US008574596B2

(12) United States Patent
Castado et al.

(10) Patent No.: US 8,574,596 B2
(45) Date of Patent: Nov. 5, 2013

(54) PERTUSSIS ANTIGENS AND USE THEREOF IN VACCINATION

(75) Inventors: Cindy Castado, Rixensart (BE); Philippe Denoel, Rixensart (BE); Fabrice Godfroid, Rixensart (BE); Jan Poolman, Rixensart (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 1017 days.

(21) Appl. No.: 10/574,297

(22) PCT Filed: Oct. 1, 2004

(86) PCT No.: PCT/EP2004/011082

§ 371 (c)(1),
(2), (4) Date: Mar. 31, 2006

(87) PCT Pub. No.: WO2005/032584

PCT Pub. Date: Apr. 14, 2005

(65) Prior Publication Data

US 2007/0116711 A1 May 24, 2007

(30) Foreign Application Priority Data

Oct. 2, 2003 (GB) .................................. 0323112.3
Oct. 2, 2003 (GB) .................................. 0323113.1

(51) Int. Cl.
*A61K 39/10* (2006.01)
*C07H 21/02* (2006.01)

(52) U.S. Cl.
USPC .................. 424/240.1; 424/253.1; 424/254.1; 536/23.1

(58) Field of Classification Search
None
See application file for complete search history.

(56) References Cited

U.S. PATENT DOCUMENTS

| | | | | |
|---|---|---|---|---|
| 5,885,587 A | 3/1999 | Eckhardt et al. | 424/240.1 |
| 6,248,329 B1 * | 6/2001 | Chandrashekar et al. | 424/191.1 |
| 7,479,283 B1 * | 1/2009 | Novotny | 424/253.1 |
| 2004/0022840 A1 * | 2/2004 | Nagy et al. | 424/450 |

FOREIGN PATENT DOCUMENTS

| | | | | |
|---|---|---|---|---|
| WO | WO/97/00697 | * 9/1997 | |
| WO | WO 0154733 | * 8/2001 | C07K 14/47 |
| WO | WO02077183 A2 | * 10/2002 | |

OTHER PUBLICATIONS

Pagliaccia et al (Arch Microbiol 168 pp. 437-440 1997).*
Burgess et al (J. of Cell Bio. 111:2129-2138, 1990).*
Lazar et al. (Molecular and Cellular Biology, 1988, 8:1247-1252).*
Bork (Genome Research, 2000,10:398-400).*
Bowie et al (Science, 1990, 247:1306-1310).*
(Chapter 29 of Vaccines, Plotkin, et al. (eds) WB Saunders, Philadelphia, 1998).*
Kinnear et al Infection and Immunity Apr. 2001 vol. 6 No. 4 pp. 1983-1993.*
Ellis (Chapter 29 of Vaccines, Plotkin, et al. (eds) WB Saunders, Philadelphia, 1998, especially p. 571, paragraph 2).*
Podda et al (Vaccine vol. 9 Oct. 2009 pp. 741-745).*
Oliver et al (Vaccine vol. 20, 2002 pp. 235-241).*
Weingart et al (Infection and Immunity Dec. 2000 vol. 68 No. 12 pp. 7175-7179).*
Kinnear et al (Infection and Immunity vol. 69 No. 4, 2001 pp. 1983-1993).*
Fernandez et al. *Infection and Immunity*, 62(11): 4727-4738 (1994).
Parkhill et al. *Nature Genetics*, 35(1): 32-40 (2003).
Heininger et al. *Clinical Infectious Diseases*, 28(3): 602-604 (1999).
Mills et al., A Murine Model in Which Protection Correlates with Pertussis Vaccine Efficacy in Children Reveals Complementary Roles for Humoral and Cell-Mediated Immunity in Portection against *Bordetella pertussis*, Infection and Immunity, 66:2, 594-602 (Feb. 1998).
Marr et al. (2008) Vaccine, 26:4306-4311.
Mooi, P.R., et al., *Adaptation of Bordetella pertussis to vaccination: a cause for its reemergence*? Emerging Infectious Diseases, vol. 7, No. 3 Supplement, pp. 526-528 (2001).
Oliver, D.C., et al., *Antibodies to BrkA augment killing of Bordetella pertussis*, Vaccine, vol. 20, pp. 235-241 (2002).
Poolman, J.T., et al., *Acellular pertussis vaccines and the role of pertactin and fimbriae*, Expert Review of Vaccines, vol. 6, No. 1, pp. 47-56 (2007).

* cited by examiner

*Primary Examiner* — Vanessa L. Ford
*Assistant Examiner* — Nina Archie
(74) *Attorney, Agent, or Firm* — Eric J. Kron

(57) ABSTRACT

The invention provides BASB232 polypeptides and polynucleotides encoding BASB232 polypeptides and methods for producing such polypeptides by recombinant techniques. Also provided are diagnostic, prophylactic and therapeutic uses. The invention further provides immunogenic compositions comprising a plurality of antigens selected from at least two different categories of antigen, having different functions within *Bordetella*. Examples of such categories of antigen are autotransporter proteins, iron acquisition proteins, lipoproteins, adhesins and toxins/invasins.

13 Claims, 6 Drawing Sheets

PERTUSSIS ANTIGENS AND USE THEREOF IN VACCINATION

This application is a 371 of International Application No. PCT/EP2004/011082, filed 01 October 2004.

FIELD OF THE INVENTION

This invention relates to polynucleotides, (herein referred to as "BASB232 polynucleotide(s)"), polypeptides encoded by them (referred to herein as "BASB232" or "BASB232 polypeptide(s)"), recombinant materials and methods for their production. In particular, the invention relates to immunogenic compositions and vaccines containing single polypeptide or nucleotides or advantageous combinations thereof. In another aspect of the invention, the invention relates to methods for using such polypeptides and polynucleotides for the treatment or prevention of *Bordetella* infections. In a further aspect, the invention relates to diagnostic assays for detecting *Bordetella* infection

BACKGROUND OF THE INVENTION

The bacterium *Bordetella pertussis* is the causative agent for whooping cough, a respiratory disease that can be severe in infants and young children. The clinical course of the disease is characterised by paroxysms of rapid coughs followed by inspiratory effort, often associated with a characteristic 'whooping' sound. In serious cases, oxygen deprivation can lead to brain damage, however the most common complication is secondary pneumonia.

Whooping cough is usually considered to be caused by *B. pertussis*, but occasionally *B. parapertussis* is isolated from patients with typical signs and symptoms of whooping cough. *B. parapertussis* infection is of lower frequency than *B. pertussis* with 5-10% of whooping cough being associated with *B. parapertussis* (Mertsola (1985) Eur J Clin Microbiol 4; 123; Lautrop (1971) Lancet 1(7711) 1195-1198). *B. parapertussis* is associated with mild clinical symptoms which, combined with its serological cross-reactivity with *B.pertussis*, makes *B. parapertussis* difficult to diagnose.

The first generation of vaccines against *B. pertussis* were whole cell vaccines, composed of whole killed bacteria. These were introduced in many countries in the 1950s and 1960s and were successful at reducing the incidence of whooping cough. A problem with whole cell *B. pertussis* vaccines is the high level of reactogenicity associated with them. Acellular vaccines containing purified *B. pertussis* proteins are less reactogenic and have been adopted for the vaccination programmes of many countries. Acellular vaccines typically containing *pertussis* toxin (PT), filamentous haemagglutinin (FHA) and quite often pertactin (PRN), are widely used and provide effective protection from the severity of whooping cough.

Despite vaccination, whooping cough remains an endemic disease (Mooi et al (2001) Emerging Infectious Diseases 7; 526). Whooping cough has re-emerged in Australia, Canada and The Netherlands; countries with highly vaccinated populations. A comparison of pre-vaccination strains with strains isolated recently, has shown antigenic drift, particularly in PT and PRN (Mooi et al (1998) Infection and Immunity 66; 670). It is widely acknowledged that current vaccines protect against severe disease but do not eliminate *Bordetella pertussis* from the body (Cherry et al (1998) Vaccine 16; 1901, Hewlett and Halperin (1998) Vaccine 16; 1899, Storsaeter et al (1998) Vaccine 16; 1907). The defence mechanisms of *Bordetella pertussis* allow it to evade elimination from the body, indicating that current vaccines do not completely disable these defence mechanisms.

Vaccination using whole cell *B. pertussis* vaccines (Pw), appears to protect against *B. parapertussis* infection, probably due to the similarity of the two bacteria. *B. parapertussis* infection in unvaccinated infants may lead to severe and fatal complications, whereas in individuals vaccinated with Pw, a milder, often subclinical course of whooping cough is seen (Long et al (1990) Pediatric Infect Dis J 9; 700). Theoretically, the introduction of acellular *pertussis* vaccines containing only two or three purified proteins could reduce the ability of vaccination to protect against *B. parapertussis*.

Accordingly, further improved acellular vaccines against whooping cough are required that combine low reactogenicity with an ability to elicit a protective response against *Bordetella*, particularly both *B. pertussis* and *B. parapertussis*, infection. The identification of new candidate antigens and particularly effective combinations of antigens will allow the development of such vaccines.

SUMMARY OF THE INVENTION

The present invention relates to immunogenic compositions containing BASB232, in particular BASB232 polypeptides or BASB232 polynucleotides, recombinant materials and methods for their production. In a further aspect, the invention relates to combination of polypeptides or nucleotides that interact advantageously in the prevention or treatment of microbial, particularly *Bordetella*, disease. In another aspect, the invention relates to methods for using such polypeptides, polynucleotides and combinations, including prevention and treatment of *Bordetella* diseases, amongst others. In a further aspect, the invention relates to diagnostic assays for detecting diseases associated with microbial infections and conditions associated with such infections, such as assays for detecting expression or activity of BASB232 polynucleotides or polypeptides.

Various changes and modifications within the spirit and scope of the disclosed invention will become readily apparent to those skilled in the art from reading the following descriptions and from reading the other parts of the present disclosure.

Panel A shows active protection against *B. parapertussis* following immunization of mice with DTPw vaccine.

Panel B shows passive protection against *B. parapertussis* by antisera raised against DTPw.

Figure 5:
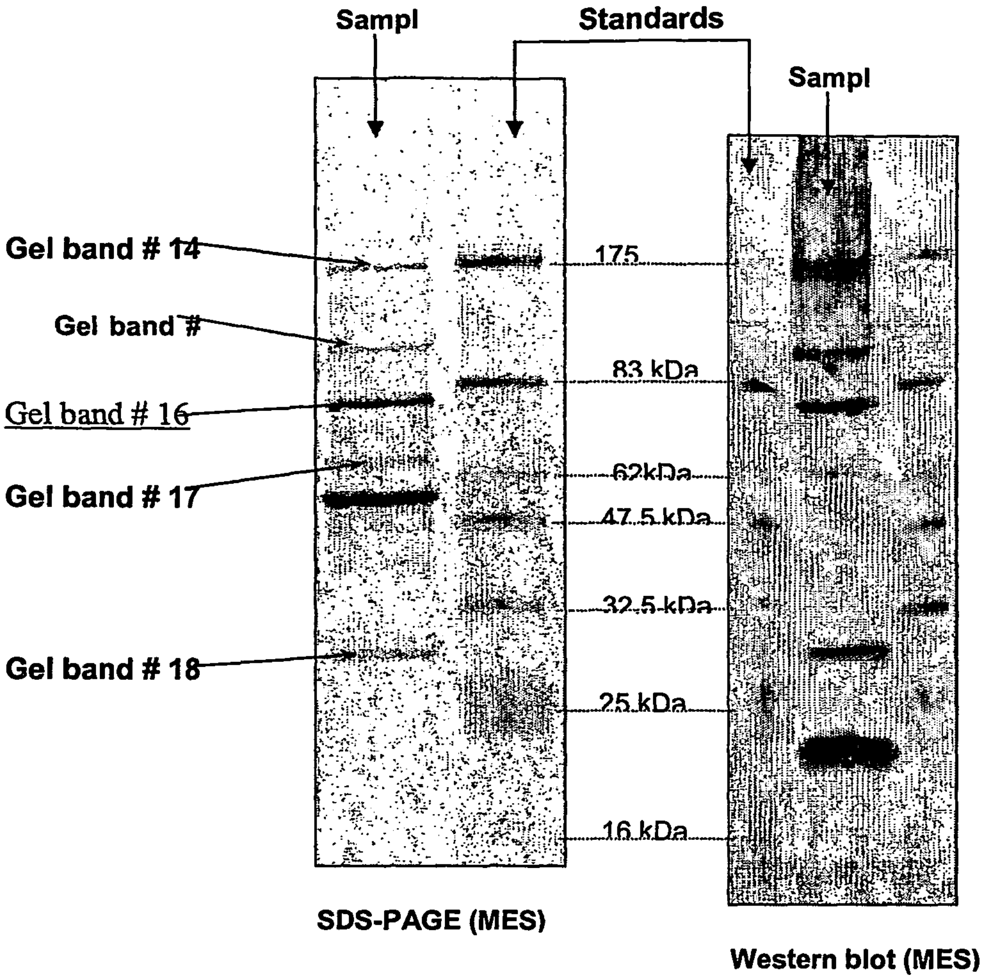

FIG. 5—Alignment of the SDS-PAGE of *B. parapertussis* OMP and the corresponding Western blot treated with sera raised against *B. pertussis* (DTPw). The running buffer used for these gels was MES. Alignment was performed using prestained molecular weight standards as reference points.

Figure 6:
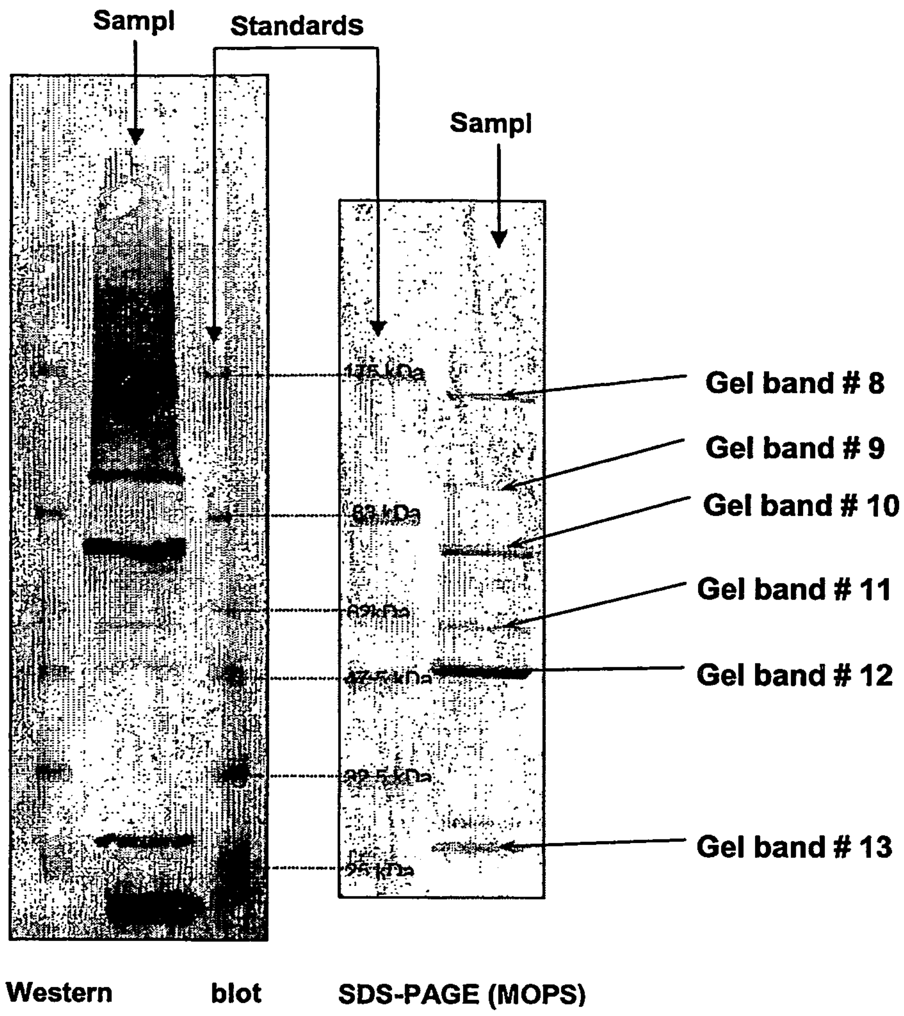

FIG. 6—Alignment of the SDS-PAGE of *B. parapertussis* OMP and the corresponding Western blot treated with sera raised against *B. pertussis* (DTPw). The running buffer used for these gels was MOPS. Alignment was performed using prestained molecular weight standards as reference points.

DESCRIPTION OF THE INVENTION

The invention relates to BASB232 polypeptides and polynucleotides as described in greater detail below. In particular, the invention relates to polypeptides and polynucleotides of BASB232 of *B. pertussis*, particularly comprised in immunogenic compositions.

The invention relates especially to BASB232 polynucleotides and encoded polypeptides listed in table 1. Those polynucleotides and encoded polypeptides have the nucleotide and amino acid sequences set out in SEQ ID NO:1 to SEQ ID NO:110 as described in table 1.

TABLE 1

| Name | Length (nT) | Length (aa) | SEQ ID nucl. | SEQ ID prot. | Description |
|---|---|---|---|---|---|
| Orf17 | 3033 | 1010 | 33 | 34 | BrkA, *Bordetella pertussis* (81%) |
| Orf1 | 2211 | 737 | 1 | 2 | Ferric enterobactin receptor (BfeA), *Bordetella pertussis* (95%) |
| Orf2 | 2475 | 812 | 3 | 4 | Probable hydroxamate-type ferrisiderophore receptor (BfrB), *Pseudomonas aeruginosa* (40%) |
| Orf3 | 2403 | 729 | 5 | 6 | Putative hydroxamate-type ferrisiderophore receptor signal peptide protein (BfrC), *Pseudomonas solanacearum* (38%) |
| Orf4 | 2304 | 734 | 7 | 8 | Putative ferric siderophore receptor (FauA), *Bordetella bronchiseptica* (97%) |
| Orf5 | 2187 | 825 | 9 | 10 | Unidentified ferric siderophore receptor, *Bordetella bronchiseptica* (94%) |
| Orf6 | 2064 | 801 | 11 | 12 | Ferric alcaligin siderophore receptor, *Bordetella pertussis* (100%) |
| Orf7 | 2229 | 743 | 13 | 14 | Hydroxamate-type ferrisidero-phore receptor (iron transport protein fiu), *Pseudomonas aeruginosa* (37%) |
| Orf8 | 2268 | 756 | 15 | 16 | Hydroxamate-type ferrisidero-phore receptor (iron transport protein fiu), *Pseudomonas aeruginosa* (41%) |
| Orf9 | 2106 | 702 | 17 | 18 | Putative hydroxamate-type ferrisiderophore receptor signal peptide protein, *Pseudomonas solanacearum* (40%) |
| Orf10 | 2610 | 870 | 19 | 20 | BhuR, outer membrane heme receptor, *Bordetella pertussis* (100%) |
| Orf11 | 2280 | 760 | 21 | 22 | Probable tonb-dependent receptor, *Pseudomonas aeruginosa* (34%) |
| Orf12 | 1887 | 629 | 23 | 24 | Probable tonb-dependent receptor, *Pseudomonas aeruginosa* (34%) |
| Orf13 | 1731 | 577 | 25 | 26 | Ferrisiderophore receptor-like protein, *Pseudomonas* sp (57%) |
| Orf14 | 1434 | 478 | 27 | 28 | Probable tonB-dependant receptor Yncd precursor, *Escherichia coli* (56%) |
| Orf15 | 2730 | 910 | 29 | 30 | Pertactin outer membrane protein, *Bordetella pertussis* (100%) |
| Orf16 | 2748 | 915 | 31 | 32 | Vag8 protein, *Bordetella pertussis* (96%) |
| Orf17 | 3033 | 1010 | 33 | 34 | BrkA, *Bordetella pertussis* (81%) |
| Orf18 | 1944 | 647 | 35 | 36 | Tcf protein, *Bordetella pertussis* (74%) |
| Orf19 | 1245 | 418 | 37 | 38 | Phg protein, *Bordetella pertussis* (81%) |
| Orf20 | 2712 | 903 | 39 | 40 | BapA protein, *Bordetella pertussis* (85%) |
| Orf21 | 1446 | 482 | 41 | 42 | BapB protein, *Bordetella pertussis* (87%) |
| Orf22 | 2277 | 759 | 43 | 44 | Putative autotransporter BapC, *Bordetella pertussis* (86%) |
| Orf23 | 1545 | 515 | 45 | 46 | Pertactin-like protein, *Bordetella pertussis* (47%) |
| Orf24 | 1191 | 397 | 47 | 48 | Tcf-like protein, *Bordetella pertussis* (56%) |
| Orf25 | 6903 | 2300 | 49 | 50 | Extracellular serine protease, *Brucella melitensis* (25%) |
| Orf26 | 2622 | 873 | 51 | 52 | Autotransporter protein, *Agrobacterium tumefaciens* (43%) |
| Orf27 | 3120 | 1039 | 53 | 54 | Autotransporter subtilisin-like protease (SphB1), *Bordetella pertussis* (93%) |
| Orf28 | 2241 | 747 | 55 | 56 | Heme/hemopexin utilization protein c precursor, *Haemophilus influenzae* (48%) |
| Orf29 | 1575 | 525 | 57 | 58 | Lipoprotein (piln protein), *Escherichia coli* (22%) |
| Orf30 | 1509 | 503 | 59 | 60 | Immunogenic protein, *Deinococcus radiodurans* (35%) |
| Orf31 | 1491 | 497 | 61 | 62 | Probable outer membrane lipoprotein precursor, *Pseudomonas aeruginosa* (48%) |
| Orf32 | 1491 | 497 | 63 | 64 | Probable outer membrane efflux protein precursor, *Pseudomonas aeruginosa* (43%) |
| Orf33 | 1380 | 460 | 65 | 66 | Oprm, *Pseudomonas aeruginosa* (45%) |
| Orf34 | 1347 | 449 | 67 | 68 | Probable outer membrane channel signal peptide protein, *Ralstonia solanacearum* (40%) |
| Orf35 | 1287 | 429 | 69 | 70 | Putative membrane-bound lytic murein transglycosylase a transmembrane protein (MltA), *Ralstonia solanacearum* (42%) |
| Orf36 | 1143 | 381 | 71 | 72 | Putative membrane-bound lytic murein transglycosylase b protein (MltB), *Ralstonia solanacearum* (40%) |

TABLE 1-continued

| Name | Length (nT) | Length (aa) | SEQ ID nucl. | SEQ ID prot. | Description |
|---|---|---|---|---|---|
| Orf37 | 1095 | 365 | 73 | 74 | Putative polysaccharide export protein yccz precursor, *Escherichia coli* (34%) |
| Orf38 | 897 | 299 | 75 | 76 | Putative serine protease transmembrane protein, *Ralstonia solanacearum* (55%) |
| Orf39 | 852 | 284 | 77 | 78 | Hypothetical protein pa4632, *Pseudomonas aeruginosa* (52%) |
| Orf40 | 846 | 282 | 79 | 80 | Competence lipoprotein coml precursor, *Neisseria meningitidis* (45%) |
| Orf41 | 813 | 271 | 81 | 82 | Probable lipoprotein precursor (vacj) transmembrane, *Ralstonia solanacearum* (43%) |
| Orf42 | 801 | 267 | 83 | 84 | Putative outer membrane lipoprotein, *Salmonella typhimurium* (24%) |
| Orf43 | 690 | 230 | 85 | 86 | Flagellar l-ring protein precursor (basal body l-ring protein), *Escherichia coli* (51%) |
| Orf44 | 678 | 226 | 87 | 88 | Hypothetical lipoprotein ydcl precursor, *Escherichia coli* (32%) |
| Orf45 | 558 | 186 | 89 | 90 | Probable peptidoglycan-associated lipoprotein precursor (Pal), *Ralstonia solanacearum* (63%) |
| Orf46 | 552 | 184 | 91 | 92 | Putative outer membrane lipoprotein (OmlA), *Bordetella pertussis* (100%) |
| Orf47 | 546 | 182 | 93 | 94 | Hypothetical transmembrane protein smc00354, *Rhizobium meliloti* (36%) |
| Orf48 | 501 | 167 | 95 | 96 | Putative outer membrane lipoprotein transmembrane, *Ralstonia solanacearum* (40%) |
| Orf49 | 456 | 152 | 97 | 98 | Lipoprotein, *Vibrio cholerae* (44%) |
| Orf50 | 5307 | 1769 | 99 | 100 | Autotransporter *Bordetella parapertussis* (100%) BPP0452 |
| Orf51 | 579 | 193 | 101 | 102 | OmpA *Bordetella pertussis* (100%) |
| Orf52 | 579 | 193 | 103 | 104 | OmpA *Bordetella parapertussis* (100%) BPP3135 |
| Orf53 | 2229 | 743 | 105 | 106 | Probable TonB-dependent receptor for iron transport *Bordetella parapertussis* (100%) BPP3376 |
| Orf54 | 1155 | 385 | 107 | 108 | Outer membrane porin protein precursor *Bordetella pertussis* (100%) |
| Orf55 | 1164 | 388 | 109 | 110 | Outer membrane porin protein precursor *Bordetella parapertussis* (100%) BPP3392 |

The percentage shown in table 1 are the identity percentage shared by each sequence of the BASB232 polypeptides and their homologous polypeptides found in *B.pertussis* or in other organisms (by a BLAST homology search).

It is understood that sequences recited in the Sequence Listing below as "DNA" represent an exemplification of one embodiment of the invention, since those of ordinary skill will recognize that such sequences can be usefully employed in polynucleotides in general, including ribopolynucleotides.

The sequences of the BASB232 polynucleotides are set out in SEQ ID NO: 33, 1, 3, 5, 7, 9, 11, 13, 15, 17, 19, 21, 23, 25, 27, 29, 31, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109. SEQ Group 1 refers herein to the group of polynucleotides set out in SEQ ID NO: 33, 1, 3, 5, 7, 9, 11, 13, 15, 17, 19, 21, 23, 25, 27, 29, 31, 35, 37, 39, 41, 43, 45,. 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109.

The sequences of the BASB232 encoded polypeptides are set out in SEQ ID NO: 34, 2, 4, 6, 8, 10, 12, 14, 16, 18, 20, 22, 24, 26, 28, 30, 32, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110. SEQ Group 2 refers herein to the group of encoded polypeptides set out in SEQ ID NO: 34, 2, 4, 6, 8, 10, 12, 14, 16, 18, 20, 22, 24, 26, 28, 30, 32, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110.

The BASB232 polynucleotides set out in SEQ ID 1, 3, 5, 7, 9, 11, 13, 15, 17, 19, 21, 23, 25, 27 and 105 belong to the iron transporter protein family.

The BASB232 polynucleotides set out in SEQ ID 33, 29, 31, 35, 37, 39, 41, 43, 45, 47, 49, 51, 53 and 99 belong to the autotransporter proteins family.

The BASB232 polynucleotides set out in SEQ ID 55, 57, 59, 61, 63, 65, 67, 69, 71, 73, 75, 77, 79, 81, 83, 85, 87, 89, 91, 93, 95 and 97 belong to the lipoproteins family.

The BASB232 polypeptides set out in SEQ ID 2, 4, 6, 8, 10, 12, 14, 16, 18, 20, 22, 24, 26, 28 and 106 belong to the iron transporter protein family.

The BASB232 polypeptides set out in SEQ ID 34, 30, 32, 36, 38, 40, 42, 44, 46, 48, 50, 52, 54 and 100 belong to the autotransporter proteins family.

The BASB232 polypeptides set out in SEQ ID 56, 58, 60, 62, 64, 66, 68, 70, 72, 74, 76, 78, 80, 82, 84, 86, 88, 90, 92, 94, 96 and 98 belong to the lipoproteins family.

Polypeptides

In one aspect of the invention there are provided polypeptides of *B. pertussis* referred to herein as "BASB232" and "BASB232 polypeptides" as well as biologically, diagnostically, prophylactically, clinically or therapeutically useful variants thereof and compositions, preferably immunogenic compositions comprising the same.

The present invention further provides for:

(a) an isolated polypeptide which comprises an amino acid sequence which has at least 85% identity, preferably at least 90% identity, more preferably at least 95% identity, most preferably at least 97, 98 or 99% or exact identity, to that of any sequence of SEQ Group 2;

(b) a polypeptide encoded by an isolated polynucleotide comprising a polynucleotide sequence which has at least 85% identity, preferably at least 90% identity, more preferably at least 95% identity, even more preferably at least 97, 98 or 99% or exact identity to any sequence of SEQ Group 1 over the entire length of the selected sequence of SEQ Group 1; or (c) a polypeptide encoded by an isolated polynucleotide comprising a polynucleotide sequence encoding a polypeptide which has at least 85% identity, preferably at least 90% identity, more preferably at least 95% identity, even more preferably at least 97-99% or exact identity, to the amino acid sequence of any sequence of SEQ Group 2.

The BASB232 polypeptides provided in SEQ Group 2 are the BASB232 polypeptides from *B. pertussis* (or *B. parapertussis*) as described in table 1. It is envisaged that *B. parapertussis* (or *B. pertussis*) sequences may be used.

The invention also provides an immunogenic fragment of a BASB232 polypeptides, that is, a contiguous portion of the BASB232 polypeptide which has the same or substantially the same immunogenic activity as the polypeptide comprising the corresponding amino acid sequence selected from SEQ Group 2; That is to say, the fragment (if necessary when coupled to a carrier) is capable of raising an immune response which recognises the BASB232 polypeptide. Such an immunogenic fragment may include, for example, the BASB232 polypeptide lacking an N-terminal leader sequence, and/or a transmembrane domain and/or a C-terminal anchor domain. In a preferred aspect the immunogenic fragment of BASB232 according to the invention comprises substantially all of the extracellular domain of a polypeptide which has at least 85% identity, preferably at least 90% identity, more preferably at least 95% identity, most preferably at least 97-99% identity, to that a sequence selected from SEQ Group 2 over the entire length of said sequence.

A fragment is a polypeptide having an amino acid sequence that is entirely the same as part but not all of any amino acid sequence of any polypeptide of the invention. As with BASB232 polypeptides, fragments may be "free-standing," or comprised within a larger polypeptide of which they form a part or region, most preferably as a single continuous region in a single larger polypeptide.

Preferred fragments include, for example, truncation polypeptides having a portion of an amino acid sequence selected from SEQ Group 2 or of variants thereof, such as a continuous series of residues that includes an amino- and/or carboxyl-terminal amino acid sequence. Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence selected from SEQ Group 2 or an isolated polypeptide comprising an amino acid sequence having at least 15, 20, 30, 40, 50 or 100 contiguous amino acids truncated or deleted from the amino acid sequence selected from SEQ Group 2.

The BASB232 polypeptides set out in SEQ ID 30, 32, 34, 36, 38, 40, 42, 44, 46, 48, 50, 52, 53 and 54 belong to an autotransporter proteins family. In this family, there are two domains: the passenger domain that is surface exposed and the beta domain that is anchored in the outer membrane protein. The passenger domain is a preferred fragment for vaccine use. The passenger domain was predicted for each of the BASB232 polypeptides set out in SEQ ID 30, 32, 34, 36, 38, 40, 42, 44, 50, 52 and 100 in table 2.

TABLE 2

| encoded peptidic sequence | $1^{st}$ amino acids of the preferred fragment | Last amino acids of the preferred fragment |
|---|---|---|
| SEQ ID NO: 30 | 35 | 604 |
| SEQ ID NO: 32 | 40 | 614 |
| SEQ ID NO: 34 | 41 | 706 |
| SEQ ID NO: 36 | 40 | 132 |
| SEQ ID NO: 38 | 36 | 114 |
| SEQ ID NO: 40 | 31 | 595 |
| SEQ ID NO: 42 | 1 | 185 |
| SEQ ID NO: 44 | 1 | 458 |
| SEQ ID NO: 50 | 38 | 1984 |
| SEQ ID NO: 52 | 43 | 561 |
| SEQ ID NO: 100 | 39 | 1453 |

Fragments described in table 2 are preferred fragments. These fragments may be readily modified by adding or removing 1, 2, 3, 4, 5, 6, 7, 8, 9, 10, 20, 30, 40 or 50 amino acids from either or both of the N and C termini.

Still further preferred fragments are those which comprise a B-cell or T-helper epitope, for example those fragments/peptides described in Example 8.

Fragments of the polypeptides of the invention may be employed for producing the corresponding full-length polypeptide by peptide synthesis; therefore, these fragments may be employed as intermediates for producing the full-length polypeptides of the invention.

The term "fragment" encompasses the fragment itself or the fragment may be part of a larger protein or a fusion protein.

Particularly preferred are variants in which several, 5-10, 1-5, 1-3, 1-2 or 1 amino acids are substituted, deleted, or added in any combination.

The polypeptides, or immunogenic fragments, of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa.

Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenzae* and the non-structural protein from influenza virus, NS1 (hemagglutinin). Another fusion partner is the protein known as Omp26 (WO 97/01638). Another fusion partner is the protein known as LytA. Preferably the C terminal portion of the molecule is used. LytA is derived from *Streptococcus pneumoniae* which synthesize an N-acetyl-L-alanine amidase, amidase LytA, (coded by the lytA gene {Gene, 43 (1986) page 265-272}) an autolysin that specifically degrades certain bonds in the peptidoglycan backbone. The C-terminal domain of the LytA protein is responsible for the affinity to the choline or to some choline analogues such as DEAE. This property has been exploited for the development of *E.coli* C-LytA expressing plasmids useful for expression of fusion proteins. Purification of hybrid proteins containing the C-LytA fragment at its amino terminus has been described {Biotechnology: 10, (1992) page 795-798}. It is possible to use the repeat portion of the LytA molecule found in the C terminal end starting at residue 178, for example residues 188-305.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

It is most preferred that a polypeptide of the invention is derived from *B. pertussis*, however, it is optionally obtained from other organisms of the same taxonomic genus. A polypeptide of the invention may also be obtained, for example, from organisms of the same taxonomic family or order (for instance *Bordetella parapertussis* or *Bordetella bronchosepaica*).

Polynucleotides

It is an object of the invention to provide polynucleotides that encode BASB232 polypeptides, particularly polynucleotides that encode polypeptides herein designated BASB232.

In a particularly preferred embodiment of the invention the polynucleotide comprises a region encoding BASB232 polypeptides comprising sequences set out in SEQ Group 1 which include full length gene, or a variant or fragment thereof.

Polynucleotides of the invention do not encompass a complete genomic DNA from a *Bordetella* species, e.g. *B. pertussis* or *B. parapertussis.*

As a further aspect of the invention there are provided isolated nucleic acid molecules encoding and/or expressing BASB232 polypeptides and polynucleotides, particularly *B. pertussis* or *B. parapertussis* BASB232 polypeptides and polynucleotides, including, for example, unprocessed RNAs, ribozyme RNAs, mRNAs, cDNAs, B- and Z-DNAs. Further embodiments of the invention include biologically, diagnostically, prophylactically, clinically or therapeutically useful polynucleotides and polypeptides, and variants thereof, and compositions, preferably immunogenic compositions, comprising the same.

Another aspect of the invention relates to isolated polynucleotides, including at least one full length gene, that encode BASB232 polypeptides having a deduced amino acid sequence of SEQ Group 2 and polynucleotides closely related thereto and variants thereof.

In another particularly preferred embodiment of the invention relates to BASB232 polypeptides from *B. pertussis* or *B. parapertussis* comprising or consisting of an amino acid sequence selected from SEQ Group 2 or a variant thereof.

Using the information provided herein, such as a polynucleotide sequence set out in SEQ Group 1, a polynucleotide of the invention encoding BASB232 polypeptide may be obtained using standard cloning and screening methods, such as those for cloning and sequencing chromosomal DNA fragments from bacteria using *B. pertussis* strain Tohama I cells as starting material, followed by obtaining a full length clone. For example, to obtain a polynucleotide sequence of the invention, such as a polynucleotide sequence given in SEQ Group 1, typically a library of clones of chromosomal DNA of *B. pertussis* strain Tohama I in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Mustrative of the invention, each polynucleotide set out in SEQ Group 1 was discovered in a DNA library derived from *B. pertussis* or *B. parapertussis.*

Moreover, each DNA sequence set out in SEQ Group 1 contains an open reading frame encoding a protein having about the number of amino acid residues set forth in SEQ Group 2 with a deduced molecular weight that can be calculated using amino acid residue molecular weight values well known to those skilled in the art.

The polynucleotides of SEQ Group 1, between the start codon and the stop codon, encode respectively the polypeptides of SEQ Group 2. The nucleotide number of start codon and first nucleotide of the stop codon are listed in table 3 for each polynucleotide of SEQ Group 1.

TABLE 3

The respective SEQ ID NO for each Orf is found in Table 1.

| Name | Start codon | 1st nucleotide of stop codon |
|---|---|---|
| Orf1 | 1 | 2212 |
| Orf2 | 1 | 2476 |
| Orf3 | 1 | 2404 |
| Orf4 | 1 | 2305 |
| Orf5 | 1 | 2188 |
| Orf6 | 1 | 2065 |
| Orf7 | 1 | 2230 |
| Orf8 | 1 | 2269 |
| Orf9 | 1 | 2107 |
| Orf10 | 1 | 2611 |
| Orf11 | 1 | 2281 |
| Orf12 | 1 | 1888 |
| Orf13 | 1 | 1732 |
| Orf14 | 1 | 1435 |
| Orf15 | 1 | 2731 |
| Orf16 | 1 | 2746 |
| Orf17 | 1 | 3031 |
| Orf18 | 1 | 1942 |
| Orf19 | 1 | 1255 |
| Orf20 | 1 | 2710 |
| Orf21 | 1 | 1447 |
| Orf22 | 1 | 2278 |
| Orf23 | 1 | 1546 |
| Orf24 | 1 | 1192 |
| Orf25 | 1 | 6901 |
| Orf26 | 1 | 2620 |
| Orf27 | 1 | 3118 |
| Orf28 | 1 | 2242 |
| Orf29 | 1 | 1576 |
| Orf30 | 1 | 1510 |
| Orf31 | 1 | 1492 |
| Orf32 | 1 | 1492 |
| Orf33 | 1 | 1381 |
| Orf34 | 1 | 1348 |
| Orf35 | 1 | 1288 |
| Orf36 | 1 | 1144 |
| Orf37 | 1 | 1096 |
| Orf38 | 1 | 898 |
| Orf39 | 1 | 853 |
| Orf40 | 1 | 847 |
| Orf41 | 1 | 814 |
| Orf42 | 1 | 802 |
| Orf43 | 1 | 691 |
| Orf44 | 1 | 679 |
| Orf45 | 1 | 559 |
| Orf46 | 1 | 553 |
| Orf47 | 1 | 547 |
| Orf48 | 1 | 502 |
| Orf49 | 1 | 457 |
| Orf50 | 1 | 5308 |
| Orf51 | 1 | 580 |
| Orf52 | 1 | 580 |
| Orf53 | 1 | 2230 |
| Orf54 | 1 | 1156 |
| Orf55 | 1 | 1165 |

In a further aspect, the present invention provides for an isolated polynucleotide comprising or consisting of:

(a) a polynucleotide sequence which has at least 85% identity, preferably at least 90% identity, more preferably at least 95% identity, even more preferably at least 97, 98 or 99% or exact identity to any sequence from SEQ Group 1 over the entire length of the polynucleotide sequence from SEQ Group 1; or (b) a polynucleotide sequence encoding a polypeptide which has at least 85% identity, preferably at least 90% identity, more preferably at least 95% identity, even more preferably at least 97, 98 or 99% or 100% exact, to any amino acid sequence selected from SEQ Group 2, over the entire length of the amino acid sequence from SEQ Group 2.

A polynucleotide encoding a polypeptide of the present invention, including homologs and orthologs from species other than *B. pertussis*, may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising any sequence selected from SEQ Group 1 or a fragment thereof; and isolating a full-length gene and/or genomic clones containing said polynucleotide sequence.

The invention provides a polynucleotide sequence identical over its entire length to a coding sequence (open reading frame) set out in SEQ Group 1. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al, *Proc. Natl. Acad Sci., USA* 86. 821-824 (1989), or an HA peptide tag (Wilson et al, *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequences encoding the BASB232 polypeptides of SEQ Group 2 may be identical to the corresponding polynucleotide encoding sequences of SEQ Group 1. The position of the first and last nucleotides of the encoding sequences of SEQ Group 1 are listed in table 4. Alternatively it may be any sequence, which as a result of the redundancy (degeneracy) of the genetic code, also encodes polypeptides of SEQ Group 2.

TABLE 4

| nucleotidic sequence | encoded peptidic sequence | Start codon | Last nucleotide of encoding sequence |
|---|---|---|---|
| SEQ ID NO: 1 | SEQ ID NO: 2 | 1 | 2211 |
| SEQ ID NO: 3 | SEQ ID NO: 4 | 1 | 2475 |
| SEQ ID NO: 5 | SEQ ID NO: 6 | 1 | 2403 |
| SEQ ID NO: 7 | SEQ ID NO: 8 | 1 | 2304 |
| SEQ ID NO: 9 | SEQ ID NO: 10 | 1 | 2187 |
| SEQ ID NO: 11 | SEQ ID NO: 12 | 1 | 2064 |
| SEQ ID NO: 13 | SEQ ID NO: 14 | 1 | 2229 |
| SEQ ID NO: 15 | SEQ ID NO: 16 | 1 | 2268 |
| SEQ ID NO: 17 | SEQ ID NO: 18 | 1 | 2106 |
| SEQ ID NO: 19 | SEQ ID NO: 20 | 1 | 2610 |
| SEQ ID NO: 21 | SEQ ID NO: 22 | 1 | 2280 |
| SEQ ID NO: 23 | SEQ ID NO: 24 | 1 | 1887 |
| SEQ ID NO: 25 | SEQ ID NO: 26 | 1 | 1731 |
| SEQ ID NO: 27 | SEQ ID NO: 28 | 1 | 1434 |
| SEQ ID NO: 29 | SEQ ID NO: 30 | 1 | 2730 |
| SEQ ID NO: 31 | SEQ ID NO: 32 | 1 | 2745 |
| SEQ ID NO: 33 | SEQ ID NO: 34 | 1 | 3030 |
| SEQ ID NO: 35 | SEQ ID NO: 36 | 1 | 1941 |
| SEQ ID NO: 37 | SEQ ID NO: 38 | 1 | 1254 |
| SEQ ID NO: 39 | SEQ ID NO: 40 | 1 | 2709 |

TABLE 4-continued

| nucleotidic sequence | encoded peptidic sequence | Start codon | Last nucleotide of encoding sequence |
|---|---|---|---|
| SEQ ID NO: 41 | SEQ ID NO: 42 | 1 | 1446 |
| SEQ ID NO: 43 | SEQ ID NO: 44 | 1 | 2277 |
| SEQ ID NO: 45 | SEQ ID NO: 46 | 1 | 1545 |
| SEQ ID NO: 47 | SEQ ID NO: 48 | 1 | 1191 |
| SEQ ID NO: 49 | SEQ ID NO: 50 | 1 | 6900 |
| SEQ ID NO: 51 | SEQ ID NO: 52 | 1 | 2619 |
| SEQ ID NO: 53 | SEQ ID NO: 54 | 1 | 3117 |
| SEQ ID NO: 55 | SEQ ID NO: 56 | 1 | 2241 |
| SEQ ID NO: 57 | SEQ ID NO: 58 | 1 | 1575 |
| SEQ ID NO: 59 | SEQ ID NO: 60 | 1 | 1509 |
| SEQ ID NO: 61 | SEQ ID NO: 62 | 1 | 1491 |
| SEQ ID NO: 63 | SEQ ID NO: 64 | 1 | 1491 |
| SEQ ID NO: 65 | SEQ ID NO: 66 | 1 | 1380 |
| SEQ ID NO: 67 | SEQ ID NO: 68 | 1 | 1347 |
| SEQ ID NO: 69 | SEQ ID NO: 70 | 1 | 1287 |
| SEQ ID NO: 71 | SEQ ID NO: 72 | 1 | 1143 |
| SEQ ID NO: 73 | SEQ ID NO: 74 | 1 | 1095 |
| SEQ ID NO: 75 | SEQ ID NO: 76 | 1 | 897 |
| SEQ ID NO: 77 | SEQ ID NO: 78 | 1 | 852 |
| SEQ ID NO: 79 | SEQ ID NO: 80 | 1 | 846 |
| SEQ ID NO: 81 | SEQ ID NO: 82 | 1 | 813 |
| SEQ ID NO: 83 | SEQ ID NO: 84 | 1 | 801 |
| SEQ ID NO: 85 | SEQ ID NO: 86 | 1 | 690 |
| SEQ ID NO: 87 | SEQ ID NO: 88 | 1 | 678 |
| SEQ ID NO: 89 | SEQ ID NO: 90 | 1 | 558 |
| SEQ ID NO: 91 | SEQ ID NO: 92 | 1 | 552 |
| SEQ ID NO: 93 | SEQ ID NO: 94 | 1 | 546 |
| SEQ ID NO: 95 | SEQ ID NO: 96 | 1 | 501 |
| SEQ ID NO: 97 | SEQ ID NO: 98 | 1 | 456 |
| SEQ ID NO: 99 | SEQ ID NO: 100 | 1 | 5307 |
| SEQ ID NO: 101 | SEQ ID NO: 102 | 1 | 579 |
| SEQ ID NO: 103 | SEQ ID NO: 104 | 1 | 579 |
| SEQ ID NO: 105 | SEQ ID NO: 106 | 1 | 2229 |
| SEQ ID NO: 107 | SEQ ID NO: 108 | 1 | 1155 |
| SEQ ID NO: 109 | SEQ ID NO: 110 | 1 | 1164 |

The term "polynucleotide encoding a polypeptide" as used herein encompasses polynucleotides that include a sequence encoding a polypeptide of the invention, particularly a bacterial polypeptide and more particularly a polypeptide of the *B. pertussis* or *B parapertussis* BASB232 having an amino acid sequence set out in any of the sequences of SEQ Group 2. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptides having a deduced amino acid sequence of any of the sequences of SEQ Group 2. Fragments of polynucleotides of the invention may be used, for example, to synthesize full-length polynucleotides of the invention.

Preferred fragments are those polynucleotides which encode a B-cell or T-helper epitope, for example the fragments/peptides described in Example 8, and recombinant, chimeric genes comprising said polynucleotide fragments.

Further particularly preferred embodiments are polynucleotides encoding BASB232 variants, that have the amino acid sequence of BASB232 polypeptides of any sequence from SEQ Group 2 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB232 polypeptides.

Further preferred embodiments of the invention are polynucleotides that are at least 85% identical over their entire length to polynucleotides encoding BASB232 polypeptides having an amino acid sequence set out in any of the sequences of SEQ Group 2, and polynucleotides that are complementary to such polynucleotides. Alternatively, most highly preferred are polynucleotides that comprise a region that is at least 90% identical over its entire length to polynucleotides encoding BASB232 polypeptides and polynucleotides complementary thereto. In this regard, polynucleotides at least 95% identical over their entire length to the same are particularly preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as mature polypeptides encoded by a DNA sequences selected from SEQ Group 1.

In accordance with certain preferred embodiments of this invention there are provided polynucleotides that hybridize, particularly under stringent conditions, to BASB232 polynucleotide sequences, such as those polynucleotides in SEQ Group 1.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 micrograms/ml of denatured, sheared salmon sperm DNA, followed by washing the hybridization support in 0.1×SSC at about 65° C.

Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in any of the sequences of SEQ Group 1 under stringent hybridization conditions with a probe having the sequence of said polynucleotide sequence set forth in the corresponding sequences of SEQ Group 1 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate fill-length cDNAs and genomic clones encoding BASB232 and to isolate cDNA and genomic clones of other genes that have a high identity, particularly high sequence identity, to the BASB232 genes. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of BASB232 genes maybe isolated by screening using a DNA sequences provided in SEQ Group 1 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., *PNAS USA* 85: 8998-9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ Group 1 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In accordance with an aspect of the invention, there is provided the use of a polynucleotide of the invention for therapeutic or prophylactic purposes, in particular genetic immunization.

The use of a polynucleotide of the invention in genetic immunization will preferably employ a suitable delivery method such as direct injection of plasmid DNA into muscles (Wolff et al., *Hum Mol Genet* (1992) 1: 363, Manthorpe et al., *Hum. Gene Ther.* (1983) 4: 419), delivery of DNA complexed with specific protein carriers (Wu et al., *J Biol Chem.* (1989) 264: 16985), coprecipitation of DNA with calcium phosphate (Benvenisty & Reshef, *PNAS USA*, (1986) 83: 9551), encapsulation of DNA in various forms of liposomes (Kaneda et al., *Science* (1989) 243: 375), particle bombardment (Tang et al., *Nature* (1992) 356:152, Bisenbraun et al., *DNA Cell Biol* (1993) 12: 791) and in vivo infection using cloned retroviral vectors (Seeger et al., *PNAS USA* (1984) 81: 5849).

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, conjugation, transduction, scrape loading, ballistic introduction and infection.

Representative examples of appropriate hosts include bacterial cells, such as cells of streptococci, staphylococci, enterococci, *E. coli*, streptomyces, cyanobacteria, *Bacillus subtilis, Neisseria meningitidis, Haemophilus influenzae* and *Moraxella catarrhalis*; fungal cells, such as cells of a yeast, *Kluveromyces, Saccharomyces, Pichia*, a basidiomycete, *Candida albicans* and *Aspergillus*; insect cells such as cells of *Drosophila* S2 and *Spodoptera* Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculovinises, papova viruses, such as SV40, vaccinia viruses, adenoviruses, fowl pox viruses, pseudorabies viruses, picornaviruses, retroviruses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

The expression system may also be a recombinant live microorganism, such as a virus or bacterium The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g; vaccinia, fowlpox, canarypox), alphaviruses (Sindbis virus, Semliki Forest Virus, Venezuelian Equine Encephalitis Virus), adenoviruses, adeno-associated virus, picomaviruses (poliovirus, rhinovirus), herpesviruses (varicella zoster virus, etc), *Listeria, Salmonella , Shigella*, BCG, streptococci. These viruses and bacteria can be virulent, or attenuated in various ways in order to obtain live vaccines. Such live vaccines also form part of the invention.

Combinations of *Bordetella* Antigens in Immunogenic Compositions

A further aspect of the invention discloses particular combinations of *Bordetella* antigens which when combined, lead to an effective immunogenic composition against *Bordetella* infection. The efficacy of the immunogenic composition is determined as by its ability to elicit a protective response against *B. pertussis* primarily, but it is preferred that they also elicit a protective effect against the related bacteria *B. parapertussis* and/or *B. bronchiseptica.*

Preferred combinations of *Bordetella* antigens, when combined in an immunogenic composition or vaccine, allow different *Bordetella* functions to be targetted by the immune response. Such an immune response is better able to treat or prevent *Bordetella* infection. For instance, known virulence factors include adhesins like FHA, fimbrae, pertactin which are involved in attachment of *Bordetella* to host cells; toxins such as *pertussis* toxin, adenylate cyclase have a role in disabling the host immune system; BrkA acts as a serum resistance factor and TcfA has a role in tracheal colonization.

In particular, combinations of certain antigens from different classes, some of which are involved in adhesion to host cells, some of which are involved in iron acquisition, some of which are antotransporters and some of which are toxins, can elicit an immune response which protects against multiple functions of *Bordetella* required to sustain infection. Such combinations of antigens can surprisingly lead to improved vaccine efficacy against *Bordetella* infection where more that one function of the bacterium is targeted by the immune response. Preferably, the improved vaccine efficacy is against *B. pertussis* and/or *B. parapertussis.*

Accordingly, the invention provides immunogenic compositions comprising at least or exactly two, three, preferably four, five, six, seven, eight, nine or ten different *Bordetella*, preferably *B. pertussis* antigens, wherein the antigens are selected from at least two, three, four or five of the following categories:

a) at least one *Bordetella* autotransporter protein selected from the group consisting of a polypeptide sharing at least 70%, 80%; 90%, 95%, 97%, 98%, 99% or 100% identity with SEQ ID 34, 30, 32, 36, 38, 40, 42, 44, 46, 48, 50, 52, 54 or 100, pertactin and BipA, or an antigenic or immunogenic fragment thereof, preferably a passenger domain thereof;

b) at least one *Bordetella* iron acquisition protein selected from the group consisting of the polypeptide sharing at least 70%, 80%, 90%, 95%, 97%, 98%, 99% or 100% identity with SEQ ID 2, 4, 6, 8, 10, 12, 14, 16, 18, 20, 22, 24, 26, 28 or 106, or an antigenic or immunogenic fragment thereof;

c) at least one *Bordetella* lipoprotein selected from the group consisting of the polypeptide sharing at least 70%, 80%, 90%, 95%, 97%, 98%, 99% or 100% identity with SEQ ID 56, 58, 60, 62, 64, 66, 68, 70, 72, 74, 76, 78, 80, 82, 84, 86, 88, 90, 92, 94, 96, or 98 or an antigenic or immunogenic fragment thereof;

d) at least one *Bordetella* adhesin selected from the group consisting of FHA, fimbriae, pertactin and BrkA or an antigenic or immunogenic fragment thereof; and e) at least one *Bordetella* toxin/invasin or antigens involved in toxin/invasin secretion selected from the group consisting of *pertussis* toxin, adenylate cyclase, dermonecrotic toxin (Dnt), Type IIIss or lipopolysaccharide or an antigenic or immunogenic fragment thereof, wherein the *Bordetella* antigens in the immunogenic composition do not consist of any combination of 2, 3, 4 or all 5 of pertactin, fimbriae 2, fimbrae 3, FHA and *pertussis* toxin.

The combinations of the invention do not include whole cell *pertussis* (Pw).

Immunogenic compositions of the invention therefore do not cover known vaccine combinations (for instance vaccines where the acellular *pertussis* component consist of 2, 3, 4 or 5 of FHA, *pertussis* toxoid, pertactin, fimbrae 2 and fimbrae 3) however a single known antigen from one group, combined with a new antigen from a different group is covered.

The *Bordetella* antigens may derived from any strain of *Bordetella* including from one or more of *B. pertussis, B. parapertussis* and *B. bronchiseptica* (preferably the former).

Preferably all five groups of antigen are represented in the immunogenic composition of the invention. Where an antigen falls into two groups, the inclusion of that one antigen into an immunogenic composition leads to the inclusion of both groups in the immunogenic composition.

Where a protein is specifically mentioned herein, it is preferably a reference to a native, full-length protein but it may also encompass antigenic, preferably immunogenic fragments thereof (particularly in the context of subunit vaccines). These are fragments containing or comprising at least 10 amino acids, preferably at least 20 amino acids, more preferably at least 30 amino acids, more preferably at least 40 amino acids or most preferably at least 50 amino acids, taken contiguously from the amino acid sequence of the protein wherein the fragment is shorter than the full length of the protein. Particularly preferred fragments are the passenger domains of autotransporter proteins as defined above. In addition, antigenic fragments denotes fragments that are immunologically reactive with antibodies generated against the *B. pertussis* proteins or with antibodies generated by infection of a mammalian host with *Bordetella*. Antigenic fragments also includes fragments that when administered at an effective dose, elicit a protective immune response against *Bordetella* infection, more preferably it is protective against *B. pertussis* and/or *B. parapertussis* and/or *B. bronchiseptica* infection. Preferably such fragments are coupled to a source of T—cell epitopes.

Also included in the invention are recombinant fusion proteins of *Bordetella* proteins of the invention, or fragments thereof. These may combine different *Bordetella* proteins or fragments thereof in the same polypeptide. Alternatively, the invention also includes individual fusion proteins of *Bordetella* proteins or fragments thereof, as a fusion protein with heterologous sequences such as a provider of T-ell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, tetanus toxoid, diphtheria toxoid, CRM197.

Antigens of the Invention

1. Autotransporter Proteins

Autotransporter proteins typically are made up of a signal sequence, a passenger domain and an anchoring domain for attachment to the outer membrane. Examples of autotransporter proteins include pertactin (SEQ ID 30), Vag8 (SEQ ID 32), BrkA (SEQ ID 34), TcfA (SEQ ID 36) (Finn and Stevens (1995) Mol. Microbiol. 16; 625-634), Phg (SEQ ID 38), BipA (Stockbauer et al 2001; Molecular Microbiology 39; 65-78), BapA (SEQ ID 40), BapB (SEQ ID 42), BapC (SEQ ID 44), pertactin-like protein (SEQ ID 46), Tcf-like protein (SEQ ID 48), extracellular serine protease (SEQ ID 50, SEQ ID 100), YapE (SEQ ID 52), SphBI (SEQ ID 54). These antigens may be derived from *Bordetella pertussis* or *Bordetella parapertussis* or other *Bordetella* strains.

It is particularly advantageous to use the passenger domain of an autotranporter when it is included in a subunit vaccine. Table 2 above defines the passsenger domains of the autotransporter proteins listed above.

BipA contains 90 amino acid tandem repeats with 5 being present in the *B. pertussis* protein and 8 being present in the *B. bronchiseptica* protein. These repeats span from amino acid 581 to 1030 in *B. pertussis* and amino acids 581 to 1300 in *B. bronchiseptica*. Preferred fragments of BipA include amino acids 1031 to 1308, amino acids 941 to 1308, amino acids 851 to 1308, amino acids 761 to 1308, amino acids 671 to 1308 and 581 to 1308 of the *B. pertusis* sequence (or sequences related to these that have 1, 2, 3, 4, 5, 6, 7, 8, 9, 10, 20, 30, 40 or 50 amino acids added or deleted from either or both of the N and C termini).

2. Iron Acquisition Proteins

Iron acquisition is of great importance to mammalian pathogens as iron is present in limiting conditions in the host and any iron that is present is sequestered by haem and other iron-chelating compounds. Iron from siderophores and host iron-binding complexes is internalised through TonB-dependent outer membrane ferric complex receptors. *Bordetella* iron aquisition proteins include BfeA (SEQ ID 2), BfrB (SEQ ID 4), BfrC (SEQ ID 6), FauA (SEQ ID 8), ferric siderophore receptor (SEQ ID 10), Ferric alcaligin siderophore receptor (SEQ ID 12), iron tranport protein fiu (SEQ ID 14, SEQ ID 106), iron tranport protein flu (SEQ ID 16), putative hydrxamate-type ferrisiderophore receptor signal peptide protein (SEQ ID 18) BhuR (SEQ ID 20) (Infection and Immunity 2001, 69; 6951), tonb-dependent receptor (SEQ ID 22), tonb-dependent receptor (SEQ ID 24), ferrisiderophore receptor-like protein (SEQ ID 26) and tonb-dependent receptor Yncd precurser (SEQ ID 28). These proteins may be derived from *Bordetella pertussiss, Bordetella parapertussis* or other *Bordetella* strains, preferably the former.

3. Lipoproteins

*Bordetella* lipoproteins include heme/hemopexin utilisation protein C presursor (SEQ ID 56), piln protein (SEQ ID 58), immunogenic protein (SEQ ID 60), outer membrane lipoprotein precursor (SEQ ID 62), outer membrane efflux protein precursor (SEQ ID 64), Oprm (SEQ ID 66), outer membrane channel signal protein (SEQ ID 68), MltA (SEQ ID 70), MTB (SEQ ID 72), yccz precursor (SEQ ID 74), serine protease transmembrane protein (SEQ ID 76), pa4632 (SEQ ID 78), coml precursor (SEQ ID 80), VacJ (SEQ ID 82), outer membrane lipoportein (SEQ ID 84), Flagelar 1-ring protein (SEQ ID 86), Ydcl (SEQ ID 88), Pal (SEQ ID 90), OmlA (SEQ ID 92), Smc00354 (SEQ ID 94), Pcp (SEQ ID 96) and lipoprotein (SEQ ID 98).

The lipoproteins having the sequence of SEQ ID 56-96 contain a lipidation motif indicating that they would be lipidated and inserted into the membrane. In its simplest form, the lipidation motif contains the concensus sequence LXXC. However, the concensus sequence is preferably close to the amino terminus of the sequence, within the larger concensus sequence:

<(M, V, L)~*{1, 40}~(D, E, R, K, *)6(L, I, V, M, F, W, S, T, A, G)2(L, I, V, M, F, Y, S, T, A, G, C, Q) (A, G, S) C

<indicates the amino terminus of the protein so that the first amino acid should be M, V or L. {1, 40} indicates that between 1 and 40 amino acids should be present between the first amino acid and the rest of the concensus sequence. (D, E, R, K, *)6 indicates that the next 6 amino acids should not be D, E, R or K. The following 2 amino acids should be one of the aliphatic amino acids indicated and is preferably L. For the following 2 amino acids, the amino acids shown in the parentheses should be present and the final amino acid of the sequence shold be C. These antigens may be derived from *Bordetella pertussis* or *Bordetella parapertussis, Bordetella bronchoseptica* or other *Bordetella* strains, preferably the former.

4. Adhesins

Adhesins have a role in attaching *Bordetella* to a host cell and hence have important roles in virulence. They include filamentous haemagglutinin (FHA) (Relman et al (1989) Proc Natl Acad Sci USA 86; 2634-2641), fimbriae (Fim) (Mooi et al (1992) Microb Pathog 12; 127-135), pertactin (Roberts et al (1991) Mol Microbiol 5; 1393-1404) and BrkA (Fernandez et al (1994) Infection and Immunity 62; 4727-4738). These antigens may be derived from *Bordetella pertussis* or *Bordetella parapertussis, Bordetella bronchoseptica* or other *Bordetella* strains, preferably the former.

Fimbriae or Fim proteins are also known as aggutinins or fimbrial adhesins. The term Fim comprises fimbriae 2 and fimbriae 3.

5. Toxins

Toxins include adenylate cyclase (CyaA) (Hewlett et al (1989) J. Biol. Chem. 264; 19379-19384), pertussis toxin (Munoz et al (1981) Infect Immun 33; 820-826), dermonecrotic toxin (Dnt) (Livey (1984) J. Med. Microbiol. 17; 91-103 and lipopolysaccharides. Toxins also include proteins that are involved in the secretion of toxins since an immune response against the secretory mechanism would prevent the efficient functioning of the secretory mechanism and lead to reduced toxin secretion. An example of such an antigen is the Type III secretion system (Yuk et al (2000) Mol. Microbiol. 35; 991-1004). These antigens may be derived from *Bordetella pertussis* or *Bordetella parapertussis, Bordetella bronchoseptica* or other *Bordetella* strains, preferably the former.

Preferred fragments of adenylate cyclase comprise amino acids 385-399 or sequences related to this that have 1, 2, 3, 4, 5, 6, 7, 8, 9, 10, 20, 30, 40 or 50 amino acids added to either or both of the N and C termini. Preferred fragments are disclosed in EP424518, EP787796 or WO 90/13312.

Where toxin is described herein, non-toxic derivatives such as toxoids or mutant toxins are also envisaged to be covered by the term.

Preferred Combinations

In any of the preferred combinations listed below, the term antigen comprises immunogenic fragments of that antigen.

In a preferred embodiment of the combination of antigens of the invention, the immunogenic composition comprises at least one *Bordetella* iron acquisition protein selected from the group consisting of the polypeptide sharing at least 70%, 80%, 90%, 95%, 97%, 98%, 99% or 100% amino acid identity with SEQ D 2, 4, 6, 8, 10, 12, 14, 16, 18, 20, 22, 24, 26, 28, 106 or an antigenic or immunogenic fragment thereof.

In a particularly preferred embodiment of the invention, the immunogenic composition comprises one, two or three of FHA, *pertussis* toxin and pertactin, (preferably FHA and PT; FHA and pertactin; PT and pertactin; or FHA, *pertussis* toxin and pertactin) and further comprises at least one *Bordetella* iron acquisition protein selected from the group consisting of the polypeptide sharing at least 70%, 80%, 90%, 95%, 97%, 98%, 99% or 100% amino acid identity with SEQ ID 2, 4, 6, 8, 10, 12, 14, 16, 18, 20, 22, 24, 26, 28, 106 or an antigenic or immunogenic fragment thereof.

In a further preferred embodiment of the invention, the immunogenic composition comprises at least one *Bordetella* autotransporter protein selected from the group consisting of BipA, the polypeptide sharing at least 70%, 80%, 90%, 95%, 97%, 98%, 99% or 100% amino acid identity with SEQ ID 32, 34, 36, 38, 40, 42, 44, 46, 48, 50, 52, 54, 100, or an antigenic or immunogenic fragment thereof, preferably the passenger domain thereof.

In a particularly preferred embodiment of the invention, the immunogenic composition comprises one, two or three of FHA, *pertussis* toxin and pertactin, (preferably FHA and PT; FHA and pertactin; PT and pertactin; or FHA, *pertussis* toxin and pertactin), and further comprises at least one *Bordetella* autotransporter protein selected from the group consisting of BipA, the polypeptide sharing at least 70%, 80%, 90%, 95%, 97%, 98%, 99% or 100% amino acid identity with SEQ ID 32, 34, 36, 38,42, 46, 48, 50, 52, 54, 100, or an antigenic or immunogenic fragment thereof, preferably the passenger domain thereof.

In a further preferred embodiment of the invention, the immunogenic composition will comprise at least one *Bordetella* lipoprotein selected from the group consisting of the polypeptide sharing at least 700%, 80%, 90%, 95%, 97%, 98%, 99% amino acid identity with SEQ ID 56, 58, 60, 62, 64, 66, 68, 70, 72, 74, 76, 78, 80, 82, 84, 86, 88, 90, 92, 94, 96, 98 or an antigenic or immunogenic fragment thereof.

In a particularly preferred embodiment of the invention, the immunogenic composition comprises one, two or three of FHA, *pertussis* toxin and pertactin, (preferably FHA and PT; FHA and pertactin; PT and pertactin; or FHA, *pertussis* toxin and pertactin) at least one *Bordetella* lipoprotein selected from the group consisting of the polypeptide sharing at least 70%, 80%, 90%, 95%, 97%, 98%, 99% amino acid identity with SEQ ID 56, 58, 60, 62, 64, 66, 68, 72, 74, 76, 78, 80, 82, 84, 86, 88, 90, 94, 96, 98 or an antigenic or immunogenic fragment thereof.

In a further preferred embodiment of the invention, the immunogenic composition comprises BrkA or an antigenic or immunogenic fragment thereof.

In a further preferred embodiment of the invention, the immunogenic composition comprises at least one *Bordetella* toxin or antigens involved in toxin secretion selected from the group consisting of adenylate cyclase, dermonecrotic toxin (Dnt), Type IIIss or lipopolysaccharide or an antigenic or immunogenic fragment thereof.

The combination of FHA, *pertussis* toxin and pertactin is known to elicit a protective immune reponse and particularly preferred combinations of the invention will contain one, two or three of these constituents, optionally further comprising fim 2, fim 3 or fim 2 and fim 3.

A preferred immunogenic composition of the invention contains TcfA and at least 1, 2, 3, 4, antigens selected from the list consisting of *pertussis* toxin, adenylate cyclase, LPS, BipA, Type IIIss, BhuR, FHA, Fim, pertactin, BrkA, MltA, MltB, VacJ, OmlA and Pcp. Preferred combinations comprise TcfA and *pertussis* toxin, (optionally with 1, 2, 3, 4 or 5 of BipA, BhuR, FHA, Fim, pertactin, BrkA, MltA, MltB, VacJ, OmlA and Pcp); TcfA and adenylate cyclase (optionally with 1, 2, 3, 4 or 5 of BipA, BhuR, FHA, Fim, pertactin, BrkA, MltA, MltB, VacJ, OmlA and Pcp); TcfA and LPS (optionally with 1, 2, 3, 4 or 5 of BipA, BhuR, FHA, Fim, pertactin, BrkA, MltA, MltB, VacJ, OmlA and Pcp); TcfA and BipA (optionally with 1, 2, 3, 4 or 5 of *pertussis* toxin, adenylate cyclase, LPS, Type IIIss, BhuR, FHA, Fim, pertactin, BrkA, MltA, MltB, VacJ, OmlA and Pcp); TcfA and Type IIIss (optionally with 1, 2, 3, 4 or 5 of *pertussis* toxin, BipA, BhuR, FHA, Fim, pertactin, BrkA, MltA, MltB, VacJ, OmlA and Pcp); TcfA and BhuR (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA, Pcp); TcfA and FHA (optionally with 1, 2, 3, 4 or 5 of *pertussis* toxin, adenylate cyclase, LPS, BipA, pertactin, BhuR, Type IIIss, MltA, MltB, VacJ, OmlA, Pcp); TcfA and a lipoprotein selected from MltA, MltB, VacJ, OmlA and Pcp (optionally with 1, 2, 3, 4 or 5 of *pertussis* toxin, adenylate cyclase, LPS, BipA, BhuR, Type IIIss, Fim, pertactin, BrkA and FHA).

A further preferred immunogenic composition of the invention contains BipA and at least 1, 2, 3, 4, antigens selected from the list consisting of *pertussis* toxin, adenylate cyclase, LPS, Type IIIss, BhuR, FHA, Fim, pertactin, BrkA, MltA, MltB, VacJ, OmlA and Pcp. Preferred combinations comprise BipA and *pertussis* toxin, (optionally with 1, 2, 3, 4 or 5 of BhuR, FHA, pertactin, Fim, BrkA, MltA, MltB, VacJ, OmlA and Pcp), BipA and adenylate cyclase (optionally with 1, 2, 3, 4 or 5 of BhuR, FHA, pertactin, Fim, BrkA, MltA, MltB, VacJ, OmlA and Pcp); BipA and LPS (optionally with 1, 2, 3, 4 or 5 of BhuR, FHA, Fim, pertactin, BrkA, MltA, MltB, VacJ, OmlA and Pcp); BipA and Type IIIss (optionally with 1, 2, 3, 4 or 5 of BhuR, FHA, Fim, pertactin, BrkA, *pertussis* toxin, MltA, MltB, VacJ, OmlA and Pcp); BipA and BhuR (optionally with 1, 2, 3, 4 or 5 of *pertussis* toxin, adenylate cyclase, LPS, Type IIIss, FHA, Fim, pertactin, BrkA, MltA, MltB, VacJ, OmlA and PCP); BipA and FHA (optionally with 1, 2, 3, 4 or 5 of *pertussis* toxin, adenylate cyclase, LPS, pertactin, BhuR, Type IIIss, MltA, MltB, VacJ, OmlA and PCP); BipA and a lipoprotein selected from MltA, MltB, VacJ, OmlA and Pcp (optionally with 1, 2, 3, 4 or 5 of *pertussis* toxin, adenylate cyclase, LPS, BhuR, Type IIIss, Fim, pertactin, BrkA and FHA).

A further preferred immunogenic composition of the invention contains BapA and at least 1, 2, 3, 4, antigens selected from the list consisting of *pertussis* toxin, adenylate cyclase, LPS, BipA, Type IIIss, BhuR, FHA, Fim, pertactin, BrkA, MltA, MltB, VacJ, OmlA and Pcp. Preferred combinations comprise BapA and *pertussis* toxin, (optionally with 1, 2, 3, 4 or 5 of BipA, BhuR, FHA, Fim, pertactin, BrkA, MltA, MltB, VacJ, OmlA and Pcp); BapA and adenylate cyclase (optionally with 1, 2, 3, 4 or 5 of BipA, BhuR, FHA, Fim, pertactin, BrkA, *pertussis* toxin, MltA, MltB, VacJ, OmlA and Pcp); BapA and LPS (optionally with 1, 2, 3, 4 or 5 of BipA, BhuR, FHA, Fim, pertactin, BrkA, MltA, MltB, VacJ, OmlA and Pcp); BapA and BipA (optionally with 1, 2, 3, 4 or 5 of *pertussis* toxin, adenylate cyclase, LPS, Type IIIss, BhuR, FHA, Fim, pertactin, BrkA, MltA, MltB, VacJ, OmlA and Pcp); BapA and Type IIIss (optionally with 1, 2, 3, 4 or 5 of *pertussis* toxin, adenylate cyclase, LPS, BipA, BhuR, FHA, Fim, pertactin, BrkA, MltA, MltB, VacJ, OmlA and Pcp); BapA and BhuR (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA and Pcp); BapA and FHA (optionally with 1, 2, 3, 4 or 5 of *pertussis* toxin, adenylate cyclase, LPS, BipA, BhuR, Fim, pertactin, BrkA, Type IIIss, MltA, MltB, VacJ, OmlA and Pcp); BapA and a lipoprotein selected from MltA, MltB, VacJ, OmlA and Pcp (optionally with 1, 2, 3, 4 or 5 of *pertussis* toxin, adenylate cyclase, LPS, BipA, Fim, pertactin, BrkA, BhuR, Type IIIss and FHA), provided that the combination is not BapA and PT and FHA.

A further preferred immunogenic composition of the invention contains BapB and at least 1, 2, 3, 4, antigens selected from the list consisting of *pertussis* toxin, adenylate cyclase, LPS, BipA, Type IIIss, BhuR, FHA, Fim, pertactin, BrkA, MltA, MltB, VacJ, OmlA and Pcp. Preferred combinations comprise BapB and *pertussis* toxin, (optionally with 1, 2, 3, 4 or 5 of BipA, BhuR, FHA, Fim, pertactin, BrkA, MltA, MltB, VacJ, OmlA and Pcp); BapB and adenylate cyclase (optionally with 1, 2, 3, 4 or 5 of BipA, BhuR, FHA, Fim, pertactin, BrkA, MltA, MltB, VacJ, OmlA and Pcp); BapB and LPS (optionally with 1, 2, 3, 4 or 5 of BipA, BhuR, FHA, Fim, pertactin, BrkA, MltA, MltB, VacJ, OmlA and Pcp); BapB and BipA (optionally with 1, 2, 3, 4 or 5 of *pertussis* toxin, adenylate cyclase, LPS, Type IIIss, BhuR, FHA, Fim, pertactin, BrkA, MltA, MltB, VacJ, OmlA and Pcp); BapB and Type IIIss (optionally with 1, 2, 3, 4 or 5 of *pertussis* toxin, BipA, BhuR, FHA, Fim, pertactin, BrkA, MltA, MltB, VacJ, OmlA and Pcp); BapB and BhuR (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA and Pcp); BapB and FHA (optionally with 1, 2, 3, 4 or 5 of *pertussis* toxin, adenylate cyclase, LPS, BipA, Fim, pertactin, BrkA, BhuR, Type IIIss, MltA, MltB, VacJ, OmlA and Pcp); BapB and a lipoprotein selected from MltA, MltB, VacJ, OmlA and Pcp (optionally with 1, 2, 3, 4 or 5 of *pertussis* toxin, adenylate cyclase, LPS, BipA, BhuR, Type IIIss, Fim, pertactin, BrkA and FHA).

A further preferred immunogenic composition of the invention contains BapC and at least 1, 2, 3, 4, antigens selected from the list consisting of *pertussis* toxin, adenylate cyclase, LPS, BipA, Type IIIss, BhuR, FHA, Fim, pertactin, BrkA, MltA, MltB, VacJ, OmlA and PCP. Preferred combinations comprise BapC and *pertussis* toxin, (optionally with 1, 2, 3, 4 or 5 of BipA, BhuR, FHA, Fim, pertactin, BrkA, MltA, MltB, VacJ, OmlA and Pcp); BapC and adenylate cyclase (optionally with 1, 2, 3, 4 or 5 of BipA, BhuR, FHA, Fim, pertactin, BrkA, MltA, MltB, VacJ, OmlA and Pcp); BapC and LPS (optionally with 1, 2, 3, 4 or 5 of BipA, BhuR, FHA, Fim, pertactin, BrkA, MltA, MltB, VacJ, OmlA and Pcp); BapC and BipA (optionally with 1, 2, 3, 4 or 5 of *pertussis* toxin, adenylate cyclase, LPS, Type IIIss, BhuR, FHA, Fim, pertactin, BrkA, MltA, MltB, VacJ, OmlA and Pcp); BapC and Type IIIss (optionally with 1, 2, 3, 4 or 5 of *pertussis* toxin, BipA, BhuR, FHA, Fim, pertactin, BrkA, MltA, MltB, VacJ, OmlA and Pcp); BapC and BhuR (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA and Pcp); BapC and FHA (optionally with 1, 2, 3, 4 or 5 of *pertussis* toxin, adenylate cyclase, LPS, BipA, BhuR, Type IIIss, pertactin, MltA, MltB, VacJ, OmlA and Pcp); BapC and a lipoprotein selected from MltA, MltB, VacJ, OmlA and PCP (optionally with 1, 2, 3, 4 or 5 of *pertussis* toxin, adenylate cyclase, LPS, BipA, BhuR, Type IIIss, Fim, pertactin, BrkA and FHA), provided that the combination is not BapC and PT and FHA.

A further preferred immunogenic composition of the invention contains pertactin and at least 1, 2, 3, 4, antigens selected from the list consisting of *pertussis* toxin, adenylate cyclase, LPS, BipA, Type IIIss, BhuR, FHA, Fim, BrkA, MltA, MltB, VacJ, OmlA and PCP. Preferred combinations comprise pertactin and pertussis toxin, (optionally with 1, 2, 3, 4 or 5 of BipA, BhuR, FHA, Fim, BrkA, MltA, MltB, VacJ, OmlA and Pcp); pertactin and adenylate cyclase (optionally with 1, 2, 3, 4 or 5 of BipA, BhuR, FHA, Fim, BrkA, MltA, MltB, VacJ, OmlA and Pcp), pertactin and LPS (optionally with 1, 2, 3, 4 or 5 of BipA, BhuR, FHA, Fim, BrkA, MltA, MltB, VacJ, OmlA and Pcp); pertactin and BipA (optionally with 1, 2, 3, 4 or 5 of *pertussis* toxin, adenylate cyclase, LPS, Type IIIss, BhuR, FHA, Fim, BrkA, MltA, MltB, VacJ, OmlA and Pcp); pertactin and Type IIIss (optionally with 1, 2, 3, 4 or 5 of *pertussis* toxin, BipA, BhuR, FHA, Fim, BrkA, MltA, MltB, VacJ, OmlA and Pcp); pertactin and BhuR (optionally with 1, 2, 3, 4 or 5 of *pertussis* toxin, adenylate cyclase, LPS, BipA, Type IIIss, FHA, Fim, BrkA, MltA, MltB, VacJ, OmlA and Pcp); pertactin and FHA (optionally with 1, 2, 3, 4 or 5 of *pertussis* toxin, adenylate cyclase, LPS, BipA, BhuR, Type IIIss, MltA, MltB, VacJ, OmlA and Pcp), pertactin and a lipoprotein selected from MltA, MltB, VacJ, OmlA and PCP (optionally with 1, 2, 3, 4 or 5 of *pertussis* toxin, adenylate cyclase, LPS, BipA, BhuR, Type IIIss, Fim, BrkA and FHA).

A further preferred immunogenic composition of the invention contains pertactin-like protein and at least 1, 2, 3, 4, antigens selected from the list consisting of *pertussis* toxin, adenylate cyclase, LPS, BipA, Type IIIss, BhuR, FHA, pertactin, Fim, BrkA, MltA, MltB, VacJ, OmlA and Pcp. Preferred combinations comprise pertactin-like protein and *pertussis* toxin, (optionally with 1, 2, 3, 4 or 5 of BipA, BhuR, FHA, pertactin, Fim, BrkA, MltA, MltB, VacJ, OmlA and Pcp); pertactin-like protein and adenylate cyclase (optionally with 1, 2, 3, 4 or 5 of BipA, BhuR, FHA, pertactin, Fim, BrkA, MltA, MltB. VacJ, OmlA and Pcp); pertactin-like protein and LPS (optionally with 1, 2, 3, 4 or 5 of BipA, BhuR, FHA, pertactin, Fim, BrkA, MltA, MltB, VacJ, OmlA and PCP); pertactin-like protein and BipA (optionally with 1, 2, 3, 4 or 5 of *pertussis* toxin, adenylate cyclase, LPS, Type IIIss, BhuR, FHA, pertactin, Fim, BrkA, MltA, MltB, VacJ, OmlA and Pcp); pertactin-like protein and Type IIIss (optionally with 1, 2, 3, 4 or 5 of *pertussis* toxin, BipA, BhuR, FHA, pertactin, Fim, BrkA, MltA, MltB, VacJ, OmlA and Pcp); pertactin-like protein and BhuR (optionally with 1, 2, 3, 4 or 5 of *pertussis* toxin, adenylate cyclase, LPS, BipA, Type IIIss, FHA, pertactin, Fim, BrkA, MltA, MltB, VacJ, OmlA, Pcp); pertactin-like protein and FHA (optionally with 1, 2, 3, 4 or 5 of *pertussis* toxin, adenylate cyclase, LPS, BipA, BhuR, pertactin, Fim, BrkA, Type IIIss, MltA, MltB, VacJ, OmlA, Pcp); pertactin-like protein and a lipoprotein selected from MltA, MltB, VacJ, OmlA and Pcp (optionally with 1, 2, 3, 4 or 5 of *pertussis* toxin, adenylate cyclase, LPS, BipA, BhuR, Type IIIss, pertactin, Fim, BrkA and FHA).

A further preferred immunogenic composition of the invention contains YapE and at least 1, 2, 3, 4, antigens selected from the list consisting of *pertussis* toxin, adenylate cyclase, LPS, BipA, Type IIIss, BhuR, FHA, pertactin, Fim, BrkA, MltA, MltB, VacJ, OmlA, Pcp. Preferred combinations comprise YapE and *pertussis* toxin, (optionally with 1, 2, 3, 4 or 5 of BipA, BhuR, FHA, pertactin, Fim, BrkA, MltA, MltB, VacJ, OmlA, Pcp); YapE and adenylate cyclase (optionally with 1, 2, 3, 4 or 5 of BipA, BhuR, FHA, pertactin, Fim, BrkA, MltA, MltB, VacJ, OmlA, Pcp); YapE and LPS (optionally with 1, 2, 3, 4 or 5 of BipA, BhuR, FHA, pertactin, Fim, BrkA, MltA, MltB, VacJ, OmlA, Pcp); YapE and BipA (optionally with 1, 2, 3, 4 or 5 of *pertussis* toxin, adenylate cyclase, LPS, Type IIIss, BhuR, FHA, pertactin, Fim, BrkA, MltA, MltB, VacJ, OmlA, Pcp); YapE and Type IIIss (optionally with 1, 2, 3, 4 or 5 of *pertussis* toxin, BipA, BhuR, FHA, pertactin, Fim, BrkA, MltA, MltB, VacJ, OmlA, Pcp); YapE and BhuR (optionally with 1, 2, 3, 4 or 5 of *pertussis* toxin, adenylate cyclase, LPS, BipA, Type IIIss, FHA, pertactin, Fim, BrkA, MltA, MltB, VacJ, OmlA, Pcp); YapE and FHA (optionally with 1, 2, 3, 4 or 5 of *pertussis* toxin, adenylate cyclase, LPS, BipA, BhuR, Type IIIss, pertactin, MltA, MltB, VacJ, OmlA, Pcp); YapE and a lipoprotein selected from MltA, MltB, VacJ, OmlA, Pcp (optionally with 1, 2, 3, 4 or 5 of *pertussis* toxin, adenylate cyclase, LPS, BipA, BhuR, Type IIIss, pertactin, Fim, BrkA and FHA).

A further preferred immunogenic composition of the invention contains BrkA and at least 1, 2, 3, 4, antigens selected from the list consisting of *pertussis* toxin, adenylate cyclase, LPS, BipA, Type IIIss, BhuR, FHA, pertactin, Fim, MltA, MltB, VacJ, OmlA, Pcp. Preferred combinations comprise BrkA and *pertussis* toxin, (optionally with 1, 2, 3, 4 or 5 of BipA, BhuR, FHA, pertactin, Fim, MltA, MltB, VacJ, OmlA, Pcp); BrkA and adenylate cyclase (optionally with 1, 2, 3, 4 or 5 of BipA, BhuR, FHA, pertactin, Fim, MltA, MltB, VacJ, OmlA, Pcp); BrkA and LPS (optionally with 1, 2, 3, 4 or 5 of BipA, BhuR, FHA, pertactin, Fim, MltA, MltB, VacJ, OmlA and Pcp); BrkA and BipA (optionally with 1, 2, 3, 4 or 5 of *pertussis* toxin, adenylate cyclase, LPS, Type IIIss, BhuR, FHA, pertactin, Fim, MltA, MltB, VacJ, OmlA, Pcp), BrkA and Type IIIss (optionally with 1, 2, 3, 4 or 5 of *pertussis* toxin, BipA, BhuR, FHA, pertactin, Fim, MltA, MltB, VacJ, OmlA, Pcp); BrkA and BhuR (optionally with 1, 2, 3, 4 or 5 of *pertussis* toxin, adenylate cyclase, LPS, BipA, Type IIIss, FHA, pertactin, Fim, MltA, MltB, VacJ, OmlA, Pcp); BrkA and FHA (optionally with 1, 2, 3, 4 or 5 of *pertussis* toxin, adenylate cyclase, LPS, BipA, BhuR, Type IIIss, pertactin, MltA, MltB, VacJ, OmlA, Pcp); BrkA and a lipoprotein selectd from MltA, MltB, VacJ, OmlA and Pcp (optionally with 1, 2, 3, 4 or 5 of *pertussis* toxin, adenylate cyclase, LPS, BipA, BhuR, Type IIIss, pertactin, Fim and FHA).

A further preferred immunogenic composition of the invention contains FHA and at least 1, 2, 3, 4, antigens selected from the list consisting of *pertussis* toxin, adenylate cyclase, LPS, BipA, Type IIIss, BhuR, BrkA pertactin, Fim, MltA, MltB, VacJ, OmlA and Pcp. Preferred combinations comprise FHA and *pertussis* toxin, (optionally with 1, 2, 3, 4 or 5 of BipA, BhuR, BrkA, pertactin, Fim, MltA, MltB, VacJ, OmlA and Pcp); FHA and adenylate cyclase (optionally with 1, 2, 3, 4 or 5 of BipA, BhuR, BrkA, pertactin, Fim, MltA, MltB, VacJ, OmlA and Pcp); FHA and LPS (optionally with 1, 2, 3, 4 or 5 of BipA, BhuR, BrkA, pertactin, Fim, MltA, MltB, VacJ, OmlA and Pcp); FHA and BipA (optionally with 1, 2, 3, 4 or 5 of *pertussis* toxin, adenylate cyclase, LPS, Type IIIss, BhuR, BrkA, pertactin, Fim, MltA, MltB, VacJ, OmlA and Pcp); FHA and Type IIIss (optionally with 1, 2, 3, 4 or 5 of *pertussis* toxin, BipA, BhuR, BrkA, pertactin, Fim, MltA, MltB, VacJ, OmlA and Pcp); FHA and BhuR (optionally with 1, 2, 3, 4 or 5 of *pertussis* toxin, adenylate cyclase, LPS, BipA, Type IIIss, BrkA, pertactin, Fim, MltA, MltB, VacJ, OmlA and Pcp); FHA and a lipoprotein selected from MltA, MltB, VacJ, OmlA and Pcp (optionally with 1, 2, 3, 4 or 5 of *pertussis* toxin, adenylate cyclase, LPS, BipA, BhuR, Type IIIss, pertactin, Fim and BrkA).

A further preferred immunogenic composition of the invention contains BhuR and at least 1, 2, 3, 4, antigens selected from the list consisting of *pertussis* toxin, adenylate cyclase, LPS, TcfA, BapA, BapB, BapC, pertactin, pertactin-like protein, YapE, BrkA, BipA, Type IIIss, FHA, Fim, MltA, MltB, VacJ, OmlA and Pcp. Preferred combinations comprise BhuR and *pertussis* toxin (optionally with 1, 2, 3, 4 or 5 of TcfA, BapA, BapB, BapC, pertactin, pertactin-like protein, YapE, BrkA, BipA, FHA, Fim, MltA, MltB, VacJ, OmlA and Pcp); BhuR and adenylate cyclase (optionally with 1, 2, 3, 4 or 5 of TcfA, BapA, BapB, BapC, pertactin, pertactin-like protein, YapE, BrkA, BipA, *pertussis* toxin, FHA, Fim, BrkA, MltA, MltB, VacJ, OmlA and Pcp); BhuR and LPS (optionally with 1, 2, 3, 4 or 5 of TcfA, BapA, BapB, BapC, pertactin, pertactin-like protein, YapE, BrkA, BipA, *pertussis* toxin, FHA, Fim, BrkA, MltA, MltB, VacJ, OmlA and Pcp); BhuR and TcfA (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA and Pcp); BhuR and BapA (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA and Pcp); BhuR and BapB (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA and Pcp); BhuR and BapC (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA and Pcp); BhuR and pertactin (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA and Pcp); BhuR and pertactin-like protein (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA and Pcp); BhuR and YapE (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA and Pcp); BhuR and BrkA (optionally with 1, 2, 3, 4 or 5 of *pertussis* toxin, adenylate cyclase, LPS, BipA, Type IIIss, FHA, Fim, pertactin, BrkA, MltA, MltB, VacJ, OmlA and Pcp); BhuR and a lipoprotein selected from MltA, MltB, VacJ, OmlA and Pcp (optionally with 1, 2, 3, 4 or 5 of *pertussis* toxin, adenylate cyclase, LPS, TcfA, BapA, BapB, BapC, pertacin, pertactin-like protein, YapE, BrkA, BipA, Type IIIss, Fim and FHA).

A further preferred immunogenic composition of the invention contains MltA and at least 1, 2, 3, 4, antigens selected from the list consisting of *pertussis* toxin, adenylate cyclase, LPS, TcfA, BapA, BapB, BapC, pertactin, pertactin-like protein, YapE, BrkA, BipA, Type IIIss, BhuR, Fim and FHA. Preferred combinations comprise MltA, and *pertussis* toxin (optionally with 1, 2, 3, 4 or 5 of TcfA, BapA, BapB, BapC, pertactin, pertactin-like protein, YapE, BrkA, BipA, FHA, Fim and BhuR); MltA and adenylate cyclase (optionally with 1, 2, 3, 4 or 5 of TcfA, BapA, BapB, BapC, pertactin, pertactin-like protein, YapE, BrkA, BipA, *pertussis* toxin, FHA, Fim and BhuR); MltA and LPS (optionally with 1, 2, 3, 4 or 5 of TcfA, BapA, BapB, BapC, pertactin, pertactin-like protein, YapE, BrkA, BipA, *pertussis* toxin, FHA, Fim and BhuR); MltA and TcfA (optionally with 1, 2, 3, 4 or 5 of *pertussis* toxin, adenylate cyclase, LPS, BipA, Type IIIss, FHA, Fim, pertactin, BrkA and BhuR); MltA and BapA (optionally with 1, 2, 3, 4 or 5 of *pertussis* toxin, adenylate cyclase, LPS, BipA, Type IIIss, FHA, Fim, pertactin, BrkA and BhuR); MltA and BapB (optionally with 1, 2, 3, 4 or 5 of *pertussis* toxin, adenylate cyclase, LPS, BipA, Type IIIss, FHA, Fim, pertactin, BrkA and BhuR); MltA and BapC (optionally with 1, 2, 3, 4 or 5 of *pertussis* toxin, adenylate cyclase, LPS, BipA, Type IIIss, FHA, Fim, pertactin, BrkA and BhuR); MltA and pertactin (optionally with 1, 2, 3, 4 or 5 of *pertussis* toxin, adenylate cyclase, LPS, BipA, Type IIIss, FHA, Fim, BrkA and BhuR); MltA and pertactin-like protein (optionally with 1, 2, 3, 4 or 5 of *pertussis* toxin, adenylate cyclase, LPS, BipA, Type IIIss, FHA, Fim, pertactin, BrkA and BhuR); MltA and YapE (optionally with 1, 2, 3, 4 or 5 of *pertussis* toxin, adenylate cyclase, LPS, BipA, Type IIIss, FHA, Fim, pertactin, BrkA and BhuR); MltA and BrkA (optionally with 1, 2, 3, 4 or 5 of *pertussis* toxin, adenylate cyclase, LPS, BipA, Type IIIss, FHA, Fim, pertactin and BhuR); MltA and BhuR (optionally with 1, 2, 3, 4 or 5 of *pertussis* toxin, adenylate cyclase, LPS, TcfA, BapA, BapB, BapC, pertacin, pertactin-like protein, YapE, BrkA, BipA, Type IIIss, Fim and FHA), provided that the combination is not MltA and PT and FHA.

A further preferred immunogenic composition of the invention contains *pertussis* toxin and at least 1, 2, 3, 4, antigens selected from the list consisting of TcfA, BapA, BapB, BapC, pertactin, pertactin-like protein, YapE, BrkA, BipA, BhuR, FHA, MltA, MltB, VacJ, OmlA and Pcp. Preferred combinations comprise *pertussis* toxin and TcfA (optionally with 1, 2, 3, 4 or 5 of BipA, BhuR, FHA, Fim, pertactin, BrkA, MltA, MltB, VacJ, OmlA and Pcp); *pertussis* toxin and BapA (optionally with 1, 2, 3, 4 or 5 of BipA, BhuR, FHA, Fim, pertactin, BrkA, MltA, MltB, VacJ, OmlA and Pcp); *pertussis* toxin and BapB (optionally with 1, 2, 3, 4 or 5 of BipA, BhuR, FHA, Fim, pertactin, BrkA, MltA, MltB, VacJ, OmlA and Pcp); *pertussis* toxin and BapC (optionally with 1, 2, 3, 4 or 5 of BipA, BhuR, FHA, Fim, pertactin, BrkA, MltA, MltB, VacJ, OmlA and Pcp); *pertussis* toxin and pertactin (optionally with 1, 2, 3, 4 or 5 of BipA, BhuR, FHA, Fim, BrkA, MltA, MltB, VacJ, OmlA and Pcp); *pertussis* toxin and pertactin-like protein (optionally with 1, 2, 3, 4 or 5 of BipA, BhuR, FHA, Fim, pertactin, BrkA, MltA, MltB, VacJ, OmlA and Pcp); *pertussis* toxin and YapE (optionally with 1, 2, 3, 4 or 5 of BipA, BhuR, FHA, Fim, pertactin, BrkA, MltA, MltB, VacJ, OmlA and Pcp); *pertussis* toxin and BrkA (optionally with 1, 2, 3, 4 or 5 of BipA, BhuR, FHA, Fim, pertactin, MltA, MltB, VacJ, OmlA and Pep); *pertussis* toxin and BhuR (optionally with 1, 2, 3, 4 or 5 of TcfA, BapA, BapB, BapC, pertactin, pertactin-like protein, YapE, BrkA, BipA, FHA, Fim, MltA, MltB, VacJ, OmlA and Pcp); *pertussis* toxin and MltA, MltB (optionally with 1, 2, 3, 4 or 5 of TcfA, BapA, BapB, BapC, pertactin, pertactin-like protein, YapE, BrkA, BipA, FHA, Fim and BhuR).

A further preferred immunogenic composition of the invention contains adenylate cyclase and at least 1, 2, 3, 4, antigens selected from the list consisting of TcfA, BapA, BapB, BapC, pertactin, pertactin-like protein, YapE, BrkA, BipA, BhuR, FHA, Fim, *pertussis* toxin , MltA, MltB, VacJ, OmlA and Pcp. Preferred combinations comprise adenylate cyclase and TcfA (optionally with 1, 2, 3, 4 or 5 of BipA, BhuR, FHA, Fim, pertactin, BrkA, *pertussis* toxin, MltA, MltB, VacJ, OmlA and Pcp); adenylate cyclase and BapA (optionally with 1,2,3,4 or 5 of BipA, BhuR, FHA, Fim, pertactin, BrkA, *pertussis* toxin, MltA, MltB, VacJ, OmlA and Pcp); adenylate cyclase and BapB (optionally with 1, 2, 3, 4 or 5 of BipA, BhuR, FHA, Fim, pertactin, BrkA, *pertussis* toxin, MltA, MltB, VacJ, OmlA and Pcp); adenylate cyclase and BapC (optionally with 1, 2, 3, 4 or 5 of BipA, BhuR, FHA, Fim, pertactin, BrkA, *pertussis* toxin, MltA, MltB, VacJ, OmlA and Pcp); adenylate cyclase and pertactin (optionally with 1, 2, 3, 4 or 5 of BipA, BhuR, FHA, Fim, pertactin, *pertussis* toxin, MltA, MltB, VacJ, OmlA and Pcp); adenylate cyclase and pertactin-like protein (optionally with 1, 2, 3, 4 or 5 of BipA, BhuR, FHA, Fim, pertactin, BrkA, *pertussis* toxin, MltA, MltB, VacJ, OmlA and Pcp); adenylate cyclase and YapE (optionally with 1, 2, 3, 4 or 5 of BipA, BhuR, FHA, Fim, pertactin, BrkA, *pertussis* toxin, MltA, MltB, VacJ, OmlA and Pcp); adenylate cyclase and BrkA (optionally with 1, 2, 3, 4 or 5 of BipA, BhuR, FHA, Fim, pertactin, *pertussis* toxin, MltA, MltB, VacJ, OmlA and Pcp), adenylate cyclase and BhuR (optionally with 1, 2, 3, 4 or 5 of TcfA, BapA, BapB, BapC, pertactin, pertactin-like protein, YapE, BrkA, BipA, FHA, Fim *pertussis* toxin, MltA, MltB, VacJ, OmlA and Pcp); adenylate cyclase and MltA, MltB (optionally with 1, 2, 3, 4 or 5 of TcfA, BapA, BapB, BapC, pertactin, pertactin-like protein, YapE, BrkA, BipA, FHA, Fim, pertussis toxin and BhuR).

A further preferred immunogenic composition of the invention contains LPS and at least 1, 2, 3, 4, antigens selected from the list consisting of TcfA, BapA, BapB, BapC, pertactin, pertactin-like protein, YapE, BrkA, BipA, BhuR, FHA, Fim, *pertussis* toxin, MltA, MltB, VacJ, OmlA and Pcp. Preferred combinations comprise LPS and TcfA (optionally with 1, 2, 3, 4 or 5 of BipA, BhuR, FHA, Fim, pertactin, BrkA, *pertussis* toxin, MltA, MltB, VacJ, OmlA and Pcp); LPS and BapA (optionally with 1, 2, 3, 4 or 5 of BipA, BhuR, FHA, Fim, pertactin, BrkA, *pertussis* toxin, MltA, MltB, VacJ, OmlA and Pcp); LPS and BapB (optionally with 1, 2, 3, 4 or 5 of BipA, BhuR, FHA, Fim, pertactin, BrkA, *pertussis* toxin, MltA, MltB, VacJ, OmlA and Pcp); LPS and BapC (optionally with 1, 2, 3, 4 or 5 of BipA, BhuR, FHA, Fim, pertactin, BrkA, *pertussis* toxin, MltA, MltB, VacJ, OmlA and Pcp); LPS and pertactin (optionally with 1, 2, 3, 4 or 5 of BipA, BhuR, FHA, Fim, BrkA, *pertussis* toxin, MltA, MltB, VacJ, OmlA and Pcp); LPS and pertactin-like protein (optionally with 1, 2, 3, 4 or 5 of BipA, BhuR, FHA, Fim, pertactin, BrkA, *pertussis* toxin, MltA, MltB, VacJ, OmlA and Pcp); LPS and YapE (optionally with 1, 2, 3, 4 or 5 of BipA, BhuR, FHA, Fim, pertactin, BrkA, *pertussis* toxin, MltA, MltB, VacJ, OmlA and Pcp); LPS and BrkA (optionally with 1, 2, 3, 4 or 5 of BipA, BhuR, FHA, Fim, pertactin, *pertussis* toxin, MltA, MltB, VacJ, OmlA and Pcp); LPS and BhuR (optionally with 1, 2, 3, 4 or 5 of TcfA, BapA, BapB, BapC, pertactin, pertactin-like protein, YapE, BrkA, BipA, FHA, Fim, *pertussis* toxin, MltA, MltB, VacJ, OmlA and Pcp); LPS and MltA (optionally with 1, 2, 3, 4 or 5 of TcfA, BapA, BapB, BapC, pertactin, pertactin-like protein, YapE, BrkA, BipA, FHA, Fim and *pertussis* toxin and BhuR).

A further preferred combination of the invention contains one, two or three of FHA, pertactin, *pertussis* toxin (preferably FHA and pertactin, FHA and *pertussis* toxin, pertactin and *pertussis* toxin or FHA, pertactin and *pertussis* toxin) and an additional 1, 2, 3 or 4 antigens selected from the group consisting of TcfA, BipA, BapA, BapB, BapC, pertactin-like protein, YapE, BhuR, Fim, BrkA, adenylate cyclase, Type IIIss, MltA, MltB, VacJ, OmlA and Pcp. A preferred combinations contains FHA, pertactin, *pertussis* toxin and BhuR. A further preferred combination contains FHA, pertactin, *pertussis* toxin, and MltA. A further preferred combination contains FHA, pertactin, *pertussis* toxin, and MltB. A further preferred combination contains FHA, pertactin, *pertussis* toxin and VacJ.

A further preferred combination contains FHA, pertactin, *pertussis* toxin and OmlA. A further preferred combination contains FHA, pertactin, *pertussis* toxin and Pcp. A further preferred combination contains FHA, pertactin, *pertussis* toxin, a lipoprotein (preferably MltA, MltB, VacJ, OmlA or Pcp) and BhuR.

A preferred immunogenic composition of the invention comprises FHA, *pertussis* toxin and BrkA or a protein sharing at least 70, 80, 90, 95, 97, 98, 99 or 100% identity with SEQ ID 34, preferably further comprising pertactin.

A preferred immunogenic composition of the invention comprises FHA, *pertussis* toxin and BhuR or a protein sharing at least 70, 80, 90, 95, 97, 98, 99 or 100% identity with SEQ ID 20, preferably further comprising pertactin.

A preferred immunogenic composition of the invention comprises FHA, *pertussis* toxin and BapB or a protein sharing at least 70, 80, 90, 95, 97, 98, 99 or 100% identity with SEQ ID 42, preferably further comprising pertactin.

A preferred immunogenic composition of the invention comprises FHA, *pertussis* toxin and YapE, preferably further comprising pertactin.

A preferred immunogenic composition of the invention comprises FHA, *pertussis* toxin and VacJ or a protein sharing at least 70, 80, 90, 95, 97, 98, 99 or 100% identity with SEQ ID 82, preferably further comprising pertactin.

A preferred immunogenic composition of the invention comprises FHA, *pertussis* toxin and Pcp or a protein sharing at least 70, 80, 90, 95, 97, 98, 99 or 100% identity with SEQ 96, preferably further comprising pertactin.

A preferred immunogenic composition of the invention comprises FHA, *pertussis* toxin and MltB or a protein sharing at least 70, 80, 90, 95, 97, 98, 99 or 100% identity with SEQ ID 72, preferably further comprising pertactin.

A preferred immunogenic composition of the invention comprises FHA, *pertussis* toxin and TcfA or a protein sharing at least 70, 80, 90, 95, 97, 98, 99 or 100% identity with SEQ ID 36, preferably further comprising pertactin.

A preferred immunogenic composition of the invention comprises FHA, *pertussis* toxin and adenylate cyclase, preferably further comprising pertactin.

A preferred immunogenic composition of the invention comprises FHA, *pertussis* toxin and Type IIIss, preferably further comprising pertactin.

It is further advantageous to combine antigens that are present at different stages of *Bordetella* life cycle in the immunogenic compositions of the invention. *Bordetella* has three identifyable stages, during which protein expression is controlled by the bvgAS locus. The Bvg+ virulent phase is characterised by the expression of a number of virulence factors including FHA, fimbrae and pertactin, a variety of toxins including adenylate cyclase, dermonecrotic toxin and *pertussis* toxin. During the Bvgi phase, some of the virulence factors are expressed and a new set of proteins including BipA are expressed (Deora et al Moledular Microbiology (2001) 40; 669-683).

immunogenic compositions comprising antigens expressed in different stages of the *Bordetella* life cycle further defines previous embodiments of the invention and is also an independent embodiment of the invention.

Antigens expressed in the Bvg phases can be determined as set out in Deora et al Molecular Microbiology (2001) 40; 669-683; Stockbauer et al Molecular Microbiology (2001) 39; 65-78; Cotter and Miller (1994) Infect. Immun. 62; 3381-3390 and Scarlato and Rappuoli (1991) J. Bacteriol. 173; 7401-7404 and U.S. Pat. No. 6,387,377.

Currently available acellular *pertussis* vaccines include FHA, adenylate cyclase, pertactin and fimbrae proteins which are all Bvg+ early genes. Accordingly, a further aspect of the invention is an immunogenic composition containing 2, 3, 4, 5, 6, 7, 8, 9, or 10 or more antigens which are expressed in two, three or four phases selected from Bvg+ early, Bvg+ late, Bvg− and Bvgi, for example, Bvg+ early and Bvg+ late; Bvg+ early and Bvg−; Bvg+ early and Bvgi: Bvg+ late and Bvg−; Bvg+ late and Bvgi; Bvg− and Bvgi; Bvg+ early and Bvg+ late and Bvg−; Bvg+ early and Bvg+ late and Bvgi; Bvg+ early and Bvg− and Bvgi; Bvg+ late and Bvg− and Bvgi; Bvg+early and Bvg+ late and Bvg− and Bvgi.

FHA, *pertussis* toxin, adenylate cyclase, Fim and pertactin are expressed in Bvg+ early phase.

Vag8, SpbB1, Tcf and Type IIISS are expressed in Bvg+ late phase.

BipA is expressed during Bvgi phase.

LPS are present in all phases including Bvg− phase.

Accordingly, preferred immunogenic compositions of the invention comprise 1, 2 or 3 antigens expressed in Bvg+ early phase (preferably selected from FHA, *pertussis* toxin, Fim and pertactin and further comprise 1, 2 or 3 antigens that are expressed during Bvg+ late phase and/or Bvgi phase and/or Bvg− phase (preferably Bvgi).

Preferred immunogenic compositions comprise BipA and an antigen expressed during Bvg+ early phase and/or Bvg+ late phase and/or Bvg− phase.

A preferred immunogenic compositions comprises FHA, PT and Tcf (optionally further comprising 1, 2, or 3 of Fim, pertactin, Vag8, SphB1, Type IIISS, BipA and LPS).

A preferred immunogenic compositions comprises FHA, PT and Vag8 (optionally further comprising 1, 2, or 3 of Fim, pertactin, Tcf, SpbB1, Type IIISS, BipA and LPS).

A preferred immunogenic compositions comprises FHA, PT and Vag8 (optionally further comprising 1, 2, or 3 of Fim, pertactin, Tct SphB1, Type IIISS, BipA and LPS).

A preferred immunogenic compositions comprises FHA, PT and SphB1 (optionally further comprising 1, 2, or 3 of Fim, pertactin, Tcf, Vag8, Type IIISS, BipA and LPS).

A preferred immunogenic compositions comprises FHA, PT and Type IIISS (optionally further comprising 1, 2, or 3 of Fim, pertactin, Tcf, Vag8, SphB1, BipA and LPS).

A preferred immunogenic compositions comprises FHA, PT and BipA (optionally further comprising 1, 2, or 3 of Fim, pertactin, Tcf, Vag8, SphB1, Type IIISS, BipA and LPS).

A preferred immunogenic compositions comprises FHA, PT and LPS (optionally further comprising 1, 2, or 3 of Fim, pertactin, Tcf, Vag8, SphB 1, Type IIISS and BipA).

The combinations listed above may be in the form of a subunit vaccine which contains isolated, preferably purified antigens. Where this is the case, it is preferred that soluble fragments of some of the antigens are used. For instance, the water soluble passenger domain of autotransporter proteins as defined above are preferred.

A further aspect of the invention is a combination of a protein involved in *Bordetella* resistance to complement (for example BrkA) and an antigen involved in *Bordetella* resistance to cellular immunity (for instance pertssis toxin). Such a combination preferably elicits a protective immune response against *Bordetella*. This aspect further defines previous embodiments of the invention and is also an independent embodiment of the invention.

A protein involved in *Bordetella* resistance to complement is defined as a *Bordetella* protein that is capable of disrupting the effective functioning of the host's complement system preferably by inhibiting the classical complement activation pathway. The degree of inhibition will be at least 10%, preferably 20%, more preferably 30%, more preferably 40%, 50%, 60%, 70%, 80%, most preferably 90% or 95%. This may be measured by the ability of the protein to inhibit a serum killing assay as described in Infect. Immun. 69; 3067 (2001). Examples of this sort of protein include BrkA and BrkB from *Bordetella* and fragments thereof eliciting an immunogenic response against said proteins, in particular a passenger domain (approximately from amino acid 41 to amino acid 706).

A protein involved in *Bordetella* resistance to cellular immunity is defined as a *Bordetella* protein which is able to inhibit (by at least 30%, 40%, 50%, 60%, 70%, 80%, preferably 90% or 95%) the effective functioning of at least one type of cell making up the host's cellular immunity system. It may act by having a toxic effect on one or more of the host's cell populations involved in cellular immunity, for instance T lymphocytes, B lymphocytes, neutrophils, eosinophils, macrophages, dendritic cells or monocytes. Examples of such antigens include *pertussis* toxin, adenylate cyclase and LPS. It may alternatively inhibit cellular immunity by disrupting the function of cell involved in immunity.

*Bordetella pertussis* is an obligate human pathogen and has developed mechanisms to survive within the hostile environment of the human host. One mechanism of doing this is through the action of *pertussis* toxin, which catalyses the ADP-ribosylation of GTP-binding proteins of mammalian cells. Since GTP-binding proteins are signalling molecules involved in regulating cellular processes, such ADP-ribosylation can lead to disruption of cellular function. Several important cells of the immune system including neutrophils, macrophages, monocytes and lymphocytes are inhibited by *pertussis* toxin (Weiss (1997) ASM News 63; 22). The action of *pertussis* toxin therefore disables the cellular immune response to *B. pertussis.*

The complement system is another important defence mechanism in the human body. The level of complement in the lung is ordinarily 10-20% of that in serum, however this increases during inflammation (Persson (1991) Eur. Respir. 4; 1268). *B. pertussis* has developed mechanisms of evading the complement system. Firstly, the lipopolysaccharides of *B. pertussis* do not activate the alternative pathway of complement (Fernandez and Weiss (1994) Infection and Immunity 62; 4727). The binding of antibodies to *B. pertussis* could however, lead to activation of the classical complement pathway. *B. pertussis* has developed a mechanism of inhibiting the classical complement pathway, using the protein BrkA.

An aspect of the invention relates to a pharmaceutical composition, preferably an immunogenic composition, more preferably a vaccine and more preferably an acellular vaccine against *Bordetella* infection, comprising an antigen involved in *Bordetella* resistance to complement and an antigen involved in *Bordetella* resistance to cellular immunity. Such antigens may be proteins, lipoproteins, polysaccharides, lipopolysaccharides or any other constituent of *Bordetella.*

In a preferred embodiment of the invention, the pharmaceutical composition comprises BrkA and/or BrkB as a protein involved in *Bordetella* resistance to complement and PT and/or adenylate cyclase as a protein involved in *Bordetella* resistance to cellular immunity. Lipopolysaccharides (LPS) are antigens that are also toxic to cells involved in immunity and in some embodiments of the invention could supplement or replace *pertussis* toxin or adenylate cyclase. In a further embodiment of the invention, the pharmaceutical composition comprises BrkA as a protein involved in *Bordetella* resistance to complement, PT as a protein involved in *Bordetella* resistance to cellular immunity and FHA. In a further embodiment of the invention, the pharmaceutical composition comprises BrkA as a protein involved in *Bordetella* resistance to complement, PT as a protein involved in *Bordetella* resistance to cellular immunity, FHA and 69 kDa pertactin.

The pharmaceutical compositions of the invention preferably comprise one or more additional cross-protective *Bordetella* antigen. It is advantageous for a vaccine to generate protection against *B. parapertussis* as well as *B. pertussis* so that a single vaccine can protect against both forms of infection. BrkA is itself well conserved between *B. pertussis* and *B. parapertussis*, however, a better level of protection is achieved by the inclusion of one or more additional antigens which are conserved between the several strains of *Bordetella.*

Several methods can be used to identify *Bordetella* cross-reactive antigens. Using genome mining, a comparison of the genomes of *B. pertussis* and *B. parapertussis* would show which antigens are conserved between the two species. Alternatively, DNA chips could be used alongside sequence information to assess the expression of candidate antigens in *B. pertussis* and *B. parapertussis*. Antisera against Pw could be used to identity cross-reactive antigens by using gel electrophoresis and western blotting. Spot microsequencing could precisely identify cross-reactive antigens. See Example 16 for one such suitable method. The invention embodies vaccines containing cross-reactive *Bordetella* antigens identified by the above methods or similar methods (preferably proteins from SEQ Group 2, most preferably proteins having an amino acid sequence having at least 80%, 85%, 90%, 95%, 96%, 97%, 98% or 99% or 100% identity to SEQ ID NO: 14, 50, 100. 102, 104, 106, 108 or 110).

Preferred ratios of antigens for inclusion into a pharmaceutical composition are 1-10 PT to 1 BrkA or BrkB, more preferred ratios are 1-5 PT to 1 BrkA or BrkB, most preferred ratio are 2.5 PT to 1 BrkA or BrkB.

The incorporation of *B. pertussis/B. parapertussis* crossprotective antigens into the immunogenic compositions of the invention further defines previously described embodiments of the invention and is also an independent embodiment of the invention, namely an immunogenic composition (or acellular vaccine) comprising one or more antigens (preferably isolated from either or both of *B. pertussis* or *B. parapertussis*, particularly those antigens described in Example 16) that is capable of generating an immune response that is crossreactive against *B. pertussis* and *B. parapertussis*, preferably crossprotective against *Bordetella* disease, more preferably against *B. pertussis* and *B. parapertussis* disease, with the proviso that the immunogenic composition does not comprise whole cell *pertussis* (Pw).

Diagnostic, Prognostic, Serotyping and Mutation Assays

This invention is also related to the use of BASB232 polynucleotides and polypeptides of the invention for use as diagnostic reagents. Detection of BASB232 polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising a BASB232 genes or proteins, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled BASB232 polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science*, 230: 1242 (1985). Sequence changes at specific locations also may be revealed by nuclease protection assays, such as RNase, V1 and S1 protection assay or a chemical cleavage method. See, for example, Cotton et al., *Proc. Natl. Acad. Sci., USA*, 85: 4397-4401 (1985).

In another embodiment, an array of oligonucleotides probes comprising BASB232 nucleotide sequences or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., *Science*, 274: 610 (1996)).

Thus in another aspect, the present invention relates to a diagnostic kit which comprises:

(a) a polynucleotide of the present invention, preferably any of the nucleotide sequences of SEQ Group 1, or a fragment thereof;

(b) a nucleotide sequence complementary to that of (a);

(c) a polypeptide of the present invention, preferably any of the polypeptides of SEQ Group 2 or a fragment thereof; or (d) an antibody to a polypeptide of the present invention, preferably to the polypeptides of SEQ Group 2.

It will be appreciated that in any such kit, (a), (b), (c) or (d) may comprise a substantial component. Such a kit will be of use in diagnosing a disease or susceptibility to a Disease, among others.

This invention also relates to the use of polynucleotides of the present invention as diagnostic reagents. Detection of a mutated form of a polynucleotide of the invention, preferably any sequences of SEQ Group 1, which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding BASB232 polypeptide can be used to identify and analyze mutations.

The invention further provides primers with 1, 2, 3 or 4 nucleotides removed from the 5' and/or the 3' end. These primers may be used for, among other things, amplifying BASB232 DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing, disease, preferably bacterial infections, more preferably infections caused by *Bordetalla*, particularly *B. pertussis*, comprising determining from a sample derived from an individual, such as a bodily material, an increased level of expression of polynucleotide having a sequence of any of the sequences of SEQ Group 1. Increased or decreased expression of a BASB232 polynucleotides can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of BASB232 polypeptides compared to normal control tissue samples may be used to detect the presence of an infection, for example.

Assay techniques that can be used to determine levels of BASB232 polypeptides, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probes obtained or derived from a bodily sample, to determine the presence of a particular polynucleotide sequence or related sequence in an individual. Such a presence may indicate the presence of a pathogen, particularly *B. pertussis*, and may be useful in diagnosing and/or prognosing disease or a course of disease. A grid comprising a number of variants of any polynucleotide sequences of SEQ Group 1 are preferred. Also preferred is a comprising a number of variants of a polynucleotide sequence encoding any polypeptide sequences of SEQ Group 2.

Antibodies

The polypeptides and polynucleotides of the invention or variants thereof, or cells expressing the same can be used as immunogens to produce antibodies immunospecific for such polypeptides or polynucleotides respectively. Alternatively, mimotopes, particularly peptide mimotopes, of epitopes within the polypeptide sequence may also be used as immunogens to produce antibodies immunospecific for the polypeptide of the invention. The term “immunospecific” means that the antibodies have substantially greater affinity for the polypeptides of the invention than their affinity for other related polypeptides in the prior art.

In certain preferred embodiments of the invention there are provided antibodies against BASB232 polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495497 (1975); Kozbor et al, *Immunology Today* 4: 72 (1983); Cole et al., pg. 77-96 in *MONOCLONAL ANTIBODIES AND CANCER THERAPY, Alan R. Liss, Inc. (*1985).

Techniques for the production of single chain antibodies (U.S. Pat. No. 4,946,778) can be adapted to produce single chain antibodies to polypeptides or polynucleotides of this invention. Also, transgenic mice, or other organisms or animals, such as other mammals, may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti-BASB232 or from naive libraries (McCafferty, et al., (1990), Nature 348, 552-554; Marks, et al., (1992) *Biotechnology* 10, 779-783). The affinity of these antibodies can also be improved by, for example, chain shuffling (Clackson et al., (1991) *Nature* 352: 628).

The above-described antibodies maybe employed to isolate or to identify clones expressing the polypeptides or polynucleotides of the invention to purify the polypeptides or polynucleotides by, for example, affinity chromatography.

Thus, among others, antibodies against BASB232 polypeptides or BASB232 polynucleotides maybe employed to treat infections, particularly bacterial infections.

Polypeptide variants include antigenically, epitopically or immunologically equivalent variants form a particular aspect of this invention.

Preferably, the antibody or variant thereof is modified to make it less immunogenic in the individual. For example, if the individual is human the antibody may most preferably be “humanized,” where the complimentarity determining region or regions of the hybridoma-derived antibody has been transplanted into a human monoclonal antibody, for example as described in Jones et al. (1986), *Nature* 321, 522-525 or Tempest et al, (1991) *Biotechnology* 9, 266-273.

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or maybe structural or functional mimetics. See, e.g., Coligan et al., *Current Protocols in Immunology* 1(2): Chapter 5 (1991).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring BASB232 polypeptides and/or polynucleotides activity in the mixture, and comparing the BASB232 polypeptides and/or polynucleotides activity of the mixture to a standard. Fusion proteins, such as those made from Fc portion and BASB232 polypeptides, as hereinbefore described, can also be used for high-throughput screening assays to identify antagonists of the polypeptide of the present invention, as well as of phylogenetically and and/or functionally related polypeptides (see D. Bennett et al., J Mol Recognition, 8:52-58 (1995); and K Johanson et al., J Biol Chem, 270(16):9459-9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of BASB232 polypeptide or polynucleotides, particularly those compounds that are bacteriostatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising BASB232 polypeptide and a labeled substrate or ligand of such polypeptides is incubated in the absence or the presence of a candidate molecule that may be a BASB232 agonist or antagonist. The ability of the candidate molecule to agonize or antagonize the BASB232 polypeptide is reflected in decreased binding of the labeled ligand or decreased production of product from such substrate. Molecules that bind gratuitously, i.e., without inducing the effects of BASB232 polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product, a reporter gene that is responsive to changes in BASB232 polynucleotide or polypeptide activity, and binding assays known in the art.

Another example of an assay for BASB232 agonists is a competitive assay that combines BASB232 and a potential agonist with BASB232 binding molecules, recombinant BASB232 binding molecules, natural substrates or ligands, or substrate or ligand mimetics, under appropriate conditions for a competitive inhibition assay. BASB232 can be labeled, such as by radioactivity or a colorimetric compound, such that the number of BASB232 molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing BASB232 induced activities, thereby preventing the action or expression of BASB232 polypeptides and/or polynucleotides by excluding BASB232 polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of BASB232.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular *Bordetella*, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial BASB232 proteins that mediate tissue damage and/or; to block the normal progression of pathogenesis in infections initiated other than by the implantation of in-dwelling devices or by other surgical techniques.

In accordance with yet another aspect of the invention, there are provided BASB232 agonists and antagonists, preferably bacteristatic or bactericidal agonists and antagonists.

The antagonists and agonists of the invention may be employed, for instance, to prevent, inhibit and/or treat diseases.

In a further aspect, the present invention relates to mimotopes of the polypeptide of the invention. A mimotope is a peptide sequence, sufficiently similar to the native antigen, preferably a peptide or LPS (sequentially or structurally), which is capable of being recognised by antibodies which recognise the native peptide; or is capable of raising antibodies which recognise the native peptide when coupled to a suitable carrier.

Peptide mimotopes may be designed for a particular purpose by addition, deletion or substitution of elected amino acids. Thus, the peptides may be modified for the purposes of ease of conjugation to a protein carrier. For example, it may be desirable for some chemical conjugation methods to include a terminal cysteine. In addition it may be desirable for peptides conjugated to a protein carrier to include a hydrophobic terminus distal from the conjugated terminus of the peptide, such that the free unconjugated end of the peptide remains associated with the surface of the carrier protein. Thereby presenting the peptide in a conformation which most closely resembles that of the peptide as found in the context of the whole native molecule. For example, the peptides may be altered to have an N-terminal cysteine and a C-terminal hydrophobic amidated tail. Alternatively, the addition or substitution of a D-stereoisomer form of one or more of the amino acids may be performed to create a beneficial derivative, for example to enhance stability of the peptide.

Alternatively, peptide mimotopes may be identified using antibodies which are capable themselves of binding to the polypeptides of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native polypeptide.

Vaccines

Another aspect of the invention relates to a method for inducing an immunological response in an individual, particularly a mammal, preferably humans, which comprises inoculating the individual with BASB232 polynucleotide and/or polypeptide, or a fragment or variant thereof, or a combination thereof as described above, adequate to produce antibody and/or T cell immune response to protect said individual from infection, particularly bacterial infection and most particularly *Bordetella* infection including *B. pertussis* and/or *B. parapertussis* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of BASB232 polynucleotide and/or polypeptide, or a fragment or a variant thereof, for expressing BASB232 polynucleotide and/or polypeptide, or a fragment or a variant thereof, or a combination thereof as described above, in vivo in order to induce an immunological response, such as, to produce antibody and/or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when iced into an individual, preferably a human, capable of having induced within it an immunological response, induces an immunological response in such individual to a BASB232 polynucleotide and/or polypeptide encoded therefrom, or a combination thereof as described above, wherein the composition comprises a recombinant BASB232 polynucleotide and/or polypeptide encoded therefrom and/or comprises DNA and/or RNA which encodes and expresses an antigen of said BASB232 polyncleotide, polypeptide encoded therefrom, or other polypeptide of the invention. The immunological response may be used therapeutically or prophylactically and may take the form of antibody immunity and/or cellular immunity, such as cellular immunity arising from CTL or CD4+ T cells.

A BASB232 polypeptide or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein D from *Haemophilus influenzae*, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein.

In a vaccine composition according to the invention, a BASB232 polypeptide and/or polynucleotide, or a fragment, or a mimotope, or a variant thereof, or a combination thereof as described above, may be present in a vector, such as the live recombinant vectors described above for example live bacterial vectors.

Also suitable are non-live vectors for the BASB232 polypeptide, or a combination thereof as described above, for example bacterial outer-membrane vesicles or "blebs". OM blebs are derived from the outer membrane of the two-layer membrane of Gram-negative bacteria and have been documented in many Gram-negative bacteria (Zhou, L et al. 1998. *FEMS Microbiol. Lett*. 163:223-228) including *C. trachomatis* and *C. psittaci*. A non-exhaustive list of bacterial pathogens reported to produce blebs also includes: *Bordetella pertussis, Borrelia burgdorferi, Brucella melitensis, Brucella ovis, Esherichia coli, Haemophilus influenzae, Legionella pneumophila, Moraxella catarrhalis, Neisseria gonorrhoeae, Neisseria meningitides, Pseudomonas aeruginosa* and *Yersinia enterocolitica*.

Blebs have the advantage of providing outer-membrane proteins in their native conformation and are thus particularly useful for vaccines. Blebs can also be improved for vaccine use by engineering the bacterium so as to modify the expression of one or more molecules at the outer membrane. Thus for example the expression of a desired immunogenic protein at the outer membrane, such as the BASB232 polypeptide, can be introduced or upregulated (e.g. by altering the promoter). Instead or in addition, the expression of outer-membrane molecules which are either not relevant (e.g. unprotective antigens or immunodominant but variable proteins) or detrimental (e.g. toxic molecules such as LPS, or potential inducers of an autoimmune response) can be downregulated. These approaches are discussed in more detail below.

The non-coding flanking regions of the BASB232 genes contain regulatory elements important in the expression of the gene. This regulation takes place both at the transcriptional and translational level. The sequence of these regions, either upstream or downstream of the open reading frame of the gene, can be obtained by DNA sequencing. This sequence information allows the determination of potential regulatory motifs such as the different promoter elements, terminator sequences, inducible sequence elements, repressors, elements responsible for phase variation, the shine-dalgarno sequence, regions with potential secondary structure involved in regulation, as well as other types of regulatory motifs or sequences. This sequence is a further aspect of the invention.

This sequence information allows the modulation of the natural expression of the BASB232 genes. The upregulation of the gene expression may be accomplished by altering the promoter, the shine-dalgarno sequence, potential repressor or operator elements, or any other elements involved. Likewise, downregulation of expression can be achieved by similar types of modification. Alternatively, by changing phase variation sequences, the expression of the gene can be put under phase variation control, or it may be uncoupled from this regulation. In another approach, the expression of the gene can be put under the control of one or more inducible elements allowing regulated expression. Examples of such regulation include, but are not limited to, induction by temperature shift, addition of inductor substrates like selected carbohydrates or their derivatives, trace elements, vitamins, co-factors, metal ions, etc.

Such modifications as described above can be introduced by several different means. The modification of sequences involved in gene expression can be carried out in vivo by random mutagenesis followed by selection for the desired phenotype. Another approach consists in isolating the region of interest and modifying it by random mutagenesis, or site-directed replacement, insertion or deletion mutagenesis. The modified region can then be reintroduced into the bacterial genome by homologous recombination, and the effect on gene expression can be assessed. In another approach, the sequence knowledge of the region of interest can be used to replace or delete all or part of the natural regulatory sequences. In this case, the regulatory region targeted is isolated and modified so as to contain the regulatory elements from another gene, a combination of regulatory elements from different genes, a synthetic regulatory region, or any other regulatory region, or to delete selected parts of the wild-type regulatory sequences. These modified sequences can then be reintroduced into the bacterium via homologous recombination into the genome. A non-exhaustive list of preferred promoters that could be used for up-regulation of gene expression includes the promoters porA, porB, lbpB, tbpB, p110, 1st, hpuAB from *N. meningitidis* or *N. gonorroheae*; ompCD, copB, lbpB, ompE, UspA1; UspA2; TbpB from *M. Catarrhalis*; p1, p2, p4, p5, p6, 1pD, tbpB, D15, Hia, Hmw1, Hmw2 from *H. influenzae* and any known strong promoter from *B. pertussis* or *B. parapertussis*. In one example, the expression of the gene can be modulated by exchanging its promoter with a stronger promoter (through isolating the upstream sequence of the gene, in vitro modification of this sequence, and reintroduction into the genome by homologous recombination). Upregulated expression can be obtained in both the bacterium as well as in the outer membrane vesicles shed (or made) from the bacterium.

In other examples, the described approaches can be used to generate recombinant bacterial strains with improved characteristics for vaccine applications. These can be, but are not limited to, attenuated strains, strains with increased expression of selected antigens, strains with knock-outs (or decreased expression) of genes interfering with the immune response, strains with modulated expression of immunodominant proteins, strains with modulated shedding of outer-membrane vesicles.

Thus, also provided by the invention is a modified upstream region of the BASB232 genes, which modified upstream region contains a heterologous regulatory element which alters the expression level of the BASB232 proteins located at the outer membrane. The upstream region according to this aspect of the invention includes the sequence upstream of the BASB232 genes. The upstream region starts immediately upstream of the BASB232 genes and continues usually to a position no more than about 1000 bp upstream of the gene from the ATG start codon. In the case of a gene located in a polycistronic sequence (operon) the upstream region can start immediately preceding the gene of interest, or preceding the first gene in the operon. Preferably, a modified upstream region according to this aspect of the invention contains a heterologous promotor at a position between 500 and 700 bp upstream of the ATG.

Thus, the invention provides BASB232 polypeptides, or a combination thereof as described above, in a modified bacterial bleb. The invention further provides modified host cells capable of producing the non-live membrane-based bleb vectors. The invention further provides nucleic acid vectors comprising the BASB232 genes having a modified upstream region containing a heterologous regulatory element.

Further provided by the invention are processes to prepare the host cells and bacterial blebs according to the invention.

Also provided by this invention are compositions, particularly vaccine compositions, and methods comprising the polypeptides and/or polynucleotides of the invention and immunostimulatory DNA sequences, such as those described in Sato, Y. et al. Science 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in animal models of infection with *B. pertussis*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *B. pertussis* infection, in mammals, particularly humans.

Immunogenic Compositions

It is advantageous for the antigens and combinations of antigens of the invention to be formulated into immunogenic compositions that comprise immunogenic, preferably immunologically effective, amounts of additional antigens to elicit immunity to other pathogens, preferably viruses and/or bacteria. Such additional antigens include diphtheria toxoid, tetanus toxoid, hepatitis B surface antigen, injectable polio vaccine, *Haemophilus influenzae* type b PRP, capsular polysaccharides or outer membranr vesicle preparations from *N. meningitidis* and capsular polysaccharides from *S. pneumoniae.*

Preferred immunogenic compositions of the invention are formulated with 1, 2, 3 or preferably all 4 of the following meningococcal capsular polysaccharides or oligosaccharides: A, C, Y or W, which may be plain or conjugated to a protein carrier. Combinations of meningococcal polysaccharides or oligosaccharides include A and C; A and Y; A and W; C and Y; C and W; Y and W; A, C and Y; A, C and W; A, Y and W; C, Y and W and A, C, Y and W. Such a vaccine containing proteins *from N. meningitidis* serogroup B may be advantageously combine a global meningococcus vaccine with a *Bordetella* vaccine.

In a further preferred embodiment, the immunogenic compositions of the invention are formulated with a conjugated or unconjugated *H. influenizae* b capsular polysaccharide or oligosaccharide, and one or more plain or conjugated pneumococcal capsular polysaccharides or oligosaccarides. Optionally, the vaccine may also comprise one or more protein antigens that can protect a host against *Streptococcus pneumoniae* infection Such a vaccine may be advantageously used as a *Bordetella/H. influenzae/streptococcus* pneumonia vaccine.

In a further preferred embodiment, the immunogenic composition of the invention is formulated with capsular polysaccharides or oligosaccharides derived from one or more of *Neisseria meningitidis, Haemophilus influenzae, Streptococcus pneumoniae*, Group A Streptococci, Group *B Strepto-*

*cocci, Staphylococcus aureus* or *Staphylococcus epidermidis*. In a preferred embodiment, the immunogenic composition comprises capsular polysaccharides or oligosaccharides derived from one or more of serogroups A, C, W and Y of *Neisseria meningitidis*. A further preferred embodiment comprises capsular polysaccharides or oligosaccharides derived from *Streptococcus pneumoniae*. The pneumococcal capsular polysaccharide or oligosaccharide antigens are preferably selected from serotypes 1, 2, 3, 4, 5, 6B, 7F, 8, 9N, 9V, 10A, 11A, 12F, 14, 15B, 17F, 18C, 19A, 19F, 20, 22F, 23F and 33F (most preferably from serotypes 1, 3, 4, 5, 6B, 7F, 9V, 14, 18C, 19F and 23F). A further preferred embodiment comprises the PRP capsular polysaccharides or oligosaccharides of *Haemophilus influenzae*. A further preferred embodiment comprises the Type 5, Type 8 or 336 capsular polysaccharides or oligosaccharides of *Staphylococcus aureus*. A further preferred embodiment comprises the Type I, Type II or Type III capsular polysaccharides of *Staphylococcus epidermidis*. A further preferred embodiment comprises the Type Ia, Type Ic, Type II or Type III capsular polysaccharides or oligosaccharides of Group B streptocoocus. A further preferred embodiment comprises the capsular polysaccharides or oligosaccharides of Group A streptococcus, preferably further comprising at least one M protein and more preferably multiple types of M protein.

Capsular polysaccharides or oligosaccharides included in pharmaceutical compositions of the invention may be unconjugated or conjugated to a carrier protein such as tetanus toxoid, tetanus toxoid fragment C, non-toxic mutants of tetaus toxin, diphtheria toxoid, CRM197, other non-texic mutant of diphtheria toxin (such as CRM176, CRM197, CRM228, CRM45 (Uchida et al J. Biol. Chem. 218; 3838-3844, 1973); CRM9, CRM45, CRM102, CRM103 and CRM107 and other mutations described by Nicholls and Youle in Geneticaly Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711), pneumolysin or Protein D (U.S. Pat. No. 6,342,224).

The polysaccharide conjugate may be prepared by any known coupling technique. For example the polysaccharide can be coupled via a thioether linkage. This conjugation method relies on activation of the polysaccharide with 1-cyano-4dimethylamino pyridinium tetrafluoroborate (CDAP) to form a cyanate ester. The activated polysaccharide may thus be coupled directly or via a spacer group to an amino group on the carrier protein. Preferably, the cyanate ester is coupled with hexane diamine and the amino-derivatised polysaccharide is conjugated to the carrier protein using heteroligation chemistry involving the formation of the thioether linkage. Such conjugates are described in PCT published application WO93/15760 Uniformed Services University.

The conjugates can also be prepared by direct reductive amination methods as described in U.S. Pat. No. 4,365,170 (Jernings) and U.S. Pat. No. 4,673,574 (Anderson). Other methods are described in EP-0-161-188, EP-208375 and EP-0-477508.

A further method involves the coupling of a cyanogen bromide activated polysaccharide derivatised with adipic acid hydrazide (ADH) to the protein carrier by Carbodiimide condensation (Chu C. et al Infect. Immunity, 1983 245 256).

The immunogenic compositions of the invention may also comprise proteins from other pathogens. Preferred pneumococcal proteins antigens are those pneumococcal proteins which are exposed on the outer surface of the pneumococcus (capable of being recognised by a host's immune system during at least part of the life cycle of the pneumococcus), or are proteins which are secreted or released by the pneumococcus. Most preferably, the protein is a toxin, adhesin, 2-component signal tranducer, or lipoprotein of *Streptococcus pneumoniae*, or fragments thereof Particularly preferred proteins include, but are not limited to: pneumolysin (preferably detoxified by chemical treatment or mutation) [Mitchell et al. Nucleic Acids Res. 1990 Jul. 11; 18(13): 4010 "Comparison of pneumolysin genes and proteins from *Streptococcus pneumoniae* types 1 and 2.", Mitchell et al. Biochim Biophys Acta 1989 Jan. 23; 1007(1): 67-72 "Expression of the pneumolysin gene in *Escherichia coli*: rapid purification and biological properties.", WO 96/05859 (A. Cyanamid), WO 90/06951 (Paton et al), WO 99/03884 (NAVA)]; PspA and transmembrane deletion variants thereof (U.S. Pat. No. 5,804,193—Briles et al.); PspC and transmembrane deletion variants thereof (WO 97/09994—Briles et al); PsaA and transmembrane deletion variants thereof (Berry & Paton, Infect Immun 1996 December;64(12):5255-62 "Sequence heterogeneity of PsaA, a 37-kilodalton putative adlesin essential for virulence of *Streptococcus pneumoniae*"); pneumococcal choline binding proteins and transmembrane deletion variants thereof; CbpA and transmembrane deletion variants thereof(WO 97/41151; WO 99/51266); Glyceraldehyde-3-phosphate—dehydrogenase (Infect. Immun. 1996 64:3544); HSP70 (WO 96/40928); PcpA (Sanchez-Beato et al. *FEMS Microbiol Lett* 1998, 164:207-14); M like protein, (EP 0837130) and adhesin 18627, (EP 0834568). Further preferred pneumococcal protein antigens are those disclosed in WO 98/18931, particularly those selected in WO 98/18930 and PCT/US99/30390.

Preferred proteins for inclusion in the immunogenic composition of the invention include adhesins, autotansporter proteins, iron acquisition proteins and toxins from *N. meningitidis* serotype B, optionally as part of an outer membrane vesicle preparation.

Adhesins include FhaB (WO98/02547), NadA (J. Exp. Med (2002) 195:1445; NMB 1994), Hsf also known as NhhA (NMB 0992) (WO99/31132), Hap (NMB 1985)(WO99/55873), NspA (WO96/29412), MafA (NMB 0652) and MafB (NMB 0643) (Annu Rev Cell Dev Biol. 16; 423457 (2000); Nature Biotech 20; 914-921 (2002)), Omp26 (No 0181), NMB 0315, NMB 0995, No 1119 and PilC (Mol. Microbiol. 1997, 23; 879-892). These are proteins that are involved in the binding of Neisseria to the surface of host cells.

Autotransporter proteins typically are made up of a signal sequence, a passenger domain and an anchoring domain for attachment to the outer membrane. Examples of autotransporter proteins include Hsf (WO99/31132) (NMB 0992), HMW, Hia (van Ulsen et al Immunol. Med. Microbiol. 2001 32; 53-64), Hap (NMB 1985) (WO99/55873; van Ulsen et al Immunol. Med. Microbiol. 2001 32; 53-64), UspA, UspA2, NadA (NMB 1994) (Comanducci et al J. Exp. Med. 2002 195; 1445-1454), AspA (Infection and Immunity 2002, 70(8); 4447-4461; NMB 1029), Aida-1 like protein, SSh-2 and Tsh. The passenger domain of an autotransporter protein is a preferred fragment for incorporation into the immunogenic composition of the invention.

Iron aquisition proteins include ThpA (NMB 0461) (WO92/03467, U.S. Pat. No. 5,912,336, WO93/06861 and EP586266), TbpB (NMB 0460) (WO93/06861 and EP586266), LbpA (NMB 1540) (Med Microbiol (1999) 32:1117), LbpB N 1541)(WO/99/09176), HpuA (U73112.2) (Mol Microbiol. 1997, 23; 737-749), HpuB (NC_003116.1)

(Mol Microbiol. 1997, 23; 737-749), P2086 also known as XthA (NMB 0399) (13$^{th}$ International Pathogenic Neisseria Conference 2002), FbpA (NMB 0634), FbpB, BfrA (NMB 1207), BfrB (NMB 1206), Lipo28 also known as GNA2132 (NMB 2132), Sibp (NMB 1882), HmbR, HemH, Bcp (NMB 0750), Iron (III) ABC transporter-permease protein (Tettelin et al Science 287; 1809-1815 2000), Iron (III) ABC transporter-periplasmic (Tettelin et al Science 287; 1809-1815 2000), TonB-dependent receptor (NMB 0964 and NMB 0293)(Tettelin et al Science 287; 1809-1815 2000) and transferrin binding protein related protein (ettelin et al Science 287; 1809-1815 2000).

Toxins include FrpA (NMB 0585; NMB 1405), FrpA/C (see below for definition), FrpC (NMB 1415; NMB 1405) (WO92/01460), NM-ADPRT (NMB 1343) (13$^{th}$ International Pathogenic Neisseria Conference 2002 Masiguani et al p135), VapD (NMB 1753), lipopolysaccharide (LPS; also called lipooligosaccharide or LOS) immunotype L2 and LPS immunotype L3. FrpA and FrpC contain a region which is conserved between these two proteins and a preferred fragment of the proteins would be a polypeptide containing this conserved fragment, preferably comprising amino acids 227-1004 of the sequence of FrpA/C.

The meningococcal proteins included in the immunogenic composition of the invention may be present as a subunit composition in which the purified protein or an immunogenic fragment of the protein is added to the immunogenic composition. Optionally, the protein is added as part of an outer membrane vesicle preparation.

The immunogenic composition optionally comprises antigens providing protection against Diphtheria and/or tetanus infections. Typically, the antigens providing protection against Diphtheria and tetanus would be Diphtheria toxoid and tetanus toxoid. The toxoids may be chemically inactivated toxins or toxins inactivated by the introduction of point mutations.

It is advantageous to combine the immunogenic composition of the invention with antigens that confer immunity against one or more of *Haemophilus influenzae* b, hepatitis B and/or polio virus. Preferred pharmaceutical compositions of the invention will further comprise one or more, most preferably all three of PRP polysaccharide or oligosaccharide of *Haemophilus influenzae* b, hepatitis B surface antigen and/or injectable polio virus (IPV).

The immunogenic composition optionally comprises one or more antigens that can protect a host against RSV and/or one or more antigens that can protect a host against influenza virus.

Preferred influenza virus antigens include whole, live or inactivated virus, split influenza virus, grown in eggs or MDCK cells, or Vero cells or whole flu virosomes (as described by R. Gluck, Vaccine, 1992, 10, 915-920) or purified or recombinant proteins thereof, such as HA, NP, NA, or M proteins, or combinations thereof.

Preferred RSV (Respiratory Syncytial Virus) antigens include the F glycoprotein, the G glycoprotein, the HN protein, or derivatives thereof.

Preferred non-typeable *H. influenzae* protein antigens include Fimbrin protein (U.S. Pat. No. 5,766,608) and fusions comprising peptides therefrom (eg LB1 Fusion) (U.S. Pat. No. 5,843,464—Ohio State Research Foundation), OMP26, P6, protein D, ThpA, TbpB, Hia, Hmw1, Hmw2, Hap, and D15.

It should be appreciated that immunogenic compositions of the invention may comprise one or more capsular polysaccharide or oligosaccharide from a single species of bacteria Immunogenic compositions may also comprise capsular polysaccharides or oligosaccharide derived from one or more species of bacteria.

Vaccines

A further embodiment of the invention provides a vaccine formulation which comprises an immunogenic recombinant polypeptide and/or polynucleotide of the invention, or a combination thereof, together with a suitable carrier/excipient, such as a pharmaceutically acceptable carrier/excipient. Since the polypeptides and polynucleotides may be broken down in the stomach, each is preferably administered parenterally, including, for example, administration that is subcutaneous, intramuscular, intravenous, or intradermal.

Formulations suitable for parenteral administration include aqueous and non-aqueous sterile injection solutions which may contain anti-oxidants, buffers, bacteriostatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

The vaccine formulation of the invention may also include adjuvant systems for enhancing the immunogenicity of the formulation. The adjuvant may be aluminium hydroxide, aluminium phosphate or a mixture of aluminium hydroxide and aluminium phosphate. Where hepatitis B surface antigen is present as part of the vaccine, the adjuvant is preferably aluminium phosphate. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses maybe characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglisotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytolines in terms of that described in murine CD4+ ve T cell clones by Mosmann and Coffman (Mosmann, T. R. and Coffman, R. L. (1989) *TH1 and TH2 cells: different patterns of lymphokine secretion lead to different functional properties. Annual Review of Immunology*, 7, p145-173). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast, TH2-type responses are associated with the secretion of IL-4, IL-5, IL-6 and IL-13.

It is known that certain vaccine adjuvants are particularly suited to the stimulation of either TH1 or TH2-type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+ cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (European Patent number 0 689 454).

3D-MPL will be present in the range of 10 μg-100 μg preferably 25-50 μg per dose wherein the antigen will typically be present in a range 2-50 μg per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with an carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21: 3D-MPL will typically be in the order of 1:10 to 10:1; preferably 1:5 to 5:1 and often substantially 1:1. The preferred range for optimal synergy is 2.5:1 to 1:1 3D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 μg-200 μg, such as 10-100 μg, preferably 10 μg-50 μg per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

While the invention has been described with reference to certain BASB232 polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides.

Compositions, Kits and Administration In a further aspect of the invention there are provided compositions comprising a BASB232 polynucleotide and/or a BASB232 polypeptide for administration to a cell or to a multicellular organism.

The invention also relates to compositions comprising a polynucleotide and/or a polypeptides discussed herein or their agonists or antagonists. The polypeptides and polynucleotides of the invention maybe employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with 1, 2, 3, 4 or 5 of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides, polynucleotides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, solutions, powders and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The dosage range required depends on the choice of peptide, the route of administration, the nature of the formulation, the nature of the subject's condition, and the judgment of the attending practitioner. Suitable dosages, however, are in the range of 0.1-100 μg/kg of subject.

A vaccine composition is conveniently in injectable form. Conventional adjuvants may be employed to enhance the immune response. A suitable unit dose for vaccination is 0.5-5 microgram/kg of antigen, and such dose is preferably administered 1-3 times and with an interval of 1-3 weeks. With the indicated dose range, no adverse toxicological effects will be observed with the compounds of the invention which would preclude their administration to suitable individuals.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Sequence Databases, Sequences in a Tangible Medium and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as the GCG program package.

Also provided by the invention are methods for the analysis of character sequences or strings, particularly genetic sequences or encoded protein sequences. Preferred methods of sequence analysis include, for example, methods of sequence homology analysis, such as identity and similarity analysis, DNA, RNA and protein structure analysis, sequence assembly, cladistic analysis, sequence motif analysis, open reading frame determination, nucleic acid base calling, codon usage analysis, nucleic acid base trimming, and sequencing chromatogram peak analysis.

A computer based method is provided for performing homology identification. This method comprises the steps of: providing a first polynucleotide sequence comprising the sequence of a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Definitions

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heine, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math*., 48: 1073 (1988). Methods to determine identity are designed to give the largest match between the sequences tested. Moreover, methods to determine identity are codified in publicly available computer programs. Computer program methods to determine identity between two sequences include, but are not limited to, the GAP program in the GCG program package (Devereux, J., et al., *Nucleic Acids Research* 12(1): 387 (1984)), BLASTP, BLASTN (Altschul, S. F. et al., *J. Molec. Biol.* 215: 403-410 (1990), and FASTA(Pearson and Lipman Proc. Natl. Acad. Sci. USA 85; 2444-2448 (1988). The BLAST family of programs is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990). The well known Smith Waterman algorithm may also be used to determine identity.

Parameters for polypeptide sequence comparison include the following:

Algorithm: Needleman and Wunsch, J. Mol Biol. 48: 443-453 (1970)

Comparison matrix: BLOSSUM62 from Henikoff and Henikoff,

Pros. Natl. Acad. Sci. USA. 89:10915-10919 (1992)

Gap Penalty: 8

Gap Length Penalty: 2

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:

Algorithm: Needleman and Wunsch, J. Mol Biol. 48: 443-453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO: 1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leq x_n - (x_n \cdot y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

The terms "comprising", "comprise" and "comprises" herein is intended by the inventors to be optionally substitutable with the terms "consisting of", "consist of", and "consists of", respectively, in every instance.

"Immunogenic composition" in the context of a polynucleotide means that when the polynucleotide is introduced into a host and protein is expresssed from that polynucleotide, the expressed protein is immunogenic.

"Individual(s)," when used herein with reference to an organism, means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxyribonucleotide, which maybe unmodified RNA or DNA or modified RNA or DNA including single and double-stranded regions.

"Toxin" preferably includes a toxoid form of the toxin.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in ammo acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Disease(s)" means any disease caused by or related to infection by a bacteria, including, for example, otitis media in infants and children, pneumonia in elderlies, sinusitis, nosocomial infections and invasive diseases, chronic otitis media with hearing loss, fluid accumulation in the middle ear, auditive nerve damage, delayed speech learning, infection of the upper respiratory tract and inflammation of the middle ear.

EXAMPLES

The examples below are carried out using standard techniques, which are well known and routine to those of skill in the art, except where otherwise described in detail. The examples are illustrative, but do not limit the invention.

Example 1

Cloning of the BASB232 Genes *B. Pertussis* Strain Tohama I

Genomic DNA is extracted from the *B. pertussis* strain Tohama I from $10^{10}$ bacterial cells using the QIAGEN genomic DNA extraction kit (Qiagen Gmbh). This material (1 μg) is then submitted to Polymerase Chain Reaction DNA amplification using two specific primers. A DNA fragment is obtained, digested by the suitable restriction endonucleases and inserted into the compatible sites of the pET cloning/expression vector (Novagen) using standard molecular biology techniques (Molecular Cloning, a Laboratory Manual, Second Edition, Eds: Sambrook, Fritsch & Maniatis, Cold Spring Harbor press 1989). Recombinant pET-BASB232 is then submitted to DNA sequencing using the Big Dyes kit (Applied biosystems) and analyzed on a ABI 373/A DNA sequencer in the conditions described by the supplier.

Example 2

Expression and Purification of Recombinant BASB232 Proteins in *Escherichia coli*

The construction of the pET-BASB232 cloning/expression vector is described in Example 1. This vector harbours the BASB232 gene isolated from *Bordetella pertussis* strain Tohama I in fusion with a stretch of 6 Histidine residues, placed under the control of the strong bacteriophage T7 gene 10 promoter. For expression study, this vector is introduced into the *Escherichia coli* strain Novablue DE3) (Novagen), in which, the gene for the T7 polymerase is placed under the control of the isopropyl-beta-D thiogalactoside (IPTG)-regulatable lac promoter. Liquid cultures (100 ml) of the Novablue (DE3) [pET-BASB232*] E. coli* recombinant strain are grown at 37° C. under agitation until the optical density at 600 nm (OD600) reached 0.6. At that time-point, IPTG is added at a final concentration of 1 mM and the culture is grown for 4 additional hours. The culture is then centrifuged at 10,000 rpm and the pellet is frozen at −20° C. for at least 10 hours. After thawing, the pellet is resuspended during 30 min at 25° C. in buffer A (6M guanidine hydrochloride, 0.1M NaH2PO4, 0.01M Tris, pH 8.0), passed three-times through a needle and clarified by centrifigation (20000 rpm, 15 min). The sample is then loaded at a flow-rate of 1 ml/min on a Ni2+-loaded Hitrap column (Pharmacia Biotech). After passage of the flowthrough, the column is washed succesively with 40 ml of buffer B (8M Urea, 0.1MNaH2PO4, 0.01M Tris, pH 8.0), 40 ml of buffer C (8M Urea, 0.1MNaH2PO4, 0.01M Tris, pH 6.3). The recombinant protein BASB232/His6 is then eluted from the column with 30 ml of buffer D (8M Urea, 0.1MNaH2PO4, 0.01M Tris, pH 6.3) containing 500 mM of imidazole and 3 ml-size fractions are collected.

Highly enriched BASB232/His6 protein can be eluted from the column. This polypeptide is detected by a mouse monoclonal antibody raised against the 5-histidine motif. Moreover, the denatured, recombinant BASB232-His6 protein is solubilized in a solution devoid of urea. For this purpose, denatured BASB232-His6 contained in 8M urea is extensively dialyzed (2 hours) against buffer R (NaCl 150 mM, 10 mM NaH2PO4, Arginine 0.5M pH6.8) containing successively 6M, 4M, 2M and no urea. Alternatively, this polypeptide is purified under non-denaturing conditions using protocoles described in the Quiexpresssionist booklet (Qiagen Gmbh).

Example 3

Production of Antisera to Recombinants BASB232

Polyvalent antisera directed against the BASB232 protein are generated by vaccinating rabbits with the purified recombinant BASB232 protein. Polyvalent antisera directed against the BASB232 protein are also generated by vaccinating mice with the purified recombinant BASB232 protein. Animals are bled prior to the first immunication ("pre-bleed") and after the last immunization.

Anti-BASB232 protein titers are measured by an ELISA using purified recombinant BASB232 protein as the coating antigen. The titer is defined as mid-point titers calculated by 4-parameter logistic model using the XL Fit software. The antisera are also used as the first antibody to identify the protein in a western blot as described in example 5 below.

Example 4

Immunological characterization: Surface Exposure of BASB232

Anti-BASB232 proteins titres are determined by an ELISA using formalin-killed whole cells of *Boydetella pertussis* (*B.pertussis*). The titer is defined as mid-point titers calculated by 4-parameter logistic model using the XL Fit software.

Example 5

Immunological Characterisation: Western Blot Analysis

Several strains of *B.pertussis*, as well as clinical isolates, are grown on Bordet Gengou agar plates for 24 hours at 36° C. and 5% $CO_2$. Several colonies are used to inoculate Tryptic Soy Agar (TSA) broth supplemented by NAD and hemin, each at 10 µg/ml. Cultures are grown until the absorbance at 620 nm is approximately 0.4 and cells are collected by centrifugation. Cells are then concentrated and solubilized in PAGE sample buffer. The solubilized cells are then resolved on 4-20% polyacrylamide gels and the separated proteins are electrophoretically transferred to PVDF membranes. The PVDF membranes are then pretreated with saturation buffer. All subsequent incubations are carried out using this pretreatment buffer.

PVDF membranes are incubated with preimmune serum and rabbit or mouse immune seruum PVDF membranes are then washed.

PVDF membranes are incubated with biotin-labeled sheep anti-rabbit or mouse Ig. PVDF membranes are then washed 3 times with wash buffer, and incubated with streptavidin-peroxydase. PVDF membranes are then washed 3 times with wash buffer and developed with 4-chloro-1-naphtol.

Example 6

Presence of Antibody to BASB232 in Human Convalescent Sera

Western blot analysis of purified recombinant BASB232 is performed as described in Example 5 above, except that a pool of human sera from children infected by *B.pertussis* is used as the first antibody preparation.

Example 7

Efficacy of BASB232 Vaccine: Enhancement of Lung Clearance of *B.pertussis* in Mice This mouse model is based on the analysis of the lung invasion by *B.pertussis* following a standard intranasal challenge to vaccinated mice.

Groups of mice are immunized with BASB232 vaccine. After the booster, the mice are challenged by instillation of bacterial suspension into the nostril under anaesthesia. Mice are killed between 30 minutes as well as 2, 5 and 8 days after challenge and the lungs are removed aseptically and homogenized individually. The log10 weighted mean number of CFU/lung is determined by counting the colonies grown on agar plates after plating of dilutions of the homogenate. The arithmetic mean of the log10 weighted mean number of CFU/lung and the standard deviations are calculated for each group. Results are analysed statistically.

In this experiment groups of mice are immunized either with BASB232 or with a killed whole cells (kwc) preparation of *B.pertussis* or sham immunized.

Example 8

Useful Epitopes

The B-cell epitopes of a protein are mainly localized at its surface. To predict B-cell epitopes of BASB232 polypeptides two methods were combined: 2D-structure prediction and antigenic index prediction. The 2D-structure prediction was made using the PSIPRED program (from David Jones, Brunel Bioinformatics Group, Dept. Biological Sciences, Brunel University, Uxbridge UB8 3PH, UK). The antigenic index was calculated on the basis of the method described by Jameson and Wolf (CABIOS 4:181-186 [1988]). The parameters used in this program are the antigenic index and the minimal length for an antigenic peptide. An antigenic index of 0.9 for a minimum of 5 consecutive amino acids was used as threshold in the program. Peptides comprising good, potential B-cell epitopes are listed in table 5. These can be useful (preferably conjugated or recombinantly joined to a larger protein) in a vaccine composition for the prevention of *Bordetella* infections, as could similar peptides comprising conservative mutations (preferably 70, 80, 95, 99 or 100% identical to the sequences of table 5) or truncates comprising 5 or more (e.g. 6, 7, 8, 9, 10, 11 or 12) amino acids therefrom or extensions comprising e. g. 1, 2, 3, 5, 10 further amino acids at either or both ends from the native context of BASB232 polypeptides which preserve an effective epitope which can elicit an immune response in a host against the BASB232 polypeptides.

TABLE 5

| Potential B-cell epitopes from SEQ ID NO:34 | |
|---|---|
| Position | Sequence |
| 56 | QDAGQEGEF |
| 84 | DDDPDELGE |
| 106 | EHKNPMS |
| 236 | PGFPPPPPPLP |
| 265 | GQDGK |
| 339 | DGANT |
| 381 | TLRQTRI |
| 404 | PQSGSG |
| 538 | DGNKPL |
| 579 | ADSRVQD |
| 599 | APEASY |
| 628 | QNDQL |
| 636 | GRADGQ |
| 653 | ADSRGA |
| 692 | AEDPKT |
| 753 | TFSERQQISNRH |
| 766 | RAYDQT |
| 785 | ASGGRW |
| 800 | YADRTYPGDGGG |
| 839 | GRYDQQY |
| 858 | DYRTSG |
| 869 | EGGRRF |
| 893 | TSGKRYRASN |
| 944 | QEFKSTGDVRTNG |
| 962 | AGRHGR |
| 1004 | AGYRYSF |

The T-helper cell epitopes are peptides bound to HLA class II molecules and recognized by T-helper cells. The prediction of useful T-helper cell epitopes of BASB232 polypeptides was based on the TEPITOPE method describe by Sturniolo at al. (Nature Biotech. 17: 555-561 [1999]). Peptides comprising good, potential T-cell epitopes are listed in table 6. These can be useful (preferably conjugated to peptides, polypeptides or polysaccharides) for vaccine purposes, as could similar peptides comprising conservative mutations (preferably 70, 80, 95, 99 or 100% identical to the sequences below) or truncates comprising 5 or more (e.g. 6, 7, 8, 9, 10, 11, 12, 14, 16, 18 or 20) amino acids therefrom or extensions comprising e. g. 1, 2, 3, 5, 10 further amino acids at either or both ends from the native context of BASB232 polypeptides which preserve an effective T-helper epitope from BASB232 polypeptides.

TABLE 6

| Potential T-helper cell epitopes from SEQ ID NO:34 | |
|---|---|
| Position | Sequence |
| 20 | WRLHALAAALA |
| 34 | MARLAAPAAA |
| 105 | VEHKNPMSK |
| 118 | VRVSGAGRA |
| 144 | VVRRGGTLELDGVTVA |
| 164 | MEPMTVSDA |
| 192 | LVRAAQGGQ |
| 208 | LQSILGPALIADGGSIS |
| 270 | VTLREVALRAHGPQAT |
| 287 | VYAYMPGSEI |
| 298 | LQGGTVSVQ |
| 329 | VRLDGTTVS |
| 347 | LVRGDAARAEVVNTVLRTAKSLAA |
| 380 | VTLRQTRIE |
| 420 | ITTTGNRAA |
| 444 | VRAEGSGSS |
| 461 | LVVSAGSLAS |
| 483 | LKLMPGALASS |
| 497 | VRLTDGATA |
| 513 | LQQHSTIPV |
| 535 | IVADGNKPL |
| 563 | VLQSATLGK |
| 576 | VVNADSRVQD |
| 586 | MSMRGGRVEFQAPAPE |
| 609 | LQTLDGNGVFVLNTNVAA |
| 644 | VLVRNAGGEA |
| 660 | LGLVHTQGQ |
| 673 | FRLANVGKAVD |
| 687 | WRYSLAEDP |
| 699 | VWSLQRAGQALS |
| 725 | IALAESNAL |
| 740 | LRLRADAGGPWARTFSERQ |
| 824 | YVGDGGYYLDTVLRLGRYDQ |
| 843 | YNIAGTDGG |
| 859 | YRTSGAAWS |
| 888 | VMLWRTSGKRYRASNGLRV |
| 915 | LGRLGLRFGRRIALAG |
| 934 | VQPYARLGW |

TABLE 6-continued

| Potential T-helper cell epitopes from SEQ ID NO:34 | |
|---|---|
| Position | Sequence |
| 952 | VRTNGIGHA |
| 996 | INIPWSFHA |

The same analyses (B-cell epitopes prediction and T-helper cell epitopes prediction) could be done for each BASB232 polypeptide sequence comprised in SEQ Group 2.

Example 9

Expression of BrkA

BrkA is a 1010 amino acid protein. A pET30b expression vector containing amino acids 60-702 of BrkA, fused at the C and N-terminal to a 6×-His tag was used to express BrkA in *E. coli*. The bacteria were grown to an OD600 of approximately 0.6 and induced with 1 mM IPTG for 2 hours. Recombinant BrkA was purified under denaturing conditions using the protocol in the Xpress System Protein Purification manual (Invitrogen, Carlsbad, Calif.). The bacteria were lysed in 6M guanidine hydrochloride and the lysate was applied to to Ni2+-nitrilotriacetic acid agarose (Qiagen, Mississauga, Ont.). After successive washes in 8M urea of decreasing pH, purified BrkA was eluted at pH 4 and the fractions were pooled. The urea was removed by slow dialysis at 4° C. against 10 mM Tris, pH 8.0 in the presence of 0.1% Triton X-100.

The purified protein was refolded so that it has a beta-structure resembling PRN (monitored by CD) and was functional in a serum assay. The protein was filter sterilized and is diluted in 10 mM Tris buffer, pH 8 at a concentration of approximately 0.4 mg/ml.

Example 10

Formulation of Vaccines

Six vaccines were formulated:

1. DTPa018A2—contains 6.25Lf DT, 2.5Lf TT, 6.25 ug PT and 6.25 ug FHA per mouse dose. All antigens were adsorbed separately onto Al(OH)3 before combining.
2. DTPa14885B9—contains 6.25Lf DT, 2.5Lf TT, 6.25 ug PT, 6.25 ug FHA and 2 ug pertactin per mouse dose. All antigens were adsorbed separately onto Al(OH)3 before combining.
3. DTPw13126A9—contains 6.25Lf DT, 2.5Lf TT and 1 I.U.whole cell *B. pertussis* per mouse dose. All antigens were adsorbed separately onto Al(OH)3 before combining.
4. DTBrkA—contains 6.25Lf DT, 2.5Lf TT and 2.5 ug BrkA per mouse dose. All antigens were adsorbed separately onto Al(OH)3 before combining.
5. DTPa-2 BrkA—contains 6.25Lf DT, 2.5Lf TT, 6.25 ug PT, 6.25 ug FHA and 2.5 ug BrkA per mouse dose. All antigens were adsorbed separately onto Al(OH)3 before combining.
6. DTPa-3 BrkA—contains 6.25Lf DT, 2.5Lf TT, 6.25 ug PT, 6.25 ug FHA, 2 ug pertactin and 2.5 ug BrkA per mouse dose. All antigens were adsorbed separately onto Al(OH)3 before combining.

Example 11

Protection Against Lung Invasion by *B. pertussis* in an Animal Model

Groups of 20 BALB/c mice (females, 5 weeks old) were immunized subcutaneously with ¼ of a human dose (125 µl of vaccine) and were boosted 3 weeks later. One week after the booster, a sample of blood was collected from each mouse for antibody determination. The mice were then challenged by instillation of 50 µl of bacterial suspension (+/−5 $10^6$ CFU/50 µl) into the left nostril under ether anesthesia. Five mice in each group were killed at 4 different times (2 hours, 2, 5 and 8 days) after challenge and the lungs were removed aseptically and homogenized individually. The log10 weighted mean number of CFU/lung was determined by counting the colonies grown on Bordet-Gengou agar plates after plating of 100 µl of 4 serial dilutions of the homogenate. The arithmetic mean of the log10 weighted mean number of CFU/lung and the standard deviation were calculated for each group and each time point.

Three experiments were performed. The same vaccine groups were included in each experiment but animals were either challenged with *B. pertussis* strain Tohama, *B. pertussis* strain 18323 or *B. parapertussis.*

The day before challenge, blood was collected from each mouse. The anti-PT, anti-FHA, anti-PRN and anti-BrkA antibody levels were determined by ELISA. The geometrc mean titre for each group of mice was calculated.

Example 12

*B. pertussis* Strain Tohama Challenge

Figure 1:
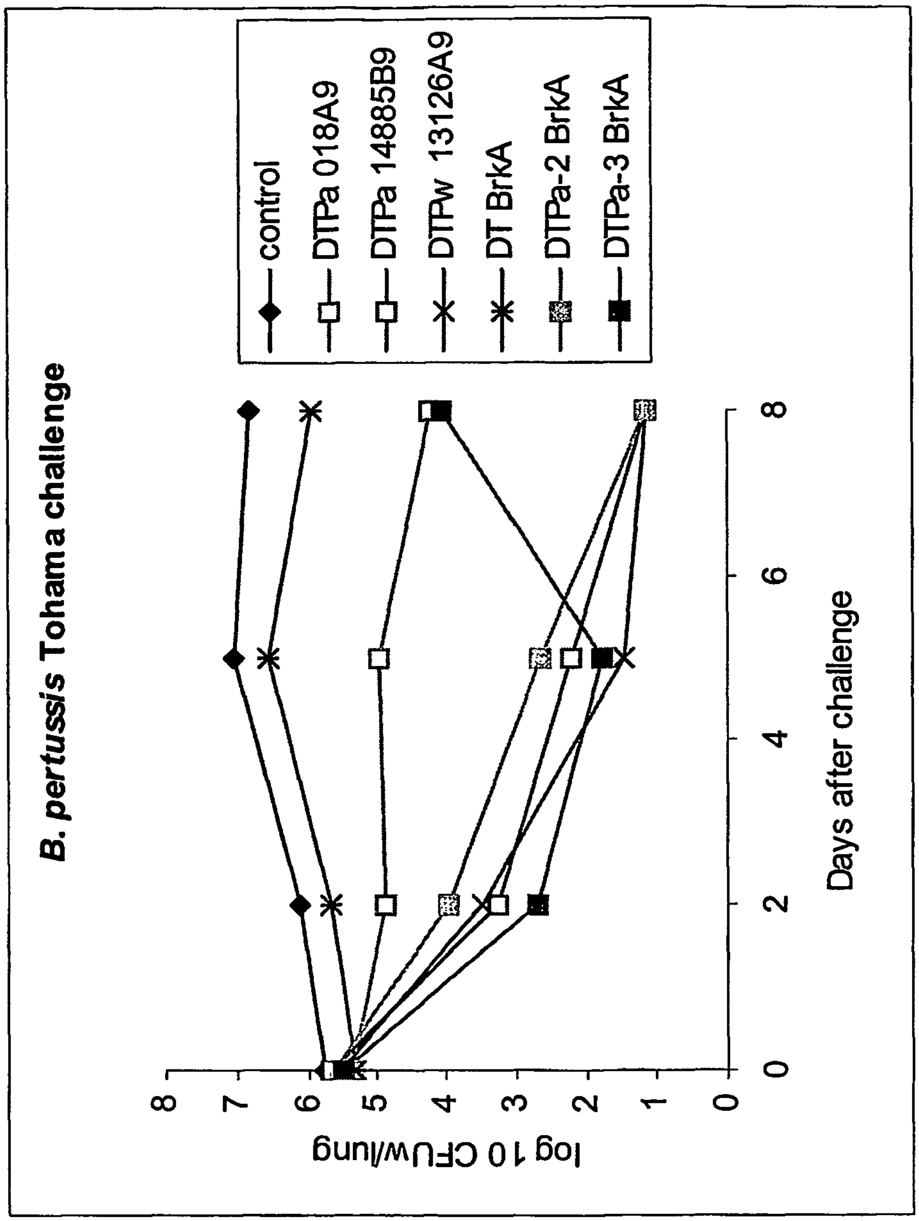
FIG. 1—is a graph showing protection against challenge with *B. pertussis* strain Tohama in groups of mice pre-immunised with carrier DT BrkA, DTPa-2, DTPa-2 BrkA, DTPa-3 or DTPa-3 BrkA. Results are expressed as the number of CFU isolated per lung at different time points after challenge. Pa-2 is a combination of *pertussis* toxin and FHA, whilst Pa-3 is a combination of *pertussis* toxin, FHA and pertactin.

In one experiment immunized mice were challenged with *B. pertussis* strain Tohama. The number of CFU/lung at each timepoint after challenge and for each group is summarized in the FIG. 1. The experiment had low variability with the data having a mean square error of is 0.450.

Statistical analysis of the data using ANOVA1 was used to assess the data. No significant difference was seen beween the protection against *B. pertussis* offered by DTBrkA compared to control, indicating that immunisation with BrkA alone is insufficient to elicit protection. In contrast, the addition of BrkA to a DTPa-2 vaccine produced a statistically significant increase in protection showing that, in combination with PT and FHA, BrkA can produce additional protection. The level of protection conferred by DTPa-2 BrkA was statistically slightly less than that conferred by DTPa-3 which conferred protection statistically equivalent to DTPw. The DTPa-3 BrkA vaccine provided excellent protection from challenge after 2 and 5 days but less protection after day 8.

Example 13

*B. pertussis* Strain 18323 Challenge

Figure 2:
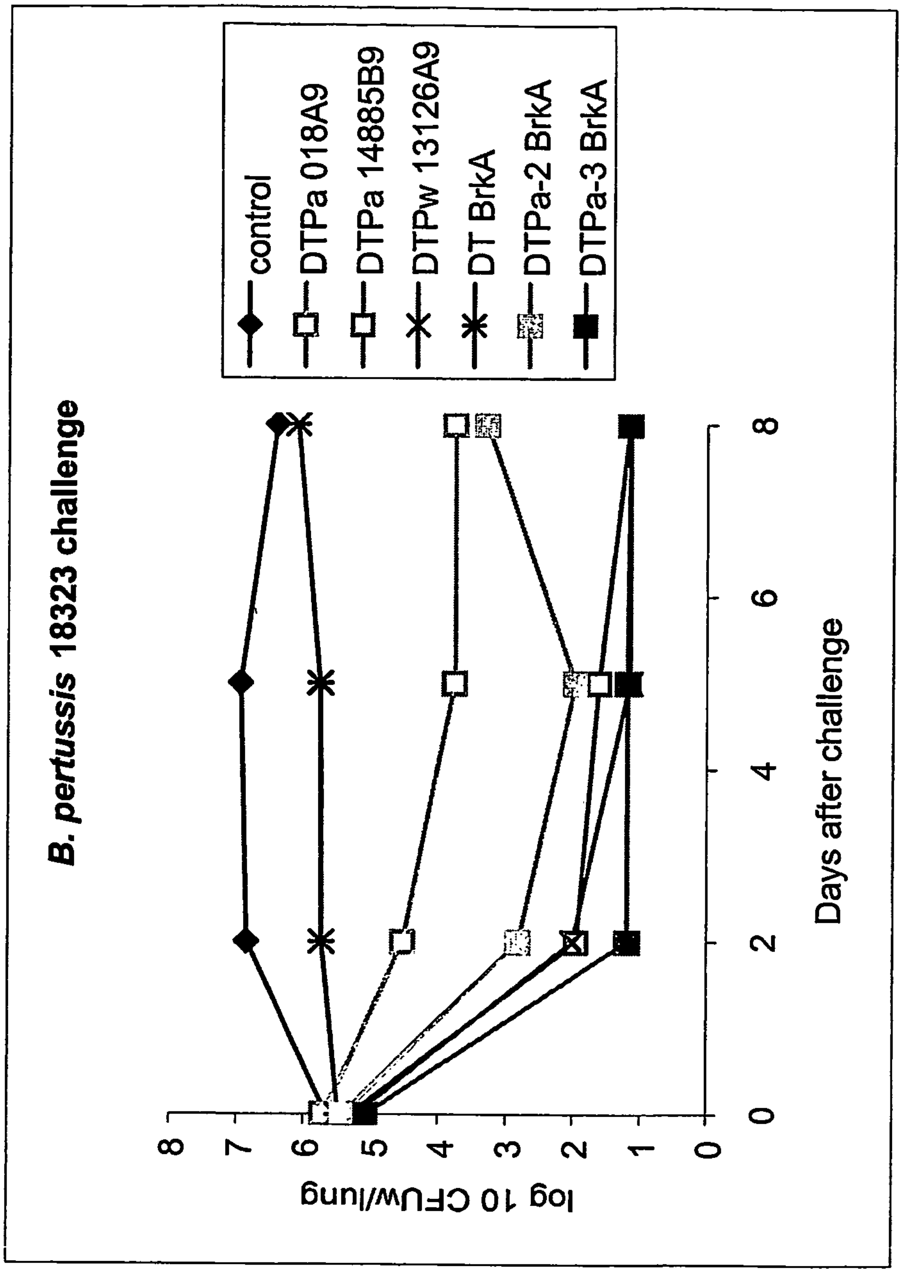
FIG. 2—is a graph showing protection against challenge with *B. pertussis* strain 18323 in groups of mice pre-immunised with carrier DT BrkA, DTPa-2, DTPa-2 BrkA, DTPa-3 or DTPa-3 BrkA. Results are expressed as the number of CFU isolated per lung at different time points after challenge.

In this experiment, immunized mice were challenged with *B. pertussis* strain 18323. The number of CFU/lung at each timepoint after challenge and for each group is summarized in FIG. 2. The experiment showed low variability with the mean square error of the experiment being 0.402. Statistical analysis using ANOVA1 showed that again DTBrkA did not provide an significant protection over the control. However, DTPa-2 BrkA provided better protection than DTPa, showing that BrkA, in combination with other *B. pertussis* antigens gives additional protection. The protection achieved by vaccination with DTPa-2 BrkAl, against challenge with *B. pertussis* strain 18323, was statistically equivalent to that provided by DTPa-3, DTPa-3 BrkA and DTPw.

Example 14

Comparison of Protection Against *B. pertussis* and *B. parapertussis* in Mice Vaccinated with DTPw or DTPa Groups of 25 or 30 BALB/c mice (females, 5 weeks old) were immunized subcutaneously with ¼ of a human dose of DT, DTPa or DTPw from different sources (125 μl of vaccine) and were boosted 3 weeks later. The sources of DTPw were Triple antigen (CSL), Tri-immune (Lederle), Pentacoq (MSD), Combivax (Behring), Infanrix (SB), DKTP (RVK, DTPw (Connaght) and Trivax (Wellcome). The sources of DTPa were Infanrix (SB), Triacel (PMCS), DI-TE-KIK (Amvax), A cell-immune (Lederle), Tropedia (Biken), Tricelluvax (Biocine/Chiron), Pentavac (PM-MSD) and DTPa-2 (SB). One or two weeks after the booster, a sample of blood was collected from each mouse for antibody determination. The mice were then challenged by instillation of 50 μl of bacterial suspension (+/−5 $10^6$ CFU/50 μl) into the left nostril under anaesthesia. Five mice in each group were killed at 5 or 6 different times (ranging from 2 hours to 14 days) after challenge and the lungs were removed aseptically and homogenized individually. The log10 weighted mean number of CFU/lung was determined by counting the colonies grown on Bordet-Gengou agar plates after plating of 100 μl of 4 serial dilutions of the homogenate. The arithmetic mean of the log10 weighted mean number of CFU/lung and the standard deviation were calculated for each group and each time point.

The day before challenge, blood was collected from each mouse for determination of the anti-PT, anti-FHA and anti-PRN antibody levels by ELISA. The geomean titre for each group of mice was calculated.

Results were analysed statistically by applying 1-way and 2-way ANOVA after assuming equality of variance (checked by Brown and Forsythe's test) and normality (checked using the Shapiro-Wilk test). Differences between groups were analysed using the Dunnet test, Tukey's studentised range test (HSD) and Student-Newman-Keuls test.

Figure 3:
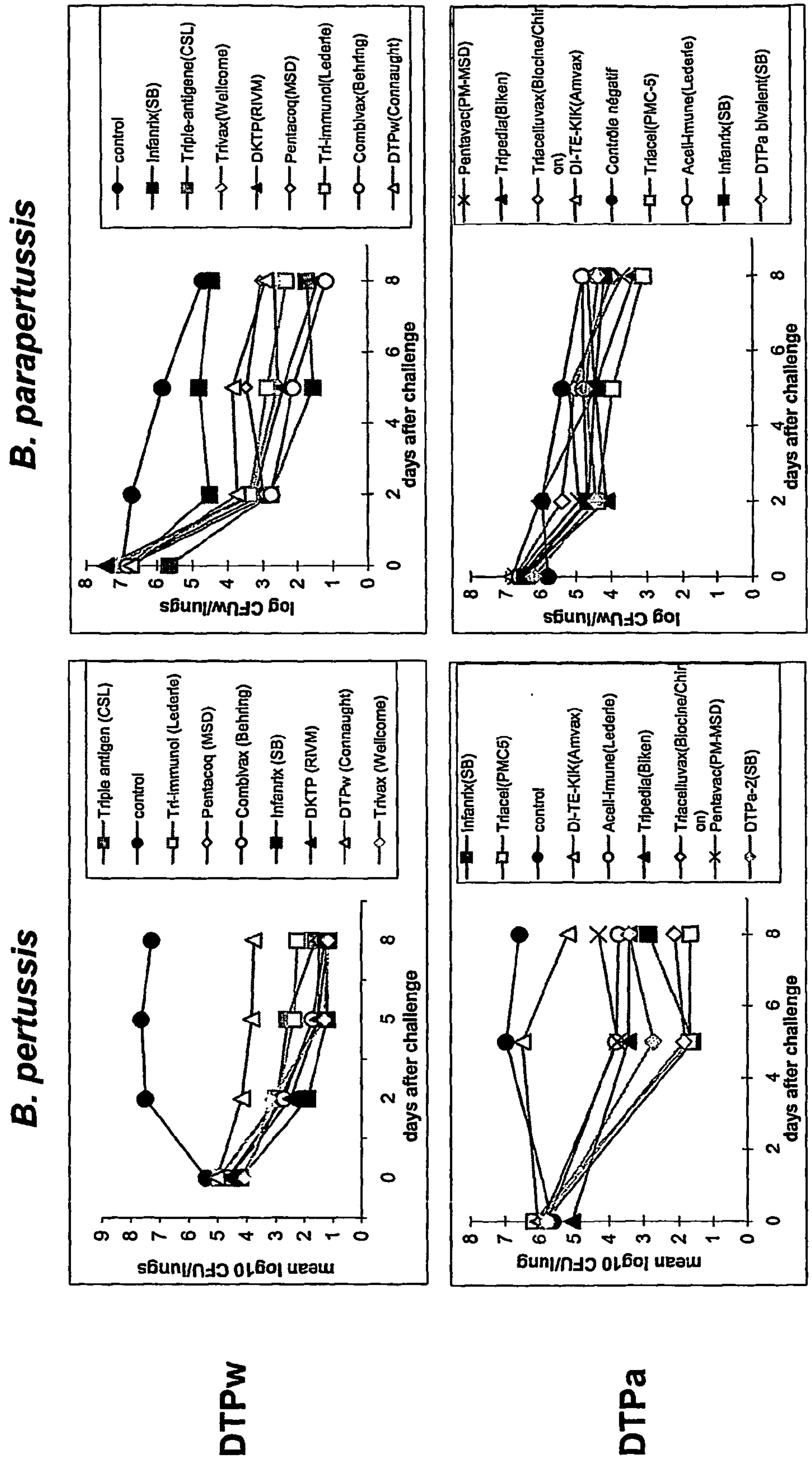
FIG. 3—graphs showing protection against challenge with *B. pertussis* or *B. parapertussis* in groups of mice preimmunised with DTPw or DTPa from several sources. Results are expressed as number of CFU isolated from the lung at different time points after challenge.
Figure 4:
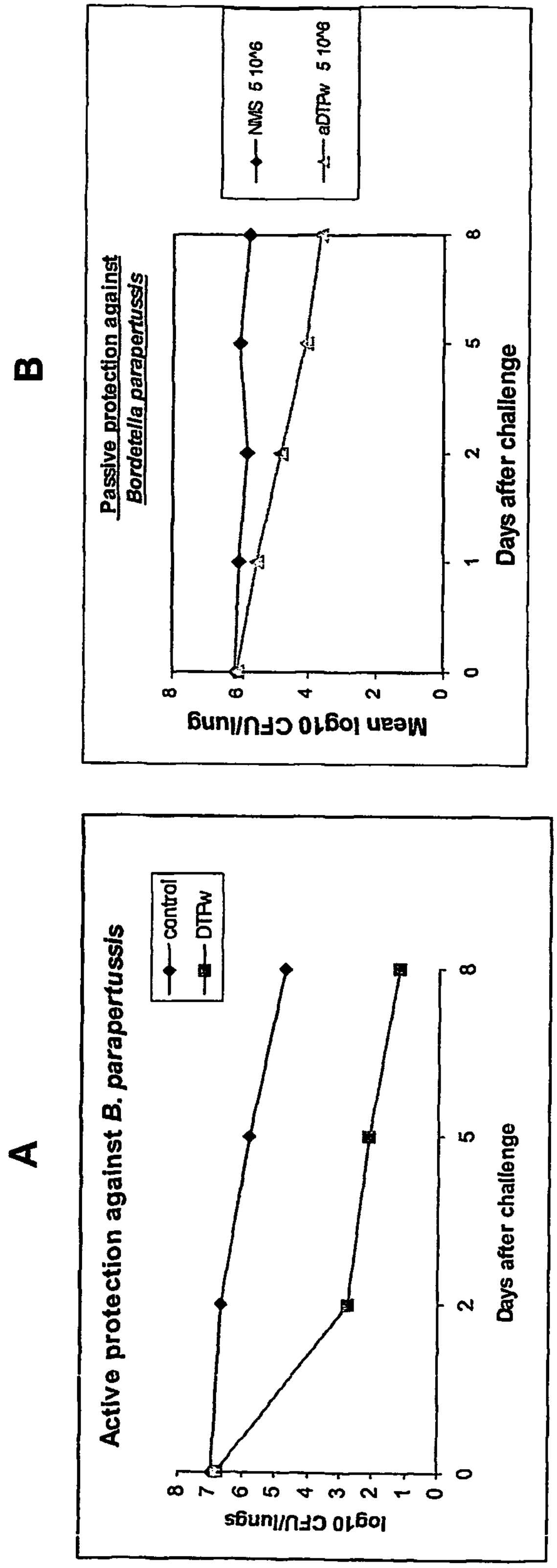
FIG. 4—graphs showing protection against *B. parapertussis* by antibodies against whole cell *B. pertussis*.

Results are shown in FIG. 3, and show that the DTPw vaccines induced good lung clearance of *B. pertussis* and *B. parapertussis*. However, DTPa vaccines induced strong lung clearance of *B. pertussis* but only limited clearance of *B. parapertussis*.

This experiment demonstrates that antigens present in the DTPw vaccine and absent from the DTPa vaccine are protective against parapertussis. Moreover, the antigens present in the DTPa vaccine, specifically FHA and pertactin, may display antigenic variability when compared to the corresponding parapertussis antigens.

Example 15

Protection Against *B. parapertussis* by Immunization with DTPw

Protection against a *B. parapertussis* challenge in the mouse lung clearance model can be obtained by active immunization with a DTPw vaccine (composed of *B. pertussis* killed whole cells).

In this experiment mice were immunnized twice (day 0 and 21) with ¼ human dose of DTPw vaccine and were intranasally challenged with *B. parapertussis* on day 28. Protection was measured by counting *B. parapertussis* in the lungs 0 (2 hours), 2, 5 and 8 days after challenge.

The results shown in FIG. 15A demonstrate that immunization with DTPw resulted in a large decrease in the number of *B. parapertussis* present in the lung, compared to control mice.

As shown in FIG. 15B, protection against *B. parapertussis* can also be obtained after passive immunization using an anti-DTPw serum. In this case, 500 μL of anti-Pw serum or normal mice serum was injected intraperitoneally to mice 20 hours before intranasal challenge with *B. parapertussis*. Bacteria remaining in the lungs were assessed 0, 1, 2, 5 and 8 days after challenge.

As shown in FIG. 15B, passive immunization with antisera against DTPw resulted in a sizeable reducetion in the number of *B. parapertussis* in the lungs of mice compared to the control group.

Protection observed against *B. parapertussis* after active and also passive immunization with a DTPw vaccine containing *B. pertussis* killed whole cells suggests that cross-protective epitopes exist between the two strains.

Example 16

Identification of Cross-protective *Bordetella* Antigens Materials and Methods

Outer Membrane Protein Samples

*B. parapertussis* outer membrane proteins (OMPs) samples were isolated from ATCC15237, using the protocol described in Inf. Imm. 1998, 66(8), 3597. This provided *B. parapertussis* OMPs at around 64 μg/ml, Gel Electrophoresis (SDS-PAGE)

Four aliquots of (ca. 13 μg each) of OMPs sample were pooled and evaporated to dryness under vacuum. The residue was solubilised in 100 μl of 0.1% w/v n-octylglucoside in water. The sample was reduced by the addition of 10 μl of 200 mM tributylphosphine and alkylated with 5 μl of 2-vinylpyridine. The reaction was performed at 4° C. for 4 hours. The mixture was then precipitated and washed with the Amersham SDS-PAGE clean-up kit. The complete sample (36 μl) was then dissolved with the SDS-PAGE sample buffer (36 μl) and reductant (7 μl) provided with the Bio-Rad Criterion XT gels. 64 μl of water were added and the mixture was heated at 95° C. for 5 min.

Two gels with lanes loaded with 14 μl (ca. 5 μg) of sample each, were run using a MES (2-morpholinethanesulfonic acid) running buffer to provide resolution for the small size range. Two other gels, also with lanes loaded with 14 μl of sample each, were run using MOPS (3-[N-morpholino]propanesulfonic acid) for resolution of the heaviest proteins. For each gel, on each side of the sample lanes, prestained and unstained standards (BioLabs cat no. P7708S and Bio-Rad cat no. 161-0317) were co-electrofocused as gel and Western alignment guides, respectively.

Gels were stained with the EZBlue Coomassie G250 colloidal reagent (Sigma).

Western Blotting

Immediately following gel electrophoresis, for each running buffer used, one gel was electroblotted onto a nitrocellulose membrane (Hybond ECL: Amersham), using a transfer buffer of 25 mM Tris, 192 mM glycine, 0.01% w/v SDS and 20% v/v methanol at 4° C. with a voltage of 100 V for 1 to 1.5 hour. Transfer was accomplished using the Trans-Blot Cell wet system from Bio-Rad.

Electroblotted proteins were revealed by pool of mouse sera raised against *B. pertussis* (αDTPw), produced as described in Example 15, followed as secondary antibody by alkaline phosphatase-conjugate goat anti-mouse IgG/IgM. Western immunoblots were visualised using AP chromogen kit nitro-blue tetrazolium (NBT)/5-bromo-4-chloro-3-indoyl phosphate potassium salt (BCIP) from Promega.

Gel and Western Blot Matching

Immunoactive bands on the Western blot membrane were matched to the corresponding Coomassie stained gel band by alignment after re-sizing of the molecular weight markers present on the scanned images.

In-gel Digestion and Peptide Extraction

The bands were excised and cut into pieces (ca. 1 $mm^3$). They were then transferred to 500 μl Protein Low Bind eppendorf tube. The gel pieces were washed three times with 300 μl of 50% v/v methanol and 5% v/v acetic acid in water for 15 min, followed by 300 μl of 100 mM ammonium bicarbonate for 5 min. Gel pieces were shrunken in 300 μl of acetonitrile for 5 min and dried under vacuum in a Speedvac evaporator for 5 min. The dried gel pieces were re-swollen in 100 μl of 5 mM tributylphosphine, 100 mM 2-vinylpyridine and 100 mM ammonium bicarbonate at 4° C. for 1 hour. The supernatant was discarded.

The gel pieces were washed with 300 μl of 100 mM ammonium bicarbonate for 5 min and shrunken in 300 μl of acetonitrile for 5 min. That step was repeated two times. The gel pieces were dried under vacuum in a Speed vac evaporator for 5 min.

In-gel digestion was performed overnight by the addition of 50 μl of a solution of native Bovin trypsin (100 mM ammonium bicarbonate, 5 mM $CaCl_2$, 0.01% w/v n-octyl glucoside). The proteolytic peptide products were extracted by sonication in 5% formic acid and acetonitrile. The combined extracts were then reduced to approximately 20 μl by vacuum evaporation.

Mass Spectrometry

Band digests were analysed by nanoLC-MS/MS using a Micromass QTof-2 tandem mass spectrometer (Micromass) operated by the Masslynx data system (Micromass). The Q-Tof was operated in survey-scan mode using a 1-s MS survey scan, from 400 to 1500 Da, followed by 1-s MS/MS scans on eight different precursor ions, from 50 to 2000 Da. MS/MS spectrum acquisition was allowed for up to a total of 4s on each precursor ion or stopped when the signal intensity fell below 3 counts/second. Precursors were excluded from any further MS/MS experiment for 200 sec. Only doubly and triply charged ions were selected as precursors for MS/MS. The cone voltage was of 35 V. The collision energy was adjusted according to the charge state and the mass of the precursor ion. The mass spectrometer was fitted with a nanospray SilicaTip emitter (New Objective). It was tuned to reach a resolution (fwhm) between 6000 and 8000 at m/z 432.9 (angiotensin). The capillary voltage was set between 2000 and 2700 V. The source temperature was 100° C.

The HPLC system was a CapLC (Micromass) using a ten port-valve enabling on-line desalting. The trapping cartridge was a C18 Symmetry (5×0.3 mm–5 μm–300 Å) (Waters) operated at 10 μl/min with 1% v/v methanol and 0.1% TFA v/v in water. After 8 min the ten-port valve was switched. The analytical columns were Atlantis C18 (150×0.075 mm–3 μm–100 Å) (Waters). They were operated at 250 nl/min at room temperature. An AB gradient was run from 5 to 40% B in 30 min. The eluent A was 0.1% v/v formic acid and 2% v/v acetonitrile in water. The eluent B was 0.1% v/v formic acid and 5% v/v water in acetonitrile. The equilibrium time after gradient elution was of 20 min.

Protein Sequence Database Search

Peak masses extracted from electrospray MS/MS spectra using the PeptideAuto macro were used for protein identification using Mascot 1.9 software (Matrix Science). The interrogation was performed against the protein sequence database of *Bordetella parapertussis* strain 12822 (4185 sequence entries) downloaded from the Sanger Institue web site (http://www.sanger.ac.uk). The mass tolerances allowed on the precursor and fragment ions were of 0.25 Da. Only proteins for which three trypsic peptides were identified were taken into account.

Results

The alignment of the Western blots and the corresponding Coomassie-stained gels for the two running buffer systems used are displayed in FIGS. 5 and 6. *B. parapertussis* OMP gel bands detected by Western blotting using sera raised against *B. pertussis* (DTPw) were excised from the gel. Trypsin was added and peptides were eluted out of the gel bands as described in the Materials and Methods section. Trypsic peptides of each bands were chromatographied by nanoLC and sequenced by MS/MS. MS/MS sequence data were used to search against the *B. parapertussis* protein sequence database. Hits were manually evaluated for their scores, ion intensity and number of matched trypsic peptides. Gel bands identification are summarised in Table 7.

For 6 MOPS gel bands and their MES equivalents , four membrane proteins were identified:

i) bands #8 (MOPS) and #14 (MES): autotransporter (13PP0452 gene);
ii) bands #9 (MOPS) and #15 (MES): TonB-dependent receptor for iron transport (BPP3376 or BFRD gene);
iii) bands #12 (MOPS): outer membrane porin protein (3PP3392 gene);
iv) bands #13 (MOPS) and #18 (MES): outer membrane protein A (BPP3135 or OMPA gene).

The identification of the autotransporter protein (BPP0452–Theor. MW=177 kDa) in gel bands at approximately 60 kDa could be tentatively assigned to a proteolytic fragment or to other autotransporter proteins displaying a high level of homology. This protein is the *B. parapertussis* homologue of SEQ ID No: 50, sharing 94% identity.

The TonB-dependent receptor for iron transport (BPP3376) is the *B. parapertussis* homologue of SEQ ID No: 14, sharing 98% identity.

A cytoplasmic chaperonin protein was identified for the gel bands #10 (MPOS) and #16 (MES) that could be associated to a contamination of the outer membrane fraction during the sample processing.

Conclusion

The method identified several antigens which generate an immune response which is crossreactive between *B. pertussis* and *B. parapertussis*. The proteins enclosed by SEQ ID NO: 50, 100, 14, 106, 108, 110, 102 and 104 are such proteins. The identified proteins isolated from either *B. pertussis* or *B. parapertussis* could be usefully incorporated into an acellular vaccine to provide protection against both *B. pertussis* and *B. parapertussis* disease.

TABLE 7

| Gel band (running buffer) | Hit # (Score[a]) | Protein description (Theor. MW in Da) | Nb peptides matched | Gene |
|---|---|---|---|---|
| #8 (MOPS) | 1 (821) | autotransporter (176978) | 15 | BPP0452 |
| | 2 (55) | translation initiation factor (103481) | 3 | BPP1862 |
| #14 (MES) | 1 (599) | autotransporter (176978) | 16 | BPP0452 |
| | 2 (112) | outer membrane protein A (20985) | 3 | BPP3135 |
| #9 (MOPS) | 1 (229) | TonB-dependent receptor for iron transport (81321) | 7 | BPP3376 or BFRD |
| | 2 (174) | polyribonucleotide nucleotidyltransferase (77294) | 4 | BPP3431 |
| | 3 (123) | probable surface antigen (86290) | 4 | BPP1535 |
| #15 (MES) | 1 (314) | TonB-dependent receptor for iron transport (81321) | 8 | BPP3376 or BFRD |
| | 2 (229) | polyribonucleotide nucleotidyltransferase (77294) | 7 | BPP3431 |
| #10 (MOPS) | 1 (938) | chaperonin (57447) | 27 | BPP0868 |
| #16 (MES) | 1 (621) | chaperonin (57447) | 16 | BPP0868 |
| #11 (MOPS) | 1 (446) | autotransporter (176978) | 10 | BPP0452 |
| | 2 (288) | elongation factor (42889) | 6 | BPP0007 |
| #17 (MES) | 1 (388) | autotransporter (176978) | 8 | BPP0452 |
| | 2 (271) | elongation factor (42889) | 6 | BPP0007 |
| | 3 (112) | putative membrane protein (47410) | 3 | BPP2847 |
| | 4 (98) | enolase (45885) | 3 | BPP3252 |
| #12 (MOPS) | 1 (528) | outer membrane porin protein (41319) | 18 | BPP3392 |
| #13 (MOPS) | 1 (209) | outer membrane protein A (20985) | 6 | BPP3135 or OMPA |
| | 2 (151) | outer membrane porin protein (41319) | 5 | BPP3392 |
| #18 (MES) | 1 (196) | outer membrane protein A (20985) | 6 | BPP3135 or OMPA |

(Score[a]) - The MOWSE score algorithm is described in DJC Pappin et al Curr. Biol., 3(6); 327-32 (1993).

DEPOSITED MATERIALS

A deposit of strain 3 (strain 3224A) has been deposited with the American Type Culture Collection (ATCC) on May 5, 2000 and assigned deposit number PTA-1816.

The *B. pertussis* strain deposit is referred to herein as "the deposited strain" or as "the DNA of the deposited strain."

The deposited strain contains a full length BASB232 gene.

The sequence of the polynucleotides contained in the deposited strain, as well as the amino acid sequence of any polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The deposited strain will be irrevocably and without restriction or condition released to the public upon the issuance of a patent The deposited strain is provided merely as convenience to those of skill in the art and is not an admission that a deposit is required for enablement, such as that required under 35 U.S.C. §112. A license may be required to make, use or sell the deposited strain, and compounds derived therefrom, and no such license is hereby granted.

SEQUENCE INFORMATION
BASB232 Polynucleotide and Polypeptide Sequences

SEQ group 1 contains SEQ ID NOS: 33, 1, 3, 5, 7, 9, 11, 13, 15, 17, 19, 21, 23, 35, 27, 29, 31, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95 and 97.

SEQ group 2 contains SEQ ID NOS: 34, 2, 4, 6, 8, 10, 12, 14, 16, 18, 20, 22, 24, 26, 28, 30, 32, 36, 38, 40, 42, 44,46, 48, 50, 52, 54, 56, 58, 60, 62, 64, 66, 68, 70, 72, 74, 76, 78, 80, 82, 84, 86, 88, 90, 92, 94, 96 and 98.

-continued

SEQ ID NO:1 polynucleotide sequence of Orf1

```
Atgtccaccccccgattcgcgctgcattacgccagcgcgtcagtcctgct

ggccgcatccGgcctggccatggcgcagacggccacccagatccacgatc

cgtcgcaggtgcagcagatgGcgacggtgcaggtgctgggcacggccgaa

gaggaaatcaaggagtcgctgggcgtctcggtcatcaccgccgaggagat

cgcccgccgcccgcccaccaatgacctgtccgacctgatccgccgcgaac

ccggcgtcaacctgaccggcaacagcgccagcggcgcgcggggcaacagc

cgccaggtcgacatccgcggcatgggccccgagaacaccctcatcctgat

cgacggcaagcccgtcacctcgcgcaatgcggtgcgctatggctggaacg

gcgaccgggacacgcgcggggacaccaactgggtgcccgccgaggaagtc

gagcgcatcgaagtgatccgcggcccggccgcccgcccgctacggttccgg

ggccatgggcggcgtggtcaacatcatcaccaagcgccccgccgatcgcg

ccaccggctccatcacctactacacgaaccagccggaagacagccgcgag

ggcaacaccaaccgcgtcaatgcgcgcatcagcgcgccgatcagcgacac

gctgagcatgcggctgtacggcaactacaacaagaccaatccggatgccc

gcgacatcaacgccggccacgcgaacaccagcgacaacggcaacccctcg

accgccggacgcgagggcgtcatcaaccaggacctgagcgcgctgttctc

gtggaaagccgacagccacaacaccgtggacctggacatgggcttcagcc

ggcagggcaacctgttcgccggcgacaccatgaacaacgccaacagcgac

ttctcggacagcctgtacggcaaggaaaccaatgcgatgtaccgcgagaa

ctatgcgctgacgcaccgcggcgtctacgactggggcacctcgcgcgcca

gcgtcggctatgactacacgcgcaacgcgcgccagcgcgaaggcctggcc

ggcggccccgagggcgcgcccaccgcgggcggctacgacaccgcgcgcct
```

-continued gaagaactggcgcgccgcggccgaggccagcgtgccgttccatctcggtt
tcgagcaggtcgccacggtcggcgtggaatggctgcgcgaatcgctggaa
gaccccgccggcacgcgccagacctataccggcggcgccatcggcggcac
ggccccggccgaccgcgacccgaaatcgcgccagaccagctatgcgctgt
tcgccgaggacaacatcgagatcgacgagcgcaccatgctcacgcccggc
gtgcgcctggaccacaacagcgaattcggcagcaactggagtcccagcct
gaacgcctcgtacgccgtcaccgacgcgctcaagctcaagggtggcatcg
cgcgcgcctacaaggcgcccaacctctaccaatccaaccccaactacctg
ctgtacagccgcggcaatggctgcctggcctcgcagaccaacaccaacgg
ctgctatctggtcggcaacgaggacctctcgccggaaaccagcgtcaaca
aggaaatcggcttcgagtacgacccgggcacgtggcgcaccagcatggcc
tatttccgcaacgactaccgcaacaagatcgtcgccggcaccgacgtcca
gtaccgcctggccaatggcgcccgggtgctgcaatggaccaacagcggca
aggccgtggtcgaagggctggaaggcaacctgttcattccgctggccagc
aatctcgactggaacaccaacttcacctacatgatccagtccaaggaaaa
ggctaccggcgaacccttgagcgtgattcccgaatacaccatcaacagca
cgctggactggttctacacgccgcagctgtcgttccaggccaatctcacc
tattacggcaagcaggaaggcccgtccaccaatgtacgcaccggcgtcga
actgaacggcgacggccgccagaccatcagtccgtatgccctggcgggcc
tgagcatgggctacgaagtcaaccggaacctgaagttccgcgtcggcgtg
agcaacctgttcgacaagcagctgtaccgcgaaggcaatgccagcagcgc
gggcgcggccacctacaacgaaccggggcgcgcctattacgccacggcga
cggtgtcgttctga SEQ ID NO:2 polypeptide sequence of Orf1
MSTPRFALHYASASVLLAASGLAMAQTATQIHDPSQVQQMATVQVLGTAE
EEIKESLGVSVITAEEIARRPPTNDLSDLIRREPGVNLTGNSASGARGNS
RQVDIRGMGPENTLILIDGKPVTSRNAVRYGWNGDRDTRGDTNWVPAEEV
ERIEVIRGPAAARYGSGAMGGVVNIITKRPADRATGSITYYTNQPEDSRE
GNTNRVNARISAPISDTLSMRLYGNYNKTNPDARDINAGHANTSDNGNPS
TAGREGVINQDLSALFSWKADSHNTVDLDMGFSRQGNLFAGDTMNNANSD
FSDSLYGKETNAMYRENYALTHRGVYDWGTSRASVGYDYTRNARQREGLA
GGPEGAPTAGGYDTARLKNWRAAAEASVPFHLGFEQVATVGVEWLRESLE
DPAGTRQTYTGGAIGGTAPADRDPKSRQTSYALFAEDNIEIDERTMLTPG
VRLDHNSEFGSNWSPSLNASYAVTDALKLKGGIARAYKAPNLYQSNPNYL
LYSRGNGCLASQTNTNGCYLVGNEDLSPETSVNKEIGFEYDPGTWRTSMA
YFRNDYRNKIVAGTDVQYRLANGARVLQWTNSGKAVVEGLEGNLFIPLAS
NLDWNTNFTYMIQSKEKATGEPLSVIPEYTINSTLDWFYTPQLSFQANLT
YYGKQEGPSTNVRTGVELNGDGRQTISPYALAGLSMGYEVNRNLKFRVGV
SNLFDKQLYREGNASSAGAATYNEPGRAYYATATVSF SEQ ID NO:3 polynucleotide sequence of Orf2
Gtgttttctcgcagtcagaagcatccgtcctggcgcctgtcgccatgcgt -continued acttgcggccGccttgtgcgccgtcgcggtcggtagcgcggacaccgccc
gcgcgcaggcgcccgccgccAgcgcccagcattatgaaatcgcggccgga
ccgctggccgacgcactgacccgcttcgcgcgccgtgccggcgtggtgct
gtcgttcgacccggccctggtgcaggggcgcagcacggcgggcctgcagg
gcgtgtacggcgtgcgcgacgggttcgcggcgctgctggccggctcgggc
ctgcaggcgcgcgccggcggcggcaacaactggtcgctggcggcgctgcc
gcgcggcggcgatgcgcagacgctggcgccggtgacggtgctgggcctgg
agggcgcgctggcgcccacggtcggctatgtcgccagtgccagcctgagc
ggcaccaagaccgatacgccgctgatcgaaacgccgcaatcgatttcggt
ggtgactcgcgaccagataaccgagcagggcgcccagacgctgaaccagg
tgctgcgctataccgccggcgtggcgaccgagacgcgcggcgcgaccgcg
acgcggctggaccagttcagcgtgcgcggtttctccgccgccacctatct
ggacggcatgcgcgtgttcggcggccgggacgccttgccccaggtcgacg
cctaccggctcgaacgggtcgatgtgctcaaggggccggcttccgtgctg
tatggccagggcggcccgggcggcgtggtcaaccaggtcagcaagcgtcc
cctggacgagcctttgcgcgagatcgaagtgcaggcgggcaatttcgatt
tccggcgggtcaacatggatttttccggcccggtggacgaggaccggcgc
ttcctgtaccgggtaaccggcgcggcctatatgtccgatggccaggtgga
tcacaccagggagcgccgctacttcgtctcgccgtcgttcacgtggcggc
ccagcgcggataccacgctgaccgtgctgaccaacttccagcgcgacccc
gacatgggttcgtacggatcgatctcggccatgcgcacgctgctgtcggc
gcccgacggcaggcggctgggcccgaaccactacgacggcgacgccgatt
tcgaaaagagcgaccgcccgcagctattcgctgggctatcaactggagcat
cgcttcaacgataccttcaaggcctcgcagaacctgcgtttccagcatgc
cgagggcgtctatcgcagcatctacggcgccagcaacaacaattacggct
atctcgacaaggactaccgctactcgcagcgcggcctggccatcagcgac
gtggacgtggatgcgttcacgatcgacaacaacctgcaggcgcgcttcga
taccggggcgctggcgcatacggtgctggtggggttcgactaccagcgcg
tgcagaccgacaccttgtcgggctatggcagcgcgccgccgctcgacgtg
ttcgatccggactatcacatgggtatcgagcggccgccgtttacgtccga
tcagacccagtacaactaccagaccggcctctacctgcaggaccagatca
ggctggatcgcctgtcgttgctgctgggcgggcgctacgactggtcgcgc
acccacaccggcaccgacaacctggccaacggctcgcacagcagctcggc
gctcgccgccgaggcgttcaccggccgggtcggggcgatctacaacttcg
acaacggcgtggcgccgtacgccagctactcggagtcgttcgagccgcag
accggcacgggctggaacaacacgccgttcaagccgaccgaaggcaagca
gtatgaggtcggcgtgaaataccagccgccgggctcggccacgctgctca
cgctggcggccttcgacatccggcgcaagaacctgcccaccaccgacccg
gatcccacccatatgtgcggcgtttcgcgctgctcgatacaggccggcga
agtgcgcacccgcggcatcgaactggaggccaagaccgaaccgctgcgcg
gcctgagcctgatcgccgcctattcgtacctcgacaacgaatacgagaag -continued gcctatccgaacacgaccgggttggacctcaagggcaagaagccggtggc
cgtgccggcgcaccaggcgtcggcctgggcccgctatcaactgcaggagg
gcccgctggccggcctgggcatgggcgcgggggtgcgctacatcggcagt
tcgtacgccaacgaaaccaacacgctcaaggtgccatcggtgacgctggt
ggacatgatgctcgactacgacctgggccgggccagccccgcgctcaagg
gcatgcaggtggcgttgaacgtctccaacctgttcgacaaggaatacatc
ggctcgtgcctgtccgattcgtggtgctggtatggctaccagcgttcgat
caaggccagcttgcgctatcgctggtga SEQ ID NO:4 polypeptide sequence of Orf2
VFSRSQKHPSWRLSPCVLAAALCAVAVGSADTARAQAPAASAQHYEIAAG
PLADALTRFARRAGVVLSFDPALVQGRSTAGLQGVYGVRDGFAALLAGSG
LQARAGGGNNWSLAALPRGGDAQTLAPVTVLGLEGALAPTVGYVASASLS
GTKTDTPLIETPQSISVVTRDQITEQGAQTLNQVLRYTAGVATETRGATA
TRLDQFSVRGFSAATYLDGMRVFGGRDALPQVDAYRLERVDVLKGPASVL
YGQGGPGGVVNQVSKRPLDEPLREIEVQAGNFDFRRVNMDFSGPVDEDRR
FLYRVTGAAYMSDGQVDHTRERRYFVSPSFTWRPSADTTLTVLTNFQRDP
DMGSYGSISAMRTLLSAPDGRRLGPNHYDGDADFEKSDRRSYSLGYQLEH
RFNDTFKASQNLRFQHAEGVYRSIYGASNNNYGYLDKDYRYSQRGLAISD
VDVDAFTIDNNLQARFDTGALAHTVLVGFDYQRVQTDTLSGYGSAPPLDV
FDPDYHMGIERPPFTSDQTQYNYQTGLYLQDQIRLDRLSLLLGGRYDWSR
THTGRDNLANGSHSSSALAAEAFTGRVGAIYNFDNGVAPYASYSESFEPQ
TGTGWNNTPFKPTEGKQYEVGVKYQPPGSATLLTLAAFDIRRKNLPTTDP
DPTHMCGVSRCSIQAGEVRTRGIELEAKTEPLRGLSLIAAYSYLDNEYEK
AYPNTTGLDLKGKKPVAVPAHQASAWARYQLQEGPLAGLGMGAGVRYIGS
SYANETNTLKVPSVTLVDMMLDYDLGRASPALKGMQVALNVSNLFDKEYI
GSCLSDSWCWYGYQRSIKASLRYRW SEQ ID NO:5 polynucleotide sequence of Orf3
Atgcgagccagaccgagcgcggcaacccgcgccctgcactcatcgtcgcg
cccccgccgcCtgatccctgccctgctgggcgcgcttgcctgcctgggca
ctggcgtacaggccgcgcccAtcgacgtcgatatcccgccccagaacctg
gcccaagccctgcaccagcttggccggcaagccaacctgcaggtcctgta
cagccaggacctggtcgatggccagcgcagccccgccgtgcagggccgca
tggaacctgccgaagcgctggaacgcctgctgaaaggccgcaacatccgc
tattcgatccagcacaacaccgtcacgctcacgcccatgccgctgactgc
gacgctgccggcaatcagcgtggtcggcgccctgcctgactccgacacct
acgtggccacaggcacgacagccggcaccaagacggacacgccgctgatc
gaaataccgcaatccatttcggtggtgaccgccgcgcagatccgcgagca
gaatccgcagacgctgggcgacgccgtgcgctacacgcccggtatcgtgg
tgcaggaaggattcaaccgcaccgacgatcctttcatcatccgcggcttc
gacgtccgcaccaatcccggcgtcatgttccgcgacgggctgaaaatccc
cctgccccattacagcgcgatgtccgaaccctacgcgctcgaacgcatcg -continued aggtcgtgaaaggccccgcttcggtgctgtacggacaggcctcgccaggc
ggcatcgtcaacgtggtatccaagcggccgacagacagcccgctgcgcga
gctgcagctgagcggcggctcgcacagcaacaggcagctcgccggcgact
tcggcggacgcatcgacgacgagggacggctgacctaccgcctgaccggc
ctggcgcgcaatgccgacacgatgatcgaccatgtcccggacgaccgcta
ctatctcgcccccgcgctgacctggcgcatcagcccggacacctcgctga
cgctgctggcgagctacatgaagaacaagaccatcaacaacgccggctac
ccgctcgaaggcacggtcaagtacaaccccaacggccgcatcccgcgtca
ccgcttcaccggcgagccggactggagcaagtgggaccaggaggtcgcca
acgtggggtaccagtttgcgcaccgcttcaacgacacctggcaattcaag
cagaacctgggctacgcccagtcgcgcaaccgcgtcaaccacgcctactg
gtggacctgggtgcccggaagcgacttctccacggccgagcgcggcgcct
accgccgcgacgatgacgcccacggcgtgagcatcgacaaccagttcgag
gccacgtggcaatccggccgcttcaggcacaacacgctgttcggcctcga
ttacaccgaaacctcgttcacccgcaaacagtacgccggctacaacaacc
tcgccccgatcgacttcttcgatccggcgtacggctcggacgtactgctg
ccggcgaagccggacacctacaccaacgagaagcgcagccagctcggcct
gtacttgcaggaccagataaagttcgacgacaaactggtggtggtgctca
gcggccgctacgacaatgccgacggctcgacgctgaacaagctgagcggc
gtcaatacccgcaccggcgacaacgcgttcacgtggcgcaccggcctgct
ctaccttgcggacaacggtctggcgccctataccagctattcgacttcgt
tccagccgcaggccggcaccacctcgcccgcacgcggcaccacgcccttc
gacccgaccaagggcaagcagtgggaagccggcgtgaagtaccagcccaa
tggttcgaactcgttcatcaccgcatccgtcttcgagctgacgcgcacca
acgtccccacgaccgaccccgccaacccgtctacagcgtgcaggaaggc
gaggtgcgctcgcgcggcctcgaattgtcggccaccgccaacctggcctc
gggctggaacctgatcgcggcctacacgtataccgacgcggaaatcacca
agagcaactccaacacgctaggcaacacgcccgaggccgtgccgcgcaac
atggcgtcgctatggtccgactacaccgtcccgtccggtgcgctggcggg
gctgaatatcggcgccggcgtgcgctacatgggctcgacctacaacaaca
ccaatgccgccaaggtcggcgactacaccgtgttcgacgccgccctgcgc
tacgacttcggggcgcgcagcccgtccctgaaaggctggacggccgatct
caccgtgcgcaacctgttcgacaaggactacgtggcctcgtgcacctatg
cctgcttctacggagaaggcaggaccgtgctgggccgggtcacgtacaaa
tggtag SEQ ID NO:6 polypeptide sequence of Orf3
MRARPSAATRALHSSSRPRRLIPALLGALACLGTGVQAAPIDVDIPPQNL
AQALHQLGRQANLQVLYSQDLVDGQRSPAVQGRMEPAEALERLLKGRNIR
YSIQHNTVTLTPMPLTATLPAIDVVGALPDSDTYVATGTTAGTKTDTPLI
EIPQSISVVTAAQIREQNPQTLGDAVRYTPGIVVQEGFNRTDDPFIIRGF
DVRTNPGVMFRDGLKIPLPHYSAMSEPYALERIEVVKGPASVLYGQASPG -continued

GIVNVVSKRPTDSPLRELQLSGGSHSNRQLAGDFGGRIDDEGRLTYRLTG

LARNADTMIDHVPDDRYYLAPALTWRISPDTSLTLLASYMKNKTINNAGY

PLEGTVKYNPNGRIPRHRFTGEPDWSKWDQEVANVGYQFAHRFNDTWQFK

QNLGYAQSRNRVNHAYWWTWVPGSDFSTAERGAYRRDDDAHGVSIDNQFE

ATWQSGRFRHNTLFGLDYTETSFTRKQYAGYNNLAPIDFFDPAYGSDVLL

PAKPDTYTNEKRSQLGLYLQDQIKFDDKLVVVLSGRYDNADGSTLNKLSG

VNTRTGDNAFTWRTGLLYLADNGLAPYTSYSTSFQPQAGTTSPARGTTPF

DPTKGKQWEAGVKYQPNGSNSFITASVFELTRTNVPTTDPANPVYSVQEG

EVRSRGLELSATANLASGWNLIAAYTYTDAEITKSNSNTLGNTPEAVPRN

MASLWSDYTVPSGALAGLNIGAGVRYMGSTYNNTNAAKVGDYTVFDAALR

YDFGARSPSLKGWTADLTVRNLFDKDYVASCTYACFYGEGRTVLGRVTYK

W

SEQ ID NO:7 polynucleotide sequence of Orf4
Atgacaggctttcatgcacgcaagccggtgggcggtggccatggccggcc cgcgcacggcAggccgcttgcgtggccgcgcatcccccctacggacaacca ccatgaagccattaccgctcGcttatctcgccgcgctgctgccctggtac gcaggcgtcatccaggcgcaatccgcgcccgccgccggcgacgatgcctc gatcaccctggaagccgtcagggtcgaggccagcgccgacgcctccgccg gcggcctggcgccggccttcgcgggcggccaggtcgccacgggcgcgaag gtcggcatcctcggcacgcgcgacaacctggaaaccccgttctccatcac cgcctacaccaacgaactgatccaggaccgccaggccaagggggtgggcg acgtcctgcagaacgaccccggcgtgcgggtggcgcgcgggttcggcaac ttccaggagtcgtatttcatccgcggcttcatcctcagctcggacgacat cgcgtacaacggcctctatggcctgttgccgcgccagtacatctcgaccc agctgttcgagcgcgtcgaggtgctgcgcggtgcctcggcgtttctcacc ggcgcgccgccgtccggcggcgggatcggcggggtgatcaacctggttcc caagcgcgcgcccaacgagccgctgacgcgcttttcggccggctacggca gcgacagcgtgctcgaggcttcggccgacatcggccggcgcttcggcccg gacgacagcgtcgggatccgcatcaacgccgcccagcgcggcggcgagac cgccatcgacggcgagcgcacccgcaccacggtgttcgcgctgggcctgg actggcgcggcgagcgcgcgcgcctgtcggccgatatcggctaccaggac aaccgcctgaagcgggcgcgccccaatgtcacgctggccggcgacgccgc caaggtgcccggcgcgcccgacgccggctccaactatgcccagccctggt cgtactccaacgaacgcgacgtgttcggcaccctgcgcggcgaatacgac ttcaacggccgcataacgggctgggtcgcctatggcatgcgccagagcaa ggaggagaactagctggccaaccccaataacgtcaacggcgcggggcagg gcaagttctaccgcttcgacaacgcccgcgaggataccgtcaacaccggc gagatcggcctgcgcgccaaggcgcgcaccggcccggtgggccacgaact ggtcgcctcggcgtcgtatttcgacctcgagaagaagaacgcctatgtca tggacttcttcaaccagttcgacaccagcatctacgaccccgtcagctac gccaagccggccatcagcagcaccgcgtttcgcggcaacgacatggacga tcccgccaagcagggcgtcatccggctggccagctatgcgctgggcgaca ccatgtcgttcttcgacgacaaggtgctgctgaccgccggcatccgccac cagcgcctctaccagcgcgactacagctacgacacgggcatcggcggcac cccctacgagcaaagccacaactcgcccgccgccggcctggtggtgcgcg tgacgccccaggtgtcgctgtacgccaactacatcgaggccctgtcggcg ggcgacaccgcgccgcagaccgccaacggcctgccggtggtcaaccacgg cgaatcgctggcgccctatgtgtccaagcagaaggaagtgggcgtcaagt tcgagcacgacggcctgggcggcggcctggcgctcttttccaccgacaag ccgcgcgggttcgtgggcgatgaccaggtcttccgcgcttcgggcaagga ccgccaccgcggggtcgaactgacgacttacggcgagctcacgcgcagcg tgcgcgtgctgggcgggctgacctggctggacgccaagcagctcagcacc ggcaacgccgccaccgacggcaagcgcgtcatcggcgtgccccgcttcca ggccaacctcggcgtggagtgggacatccccggcgtgcagggcctgaccg tggacgggcgtgtggtctatacgggctcgtcctatgcggatgcggccaac accctcgaggtgccgggctggacgcgcctggacgccggcctgcgttacat gaccgatatcggcggccatctggtgacctggcgcgcccgcgtcgagaaca tcgccaaccgcgactactggtcctccgtgggcggctaccccggcaatggc tacctggtgctgggcggcccgcgcaccttcacgctgtcggcatcgatgga gttctga SEQ ID NO:8 polypeptide sequence of Orf4
MTGFHARKPVGGGHGRPAHGRPLAWPRIPLRTTTMKPLPLAYLAALLPWY

AGVIQAQSAPAAGDDASITLEAVRVEASADASAGGLAPAFAGGQVATGAK

VGILGTRDNLETPFSITAYTNELIQDRQAKGVGDVLQNDPGVRVARGFGN

FQESYFIRGFILSSDDIAYNGLYGLLPRQYISTQLFERVEVLRGASAFLT

GAPPSGGGIGGVINLVPKRAPNEPLTRFSAGYGSDSVLEASADIGRRFGP

DDSVGIRINAAQRGGETAIDGERTRTTVFALGLDWRGERARLSADIGYQD

NRLKRARPNVTLAGDAAKVPGAPDAGSNYAQPWSYSNERDVFGTLRGEYD

FNGRITGWVAYGMRQSKEENSLANLNNVNGAGQGKFYRFDNAREDTVNTG

EIGLRAKARTGPVGHELVASASYFDLEKKNAYVMDFFNQFDTSIYDPVSY

AKPAISSTAFRGNDMDDPAKQGVIRLASYALGDTMSFFDDKVLLTAGIRH

QRLYQRDYSYDTGIGGTPYEQSHNSPAAGLVVRVTPQVSLYANYIEALSA

GDTAPQTANGLPVVNHGESLAPYVSKQKEVGVKFEHDGLGGGLALFSTDK

PRGFVGDDQVFRASGKDRHRGVELTTYGELTRSVRVLGGLTWLDAKQLST

GNAATDGKRVIGVPRFQANLGVEWDIPGVQGLTVDGRVVYTGSSYADAAN

TLEVPGWTRLDAGLRYMTDIGGHLVTWRARVENIANRDYWSSVGGYPGNG

YLVLGGPRTFTLSASMEF

SEQ ID NO:9 polynucleotide sequence of Orf5
Gtgcctcgtcctacttcccgccgtacgcgccctgcgcgccggcaggcgca gcccgccttcGtgcccgcgctcttcatgcttgccctgggcgccgttgccg ccggcgcgcgcgcccagcccGctgcggcgggtgtcccggatacgcaaggc gtggcgcaaatgccggccgtcacggtcaacGccgcgccggtggacgacac gctggagcatctggaggcgccggtcgataccggcgcgctgGgacggcgca -continued cccagctggagacgcctttttccaccacggtggtgactgcccgcgacatg
Gaggagcgccaggtcaacaagctgggagacgtgttcgcgctggatgcctc
ggtgacggacAacagcgcgtcctatggcgcgtgggccagctacctgacgg
tgcgcggcctgccgctggatTggcagaattcgtaccgcatcgatggccgg
ccgttcctgagctacgtcacgacgctgccgTtcgagcacttcgagcagat
cgacctgctcaaggggggcgtcgggcttcatgtacggtttcGgctcgccgg
gcggcctggtcaactatgtcaccaagaagccgaccgacgaagcggtgcgc
Agcgtcgagctgggctacgtgtccaaggggttgctgcgcgagcacgtgga
cctgggcggcAgggtgggccagagcggcgcgtttggctatcggctgaatg
ccacgcacgaggagggcaatAcctacaacggtggatcgctgtaccgcgat
tcggtgtcgctggcgctggatgcgcgcctgAgcgaccggttgacctggga
cttccaatccatctaccaggaccgcaaggccatcgggcagGagcccacga
tctatgcgggcaccatggccggcagcgagttgccatcgccggtgcgcaac
Gacaatgacaggctggtcggcagggaccgtatgcggacaatgcgttccg
ctattactcgAccggcttgaagtaccaattggcggacgaatggacgctga
gcaccaattacagctacagcTccacgcgtacccgccgcaacgagtcggtg
ctgttcctgcgcgaccaggcgggcgactatGacgattaccgctcggacta
tggcgaggcctatggctacaaccagtggcaggccatgctgGagggcaagt
tcgctaccggtcccttgaagcaccacgtggtggccggcgcgtcgtggcag
Aagcagaagaacgactacagcgccaacggggtctatcaattgcagggcac
gggcaacctgCgcgcgcgcaataccaacacgtactacagcgaaggccagc
tgcacctgtaccgcgcggccGagatcacgcagaaggcgctgttcgccagc
gacacggtcgacctgaccggcggctggtcgGtgctgggcgggctgcgcta
tacgaattatgcgcagcaaggattcgatgccacgggcgcgCgaacatcgc
gctacgacaagaacggcgtgctgacgccgacctttgccctgatgtacaag
Ctgacgccgcgcaccatggcctatgccagctacatcgaatccttggagcc
gggctcgtcgGtgggcgccgcgtacgccaacttcggcgcattgctcgatc
cgttgaagagcaagcagtacGagctgggcatcaagaccgaacaggacggc
tgggccgccacggcggcgctgtttcgcatcGagaagaaggcggaatacgc
gaatgccgccaacgagctggtgcaggacggcaagacgctctTatcaggggt
tggaactgggcgcctccacgcgtatcgcccgcgactggaacgtgggaggc
Agcctgatgttgctggattcggaatacaagaaaggctcggatttcaccgg
caaccgcgtgGcgggagcgccgaagttcgtggcggccgcgcaactggcgt
actcggtgccgcaggtgccgGggctgaagctgcgcgccgatgtgaagtac
accggcaacacgatgctgggcgccagcaacCgggtgcaggtggacgacta
cgccatcgtcaatatcggcgccacctacgacacgcagatcCacggctacg
aggcgaccttcaccgccggcatcaacaacgtggccaacaagcgctactgg
Ctgtaccagtcgtctgactacgtgaaggcgggcgacccgcggacctatgg
cctgacgtctatatccagatatccggatatctggatataa SEQ ID NO:10 polypeptide sequence of Orf5
VPRPTSRRTRPARRQAQPAFVPALFMLALGAVAAGARAQPAAAGVPDTQG
VAQMPAVTVNAAPVDDTLEHLEAPVDTGALGRRTQLETPFSTTVVTARDM
EERQVNKLGDVFALDASVTDNSASYGAWASYLTVRGLPLDWQNSYRIDGR
PFLSYVTTLPFEHFEQIDLLKGASGFMYGFGSPGGLVNYVTKKPTDEAVR
SVELGYVSKGLLREHVDLGGRVGQSGAFGYRLNATHEEGNTYNGGSLYRD
SVSLALDARLSDRLTWDFQSIYQDRKAIGQEPTIYAGTMAGSELPSPVRN
DNDRLVGQGPYADNAFRYYSTGLKYQLADEWTLSTNYSYSSTRTRRNESV
LFLRDQAGDYDDYRSDYGEAYGYNQWQAMLEGKFATFPLKHHVVAGASWQ
KQKNDYSANGVYQLQGTGNLRARNTNTYYSEGQLHLYRAAEITQKALFAS
DTVDLTGGWSVLGGLRYTNYAQQGFDATGARTSRYDKNGVLTPTFALMYK
LTPRTMAYASYIESLEPGSSVGAAYANFGALLDPLKSKQYELGIKTEQDG
WAATAALFRIEKKAEYANAANELVQDGKTLYQGLELGASTRIARDWNVGG
SLMLLDSEYKKGSDFTGNRVAGAPKFVAAAQLAYSVPQVPGLKLRADVKY
TGNTMLGASNRVQVDDYAIVNIGATYDTQIHGYEATFTAGINNVANKRYW
LYQSSDYVKAGDPRTYGLTSISRYPDIWI SEQ ID NO:11 polynucleotide sequence of Orf6
Ttgcccgccataagcgtcacgggtcgtgagatttccgacctcaccgaggg
tacaaacgccTacacaaccgaggccatgagcacggccacgggcctgacac
tctcgccacgcgaaacaccaCaatccgtcagtgtggtcacccgacagcag
atcgaggatcagggcctcaccgacaccggcGccatcctggcgaccgcgcc
agggatttccgtcacgcgcagcgacagcaaccgctattcaTtctcggccc
gcggcttcaccatcgacaacttccagtttgacggcctggtatcgcccatc
Ctgagccaatggaactatggttcgaccgatatggacgccgccatctacga
tcacgtggaaAtcgtacgtggcgcccacaggcctgatgacaggctcgggca
atccttcagccgccgtgaacTtcgtgcgcaagcgtcccttgcgtgagttc
gcggctacgttcaatgcgagtgtcggcagcTgggactatgtgcgcggcga
tgccgacatctccgtgcccatcacggaagacggcagaataCggtcacgct
tggtggccgcctacagtcagggcgacagctatgtgcactttttagatacg
Cgccggcgcacattctatggcgtggtcagcgccgatctgacgccggatac
ggtgctgacgAccagcgtggagtaccagcacaaccacagcaatgggtttg
gcagcggctttccgctgttcTatagcgacggttcgcgcaccgatttcaac
cgctcggtggccaacaacgctccctgggccCggcaggataccgaagccac
cacctatttcgtggacctcacgcaccgcttcaccaatgacTggaagctgc
gcgcggcctatagccacactgatggccgctatcccatgaaacatgtgtac
Cggggcggctaccccgatcgccatactggcatcatcgctgccccccctgc
attttccaacTacgacggcaacctcgatcgggatgacatccatttttcct
tgtccgctcctttcgaggccTtcggcctgcgccacgaagttgccctgggc
tggatgagcatcgacaaccatagcgacatcCagcgatacgcaatggtcgg
accggccccagccatcggcagcttcttcgactggcgccgcGcccacatcc
aagagcccagctgggccgacacgctgtcgcccgccgacgacgtgcgcacc
Aagcagaccggcgcctatctggtcggccggtttgcactagccgaacccct
gcacctcatcGtgggcgaccgttggagcgactggaaaaccaaacagatgt -continued attttggctcgcgccgcgaaTacaggatcaagaatcagttcacccccctat gccggtctgacctacgacatcaacgacaccTacacggcgtacgccagcta tacggagatcttccagccgcagaacgcgcgcgacaccagcGgcggcattc ttcctcccatcaaaagcaagagctatgagctgggtctgaaggcagcctat Ctggagggacggctcaatacctccgccgcgctctttcagacgcggcagga taacctggccCaggtcatcccgggctcatccattccgggctttccgaaca tgcaggcctcacgtgccgccTccggcgccaaggtcgaggggatagacctg gaggccagcggccagatcctgcccgaccggAacatcggcgccagctatac acacttcaccaccaaggacgccagcggcaaccccatcaacAccaatcatc cgcgcagcctgttcaagctctacaccacgtaccgcctgccgggcgccctg Caccggcttaccgtgggcggcggcgttgactggcaaagtcgcatgtacca ggccgcagccAgtccgcgcggcaatgtcgaagtcgaacaggacagctacg cactcgtgagcctcatggcgCgcttcgactttaacaaaaaactgtcggca acactgaacgtgaacaatctgttcgacaaaAagtactacgatcagatcgg cttctacagccagggttggtggggtgcgccacgcaatgtaatgctcaact tgcgggcgcagtattga SEQ ID NO:12 polypeptide sequence of Orf6
LPAISVTGREISDLTEGTNAYTTEAMSTATGLTLSPRETPQSVSVVTRQQ

IEDQGLTDTGAILATAPGISVTRSDSNRYSFSARGFTIDNFQFDGLVSPI

LSQWNYGSTDMDAAIYDHVEIVRGATGLMTGSGNPSAAVNFVRKRPLREF

AATFNASVGSWDYVRGDADISVPITEDGRIRSRLVAAYSQGDSYVHFLDT

RRRTFYGVVSADLTPDTVLTTSVEYQHNHSNGFGSGFPLFYSDGSRTDFN

RSVANNAPWARQDTEATTYFVDLTHRFTNDWKLRAAYSHTDGRYLMKHVY

RGGYPDRHTGIIAAPPAFSNYDGNLDRDDIHFSLSAPFEAFGLRHEVALG

WMSIDNHSDIQRYAMVGPAPAIGSFFDWRRAHIQEPSWADTLSPADDVRT

KQTGAYLVGRFALAEPLHLIVGDRWSDWKTKQMYFGSRREYRIKNQFTPY

AGLTYDINDTYTAYASYTEIFQPQNARDTSGGILPPIKSKSYELGLKAAY

LEGRLNTSAALFQTRQDNLAQVIPGSSIPGFPNMQASRAASGAKVEGIDL

EASGQILPDWNIGASYTHFTTKDASGNPINTNHPRSLFKLYTTYRLPGAL

HRLTVGGGVDWQSRMYQAAASPRGNVEVEQDSYALVSLMARFDFNKKLSA

TLNVNNLFDKKYYDQIGFYSQGWWGAPRNVMLNLRAQY

SEQ ID NO:13 polynucleotide sequence of Orf7
Atgaagttctactcttcccatccgatgcccgagtcgctcgcggctgcgat cgcagtgcctCtgttgggcctgctgccggcggcgcaggccgcgtccacgg cggtccagctgccatccgtcAcggtcgagggcgagtactcgtcctatcaa ccggaaagcgcccagtcgcccaagttcaccGcgcccctggcggacacgcc gcgcacggtgcaggtcatccctgagcggctcatccaggacCagggggcca gcgacctcgaagcggtactgcgcaatgcgccagggatatcgatgaccgcc Ggcgaaggcggccgtccggccagcgacctgccgttcatccgcggccagaa ttcggccagcAgccttttttgtcgacggcctgcgcgatcccagcacgcaat cgcgcgataccttcaacctgGaacaggtcgacgtcgtcaaggggcccgat tcggtattttccgggcgcggcggcgccggcGgaagcatcaacctcgtcac caagacgcccaggaaccaggatttcaccgaagtccaggccGgcatcggga cggccgagacctaccgaggcaccatagacggcaactgggtgctgggcgag Aacacggcgctgcgcctcaacctgctgggcaccagggacaccgtgccggg ccgcgacaagGcggtcgagttcagccgcgtgggtatcgcgccatcgctgc gcctgggcctgagcggccccAcccgcgtgacgctgggcctgtaccactat cgccaccggcgggttcccgattattcgattCcgtacgatccgcgcaccgg cacgccgatcaccgagaccatcggcgtcagccgccgcaacTtctacggcc tggtgcggcgcgactccggcgataccgaggactacgccgccaccgtcaaa Tgggagcacgacctcgccaatggcttcaaggtggagaacctggcgcgcta ctcgcgtgccAcggtggagcagatcaccaccatgcccgaactgaaaaccg ccgatctggccaaggggctgGtgtaccgcaatctgcgcgccagctaccag gtcaacgacagtttcgccaaccgcaccgacCtgcgcggtacattcgacac ggggcagtggcgccataccttcgatctgggcggggagttcGccaccagcc ggcgcagtcgcgaccgctacaagcaagaaatccccgacgccgccagtcct Tgctcgcccgtgacggacggcaacaatcccgccctgtgcgcctcgctccg ggatccggatCcgcacgtggatttcccgggaacggtgcggcgcaaccata acccggcccgctaccacaccGacatcctgtccctgtacggtttcgacacc atcgccttcgacgagcagtggcagctgaatCtcggcctgcgctgggacca ctacaagaccagcggacgcaacctgccggtacgaggcgccAagccgcccg tctacgagcgtgccgcgcgcaccgacaacctgttcaactaccagctcggc Ctggtctacaagcctcgtccggacggctcggtgtatgcgagttacggcac ggcgtccacgCcgtcggccgtgtccgactacgccccggcggacagcatct ccggcacaagccagcagctcAagccggagcgcagcgaggcgatcgagatc gggaccaagtggcaggtgctggaccggcggCtgctggtgacgggcgccat gttccgcgagacgcgcaagaacaccagcatcgaagtcgccGaaggcctgc gcgcaccagccggcaagagccgcgtcaccggcatggagccgggcgtggcg Ggcagcctgacgccgcgctgggacgtctacggcggctacgcgctgctcga cagcaagctgGtcagggccagccataagagcggggcgcaaggccagccgc tgcccagcgcgccccggcacGcattcagcatctggagcacctacaagctg ctgccggaactgaccgtgggggccggcgcgTtctatcgcagcaaggtcta tggcaacgcagatgccggctacaacaaggacggcacgcccAaggcgcgct gggtgccggcgtactggcgcttcgacgccatggcggcgtaccagcttaac Aagcaccttacggcccagttgaacgtctacaacctgctcgacaagaccta ttacgccaagAcctaccgcagccattacgcggcgctgggcccggggcggt ccgccatgctgacgttcaagctgagctactga SEQ ID NO:14 polypeptide sequence of Orf7
MKFYSSHPMPESLAAAIAVPLLGLLPAAQAASTAVQLPSVTVEGEYSSYQ

PESAQSPKFTAPLADTPRTVQVIPERLIQDQGASDLEAVLRNAPGISMTA

GEGGRPASDLPFIRGQNSASSLFVDGLRDPSTQSRDTFNLEQVDVVKGPD

SVFSGRGGAGGSINLVTKTPRNQDFTEVQAGIGTAETYRGTIDGNWVLGE

-continued

NTALRLNLLGTRDTVPGRDKAVEFSRVGIAPSLRLGLSGPTRVTLGLYHY

RHRRVPDYSIPYDPRTGTPITETIGVSRRNFYGLVRRDSGDTEDYAATVK

WEHDLANGFKVENLARYSRATVEQITTMPELKTADLAKGLVYRNLRASYQ

VNDSFANRTDLRGTFDTGQWRHTFDLGGEFATSRRSRDRYKQEIPDAASP

CSPVTDGNNPALCASLRDPDPHVDFPGTVRRNHNPARYHTDILSLYGFDT

IAFDEQWQLNLGLRWDHYKTSGRNLPVRGAKPPVYERAARTDNLFNYQLG

LVYKPRPDGSVYASYGTASTPSAVSDYAPADSISGTSQQLKPERSEAIEI

GTKWQVLDRRLLVTGAMFRETRKNTSIEVAEGLRAPAGKSRVTGMELGVA

GSLTPRWDVYGGYALLDSKLVRASHKSGAQGQPLPSAPRHAFSIWSTYKL

LPELTVGAGAFYRSKVYGNADAGYNKDGTPKARWVPAYWRFDAMAAYQLN

KHLTAQLNVYNLLDKTYYAKTYRSHYAALGPGRSAMLTFKLSY

SEQ ID NO:15 polynucleotide sequence of Orf8
Atggagaagccgttgaaatccctggactcgtattcagcgagcacgctcgc caactcgctgGccgccgccattgcggtgccggccctgtgcctgatgcccg gtgctcaggcacagaccagcGcgggcgttacccaattggcgccggtgcag gtagagggcgaagcgtcccccctatcaggccAccaccgtccagtcgtccaa gatgacggcgcccttgctggatacgcccaggaccgtgcagGtcgtgccgc agcaggtcatccaggaccaggccgccaccaatctgcaggacgtgctgcgc Aactcgccgggcatcaccatgggcgccggcgagggcgggcgcgccggcgg cgacctgcccAtcatccggggccagaatgcggcgggcagcatcttcgtcg acggcgtgcgcgaccccagcAcccagatacgcgatacgttcaacctggag caggtcgagatcatcaaggggcctgattcgGtctactccggccgcggcgg agccggcggcagcatcaacctggtcagcaagacgccgaagGcgcgcgact tcgccgagggctcggtgcagatcggcaccgacagcaattaccgcgccacc Gccgacggcaactggctgctgggcgacaacgccgccttccgcctgaacct gatgggcaacAagggcgacgtgccgggccgcgaccatgcggtcgatttca gccgctggggcgtggcgcccAccctgcaactgggcgtgggcacgcccacc cgcatcaccctggggtactaccactaccagGatgacagcatgcccgatta cgcgatcccgtacgatccgaagtcggggcagccggtcaccGagacccagg gcgtcagccgcaagaatttctacgggctgaccggccgcgacttcatgaag Tcgcgcgacgacgtggccacgctggccatcgatcacgatttcagcagcaa gctgcgcctgCgcaacgtcacccgctacgggcgctcggtgaccgactacg ccgccaccaatccggatgacAgcaagggcaacgtgcccaacgggctggtg taccgggcgctgaaggcgggctactacaccAacaagacgttcaccaacca gaccgacctgagcggcgaattcgagacgggcagcctgcagCactcgttcg acgtgggcttcgagtacagcaacatcaagcaggacaaggactcgtatacc Cagactatcgccaagggcgcgatgccttgcaaggtgggcgccaacgatgc cagcaatccgGccttgtgcacctcgctgtgggatccggatccgcatgact attatcccggccacctgtcgCgcaacgacaacccggcccgctattccacc gacacgatcgcgctctacggcttcgacacgAtcaagttcaacgagcaatg gcaggccagcgtcggactgcgttgggacaattaccgcgtaAgcggcagca atatcgcccgcggccgcaacgatcccgccagcacgccggcgttctacagc Accagccgcgaagacaatctgttcaattaccagctgggcctggcctacaa gccggtgcccAacggcacgatctacgcctcgtatggcacctcgtcgacgc cgtcggccgtcgccggctcgAacgtgagcgacgccgtgacggtgagcaac gagtcgctggcgccggagaaaagccgcaccGtcgaggtcggcaccaagtg gcaattgttcgacgaccgcctgaccctgtcgggcgcgttgTtccaggaca tccgcaagaacaccagcgtggccgtgtcggcgaccgaaacggagcagatc Ggcaaggccaaggtgcgcggcatcgaactgggcttctcgggcagcatcac gcccaagtggAacgtctacggcggctataccttcatggacagcgaactgg tcgagggcgcctacaacagcGgcgcggtgggccaggacctgcccaacacg ccgcgcaatgccttcagcctgtggaccaccTacaagctggtgcctcagct gaccgtgggcggcggcgcctattacgtggacaaggtatatGgcaacgcgg acaacggtcgcaatgccgacggcacgccgaaggcgcgctgggtaccgtcg Tactggcgcttcgacgccatggccgcgtacgagttcaacgaccacctgac cgcgcagctcAacgtgatgaacatcttcgacaagacgtactacaccaagg cctacgcggcgcactacgcggcgctgggcacgggccgcgccgcggtgctg tcgttcaatatcaagtattga SEQ ID NO:16 polypeptide sequence of Orf8
MEKPLKSLDSYSASTLANSLAAAIAVPALCLMPGAQAQTSAGVTQLAPVQ

VEGEASPYQATTVQSSKMTAPLLDTPRTVQVVPQQVIQDQAATNLQDVLR

NSPGITMGAGEGGRAGGDLPIIRGQNAAGSIFVDGVRDPSTQIRDTFNLE

QVEIIKGPDSVYSGRGGAGGSINLVSKTPKARDFAEGSVQIGTDSNYRAT

ADGNWLLGDNAAFRLNLMGNKGDVPGRDHAVDFSRWGVAPTLQLGVGTPT

RITLGYYHYQDDSMPDYAIPYDPKSGQPVTETQGVSRKNFYGLTGRDFMK

SRDDVATLAIDHDFSSKLRLRNVTRYGRSVTDYAATNPDDSKGNVPNGLV

YRALKAGYYTNKTFTNQTDLSGEFETGSLQHSFDVGFEYSNIKQDKDSYT

QTIAKGAMPCKVGANDASNPALCTSLWDPDPHDYYPGHLSRNDNPARYST

DTIALYGFDTIKFNEQWQASVGLRWDNYRVSGSNIARGRNDPASTPAFYS

TSREDNLFNYQLGLAYKPVPNGTIYASYGTSSTPSAVAGSNVSDAVTVSN

ESLAPEKSRTVEVGTKWQLFDDRLTLSGALFQDIRKNTSVAVSATETEQI

GKAKVRGIELGFSGSITPKWNVYGGYTFMDSELVEGAYNSGAVGQDLPNT

PRNAFSLWTTYKLVPQLTVGGGAYYVDKVYGNADNGRNADGTPKARWVPS

YWRFDAMAAYEFNDHLTAQLNVMNIFDKTYYTKAYAAHYAALGTGRAAVL

SFNIKY

SEQ ID NO:17 polynucleotide sequence of Orf9
Ttgcatactcgcacgccacagcggcagcgcccggtcgcgccgcgcctgct gcatctatcgCtggccgcctcgctggcggccggcgccgcccaggcgcaga ccgccaccgaagccaccacccCtgcccaccgtgcaggtcaccggcaggggc gagaccgccaccggcccggtcgacggctatgccgccacgcgcagcgccac cgccaccaagaccgataccccgctgtcggaaaccccgcaggccgtcacgg tgatcccgcgcgagcagatcatcgaccagggcgcgcagaacgtgcaggac accatgaactacgccgcgggggtgcgccccaacgcctatggcgtggacaa -continued ccgcggcgactacgtgcgggtgcgcggggtggagccggtccagtatctcg acggcctgaagcagttcttcaactacaacaatccgcgcaccgaggtctac gggctcgagcgcgtcgaagtcctgcgcggcccggcctcgatgctgtacgg ccagggcagcaccggcggcgtggtcaacctcgtcagcaagcggccgcagc ccgaggccatgcgcgagatcggcgtgaccgtgggcaaccacaaccgcaag gagatccaggccgatctcaccggcccgctgaccgaggacggcacctggct gtaccaggtggtggccctcggacgcgacagcgacacgcaggtccagtaca ccaaggacgaccgcatgatgctcgcgccgtcgctgacctggcagcccagc gccgccacctcgctgacgctgcaggcctactggcagaaggacaagtcggg cacgacccaggccttcctgccctggagcggcacggtcagcggcaacccca acggccgcatccccacccgccgcttcaccagcgaacccggcttcgaccgc tacgacaccgagcaattcagcgtgggctggcagttcgagcacaagttcaa cgacaactggaaagtgcgccagaacctgcgccacacatccagcaaggtcg actacagcacgctgtatccggcggtctacggcaaccccgacaaccccttc atcgacgccgaccagcgcgtggtcaatcgctacctgtacatcaagaaccc gcgcatgcgttccttgctggccgaccagaacctcgaaggcaaggtgaact ggggccgcgcgccgaacataccctgctgatgggcgtggactacagccgctat cgcgagaccggcgagaccggcagcgggttcggcgcgccgctggacctgta ccagccggtctacggcaccctgcccgactatgccatgtcggacgtgccca agaacaagcagcagcagatcggcgtctacctgcaggaccagatcaagttc gaccgcaactggatcgtggtggcgggcctgcgccacgaccgcgtcgccaa cagcgtcgagggcgccgacaaggaaaccgacaacgccaccaccaagcggc tgggcctgatgtacgccgccgacaacggctggtcgccctacctcagctac agcgagtcgttcaccccccatcgccggcaccgacaacagcggcaaccgctg ggtgccgatgcgcggcaagcaatgggaagcaggcctgaagtacatgccgc aggacaccggctatgaggccaccctggcggcctacgacctgcgcgagcgc aaccgccagaccaacgacccgtccgatcccaccaaccaggtgcagaccgg caagaccaagacgcgcggcatcgaactggaattccgcggccgcgtcacgc cgcagatggatgtgatcgccaactacaactacaccgacatcgacccgcag ctcgaaggcctgcccaagcacacgttctcgctgtggagcaaataccggtt cagcgtgggcgatgtgcatggctttgccgccggcgccggcgtgcgctacc tgaacgcgtttcgcgacgggtccgcgcccgagaccggctcggtggccctg ttcgacgccatgctcagctacgacaccggttcgtggcgctatgcgctgaa cgtcgccaacatcgccgacaagacctacgaggtggtgtgcctgcggcgcg gcgattgcttctacggccagcgccgcacggtcaccctgagcgccatgtac cgcttctag SEQ ID NO:18 polypeptide sequence of Orf9
LHTRTPQRQRPVAPRLLHLSLAASLAAGAAQAQTATEATTLPTVQVTGRG

ETATGPVDGYAATRSATATKTDTPLSETPQAVTVIPREQIIDQGAQNVQD

TMNYAAGVRPNAYGVDNRGDYVRVRGVEPVQYLDGLKQFFNYNNPRTEVY

GLERVEVLRGPASMLYGQGSTGGVVNLVSKRPQPEAMREIGVTVGNHNRK

EIQADLTGPLTEDGTWLYQVVALGRDSDTQVQYTKDDRMMLAPSLTWQPS

AATSLTLQAYWQKDKSGTTQAFLPWSGTVSGNPNGRIPTRRFTSEPGFDR

YDTEQFSVGWQFEHKFNDNWKVRQNLRHTSSKVDYSTLYPAVYGNPDNPF

IDADQRVVNRYLYIKNPRMRSLLADQNLEGKVNWGRAEHTLLMGVDYSRY

RETGETGSGFGAPLDLYQPVYGTLPDYAMSDVPKNKQQIGVYLQDQIKF

DRNWIVVAGLRHDRVANSVEGADKETDNATTKRLGLMYAADNGWSPYLSY

SESFTPIAGTDNSGNRWVPMRGKQWEAGLKYMPQDTGYEATLAAYDLRER

NRQTNDPSDPTNQVQTGKTKTRGIELEFRGRVTPQMDVIANYNYTDIDPQ

LEGLPKHTFSLWSKYRFSVGDVHGFAAGAGVRYLNAFRDGSAPETGSVAL

FDAMLSYDTGSWRYALNVANIADKTYEVVCLRRGDCFYGQRRTVTLSAMY

RF

SEQ ID NO:19 polynucleotide sequence of Orf10
Atggtttacgcttgcgatcagggcgcccgccgcgcccgtcccgcgccgcc aaggcgccccCaaacggcactggccatgcgcggcgcgctggcggcatgcg cactggccggtacgctggcgGccgctcccgccgccgcgcagccgacggcg gcgcccgcatcggcgggcgcgcgcgcctggcacatcgacgccggcccccct gggcgaggccctggcgcgctttgccgaccaggccggcattaccctgctgt acgaccccgccgcggtgcgcggccgcgccagcgccggcctgcaaggcgtg tactcggtgcccgacggcctggcgcgcctgctcgatggcagcggcctgga cgcgcgccagcgcggcgccggcacctacgtgctgcaggcgctgcccgccg gcccggtcgcccagctggcgccggtcaccatcgaggctgacggcgtgcgc gccgatcccgcctgggcccgcaccgccacgcgccgcgagctcgacgcgcg ccaggtgctcgactggagcgatatcggcaagcgcgtcgatcccggcgtca actacaaccgccgcaccaagagcatcaacatccgcggcctggacgaaaac cgcgtggtcacgcgcatcgacggcatccgcctgccctggctcgacgacgg cgcgcgcggcatccagggcgggctgaacgcggtggacttcaacaccctgt cgcgcctggacgtcgtgcgcggcgccgactccagcgcggccggctccggc gcgctgggcggcctggccgacctgcgcacgctcgaacccgccgacctgct gcgcgacgggcgccgcttcggcgcgctggccaagtccgactatgactcgg ccgacgccagctggggcctgaacgcggccctggccgggcaggtccacgac gacaccagctggctgttgcaggcgggcacccgcaatgggcacgacctgga caaccgcgccgacacgggcggctacggcagcaagcgcagccagcccagcc ccgaggactacgcccagaacaacttcctgctcaagctgcagcagcgcatc gacggcggccatcgcctcggcctgacgggcgaatacttcaagcgccgcgc cgacctcgaccagatgtaccagcagggcgccggcaccagctaccagtacg gcgccaaccgcacccacgaggaaaccacgcgcaagcgcgtctcgctggac taccagtacaacgccccgcaggccggcgccgcgatcgacagcgcccgggc catggtgtattggcagcggctgcggctggacagctcgcaggacgcccgcc gcacgcgcgacgggcgcgcctacgcccgccccggcgacccgtacttctac ggctaccccagcggcccctacgggcgcagcaactcgatccaggaatcgat cctcggcgtcaacggcgagctctccagccgcttcgaaggcatggtgtcgc -continued agcgcgtgacgataggcggcgaatggtacggcaaccgcaccgagcagtac tcggacggctacgacaactgccccgccatcccgcccggcacgcccgcgcc gatggggccgcgcctgtgcgacatgctgcataccaaccaggccgacatgc cccgggtcaagggcagccagtgggccatctgggcgcaggacgaaatcgcc ttcgccgacgggcgctacatcctgaccccgtcactgcgctacgaccatta cgagcagaagccgcagcaaggcggcggctaccagaacaaccccaacgccg gcgcgctgccgccgtcgtcgtcggggggccgcttctcgcccaagctgctg ggcacctggaaggcgcgcgaggcgctgacgctgtatgcgcaatacggctt cggctaccgggcgccgtcggccaccgagctgtacaccaactacggcggcc cgggaacctatctgcgcgtgggcaatccctccttgaagcccgagaccagc aagggctgggaactgggcgcccgcctgggcgacgaccagttgggaggcgc cgtatcgctgttcgacaaccgctaccagaacttcatcgacaagaacgtgc cgctgggcaagggttcgccgcaatggcagccggcctgggacggccagtac ccgctgggcgtcaccgggctggccaaccgggcgcgcgtgcgcatctatgg cgccgaagcctcggcgcactggcggttcgcgcccaactggcgcacctggg gctcgctggcctgggccgtgggcaaggacgaaaacaccggccagcacctg aattcggtgccgccgctcaaggccatcctcggcctgggctaccagcgcga cgaatggggcatcgacgccatgctgacggccgccacgcgccgcgacgacg tgcaataccccgaggcctccgccagcgcgcgctacgccgatttccaggcc ccgggctacggcgtggtggatctgtccgcctactggcgcccggccgccgt caagggcctgcagctgcaggcgggcgtgttcaacctgttcgacaagaaat actgggaagccatcaacgtgcccacggcgggtgccattgcgattccgcga ccgttagactggtacaacgagccaggccgcagcgtgcgcgtatcgttgac ctaccagtattga SEQ ID NO:20 polypeptide sequence of Orf10
MVYACDQGARRARPAPPRRPQTALAMRGALAACALAGTLAAAPAAAQPTA

APASAGARAWHIDAGPLGEALARFADQAGITLLYDPAAVRGRASAGLQGV

YSVPDGLARLLDGSGLDARQRGAGTYVLQALPAGPVAQLAPVTIEADGVR

ADPAWARTATRRELDARQVLDWSDIGKRVDPGVNYNRRTKSINIRGLDEN

RVVTRIDGIRLPWLDDGARGIQGGLNAVDFNTLSRLDVVRGADSSAAGSG

ALGGLADLRTLEPADLLRDGRRFGALAKSDYDSADASWGLNAALAGQVHD

DTSWLLQAGTRNGHDLDNRADTGGYGSKRSQPSPEDYAQNNFLLKLQQRI

DGGHRLGLTGEYFKRRADLDQMYQQGAGTSYQYGANRTHEETTRKRVSLD

YQYNAPQAGAAIDSARAMVYWQRLRLDSSQDARRTRDGRAYARPGDPYFY

GYPSGPYGRSNSIQESILGVNGELSSRFEGMVSQRVTIGGEWYGNRTEQY

SDGYDNCPAIPPGTPAPMGPRLCDMLHTNQADMPRVKGSQWAIWAQDEIA

FADGRYILTPSLRYDHYEQKPQQGGGYQNNPNAGALPPSSSGGRFSPKLL

GTWKAREALTLYAQYGFGYRAPSATELYTNYGGPGTYLRVGNPSLKPETS

KGWELGARLGDDQLGGAVSLFDNRYQNFIDKNVPLGKGSPQWQPAWDGQY

PLGVTGLANRARVRIYGAEASAHWRFAPNWRTWGSLAWAVGKDENTGQHL

NSVPPLKAILGLGYQRDEWGIDAMLTAATRRDDVQYPEASASARYADFQA

-continued

PGYGVVDLSAYWRPAAWKGLQLQAGVFNLFDKKYWEAINVPTAGAIAIPR

PLDWYNEPGRSVRVSLTYQY

SEQ ID NO:21 polynucleotide sequence of Orf11
Ttgcggccgggccggcggcgcgccgcgcgctgcccgtcatcgacatgccc gccggctgccGgcgcggcgccacaacgtgtgatcatgaaacagacttccc tttactacgccaccctgggcCtggtcggactggcgctggccgcgcccgcg cgcgcgcaggagcaatcgcttcccgtccaactcgcgccggtggtcgtgca tggcgcgcccgaggccaacggcccgctgaatctcgacgcggtcgacagca ccggcagccgcctgggcctgaccctgcgcgagacgcccgccccggtgacc gtcatcaaccgcgagcagatcgaggcgcgcggcgcgctcgacacgcagga aatcgcccgcggcatcgtcggcgtggacaatgcctcgccgcccggctcgg ccggctcggtgagctaccgcggtttctcgggttcgcaggtcagccagttg ttcaacggcatttcggtgcagtacgacgtggtcgccgcgcgtccgatcga cagctggatctacgaccgcgtcgaagccatcggcgggccgtccagcttcc tgttcggcgcgggcgcggtgggcggcgccatcaactacgtgaccaaggtg gcgcagcgcgatacgttctacgacggccagctgcgcctgggttcgtacgg cgcgcgccaggcatccgtgggccttaaccggcaattggccggcgagccgg gcgggcgcggccagtacctgcgcatcgacgccaacgccaacgcgagcgac ggctgggtcgacggcaatcgctcgcacgccgagcaggtggcggcctcgct gctgtcggacctgggcgaacgcgtgacccatacgctggcgctggagtacc agcacgagatggtgcaccggccttactggggtacgccgctgaccaccgac ggcgacggcgtggtgcgcggcgaaggccacatccgcggcgggacgcgctg gaagaactacaacgtcgacgacggccggtacgagcaatcggtgtggtggc tgcgttcgctgaccgaatggcaggccagcgaccgcctgagtttccgcaat acgctgtactactatcgcgccgatcgcgatttccagaacctcgagaccta ccgctacaacccgggcaacagccaggtgctgcgctccggcgcgctgctgc agcgccacgagcagcgcctgctgggcaaccgcatcgaaggcctgtaccac ggcagcctgggcggcctgcgcagcgactggtcgttcggcgccgactacag cgtcaaccgccagacgcgctaccccaccagcgtggccgggcaagtcgata gcgtggacccgtacgagttcgacccgggcgagttctacgacattccgggc atgcggcgcggccacgtgcccgaccgcgacaacaaggtgcgcacgctggc cttcatgctggaaaaccgcaccgaagtgggcggcggggtcgcgctggtga cggctctgcggcacgacatcatcgacctggacctgaccaaccggcgcgcg gccagcgcggcttcgcccgggcacgcctcgcgccgctacaacccgaccac ggggcgcgtcgccgtcaattgggaggtcagtcccggcgcgaccctgtacg cgcaatacgccaccgccgccgacccgccttccggcgtactgtcgaccgcg accttcgccgatgtgctgaacaacgacaagctgaccaccggcacccaggt cgaggccggcggcaagttcgcgttctgggacggccgcggcacggcgaccg tggcggtctacgagatcaagcgcaagaacctcgccacgcccgatcccctc aaccccggcagcagcctgccggtgggcagccagtctgcccgcgggctgga gctggccggcggattgcagttgacgcgcgccttgtcgctgcaggccaacc -continued tggcgctggtcgacccccgctatgacgatttctcgcagaacgtcggcggg gtggcggtctcgcgcaacggcaaggtgccggtcaacacgccgcgccggct ggccaacgtgtggctggactacgccttcgcgcccgactggcgcgccagcc tggcggcgcgccacgtgggcaagacctatgcggacgcggccaatacggtg tgggcgccggcctataccgtgttcgacgcggcgctgtcgcatcgcatcga ccgccatttcagcgtgacggcgcgggtgcgcaacctgaccgacaaggtct atgccgccagcgtgaccggcgcgcccatgcattacctgggcgcgccgcgc agcgtcgaactcgcgctgcaggcgcgcttctga SEQ ID NO:22 polypeptide sequence of Orf11
LRPGRRRAARCPSSTCPPAAGAAPQRVIMKQTSLYYATLGLVGLALAAPA

RAQEQSLPVQLAPVVVHGAPEANGPLNLDAVDSTGSRLGLTLRETPASVT

VINREQIEARGALDTQEIARGIVGVDNASPPGSAGSVSYRGFSGSQVSQL

FNGISVQYDVVAARPIDSWIYDRVEAIGGPSSFLFGAGAVGGAINYVTKV

AQRDTFYDGQLRLGSYGARQASVGLNRQLAGEPGGRGQYLRIDANANASD

GWVDGNRSHAEQVAASLLSDLGERVTHTLALEYQHEMVHRPYWGTPLTTD

GDGVVRGEGHIRGGTRWKNYNVDDGRYEQSVWWLRSLTEWQASDRLSFRN

TLYYYRADRDFQNLETYRYNPGNSQVLRSGALLQRHEQRLLGNRIEGLYH

GSLGGLRSDWSFGADYSVNRQTRYPTSVAGQVDSVDPYEFDPGEFYDIPG

MRRGHVPDRDNKVRTLAFMLENRTEVGGGVALVTALRHDIIDLDLTNRRA

ASAASPGHASRRYNPTTGRVAVNWEVSPGATLYAQYATAADPPSGVLSTA

TFADVLNNDKLTTGTQVEAGGKFAFWDGRGTATVAVYEIKRKNLATPDPL

NPGSSLPVGSQSARGLELAGGLQLTRALSLQANLALVDPRYDDFSQNVGG

VAVSRNGKVPVNTPRRLANVWLDYAFAPDWRASLAARHVGKTYADAANTV

WAPAYTVFDAALSHRIDRHFSVTARVRNLTDKVYAASVTGAPMYYLGAPR

SVELALQARF

SEQ ID NO:23 polynucleotide sequence of Orf12
Atgaaatcccgctcactccggcgctgcgccggtgtcctggcctgtgtcgc tccgttggccGgccacgcccaggccggcgccgccgccggccaacccatcc ccgaactcgatccggtcgtcGtcaccgccgcgcgatcgccccagctgctc aagaatgtgctggccgacgccagcgtgatcgagcgcgatacgctggcgcg cgccggccagtccagcctggccgaagtgctggcgcagcagcacggcatcg aattcgccgacagcggcggcccgcaaagcgtcaccagcctgttcatgcgc ggcgccaacagcaaccagaccctggtcctgctcaacggccagcgcatcaa caacgccaacggcggcggcattgcgctcaacgcgctgccgccggaagcca tcgaacgcatcgagatcatgcgtggcgcggccagcagcctgtacggggcc gacgcgatcggcggcgtgatcaacatcattacccgcgagccgggcgacaa ggcgctgtcggcctatgccaacgccggttacggcacctacggcaccagcc gctacgacgccggcgtctcgggcgcggccgacggcttcagctacagcctg tccaccggctatggccagagccatggcttcaacgccaccaaccgccgctc gttctcgtacaacccggacaaggacagctactaccagaactacgccaccg gcacgctgggctacgaatggcggcccgagcagaaagtggtggcgcaggtc -continued taccgcagccgcatcaacggcggctacgacgcctcggcctcgtacgacta caacgaccgctacatccaggacctgcaggcctattcgctggccagcgaaa accgcctgacccgctactggaagagcacgctgcgcgccggctatgtggaa gacaagaacgattcgcgcgccgaaggcatgttcgaagacaacaacacgcg cttccggacccgccagatgcagtacctgtggcagaacgacttcaccctgg ccgccggccagacgctgacgctggcctacgagcacctggaccagcgcgcc gacggccagatgagcaccgccaccggcatcggcaactacaccgagacgcg ccgccacgtgaactcgtacaccggcgtctacctgggcgatttcggccgcc accatgtgcaggccagcctgcgcaacgacaacaactcgcagttcggcagc cacaccaccggcggcctggcctacgggttcgacctgacgcccaacctgcg cgccaccgtggccgccaacacgggctttcgggcgccgtcgttcaacgatc tgtacacgccgaccagcgcgttcggctatcgcggcaaccccgacctcaag ccggaagagtcgcgcaacgccgagatcggcctgaaataccaggacgagga cagcgaactgggcgtggtgtattaccagacccgcatcaagaacctgatcc aggtgaccgaggacttcagcacggtcgagaacgtcggcgcgcgcccgcctg caaggcttcaccatcagcggcgcgcaccgcttcggcaacacgcgcctgcg cgccagcctggacctgagcaacccgcgcaacgaagacaccggcaagcaat tgctgcgccgcgcccgcacggtgctgcgcgccggcatcgaccatcgcttc gaccgcctgctggtgggcgccgagtggtacgcctcggacgagcgctacga ctacggcttccccgaggaaaagcgcctgggcggctacggcctggtcaacc tgaccgcggcctacgacctgagccgcaacatgcaggtgcaggtgcgctgg aacaacgtgctcggccagcgctacaccttggccgacggctacaacacggc cggctcgaacgccttcgtcaacccgtcgtggcgcatgtag SEQ ID NO:24 polypeptide sequence of Orf12
MKSRSLRRCAGVLACVAPLAGHAQAGAAAGQPIPELDPVVVTAARSPQLL

KNVLADASVIERDTLARAGQSSLAEVLAQQHGIEFADSGGPQSVTSLFMR

GANSNQTLVLLNGQRINNANGGGIALNALPPEAIERIEIMRGAASSLYGA

DAIGGVINIITREPGDKALSAYANAGYGTYGTSRYDAGVSGAADGFSYSL

STGYGQSHGFNATNRRSFSYNPDKDSYYQNYATGTLGYEWRPEQKVVAQV

YRSRINGGYDASASYDYNDRYIQDLQAYSLASENRLTRYWKSTLRAGYVE

DKNDSRAEGMFEDNNTRFRTRQMQYLWQNDFTLAAGQTLTLAYEHLDQRA

DGQMSTATGIGNYTETRRHVNSYTGVYLGDFGRHHVQASLRNDNNSQFGS

HTTGGLAYGFDLTPNLRATVAANTGFRAPSFNDLYTPTSAFGYRGNPDLK

PEESRNAEIGLKYQDEDSELGVVYYQTRIKNLIQVTEDFSTVENVGRARL

QGFTISGAHRFGNTRLRASLDLSNPRNEDTGKQLLRRARTVLRAGIDHRF

DRLLVGAEWYASDERYDYGFPEEKRLGGYGLVNLTAAYDLSRNMQVQVRW

NNVLGQRYTLADGYNTAGSNAFVNPSWRM

SEQ ID NO:25 polynucleotide sequence of Orf13
Atgattccaccttgccgcttatccctgatcccggcgctggccgccatggc gctggcaggcGcctttcccgcgccgagcggggccgcgccggctgaattgg cgcccatcgcggtcatcggcGacgatcccgacgatccgcgggtattcgaa ggcagcaccgccacccgtaccgccacaccgctgcgggaggtgccgcagac -continued ggtcgacaccgtgaaggtgccggacgccctgaactatggcgcgcgcacgc
tgggcgaggcgctggccggcgtgcccaatgtcaccgacgccagcgatacc
cgcttcgacggcttgcgcatacgcgggttcgacgccggcagcgacttcta
cctggacggggtgcgcgatgacagccagtacgtgcgcgacctgcacaaca
tcgagcgcatcgaggtgctcaagggggccggccggcgttctgtacggccgc
ggcagccagggcggcatcgtcaatcgggtgagcaaggcgcccgggccggg
ccgcgcttccaccctcgaagtccggctgggcggcgaggactttcgcagcc
tgtacgccgacctgagcgcggacccttccgacacggtcagcctgcgcctg
aacgtgggcggcgagaatgcgggcagtttcaggcacggggtcagctcgcg
ccgccgcctggcgtcgcccgccttggcgtggcgcattacgccacggctcg
attggctggcgcagtacgaacacagccgctacgaccgcgtgcccgaccgc
ggcattccctcggtggacggccggcccgcgccggtcgggcgctcgaccgt
ctacggcgaccccgggcgcgacaatatcgacgatcgggtccaggtgctgc
gctcgcgcctgcgctaccgggcggccaatggatgggagctgcgccatacc
ctgtcgacgttccggctgcatagcgatttcgacaacacctatctgtccgg
ctggcgcgccgagaccgggctggtgcaacgccagcgctggcagcagcacc
tgcgcgcccggcatctttacaacgtcttcgaggccgagggcacgttcgcc
accggctggctcgaacaccgcttgctggccggcgtcgagctgggcagcca
gcatcgcgatccgacgctgcaccgcgcggccaccaaaggccccggcgcgc
agccggtgcccgggctggcgctgcaccaccccgacttgagccagcagcac
cacggccgcatggagcgcgccagcgatgcgcgtcaccgcgtgcgtacgca
aggctactacttgcaggatcaactgcgattgagcgagtcctggcaggtgg
tggcgggcgcgcgcctggaccggttcggggtgcgcacgcgcaatcgcctg
ctgggcctggaaggcagccgtggcgaccgcagtgtgagtccgcgcctggg
agtggtctggacgccctggccggcgcacgcgttctacgcgtcgtacagca
agactttctcgcccaccggcggcggcaccataggcatcacgccggacgcg
cggggcaacgccaatgatctgccgcccgaacatacgcgccagtacgaagc
cggggtcaagagcgactggctggacgggcgcctgagcaccatgctggccg
tctaccagctcgaactctacaaccgccgcacgcgcgcgccccacgatccc
acgcggatactcctgacgggcctgcagcgctcgcgcggcctggaaatgag
cggggcggggcggctagctgtgaagattcaatag SEQ ID NO:26 polypeptide sequence of Orf13
MIPPCRLSLIPALAAMALAGAFPAPSGAAPAELAPIAVIGDDPDDPRVFE
GSTATRTATPLREVPQTVDTVKVPDALNYGARTLGEALAGVPNVTDASDT
RFDGLRIRGFDAGSDFYLDGVRDDSQYVRDLHNIERIEVLKGPAGVLYGR
GSQGGIVNRVSKAPGPGRASTLEVRLGGEDFRSLYADLSADPSDTVSLRL
NVGGENAGSFRHGVSSRRRLASPALAWRITPRLDWLAQYEHSRYDRVPDR
GIPSVDGRPAPVGRSTVYGDPGRDNIDDRVQVLRSRLRYRAANGWELRHT
LSTFRLHSDFDNTYLSGWRAETGLVQRQRWQQHLRARHLYNVFEAEGTFA
TGWLEHRLLAGVELGSQHRDPTLHRAATKGPGAQPVPGLALHHPDLSQQH
HGRMERASDARHRVRTQGYYLQDQLRLSESWQVVAGARLDRFGVRTRNRL
LGLEGSRGDRSVSPRLGVVWTPWPAHAFYASYSKTFSPTGGGTIGITPDA
RGNANDLPPEHTRQYEAGVKSDWLDGRLSTMLAVYQLELYNRRTRAPHDP
TRILLTGLQRSRGLEMSGAGRLAVKIQ SEQ ID NO:27 polynucleotide sequence of Orf14
Atgaacacgctgcgacgcctgcgcatcctgggcgccgccgccacgctggg
cggccggccGccgcgcaggaggcgcccgccatgctggagccggtgcgca
tcagcggcacgcgcaccggcAcctcggtgctcgatacgcccgcgtccgtg
gacgtggtcgatggccacgagctgcgcgcgCgcaacctgcaggtcaacct
gtccgaaggcttggccggcgtgcccggactgcagctgcagAaccgccaga
attacgcgcaggacctgcagctgtcgatacgcggcttcggcgcgcgctcg
Accttcggcgtgcgcggcgtgcggctgtacgtggacggcatcccggccac
catgcccgacGgccagggccagacctcgaacatcgacatcggctcggccg
gccgcgtggaagtgctgcgcGgcccgttctcggccctgtacggcaattcg
tcgggcggcgtggtgcaggtgttcaccgaaCagggcagcgatccgcccga
ggcgacgggcagcgcggcggcgggcagcttcggcacctggCgctacggcg
ccaagctgcgcggcgccagcgcggcagacggcctggattacgtgctggac
Ttcaatcgcttcacgaccgagggctatcgcgaccacagcgccgcgcgcaa
gaacctgggcAacgcgcggctgggcctgcgcatggacgacggcagccgcc
tgacgctgagcgccaaccacGtggacctgaccgcgcaggatccgctgggc
ctgacgcgcgagcaattcgaggacgacccgCgcagcgcgccggtggccga
gcgcttcgatacgcgcaagaccgtgcgccagacccagggcGgcctgctgt
acgagcgcgccttcgacacgcgcaacgacctgcgcgtgatgctgtactac
Ggacaacgccgcaccacgcaataccaatccatcccggtggccgtgcagca
aagccccacgCaggccggcggcgtgatcgacctgggccgcgactacggcg
gcgccgacctacgctggaccTcgcgccagcaggtggccggcctgccgctg
accctgatcggcggactggcctatgacaccAtgaaggagcagcgccgcgg
ctacgacaactacaccggcccgcccgctgcgcccaccggcCatgggcgtc
aagggcgcgttgcggcgcgacgagaccaacacggtctacaacctggaccc
Gtacctgcaggcctcgtggcagttcgccgagcgctggacgctggacgcgg
ggctgcgctaCagcacggtgcgcttcgactcggacgatcattaccaggcg
ccgggcaacggcgacgacagCggacgcgccacctatcgcaaggccttgcc
ggtggcggcgctgcgctatgcggccaacgagaacctgagcctgtacgcct
cgtacggacgcggcttcgagacgcccacgctcaatga SEQ ID NO:28 polypeptide sequence of Orf14
MNTLRRLRILGAAATLGGPAAAQEAPAMLEPVRISGTRTGTSVLDTPASV
DVVDGHELRARNLQVNLSEGLAGVPGLQLQNRQNYAQDLQLSIRGFGARS
TFGVRGVRLYVDGIPATMPDGQGQTSNIDIGSAGRVEVLRGPFSALYGNS
SGGVVQVFTEQGSDPPEATGSAAAGSFGTWRYGAKLRGASAADGLDYVLD
FNRFTTEGYRDHSAARKNLGNARLGLRMDDGSRLTLSANHVDLTAQDPLG
LTREQFEDDPRSAPVAERFDTRKTVRQTQGGLLYERAFDTRNDLRVMLYY
GQRRTTQYQSIPVAVQQSPTQAGGVIDLGRDYGGADLRWTSRQQVAGLPL -continued TLIGGLAYDTMKEQRRGYDNYTGPPAAPTGHGRQGRVAARRDQHGLQPGP
VPAGLVAVRRALDAGRGAALQHGALRLGRSLPGAGQRRRQRTRHLSQGLA
GGGAALCGQREPEPVRLVRTRLRDAHAQ SEQ ID NO:29 polynucleotide sequence of Orf15

Atgaacatgtctctgtcacgcattgtcaaggcggcgcccctgcgccgcac
cacgctggccAtggcgctgggcgcgctgggcgccgccccggcggcgcatg
ccgactggaacaaccagtccAtcgtcaagaccggtgagcgccagcatggc
atccatatccagggctccgacccgggcggcgtacggaccgccagcggaac
caccatcaaggtaagcggccgtcaggcccagggcatcctgctagaaaatc
ccgcggccgagctgcagttccggaacggcagtgtcacgtcgtcgggacag
ttgtccgacgatggcatccggcgctttctgggcaccgtcaccgtcaaggc
cggcaagctggtcgccgatcacgccacgctggccaacgttggcgacacct
gggacgacgacggcatcgcgctctatgtggccggcgaacaggcccaggcc
agcatcgccgacagcaccctgcagggcgctggcggcgtgcagatcgagcg
cggcgccaatgtcacggtccaacgcagcgccatcgtcgacggggggcttgc
atatcggcgccctgcagtcattgcagccggaagaccttccgcccagccgg
gtggtgctgcgcgacaccaacgtgaccgccgtgcccgccagcggcgcgcc
cgcggcggtgtctgtgttgggggccagtgagcttacgctcgacggcgggc
acatcaccggcgggcgggcagcgggggtggcggccatgcaaggggcggtc
gtgcatctgcagcgcgcgacgatacggcgcggggacgcgcctgccggcgg
tgcggttcccggcggtgcggttcccggtggtgcggttcccggcggcttcg
gtcccggcggcttcggtcccgtcctcgacggctggtatggcgtggacgta
tcgggctccagcgtggagctcgcccagtcgatcgtcgaggcgccggagct
gggcgccgcaatccgggtgggccgcggcgccagggtgacggtgtcgggcg
gcagcttgtccgcaccgcacggcaatgtcatcgagaccggcggcgcgcgt
cgctttgcgcctcaagccgcgcccctgtcgatcaccttgcaggccggcgc
gcatgcccaggggaaagcgctgctgtaccgggtcctgccggagcccgtga
agctgacgctgaccgggggcgccgatgcgcagggcgacatcgtcgcgacg
gagctgccctccattcccggcacgtcgatcgggccgctcgacgtggcgct
ggccagccaggcccgatggacgggcgctacccgcgcggtcgactcgctgt
ccatcgacaacgccacctgggtcatgacggacaactcgaacgtcggtgcg
ctacggctggccagcgacggcagcgtcgatttccagcagccggccgaagc
tgggcggttcaaggtcctgacggtcaatacgctggcgggttcggggctgt
tccgcatgaatgtcttcgcggacctggggctgagcgacaagctggtcgtc
atgcaggacgccagcggccagcacaggctgtgggtccgcaacagcggcag
cgagccggccagcgccaacaccctgctgctggtgcagacgccactaggca
gcgcggcgacctttacccttgccaacaaggacggcaaggtcgatatcggt
acctatcgctatcgattggccgccaacggcaatgggcagtggagcctggt
gggcgcgaaggcgccgccggcgcccaagcccgcgccgcagccgggtcccc
agccgccgcagccgccgcagccgcagccggaagcgccggcgccgcaaccg
ccggcgggcagggagttgtccgccgccgccaacgcggcggtcaacacggg
tggggtgggcctggccagcacgctctggtacgccgaaagcaatgcgttgt
ccaagcgcctgggcgagttgcgcctgaatccggacgccggcggcgcctgg
ggccgcggcttcgcgcaacgccagcagctggacaaccgcgccgggcggcg
cttcgaccagaaggtggccggcttcgagctgggcgccgaccacgcggtgg
cggtggccggcggacgctggcacctgggcgggctggccggctatacgcgc
ggcgaccgcggcttcaccggcgacggcggcggccacaccgacagcgtgca
tgtcgggggctatgccacatatatcgccgacagcggtttctacctggacg
cgacgctgcgcgccagccgcctggagaatgacttcaaggtggcgggcagc
gacgggtacgcggtcaagggcaagtaccgcacccatggggtgggcgcctc
gctcgaggcgggccggcgctttacccatgccgacggctggttcctcgagc
cgcaggccgagctggcggtattccgggccggcggcggtgcgtaccgcgcg
gccaacggcctgcgggtgcgcgacgaaggcggcagctcggtgctgggtcg
cctgggcctggaggtcggcaagcgcatcgaactggcaggcggcaggcagg
tgcagccatacatcaaggccagcgtgctgcaggagttcgacggcgcgggt
acggtacacaccaacggcatcgcgcaccgcaccgaactgcgcggcacgcg
cgccgaactgggcctgggcatggccgccgcgctgggccgcggccacagcc
tgtatgcctcgtacgagtactccaagggcccgaagctggccatgccgtgg
accttccacgcgggctaccggtacagctggtaa SEQ ID NO:30 polypeptide sequence of Orf15

MNMSLSRIVKAAPLRRTTLAMALGALGAAPAAHADWNNQSIVKTGERQHG
IHIQGSDPGGVRTASGTTIKVSGRQAQGILLENPAAELQFRNGSVTSSGQ
LSDDGIRRFLGTVTVKAGKLVADHATLANVGDTWDDDGIALYVAGEQAQA
SIADSTLQGAGGVQIERGANVTVQRSAIVDGGLHIGALQSLQPEDLPPSR
VVLRDTNVTAVPASGAPAAVSVLGASELTLDGGHITGGRAAGVAAMQGAV
VHLQRATIRRGDAPAGGAVPGGAVPGGAVPGGFGPGGFGPVLDGWYGVDV
SGSSVELAQSIVEAPELGAAIRVGRGARVTVSGGSLSAPHGNVIETGGAR
RFAPQAAPLSITLQAGAHAQGKALLYRVLPEPVKLTLTGGADAQGDIVAT
ELPSIPGTSIGPLDVALASQARWTGATRAVDSLSIDNATWVMTDNSNVGA
LRLASDGSVDFQQPAEAGRFKVLTVNTLAGSGLFRMNVFADLGLSDKLVV
MQDASGQHRLWVRNSGSEPASANTLLLVQTPLGSAATFTLANKDGKVDIG
TYRYRLAANGNGQWSLVGAKAPPAPKPAPQPGPQPPQPPQPQPEAPAPQP
PAGRELSAAANAAVNTGGVGLASTLWYAESNALSKRLGELRLNPDAGGAW
GRGFAQRQQLDNRAGRRFDQKVAGFELGADHAVAVAGGRWHLGGLAGYTR
GDRGFTGDGGGHTDSVHVGGYATYIADSGFYLDATLRASRLENDFKVAGS
DGYAVKGKYRTHGVGASLEAGRRFTHADGWFLEPQAELAVFRAGGGAYRA
ANGLRVRDEGGSSVLGRLGLEVGKRIELAGGRQVQPYIKASVLQEFDGAG
TVHTNGIAHRTELRGTRAELGLGMAAALGRGHSLYASYEYSKGPKLAMPW
TFHAGYRYSW

SEQ ID NO:31 polypeptide sequence of Orf16

Atggcaggacaagcgaggggatggtacggcgcaggcggacgccacccaat
acattttcaaAtttcggcgggcgctgcgttgatgctgggcctgctggacg
tcgccggcgccgccgctgtcAcggcagcgcagcgaatagatggcggcgcg -continued gcgtttctgggcgatgtcgccatagcgacgAccaaggcgtccgagcacgg
tatcaacgtgactggccgcacggcagaggttcgggtgacgGgcggcacca
tacggacgagcggcaaccaggcccagggcttgcgggtcggcacggagaat
Gcaccggacaacaccgcgctgggcgcgtcggtctttttgcagaacctgat
catcgagactTccgggaccggggcattgggcgtctctgtccacgagccac
agggaggaggaggcacgcgcttgtccatgtccgggacgacggtgcgcacg
cgcggcgatgacagtttcgccctgcagctttcagggcctgccagcgccac
cttgaatgacgtggcgctggagacggccggccagcaggcgcccgcggtgg
tgctgtggcaaggcgcacagttgaacgcacaggggctggtggttcaggtc
aacggggcaggcgtttccgcgatacatgcgcaggatgccggcagcttcac
gttgtcgggctcggatattaccgcccggggcctggaagtcgccgggatct
atgtgcaggaaggcatgcaggggacgttgacgggtacgcgggtcacgacg
cagggcgataccgcgcccgccttgcaggtggaggacgcgggtacgcacgt
cagcatgaacggcggcgcgttgtcgacctccggcgcgaattcgcccgctg
catggctgctggctggcggttccgcgcagttccgcgatacggtattgagg
accgtcggcgaggcctcgcatggcgtggacgtcgctgcgcacagcgaggt
cgaactggcgcatgcgcaggtgcgggccgacgggcaaggggctcatggcc
tggtggtgacgcgaagcagcgcgatggtgcgggcgggttcactggtagag
agcaccggagacggcgccgcggcgctgctggaaagcgggcatcttacggt
ggacggcagcgtggtccatggccacggcgcggccgggttggaggtcgacg
gcgagagtaatgtgtccctgctcaacggcgcacgcctgtcgtcggaccag
ccgacggcgatcaggctgatcgaccctcggtcggtcctgaacctcgacat
caaggaccgggcgcagctattgggcgacattgcgccagaggcgcagcagc
cggacggttcgcccgagcaggccagggttcgtgtggcgctcgccgacggg
gggacgtgggcgggccgcacggacggcgcggtccatacggtgcgattgct
cgatcgtggcgtctggaccgtgacgggcgattcccgggtggccgaggtca
agctggagggcggcacgctggcgtttgcgccacctgcgcagcccaagggc
gctttcaagacactggtcgcgacgcagggcatttccggtacgggcacgat
agtcatgaatgcacatttgcccagcggcacggccgatgtgctggtggcgc
cgcagggattcggcgaccggcaggtgctggtggtcaacaacacggatgat
ggcaccgagagcggcgcgaccaaggtgccgctgatcgaagacgaacaagg
ccatacggcgttcacgctgggcaacatgggggggacgggtggacgcgggtg
cgcgccagtacgaattgaccgcgagcgaggcgcaggccgacaaggcccgc
acctggcagctgacgccgaccaacgagttgtccaccacggcgaccgccgc
cgtgaatgcgatggcgatcgcggcgtcgcagcgcatctggcaggccgaaa
tggacgtgttgctgcgccatatgagcggcctgcattcgatcgggtcgccg
ggcggattctgggcgcgcggcctgagccagcgccagaggctcgataccgg
ttacggaccctggcagaagcagaccgtcagcggaatagagctgggcctcg
acaggcgggtggccggcggcgcaacgacggcgtggtccgtcggcatgctg
gccggctacagcgagacccggcgcgatggcggcgcataccgcgccgggca
tgtgcacagcgcgcacgtcggcgcgtatgtctcctacctgaatgattcgg
gctcgtatgtggatggcgtggtcaagtacaaccgctttcggcatggtttc
gacattcgcacgaccgacctgaagcgggtcgatgccaagcaccgcagcca
cggcctgggcgcgttgctgcgcggcgggcgccgtatcgatatcgatggcg
gctggtatgtcgagccgcaggcttcggtggcgtggttccacgccggcggg
agccgctatgaggccagcaatggcctgcgcgtgcgcgccgacggcgcgca
ttcatgggtgttgcgcgccggggcggaggcgggccggcagatgaggttgg
ccaatggcaatatcgttgaaccctatgcgcgcttgggctgggcccaggag
ctgggggccgataacgcggtctacaccaacggcatcaggcatgtcacgcg
ttcgcgtggcggattcgccgaggcccgcgtgggggtgggcgccttgctgg
gcaagcggcatgccttgtacgccgactacgagtatgccaagggcgcgcgg
ttcgaggcgccctggaccttgcagctggggtatcgctacagctggtga SEQ ID NO:32 polypeptide sequence of Orf16

MAGQARGWYGAGGRHPIHFQISAGAALMLGLLDVAGAAAVTAAQRIDGGA
AFLGDVAIATTKASEHGINVTGRTAEVRVTGGTIRTSGNQAQGLRVGTEN
APDNTALGASVFLQNLIIETSGTGALGVSVHEPQGGGGTRLSMSGTTVRT
RGDDSFALQLSGPASATLNDVALETAGQQAPAVVLWQGAQLNAQGLVVQV
NGAGVSAIHAQDAGSFTLSGSDITARGLEVAGIYVQEGMQGTLTGTRVTT
QGDTAPALQVEDAGTHVSMNGGALSTSGANSPAAWLLAGGSAQFRDTVLR
TVGEASHGVDVAAHSEVELAHAQVRADGQGAHGLVVTRSSAMVRAGSLVE
STGDGAAALLESGHLTVDGSVVHGHGAAGLEVDGESNVSLLNGARLSSDQ
PTAIRLIDPRSVLNLDIKDRAQLLGDIAPEAQQPDGSPEQARVRVALADG
GTWAGRTDGAVHTVRLLDRGVWTVTGDSRVAEVKLEGGTLAFAPPAQPKG
AFKTLVATQGISGTGTIVMNAHLPSGTADVLVAPQGFGDRQVLVVNNTDD
GTESGATKVPLIEDEQGHTAFTLGNMGGRVDAGARQYELTASEAQADKAR
TWQLTPTNELSTTATAAVNAMAIAASQRIWQAEMDVLLRHMSGLHSIGSP
GGFWARGLSQRQRLDTGYGPWQKQTVSGIELGLDRRVAGGATTAWSVGML
AGYSETRRDGGAYRAGHVHSAHVGAYVSYLNDSGSYVDGVVKYNRFRHGF
DIRTTDLKRVDAKHRSHGLGALLRGGRRIDIDGGWYVEPQASVAWFHAGG
SRYEASNGLRVRADGAHSWVLRAGAEAGRQMRLANGNIVEPYARLGWAQE
LGADNAVYTNGIRHVTRSRGGFAEARVGVGALLGKRHALYADYEYAKGAR
FEAPWTLQLGYRYSW

SEQ ID NO:33 polynucleotide sequence of Orf17

Atgtatctcgatagattccgtcaatgtccgtcttccttgcagatcccgcg
ttccgcgtggCgcctgcatgcgctggccgcagctctggcgctggccggca
tggcccggctggcgcccgcgGcggcgcaggcgccgcagccgcccgtggcc
ggcgcgccgcatgcgcaggacgccgggcagGaaggagagttcgaccaccg
ggacaacacgctcattgcagtctttgacgacggcgtcggcAtcaatctcg
acgacgatcccgacgagctcggcgagacggcgccccccacgctcaaggac
Atccacatctcggtggagcacaagaacccgatgagcaagccggccatcgg
ggtgcgtgtcAgcggcgccggccgcgcgctgacgctggccggctcgacca
tcgatgccaccgagggcggcAttcccgcagtggtacggcgcggcggcacg -continued ctggagctggatggcgtcaccgtggcgggcGgggaagggatggagccgat gacggtctctgacgccggcagccgcctgagcgtgcgcggcGgcgtgctgg gcggcgaagcgccgggcgtcggcctggtccgggccgcgcaaggcggccag Gcgagcatcatcgacgcgacgctgcagagcatcctcgggcccgcgctcat tgccgacggcGgctccatttccgtcgccggcggttcgatcgacatggaca tgggcccgggattcccgccgCcgcctccaccgcttcccggggcgccgctg gccgcgcatccgccgctcgatcgcgttgccGcggtgcacgccggccagga cggcaaggtgacactgcgggaggtggcgctgcgggctcacGgccgcagg cgacgggcgtctatgcgtatatgcctggcagcgaaatcaccctgcaggga Ggcacagtcagcgtgcagggcgatgacggggccggcgtggtcgccggcgc gggcctgctcGacgccttgccgcccggcggcacggtgcggctggacggaa ccacggtgtcgaccgatggcGccaacaccgatgccgtgctggttcgcggc gacgcggcgcgcgccgaggtcgtcaacaccGtgctgcgcaccgccaagag cctggccgccggcgtatcggcccagcatggaggccgcgtcAcgctgcggc agacccgcatcgagaccgcgggcgcgggggccgagggcatctccgtgctg Ggcttcgagccgcagtccggctccggcccggccagcgtcgacatgcaggg cggcagcatcAccacgaccggcaaccgcgccgccggcatcgcgctcaccc acggcagcgcccgcctggaaGgcgtggcggtgcgcgccgagggcagcggc tcgagcgccgcgcagctggccaacggcacgCtggtcgtcagcgcagggtc gctggcctcggcccagtccggcgcgatcagcgtgaccgacAcgccgctga agctgatgccgggcgccctggccagcagcacggtctcggtccggttgacc Gacggcgccacggcgcaaggcggcaatggcgtgttcctccagcagcattc caccattccgGtggcggttgccctcgagagcggcgccctggctcgcggcg atatcgtcgccgacggcaacAagcccctcgatgccgggatctccctcagc gtggccagcggcgccgcctggcacggcgccAcccaggtgctccagtcggc cacgctgggcaagggcggaacctgggtcgtgaacgccgacTcccgggtgc aggacatgtcgatgcgcggcgggcgggtcgaattccaggcgcccgcgccc Gaggcctcttacaagaccctgaccctgcaaaccctggacggcaacggcgt gttcgtgctgAacaccaacgtcgccgccgggcagaacgaccagttgcggg tcaccggccgcgccgatggcCagcaccgcgtgctggtgcgcaatgccgga ggcgaggccgacagccggggcgcccgcctgGgcctggtgcatacccaggg gcagggcaacgccaccttccggctggccaacgtcggcaagGcggttgacc tgggcacgtggcgctacagcctggcggaggatccgaagacgcatgtctgg Agcttgcagcgcgcgggccaggccctgtcgggggcggccaatgccgccgt gaacgcggcgGatctttccagcatcgccctggccgagtccaacgcgctgg acaagcgcctgggcgagctgCgcctgcgcgccgacgccggcgggccatgg gcgcgtacgttcagcgagcgccagcagatcAgcaaccgccacgcccgcgc ctacgaccagacggtcagcgggctggagatcggcctggacCgtggctgga gcgcgtcgggcgggcgctggtacgccggcggcctgctcggctacacctat Gccgaccgcacctatcccggcgacggtggcggcaaggtcaagggcctgca cgtcggcggcTacgccgcctatgtcggcgatggcggctactatctcgaca ccgtgctgcggctgggccgcTacgatcagcaatacaacattgccggcacc gatggcggccgcgtcaccgccgactaccgcAcaagcggcgccgcatggtc gctcgaaggcgggcgccggttcgagctgcccaacgactggTtcgccgaac cgcaggccgaggtcatgctgtggcgcacgtcaggcaagcgctatcgcgcc Agcaatggcctgcgcgtcaaggtggacgccaacaccgccacgctgggccg cctgggcttgCgcttcggccgccgcatcgccctggccggcggcaacatcg tgcagccctacgccaggctcGgctggacgcaggagttcaaaagcacgggc gatgtgcgcaccaatggcattggccatgccGgcgcaggccgccacggccg cgtggaactgggcgcgggcgtcgacgccgcgttgggcaagGggcacaacc tctatgcttcgtacgagtacgcggcgggcgaccggatcaacattccgtgg tcgttccacgccggctaccgctacagcttctga SEQ ID NO:34 polypeptide sequence of Orf17

MYLDRFRQCPSSLQIPRSAWRLHALAAALALAGMARLAPAAAQAPQPPVA

GAPHAQDAGQEGEFDHRDNTLIAVFDDGVGINLDDDPDELGETAPPTLKD

IHISVEHKNPMSKPAIGVRVSGAGRALTLAGSTIDATEGGIPAVVRRGGT

LELDGVTVAGGEGMEPMTVSDAGSRLSVRGGVLGGEAPGVGLVRAAQGGQ

ASIIDATLQSILGPALIADGGSISVAGGSIDMDMGPGFPPPPPPLPGAPL

AAHPPLDRVAAVHAGQDGKVTLREVALRAHGPQATGVYAYMPGSEITLQG

GTVSVQGDDGAGVVAGAGLLDALPPGGTVRLDGTTVSTDGANTDAVLVRG

DAARAEVVNTVLRTAKSLAAGVSAQHGGRVTLRQTRIETAGAGAEGISVL

GFEPQSGSGPASVDMQGGSITTTGNRAAGIALTHGSARLEGVAVRAEGSG

SSAAQLANGTLVVSAGSLASAQSGAISVTDTPLKLMPGALASSTVSVRLT

DGATAQGGNGVFLQQHSTIPVAVALESGALARGDIVADGNKPLDAGISLS

VASGAAWHGATQVLQSATLGKGGTWVVNADSRVQDMSMRGGRVEFQAPAP

EASYKTLTLQTLDGNGVFVLNTNVAAGQNDQLRVTGRADGQHRVLVRNAG

GEADSRGARLGLVHTQGQGNATFRLANVGKAVDLGTWRYSLAEDPKTHVW

SLQRAGQALSGAANAAVNAADLSSIALAESNALDKRLGELRLRADAGGPW

ARTFSERQQISNRHARAYDQTVSGLEIGLDRGWSASGGRWYAGGLLGYTY

ADRTYPGDGGGKVKGLHVGGYAAYVGDGGYYLDTVLRLGRYDQQYNIAGT

DGGRVTADYRTSGAAWSLEGGRRFELPNDWFAEPQAEVMLWRTSGKRYRA

SNGLRVKVDANTATLGRLGLRFGRRIALAGGNIVQPYARLGWTQEFKSTG

DVRTNGIGHAGAGRHGRVELGAGVDAALGKGHNLYASYEYAAGDRINIPW

SFHAGYRYSF

SEQ ID NO:35 polynucleotide sequence of Orf18

Atgcacatttacggaaatatgaatcgagcaacaccttgccgcggtgcggt gcgtgcccttGcgcttgccctgctgggagcgggtatgtggacactttctc ctccctcggcatgggcgcttAagctcccgtcgctgctgacggacgacgag ctgaagctggttctgccgactggcatgtctctggaggatttcaagcgcag ccttcaggagtccgcgccgagcgcgctggcaacgccgccgtcgtcttcgc ctccggttgcgaagccaggtccgggctccgttgccgaggctccgtcgggg tcgggccacaaggacaacccatcccctcccgtcgtcggcgtcggtccagg -continued tatggcggagtcgtctggcggacataaccccggcgtgggggggggcacgc atgaaaatgggttgcccggtataggaaaggtcggcgggtctgcgcccgga ccggataccagtacgggctcgggtcccgacgccggcatggcgtccggagc gggttcgacgtcgcccggcgcatcgggtggggcgggcaaggatgcgatgc cgccctcggaaggcgagaggccggactccggtatgtccgattcggggcgg ggtggcgaatcgtcggctggaggcttgaatccggacggcgctggcaagcc accgcgggaggaaggcgagccgggttccaagtctcctgcggacggtggcc aggacgggccgccgccgccccgggacggcggcgatgcggatccgcaacct ccgcgggacgatggcaatggggaacagcagccgcccaagggcggcgggga tgaggggcagcgcccgccgcctgccgccggaaacggtggcaacggtggca acgggaacgcgcagcttcccgagcgcggcgacgacgcgggtccgaagcct cccgagggagagggcggcgatgaaggtccgcaaccgccgcagggcggcgg cgagcaggacgcgccggaggttcctcccgtcgcgccggcgccgcccgcgg gcaacggtgtctatgacccgggcacgcataccttgaccacgccggcctct gcggcggtgagcctggccagcagttcgcatggcgtatggcaggccgagat gaacgcgttgagcaagcgcatgggcgagttgcgcctgacgccggttgcgg gcggcgtatggggccgcgcttttggccggcgccaggacgtcgacaaccgc gtgtcgcgcgagttccgccagaccatcagcggtttcgaactgggcgccga taccgccttgccggtggccgacgggcgctggcacgtgggcgcggtggctg gctacaccaacggccgcatcaagttcgaccggggcggcacgggcgatgac gacagcgtgcacgtgggcgcttacgctacctacatcgaggacggcggttt ctatatggatggcatcgtgcgggtcagccgcattcgccacgcgttcaagg tggacgacgccaagggccggcgcgtgcgcggccagtaccgcggcaatggc gtgggcgcgtcgctggaactgggcaagcgcttcacgtggcccggcgcctg gtacgtggagccgcagctggaggtggccgccttccatgcgcaaggggccg actacaccgccagcaacggcctgcgcatcaaggacgacggcacgaactcc atgctgggccgcctgggcctgcacgtggggcggcagttcgacctgggcga tggccgcgtggtgcagccctacatgaagctgagctgggtgcaggagttcg acggcaagggcacggtgcgcaccaacgacatccggcacaaggtgcggctc gatggcggccgcaccgaactggccgtaggggtggcttcgcaactgggcaa gcacggcagcctgttcggctcgtacgagtacgccaagggcagccgccaga ccatgccgtggaccttccacgtcggctatcgctacgcctggtag SEQ ID NO:36 polypeptide sequence of Orf18
MHIYGNMNRATPCRGAVRALALALLGAGMWTLSPPSAWALKLPSLLTDDE

LKLVLPTGMSLEDFKRSLQESAPSALATPPSSSPPVAKPGPGSVAEAPSG

SGHKDNPSPPVVGVGPGMAESSGGHNPGVGGGTHENGLPGIGKVGGSAPG

PDTSTGSGPDAGMASGAGSTSPGASGGAGKDAMPPSEGERPDSGMSDSGR

GGESSAGGLNPDGAGKPPREEGEPGSKSPADGGQDGPPPPRDGGDADPQP

PRDDGNGEQQPPKGGGDEGQRPPPAAGNGGNGGNGNAQLPERGDDAGPKP

PEGEGGDEGPQPPQGGGEQDAPEVPPVAPAPPAGNGVYDPGTHTLTTPAS

AAVSLASSSHGVWQAEMNALSKRMGELRLTPVAGGVWGRAFGRRQDVDNR

-continued

VSREFRQTISGFELGADTALPVADGRWHVGAVAGYTNGRIKFDRGGTGDD

DSVHVGAYATYIEDGGFYMDGIVRVSRIRHAFKVDDAKGRRVRGQYRGNG

VGASLELGKRFTWPGAWYVEPQLEVAAFHAQGADYTASNGLRIKDDGTNS

MLGRLGLHVGRQFDLGDGRVVQPYMKLSWVQEFDGKGTVRTNDIRHKVRL

DGGRTELAVGVASQLGKHGSLFGSYEYAKGSRQTMPWTFHVGYRYAW

SEQ ID NO:37 polynucleotide sequence of Orf19
Atgaaaccgacttccatcctggcacgtttgccccgctatctcggcgcctg cgcgctggccGcgctggccgcgctggctgtcgcgccgctcgcgccggcgc aggcacagactccgctgcccGcgggactcggcgccgccgaggtgcggcag tatttgtccggcctgccgtccgatgccctgcgccagcaggcgtcgtggct ggcgccggcgctgttgcgcccctatctgtcaggcctgacggatgcgcaat tgcggcaatatgtgcaggcgctgacacccgggcagatcacgcaggggctg gcggcgttgacgcctgcgcagcgtgcgcggctgcagcgcgaattcgaacg gcaggcgcgccggcaggtgcagcaggcggtacgggccgaggtcgccgcgc gcagcgcgcgggcggtggcgatggggcagagcgcatcgatgctgctgctc gacgccgagatgggaaccctggcgcaacgccagggcgatctgcgccgcgg ccacgacgagggcgccttctgggcgcgcggcagcgcgaaccgcttcaagg tcgatacgccggacacaccggcgttcgacctgcgcgtggagtacctgacg ctgggcgccgaccatggctggcgcctggacacggggcggctctatctggg cgcctacgccggcgtctcgcgcgcccgcatggatgacaacgacatcatgc acggccggatcgaaagccggttcctgggcacgtacctgacttatgtggac aacggcgggttctacgtcgatgcggtcagcaagctggggcgtatcgacga gtccgtgtcgttcgacctgccgctggggctgggcgactacgacgacgata tatcgcatacaacgtatacgggcagtgccgaggccggctatcacttcaag ttgccgcaacgctggttcgtcgagccgcaggcgcaggtgatctactcgcg cagcagccagacgtcggtgcaggggcgggccggcgtgcgcgccggccggg atttcaccctggccggcggcgcgaccttgcgtccttatgtcagcgcctcg tacctgcacgagttctcgcacgacgactcggtcgatttcggcggcaagtc gtacgatgccgaactgcccggcagccgctggcagctgggtgccggcgcgg cgctggacgtgggggcgcatcgcgcctacgcggatctgcgctatgggcac ggcgccaacatcagccaggacctgtcgctgaacatcggctacgcgtaccg cttctag SEQ ID NO:38 polypeptide sequence of Orf19
MKPTSILARLPRYLGACALAALAALAVAPLAPAQAQTPLPAGLGAAEVRQ

YLSGLPSDALRQQASWLAPALLRPYLSGLTDAQLRQYVQALTPGQITQGL

AALTPAQRARLQREFERQARRQVQQAVRAEVAARSARAVAMGQSASMLLL

DAEMGTLAQRQGDLRRGHDEGAFWARGSANRFKVDTPDTPAFDLRVEYLT

LGADHGWRLDTGRLYLGAYAGVSRARMDDNDIMHGRIESRFLGTYLTYVD

NGGFYVDAVSKLGRIDESVSFDLPLGLGDYDDDISHTTYTGSAEAGYHFK

LPQRWFVEPQAQVIYSRSSQTSVQGRAGVRAGRDFTLAGGATLRPYVSAS

YLHEFSHDDSVDFGGKSYDAELPGSRWQLGAGAALDVGAHRAYADLRYGH

-continued

GANISQDLSLNIGYAYRF

SEQ ID NO:39 polynucleotide sequence of Orf20
Atggtcggcaggagttgtcatcgtgcagggtggttataccgggcgacctt
cctcTtatacGccgcaaactgtgcttatcccgcgaacgcccaatcggttt
ctggttccggtcagGtgtcgAacgggccgatcacgtcaccgcactgggtg
gtgggcggggaactgatcgtcggggatacgGgcgccgggaccttgctcat
cgaggccggcggtaccgtgctcaacgactgggcctatatcGgcagtgaca
atggcgctgtgggcaccctgacggtgtcgggccgcgacggcgccggggcc
Gcgtcgacctggacgactgtcgacgatgtgtcgatcggcgttgcggcggg
cagcaggggcAcgctcgaggtgctcggcggggccagggcgcaaagcggat
ggggcaccatcggcgtcgctGcaggcagcgtcggaagcgtgaccgtgtcc
gggcccgggtcggtgtggaatatcgccacgGtcaattcgttccagatcgg
ctcgggcggcagcgggacgctgtggatcgaccagggcggcGcagtgtata
gcgggcagggcgtcatcggttggaaccccggcagcgacgggcacgtcacg
Gtattgggtccggcaacggtatggaacccgctgaacaatatctatgtcgg
tctcggcgggActggtgaactggatatccgggacggcgcggccgttgcga
ctgcagggtcgagcccgccgGgcgccgcggcatcgatctacatcgggacg
agcgcagggagcgccggcacggtaacggtgTcgagcgcgacggccgtcac
ctcgacgctcacgtcgaccgaccgtatcgaaatcggctcgGccggcgccg
gggtgctgactgtcgccaaaggcgggatggtgggcgtcgccagcgacgcc
Tggatagccatcaccggcacgtcctccggaacgctgaacctgaccggcga
tgccagcggcCgaggcgtgctggaaacgggctcggtcatcaagggcgccg
gcaacgcgaccttcaacctgGatggcggggtcctgcgcgccaatcgtgac
gaggccaatttcctcaatggtttctccacgCaggcggtgggaagcggcgg
cgcctggttcgatacgaatgcccatgacgtgggcgttgtcAccgccttct
cgggtacgtccagcttcaacaagctgggagccggcacgctgacgctgtca
Ggcaacagcgccgcgttcacggggaacaccgatatccaggccggaacgct
gcaggtggacGgcgttcttggcgggccggtggatgtgctggcgggggcgc
ggttgaccggtaccgggcgcGtcggtgcgacggccaacaagggcaccatt
gcgccgggcccgcgcagcggctttggcaccCtgacgatcgccggggatta
cgcggcccagggcggcaacctggaaatccgtacgcagcttGgcgccgacg
actcgccgaccgacaggctggtgatcacgggcgccagcgctggcgtgaca
Ccggtcacggtcgagaatatcggcggcacgggcgcctcgacccagcgggg
catacaggtcGtgcaggtcaatggcgcttcggcaggccggttcaacctcg
ccaacggcgattacgtcatcGaggggcgtccggcgctggtggccggcgcc
tatggctatgtgctgcagcaggacgccgccGacggcgattggtatctgaa
atcgtcgctgcccgaccctggggctccccaaggcgggggcGgtctgccgg
gcgccggggagcccgtgctttatcagcccggcgtgccggtctatgaagcc
Tatgccaacacgctgctgcatctgagccggctttccaccttgcgccaacg
ggtcggcaatCgcctttatgatccggcagatgtcggccgcaacggcgtat
ggagccgcgtcgagggctccGcgagccagctcgatccttccgcgtccacg
actggcgaacgccaggacgtcgatagctggAaagtgcagttcggtgtcga
ccgtatcctggccggcgggcaagagggctcccgcctggtgGgcggattgg
cgctgcagtacggcaaggccgacacgcgcgtgtcgtcgatatacggcaat
Ggcactgtcgacgccacggcctatggcctgaccccgacgctgacctggta
cggcagggacGgcgcctatgtcgatgcccaggcccaggcgatctggttcg
acagcgacctgagttcacggCtggccggcaagctcaaggatggccggaaa
gcgcatggctatgggctgggtatCgaagcgGgcaaggccttcggattgcg
ggaggggctggccctgatcccgcaggcgcaattgtcgtacGcatcgaccc
gcttcgacagcttcgacgacagattcggcgcccgcgtcgaagacgataag
Ggcgacagcctgcagggccgtctcggcatcgcgctggactacaagagcag
ctggcaagcgGgcggcgcgaaccgggagtcgagtgtcttcggcatcgtca
atgtgaagcatgagttcctgGatggcacgcgcgtgcgcgttgccggcgtg
ccggtaagcagccgcatggcgcgcacctggGgcagcgtgggagtgggggc
cgattacggttggggagaacgctacgccatttacggccagGtggacgccg
atgcagatttcgccggcagctacatcgtcaccgcgaccgcggggttcagg
atgatgttctag SEQ ID NO:40 polypeptide sequence of Orf20
MVGRSCHRAGWLYRATFLLYAANCAYPANAQSVSGSGQVSNGPITSPHWV
VGGELIVGDTGAGTLLIEAGGTVLNDWAYIGSDNGAVGTLTVSGRDGAGA
ASTWTTVDDVSIGVAAGSRGTLEVLGGARAQSGWGTIGVAAGSVGSVTVS
GPGSVWNIATVNSFQIGSGGSGTLWIDQGGAVYSGQGVIGWWPGSDGHVT
VLGPATVWNPLNNIYVGLGGTGELDIRDGAAVATAGSSPPGAAASIYIGT
SAGSAGTVTVSSATAVTSTLTSTDRIEIGSAGAGVLTVAKGGMVGVASDA
WIAITGTSSGTLNLTGDASGRGVLETGSVIKGAGNATFNLDGGVLRANRD
EANFLNQFSTQAVGSGGAWFDTNAHDVGVVTAFSGTSSFNKLGAGTLTLS
GNSAAFTGNTDIQAGTLQVDGVLGGPVDVLAGARLTGTGRVGATANKGTI
APGPRSGFGTLTIAGDYAAQGGNLEIRTQLGADDSPTDRLVITGASAGVT
PVTVENIGGTGASTQRGIQVVQVNGASAGRFNLANGDYVIEGRPALVAGA
YGYVLQQDAADGDWYLKSSLPDPGAPQGGGGLPGAGEPVLYQPGVPVYEA
YANTLLHLSRLSTLRQRVGNRLYDPADVGRNGVWSRVEGSASQLDPSAST
TGERQDVDSWKVQFGVDRILAGGQEGSRLVGGLALQYGKADTRVSSIYGN
GTVDATAYGLTPTLTWYGRDGAYVDAQAQAIWFDSDLSSRLAGKLKDGRK
AHGYGLGIEAGKAFGLREGLALIPQAQLSYASTRFDSFDDRFGARVEDDK
GDSLQGRLGIALDYKSSWQAGGANRESSVFGIVNVKHEFLDGTRVRVAGV
PVSSRMARTWGSVGVGADYGWGERYAIYGQVDADADFAGSYIVTATAGFR
MMF SEQ ID NO:41 polynucleotide sequence of Orf21
Atgccgtcacccgatgccttgccgcacacgccgcctgcttcaggcggcga
tcgcgtgatcAgcgggatcctgcagcaggacctcggcagttggctggcgc
cggatgccgcaaagcgcagcCcctccgagcctggcaaggcggccgaaaaa
atcggggtaatgccgaacgaggacctcggcAagtggctggttccgggggc
gcaaaagaacaatccgcccgagcctggcaagacgctggacGaaatccgTg -continued cgggtctcgaaaaatgggtggcgcccgggtccaagccgcccgtcgaaccg Gatccggacaaggcgacgcaggcgtatcgcaaagacctcgataaatggct ggcgcctccgGccaagtccggcccgcccgaagcgccacccgtcgtccaac ccgaagcgccgccgcaagcgCaacctgaggcgccgcctgtcgtgccgccg ccggccgagccgccagcagctcgaccgccgGccgttccgcccgcgcggcc ggccggcgacgcggtgtacgtgccgggcacgcgcacgctgAcgccgacgg ccaacgcggcggtgggcacggccagcgccgcgcaaggtctgtggcaggcc Gagatgaacgcgttgagcaagcgcatgggcgagttgcgcctgacgccggt tgcgggcggcGtatggggccgcgcttttggccggcgccaggacgtcgaca accgcgtgtcgcgcgagttcCgccagaccatcagcggtttcgaactgggc gccgataccgccttgccggtggccgacgggCgctggcacgtgggcgcggt ggctggctacaccaacggccgcatcaagttcgaccggggcGgcacgggcg atgacgacagcgtgcacgtgggcgcttacgctacctacatcgaggacggc Ggtttctatatggatggcatcgtgcgggtcagccgcattcgccacgcgtt caaggtggacGacgccaagggccggcgcgtgcgcggccagtaccgcggca atggcgtgggcgcgtcgctgGaactgggcaagcgcttcacgtggcccggc gcctggtacgtggagccgcagctggaggtgGccgccttccatgcgcaagg ggccgactacaccgccagcaacggcctgcgcatcaaggacGacggcacga actccatgctgggccgcctgggcctgcacgtggggcggcagttcgacctg Ggcgatggccgcgtggtgcagccctacatgaagctgagctgggtgcagga gttcgacggcAagggcacggtgcgcaccaacgacatccggcacaaggtgc ggctcgatggcggccgcaccGaactggccgtaggggtggcttcgcaactg ggcaagcacggcagcctgttcggctcgtacGagtacgccaagggcagccg ccagaccatgccgtggaccttccacgtcggctatcgctacgcctggtag SEQ ID NO:42 polypeptide sequence of Orf21

MPSPDALPHTPPASGGDRVISGILQQDLGSWLAPDAAKRSPSEPGKAAEK

IGVMPNEDLGKWLVPGAQKNNPPEPGKTLDEIRAGLEKWVAPGSKPPVEP

DPDKATQAYRKDLDKWLAPPAKSGPPEAPPVVQPEAPPQAQPEAPPVVPP

PAEPPAARPPAVPPARPAGDAVYVPGTRTLTPTANAAVGTASAAQGLWQA

EMNALSKRMGELRLTPVAGGVWGRAFGRRQDVDNRVSREFRQTISGFELG

ADTALPVADGRWHVGAVAGYTNGRIKFDRGGTGDDDSVHVGAYATYIEDG

GFYMDGIVRVSRIRHAFKVDDAKGRRVRGQYRGNGVGASLELGKRFTWPG

AWYVEPQLEVAAFHAQGADYTASNGLRIKDDGTNSMLGRLGLHVGRQFDL

GDGRVVQPYMKLSWVQEFDGKGTVRTNDIRHKVRLDGGRTELAVGVASQL

GKHGSLFGSYEYAKGSRQTMPWTFHVGYRYAW

SEQ ID NO:43 polynucleotide sequence of Orf22

Atgtgcgacacctgcagagatgatgatggcacctcgccttcgattcgcgt ccaaggcgggGttgttcagggcggcatgggtgcaaataacgtcgctgtgg tggcaacagggtctggaaagGtcgcgatcgagaatgcggaactgctcgga gccagcggcatgtacgccacgttcggcgcgcaggtcgatatgaaaggcgg gcgcattctggcgcacaacaccaatatcctgggaagccagggttacgccg -continued atggtccctatggcggcgtggtcgtgacagaggacggtcaagtcaacctg gagggcgccaaggtcagtgcaactggcctgggggccgccggcttgtggtt gctgggcgacaaggacaccagcccgcgagccagcctgcgcaacaccgacg tccacggagaggtcgccgccattgcgctggggttcaatggcgaggcgaac atctcgggcggcagcttgagcgtagaggatggggccgtgctcaccaccct gacgcccgatgcagtcgagtattactacgactacgccttgtccatggagc atctgccagctgatgcgccgttgacgccggtccgcgtcacgctgtccgat ggcgcgcgcgccagcggagaaacgttgatcgcgcatggcgggttgttgcc catgacgctgcgcttgagcagcggggtcgacgcccgcggcgacatcgtca cgctgccgccttccgcgccgcccgattccgcggagcaaccggatgccgag ccggaaccggatgccgagctggaaccggacgccgcggcgcagtcggacgc caaggcgaatgcgcgggtcatggcgcaggtagatggcggggaacctgttg ccgtgccgatcccggccccttcgcatcccgatgccccgatcgacgtgttc atcgacagcggtgcccaatggcggggcatgaccaagaccgtcaatgcgtt gcgcatcgaggacggcacctggaccgtcaccgggtcgtccacggtgaaca gcctgcacctgcaggcaggcaaggtggcgtacgcaacgcctgccgaaagc gacggagaattcaaacacctgcgggtcaagaccctctcgggaagcggcct gttcgagatgaacgccagcgccgacctgagcgatggcgacctgctggtcg tgtccgacgaggccagcgggcagcacaaggtgctggtgcgaggagccggc acggaacccaccggtgtggaaagcctgacgctggtcgagctgcccgaggg cagccagacgaagttcacgcttgccaaccggggcggggtggtcgacgccg gcgcgttccgctatcgcctgacgccggacaacggtgtctggggcctggaa cggaccagccagctttcggccgtcgccaacgcggccttgaataccggggg cgtgggcgcggccagcagcatctggtatgcggaaggcaatgcgctctcca agcgcctgggcgagttgcggctcgatcccggcgcgggcggcttctggggg cgcacgttcgcccagaagcagcagctcgacaacaaggctggccgacgctt cgaccagaaggtgtacggtttcgagctggggggccgaccatgccatcgcag gacagcaagggcgctggcacgtgggcggcctgctgggctatacccgcgca aggcgcagcttcatcgatgacggcgcccgggcataccgacagcgcgcatat cggggcctacgcggcgtacgtggcggacaacggcttctatttcgattcga ccctgcgcgccagccgcttcgagaacgacttcacggtaacggccaccgac gccgtttccgtacggggcaagtaccgggccaatggggtaggcgccacctt ggaggccggcaaacgtttcacgttgcacgacggctggttcgtcgaacctc agtccgaggtgtcgctgttccatgccagcggcggaacctaccgtgccgcg aacaacctgtcggtcaaggacgaaggcggcacctccgccgtgctgcgcct gggcttggcggccgggcgacgcatcgacctgggcaaggaccgcgtgatcc agccctatgccaccctgagctggctgcaggaattcaaaggcgtcacgacc gttcgcaccaacgggtacgggctgcgcaccgacctgagcggtggccgggc tgaattggcgctgggcctggccgccgcgttggggcgcggccaccagctct acacttcgtacgagtacgccaagggcaacaagctgaccttgccttggacg ttccacctgggctatcgctacacctggtag -continued SEQ ID NO:44 polypeptide sequence of Orf22
MCDTCRDDDGTSPSIRVQGGVVQGGMGANNVAVVATGSGKVAIENAELLG
ASGMYATFGAQVDMKGGRILAHNTNILGSQGYADGPYGGVVVTEDGQVNL
EGAKVSATGLGAAGLWLLGDKDTSPRASLRNTDVHGEVAAIALGFNGEAN
ISGGSLSVEDGAVLTTLTPDAVEYYYDYALSMEHLPADAPLTPVRVTLSD
GARASGETLIAHGGLLPMTLRLSSGVDARGDIVTLPPSAPPDSAEQPDAE
PEPDAELEPDAAAQSDAKANARVMAQVDGGEPVAVPIPAPSHPDAPIDVF
IDSGAQWRGMTKTVNALRIEDGTWTVTGSSTVNSLHLQAGKVAYATPAES
DGEFKHLRVKTLSGSGLFEMNASADLSDGDLLVVSDEASGQHKVLVRGAG
TEPTGVESLTLVELPEGSQTKFTLANRGGVVDAGAFRYRLTPDNGVWGLE
RTSQLSAVANAALNTGGVGAASSIWYAEGNALSKRLGELRLDPGAGGFWG
RTFAQKQQLDNKAGRRFDQKVYGFELGADHAIAGQQGRWHVGGLLGYTRA
RRSFIDDGAGHTDSAHIGAYAAYVADNGFYFDSTLRASRFENDFTVTATD
AVSVRGKYRANGVGATLEAGKRFTLHDGWFVEPQSEVSLFHASGGTYRAA
NNLSVKDEGGTSAVLRLGLAAGRRIDLGKDRVIQPYATLSWLQEFKGVTT
VRTNGYGLRTDLSGGRAELALGLAAALGRGHQLYTSYEYAKGNKLTLPWT
FHLGYRYTW SEQ ID NO:45 polynucleotide sequence of Orf23
Ttgcgccagaccacgccggtgccggtgcggctcgtcctgcgcggcgcggc
ggtcgcgcagGgcgatgtcgtgcgcgcgcccgagacggcgccggagaagg
atgggttcggcacgcccgtgCggccgggcttgcgcgtcgggctggaccag
gcgccgctcgagctcgatgtggccgacggcgcgcagtggcatggcgcgac
tcagtcgcttgacaggctggccctgggcgcgggcggccaatggcgcatga
gcgcggcatccagcgtgggcgaactgagcatggagcctggcgcggccgtc
gtgttcggcgatgcggccggaccgggttttcaaacgctgacggtgcgcac
cctggcgggcgccggttcgttcgagatgcgtgcggacgccgcgctggagc
atgccgatcaactggtggtgaccgaccaggccgaagggcggcatcgcgtg
tggttgcgcgcgccggccggcgccgagccgtcgaaggcacaggccgtgct
ggtgcgcgcgcccgcagacggcaaggccagtttcgaactcgacggcagcg
acggcagggccgacttcggcacctatcgctacgggctggcgcagcagccg
ggcggcgcctggggcctagtcaggacggggtattcgtccaccgccgccgc
ggcgctggataccggcggactgggcgcggtgcaggggttgtggtatgccg
aatccaacgcgttgggcaagcgcatgggcgaattgcgcctgaacccggac
gccggcggcgcctggggccgggcgttcagccagcgccagcgcatcagtcc
gcgcgcgggccggcatttccagcaaggcgtcagcggcatcgagctgggcg
ccgaccgggcctggcccgtggccggcggccgttggcatgcgggctggttg
ctgggctacacgcgcgcgtcacgcgggttttccggccagggaaaggggca
caccgacagcgtgcacgtgggcggctatgccacctatatcggcgccaatg
gcgtgtacgccgatgccacgctgcgcgccagccgcttcgagaattcgttc
gacgcacctggctgggcggggcgcaccgtgtccggcagctaccgcgccaa
tggcgtgggcgtgacgctggaggccggccggcgtctggcgctggaccggc
actggttcgtcgagccgcaggccgaactggcgtggtttcgtgccggcggc
ggtacgtacacggccagcaatggcctgcgtatcgaggatgacggcggcac
gtcgctgcaggcgcgggtaggcgcgcaagccggccgccgcttcgacttgc
gcggcggcgcggtggtgcagccctacgcgcagctgagttgggtgcaggaa
ctcaagggcgtgagcacggtgcgcaccaacggcatcgcgcaccgtaccga
cctgggcgcgggccgcgtcgaactgggactgggcgtggcggccgcgctgg
gcaagggccacaatctgtacgcgtcgtacgagtacgcgcacgggcccagg
ctcagcctgccgtggaccgtgcagctgggttaccgctacgcttggtaa SEQ ID NO:46 polypeptide sequence of Orf23
LRQTTPVPVRLVLRGAAVAQGDVVRAPETAPEKDGFGTPVRPGLRVGLDQ
APLELDVADGAQWHGATQSLDRLALGAGGQWRMSAASSVGELSMEPGAAV
VFGDAAGPGFQTLTVRTLAGAGSFEMRADAALEHADQLVVTDQAEGRHRV
WLRAPAGAEPSKAQAVLVRAPADGKASFELDGSDGRADFGTYRYGLAQQP
GGAWGLVRTGYSSTAAAALDTGGLGAVQGLWYAESNALGKRMGELRLNPD
AGGAWGRAFSQRQRISPRAGRHFQQGVSGIELGADRAWPVAGGRWHAGWL
LGYTRASRGFSGQGKGHTDSVHVGGYATYIGANGVYADATLRASRFENSF
DAPGWAGRTVSGSYRANGVGVTLEAGRRLALDRHWFVEPQAELAWFRAGG
GTYTASNGLRIEDDGGTSLQARVGAQAGRRFDLRGGAVVQPYAQLSWVQE
LKGVSTVRTNGIAHRTDLGAGRVELGLGVAAALGKGHNLYASYEYAHGPR
LSLPWTVQLGYRYAW SEQ ID NO:47 polynucleotide sequence of Orf24
Ttgccttcgccgcccgaagaggcgcctcaggcggggcccgacgcgtccaa
gcagcggccgGagggcctgcccgcgcccgatgccaatccccaacccgatg
caaagcccggagctgagatgAaaccccggcctggggtggaacccggacct
gaggcggaacctggtccgcaggggcagcctggcccccagcctggagcccg
gccgcaggacgagccgcacgcgcagccgctgccgcccgccggcaaccccg
gcgctgggatttacatgccccgcagcggcatcttgaccgcaccggttctg
gccgtgctgggcacggccagtgcgccgcaaggtatctggcaggcagagat
gaacgccctgagcaagcgcatgggtgaattgcggcttacgccggcagccg
gcggcgtgtgggcacgctcgttcgcgcaacgccaacgcctggacaatcag
gtggtggacaggttcacccagaccgtgggcgggatcgagattggcgccga
cacggccttgccggcggccgaggggcgctggcatgtaggcgcggtggccg
gctacagccgtgcgcgcgccgcaagctggcgcacagcgcccgtggcaacagc
gacagcctgcatgtgggcgcctatgcgacgtatatcggcgacggcggctt
ctacctcgacgggattgtgcgggtgaaccgctacgagcacgatttcaggg
ctgacggccagcgcggcgcgcgcgtgacgggcaagtatcgcgccaatggc
atcgggctgtcgctggagaccggcaggcgtttcacatgggccggcgactg
gttcgtggaaccgcaggtcgaagtggcgttgttccgttcgggcggggcag
actacacggccagcaatggcgtgcgcgtcgacgtggcaagcaccaagtcg
ttgctgggccgggcaggcctgcaggtgggacgcaagctggatctgggcaa
cggcaaactggtgcagccgtacgccaagctgagctggttgcaggagttcg
atggcgtgggcaaggtgcgcaccaacgatatcggccatgacgtcaaactg -continued cggggcgggcgcgccgaactcgacttgggcgtggccgcggcgcttggcag gcacagcagcctgtttgcttcgtacgagtacagcaagggcagccgcttga ccattccgtggagctttcacgtcggctatcgatacgcctggtaa SEQ ID NO:48 polypeptide sequence of Orf24
LPSPPEEAPQAGPDASKQRPEGLPAPDANPQPDAKPGAEMKPRPGVEPGP

EAEPGPQGQPGPQPGARPQDEPHAQPLPPAGNPGAGIYMPRSGILTAPVL

AVLGTASAPQGIWQAEMNALSKRMGELRLTPAAGGVWARSFAQRQRLDNQ

VVDRFTQTVGGIEIGADTALPAAEGRWHVGAVAGYSRARRKLAHSARGNS

DSLHVGAYATYIGDGGFYLDGIVRVNRYEHDFRADGQRGARVTGKYRANG

IGLSLETGRRFTWAGDWFVEPQVEVALFRSGGADYTASNGVRVDVASTKS

LLGRAGLQVGRKLDLGNGKLVQPYAKLSWLQEFDGVGKVRTNDIGHDVKL

RGGRAELDLGVAAALGRHSSLFASYEYSKGSRLTIPWSFHVGYRYAW

SEQ ID NO:49 polynucleotide sequence of Orf25
Atgagacggttaaaggcccaggctttcgagggcagccgcagcaggccggc aggacatgggGtggcgcctaccttgctggcgctggccctggggttccagg gggcggcggcgtgggccaatTgcacgacgtcaaacggtgctaccacttgc accaacgccaacggctctcataccaacaagGtgggcagtggaccgagcgg gatgaacgaacgcgtcaccgtgaatcagggggcgcgcatcGAgacaaacg ccagcgcggcgatcagtgtgggaacgagcgggcaggtacgaatcgagggc Ggtgcagtagtgcaaagcacggtcaatactgctgcgtccggccagtacgc caaaacgctgGaagcagcaagcaataacaatatttccatccaagtaaacg cgcagctcctggccaagggcAgcgcttcgcagtccagcgcgttgggattg tcaggcgccggcaataccgtcaccaaccatGgcacgatccgggccgataa tgccgcggcaatctgggtcactgccaataccgccaatgcgGccaatacca tcgataactacgggactatcgaaacagtgctcaatggcggctacgccaac Gccatcggcagcacgcggaacaacagtgccacgggcgctggcgtgacggt acgcaatcatGccaacggacgcatcgtcggcaacgtgaagttcgaggctg gcgacgacagcgtcatactcGacggcggctctaccatcaccggatccttg aacggtggcagcggcaacaacagcctgacgCtgaaagccggcgacggcac gctgggccgcgcaatccgcaacttcggcacgatcaccaagCaggaggctg gaacctggaccctgaatggccaggtcggccgcaacgacaacaacctcaag tccacggtcaaggtggagggcggcacgctggtcttgcgcggcgataacag cggcgccacccagggcggcgtgttgcaggtgtccgccggcgctacggcgg acgtaactgccgccagcgccatgcagtccatcagcaacgccggcacggtt cagttcacgcaggacagcaatgccgcctacgccggcgtgctgagcgggac cgggagcatcgtcaagcgcggcggcggcgacctgacgttgacgggcaaca acacccataccggcaaggtggtggtggaggcgggcagcctcagcgtatcg gcggccaacaacctgggtggcgcaggtagttcggtacagctcaagggcgg cgccctcgccctcaagaaaaccatcgtcgtcaatcgcggcctgacgctcg attccggggcgcagacgttgatcatcgagccgggaacaaccacgacctgg caaggccaggttagcggcgccggcaaactggtgacccagggcggcacgct -continued ggtgctggagcacgcgtccaatacgtatagcggcggtacggagatcaaca acggaacgctgcgggcggcgcatgatgccagcctgggttccggcacgttg gcgctcaagaacagccagctggccgccacggacagcttcacggccacgcg tgcattgacgctcgctggaaacgaaagcatagacgtcgcagccaccaaga tactcagttggaacggcgaaatcagcggcgccggcaccctggtgaaggaa ggccaggggaccttgctgctgcgcggaaccaatcagcaaaatggcggcac gaccgtcaatgccggtacgctgcagatatcccgcgacgccaatcttggcc gaggggcgctggcgctgaacgacggcacgctgcagagcaccggcagcttc gcgacctcgcgcgcggccaccttgcgcggccaggccaccatggaggtcga cgcttcgcataccgtgacctggaatggcgagctgagcggcggcggcatgt tgcgcaagtcaggccagggcacgctggtcctggccggcgccaacacgtac tcgggtggcacggtggtcgaggccggcgcgcttcgggcaggacacgaaga caacctgggacggggcgcaataaccctgcagggcggagatctgcttgccg gcggcagtttttcgagcaaccgcgatctcacgcttgtccgcggttccttg gacgtggctcgcgacgctaccctgacctggagcggcgcgatatcgggcgc cggcgatctggtcaagaaaggggacgggcgcctgacactcacgggcgtca acgagtacgccggccagaccgtgctccggggcggcaagctgcgtgtggcc agggacgaaaacctgggccgcggagcactggtgctggaagacaataccgt gttcgagagcatgggctcgcatgccgccacgcggcaggtcacgctcaagg gcgcgcccaaggtagagacgcttgacggcactacgctcgaatggcgcggc acggtcgacggcgacggcaagctgtacaagcaaggcggcggcacgctcgt gctgagcggcaacaatacctacgccaagggcgtcgaggtctggggcgggg tcgtgcaagtctctcgcgaccagaacctgggcgcggccaatggcgcggtc acgctcaacggcggcgggttggcggccaacggggatttcaccagcaatcg ccagctggagctgaccgccggggccaaggccatcgacgtcgcggccggca aggacgtgacgtggcgcggtgtcgtcaacggcgccggcgcgctgaccaag gccggcgacggtacgctggcgctggccggcgccaacacctacaccggcgg cacgcgcttgcagggcggcaccgtgcaggtatcgcgcgacaacaacctcg gccaggccgccggcgcggtcacgttcgacggcgggcggctggccaacacg ggcagctttgcgaccgcgcgcacggccacgctcaacaaggctggccagat cgataccgaccgggacaccacgctgacatggaacggcgccatcggcggca agggcgagctgcgcaagcaaggggcgggcaccctggtgctgggcggagcc aacacttaccagggcgacacccgcgtcgaggccggcacgctgcaagtgtc ggccgacgccaatctgggccagggcgccgtgcatctgcacgacagccggc tggcgacgaccggtacgttcgcgacctcgcgccgtctggagttgaccgga cgtggcgcggtgcaagcggctgccgccgccacgctggattggcgcgggac ggtcgctggcgccggcacgctggtcaaggagggcgcaggcacgctggtgc tggccggtgacaaccagcatgccggcggcaccgaggtcagggccggcacg ctgcaggtatcgcgcgccaccaacctggggcccggcgcgctggcgctgga gaacgcggcgctggccacgaccgccagcttcacggccacgcaggcagcca ccctgactggcaacgccgccatcgacacggccgccggcaccacgctggga -continued tgggaggggggccatcggcggaaccggcagcctgcacaaaaagggcgaggg caagctggtgctggtcaaggacaaccaccatgacggcggcaccacgatcc acgccggtaccctgcaggtgtcgcgcgacgccaacctgggctcgggacag agcgcggtgacgctggatggcggcgccctggcggtttctgccgggttctc cagcgggcgcgagatcgtcgtgggcgccgggcacggcgcgctttcggtga cgggcggccacaccctgcaatggcagggccaggtcggcggggcgggggcg ttgaccaagacgggcgacggcacgctcgtgctggagcacgacaataccca cgccggcggtacccggattaccggcggggtgctgcgcgtctcgcgcgatg agaacctgggcgaggcgcatggcatgctgacgctcgacggcggcacgctg tcgaccaccgccgggttcgcgagccggcgcaacgccaccgtgggcaacgg cggcggccggatcgtcgtcgccgacgccgccacgctggatttgcagggcg acgttgccggcgcgggccggctggtcaaagagggcgcgggcacgctggcc ttgggcggcacgaacacctatgccggcggcaccgtggtcgaggccggcac gctgcgggtcgcgcgcgacgccaacctgggcggcggcgcgctgaccctga acaacagccgcctgcatgcgaccgccggctttgccaccggccgcgatgcg accctctccgggcgcgcctcgatcgacaccgacgaccgggcgacgctgca atggcgcggcacggtcaatggcgccggcaggctggtcaagcagggcctgg gcaccctggtactggacggcgacaaccggtacgcgggaggcaccgaggtc aatgccggcacgctgcaggtcgcgcgcgacgccaacctgggcgcgggcga cgtggcgctcaatggcagcagcctggccgcgaccgccagcttcgccaccg cgcgcacggccacgctgagcggcgcggccgccatcgacacggccgacggc gccaccttggactggaatggcctgctcgacggtgacggcgccctggtcaa gcagggcaacggcaccctggcgctggccgcggccaaccgctatggcggcg gcaccatcgtcaaggcgggcgccgtgcggatcgcccgcgacgccaacctg gggcgggccggcaccggcgtaacgctggacggcggcgcgctggccaccac ggcggatctcgcgaccggccgcgcggcgaccctgggcgcggccaacggca cgctggacgtggccgccggcacccgcctggactggaacggggcgatcggc ggcgccggcgcgctgaccaagaccggcgccggcaccctggcgctcaacca cgacaaccagcatgccggcggcaccctggtccatggcggcacgctgcgga tcgcccgcgacgccaacctaggcgcggcgggcacggcggtgacgctggac ggcggcacgctggccaccacggcgtcgttggcgcccgagcgcgcgctgcg cgtcggggcgcgcaacggcgtattgctgccggacgcgggcacgaccctgg attggcggggcgtggtcgccggcgcgggcaagctgaccaaggccggtccg ggcacgctggtgctcagcgccgataaccgccatggcggcggcacggcagt caccggcggtacgctgcaagtttcgcgcgacgccaacctgggcgcggcgg ccggcgccctgacgctggacggcggcaccttgctgagcaccgccagcttt gcctcggcgcgtgtcgccaccctcgatgccgcgggcggcaccttcgtcac ccgcgacggcacccggctggattgggacggcgcgataggcggggcgggtg gcctggtcaaggaaggcgccggcgagctgcggcttggcaatgccaatacc taccaggggccgacccgcatcgccgccggccgcctggccgtcaacggcag -continued catcgccagcccggtcacggtcgagcaggccggcgtgctgggcggcacgg gccgcatcgtcggggatgtggccaaccgcggcgtggtcgcgccgggcaac tcgatcggcgcgttgacggtggccggcaattacgctggtacgggcggcag cctggaagtggaggcggtgcttggcggcgacgccgcgccggccgatcggc tggtgctcgacggcggcgcggccagcggcgtcacgccggtcgtagtcaag ccgcagggcggggtgggcggcctgaccctgcgcggcattccggtggtcgt ggcccagggtggcgccacgaccgcgcccggggccttccgcctggcgcagc cgctggtcgcgggcgcctacgagtaccagttgctgcgcggcgcgggcgac ggcgccgcggcgcaggcgcaagactggtacctgcgtacctcccgcgtcga gcgcgacaaggcgggcaggatcgtcaaggtcgtgcccttctaccggcccg aggtggcgctgtatgccggcacgcccatgctgatgcgcatggtcggcacg gaagcgctgggcagctaccgcgaacgcgcgggccagcccggcgcggccgc gaccgaggcaggcgccgcagcccggcgtggcgtgtgggcacgtaccttcg ggcgtcgtttcgagcgctccgcgggcagcgaagcggcgccgtccttcaac ggcagcctggccggcatgcagctgggcgcggacctctacacgcgtcgctc ggccacccggcatgccgacgccttcggcgtgttcggcggatacgccacgg cccgcggcgatgtgcggggcctggcgcgcggcgagatccaggcggtgggc acgtccacgctgcgggccgcccagctgggcgcctactggacgcacactgg tccgagcggctggtacgtcgacacggtgctggcgggcacgcgctacaagc agcagaccagctcgtcggcccatgtcggcgcgaccagccgcggctggggc atgatggcctcggtggaggccggctacccgtggcagctcaatccgcgctg gcaaatcgagccgcaggcccagttggtgtatcagcagcttggcatcgcca atggcgccgaccgcgtgtcttcggtgtcgtacaagacgcccgatgcgctg acggggcggctgggcacgcgcctggcgggccagtacgcatacgggaaggc gcagttgcggccgttcatgggcgtatcgctgctgcacgatttcaccggcg ccgacaccgtcacgttcgcgggcgtgcacagcgtacgcgccagccgccag aacacggccgtggatctgaaggcgggcgtggacacgcagctgggcaagag cgtaggcctgtgggggcaggtcggctacggcaagtcggtcggcagcggcg acggcagcgaccgtggctggagcgccaacctggggctgcgcgtggcgtat tga SEQ ID NO:50 polypeptide sequence of Orf25

MRRLKAQAFEGSRSRPAGHGVAPTLLALALGFQGAAAWANCTTSNGATTC

TNANGSHTNKVGSGPSGMNERVTVNQGARIETNASAAISVGTSGQVRIEG

GAVVQSTVNTAASGQYAKTLEAASNNNISIQVNAQLLAKGSASQSSALGL

SGAGNTVTNHGTIRADNAAAIWVTANTANAANTIDNYGTIETVLNGGYAN

AIGSTRNNSATGAGVTVRNHANGRIVGNVKFEAGDDSVILDGGSTITGSL

NGGSGNNSLTLKAGDGTLGRAIRNFGTITKQEAGTWTLNGQVGRNDNNLK

STVKVEGGTLVLRGDNSGATQGGVLQVSAGATADVTAASAMQSISNAGTV

QFTQDSNAAYAGVLSGTGSIVKRGGGDLTLTGNNTHTGKVVVEAGSLSVS

AANNLGGAGSSVQLKGGALALKKTIVVNRGLTLDSGAQTLIIEPGTTTTW

QGQVSGAGKLVTQGGTLVLEHASNTYSGGTEINNGTLRAAHDASLGSGTL

-continued

ALKNSQLAATDSFTATRALTLAGNESIDVAATKILSWNGEISGAGTLVKE

GQGTLLLRGTNQQNGGTTVNAGTLQISRDANLGRGALALNDGTLQSTGSF

ATSRAATLRGQATMEVDASHTVTWNGELSGGGMLRKSGQGTLVLAGANTY

SGGTVVEAGALRAGHEDNLGRGAITLQGGDLLAGGSFSSNRDLTLVRGSL

DVARDATLTWSGAISGAGDLVKKGDGRLTLTGVNEYAGQTVLRGGKLRVA

RDENLGRGALVLEDNTVFESMGSHAATRQVTLKGAPKVETLDGTTLEWRG

TVDGDGKLYKQGGGTLVLSGNNTYAKGVEVWGGVVQVSRDQNLGAANGAV

TLNGGGLAANGDFTSNRQLELTAGAKAIDVAAGKDVTWRGVVNGAGALTK

AGDGTLALAGANTYTGGTRLQGGTVQVSRDNNLGQAAGAVTFDGGRLANT

GSFATARTATLNKAGQIDTDRGTTLTWNGAIGGKGELRKQGAGTLVLGGA

NTYQGDTRVEAGTLQVSADANLGQGAVHLHDSRLATTGTFATSRRLELTG

RGAVQAAAAATLDWRGTVAGAGTLVKEGAGTLVLAGDNQHAGGTEVRAGT

LQVSRATNLGPGALALENAALATTASFTATQAATLTGNAAIDTAAGTTLG

WEGAIGGTGSLHKKGEGKLVLVKDNHHDGGTTIHAGTLQVSRDANLGSGQ

SAVTLDGGALAVSAGFSSGREIVVGAGHGALSVTGGHTLQWQGQVGGAGA

LTKTGDGTLVLEHDNTHAGGTRITGGVLRVSRDENLGEAHGMLTLDGGTL

STTAGFASRRNATVGNGGGRIVVADAATLDLQGDVAGAGRLVKEGAGTLA

LGGTNTYAGGTVVEAGTLRVARDANLGGGALTLNNSRLHATAGFATGRDA

TLSGRASIDTDDRATLQWRGTVNGAGRLVKQGLGTLVLDGDNRYAGGTEV

NAGTLQVARDANLGAGDVALNGSSLAATASFATARTATLSGAAAIDTADG

ATLDWNGLLDGDGALVKQGNGTLALAAANRYGGGTIVKAGAVRIARDANL

GRAGTGVTLDGGALATTADLATGRAATLGAANGTLDVAAGTRLDWNGAIG

GAGALTKTGAGTLALNHDNQHAGGTLVHGGTLRIARDANLGAAGTAVTLD

GGTLATTASLAPERALRVGARNGVLLPDAGTTLDWRGVVAGAGKLTKAGP

GTLVLSADNRHGGGTAVTGGTLQVSRDANLGAAAGALTLDGGTLLSTASF

ASARVATLDAAGGTFVTRDGTRLDWDGAIGGAGGLVKEGAGELRLGNANT

YQGPTRIAAGRLAVNGSIASPVTVEQAGVLGGTGRIVGDVANRGVVAPGN

SIGALTVAGNYAGTGGSLEVEAVLGGDAAPADRLVLDGGAASGVTPVVVK

PQGGVGGLTLRGIPVVVAQGGATTAPGAFRLAQPLVAGAYEYQLLRGAGD

GAAAQAQDWYLRTSRVERDKAGRIVKVVPFYRPEVALYAGTPMLMRMVGT

EALGSYRERAGQPGAAAPEAGAAARRGVWARTFGRRFERSAGSEAAPSFN

GSLAGMQLGADLYTRRSATRHADAFGVFGGYATARGDVRGLARGEIQAVG

TSTLRAAQLGAYWTHTGPSGWYVDTVLAGTRYKQQTSSSAHVGATSRGWG

MMASVEAGYPWQLNPRWQIEPQAQLVYQQLGIANGADRVSSVSYKTPDAL

TGRLGTRLAGQYAYGKAQLRPFMGVSLLHDFTGADTVTFAGVHSVRASRQ

NTAVDLKAGVDTQLGKSVGLWGQVGYGKSVGSGDGSDRGWSANLGLRVAY

SEQ ID NO:51 polynucleotide sequence of Orf26

Atgttgcgaactggagccccgatgcgtagcgcccgccgccgtaccccagc acgacttgccCcgttgccggccatgctggccgccgccggcctgctgcaat ccttgggcgcgacgcccgcgGccgcggcctgtgcgcccacgctggcgcca gccagcgggcagagcgtgcaatgcgacggcGccgtggtcaaccagtcggt -continued cgaggcggcggccggcagccagaacgtaaccatcacggtgGcgcccggcg cgctgttctcgaccaacgcgacgcgggcgctgtcggtcgatgaccgcagc Cgtatcgtcaacgagggcacgatccagatggccggcggcgccggcgcctc gcgcggcgccAtggtgggtttcggcgacaacaaccagttgatcaaccgcg gatcgatcacgacatcgggcAgcggcgtgcgcggcatctcggtgcccaac gtcggcagtaccgggacgctggtcgacaacAgcggcagcatccgcaccca gggcgccagcgcgcacggcatcgccatcaacggcccgggcAaccgcgtcc agaacagcggcgccatcaccgtcaacggcaccgacgccaagggcgtgtat Ctgcaaggcggcagccccgcggccaacgtactggtcaacggcggcaccat ccatgcgcgcGgcgccagcagcaacggcatattcggccccgacggcgtgc atgtgaacaccaccaacgccAacggctttcatgcccgcgtcgagaacctg cccggcgggcgcatcctcagcgatcactcgTatgcgctgcgcgggcagaa cggcaacgataccttcatcaacgccggctacctgcaagggCacggcgggg ccggccgcgacacggccgtctacatgggcccccagggcacgggcacgctg Atcctgcgcaccggctcggccatcgccggcctggccgacggcggcggggc ggccagccacGcgtatctggagggcagcggcacggtggacaaccggttcg ccaacttccgcaccctgaccAtgcgcggcgccgactggcgctggacctcg gacgccgcgttcaccgaaagcgtggacctgCgcaccggcacattctttct tgccggcacgctcgccagcccggccaaccgcctggccgccGgcgcggtgc tggccggcaccggcacgctggccggcgcattgcgcaacgccggcgaaatc Cggcccggcccgaacgacggcagcggctacggcgcgctgacggtgcgcgg cgattacaccGgcgcgggcggcgcgctgcgcgtcaacacggtgctggccg gcgacggggccgcctcggacAggctggtcatcgatggcgggcacgccggc ggcagcaccccggtcacggtggtcaaccggGgcgggcagggcgcgctgac cgcggccgacggcatcctggtggtccaggccatcaatggcGcaagctcgg acgccggcgccttctcgctggccgccccctcaacgccggcgcatacgag Tacaggctgtaccgcggcggcgccacgggcgccgcgccggacagctggta cctgcgctcgCgggcctatctggtcgaggaccaactggccggcagccttg ccgaagccgaggcgatcgccGacgacatcggccggcgcaccggcgagcgg ccgagcatcgaggacacgccgctgtaccggCccgaggtggcgctgtacag cagcattcccatgctggcgcggcgcatgggcctggcccagCtgggcacct tccacgaacggcagggcaaccaggcgctgctggcgcgcgacggcgaacgc Gtcgcggcctgggcgcgcgcctatggcggcaacagcaagcaggcgctcga cggcgatgcgCaacccggcatcgacgcccgcctggccggcgtgcaactgg ggcaggacctctacagcagcGtgcgcccggacggcggacagcaccgcttc gggctgttcggcggctatggccaggcgcgcGgcgacacccacggctcggc cggcggcgagcgcgacgccgctaccggccggctgaccatcGacggctaca gcgtcggcggctactggacctatgtcggcccgcgcgggtggtacgtggat Gccgtgctggccaacacctggatggacatcgacaccgactccaaggccgg gcgcgacgccGatacgcgcggccaggcgttcacggcttcgctggaaagtg gctacccgctggcgctgtccGagcgctggacgctggagccgcaggcgcag -continued ctcatctaccagcacacgcgcgtcgacggtTtctcggacgccgtgtccga ggtgcgcatccgcgacgacaacgcgctgaccgcccgcctgGgcgcccggc tgcagggcgagtacgcggccgccgcgcaggtgtggcgcccctacgcggcg Ctgaatttctggcgcaccttcagcggcgagaacaccgtcgtgctgggcga agacagcatcGatacccggcgcggcgcgacctcgctcgaactggcggccg gcgccagcgtgacgctggccCgcagcctggccctctacggcaggctggcc tatgccaccagcatcgacagccagtatctgCgcggcgcttcggcgcagct ggggatgcgctacacctggtaa SEQ ID NO:52 polypeptide sequence of Orf26
MLRTGAPMRSARRRTPARLAPLPAMLAAAGLLQSLGATPAAAACAPTLAP

ASGQSVQCDGAVVNQSVEAAAGSQNVTITVAPGALFSTNATRALSVDDRS

RIVNEGTIQMAGGAGASRGAMVGFGDNNQLINRGSITTSGSGVRGISVPN

VGSTGTLVDNSGSIRTQGASAHGIAINGPGNRVQNSGAITVNGTDAKGVY

LQGGSPAANVLVNGGTIHARGASSNGIFGPDGVHVNTTNANGFHARVENL

PGGRILSDHSYALRGQNGNDTFINAGYLQGHGGAGRDTAVYMGPQGTGTL

ILRTGSAIAGLADGGGAASHAYLEGSGTVDNRFANFRTLTMRGADWRWTS

DAAFTESVDLRTGTFFLAGTLASPANRLAAGAVLAGTGTLAGALRNAGEI

RPGPNDGSGYGALTVRGDYTGAGGALRVNTVLAGDGAASDRLVIDGGHAG

GSTPVTVVNRGGQGALTAADGILVVQAINGASSDAGAFSLAAPLNAGAYE

YRLYRGGATGAAPDSWYLRSRAYLVEDQLAGSLAEAEAIADDIGRRTGER

PSIEDTPLYRPEVALYSSIPMLARRMGLAQLGTFHERQGNQALLARDGER

VAAWARAYGGNSKQALDGDAQPGIDARLAGVQLGQDLYSSVRPDGGQHRF

GLFGGYGQARGDTHGSAGGERDAATGRLTIDGYSVGGYWTYVGPRGWYVD

AVLANTWMDIDTDSKAGRDADTRGQAFTASLESGYPLALSERWTLEPQAQ

LIYQHTRVDGFSDAVSEVRIRDDNALTARLGARLQGEYAAAAQVWRPYAA

LNFWRTFSGENTVVLGEDSIDTRRGATSLELAAGASVTLARSLALYGRLA

YATSIDSQYLRGASAQLGMRYTW

SEQ ID NO:53 polynucleotide sequence of Orf27
ATGCCTGCTCAACGCACTCCTCGCACCGCGGTTTGTGAGGCCACCGTCCG

TTCATCGCCACGTTGGATCCATTGCACCGGATTCGTGCTGTGCGCGCTGC

TGGCGGCATGCGGAGGCGGTGGCGGCGGAGGTGGCGGCGGAGGCGGTGGC

GGCAGCCCGGGCGGCCGTGCGCCATCGGCGCCGCAACCCGCCCCTTCGCC

ACGCCCCGAACCTGCACCCGAGCCGGCACCCAATCCTGCGCCCAGGCCTG

CTCCGCAACCGCCGGCGCCCGCGCCTGGAGCGCCCCGTCCTCCCGCGCCG

CCACCGGAGGCTCCCCCGCCCGTGATGCCGCCGCCGGCCGTGCCGCCTCA

GCTGCCCGAAGTGCCGGCCGCAGACCTGCCCCGCGTGCGCGCGCCGCTGT

CGACATACCGGCGGCCGCAACGCACCGACTTCGTCACGCCCACCGGCGGG

CCGTTCTTCGCCAAGCAGGACAAAGCCCTCAACACCATCGACCTGAAGAT

GGCGCACGACCTGAAGCTGCGGGGCTACCGCGTCAAAGTCGCGGTCGTCG

ACGAAGGCGTGCGCAGCGACCATCCGCTCCTGAACGTCGAGAAGAAATAC

GGTGGCGATTACATGGCCGACGGCACCCGCACCTACCCCGACCCCAAGCG

-continued

CCAGGGCAGGCACGGAACCTCGGTCGCCCTGGTACTGGCCGGACAGGACA

CCGACACGTATCGCGGCGGCGTTGCGCCCAATGCCGACCTCTATTCGGCC

AACATCGGCACGCGGGCCGGCCACGTCTCCGACGAAGCCGCATTCCACGC

CTGGAACGACCTGCTCGGGCACGGCATCAAGATCTTCAACAACAGTTTCG

CCACCGAAGGTCCGGAAGGCGAGCAGCGCGTCAAGGAGGACCGCAACGAA

TACCATAGCGCCGCCAACAAGCAGAACACCTACATCGGACGGCTCGATCG

CCTGGTGCGCGACGGCGCGCTCCTCATTTTCGCCGCCGGCAACGGCAGGC

CATCGGGTCGCGCCTACAGTGAGGTCGGCTCGGTCGGACGCACCCCTCGC

GTCGAGCCGCACCTGCAACGCGGCCTGATCGTGGTCACCGCGGTGGACGA

AAACGGCAGGCTCGAAACATGGGCCAACCGCTGCGGGCAAGCGCAGCAAT

GGTGCCTGGCCGCGCCCAGCACCGCCTACCTGCCCGGCCTCGACAAGGAC

AACCCCGACAGCATCCACGTCGAACAGGGCACGTCGCTATCCGCGCCGCT

GGTCACCGGCGCCGCCGTACTGGTGCAGGATCGCTTTCGCTGGATGGACA

ACGACAACCTGCGCACCACCTTGCTGACCACGGCGCAGGACAAGGGCCCG

TACGGCGTCGACCCGCAGTACGGCTGGGGCGTGCTCGACGTGGGCCGCGC

CGTGCAGGGCCCGGCGCAGTTCGCCTTCGGCGACTTCGTCGCCCGGGTTA

CGGATACCTCCACGTTCGGCAACGACATCTCCGGCGCCGGCGGGCTGGTC

GTCGACGGCCCCGGCGCGCTGGTCCTGGCCGGCTCCAATACCTATGCCGG

CCGCACCACCATCAAGCGCGGCACCCTCGACGTCTTTGGCAGCGTCACGT

CCGCCGTCACCGTCGAGCCTGGCGGCACGCTGACCGGCATCGGCACCGTC

GGCACGGTGACCAACCAGGGCACGGTGGTCAACAAGGAGGCCGGCCTGCA

CGTCAAGGGAGATTACTCACAGACCGCGCAGGGCCTGCTGGTCACCGACA

TCGGCTCGCTGCTCGACGTATCCGGCAGGGCCAGCCTGGCCGGCCGGCTG

CATGTGGACGACATCCGCCCCGGCTACGTCGGCGGCGACGGGAAAAGCGT

CCCGGTCATCAAGGCCGGCGCGGTGTCCGGCGTCTTCGCCACGCTGACGC

GCAGTCCGGGCCTGCTGCTCAACGCCCGGCTGGACTACCGGCCCCAGGCC

GTCTACCTGACCATGCGGCGCGCCGAGCGCGTCCATGCCGCGGCGCAGCG

GGGCGCGGACGACGGGCGTCGCGCGTCGGTGCTGGCCGTGGCCGAGCGGC

TCGACGCCGCGATGCGCGAACTCGATGCCCTGCCCGAGTCGCAGCGCGAC

GCCGCGGCGCCGGCGGCCGCCATCGGACGCATCCAGCGCGTGCAAAGCCG

CAAGGTGCTGCAGGACAACCTGTATTCGCTGGCCGGCGCCACCTACGCCA

ACGCCGCCGCGGTCAACACGCTGGAGCAGAACCGCTGGATGGACCGCCTC

GAGAACCACCTGGCCCAGGCCGGCGGCGAGCGCGTGGCGGCCATCGCCGA

GTATCGCCACGGCCAGTTGCGCTGGCGCCCCGATGGCCTGCAAGGCCGCC

AGCGCGGCAACGGCATCATGCTGGGCCTGGCGCGCGAAGTCTCGGCCGGC

CTGAGCCTGGCCGCGGCGCTGACCCACAGCCGCACGCACTGGGACGAGTC

GTCCGGCGCGCCGGCCCGCGACAACGCCGCCATGACCACGCCGGGCGTAC

TGCTGGGCGCGCGCCCGCGCCTGGGAGGACGGCTGGTTCGTGCAGGGCGCA

CTGGGCTATAGCCGCTACCGCAACCAGGCCACGCGCCACATCTCGCTCGG

CGATGCCGGCCACACCGTCGGCGCCACCGCCCGGGGCCACGTCTGGCAGG

CCGACGCCGGCCTGGGACGCCAGTGGACGCTCGCCCCCGGACACACGCTG

-continued

GCGCCTCGGGCGGGCCTGCAACTCACGCATCTGCGCCAGCAAGGTTTCAG
CGAGAGCGGCGCGCAAGGACTGGGGCTGCGCGCCCACGCCTTGACGCGCA
CCGTGCCCACGCTGTGGGCGCAACTGCAAAGCCGCCATGCCTTCATGCTG
GGAGCCACGCCCATGACGGCGCAGCTGCAACTGGGCGTCTGGCATGACCT
GCGCGCGCGGCGCTACGCCGCCTCCGGCGGTTTCGCCGGCCTGGCGCAGG
ACCAGGGCGCCAGCGGCTACTGGCCCGTGCCGCGCACACGCGTACAGGGC
GCGCTCGGCCTGCGCGCCGAGTTCGCGCCAGGCCTCGTGCTGGGGCTGGG
CTACACGGGCCAGCTTGCCACGCACTGGGTCGATCACCAGCTCAGCGCCA
GCCTCACTTACCGCTACTGA

SEQ ID NO:54 polypeptide sequence of Orf27
MPAQRTPRTAVCEATVRSSPRWIHCTGFVLCALLAACGGGGGGGGGGGGG
GSPGGRAPSAPQPAPSPRPEPAPEPAPNPAPRPAPQPPAPAPGAPRPPAP
PPEAPPPVMPPPAVPPQLPEVPAADLPRVRAPLSTYRRPQRTDFVTPTGG
PFFAKQDKALNTIDLKMAHDLKLRGYRVKVAVVDEGVRSDHPLLNVEKKY
GGDYMADGTRTYPDPKRQGRHGTSVALVLAGQDTDTYRGGVAPNADLYSA
NIGTRAGHVSDEAAFHAWNDLLGHGIKIFNNSFATEGPEGEQRVKEDRNE
YHSAANKQNTYIGRLDRLVRDGALLIFAAGNGRPSGRAYSEVGSVGRTPR
VEPHLQRGLIVVTAVDENGRLETWANRCGQAQQWCLAAPSTAYLPGLDKD
NPDSIHVEQGTSLSAPLVTGAAVLVQDRFRWMDNDNLRTTLLTTAQDKGP
YGVDPQYGWGVLDVGRAVQGPAQFAFGDFVARVTDTSTFGNDISGAGGLV
VDGPGALVLAGSNTYAGRTTIKRGTLDVFGSVTSAVTVEPGGTLTGIGTV
GTVTNQGTVVNKEAGLHVKGDYSQTAQGLLVTDIGSLLDVSGRASLAGRL
HVDDIRPGYVGGDGKSVPVIKAGAVSGVFATLTRSPGLLLNARLDYRPQA
VYLTMRRAERVHAAAQRGADDGRRASVLAVAERLDAAMRELDALPESQRD
AAAPAAAIGRIQRVQSRKVLQDNLYSLAGATYANAAAVNTLEQNRWMDRL
ENHLAQAGGERVAAIAEYRHGQLRWRPDGLQGRQRGNGIMLGLAREVSAG
LSLAAALTHSRTHWDESSGAPARDNAAMTTPGVLLGARRAWEDGWFVQGA
LGYSRYRNQATRHISLGDAGHTVGATARGHVWQADAGLGRQWTLAPGHTL
APRAGLQLTHLRQQGFSESGAQGLGLRAHALTRTVPTLWAQLQSRHAFML
GATPMTAQLQLGVWHDLRARRYAASGGFAGLAQDQGASGYWPVPRTRVQG
ALGLRAEFAPGLVLGLGYTGQLATHWVDHQLSASLTYRY SEQ ID NO:55 polynucleotide sequence of Orf28
Atgtcgtccccgcgtccccccgcaccttggcgcgcaccgctcgcgcttgc
cggcctgtcgCttggttgcgctgccggcgcatacggcgcgcccgcgccgg
cacaaaccgtcgtcaccctgCccgcgcaagaggtcatcggcgacagcgtc
gcggcggcccggtccgtgctgcgcctgccggagatcgagcgcgcgcaggc
cgacaacttcgcctccctggtcgatcagctgccgggcatctcgatggccg
gctctccgcgccccggcgggcaaagcctgaacatctggggcatgggcgat
accgaggacgtgaaaatcgtcctcgatggcgcgcccaagggtttcgagaa
gtaccgccagggctcggtcttcatcgaacccgaactgatccggcgcatcg
aggtcgacaaggggccgcacaacctggtcgacggcaatggcgggttcggc -continued ggcaccgtcaagatcgataccaaggatgcggccgacctgttgccgccggg
cgcgcgcttcggcgcgctggccaagtacggccgccattcgaacgacggcc
aggacatctacagcgtggcgctgtacggccgcacccgcgccgacggggcc
gacggcctgctgtatgccaaccgccgcgacggcggcgatctgcgcgccgcc
cgacggcacccgcttcgcatactcgcgcaacaaccagcgctcgctgctcg
ccaaggtcaacctctatccggacgacgcccagaccatcaccctgtcggcc
atgcgttcgaatgcggcgggttggcaacccttcgcggccaagcgcgacga
tcttcccgcgccttcgcaggccgatatcgaccgctacggcctgaccgaag
catggcggcgcaagctggtccatcgcgaccagctcgaccagaactacagc
gcgaaatggaacatcgccccatccgcccatccctgggtgaacctcacgct
ggcctatgcccgctcggacacccggcagcgcgaccggcgctcgtcccggg
cgtcgcagtcggcctttctcggcacgctgggcaacaagagttgggtcgac
taccgcgacgaccggttcgacctcagcaacgaaagccacgtggccctggg
cacggccgagcatgtcctgctggcgggcctgcgctggcaccggcatcgcc
gcgacacgctcatgtactacccgcccggccgcggcgagcccgattacaac
cacgggtacttccagccgcactacatgccttcgggcacgcagaccgtgcg
cagcctgtacctgcaggacgccgtcaccgtcggcggccttaccgtcacgc
ccggcgtgcggtacgaccatgtcgccaataccggcaggccaaacgacgcg
ccccgctacaacaaccccgcccccgtggccgggcatgactaccgccgcgt
ctcgtacgcgggctggaccccgcacctgggcgtggtctggaaggcggcgc
gaggcgtggcgctgttcgccgacgccggccgcacctggcgcgcacccgtc
atcgacgaacagtacgaagtgcaatatgcgaagtccaatgtgtcgggcag
cagccgggcgctgcggcccgagcgcatcgtgggcctgcgcgccggcgccg
tactggattacaacgatatcgcgacgcgcggcgacagcgtgcagatacgg
accacgctgtttcgcaatcgcggcaagcacgagatcttccagcgccgtgg
cgtggcatgccgcgggcaggccgagggcggcgccgcctcggactgcccca
agcccttgtccaactaccgcaacctgcccggctacaccatcgaagggctg
gaactggagacctactacgacagcccggcgatgttcgccagcctgtcgct
ttcggccatgcgcgggcaccgcgacgcctcgccgcgcgatccatgggggc
cgcgcacctggatcgccgagatcccgccggtctcggcgcgcgcgatgctg
ggcgtgaaactgccgcgcctggacatggtcctgggatggcgcggcgaatt
cgtgcgccgccaggaccgctcgccgaccgacggcgacccgctggccggct
actgggccttgcccaagaccgccggctacgcgctgcacggcctgttcgca
agctggcaaccccggcatgtcaaaggcctggacgtgcgcctggccgccga
caacctcttcaaccggccctatcatccctacctgggcgaagcggtatcgg
gcacgggccgcaacatcaagctgagcatcgcccagcgcttctag SEQ ID NO:56 polypeptide sequence of Orf28
MSSPRPPAPWRAPLALAGLSLGCAAGAYGAPAPAQTVVTLPAQEVIGDSV
AAARSVLRLPEIERAQADNFASLVDQLPGISMAGSPRPGGQSLNIWGMGD
TEDVKIVLDGAPKGFEKYRQGSVFIEPELIRRIEVDKGPHNLVDGNGGFG
GTVKIDTKDAADLLPPGARFGALAKYGRHSNDGQDIYSVALYGRTRADGA -continued

DGLLYANRRDGGDLRRPDGTRFAYSRNNQRSLLAKVNLYPDDAQTITLSA

MRSNAAGWQPFAAKRDDLPAPSQADIDRYGLTEAWRRKLVHRDQLDQNYS

AKWNIAPSAHPWVNLTLAYARSDTRQRDRRSSRASQSAFLGTLGNKSWVD

YRDDRFDLSNESHVALGTAEHVLLAGLRWHRHRRDTLMYYPPGRGEPDYN

HGYFQPHYMPSGTQTVRSLYLQDAVTVGGLTVTPGVRYDHVANTGRPNDA

PRYNNPAPVAGHDYRRVSYAGWTPHLGVVWKAARGVALFADAGRTWRAPV

IDEQYEVQYAKSNVSGSSRALRPERIVGLRAGAVLDYNDIATRGDSVQIR

TTLFRNRGKHEIFQRRGVACRGQAEGGAASDCPKPLSNYRNLPGYTIEGL

ELETYYDSPAMFASLSLSAMRGHRDASPRDPWGPRTWIAEIPPVSARAML

GVKLPRLDMVLGWRGEFVRRQDRSPTDGDPLAGYWALPKTAGYALHGLFA

SWQPRHVKGLDVRLAADNLFNRPYHPYLGEAVSGTGRNIKLSIAQRF

SEQ ID NO:57 polynucleotide sequence of Orf29

Atgaaggcgcggcgcctggccatggcgggtctgtcgctggcgctcggcgg ctgctcgctgTcgcagcagatgcaggccatgcgcgacgccgcgacgtccc tgcgcgcacgcctgctcgaaGggcagcaggccgtgggccgggccggcgag cggccggcgcgcgaagccgcccaggacgtcgcgcggccctggctggccgg gcgcgcccagccgctggcacgcgaggtgctgctgccgccggcgctgcgcg ccgatgtcgatacgaccctgctgttcgcgggcaaggccacgctgcccgtg ctggccgagcgcctgcatcgcgccaccggcatcgccgtgcgcgtgcatcc cgacgcgctgctgccgcgcgccgccttcctgccgcgcctggcggggcagg ccgagctggcggccgagcctcccgcccaggccgaactgcgggccgggccg cgtccgctggccgacacgctcgacgcgctggccgcgcagctgtacgtgca ctggcgctaccatcgcggcgccatcgagttctaccgcaccgaaacgcggg tcttcgatgtgcgcacgctggcgctggccgccagcgcgcaggctcggctg ggccgcgccggcagcggcgagacgggcagtttcgaccatgcctcgagcac ggtgctcagcgccgacgccggcaaggcgctgcaggccgtgcgggaccgcg tcgccgctttcctgacgcgcgccggcgtcatcgccgagatcgaggcgggc ggaagcacgctcgcggtcacggatacgccggaggcgctcgcgcgcatcga aaaatacctgcaaggcgagaaccgcgccctgacgcgccgggtacgcctgg tgttcgaagagctcacggtgcgcaccacggccgccgccgaaggcggcatc gattggcaggcggtctacgccagcgcgcgcgccgcggcgtcgtacgccat gcccggcggggccggcgcggcaggcgcgctcggggcccgcgtgctggccg ggccctggcgcgacgcgcgcgccctgatcgccgcgctgagcaccatggga gcggtactgcgccatcgcagcatacccatgctgacgctgaaccggcgcgc cgtcacccacgccgtgcgcaccacgttttcctacgtggaccaggtgcagc gcctgagcccgaccgcggcggcgcccggtgggcgcgatgccgtgcccggg ctggcggtgcagcagaagcgcgagacggtgggcacgttcctcacgctgtt gcccgaggcgcgcgatgacggccgcatcctgctctccatttcctatgaca acaccattgcccagccgctgcgcaccctgaccttcggcgagggcggccag caagtgtcgctgcagcagatcgccatcgacggcagcggcatcgtgcagca ggtcgagctgctgcccggccagcccgtcatcctgtcgggcttcgaccaca gcgaagaccaatacgaacgccaccgcctgtttcccgatgcgccgctcgcg gccggcgggcacgaccgcacggcgcgcgagcgggtcacgaccgtggtcat ggtcaccgcgcagatcgacgagggttga SEQ ID NO:58 polypeptide sequence of Orf29

MKARRLAMAGLSLALGGCSLSQQMQAMRDAATSLRARLLEGQQAVGRAGE

RPAREAAQDVARPWLAGRAQPLAREVLLPPALRADVDTTLLFAGKATLPV

LAERLHRATGIAVRVHPDALLPRAAFLPRLAGQAELAAEPPAQAELRAGP

RPLADTLDALAAQLYVHWRYHRGAIEFYRTETRVFDVRTLALAASAQARL

GRAGSGETGSFDHASSTVLSADAGKALQAVRDRVAAFLTRAGVIAEIEAG

GSTLAVTDTPEALARIEKYLQGENRALTRRVRLVFEELTVRTTAAAEGGI

DWQAVYASARAAASYAMPGGAGAAGALGARVLAGPWRDARALIAALSTMG

AVLRHRSIPMLTLNRRAVTHAVRTTFSYVDQVQRLSPTAAAPGGRDAVPG

LAVQQKRETVGTFLTLLPEARDDGRILLSISYDNTIAQPLRTLTFGEGGQ

QVSLQQIAIDGSGIVQQVELLPGQPVILSGFDHSEDQYERHRLFPDAPLA

AGGHDRTARERVTTVVMVTAQIDEG

SEQ ID NO:59 polynucleotide sequence of Orf30

Gtgaccatgttcatccgctggctcattctctccgcgtgcctgctgctggc cgcctgcagcCgcgctcccgataccgagatcctgcagcgcgatgtcggcc agaccctggccgccacgtacGgcccggacctgttcgacatcgtcgcgctg cgccgcatgggctcggccaccgacagcacggccccgccgggccagacgcg ccgggtggtctattacgatgtggtgctgggcctgaagaaggacctcaccc tgggcgcctgggaccagcccggcgccgccgcgctggtcagcctgctgggc gccgggccgcgcagcatctcgggggtgaaatccagcggcaatgccgccgg cgaccagatcgtcgcccacgccagcgccatctaccagcgcgacgcagagc aatgggtgcacgtcgccccggccagcttcacggccaccgaagcgccctcg ctggacaccggcgcgccgccgccggtgacgcgccagctgctccagacgct ggagcagatcacgcgttccgtgccctacagcgcctccagcaccgcccagc acgtggtgcaacaggagctggagcgctcggtggcgcgcatcaatggccgg cttgcccgcctgcaaaagggctacccgctggcgaccggccccgacaaggg cgagtacctggcgttcggccaggcgctggccgcgatcgggcgcaacgagc aggtgcgcgtcattcccctcattaccggcggcagcgcggacaacatggcc atgctgcgcagcggcgcggcggtggccgccctgtcgcaggccgacatcgc gcaactggcctacgagggcaaggggccgttcgaaagccagggaccgttct ccgggttgcgcgcgctgggcagcctgtatccggagctggtgcacatcgtg gtgcgccagggcgatggcatcgccacggtgggcgcgctgcgcggcaagaa gattgccctgggcccgtcgggctcggcggtacgcaccacgctggagaccg tgctggcagcccatgggctgcagccggggcgcgactatgcagtcatcgac acgccggccgccgcggccctgccgcagctgagcgaaggacgggtcgacgc ggtggcgcaggtcatcggtacgccggccgcgcccttgcgcgcggcgctga cccaggcgcgcctggcgctgctgccgctggaccgggctgcgatcgacaag ctggtgcaggccgatccgaccctgatggcgctggacatcccggccaacac ctaccccagccaggccgcggccatccccacggtgggcatggcggcgctgc -continued tggtcaccacggccgatctgacgcgcgacgaggccgcgcatatggtggac gtggtataccgggccgggcaggacctgctggccgccgggtccgcgcaggg cgcgcaggtatccgcggccaacgccgggcgcggattgagcattcccctgc acgacggcgccgtggaagccttcgagaaactgggcgcgccgcccctgccc gagggcaggtag SEQ ID NO:60 polypeptide sequence of Orf30
VTMFIRWLILSACLLLAACSRAPDTEILQRDVGQTLAATYGPDLFDIVAL

RRMGSATDSTAPPGQTRRVVYYDVVLGLKKDLTLGAWDQPGAAALVSLLG

AGPRSISGVKSSGNAAGDQIVAHASAIYQRDAEQWVHVAPASFTATEAPS

LDTGAPPPVTRQLLQTLEQITRSVPYSASSTAQHVVQQELERSVARINGR

LARLQKGYPLATGPDKGEYLAFGQALAAIGRNEQVRVIPLITGGSADNMA

MLRSGAAVAALSQADIAQLAYEGKGPFESQGPFSGLRALGSLYPELVHIV

VRQGDGIATVGALRGKKIALGPSGSAVRTTLETVLAAHGLQPGRDYAVID

TPAAAALPQLSEGRVDAVAQVIGTPAAPLRAALTQARLALLPLDRAAIDK

LVQADPTLMALDIPANTYPSQAAAIPTVGMAALLVTTADLTRDEAAHMVD

VVYRAGQDLLAAGSAQGAQVSAANAGRGLSIPLHDGAVEAFEKLGAPPLP

EGR

SEQ ID NO:61 polynucleotide sequence of Orf31
Atgatccgtatgcctggtttccgattctccgttccgccgcgccgccggct ggccgtcgcgGcgctgtgcgcggcgctgggcggctgtgcggtcgggcccg actaccagcgacccgccatcGacgtgggggccgcctacaaggaggccgcc gcgccgcagcccggctggacgcccgcgcagcccagcgacgagagcgcgcg cgggcaatggtggcaggtgtatggcgacccggtgctcgacggcctggtgc agcaattgaaccagggcaactactccgtggcgcaggccgaggccaattat cgccaggcccaggcgctggtgcgcaatgcgcgcgccggcttcttccccac cataggcgcgggcgccgacgtgacgcggtccggctcgggcggcggcagcg gcgccggctcgaacggcagctcggtcggcaaccagtactcgctcagtggg tcggtcagctgggaagtcgatgtgtggggccgggtgcgccgcgaagtcga gtccagccgcgccgaggcgcaggccagcgcggcggacctggccgtcaccc gcctgagcgcgcaggccgccctggtgcagaactacctgcaattgcgcgtg ctcgacgagcagaaacgcctgctcgacgccacggtgctggcctacgagcg ctcgctgcgcctgacgcagaaccgctacgaagccggcgtggtgggcaagt ccgacgtggcggtggcgcgcacccagctggagaacacgcgggcccagtcc atcgacctggactggcagcgcggccagttcgagcacgccatcgcggtgct gatggggcaggcgccttcgcgcttcgccctgccggcgcagccgttcgcgc agcaactgccggacatcccggcgggcctgccctcgcaactgctggagcgc cggcccgacgtggcggccgccgagcggcgcgcggccgccgccaatgcgca gatcggcgtggcgcaggcggcctggttcccggacctgaccttgtcggcca gcggcggttttcgcagcggccagttcgccgagtggctgaccgcgccggcg cgcttctggaccctcggcccggcgctggccatgacgctgttcgacggcgg cgcgcgttcggcgcgcgtcgagcaggcccgcgccgcctatgacgcgcagg -continued cggccgcctaccgccagagcgtgctgacggcgctgcgcgaggtggaggat tacctggtgcagctgcgcgtgatggagcacgagcagcaggtgcagcgcaa tgcgctcgagtccgcgcgcgaatcgctgcgcctggcgcgcaaccagtacg agcaggggctgatcgactacctgagcgtggcggtgctggaaaccaccgcg ctgaacaccgagcgcaacgccatcagcctgctgggcagccggctcaacgc cagcgtgcagctgatcgcggcgctgggcggcgggtggcagggcttgccgg ccgaggcggcggccagcgcggcggccgagccgt7ccgcgccctag SEQ ID NO:62 polypeptide sequence of Orf31
MIRMPGFRFSVPPRRRLAVAALCAALGGCAVGPDYQRPAIDVGAAYKEAA

APQPGWTPAQPSDESARGQWWQVYGDPVLDGLVQQLNQGNYSVAQAEANY

RQAQALVRNARAGFFPTIGAGADVTRSGSGGGSGAGSNGSSVGNQYSLSG

SVSWEVDVWGRVRREVESSRAEAQASAADLAVTRLSAQAALVQNYLQLRV

LDEQKRLLDATVLAYERSLRLTQNRYEAGVVGKSDVAVARTQLENTRAQS

IDLDWQRGQFEHAIAVLMGQAPSRFALPAQPFAQQLPDIPAGLPSQLLER

RPDVAAAERRAAAANAQIGVAQAAWFPDLTLSASGGFRSGQFAEWLTAPA

RFWTLGPALAMTLFDGGARSARVEQARAAYDAQAAAYRQSVLTALREVED

YLVQLRVMEHEQQVQRNALESARESLRLARNQYEQGLIDYLSVAVLETTA

LNTERNAISLLGSRLNASVQLIAALGGGWQGLPAEAAASAAAEPSAP

SEQ ID NO:63 polynucleotide sequence of Orf32
Atgacgcatcccgtcccgacgacctttgcacgtaccgccggcgcgctgct tgccgcgctgGcgctggccggctgcgccgtggggccgcagtaccaggcgc ccacgcccgcgccggtgaagCtggccagccccgaacaggcgctgttctcg gccgaccggttgcaacgcgaatggtggcgccagttgcaggatgcccggct ggacgcgttgatcggcctggcgctggcgcgcaacctcgatatcggcctgg cgctggcgcgcaacctcgatatccgccaggcgcaggcgcgcctgcgcgaa gcgcgcgcccgcgctcgacgaaaaggaactggaccgctggccgaccgtgac cgcggccggcggctacacgcgcagcctgtcgcagatcaaccccggccccg accagcgcaacctcgcgcaaagctaccgcgcgggcttcgacgcgacctgg gaaatcgatttgttcggccgcctgcagcgacgggccgaggccgcggccgc gcgcgaccaggccgccgccgccgacctggcccagacgcgcctggtggtgg tggccgagctggcacgcaactatttcgagatgcgcggcgccgagcaacgg ctggccgtggcgcgcgccaacctcgccacccagcaggagacgctgcgcgt caccgcggcgctggtggaaaccggccgcggctatgccggcgacctggcca gcgcacgggccgagctggccggcacgcgggcgctgctcgcgccgctggag acgcaacggcgcctggcccagtaccacatcgccgtcctggcggccatgcg gccggccgagctgggcgagctgcggcaggagcagccgctggcgccgctgg ccgcgcaattgcccatcggcgacgtggccatgctgctgcaacgccgcccc gacgtgcgcgccgccgagcgcctgctggccgccaccaacgccgacgtcgg cgccatcaccgccgaactgtatccgcgcatcgacctgggcgggttcctcg gtttcattgccttgcgcggcggcgacctgggccaggccagcagcaaggcc ttcgcgctggcgccgacgatcagctggccggcgttgcacctgggcagcgt ccaggcgcagctgcgcgcgggccaggcccggcacgacgcggcgcgggcgc -continued gctacgaacaggtggcgctgcaggccatcgaggaagtggaaggcgcgttg
acgcgctatggacagaaccagcagcggctgcgcgacctgcttgacagcgc
cacgcagagccagcgcgccgccgacctggcgcaaacgcgctatcgtgaag
gggccgcgccgtatttgacggtgctggacgcgcagcgtactcttttgcgc
gcacaggatgccgtggcgcaatccgagtcggagtcctataccagcctggt
cgcgctctacaaggccctgggcggaggctggaataccgacgccgccgcgc
ccgcccgttccgcccgcaccgccgccctgccggccagcccctga SEQ ID NO:64 polypeptide sequence of Orf32
MTHPVPTTFARTAGALLAALALAGCAVGPQYQAPTPAPVKLASPEQALFS
ADRLQREWWRQLQDARLDALIGLALARNLDIGLALARNLDIRQAQARLRE
ARAALDEKELDRWPTVTAAGGYTRSLSQINPGPDQRNLAQSYRAGFDATW
EIDLFGRLQRRAEAAAARDQAAADLAQTRLVVVAELARNYFEMRGAEQR
LAVARANLATQQETLRVTAALVETGRGYAGDLASARAELAGTRALLAPLE
TQRRLAQYHIAVLAAMRPAELGELRQEQPLAPLAAQLPIGDVAMLLQRRP
DVRAAERLLAATNADVGAITAELYPRIDLGGFLGFIALRGGDLGQASSKA
FALAPTISWPALHLGSVQAQLRAGQARHDAARARYEQVALQAIEEVEGAL
TRYGQNQQRLRDLLDSATQSQRAADLAQTRYREGAAPYLTVLDAQRTLLR
AQDAVAQSESESYTSLVALYKALGGGWNTDAAAPARSARTAALPASP SEQ ID NO:65 polynucleotide sequence of Orf33
Atgaaacctgtcgtcatgagaaccttgttgtcccttgccgtggccacggc
cctggccggcTgctcgctggcgcccacctacgagcgcccgcaggcgccgg
tcgacgcggcctatccgtccGgcccggcctacggcgcgccgggccaggcc
gccgcgggcgcgccggccgccgccgacgtgggctggcgcgacttcttcgg
cgacccgctgctgcaggagctgctggcgctgtcgctggccaacaaccgcg
acctgcgggtcgccgcgctcaacgtggaggcggcgcgcctcaacccgagc
ggacaggccggcatcagccgcagctaccaggtcggtgccagcctgtcgac
ctgggagctggacctgttcgggcgcatccgcagcctcagcgaacaggcgc
tgcagctctatctggcccaggacgaaacgcgcctggccacccagctgacg
ctggtggccgagaccgccaacgcctacccgaccctgcgcgccgaccagga
actgctggcgctgacgcgccagacgctggcggcccagcaggagtcgtaca
agctgacccgccagagctacgacctgggcgtggcgaccgagctggacctg
agccaggccgagatttcgctgcgcaccgccgagcgcaatctgtcgcagta
cacgcgcatggcggcgcaggaccgcaacgcgctggtgctgctggtgggcc
agccgctgccggccggcatcggcgcgcagctggaccaggccgtggcgctg
cccgacggcgtggtcctggccgacctgccggcgggcctgccgtcggatct
gctcgcgcgccggccggatatccgcgcggcggagcaccagctgcaagccg
ccaacgccagcatcggcgcggcgcgcgcggcgttcttcccgcgcatcagc
ctgaccggctcggccggcacggccagcgccagcctgggcggcctgttcga
tgccgggtcgggggcctggagtttcgcgccgcagatcagcgtgccgatct
tcgcgggcggggcgctgcgcgccagcctggacctggccaagatccagaag
gacatcggcatcgcgcgctacgagcaggccatccagagcgggttccgcga
ggtctccgacgcgctggccggccgcggcacattgcaggagcagatccggt
cgcaggaactgctggtgcaggccaaccagcgcgcctacgacctgtcgcag
cagcgttaccagcagggcatcgacaactatctcagcgtgctggattcgca
gcgttcgctgtatacggcgcagcagacgctggtcgagacgcggctggcgc
gcctgtccaacctgatccagctctacaaggcgctgggcggcggctggtcc
gagcgcacggtggcggcggcgcaggccggctga SEQ ID NO:66 polypeptide sequence of Orf33
MKPVVMRTLLSLAVATALAGCSLAPTYERPQAPVDAAYPSGPAYGAPGQA
AAGAPAAADVGWRDFFGDPLLQELLALSLANNRDLRVAALNVEAARLNPS
GQAGISRSYQVGASLSTWELDLFGRIRSLSEQALQLYLAQDETRLATQLT
LVAETANAYPTLRADQELLALTRQTLAAQQESYKLTRQSYDLGVATELDL
SQAEISLRTAERNLSQYTRMAAQDRNALVLLVGQPLPAGIGAQLDQAVAL
PDGVVLADLPAGLPSDLLARRPDIRAAEHQLQAANASIGAARAAFFPRIS
LTGSAGTASASLGGLFDAGSGAWSFAPQISVPIFAGGALRASLDLAKIQK
DIGIARYEQAIQSGFREVSDALAGRGTLQEQIRSQELLVQANQRAYDLSQ
QRYQQGIDNYLSVLDSQRSLYTAQQTLVETRLARLSNLIQLYKALGGGWS
ERTVAAAQAG SEQ ID NO:67 polynucleotide sequence of Orf34
Atgaaacagcataaggtcggcaggcactgggcaggatgggcgatggcgct
ggcgtgcctgGgcgcggccgcgccgctggcggcgcagccggcggcaccag
ctggggccgcgcaggcgcgcGaactgctgctggaggtcaagggccagcag
ccgttgcgcctggacgccgcgccatcgcgcgtggcgatcgccgatccgca
ggtcgccgacgtcaaggtgctggcgcccggcgtgggccgcccgggcgagg
tgctgctgatcggccggcaggccggcaccaccgagctgcgggtctggagc
cgcggctcgcgcgacccgcaggtctggaccgtgcgcgtgctgccgcaagt
gcaggccgcgctggcgcggcgcggcgtcggcggcggcgcgcaggtcgaca
tggctggcgacagcggcgtggtcaccggcatggcgccctcggccgaggcg
catcgcggcgcggccgaggctgccgcggccgccgcgggcggcaacgacaa
ggtggtcgacatgtcgcagatcaacaccagcggcgtggtgcaggtggaag
tgaaagtggtcgagctggcgcgctcggtcatgaaggatgtcgggatcaat
ttcagggccgacagcggcccgtggtcgggcggcgtgtcgctgctgccgga
cctggccagcggcggcatgttcggcatgctgtcctataccagccgcgatt
tcagcgcgtcgctggcgctgctgcaaaacaacggcatggcgcgcgtcctg
gccgagccgacgctgctggccatgtcgggccagagcgccagcttcctggc
cggcggcgagattccgattccggtatcggccggcctgggtacgacctcgg
tgcagttcaagcccttcggcatcggcctgacggtcacgcccacggtcatc
tcgcgcgagcgcatcgcgctgaaggtggcgcccgaagccagcgagctgga
ctacgccaacggcatttccagcatcgacagcaacaatcgcatcacggtga
tcccggcgttgcgaacccgcaaggccgacaccatggtggagctgggcgat
ggcgagacattcgtcatcagcggcctggtttcgcgccagaccaaggccag
cgtcaacaaggtgccgctgttgggcgacctgcccatcatcggggcgttct
tccgcaacgtgcagtattcccaggaggatcgcgaattggtgatcgtggtc -continued acgccgcgcctggttcgccccatcgcgcgcggtgtcacgctgcccttgcc gggcgcgcgccaggaggtcagcgacgctggcttcaacgcctggggctatt acctgctgggtccgacgagcggccagcagatgccgggcttttcacagtga SEQ ID NO:68 polypeptide sequence of Orf34
MKQHKVGRHWAGWAMALACLGAAAPLAAQPAAPAGAAQARELLLEVKGQQ

PLRLDAAPSRVAIADPQVADVKVLAPGVGRPGEVLLIGRQAGTTELRVWS

RGSRDPQVWTVRVLPQVQAALARRGVGGGAQVDMAGDSGVVTGMAPSAEA

HRGAAEAAAAAAGGNDKVVDMSQINTSGVVQVEVKVVELARSVMKDVGIN

FRADSGPWSGGVSLLPDLASGGMFGMLSYTSRDFSASLALLQNNGMARVL

AEPTLLAMSGQSASFLAGGEIPIPVSAGLGTTSVQFKPFGIGLTVTPTVI

SRERIALKVAPEASELDYANGISSIDSNNRITVIPALRTRKADTMVELGD

GETFVISGLVSRQTKASVNKVPLLGDLPIIGAFFRNVQYSQEDRELVIVV

TPRLVRPIARGVTLPLPGARQEVSDAGFNAWGYYLLGPMSGQQMPGFSQ

SEQ ID NO:69 polynucleotide sequence of Orf35
Atgaagcgacttctctgtctgtccctgctgtccgtattgctggcggcgtg cacgaccccaTcgcagattccgcccgagacggcgcccggcggcgtgccgc cggcggccgaaggtccgctgGtcgtgccgccgctgtcggcgctgtccgac accccgccgcgcgcgctggccgggcgctaccagcgcgttgcctggaccga gctgcccaactgggagagcgacgacctgtcgcgctggtggccgctgttcc tgcgcaattgcaaaggcctgatgcggccgaccagcggtaacctggcggcg ccggcacgcgccacgccgcgcgcctggcagcccgtgtgcgcggcggcggt cgacccgtccaaggcgccggccgccggcgacagcgcggcggtgcggcgct tcctgcagacctggctgcagccctggcgcatcgccggcgccgacggccgt cccgccaccaataccgtcaccggctactacgagccgctggtgcgcggctc gcgccgccagggcggccgctaccagtggccgctgtatgccgtgccggccg acctgctcgtcgtcgacctgggctcggtctatcccgacctgaccggcaag cgcgtgcgcggccggctcgacggccgccgggtcgtgccctacgacacgcg cgccgcgatcgaggcgggcgaccgcaagccgccggccatcgtctgggtgg acgatccggtcgacaatttcttcctgcaggtccaggggtcgggccgggtg cagctgaccgatggccccgaccgcggcaccacgatccgcgtcgcgtacgc cgaccataacggccagccctatgcctccatcggccgctggctcatcgaca agggcgagctgcgcgccgaccaggcatcgatgcagaacatccgtgcctgg gcccaacgcaatccctcgcgcgtgcaggaaatgctcaacgccaacccggc ggtggtcttcttccgcgaagaggcggtggtcgatccggagcaagggccca agggggcctatggcatcccgttggcgccgcagcgctcgatcgcggtcgac gccggtttcgtgccgctgggcacgccggtctacctgtcgaccacgctgcc ggcctccgaccggcccctgcagcgcaccgtgttcgcgcaggacaccggca cggccattcgcggcgcggcgcgcgccgacttctattggggctacggcgag gaagccggccagcaggccgggcgcatgaagcagcgcggccagatgtggct gctgtggcccaagcaggccggggagccgtcggcgcgatga SEQ ID NO:70 polypeptide sequence of Orf35
MKRLLCLSLLSVLLAACTTPSQIPPETAPGGVPPAAEGPLVVPPLSALSD -continued

TPPRALAGRYQRVAWTELPNWESDDLSRWWPLFLRNCKGLMRPTSGNLAA

PARATPRAWQPVCAAAVDPSKAPAAGDSAAVRRFLQTWLQPWRIAGADGR

PATNTVTGYYEPLVRGSRRQGGRYQWPLYAVPADLLVVDLGSVYPDLTGK

RVRGRLDGRRVVPYDTRAAIEAGDRKPPAIVWVDDPVDNFFLQVQGSGRV

QLTDGPDRGTTIRVAYADHNGQPYASIGRWLIDKGELRADQASMQNIRAW

AQRNPSRVQEMLNANPAVVFFREEAVVDPEQGPKGAYGIPLAPQRSIAVD

AGFVPLGTPVYLSTTLPASDRPLQRTVFAQDTGTAIRGAARADFYWGYGE

EAGQQAGRMKQRGQMWLLWPKQAGEPSAR

SEQ ID NO:71 polynucleotide sequence of Orf36
Atgttcaactgtcggcgattcctgcaaatcggcacgctgtcggccctgct ggccggctgtGccacctccagccaaacaccccaagcccagcatcttcccg cgcaggccgccacaggccagGccgaccgcgtccgcatcggcccggacaaa cccgtatcgagcgacgaaggccccgccacgctgacgccgaccggcgaact gcggcccgacgtccgcgccttcgccgaacagctggcggcgcagcgcgagc tgccccctgccgcaagtgctggccagcctggaaagcacgcgctacaacgcg accgtcgcccgcctcatcgccccgtccggcgcgtcgggcaagaaaatctg gcgcagctggctgacctatcgcgggcgtttcgtcgaacccaagcgcatcg cctggggcgtggaattctggaacgccaaccaggacctgctcaaccgcgcc gcccagcgctacggcgtgccggcctcgatcatcgcctccatcatcggcgt ggaaaccctgtatggccgcaacgtgggcaacttccgcgtggtcgacgccc tggcgacgctggcattcgactacctcgatcccgccaagcccgagcgcgcc gacatgttccgcggccagctcggcgacttcatcaccctggcgctgcagga caagctggaccccgagacgcgcggctcgtacgccggcgccatcggcatgc cgcaattcatgcccggcagcatcatgcgctatgcggtcgatggcgatgac gacggccacatcgacctgaccaacagcgtcgcggacgcggtcatgtcggt gggcaacttcctggtcgaacatggctggcagcgcggcctgccggtgttcg cgccggtcgcgctgccggccgatccggcgccgctggtggccggcggcctt acgccgacgctggactggaacggcctgcaggccgccggcgcgcgcccggc ggcgggcgccggacgcggcgcctggcaggagcaccccatgggcatcgtgg acctggtcgaggaagcgcgcggcaccgtgcaataccgtaccgccacgccc aatttctttgccctgacgcaatacaaccgcagctacttctatgccacggc ggtggccgacctggcggccgaactgcaggcccgcacgggctattga SEQ ID NO:72 polypeptide sequence of Orf36
MPNCRRFLQIGTLSALLAGCATSSQTPQAQHLPAQAATGQADRVRIGPDK

PVSSDEGPATLTPTGELRPDVRAFAEQLAAQRELPLPQVLASLESTRYNA

TVARLIAPSGASGKKIWRSWLTYRGRFVEPKRIAWGVEFWNANQDLLNRA

AQRYGVPASIIASIIGVETLYGRNVGNFRVVDALATLAFDYLDPAKPERA

DMFRGQLGDFITLALQDKLDPETRGSYAGAIGMPQFMPGSIMRYAVDGDD

DGHIDLTNSVADAVMSVGNFLVEHGWQRGLPVFAPVALPADPAPLVAGGL

TPTLDWNGLQAAGARPAAGAGRGAWQEHPMGIVDLVEEARGTVQYRTATP

NFFALTQYNRSYFYATAVADLAAELQARTGY

-continued

SEQ ID NO:73 polynucleotide sequence of Orf37
Atgaaccatagactcatacgttgcctgagcatcgcgctgctggccctgct
gtcgggctgcAgcattctctccgggtcgggcccgacgcgatcggccatca
tggacggcgggtcgaccgacGcgaccggcgccaagctcggctcctacgac
ctggtggacctgcgcgccgacaccattgcgccctatgtgctggtcaaggc
ggtgtccaaggatggcgccacctcggacggctacgtgggcaatatgcgcg
tgatgccgggcgatgtgctgcgcatcctggtagccgacagcatggagacc
ggactgttcgcgccgctggccgccggcggcacggtgttcgaagccgtgcg
ggtcgcggccgacggcagcatctcgctgccctatgcgggccgcctgaaag
tgcagggcaagtcgctggcgcagatcgagcagctcgtcaagggcagcctg
cgcaataccgcggcggtgcagccgcaggccatggtggatctggccgacga
ccgctccaattcggtgctggtggccggggcggtgccgcgcccgggacgct
tcggcggcaacaagggcccgctgacggcgctggatgcgatcacgcaggcg
ggcggctcgaccctgccggcttaccaggccgacgtagtgatccggactgg
cagcaaggtgcagcgcattccttaccagcaattgctcaacggccgcaacg
tggcggtggagccgcgctccgaactggtggtcgaaccgaacctgaagcgt
ttcgtggcgatgggggcccttaccaagccgggcctgcacgaactgccgtc
gaaccagaccaatctgctcgacgccctgggcgtggccggaggcctgaacg
accgcgcggccgacgccaccggggtattcgtttttcgcctggacggccgc
aacgccgatggccgcccgcggcccacggtgttcaggctgaatatgcgcaa
tccggagtccatgttcctggccaagcaattcgagctgctgccggaggacg
tggtgtatgtcagtaatgcgcccatgtacgaatgggaaaagatcattacg
cctatcgtgcaggtcctgatcgtgggccaacgcgtgggtacttactaa SEQ ID NO:74 polypeptide sequence of Orf37
MNHRLIRCLSIALLALLSGCSILSGSGPTRSAIMDGGSTDATGAKLGSYD
LVDLRADTIAPYVLVKAVSKDGATSDGYVGNMRVMPGDVLRILVADSMET
GLFAPLAAGGTVFEAVRVAADGSISLPYAGRLKVQGKSLAQIEQLVKGSL
RNTAAVQPQAMVDLADDRSNSVLVAGAVPRPGRFGGNKGPLTALDAITQA
GGSTLPAYQADVVIRTGSKVQRIPYQQLLNGRNVAVEPRSELVVEPNLKR
FVAMGALTKPGLHELPSNQTNLLDALGVAGGLNDRAADATGVFVFRLDGR
NADGRPRPTVFRLNMRNPESMFLAKQFELLPEDVVYVSNAPMYEWEKIIT
PIVQVLIVGQRVGTY SEQ ID NO:75 polynucleotide sequence of Orf38
Atgcaacgtctcatgcccatcctggtcggactgctcgtcgtcctggccgt
cctgtcttcaTgcgtcttcgtggtccgcgagcgcgactacgccctggtgt
tctcgctgggcgaggtgcgcCaggtcatcagcgagcctggcctgtatttc
aaggcgccgccgccgttccagaacgtcgtcacgctggacaagcgcatcct
caccatcgagtccagcgatgccgagcgcatccagacctccgagaagaaga
acctgctgatcgactcgtacgtcaagtggcgcatcgccgatccgcgcctg
tactacgtgaccttcggcggcaacgagcgcgccgcccaggagcgtctgca
ggcgcagatccgcgacgcgctgaacgcggcggtcaacgtgcgcacggtca
aggacgtggtctcggccgagcgtgacaaggtcatggccgaaatcctcacc
aacgtcgtcaagcgcgccgagccgctgggcgtgcaggtggtcgacgtgcg
cctgcgccgcatcgagttcgcgcccgagatttccgagtcggtctatcgcc
gcatggaagccgagcgcacccgcgtggccaacgagctgcgttcgatcggc
gcggccgaaagcgagaagatccgcgccgaggccgaccgccagcgcgaggt
catcgtggcccaggcctatgcgcgcgcccagggcatcatgggcgagggcg
acgcccaggccggcagcatctacgcccaggccttcggccgcaataccgag
ttctacacctattacaagagcctggaagcctatcgcgccgcgttcggcaa
aaccggtgacgtattggtggtcgatccgacgtcggagttcttccagttct
tcaagaaccccggcaagggcgcggcgggcgccccggcaccggcgaattga SEQ ID NO:76 polypeptide sequence of Orf38
MQRLMPILVGLLVVLAVLSSCVFVVRERDYALVFSLGEVRQVISEPGLYF
KAPPPFQNVVTLDKRILTIESSDAERIQTSEKKNLLIDSYVKWRIADPRL
YYVTFGGNERAAQERLQAQIRDALNAAVNVRTVKDVVSAERDKVMAEILT
NVVKRAEPLGVQVVDVRLRRIEFAPEISESVYRRMEAERTRVANELRSIG
AAESEKIRAEADRQREVIVAQAYARAQGIMGEGDAQAGSIYAQAFGRNTE
FYTYYKSLEAYRAAFGKTGDVLVVDPTSEFFQFFKNPGKGAAGAPAPAN SEQ ID NO:77 polynucleotide sequence of Orf39
Ttgcccagggaggcaaccatgaaacccgtcatccagactttcctgcgcgc
cgccgccgtgGccggcctggcgctgctggccggctgcgccggcgtcagca
cgacgcagtccggcgcgatcGgcgtggaccgcacccaatacatgtcgagc
ctggtgcccgagcaggcgctggtgcaggaggccgggcagcagtatgccga
gatcgtccaggaggcccgcgccaaggggctgcttgaccgcgacccggcgc
aattgtcgcgcgtgcgcgccatttcccagcgcctgatcgcgcagaccggg
gtgtttcgcgccgacgcggccaactggccatgggaagtgcatgtgctgtc
ggtcgacgaggtcaacgcctggtgcatgcccggcggcaagattgccgtct
acacgggcctgctcgcccatatcaagccgaccgacgacgaactggcggcg
gtgctgggccacgagatcgcgcatgcgttgcgcgagcacgcgcgcgagcg
cgtctcgcagcagatggcgaccagcatcggcctgtcggtgctgtccatgg
ccaccggttcgcccggcgcgtccgacctgggcggcaagctgaccgaagtc
atgttcaccttgcccaacagccgcacgcacgagaccgaggccgatcgcat
gggcgtcgaactggccgcgcgcgccggtttcgatccgcgcgccgccgtca
cgctgtggcagaaaatgggcgcggccgacggcaatgcgccgccggagttc
ctgtccacccacccgtcggccagtacccgcatcggcgaattgcagcaggc
cttgcagaaggtattgccgctgtacgagcaggcgcgcggccaggccgcca
aatag SEQ ID NO:78 polypeptide sequence of Orf39
LPREATMKPVIQTFLRAAAVAGLALLAGCAGVSTTQSGAIGVDRTQYMSS
LVPEQALVQEAGQQYAEIVQEARAKGLLDRDPAQLSRVRAISQRLIAQTG
VFRADAANWPWEVHVLSVDEVNAWCMPGGKIAVYTGLLAHIKPTDDELAA
VLGHEIAHALREHARERVSQQMATSIGLSVLSMATGSPGASDLGGKLTEV
MFTLPNSRTHETEADRMGVELAARAGFDPRAAVTLWQKMGAADGNAPPEF
LSTHPSASTRIGELQQALQKVLPLYEQARGQAAK -continued SEQ ID NO:79 polynucleotide sequence of Orf40
Gtgactcaccgtcccgctgcactctcgaagcccgcctcccgccgcggggt
ggccctgcgcGcggcgatcgcgctgtcaaccattctgatcgtggccggct
gcggctcgtcaagcaccaaaTacgacaagaccgcgggctggagcgccgaa
cagttgtacgccgacgccaagcaggaagtcgcggcgggcaactggaccga
tgcccgggagcgcctgaccgccatcgaaagccgctacccgttcggcacgt
acgcccagcaggccctgatcgaactggcttacgtcaactggaaagacggc
gagaacgaacaggcgctggccgccatcgaccgcttccagcagctctatcc
caaccacccgggcacggactacgtgctgtacctgaaggggctggtcaact
tcacgccggccagcgccttcatgagcaacctgaccggccaggaccccgcc
gagcgcgatcccaagggcctgcgcgcgtcctacgatgcgttcaacgaact
ggtccagcgcttccccaacagcaagtacacgcccgatgcgcagaagcgca
tgacctggctggtcaacgccatcgccatgaacgaagtccacgtggcgcgc
tactactacgagcggggcgcctacgtggcggccgccaaccgggcgcagac
cgtgatcaccgatttcgaggggcccccgcctcggaagaagcgctctata
tcatggtcgagtcgtatgacaagctgggaatgaccgaactgaagggcgac
gccgaacgcgtgctcgaccagaactatcccaacagcaaattcaagacgca
aggcctgtcggccgacaagagctggtggaacccgttctcgtggcgctga SEQ ID NO:80 polypeptide sequence of Orf40
VTHRPAALSKPASRRGVALRAAIALSTILIVAGCGSSSTKYDKTAGWSAE
QLYADAKQEVAAGNWTDARERLTAIESRYPFGTYAQQALIELAYVNWKDG
ENEQALAAIDRFQQLYPNHPGTDYVLYLKGLVNFTPASAFMSNLTGQDPA
ERDPKGLRASYDAFNELVQRFPNSKYTPDAQKRMTWLVNAIAMNEVHVAR
YYYERGAYVAAANRAQTVITDFEGAPASEEALYIMVESYDKLGMTELKGD
AERVLDQNYPNSKFKTQGLSADKSWWNPFSWR SEQ ID NO:81 polynucleotide sequence of Orf41
Ttgcccccacaggttgaccttgccatgacgaagcactctgccgctcgaat
cgccaccatcGccgccgcaggcgtcctgctggccggctgcgcagcgccca
agaaccccgatccgcgcgatCcctgggaaggcttcaaccggggcgtctac
aagttcaacgacacggtcgaccgcgcgctgttcaagccggtggcccaggc
ctataccttcgtcaccccgcagccggtgcgcagctgcgtgcacaatatgt
tcagcaacgtgggcgacctgtggtcggccaccaacagcttcctgcaaggc
cgcgggcacgatttcgtcaacacgatcggccgcttcctgttcaataccac
catggggatcggcggctgcttcgacgtcgcgtcgaccaccggggcgcgca
agatccccaacgacttcggcgtgacgctgggcgtctggggcttcggccag
ggaccgtacctggtgctgccgatctggggcgccagcagcctgcgcgacgg
cgtcggcctgatcggcgactggaccggcaaccagggcgcgaccatcggcg
cgatcgacaacgtgccgctgcgcaactcgctgtggggcctggaggccgtc
gacctgcgcgccagcctgctcgataccaccgacaccgtggaccgcgtggc
gctggatccctacagcttcgtgcgcgacgcctacctgcagcgccgcgccg
ccatggtgcgcggcaccaagacgggcgacgacacgctgcccacctatgaa
gacgagggcgatgacgacgcggcccccgccgcgccggccgcccagccggc
cgcccagccgcagtaa SEQ ID NO:82 polypeptide sequence of Orf41
LPPQVDLAMTKHSAARIATIAAAGVLLAGCAAPKNPDPRDPWEGFNRGVY
KFNDTVDRALFKPVAQAYTFVTPQPVRSCVHNMFSNVGDLWSATNSFLQG
RGHDFVNTIGRFLFNTTMGIGGCFDVASTTGARKIPNDFGVTLGVWGFGQ
GPYLVLPIWGASSLRDGVGLIGDWTGNQGATIGAIDNVPLRNSLWGLEAV
DLRASLLDTTDTVDRVALDPYSFVRDAYLQRRAAMVRGTKTGDDTLPTYE
DEGDDDAAPAAPAAQPAAQPQ SEQ ID NO:83 polynucleotide sequence of Orf42
Atggcaacaaagtgcctgctccaggggagttttccggatgccagcccgat
aatgccggcaAtgcgtagtggcgccgcatgggtgctggaagggaggttta
tgcggtttggatggggattgCcggcgctggccgtcgtgcttgcgctggcc
ggatgcgtgaatcgcgagccagaggagcgcgcggccttcatcgcgtatct
ggaacaagtggccgcgccgcaggcgggcgtcgtggccgcgccgcccgacc
cgcccacgcgcaaggccctgggcgactacgaggcgcagtacgagccgatg
gaagcggcgcacgccgccgtgcgcgaagcgttggcggcgcagcaggcggc
gctgcaggcgctgcggctgcattcggtcgacgagatcgtcgcacgccagg
acggctgggacaggctggccgagcgcctggcggccgcgcgcaccgggctc
gaacaggcgcgcgccgccgccgacgccgcgcgcgccgggatggagcagcc
tcccgacctgcgcaacgcctacgcgcgcgcctatgaacacagcgtcacgg
cgccggcacaggccttggcgcggatatccggcctgctcgaacccgccgtg
gaggatgcgcggcgcgtggccgggttcgttgcgcgccatcgcgatcaggt
cgataccgatggtccgctgacccaggtgcgcgatccctcggtgcgcagcg
agctcaatgtactgctgcaggcgctcaatggccgctccgaccaggtttcg
caggcgcaggccttgctcaatggcctggcgggaccggctcgccaggcgcc
ctga SEQ ID NO:84 polypeptide sequence of Orf42
MATKCLLQGSFPDASPIMPAMRSGAAWVLEGRFMRFGWGLPALAVVLALA
GCVNREPEERAAFIAYLEQVAAPQAGVVAAPPDPPTRKALGDYEAQYEPM
EAAHAAVREALAAQQAALQALRLHSVDEIVARQDGWDRLAERLAAARTGL
EQARAAADAARAGMEQPPDLRNAYARAYEHSVTAPAQALARISGLLEPAV
EDARRVAGFVARHRDQVDTDGPLTQVRDPSVRSELNVLLQALNGRSDQVS
QAQALLNGLAGPARQAP SEQ ID NO:85 polynucleotide sequence of Orf43
Gtgatgctgaagaccgtattgcgcctgccggtctgcgccgcgctgctggc
gctggccgcgGgctgcgcgatgattccgccccgaaccggtggtgatctgtc
cgctgaccgcgccgcctccgTcgccgccgcaaccctcggcgcggcccaac
ggctcgatctaccagccttcggcctacggcaactatccgctgttcgagga
ccgccggccgcgcaacgtgggcgacatcgtcaccatcgtgctggaggaaa
agaccaacgccgccaagggcgtggccaccaataccagccgcgacggctcg
gccacgctgggcgtggcggccgcgccgcgcttcatggacggcatcatcaa
cgacaagctggataccgatatctcgggcggcaataccgccaacggcaccg
gcaagagcagcgccaacaacaccttcaccggcaccatcacgaccaccgtg -continued atcggggtgctgcccaacggcaatctgcagatcgccggcgagaagcagat cgccatcaaccgcggcagcgagtacgtgcgcttctcgggcgtggtcgacc cgcgatcgatcaccggcagcaatacggtgtcgtcgacccgggtggccgac gcgcgcatcgaataccgcagcaagggcgtcatggacgaagtccagaccat gggctggctgcaacgcttttttcctgatcgcttcgccgttctga SEQ ID NO:86 polypeptide sequence of Orf43
VMLKTVLRLPVCAALLALAAGCAMIPPEPVVICPLTAPPPSPPQPSARPN

GSIYQPSAYGNYPLFEDRRPRNVGDIVTIVLEEKTNAAKGVATNTSRDGS

ATLGVAAAPRFMDGIINDKLDTDISGGNTANGTGKSSANNTFTGTITTTV

IGVLPNGNLQIAGEKQIAINRGSEYVRFSGVVDPRSITGSNTVSSTRVAD

ARIEYRSKGVMDEVQTMGWLQRFFLIASPF

SEQ ID NO:87 polynucleotide sequence of Orf44
Atgaagtcgtccctgtatcgaatcgcagcgctcagcgccgctgccctgtt gctggccggcTgcgccaaccagcgcgctccgaaggagtcgggcttcctcg gcgattactcgcagttgcgcGaggagcaggtgcccggcggcgcgcggctg atctaccgcgacgccgcgctcaagccgcgccagtacaccgccatgtggct gtcgccggtcgagtactaccccagcccgcaaccgtcggcgcaggtgtcga tggaaacgctgaccgaactgcagaactacctggaccagtcgctgcgccgc aagatcggccgcgagatccgcctggtcaacggccccggcccgggcgtggc caaggcgcgcatcgcgatcacagcggtcggcagcgaaagcgaggcgctgg cggcctaccagtacatccccgtggcgctggccgtcaccggcgccagggcc gtgctggaaggcggccggccgcagcaggccaccatcgcgatcgaaagcaa ggtcaccgacagccagacgggccagctgctgtgggcgtcggtgcgcgggg gcaccggcgagcgcgtacgcgccatcgcccagggccaggcctcggtgccg gcctcggcgctcaagccgctgatcgacgaatggaccgataacgtcgcacg tgaaatacgcaactacgtgcgcagcaaataa SEQ ID NO:88 polypeptide sequence of Orf44
MKSSLYRIAALSAAALLLAGCANQRAPKESGFLGDYSQLREEQVPGGARL

IYRDAALKPRQYTAMWLSPVEYYPSPQPSAQVSMETLTELQNYLDQSLRR

KIGREIRLVNGPGPGVAKARIAITAVGSESEALAAYQYIPVALAVTGARA

VLEGGRPQQATIAIESKVTDSQTGQLLWASVRGGTGERVRAIAQGQASVP

ASALKPLIDEWTDNVAREIRNYVRSK

SEQ ID NO:89 polynucleotide sequence of Orf45
Gtgaaccaacgtggggcccttttacccgttaacacgtgtgactctctttg caaaggaactAtcatgaagtcgcgcattgccaaaagcctaaccatagctg cgctggccgccacgctggcaGcctgcagttccgtccctctcgacgacaag gcaggtcaagctggaggctccggccagggttcggcctccggccagatcct ggatcccttcaacccgcaaagcattctggcgcaacagcgctcggtgtact ttgacttcgacagctatacggtgtcggaacagtatcgcggcctggtcgaa acccacgcccgctacctggcttcgaacaaccagcagcgcatcaagatcga aggcaataccgacgaacgcggcggcgccgagtacaacctcgcactgggcc aacgccgtgccgacgctgtccgtcgcatgatgaccctgctgggtgtgtcg gacaaccagatcgaaaccattagtttcggcaaggaaaagccgaaggcgac gggttcgagcgaggctgatttcgccgagaaccgccgcgccgatatcgttt atcagcgctaa SEQ ID NO:90 polypeptide sequence of Orf45
VNQRGALLPVNTCDSLCKGTIMKSRIAKSLTIAALAATLAACSSVPLDDK

AGQAGGSGQGSASGQILDPFNPQSILAQQRSVYFDFDSYTVSEQYRGLVE

THARYLASNNQQRIKIEGNTDERGGAEYNLALGQRRADAVRRMMTLLGVS

DNQIETISFGKEKPKATGSSEADFAENRRADIVYQR

SEQ ID NO:91 polynucleotide sequence of Orf46
Gtgtccatgatcgcacgtatttccctgcggcctctgaaggggctcgcggt ggctgtcctgGcagcctccgccctgaccgcctgctcgtccggcaaatggg gattcccctacaaggccggcGtccagcaaggcaactggatcaccaaagag caggtcgccctgctgcagcaaggcatgtcgcgcgaacaggtgcgcttcgc cctgggcagccccacgctgaccagcgtgctgcacgccgatcgctgggatt acccctactacttcaagcccggctacggcaaggcgcaggaacgccagttc accgtgtggttcgagaacgaccacctggtacgctggagcggggatgaaca gcccgacctccagccgttccagatcgagaaagtgaacgccaaacaggaag aaaaagccgacgcccaggtggatacggccgagaagcgccaggaaggcatc gacaaggctgaaaaagtccggccccatgtcgatgtcacgacgccggacaa ccccaccctcgactacccgggcgagccgggccaaaccttcgaaccgctca agtaa SEQ ID NO:92 polypeptide sequence of Orf46
VSMIARISLRPLKGLAVAVLAASALTACSSGKWGFPYKAGVQQGNWITKE

QVALLQQGMSREQVRFALGSPTLTSVLHADRWDYPYYFKPGYGKAQERQF

TVWFENDHLVRWSGDEQPDLQPFQIEKVNAKQEEKADAQVDTAEKRQEGI

DKAEKVRPHVDVTTPDNPTLDYPGEPGQTFEPLK

SEQ ID NO:93 polynucleotide sequence of Orf47
Atggcgacccatcctgtcgggccaacgttgctggcggcgctgacgctgct tgccgcctgcAgcggttccatggcgcaagagccgccctacaagagcacga tactgggcttgcaggcgaccAtcctggacctgaagggcttgccgtccgac accgacggcggcatatcggacctgagcgcccaagtgggtgcgctggccgc gcgccatgaaggcgtgtcggtacggcagggcaaggatgccgtcaccatcg ccatgatgggcgacgtactcttcgatttcgacaaggccgacatactcgcc gcggccgaacccactctgcgggacatcgcggagctgatcaaatcccccgc caccggcatcgtcgccattgaaggtcacacggactccaagggctcggatt cctataacaagggcctgtcattgcgacgggcccaggccgttgcgcagtgg ctgggcgctcacggggtggatgcagcgaaactgtcggtcaggggcctggg ggctgccaggcccgtacagcccaaccagctagctgtgaagattcaatag SEQ ID NO:94 polypeptide sequence of Orf47
MATRPVGPTLLAALTLLAACSGSMAQEPPYKSTILGLQATILDLKGLPSD

TDGGISDLSAQVGALAARHEGVSVRQGKDAVTIAMMGDVLFDFDKADILA

AAEPTLRDIAELIKSPATGIVAIEGHTDSKGSDSYNKGLSLRRAQAVAQW

LGAHGVDAAKLSVRGLGAARPVQPNQLAVKIQ

-continued

SEQ ID NO:95 polynucleotide sequence of Orf48
Atgaactatatgcattccccctctgtagttgccgggcgcgcccgccgcct
gctggcggtaGcggcggttgccggctcggtggccgttctggccggctgcg
ccaatcccagcgcatcgagtGgggtgtacacgtacggccaggcgcagcgc
gagcagatcgtgcgcaccggcacggtcaccggcgtgcgtccgattaccat
ccagaacgacaagtccagcggcgtcggcttggtggccggtggcgcgctgg
gcggggtagcgggcaatgccgtcggcggcggcaccggccgcaccatcgcc
acggtgggcggcgtcatcctcggcgcgctggcgggcaacgccatcgagaa
ccgcgcgggcaagtcctccggctacgaaatcacggtgcgcctggacaacg
gcgaaacccgggtcgtggcgcaggaagccgacgtgcccatcagcgtgggc
cagcgcgtgcaggtcatcagcggcgcgggcccgacccgcgtgacaccgta
ttga SEQ ID NO:96 polypeptide sequence of Orf48
MNYMHSPSVVAGRARRLLAVAAVAGSVAVLAGCANPSASSGVYTYGQAQR
EQIVRTGTVTGVRPITIQNDKSSGVGLVAGGALGGVAGNAVGGGTGRTIA
TVGGVILGALAGNAIENRAGKSSGYEITVRLDNGETRVVAQEADVPISVG
QRVQVISGAGPTRVTPY SEQ ID NO:97 polynucleotide sequence of Orf49
Ttggcgttgatcagcaaaaaggagcgcatcttgaaaaccctgctacccgt
attggcgcttGccgccctgctgtcggcctgcaacgcgaacgccccctcgg
atacgcccgagggcgcgccgCcgcccgatacgcatacctcgcgcaattcg
ctggactggcaaggcacgtaccagggcgtgctgccgtgcgccgactgccc
cggcatccgcacggtgctgaccctgcgcgccgacaacacctaccagttgc
agacccagtacctggagcgccagccccgcccggacacggtgcaaggcaga
ttcggctggctgacgggcgacaacgccatcgagctcgacagcgccggcga
tcactaccgttaccaggtcggcgaaaaccggctgaccatgatgtcgcaag
acggcaccctgcccagcggcccgttggccgagcactacgtgctcaagcgc
agccagtga SEQ ID NO:98 polypeptide sequence of Orf49
LALISKKERILKTLLPVLALAALLSACNANAPSDTPEGAPPPDTHTSRNS
LDWQGTYQGVLPCADCPGIRTVLTLRADNTYQLQTQYLERQPRPDTVQGR
FGWLTGDNAIELDSAGDHYRYQVGENRLTMMSQDGTLPSGPLAEHYVLKR
SQ SEQ ID NO:99 polynucleotide sequence of Orf50
ATGAGACGGTTAAAGGCCCAGGCTTTCGAAGGCAGCCGCAGCAGGCCGGC
AGGACATGGGGTGGCGCCTACCTTGCTGGCGCTGGCCCTGGGGTTCCAGG
GGGCGGCGGCGTGGGCCAATTGCACCACCTCGGGGTCCAACACCACTGCA
CCGCAGCCGGCGGAGCGCATCGCGCCAAGGTAGGGGGCGGCTCTACCGGG
AACAAACCAACACGTCACGGTGCAGGCCGGTGCGCGGATCGAGGCCGGCG
ACAGCGGGGCCATCAGCGTGGGCAATAACAGCCGAGTCCAGATCCAGGAC
GGCGCCGTCGTGCAAAGCACGGTCAATACTGCTGCGTCCGGCCAGTACGC
CAAAACGCTGGAAGCAGCAAGCAATAACAATATTTCCATCCAAGTAGGCG
CGCAGCTCCTGGCCAAGGGCAGCGCTTCGCAGTCCAGCGCGTTGGGATTG -continued TCAGGCGCCGGCAATACCGTCACCAACCATGGCACGATCCGGGCCGATAA
TGCCGCGGCAATCTGGATCACTGCCAATACCGCCAATGCGGCCAATACCA
TCGATAACTACGGGACTATCGAAACAGTGCTCAATGGCGGCTACGCCAAC
GCCATCGGCAGCACGCGGAACAACAGCGCCACGGGCGCTGGCGTGACGGT
ACGCAATCATGCCAACGGGCGCATCGTCGGCAACGTGAAGTTCGAGGCTG
GCGACGACAGCGTCATACTCGACGGCGGCTCTACCATCACCGGATCCTTG
AACGGTGGCAGCGGCAACAACAGCCTGACGCTGAAAGCCGGCGACGGCAC
GCTGGGCCGCGCAATCCGCAACTTCGGCACGATCACCAAGCAGGAGGCTG
GAACCTGGACCCTGAATGGCCAGGTCGGCCGCAACGACAACAACTTCAAG
TCCACGGTCAAGGTGGAGGGCGGCACGCTGGTCTTGCGCGGCGATAACAG
CGGCGCCACCCAGGGCGGCGTGTTGCAGGTGTCCGCCGGCGGTACGGCGG
ACGTAACTGCCGCCAGCGCCATGCAGTCCATCAGCAACGCCGGCACGGTT
CAGTTCACGCAGGACAGCAATGCCGCCTACGCCGGCGTGCTGAGCGGGAC
CGGGAGCATCGTCAAGCGCGGCGGCGGCGACCTGACGTTGACGGGCAACA
ACACCCATACCGGCAAGGTGGTGGAGGCGGGCAGCCTCAGCGTATCG
GCGGCCAACAACCTGGGTGGCGCAGGTAGTTCGGTACAGCTCAAGGCCGG
CGCCCTCGCCCTCAAGAAAACCATCGCCGTCAATCGCGGCCTGACGCTCG
ATTCCGGGGGCGCAGACGTTGATCATCGAGCCGGGAACAACCACGACCTGG
CAAGGCCAGGTCAGTGGCGCCGGCAAACTGGTGACCCAGGGCGGCACGCT
GGTGCTGGAGCACGCGTCCAATACGTATAGCGGCGGTACGGAGATCAACA
ACGGAACGCTGCGGGCGGCGCATGACGCCAGCCTGGGTTCCGGCACGTTG
GCGCTCAAGAACAGCCAGCTGGCCGCCACGGACAGCTTCACGGCCACGCG
TGCATTGACGCTCGCTGGAAACGAAAGCATAGACGTCGCAGCCACCAAGA
TACTCAGTTGGAACGGAGAAATCAGCGGCGCCGGCACCCTGGTGAAGGAA
GGCCAGGGGACCTTGCTGCTGCGCGGAACCAATCAGCAAAATGGCGGCAC
GACCGTCAATGCCGGTACGCTGCAGATATCCCGCGACGCCAATCTTGGCC
GAGGGGCGCTGGCGCTGAACGACGGCACGCTGCAGAGCACCGGCAGCTTC
GCGACCTCGCGCGCGGCCACCTTGCGCGGCCAGGCCACCATGGAGGTCGA
CGCTTCGCATACCGTGACCTGGAATGGCGAGCTGAGCGGCGGCGGCATGT
TGCGCAAGTCAGGCCAGGGCACGCTGGCCCTGGCCGGCGCCAACACGTAC
TCGGGTGGCACGGTGGTCGAGGCCGGCGCGCTTCGGGCAGGACACGAAGA
CAACCTGGGACGGGGCGCAATAACCCTGCAGGGCGGAGATCTGCTTGCCG
GCGGCAGTTTTTCGAGCAACCGCGATCTCACGCTTGTCCGCGGTTCCTTG
GACGTGGCTCGCGACGCTACCCTGACCTGGAACGGTGCGATATCGGGCGC
CGGCGATCTGGTCAAAACGGGGGACGGACCCTGGCGCTCACTGGCGTCA
ACGAGTACGCCGGCCAGACCGTGCTCAGGCAAGGCAAGCTGCGCGTGGCC
AGGGAAGAAAGCCTGGGCGGCGCTGCGCTGGTGCTGGAAAACAATACGGT
GTTCGAGAGTGCGGGCTCGTATGCCATCGGGCGGCGAGTCACGCTCAAGG
GCGCGCCCAAGGTGGCAACGCCCGCGGGCGACACGCTCGAATGGCGCGGC
ACGGTCGACGGCGACGGCAAGCTGTACAAGCAAGGCGGCGGCACGCTCGT
GCTGAGCGGCAACAATACCTACGCCAAGGGCGTCGAGGTCTGGGGCGGGG -continued

TCGTGCAAGTCTCTCGCGACCAGAACCTGGGCGCGGCCAATGGCGCGGTC

ACGCTCAACGGCGGCGGGTTGGCGGCCAACGGGGATTTCACCAGCAATCG

CCAGCTGGAGCTGACCGCCGGGGCCAAGGCCATCGACGTCGCGGCCGGCA

AGGACGTGACGTGGCGCGGTGTCGTCAACGGCGCCGGCGCGCTGACCAAG

GCCGGCGACGGCACCTTGAGGTTGGAGAGCGTCAACACCTACACCGGTGG

CACGCGCTTGCAGGGCGGCACCGTGCAGGTATCGCGCGACAACAACCTAG

GCCAGGCCGCCGGCGCGGTCACGTTCGACGGCGGGCGGCTGGCCAGCACC

GGCAGCTTTGCGACCGCACGCGCGGCCACGCTCAACAACGCCGGCCAGAT

CGATACCGCCCAGGGCACCACGCTGACGTGGAACGGCGCCATTGGCGGCA

AGGGCGAGCTGCGCAAGCAAGGGGCGGGCACCCTGGTGCTGGGCGGCGCC

AACACTTACCAGGGCGACACCCGCGTCGAGGCTGGCACGCTGCAGGTGTC

GGCCGACGCCAATCTGGGCCAGGGCGCCGTGCATCTGCACGACAGCCGGC

TGGCGACGACCGGTACCTTCGCGACCTCGCGCCGTCTGGAGTTGACCGGA

CGTGGCACGGTGCAAGCGGCTGCCGCCGCCACGCTGGATTGGCGCGGGAC

GGTGGCTGGCGCCGGCACGCTGGTCAAGGAAGGCGCAGGCACGCTGGTGC

TGGCCGGCGACAACCAGCATGCCGGCGGCACCCTGGTCCACGGCGGCACG

CTGCGCATCGCCCGCGACGCCAACCTGGGCGCGGCGGGCACGGCGGTGAC

GCTGGACGGCGGCACGCTGGCCACCACGGCATCGTTGGCGCTGGATCGCG

CGCTGCGCGTCGGGGCGCGCAATGGCGTATTGCTGCCGGACGCGGGCACG

ACCCTGGATTGGCGGGGCGTGGTCGCCGGCGCGGGCAAGCTGACCAAGGC

CGGTCCGGGCATGCTGGTGCTCAGCGCCGACAACCGCCATGGCGGCGGCA

CGGCAGTCACCGGCGGTACGCTGCAAGTCTCGCGCGACGCCAACCTGGGC

GCGGCGGCCGGCGCCCTGACGCTGGACGGCGGCACTTTGCTGAGCACCGC

CAGCTTTGCCTCGGCGCGTGCCGCCACCCTCGATGCCGCGGGCGGCACCT

TCGTCACCCGCGACGGCACCCGGCTGGATTGGGACGGCGCGATAGGCGGG

GCGGGTGGCCTGGTCAAGGAGGGCGCCGGCGAGCTGCGGCTTGGCAATGC

CAATACCTACCAGGGGCCGACCCGCATCGCCGCCGGCCGCCTGGCCGTCA

ACGGCAGCATCGCCAGCCCGGTCACGGTCGAGCAGGCTGGCGTGCTGGGC

GGCACGGGCCGCATCGTCGGGGATGTGGCCAACCGCGGCGTGGTCGCGCC

GGGCAACTCGATCGGCGCGTTGACGGTAGCCGGCAATTACGCTGGTACCG

GCGGCAGCCTGGAAGTGGAGGCGGTGCTTGGCGGCGACGCCGCGCCGGCC

GATCGGCTGGTGCTTGACGGCGGCGCGGCCAGCGGTGTCACGCCGGTCGT

GGTCAAGCCGCAGGGCGGGGTGGGCGGCCTGACCCTGCGCGGCATTCCGG

TGGTCGTGGCCCAGGGTGGCGCCACGACCGCGCCCGGGGCCTTCCGCCTG

GCGCAGCCGCTGGTCGCGGGCGCGTACGAGTACCAGTTGCTGCGCGGCGC

GGGCGACGGCGCCGCGGCGCAGGCGCAGGACTGGTACCTGCGTACGTCCC

GCGTCGAGCGCGACAAGGCGGGCAGGATCGTCAAGGTCGTGCCCTTCTAC

CGGCCCGAGGTGGCGCTGTATGCCGGCACGCCGATGCTGATGCGCATGAC

AGGCACGGAAATGCTGGGCAGCTATCGCGAGCGGGCGGGCCAGACTGGTG

CGGTGTCGCCCGAAGCGGGCGCCACGGCCGCGCGCGGTGGATGGGCGCGC

-continued

ACCTTCGGCCGCCGTTTCGAGCGTTCCGCCGGCGGCGAGGCCGCGCCGTC

CTTCGACGGCCATTTGGCCGGCGCGCAACTGGGCGCGGACCTCTACGCGC

GCAGCTCGGGCACGCGGCATACCGACGCCTTCGGGGTGTTCGGCGGATAT

GCCACGGTGCGCGGCGACGTGCATGGCCTGGCGCGTGGCGAAATCCAGGC

CGTGGGGACGTCCACGCTGCGGGCCACCCAATTGGGCGCCTATTGGACCC

ACACTGGTCCGGGCGGCTGGTACATCGACACGGTGCTGGCCGGCACGCGC

TACAGGCAGCAGACGAAGTCGTCCGCTCAGGTCGGCGCTGTCAGCCGCGG

CTGGGGGATGACGGCTTCGGTGGAGGCGGGCTATCCGTGGCAGCTCAACC

CGCGCTGGCGCATCGAACCGCAGGCCCAGGTGGTGTATCAGCAACTGGGC

ATTGCCAATGGCGCCGACCGCGTGTCCACGGTGTCGTACAAGACGCCCGA

TGCGCTGACGGCTCGGTTAGGTACGCGCCTGTCGGGCCAGTACGCATACG

GGAAGGCGCAGTTGCGGCCGTTCATGGGCGTATCGCTGCTGCACGATTTC

ACCGGCGCGGACACCGTCACGTTCGCGGGCGCGCATGGCGTACGCGCCAG

CCGCCAGAACACGGCCGTGGATCTGAAGGCGGGCGTGGACACGCAGCTGG

GCAAGAGCGTAGGCCTGTGGGGGCAGGTAGGCTACGGCAAGTCGGTCGGC

AGCGGCGACGGCAGCGACCGTGGCTGGAGCGCCAACCTGGGGCTGCGCGT

GGCGTATTGA

SEQ ID NO:100 polypeptide sequence of Orf50

MRRLKAQEFEGSRSRPAGHGVAPTLLALALGFQGAAAWANCTTSGSNTTC

TAAGGAHRAKVGGGSTGNNQHVTVQAGARIEAGDSGAISVGNNSRVQIQD

GAVVQSTVNTAASGQYAKTLEAASNNNISIQVGAQLLAKGSASQSSALGL

SGAGNTVTNHGTIRADNAAAIWITANTANAANTIDNYGTIETVLNGGYAN

AIGSTRNNSATGAGVTVRNHANGRIVGNVKFEAGDDSVILDGGSTITGSL

NGGSGNNSLTLKAGDGTLGRAIRNFGTITKQEAGTWTLNGQVGRNDNNFK

STVKVEGGTLVLRGDNSGATQGGVLQVSAGATADVTAASAMQSISNAGTV

QFTQDSNAAYAGVLSGTGSIVKRGGGDLTLTGNNTHTGKVVVEAGSLSVS

AANNLGGAGSSVQLKGGALALKKTIAVNRGLTLDSGAQTLIIEPGTTTTW

QGQVSGAGKLVTQGGTLVLEHASNTYSGGTEINNGTLRAAHDASLGSGTL

ALKNSQLAATDSFTATRALTLAGNESIDVAATKILSWNGEISGAGTLVKE

GQGTLLLRGTNQQNGGTTVNAGTLQISRDANLGRGALALNDGTLQSTGSF

ATSRAATLRGQATMEVDASHTVTWNGELSGGGMLRKSGQGTLALAGANTY

SGGTVVEAGALRAGHEDNLGRGAITLQGGDLLAGGSFSSNRDLTLVRGSL

DVARDATLTWNGAISGAGDLVKTGDGTLALTGVNEYAGQTVLRQGKLRVA

REESLGGAALVLENNTVFESAGSYAIGRRVTLKGAPKVATPAGDTLEWRG

TVDGDGKLYKQGGGTLVLSGNNTYAKGVEVWGGVVQVSRDQNLGAANGAV

TLNGGGLAANGDFTSNRQLELTAGAKAIDVAAGKDVTWRGVVNGAGALTK

AGDGTLRLESVNTYTGGTRLQGGTVQVSRDNNLGQAAGAVTFDGGRLAST

GSFATARAATLNNAGQIDTAQGTTLTWNGAIGGKGELRKQGAGTLVLGGA

NTYQGDTRVEAGTLQVSADANLGQGAVHLHDSRLATTGTFATSRRLELTG

RGTVQAAAAATLDWRGTVAGAGTLVKEGAGTLVLAGDNQHAGGTLVHGGT

LRIARDANLGAAGTAVTLDGGTLATTASLALDRALRVGARNGVLLPDAGT

-continued

TLDWRGVVAGAGKLTKAGPGMLVLSADNRHGGGTAVTGGTLQVSRDANLG
AAAGALTLDGGTLLSTASFASARAATLDAAGGTFVTRDGTRLDWDGAIGG
AGGLVKEGAGELRLGNANTYQGPTRIAAGRLAVNGSIASPVTVEQAGVLG
GTGRIVGDVANRGVVAPGNSIGALTVAGNYAGTGGSLEVEAVLGGDAAPA
DRLVLDGGAASGVTPVVVKPQGGVGGLTLRGIPVVVAQGGATTAPGAFRL
AQPLVAGAYEYQLLRGAGDGAAAQAQDWYLRTSRVERDKAGRIVKVVPFY
RPEVALYAGTPMLMRMTGTEMLGSYRERAGQTGAVSPEAGATAARGGWAR
TFGRRFERSAGGEAAPSFDGHLAGAQLGADLYARSSGTRHTDAFGVFGGY
ATVRGDVHGLARGEIQAVGTSTLRATQLGAYNTHTGPGGWYIDTVLAGTR
YRQQTKSSAQVGAVSRGWGMTASVEAGYPWQLNPRWRIEPQAQVVYQQLG
IANGADRVSTVSYKTPDALTARLGTRLSGQYAYGKAQLRPFMGVSLLHDF
TGADTVTFAGAHGVRASRQNTAVDLKAGVDTQLGKSVGLWGQVGYGKSVG
SGDGSDRGWSANLGLRVAY

SEQ ID NO:101 polynucleotide sequence of Orf51
ATGAACAAACCCTCCAAATTCGCTCTGGCGCTCGCCTTCGCCGCTGTTAC
GGCCTCTGGTGCAGCTTCCGCGCAAACCGTGGACAACTGGCGCAATCCGT
TTGGCGACGTTTGGAAGAACGGCACCAATGAACTGTGCTGGCGCGATGCG
TTCTGGACCCCGGCTACCGGCATCCCCGGTTGCGACGGCGTTCCGGTCGC
TCAGAAGGAAAAGTCCGCTCCCATGGCCGCCAAGGTCGTGTTCAATGCTG
ACACCTTCTTCGACTTCGACAAGTCGACGCTGAAGCCGGAAGGCCGCCAG
CTGCTGGATCAAGTCGCCCAGCAAGCCGGCACGATCGATCTGGAAACGAT
CATCGCCGTTGGCCACACGGACTCGATCGGCACCGAAGCCTACAACCAGA
AGCTGTCCGAGCGCCGTGCCGCTGCGGTCAAGACCTACCTGGTCAGCAAG
GGTATCGACCCCAACCGTATCTACACGGAAGGCAAGGGCGAACTGCAACC
GATCGCTTCGAACAAGACGCGTGAAGGCCGTGCCCAGAACCGTCGCGTGG
AAATCGAAATCGTCGGTAGCCGCAAGAACTAA SEQ ID NO:102 polypeptide sequence of Orf51
MNKPSKFALALAFAAVTASGAASAQTVDNWRNPFGDVWKNGTNELCWRDA
FWTPATGIPGCDGVPVAQKEKSAPMAAKVVFNADTFFDFDKSTLKPEGRQ
LLDQVAQQAGTIDLETIIAVGHTDSIGTEAYNQKLSERRAAAVKTYLVSK
GIDPNRIYTEGKGELQPIASNKTREGRAQNRRVEIEIVGSRKN SEQ ID NO:103 polynucleotide sequence of Orf52
ATGAACAAACCCTCCAAATTCGCTCTGGCGCTCGCCTTCGCCGCTGTTAC
GGCCTCTGGTGCAGCTTCCGCGCAAACCGTGGACAACTGGCGCAATCCGT
TTGGCGACGTTTGGAAGAACGGCACCAATGAACTGTGCTGGCGCGATGCG
TTCTGGACCCCGGCTACCGGCATCCCCGGTTGCGACGGCGTTCCGGTCGC
TCAGAAGGAAAAGCCCGCTCCCATGGCCGCCAAGGTCGTGTTCAATGCTG
ACACCTTCTTCGACTTCGACAAGTCGACGCTGAAGCCGGAAGGCCGCCAG
CTGCTGGATCAAGTCGCCCAGCAAGCCGGCACGATCGATCTGGAAACGAT
CATCGCCGTTGGCCACACGGACTCGATCGGCACCGAAGCCTACAACCAGA
AGCTGTCCGAGCGCCGTGCCGCTGCGGTCAAGACCTACCTGGTCAGCAAG
GGTATCGACCCCAACCGTATCTACACGGAAGGCAAGGGCGAACTGCAACC -continued GATCGCTTCGAACAAGACGCGTGAAGGCCGTGCCCAGAACCGTCGCGTGG
AAATCGAGATCGTCGGTAGCCGCAAGAACTAA SEQ ID NO:104 polypeptide sequence of Orf52
MNKPSKFALALAFAAVTASGAASAQTVDNWRNPFGDVWKNGTNELCWRDA
FWTPATGIPGCDGVPVAQKEKPAPMAAKVVFNADTFFDFDKSTLKPEGRQ
LLDQVAQQAGTIDLETIIAVGHTDSIGTEAYNQKLSERRAAAVKTYLVSK
GIDPNRIYTEGKGELQPIASNKTREGRAQNRRVEIEIVGSRKN SEQ ID NO:105 polynucleotide sequence of Orf53
ATGAAGTTCTACCCTTCCCATCCGATGCCCGAGTCGCTCGCGGCTGCGAT
CGCAGTGCCTCTGTTGGGCCTGCTGCCGGCGGCGCAGGCCGCGTCCACGG
CGGTCCAGCTGCCATCCGTCACGGTCGAGGGCGAGTACTCGTCCTATCAA
CCGGAAAGCGCCCAGTCGCCCAAGTTCACCGCGCCCCTGGCGGACACGCC
GCGCACGGTGCAGGTCATCCCTGAGCGGCTCATCCAGGACCAGGGGGCCA
GCGACCTCGAAGCGGTACTGCGCAATGCGCCAGGGATATCGATGACCGCC
GGCGAAGGCGGCCGTCCGGCCAGCGACCTGCCGTTCATCCGCGGCCAGAA
TTCGGCCAGCAGCCTGTTTGTCGACGGCCTGCGCGATCCCAGCACGCAAT
CGCGCGATACCTTCAACCTGGAACAGGTCGACGTCGTCAAGGGGCCCGAT
TCGGTATTTTCCGGGCGCGGCGGCGCCGGCGGAAGCATCAACCTCGTCAC
CAAGACGCCCAGGAACCAGGATTTCACCGAAGTCCAGGCCGGCATCGGGA
CGGCCGAGACCTACCGAGGCACCATAGACGGCAACTGGGTGCTGGGCGAG
AACACGGCGCTGCGCCTCAACCTGCTGGGCACCAGGGGCACCGTGCCGGG
CCGCGACAAGGCGGTCGAGTTCAGCCGCGTGGGTATCGCGCCATCGCTGC
GCCTGGGCCTGAGCGGCCCCACCCGCGTGACGCTGGGCCTGTACCTCTAT
CGCCACCGGCGGGTTCCCGATTATTCGATTCCGTACGATCCGCGCACCGG
CACGCCGATCACCGAGACCATCGGGGTCAGCCGCCGCAACTTCTACGGCC
TGGTGCAGCGCGACTCCGGCGATACCGAGGACTACGCCGCCACCGTCAAA
TGGGAGCACGACCTCGCCAATGGCTTCAAGGTGGAGAACCTGGCGCGCTA
CTCGCGCGCCACGGTGGAGCAGATCACCACCATCCCCGAACTGAAAACCG
CCGATCTGGCCAAAGGGCTGGTGTACCGCAATCTGCGCGCCAGCTACCAG
GTCAACGACAGTTTCGCCAACCGCACCGACCTGCGCGGCACATTCGACAC
GGGGCAGTGGCGCCATACCTTCGATCTGGGCGGGGAGTTCGCCACCAGCC
GGCGCAGTCGCGACCGCTACAAGCAGGAAATCCCCGACGCCGCCAGTCCT
TGCTCGCCCGTGACGGGCGGCAACAATCCCGCCCTGTGCGCCTCGCTCCG
GGATCCGGATCCGCACGTGGATTTCCCGGGAACGGTGCGGCGCAACCATA
ACCCGGCCCGCTACCACACCGACATCCTGTCCCTGTACGGTTTCGACACC
ATCGCCTTCGACGAGCAGTGGCAGCTGAATCTCGGCCTGCGCTGGGACCA
CTACAAGACCAGCGGACGCAACCTGCCGGTACGAGGCGCCAAGCCGCCCG
TCTACGAGAGCGCCGCGCGTACCGACAACCTGTTCAACTACCAGCTCGGC
CTGGTCTACAAGCCTCGTCCGGACGGCTCGGTGTATGCGAGCTACGGCAC
GGCGTCCACGCCGTCGGCCGTGTCCGACTACGCCCCGGCGGACAACATCT
CCGGCACAAGCCAGCAGTTCAAGCCGGAGCGCAGCGAGGTGATCGAGGTC
GGGACCAAGTGGCAGGTGCTGGACCGGCGGCTGCTGGTGACGGGCGCCAT -continued

GTTCCGCGAAACGCGCAAGAACACCAGCATCGAAGTCGCCGAAGGCCTGC

GCGCACCGGCCGGCAAGAGCCGCGTCACCGGCATGGAGCTGGGCGTGGCG

GGCAGCCTGACGCCGCGCTGGGACGTCTACGGCGGCTACGCGCTGCTCGA

CAGCAAGCTGGTCAGGGCCAGCCATAACAGCGGGGCGCAAGGCCAGCCGC

TGCCCAGCGCGCCCCGGCACGCATTCAGCATCTGGAGCACCTACAAGCTG

CTGCCGGAGCTGACCGTGGGGGCCGGCGCGTTCTATCGCAGCAAGGTCTA

TGGCAACGCAGATGCCGGCCACAACAAGGACGGCACGCCCAAGGCGCGCT

GGGTGCCGGCGTACTGGCGCTTCGACGCCATGGCGGCGTACCAGCTCAAC

AAGCACCTTACGGCCCAGTTGAACGTCTACAACCTGCTCGACAAGACCTA

TTACGCCAAGACCTACCGCAGCCATTACGCGGCGCTGGGTCCGGGGCGGT

CCGCCATGCTGACGTTCAAGCTGAGCTACTGA

SEQ ID NO:106 polypeptide sequence of Orf53

MKFYPSHPMPESLAAAIAVPLLGLLPAAQAASTAVQLPSVTVEGEYSSYQ

PESAQSPKFTAPLADTPRTVQVIPERLIQDQGASDLEAVLRNAPGISMTA

GEGGRPASDLPFIRGQNSASSLFVDGLRDPSTQSRDTFNLEQVDVVKGPD

SVFSGRGGAGGSINLVTKTPRNQDFTEVQAGIGTAETYRGTIDGNWVLGE

NTALRLNLLGTRGTVPGRDKAVEFSRVGIAPSLRLGLSGPTRVTLGLYLY

RHRRVPDYSIPYDPRTGTPITETIGVSRRNFYGLVQRDSGDTEDYAATVK

WEHDLANGFKVENLARYSRATVEQITTIPELKTADLAKGLVYRNLRASYQ

VNDSFANRTDLRGTFDTGQWRHTFDLGGEFATSRRSRDRYKQEIPDAASP

CSPVTGGNNPALCASLRDPDPHVDFPGTVRRNHNPARYHTDILSLYGFDT

IAFDEQWQLNLGLRWDHYKTSGRNLPVRGAKPPVYESAARTDNLFNYQLG

LVYKPRPDGSVYASYGTASTPSAVSDYAPADNISGTSQQFKPERSEVIEV

GTKWQVLDRRLLVTGAMFRETRKNTSIEVAEGLRAPAGKSRVTGMELGVA

GSLTPRWDVYGGYALLDSKLVRASHNSGAQGQPLPSAPRHAFSIWSTYKL

LPELTVGAGAFYRSKVYGNADAGHNKDGTPKARWVPAYWRFDAMAAYQLN

KHLTAQLNVYNLLDKTYYAKTYRSHYAALGPGRSAMLTFKLSY

SEQ ID NO:107 polynucleotide sequence of Orf54

ATGAAAAAGACTCTGCTCGCTGCCGCCCTGCTCGCCGGTTTCGCCGGTGC

CGCTCAGGCAGAAACGTCGGTCACCCTGTACGGTATCATCGACACGGGTA

TCGGCTACAACGATGTCGATTTCAAGGTGAAAGGCGCTAACGCCGACGAC

AGCGACTTCAAGTACAACCACAGCCGCTTCGGCATGATCAACGGCGTGCA

GAACGGTTCGCGCTGGGGTCTGCGTGGTACGGAAGATCTGGGTGACGGCC

TGCAAGCTGTGTTCCAACTGGAATCGGGCTTCAACTCGGGCAACGGTAAC

TCGGCCCAAGACGGCCGCCTGTTCGGTCGCCAAGCCACCATCGGTCTGCA

AAGCGAAAGCTGGGGCCGTCTGGACTTCGGTCGCCAAACCAACATCGCCT

CGAAGTACTTCGGCTCGATCGATCCGTTCGGCGCTGGCTTCGGTCAAGCC

AACATCGGCATGGGCATGAGCGCGATGAACACCGTTCGCTACGACAACAT

GGTCATGTACCAGACCCCGTCGTACAGCGGCTTCCAGTTCGGTATCGGCT

ACTCGTTCAGCGCGAACGACAAGGATGCTGACGCCGTCAACCGCGTTGGC

TTCGCCACCGCCGACAACGTTCGTGCCATCACGACCGGTCTGCGCTACGT

-continued

GAACGGCCCGCTGAACGTCGCTCTGTCGTACGACCAGCTGAACGCCTCGA

ACAACCAAGCCCAAGGCGAAGTTGACGCGACCCCGCGCAGCTACGGCCTC

GGCGGTTCGTATGACTTCGAAGTCGTGAAGCTGGCTCTGGCCTACGCTCG

CACGACCGACGGCTGGTTCGGTGGCCAAGGCTACCCGGTCGCCGTCACGC

TGCCCTCGGGCGACAAGTTCGGCGGCTTCGGCGTGAACACCTTCGCTGAC

GGCTTCAAGGCCAACTCGTACATGGTCGGCCTGTCGGCCCCCATCGGCGG

CGCCAGCAACGTGTTCGGTTCGTGGCAGATGGTTGACCCCAAGCTGACCG

GCGGCGACGAGAAGATGAACGTCTTCTCGCTGGGCTACACCTACGACCTG

TCCAAGCGCACCAACCTGTACGCCTACGGTTCGTACGCCAAGAACTTCGC

GTTCCTGGAAGATGCCAAGTCGACCGCTGTCGGCGTCGGTATCCGTCACC

GCTTCTAA

SEQ ID NO:108 polypeptide sequence of Orf54

MKKTLLAAALLAGFAGAAQAETSVTLYGIIDTGIGYNDVDFKVKGANADD

SDFKYNHSRFGMINGVQNGSRWGLRGTEDLGDGLQAVFQLESGFNSGNGN

SAQDGRLFGRQATIGLQSESWGRLDFGRQTNIASKYFGSIDPFGAGFGQA

NIGMGMSAMNTVRYDNMVMYQTPSYSGFQFGIGYSFSANDKDADAVNRVG

FATADNVRAITTGLRYVNGPLNVALSYDQLNASNNQAQGEVDATPRSYGL

GGSYDFEVVKLALAYARTTDGWFGGQGYPVAVTLPSGDKFGGFGVNTFAD

GFKANSYMVGLSAPIGGASNVFGSWQMVDPKLTGGDEKMNVFSLGYTYDL

SKRTNLYAYGSYAKNFAFLEDAKSTAVGVGIRHRF

SEQ ID NO:109 polynucleotide sequence of Orf55

ATGAAAAAGACTCTGCTCGCTGCCGCCCTGCTCGCCGGTTTCGCCGGTGC

CGCTCAGGCAGAAACGTCGGTCACCCTGTACGGTATCATCGACACGGGTA

TCGGCTACAACGATGTCGATTTCAAGGTGAAAGGCGCTAACGCCGACGGC

AGCGACTTCAAGTACAACCACAGCCGCTTCGGCATGATCAACGGCGTGCA

GAACGGTTCGCGCTGGGGTCTGCGTGGTACGGAAGATCTGGGTGACGGCC

TGCAAGCTGTGTTCCAACTGGAATCGGGCTTCAGCTCGGCCAACGGTAAC

TCGGCCCAAGACGGTCGCCTGTTCGGTCGTCAAGCCACCATCGGTCTGCA

AAGCGAAAGCTGGGGCCGTCTGGACTTCGGTCGCCAAACCAACATCGCCT

CGAAGTACTTCGGCTCGATCGATCCGTTCGGCGCTGGCTTCGGTCAAGCC

AACATCGGCATGGGCATGAGCGCGATGAACACCGTTCGCTACGACAACAT

GGTCATGTACCAGACCCCGTCGTACAGCGGCTTCCAGTTCGGTATCGGCT

ACTCGTTCAGCGCGAACGACAAGGACGCTGACGCCGTCAACCGCGTTGGC

TTCGCCACCGCCGACAACGTTCGTGCCATCACGACCGGTCTGCGCTACGT

GAACGGCCCGCTGAACGTCGCTCTGTCGTACGACCAGCTGAACGCCTCGA

ACAACCAAGCCCAAGACGAAGTTGACGCCACCCCGCGCAGCTACGGCATC

GGCGGTTCGTATGACTTCGAAGTCGTGAAGCTGGCTCTGGCCTACGCTCG

CACGACCGACGGCTGGTTCGGTGGCCAAGGCTACCCGGTCGCTGTCACGC

TGCCCTCGGGCGACAAGTTCGGCGGCTTCGGCGTGAACACCTTCGCTGAC

GGCTTCAAGGCCAACTCCTACCTGTTGGGCCTGTCGGCTCCGATCGGCGG

CGCCAGCAACGTGTTCGGTTCGTGGCAGATGGTTGACCCCAGCAACGACA

AGCTGACCGGCGGCGACGAGAAGATGAACGTCTTCTCGCTGGGCTACACC

-continued

TACGACCTGTCCAAGCGCACCAACCTGTACGCCTACGGTTCGTACGCCAA

GAACTTCGCGTTCCTGGAAGATGCCAAGTCGACCGCTGTCGGCGTCGGTA

TCCGTCACCGCTTCTAA

SEQ ID NO:110 polypeptide sequence of Orf55
MKKTLLAAALLAGFAGAAQAETSVTLYGIIDTGIGYNDVDFKVKGANADG

SDFKYNHSRFGMINGVQNGSRWGLRGTEDLGDGLQAVFQLESGFSSANGN

SAQDGRLFGRQATIGLQSESWGRLDFGRQTNIASKYFGSIDPFGAGFGQA

NIGMGMSAMNTVRYDNMVMYQTPSYSGFQFGIGYSFSANDKDADAVNRVG

FATADNVRAITTGLRYVNGPLNVALSYDQLNASNNQAQDEVDATPRSYGI

GGSYDFEVVKLALAYARTTDGWFGGQGYPVAVTLPSGDKFGGFGVNTFAD

GFKANSYLLGLSAPIGGASNVFGSWQMVDPSNDKLTGGDEKMNVFSLGYT

YDLSKRTNLYAYGSYAKNFAFLEDAKSTAVGVGIRHRF

BPP0452: Autotransporter
>BPP0452 *B.parapertussis* np_882803

-continued

>BPPP0452_n

*B.pertussis* homologous sequence: SEQID50 in V860452

BPP3135: OmpA
>BPP3135 *B.parapertussis* np_885310
>BPP3135_n

>BP0943 *B.pertussis*
>BP0943_n

BPP3376: Probable TonB-dependant receptor for iron transport
>BPP3376 *B.parapertussis* np_885539
>BPP3376_n

*B.pertussis* homologous sequence: SEQID14 in VB60452

BPP3392: Outer membrane porin protein precursor
>BPP3392 *B.parapertussis* np_885555
>BPP3392_n >BP0840 *B.pertussis*
>BP0840_n

---

The invention claimed is:

1. An immunogenic composition comprising:

a) a fragment of SEQ ID NO:34, wherein the fragment comprises amino acids 41 to 706 of SEQ ID NO:34;

b) filamentous haemagglutinin (FHA); and c) pertussis toxin.

2. The immunogenic composition of claim 1 comprising a polypeptide that is expressed during the Bvg+ early phase of *Bordetella* infection.

3. The immunogenic composition of claim 1 comprising a polypeptide that is expressed during the Bvg+ late phase of *Bordetella* infection.

4. A vaccine comprising the immunogenic composition of claim 1.

5. The vaccine of claim 4 comprising an adjuvant.

6. The fragment of claim 1, wherein the fragment is recombinantly produced.

7. An immunogenic composition comprising:

a) a fragment of SEQ ID NO:34, wherein the fragment comprises amino acids 60 to 702 of SEQ ID NO:34;

b) filamentous haemagglutinin (FHA); and c) pertussis toxin.

8. The immunogenic composition of claim 7 comprising a polypeptide that is expressed during the Bvg+ early phase of *Bordetella* infection.

9. The immunogenic composition of claim 7 comprising a polypeptide that is expressed during the Bvg+ late phase of *Bordetella* infection.

10. A vaccine comprising the immunogenic composition of claim 7.

11. The vaccine of claim 10 comprising an adjuvant.

12. The fragment of claim 7, wherein the fragment is recombinantly produced.

13. An immunogenic composition comprising:

a) a fragment of SEQ ID NO:34, wherein the fragment comprises amino acids 41 to 706 of SEQ ID NO:34 from which 1, 2, 3, 4, 5, 6, 7, 8, 9, 10, 20, 30, 40, or 50 amino acids have been removed from either or both of the N and C termini;

b) filamentous haemagglutinin (FHA); and c) pertussis toxin.

* * * * *

SEQUENCE LISTING

<160> NUMBER OF SEQ ID NOS: 110

<210> SEQ ID NO 1
<211> LENGTH: 2214
<212> TYPE: DNA
<213> ORGANISM: Bordetella Pertussis

<400> SEQUENCE: 1
atgtccaccc cccgattcgc gctgcattac gccagcgcgt cagtcctgct ggccgcatcc 60
ggcctggcca tggcgcagac ggccacccag atccacgatc cgtcgcaggt gcagcagatg 120
gcgacggtgc aggtgctggg cacggccgaa gaggaaatca aggagtcgct gggcgtctcg 180
gtcatcaccg ccgaggagat cgcccgccgc ccgcccacca atgacctgtc cgacctgatc 240
cgccgcgaac ccggcgtcaa cctgaccggc aacagcgcca gcggcgcgcg gggcaacagc 300
cgccaggtcg acatccgcgg catgggcccc gagaacaccc tcatcctgat cgacggcaag 360
cccgtcacct cgcgcaatgc ggtgcgctat ggctggaacg gcgaccggga cacgcgcggg 420
gacaccaact gggtgcccgc cgaggaagtc gagcgcatcg aagtgatccg cggcccggcc 480
gccgcccgct acggttccgg ggccatgggc ggcgtggtca acatcatcac caagcgcccc 540
gccgatcgcg ccaccggctc catcacctac tacacgaacc agccggaaga cagccgcgag 600
ggcaacacca accgcgtcaa tgcgcgcatc agcgcgccga tcagcgacac gctgagcatg 660
cggctgtacg gcaactacaa caagaccaat ccggatgccc gcgacatcaa cgccggccac 720
gcgaacacca gcgacaacgg caacccctcg accgccggac gcgagggcgt catcaaccag 780
gacctgagcg cgctgttctc gtggaaagcc gacagccaca acaccgtgga cctggacatg 840
ggcttcagcc ggcagggcaa cctgttcgcc ggcgacacca tgaacaacgc caacagcgac 900
ttctcggaca gcctgtacgg caaggaaacc aatgcgatgt accgcgagaa ctatgcgctg 960
acgcaccgcg gcgtctacga ctggggcacc tcgcgcgcca gcgtcggcta tgactacacg 1020
cgcaacgcgc gccagcgcga aggcctggcc ggcggccccg agggcgcgcc caccgcgggc 1080
ggctacgaca ccgcgcgcct gaagaactgg cgcgccgcgg ccgaggccag cgtgccgttc 1140

-continued

```
catctcggtt tcgagcaggt cgccacggtc ggcgtggaat ggctgcgcga atcgctggaa   1200

gaccccgccg gcacgcgcca gacctatacc ggcggcgcca tcggcggcac ggccccggcc   1260

gaccgcgacc cgaaatcgcg ccagaccagc tatgcgctgt tcgccgagga caacatcgag   1320

atcgacgagc gcaccatgct cacgcccggc gtgcgcctgg accacaacag cgaattcggc   1380

agcaactgga gtcccagcct gaacgcctcg tacgccgtca ccgacgcgct caagctcaag   1440

ggtggcatcg cgcgcgccta caaggcgccc aacctctacc aatccaaccc caactacctg   1500

ctgtacagcc gcggcaatgg ctgcctggcc tcgcagacca acaccaacgg ctgctatctg   1560

gtcggcaacg aggacctctc gccggaaacc agcgtcaaca aggaaatcgg cttcgagtac   1620

gacccgggca cgtggcgcac cagcatggcc tatttccgca acgactaccg caacaagatc   1680

gtcgccggca ccgacgtcca gtaccgcctg gccaatggcg cccgggtgct gcaatggacc   1740

aacagcggca aggccgtggt cgaagggctg gaaggcaacc tgttcattcc gctggccagc   1800

aatctcgact ggaacaccaa cttcacctac atgatccagt ccaaggaaaa ggctaccggc   1860

gaacccttga gcgtgattcc cgaatacacc atcaacagca cgctggactg gttctacacg   1920

ccgcagctgt cgttccaggc caatctcacc tattacggca agcaggaagg cccgtccacc   1980

aatgtacgca ccggcgtcga actgaacggc gacggccgcc agaccatcag tccgtatgcc   2040

ctggcgggcc tgagcatggg ctacgaagtc aaccggaacc tgaagttccg cgtcggcgtg   2100

agcaacctgt tcgacaagca gctgtaccgc gaaggcaatg ccagcagcgc gggcgcggcc   2160

acctacaacg aaccggggcg cgcctattac gccacggcga cggtgtcgtt ctga         2214
```

```
<210> SEQ ID NO 2
<211> LENGTH: 737
<212> TYPE: PRT
<213> ORGANISM: Bordetella Pertussis

<400> SEQUENCE: 2

Met Ser Thr Pro Arg Phe Ala Leu His Tyr Ala Ser Ala Ser Val Leu
1               5                   10                  15

Leu Ala Ala Ser Gly Leu Ala Met Ala Gln Thr Ala Thr Gln Ile His
            20                  25                  30

Asp Pro Ser Gln Val Gln Gln Met Ala Thr Val Gln Val Leu Gly Thr
        35                  40                  45

Ala Glu Glu Glu Ile Lys Glu Ser Leu Gly Val Ser Val Ile Thr Ala
    50                  55                  60

Glu Glu Ile Ala Arg Arg Pro Pro Thr Asn Asp Leu Ser Asp Leu Ile
65                  70                  75                  80

Arg Arg Glu Pro Gly Val Asn Leu Thr Gly Asn Ser Ala Ser Gly Ala
                85                  90                  95

Arg Gly Asn Ser Arg Gln Val Asp Ile Arg Gly Met Gly Pro Glu Asn
            100                 105                 110

Thr Leu Ile Leu Ile Asp Gly Lys Pro Val Thr Ser Arg Asn Ala Val
        115                 120                 125

Arg Tyr Gly Trp Asn Gly Asp Arg Asp Thr Arg Gly Asp Thr Asn Trp
    130                 135                 140

Val Pro Ala Glu Glu Val Glu Arg Ile Glu Val Ile Arg Gly Pro Ala
145                 150                 155                 160

Ala Ala Arg Tyr Gly Ser Gly Ala Met Gly Gly Val Val Asn Ile Ile
                165                 170                 175

Thr Lys Arg Pro Ala Asp Arg Ala Thr Gly Ser Ile Thr Tyr Tyr Thr
            180                 185                 190
```

```
Asn Gln Pro Glu Asp Ser Arg Glu Gly Asn Thr Asn Arg Val Asn Ala
        195                 200                 205

Arg Ile Ser Ala Pro Ile Ser Asp Thr Leu Ser Met Arg Leu Tyr Gly
    210                 215                 220

Asn Tyr Asn Lys Thr Asn Pro Asp Ala Arg Asp Ile Asn Ala Gly His
225                 230                 235                 240

Ala Asn Thr Ser Asp Asn Gly Asn Pro Ser Thr Ala Gly Arg Glu Gly
                245                 250                 255

Val Ile Asn Gln Asp Leu Ser Ala Leu Phe Ser Trp Lys Ala Asp Ser
            260                 265                 270

His Asn Thr Val Asp Leu Asp Met Gly Phe Ser Arg Gln Gly Asn Leu
        275                 280                 285

Phe Ala Gly Asp Thr Met Asn Asn Ala Asn Ser Asp Phe Ser Asp Ser
    290                 295                 300

Leu Tyr Gly Lys Glu Thr Asn Ala Met Tyr Arg Glu Asn Tyr Ala Leu
305                 310                 315                 320

Thr His Arg Gly Val Tyr Asp Trp Gly Thr Ser Arg Ala Ser Val Gly
                325                 330                 335

Tyr Asp Tyr Thr Arg Asn Ala Arg Gln Arg Glu Gly Leu Ala Gly Gly
            340                 345                 350

Pro Glu Gly Ala Pro Thr Ala Gly Gly Tyr Asp Thr Ala Arg Leu Lys
        355                 360                 365

Asn Trp Arg Ala Ala Ala Glu Ala Ser Val Pro Phe His Leu Gly Phe
    370                 375                 380

Glu Gln Val Ala Thr Val Gly Val Glu Trp Leu Arg Glu Ser Leu Glu
385                 390                 395                 400

Asp Pro Ala Gly Thr Arg Gln Thr Tyr Thr Gly Gly Ala Ile Gly Gly
                405                 410                 415

Thr Ala Pro Ala Asp Arg Asp Pro Lys Ser Arg Gln Thr Ser Tyr Ala
            420                 425                 430

Leu Phe Ala Glu Asp Asn Ile Glu Ile Asp Glu Arg Thr Met Leu Thr
        435                 440                 445

Pro Gly Val Arg Leu Asp His Asn Ser Glu Phe Gly Ser Asn Trp Ser
    450                 455                 460

Pro Ser Leu Asn Ala Ser Tyr Ala Val Thr Asp Ala Leu Lys Leu Lys
465                 470                 475                 480

Gly Gly Ile Ala Arg Ala Tyr Lys Ala Pro Asn Leu Tyr Gln Ser Asn
                485                 490                 495

Pro Asn Tyr Leu Leu Tyr Ser Arg Gly Asn Gly Cys Leu Ala Ser Gln
            500                 505                 510

Thr Asn Thr Asn Gly Cys Tyr Leu Val Gly Asn Glu Asp Leu Ser Pro
        515                 520                 525

Glu Thr Ser Val Asn Lys Glu Ile Gly Phe Glu Tyr Asp Pro Gly Thr
    530                 535                 540

Trp Arg Thr Ser Met Ala Tyr Phe Arg Asn Asp Tyr Arg Asn Lys Ile
545                 550                 555                 560

Val Ala Gly Thr Asp Val Gln Tyr Arg Leu Ala Asn Gly Ala Arg Val
                565                 570                 575

Leu Gln Trp Thr Asn Ser Gly Lys Ala Val Val Glu Gly Leu Glu Gly
            580                 585                 590

Asn Leu Phe Ile Pro Leu Ala Ser Asn Leu Asp Trp Asn Thr Asn Phe
        595                 600                 605

Thr Tyr Met Ile Gln Ser Lys Glu Lys Ala Thr Gly Glu Pro Leu Ser
    610                 615                 620
```

-continued

```
Val Ile Pro Glu Tyr Thr Ile Asn Ser Thr Leu Asp Trp Phe Tyr Thr
625                 630                 635                 640

Pro Gln Leu Ser Phe Gln Ala Asn Leu Thr Tyr Tyr Gly Lys Gln Glu
                645                 650                 655

Gly Pro Ser Thr Asn Val Arg Thr Gly Val Glu Leu Asn Gly Asp Gly
            660                 665                 670

Arg Gln Thr Ile Ser Pro Tyr Ala Leu Ala Gly Leu Ser Met Gly Tyr
        675                 680                 685

Glu Val Asn Arg Asn Leu Lys Phe Arg Val Gly Val Ser Asn Leu Phe
    690                 695                 700

Asp Lys Gln Leu Tyr Arg Glu Gly Asn Ala Ser Ser Ala Gly Ala Ala
705                 710                 715                 720

Thr Tyr Asn Glu Pro Gly Arg Ala Tyr Tyr Ala Thr Ala Thr Val Ser
                725                 730                 735

Phe
```

<210> SEQ ID NO 3
<211> LENGTH: 2478
<212> TYPE: DNA
<213> ORGANISM: Bordetella Pertussis

<400> SEQUENCE: 3

```
gtgttttctc gcagtcagaa gcatccgtcc tggcgcctgt cgccatgcgt acttgcggcc      60

gccttgtgcg ccgtcgcggt cggtagcgcg gacaccgccc gcgcgcaggc gcccgccgcc     120

agcgcccagc attatgaaat cgcggccgga ccgctggccg acgcactgac ccgcttcgcg     180

cgccgtgccg gcgtggtgct gtcgttcgac ccggccctgg tgcaggggcg cagcacggcg     240

ggcctgcagg gcgtgtacgg cgtgcgcgac gggttcgcgg cgctgctggc cggctcgggc     300

ctgcaggcgc gcgccggcgg cggcaacaac tggtcgctgg cggcgctgcc gcgcggcggc     360

gatgcgcaga cgctggcgcc ggtgacggtg ctgggcctgg agggcgcgct ggcgcccacg     420

gtcggctatg tcgccagtgc cagcctgagc ggcaccaaga ccgatacgcc gctgatcgaa     480

acgccgcaat cgatttcggt ggtgactcgc gaccagataa ccgagcaggg cgcccagacg     540

ctgaaccagg tgctgcgcta taccgccggc gtggcgaccg agacgcgcgg cgcgaccgcg     600

acgcggctgg accagttcag cgtgcgcggt ttctccgccg ccacctatct ggacggcatg     660

cgcgtgttcg gcggccggga cgccttgccc caggtcgacg cctaccggct cgaacgggtc     720

gatgtgctca aggggccggc ttccgtgctg tatggccagg gcggcccggg cggcgtggtc     780

aaccaggtca gcaagcgtcc cctggacgag cctttgcgcg agatcgaagt gcaggcgggc     840

aatttcgatt tccggcgggt caacatggat ttttccggcc cggtggacga ggaccggcgc     900

ttcctgtacc gggtaaccgg cgcggcctat atgtccgatg gccaggtgga tcacaccagg     960

gagcgccgct acttcgtctc gccgtcgttc acgtggcggc ccagcgcgga taccacgctg    1020

accgtgctga ccaacttcca gcgcgacccc gacatgggtt cgtacggatc gatctcggcc    1080

atgcgcacgc tgctgtcggc gcccgacggc aggcggctgg gcccgaacca ctacgacggc    1140

gacgccgatt tcgaaaagag cgaccgccgc agctattcgc tgggctatca actggagcat    1200

cgcttcaacg ataccttcaa ggcctcgcag aacctgcgtt tccagcatgc cgagggcgtc    1260

tatcgcagca tctacggcgc cagcaacaac aattacggct atctcgacaa ggactaccgc    1320

tactcgcagc gcggcctggc catcagcgac gtggacgtgg atgcgttcac gatcgacaac    1380

aacctgcagg cgcgcttcga taccggggcg ctggcgcata cggtgctggt ggggttcgac    1440
```

-continued

```
taccagcgcg tgcagaccga caccttgtcg ggctatggca gcgcgccgcc gctcgacgtg   1500

ttcgatccgg actatcacat gggtatcgag cggccgccgt ttacgtccga tcagacccag   1560

tacaactacc agaccggcct ctacctgcag gaccagatca ggctggatcg cctgtcgttg   1620

ctgctgggcg ggcgctacga ctggtcgcgc acccacaccg gcaccgacaa cctggccaac   1680

ggctcgcaca gcagctcggc gctcgccgcc gaggcgttca ccggccgggt cggggcgatc   1740

tacaacttcg acaacggcgt ggcgccgtac gccagctact cggagtcgtt cgagccgcag   1800

accggcacgg gctggaacaa cacgccgttc aagccgaccg aaggcaagca gtatgaggtc   1860

ggcgtgaaat accagccgcc gggctcggcc acgctgctca cgctggcggc cttcgacatc   1920

cggcgcaaga acctgcccac caccgacccg gatcccaccc atatgtgcgg cgtttcgcgc   1980

tgctcgatac aggccggcga agtgcgcacc cgcggcatcg aactggaggc caagaccgaa   2040

ccgctgcgcg gcctgagcct gatcgccgcc tattcgtacc tcgacaacga atacgagaag   2100

gcctatccga acacgaccgg gttggacctc aagggcaaga agccggtggc cgtgccggcg   2160

caccaggcgt cggcctgggc ccgctatcaa ctgcaggagg gcccgctggc cggcctgggc   2220

atgggcgcgg gggtgcgcta catcggcagt tcgtacgcca acgaaaccaa cacgctcaag   2280

gtgccatcgg tgacgctggt ggacatgatg ctcgactacg acctgggccg ggccagcccc   2340

gcgctcaagg gcatgcaggt ggcgttgaac gtctccaacc tgttcgacaa ggaatacatc   2400

ggctcgtgcc tgtccgattc gtggtgctgg tatggctacc agcgttcgat caaggccagc   2460

ttgcgctatc gctggtga                                                 2478
```

<210> SEQ ID NO 4
<211> LENGTH: 825
<212> TYPE: PRT
<213> ORGANISM: Bordetella Pertussis

<400> SEQUENCE: 4

```
Val Phe Ser Arg Ser Gln Lys His Pro Ser Trp Arg Leu Ser Pro Cys
 1               5                  10                  15

Val Leu Ala Ala Ala Leu Cys Ala Val Ala Val Gly Ser Ala Asp Thr
            20                  25                  30

Ala Arg Ala Gln Ala Pro Ala Ala Ser Ala Gln His Tyr Glu Ile Ala
        35                  40                  45

Ala Gly Pro Leu Ala Asp Ala Leu Thr Arg Phe Ala Arg Arg Ala Gly
    50                  55                  60

Val Val Leu Ser Phe Asp Pro Ala Leu Val Gln Gly Arg Ser Thr Ala
65                  70                  75                  80

Gly Leu Gln Gly Val Tyr Gly Val Arg Asp Gly Phe Ala Ala Leu Leu
                85                  90                  95

Ala Gly Ser Gly Leu Gln Ala Arg Ala Gly Gly Gly Asn Asn Trp Ser
            100                 105                 110

Leu Ala Ala Leu Pro Arg Gly Gly Asp Ala Gln Thr Leu Ala Pro Val
        115                 120                 125

Thr Val Leu Gly Leu Glu Gly Ala Leu Ala Pro Thr Val Gly Tyr Val
    130                 135                 140

Ala Ser Ala Ser Leu Ser Gly Thr Lys Thr Asp Thr Pro Leu Ile Glu
145                 150                 155                 160

Thr Pro Gln Ser Ile Ser Val Val Thr Arg Asp Gln Ile Thr Glu Gln
                165                 170                 175

Gly Ala Gln Thr Leu Asn Gln Val Leu Arg Tyr Thr Ala Gly Val Ala
            180                 185                 190
```

-continued

```
Thr Glu Thr Arg Gly Ala Thr Ala Thr Arg Leu Asp Gln Phe Ser Val
        195                 200                 205

Arg Gly Phe Ser Ala Ala Thr Tyr Leu Asp Gly Met Arg Val Phe Gly
    210                 215                 220

Gly Arg Asp Ala Leu Pro Gln Val Asp Ala Tyr Arg Leu Glu Arg Val
225                 230                 235                 240

Asp Val Leu Lys Gly Pro Ala Ser Val Leu Tyr Gly Gln Gly Gly Pro
                245                 250                 255

Gly Gly Val Val Asn Gln Val Ser Lys Arg Pro Leu Asp Glu Pro Leu
            260                 265                 270

Arg Glu Ile Glu Val Gln Ala Gly Asn Phe Asp Phe Arg Arg Val Asn
        275                 280                 285

Met Asp Phe Ser Gly Pro Val Asp Glu Asp Arg Arg Phe Leu Tyr Arg
    290                 295                 300

Val Thr Gly Ala Ala Tyr Met Ser Asp Gly Gln Val Asp His Thr Arg
305                 310                 315                 320

Glu Arg Arg Tyr Phe Val Ser Pro Ser Phe Thr Trp Arg Pro Ser Ala
                325                 330                 335

Asp Thr Thr Leu Thr Val Leu Thr Asn Phe Gln Arg Asp Pro Asp Met
            340                 345                 350

Gly Ser Tyr Gly Ser Ile Ser Ala Met Arg Thr Leu Leu Ser Ala Pro
        355                 360                 365

Asp Gly Arg Arg Leu Gly Pro Asn His Tyr Asp Gly Asp Ala Asp Phe
    370                 375                 380

Glu Lys Ser Asp Arg Arg Ser Tyr Ser Leu Gly Tyr Gln Leu Glu His
385                 390                 395                 400

Arg Phe Asn Asp Thr Phe Lys Ala Ser Gln Asn Leu Arg Phe Gln His
                405                 410                 415

Ala Glu Gly Val Tyr Arg Ser Ile Tyr Gly Ala Ser Asn Asn Asn Tyr
            420                 425                 430

Gly Tyr Leu Asp Lys Asp Tyr Arg Tyr Ser Gln Arg Gly Leu Ala Ile
        435                 440                 445

Ser Asp Val Asp Val Asp Ala Phe Thr Ile Asp Asn Asn Leu Gln Ala
    450                 455                 460

Arg Phe Asp Thr Gly Ala Leu Ala His Thr Val Leu Val Gly Phe Asp
465                 470                 475                 480

Tyr Gln Arg Val Gln Thr Asp Thr Leu Ser Gly Tyr Gly Ser Ala Pro
                485                 490                 495

Pro Leu Asp Val Phe Asp Pro Asp Tyr His Met Gly Ile Glu Arg Pro
            500                 505                 510

Pro Phe Thr Ser Asp Gln Thr Gln Tyr Asn Tyr Gln Thr Gly Leu Tyr
        515                 520                 525

Leu Gln Asp Gln Ile Arg Leu Asp Arg Leu Ser Leu Leu Leu Gly Gly
    530                 535                 540

Arg Tyr Asp Trp Ser Arg Thr His Thr Gly Thr Asp Asn Leu Ala Asn
545                 550                 555                 560

Gly Ser His Ser Ser Ser Ala Leu Ala Ala Glu Ala Phe Thr Gly Arg
                565                 570                 575

Val Gly Ala Ile Tyr Asn Phe Asp Asn Gly Val Ala Pro Tyr Ala Ser
            580                 585                 590

Tyr Ser Glu Ser Phe Glu Pro Gln Thr Gly Thr Gly Trp Asn Asn Thr
        595                 600                 605

Pro Phe Lys Pro Thr Glu Gly Lys Gln Tyr Glu Val Gly Val Lys Tyr
    610                 615                 620
```

-continued

```
Gln Pro Pro Gly Ser Ala Thr Leu Leu Thr Leu Ala Ala Phe Asp Ile
625                 630                 635                 640

Arg Arg Lys Asn Leu Pro Thr Thr Asp Pro Asp Pro Thr His Met Cys
                645                 650                 655

Gly Val Ser Arg Cys Ser Ile Gln Ala Gly Glu Val Arg Thr Arg Gly
            660                 665                 670

Ile Glu Leu Glu Ala Lys Thr Glu Pro Leu Arg Gly Leu Ser Leu Ile
        675                 680                 685

Ala Ala Tyr Ser Tyr Leu Asp Asn Glu Tyr Glu Lys Ala Tyr Pro Asn
    690                 695                 700

Thr Thr Gly Leu Asp Leu Lys Gly Lys Lys Pro Val Ala Val Pro Ala
705                 710                 715                 720

His Gln Ala Ser Ala Trp Ala Arg Tyr Gln Leu Gln Glu Gly Pro Leu
                725                 730                 735

Ala Gly Leu Gly Met Gly Ala Gly Val Arg Tyr Ile Gly Ser Ser Tyr
            740                 745                 750

Ala Asn Glu Thr Asn Thr Leu Lys Val Pro Ser Val Thr Leu Val Asp
        755                 760                 765

Met Met Leu Asp Tyr Asp Leu Gly Arg Ala Ser Pro Ala Leu Lys Gly
    770                 775                 780

Met Gln Val Ala Leu Asn Val Ser Asn Leu Phe Asp Lys Glu Tyr Ile
785                 790                 795                 800

Gly Ser Cys Leu Ser Asp Ser Trp Cys Trp Tyr Gly Tyr Gln Arg Ser
                805                 810                 815

Ile Lys Ala Ser Leu Arg Tyr Arg Trp
            820                 825
```

<210> SEQ ID NO 5
<211> LENGTH: 2406
<212> TYPE: DNA
<213> ORGANISM: Bordetella Pertussis

<400> SEQUENCE: 5

```
atgcgagcca gaccgagcgc ggcaacccgc gccctgcact catcgtcgcg cccccgccgc      60

ctgatccctg ccctgctggg cgcgcttgcc tgcctgggca ctggcgtaca ggccgcgccc     120

atcgacgtcg atatcccgcc ccagaacctg gcccaagccc tgcaccagct tggccggcaa     180

gccaacctgc aggtcctgta cagccaggac ctggtcgatg gccagcgcag ccccgccgtg     240

cagggccgca tggaacctgc cgaagcgctg gaacgcctgc tgaaaggccg caacatccgc     300

tattcgatcc agcacaacac cgtcacgctc acgcccatgc cgctgactgc gacgctgccg     360

gcaatcagcg tggtcggcgc cctgcctgac tccgacacct acgtggccac aggcacgaca     420

gccggcacca agacggacac gccgctgatc gaaataccgc aatccatttc ggtggtgacc     480

gccgcgcaga tccgcgagca gaatccgcag acgctgggcg acgccgtgcg ctacacgccc     540

ggtatcgtgg tgcaggaagg attcaaccgc accgacgatc ctttcatcat ccgcggcttc     600

gacgtccgca ccaatcccgg cgtcatgttc cgcgacgggc tgaaaatccc cctgccccat     660

tacagcgcga tgtccgaacc ctacgcgctc gaacgcatcg aggtcgtgaa aggccccgct     720

tcggtgctgt acggacaggc ctcgccaggc ggcatcgtca acgtggtatc caagcggccg     780

acagacagcc cgctgcgcga gctgcagctg agcggcggct cgcacagcaa caggcagctc     840

gccggcgact tcggcggacg catcgacgac gagggacggc tgacctaccg cctgaccggc     900

ctggcgcgca atgccgacac gatgatcgac catgtcccgg acgaccgcta ctatctcgcc     960
```

-continued

```
cccgcgctga cctggcgcat cagcccggac acctcgctga cgctgctggc gagctacatg   1020

aagaacaaga ccatcaacaa cgccggctac ccgctcgaag gcacggtcaa gtacaacccc   1080

aacggccgca tcccgcgtca ccgcttcacc ggcgagccgg actggagcaa gtgggaccag   1140

gaggtcgcca acgtggggta ccagtttgcg caccgcttca acgacacctg gcaattcaag   1200

cagaacctgg gctacgccca gtcgcgcaac cgcgtcaacc acgcctactg gtggacctgg   1260

gtgcccggaa gcgacttctc cacggccgag cgcggcgcct accgccgcga cgatgacgcc   1320

cacggcgtga gcatcgacaa ccagttcgag gccacgtggc aatccggccg cttcaggcac   1380

aacacgctgt tcggcctcga ttacaccgaa acctcgttca cccgcaaaca gtacgccggc   1440

tacaacaacc tcgccccgat cgacttcttc gatccggcgt acggctcgga cgtactgctg   1500

ccggcgaagc cggacaccta caccaacgag aagcgcagcc agctcggcct gtacttgcag   1560

gaccagataa agttcgacga caaactggtg gtggtgctca gcggccgcta cgacaatgcc   1620

gacggctcga cgctgaacaa gctgagcggc gtcaataccc gcaccggcga caacgcgttc   1680

acgtggcgca ccggcctgct ctaccttgcg gacaacggtc tggcgcccta taccagctat   1740

tcgacttcgt tccagccgca ggccggcacc acctcgcccg cacgcggcac cacgcccttc   1800

gacccgacca agggcaagca gtgggaagcc ggcgtgaagt accagcccaa tggttcgaac   1860

tcgttcatca ccgcatccgt cttcgagctg acgcgcacca acgtccccac gaccgacccc   1920

gccaaccccg tctacagcgt gcaggaaggc gaggtgcgct cgcgcggcct cgaattgtcg   1980

gccaccgcca acctggcctc gggctggaac ctgatcgcgg cctacacgta taccgacgcg   2040

gaaatcacca agagcaactc caacacgcta ggcaacacgc ccgaggccgt gccgcgcaac   2100

atggcgtcgc tatggtccga ctacaccgtc ccgtccggtg cgctggcggg gctgaatatc   2160

ggcgccggcg tgcgctacat gggctcgacc tacaacaaca ccaatgccgc caaggtcggc   2220

gactacaccg tgttcgacgc cgccctgcgc tacgacttcg ggcgcgcgag cccgtccctg   2280

aaaggctgga cggccgatct caccgtgcgc aacctgttcg acaaggacta cgtggcctcg   2340

tgcacctatg cctgcttcta cggagaaggc aggaccgtgc tgggccgggt cacgtacaaa   2400

tggtag                                                              2406
```

<210> SEQ ID NO 6
<211> LENGTH: 801
<212> TYPE: PRT
<213> ORGANISM: Bordetella Pertussis

<400> SEQUENCE: 6

```
Met Arg Ala Arg Pro Ser Ala Ala Thr Arg Ala Leu His Ser Ser Ser
 1               5                  10                  15

Arg Pro Arg Arg Leu Ile Pro Ala Leu Leu Gly Ala Leu Ala Cys Leu
            20                  25                  30

Gly Thr Gly Val Gln Ala Ala Pro Ile Asp Val Asp Ile Pro Pro Gln
        35                  40                  45

Asn Leu Ala Gln Ala Leu His Gln Leu Gly Arg Gln Ala Asn Leu Gln
    50                  55                  60

Val Leu Tyr Ser Gln Asp Leu Val Asp Gly Gln Arg Ser Pro Ala Val
65                  70                  75                  80

Gln Gly Arg Met Glu Pro Ala Glu Ala Leu Glu Arg Leu Leu Lys Gly
                85                  90                  95

Arg Asn Ile Arg Tyr Ser Ile Gln His Asn Thr Val Thr Leu Thr Pro
            100                 105                 110

Met Pro Leu Thr Ala Thr Leu Pro Ala Ile Ser Val Val Gly Ala Leu
```

-continued

```
        115                 120                 125

Pro Asp Ser Asp Thr Tyr Val Ala Thr Gly Thr Thr Ala Gly Thr Lys
    130                 135                 140

Thr Asp Thr Pro Leu Ile Glu Ile Pro Gln Ser Ile Ser Val Val Thr
145                 150                 155                 160

Ala Ala Gln Ile Arg Glu Gln Asn Pro Gln Thr Leu Gly Asp Ala Val
                165                 170                 175

Arg Tyr Thr Pro Gly Ile Val Val Gln Glu Gly Phe Asn Arg Thr Asp
            180                 185                 190

Asp Pro Phe Ile Ile Arg Gly Phe Asp Val Arg Thr Asn Pro Gly Val
        195                 200                 205

Met Phe Arg Asp Gly Leu Lys Ile Pro Leu Pro His Tyr Ser Ala Met
    210                 215                 220

Ser Glu Pro Tyr Ala Leu Glu Arg Ile Glu Val Val Lys Gly Pro Ala
225                 230                 235                 240

Ser Val Leu Tyr Gly Gln Ala Ser Pro Gly Gly Ile Val Asn Val Val
                245                 250                 255

Ser Lys Arg Pro Thr Asp Ser Pro Leu Arg Glu Leu Gln Leu Ser Gly
            260                 265                 270

Gly Ser His Ser Asn Arg Gln Leu Ala Gly Asp Phe Gly Gly Arg Ile
        275                 280                 285

Asp Asp Glu Gly Arg Leu Thr Tyr Arg Leu Thr Gly Leu Ala Arg Asn
    290                 295                 300

Ala Asp Thr Met Ile Asp His Val Pro Asp Asp Arg Tyr Tyr Leu Ala
305                 310                 315                 320

Pro Ala Leu Thr Trp Arg Ile Ser Pro Asp Thr Ser Leu Thr Leu Leu
                325                 330                 335

Ala Ser Tyr Met Lys Asn Lys Thr Ile Asn Asn Ala Gly Tyr Pro Leu
            340                 345                 350

Glu Gly Thr Val Lys Tyr Asn Pro Asn Gly Arg Ile Pro Arg His Arg
        355                 360                 365

Phe Thr Gly Glu Pro Asp Trp Ser Lys Trp Asp Gln Glu Val Ala Asn
    370                 375                 380

Val Gly Tyr Gln Phe Ala His Arg Phe Asn Asp Thr Trp Gln Phe Lys
385                 390                 395                 400

Gln Asn Leu Gly Tyr Ala Gln Ser Arg Asn Arg Val Asn His Ala Tyr
                405                 410                 415

Trp Trp Thr Trp Val Pro Gly Ser Asp Phe Ser Thr Ala Glu Arg Gly
            420                 425                 430

Ala Tyr Arg Arg Asp Asp Asp Ala His Gly Val Ser Ile Asp Asn Gln
        435                 440                 445

Phe Glu Ala Thr Trp Gln Ser Gly Arg Phe Arg His Asn Thr Leu Phe
    450                 455                 460

Gly Leu Asp Tyr Thr Glu Thr Ser Phe Thr Arg Lys Gln Tyr Ala Gly
465                 470                 475                 480

Tyr Asn Asn Leu Ala Pro Ile Asp Phe Phe Asp Pro Ala Tyr Gly Ser
                485                 490                 495

Asp Val Leu Leu Pro Ala Lys Pro Asp Thr Tyr Thr Asn Glu Lys Arg
            500                 505                 510

Ser Gln Leu Gly Leu Tyr Leu Gln Asp Gln Ile Lys Phe Asp Asp Lys
        515                 520                 525

Leu Val Val Val Leu Ser Gly Arg Tyr Asp Asn Ala Asp Gly Ser Thr
    530                 535                 540
```

-continued

```
Leu Asn Lys Leu Ser Gly Val Asn Thr Arg Thr Gly Asp Asn Ala Phe
545                 550                 555                 560

Thr Trp Arg Thr Gly Leu Leu Tyr Leu Ala Asp Asn Gly Leu Ala Pro
                565                 570                 575

Tyr Thr Ser Tyr Ser Thr Ser Phe Gln Pro Gln Ala Gly Thr Thr Ser
            580                 585                 590

Pro Ala Arg Gly Thr Thr Pro Phe Asp Pro Thr Lys Gly Lys Gln Trp
        595                 600                 605

Glu Ala Gly Val Lys Tyr Gln Pro Asn Gly Ser Asn Ser Phe Ile Thr
    610                 615                 620

Ala Ser Val Phe Glu Leu Thr Arg Thr Asn Val Pro Thr Thr Asp Pro
625                 630                 635                 640

Ala Asn Pro Val Tyr Ser Val Gln Glu Gly Glu Val Arg Ser Arg Gly
                645                 650                 655

Leu Glu Leu Ser Ala Thr Ala Asn Leu Ala Ser Gly Trp Asn Leu Ile
            660                 665                 670

Ala Ala Tyr Thr Tyr Thr Asp Ala Glu Ile Thr Lys Ser Asn Ser Asn
        675                 680                 685

Thr Leu Gly Asn Thr Pro Glu Ala Val Pro Arg Asn Met Ala Ser Leu
    690                 695                 700

Trp Ser Asp Tyr Thr Val Pro Ser Gly Ala Leu Ala Gly Leu Asn Ile
705                 710                 715                 720

Gly Ala Gly Val Arg Tyr Met Gly Ser Thr Tyr Asn Asn Thr Asn Ala
                725                 730                 735

Ala Lys Val Gly Asp Tyr Thr Val Phe Asp Ala Ala Leu Arg Tyr Asp
            740                 745                 750

Phe Gly Ala Arg Ser Pro Ser Leu Lys Gly Trp Thr Ala Asp Leu Thr
        755                 760                 765

Val Arg Asn Leu Phe Asp Lys Asp Tyr Val Ala Ser Cys Thr Tyr Ala
    770                 775                 780

Cys Phe Tyr Gly Glu Gly Arg Thr Val Leu Gly Arg Val Thr Tyr Lys
785                 790                 795                 800

Trp
```

<210> SEQ ID NO 7
<211> LENGTH: 2307
<212> TYPE: DNA
<213> ORGANISM: Bordetella Pertussis

<400> SEQUENCE: 7

```
atgacaggct ttcatgcacg caagccggtg ggcggtggcc atggccggcc cgcgcacggc      60

aggccgcttg cgtggccgcg catcccccta cggacaacca ccatgaagcc attaccgctc     120

gcttatctcg ccgcgctgct gccctggtac gcaggcgtca tccaggcgca atccgcgccc     180

gccgccggcg acgatgcctc gatcaccctg gaagccgtca gggtcgaggc cagcgccgac     240

gcctccgccg gcggcctggc gccggccttc gcgggcggcc aggtcgccac gggcgcgaag     300

gtcggcatcc tcggcacgcg cgacaacctg gaaaccccgt tctccatcac cgcctacacc     360

aacgaactga tccaggaccg ccaggccaag ggggtgggcg acgtcctgca gaacgacccc     420

ggcgtgcggg tggcgcgcgg gttcggcaac ttccaggagt cgtatttcat ccgcggcttc     480

atcctcagct cggacgacat cgcgtacaac ggcctctatg gcctgttgcc gcgccagtac     540

atctcgaccc agctgttcga gcgcgtcgag gtgctgcgcg gtgcctcggc gtttctcacc     600

ggcgcgccgc cgtccggcgg cgggatcggc ggggtgatca acctggttcc caagcgcgcg     660
```

```
cccaacgagc cgctgacgcg cttttcggcc ggctacggca gcgacagcgt gctcgaggct    720

tcggccgaca tcggccggcg cttcggcccg gacgacagcg tcgggatccg catcaacgcc    780

gcccagcgcg gcggcgagac cgccatcgac ggcgagcgca cccgcaccac ggtgttcgcg    840

ctgggcctgg actggcgcgg cgagcgcgcg cgcctgtcgg ccgatatcgg ctaccaggac    900

aaccgcctga agcgggcgcg ccccaatgtc acgctggccg gcgacgccgc caaggtgccc    960

ggcgcgcccg acgccggctc caactatgcc cagccctggt cgtactccaa cgaacgcgac   1020

gtgttcggca ccctgcgcgg cgaatacgac ttcaacggcc gcataacggg ctgggtcgcc   1080

tatggcatgc gccagagcaa ggaggagaac tcgctggcca acctcaataa cgtcaacggc   1140

gcggggcagg gcaagttcta ccgcttcgac aacgcccgcg aggataccgt caacaccggc   1200

gagatcggcc tgcgcgccaa ggcgcgcacc ggcccggtgg gccacgaact ggtcgcctcg   1260

gcgtcgtatt tcgacctcga gaagaagaac gcctatgtca tggacttctt caaccagttc   1320

gacaccagca tctacgaccc cgtcagctac gccaagccgg ccatcagcag caccgcgttt   1380

cgcggcaacg acatggacga tcccgccaag cagggcgtca tccggctggc cagctatgcg   1440

ctgggcgaca ccatgtcgtt cttcgacgac aaggtgctgc tgaccgccgg catccgccac   1500

cagcgcctct accagcgcga ctacagctac gacacgggca tcggcggcac cccctacgag   1560

caaagccaca actcgcccgc cgccggcctg gtggtgcgcg tgacgcccca ggtgtcgctg   1620

tacgccaact acatcgaggc cctgtcggcg ggcgacaccg cgccgcagac cgccaacggc   1680

ctgccggtgg tcaaccacgg cgaatcgctg gcgccctatg tgtccaagca gaaggaagtg   1740

ggcgtcaagt tcgagcacga cggcctgggc ggcggcctgg cgctcttttc caccgacaag   1800

ccgcgcgggt tcgtgggcga tgaccaggtc ttccgcgctt cgggcaagga ccgccaccgc   1860

ggggtcgaac tgacgactta cggcgagctc acgcgcagcg tgcgcgtgct gggcgggctg   1920

acctggctgg acgccaagca gctcagcacc ggcaacgccg ccaccgacgg caagcgcgtc   1980

atcggcgtgc cccgcttcca ggccaacctc ggcgtggagt gggacatccc cggcgtgcag   2040

ggcctgaccg tggacgggcg tgtggtctat acgggctcgt cctatgcgga tgcggccaac   2100

accctcgagg tgccgggctg gacgcgcctg gacgccggcc tgcgttacat gaccgatatc   2160

ggcggccatc tggtgacctg gcgcgcccgc gtcgagaaca tcgccaaccg cgactactgg   2220

tcctccgtgg gcggctaccc cggcaatggc tacctggtgc tgggcggccc gcgcaccttc   2280

acgctgtcgg catcgatgga gttctga                                       2307
```

<210> SEQ ID NO 8
<211> LENGTH: 768
<212> TYPE: PRT
<213> ORGANISM: Bordetella Pertussis

<400> SEQUENCE: 8

```
Met Thr Gly Phe His Ala Arg Lys Pro Val Gly Gly Gly His Gly Arg
 1               5                  10                  15

Pro Ala His Gly Arg Pro Leu Ala Trp Pro Arg Ile Pro Leu Arg Thr
            20                  25                  30

Thr Thr Met Lys Pro Leu Pro Leu Ala Tyr Leu Ala Ala Leu Leu Pro
        35                  40                  45

Trp Tyr Ala Gly Val Ile Gln Ala Gln Ser Ala Pro Ala Ala Gly Asp
    50                  55                  60

Asp Ala Ser Ile Thr Leu Glu Ala Val Arg Val Glu Ala Ser Ala Asp
65                  70                  75                  80

Ala Ser Ala Gly Gly Leu Ala Pro Ala Phe Ala Gly Gly Gln Val Ala
```

-continued

```
                85                  90                  95

Thr Gly Ala Lys Val Gly Ile Leu Gly Thr Arg Asp Asn Leu Glu Thr
            100                 105                 110

Pro Phe Ser Ile Thr Ala Tyr Thr Asn Glu Leu Ile Gln Asp Arg Gln
        115                 120                 125

Ala Lys Gly Val Gly Asp Val Leu Gln Asn Asp Pro Gly Val Arg Val
    130                 135                 140

Ala Arg Gly Phe Gly Asn Phe Gln Glu Ser Tyr Phe Ile Arg Gly Phe
145                 150                 155                 160

Ile Leu Ser Ser Asp Asp Ile Ala Tyr Asn Gly Leu Tyr Gly Leu Leu
                165                 170                 175

Pro Arg Gln Tyr Ile Ser Thr Gln Leu Phe Glu Arg Val Glu Val Leu
            180                 185                 190

Arg Gly Ala Ser Ala Phe Leu Thr Gly Ala Pro Pro Ser Gly Gly Gly
        195                 200                 205

Ile Gly Gly Val Ile Asn Leu Val Pro Lys Arg Ala Pro Asn Glu Pro
    210                 215                 220

Leu Thr Arg Phe Ser Ala Gly Tyr Gly Ser Asp Ser Val Leu Glu Ala
225                 230                 235                 240

Ser Ala Asp Ile Gly Arg Arg Phe Gly Pro Asp Asp Ser Val Gly Ile
                245                 250                 255

Arg Ile Asn Ala Ala Gln Arg Gly Gly Glu Thr Ala Ile Asp Gly Glu
            260                 265                 270

Arg Thr Arg Thr Thr Val Phe Ala Leu Gly Leu Asp Trp Arg Gly Glu
        275                 280                 285

Arg Ala Arg Leu Ser Ala Asp Ile Gly Tyr Gln Asp Asn Arg Leu Lys
    290                 295                 300

Arg Ala Arg Pro Asn Val Thr Leu Ala Gly Asp Ala Ala Lys Val Pro
305                 310                 315                 320

Gly Ala Pro Asp Ala Gly Ser Asn Tyr Ala Gln Pro Trp Ser Tyr Ser
                325                 330                 335

Asn Glu Arg Asp Val Phe Gly Thr Leu Arg Gly Glu Tyr Asp Phe Asn
            340                 345                 350

Gly Arg Ile Thr Gly Trp Val Ala Tyr Gly Met Arg Gln Ser Lys Glu
        355                 360                 365

Glu Asn Ser Leu Ala Asn Leu Asn Asn Val Asn Gly Ala Gly Gln Gly
    370                 375                 380

Lys Phe Tyr Arg Phe Asp Asn Ala Arg Glu Asp Thr Val Asn Thr Gly
385                 390                 395                 400

Glu Ile Gly Leu Arg Ala Lys Ala Arg Thr Gly Pro Val Gly His Glu
                405                 410                 415

Leu Val Ala Ser Ala Ser Tyr Phe Asp Leu Glu Lys Lys Asn Ala Tyr
            420                 425                 430

Val Met Asp Phe Phe Asn Gln Phe Asp Thr Ser Ile Tyr Asp Pro Val
        435                 440                 445

Ser Tyr Ala Lys Pro Ala Ile Ser Ser Thr Ala Phe Arg Gly Asn Asp
    450                 455                 460

Met Asp Asp Pro Ala Lys Gln Gly Val Ile Arg Leu Ala Ser Tyr Ala
465                 470                 475                 480

Leu Gly Asp Thr Met Ser Phe Phe Asp Asp Lys Val Leu Leu Thr Ala
                485                 490                 495

Gly Ile Arg His Gln Arg Leu Tyr Gln Arg Asp Tyr Ser Tyr Asp Thr
            500                 505                 510
```

```
Gly Ile Gly Gly Thr Pro Tyr Glu Gln Ser His Asn Ser Pro Ala Ala
        515                 520                 525

Gly Leu Val Val Arg Val Thr Pro Gln Val Ser Leu Tyr Ala Asn Tyr
    530                 535                 540

Ile Glu Ala Leu Ser Ala Gly Asp Thr Ala Pro Gln Thr Ala Asn Gly
545                 550                 555                 560

Leu Pro Val Val Asn His Gly Glu Ser Leu Ala Pro Tyr Val Ser Lys
                565                 570                 575

Gln Lys Glu Val Gly Val Lys Phe Glu His Asp Gly Leu Gly Gly Gly
            580                 585                 590

Leu Ala Leu Phe Ser Thr Asp Lys Pro Arg Gly Phe Val Gly Asp Asp
        595                 600                 605

Gln Val Phe Arg Ala Ser Gly Lys Asp Arg His Arg Gly Val Glu Leu
    610                 615                 620

Thr Thr Tyr Gly Glu Leu Thr Arg Ser Val Arg Val Leu Gly Gly Leu
625                 630                 635                 640

Thr Trp Leu Asp Ala Lys Gln Leu Ser Thr Gly Asn Ala Ala Thr Asp
                645                 650                 655

Gly Lys Arg Val Ile Gly Val Pro Arg Phe Gln Ala Asn Leu Gly Val
            660                 665                 670

Glu Trp Asp Ile Pro Gly Val Gln Gly Leu Thr Val Asp Gly Arg Val
        675                 680                 685

Val Tyr Thr Gly Ser Ser Tyr Ala Asp Ala Ala Asn Thr Leu Glu Val
    690                 695                 700

Pro Gly Trp Thr Arg Leu Asp Ala Gly Leu Arg Tyr Met Thr Asp Ile
705                 710                 715                 720

Gly Gly His Leu Val Thr Trp Arg Ala Arg Val Glu Asn Ile Ala Asn
                725                 730                 735

Arg Asp Tyr Trp Ser Ser Val Gly Gly Tyr Pro Gly Asn Gly Tyr Leu
            740                 745                 750

Val Leu Gly Gly Pro Arg Thr Phe Thr Leu Ser Ala Ser Met Glu Phe
        755                 760                 765
```

<210> SEQ ID NO 9
<211> LENGTH: 2190
<212> TYPE: DNA
<213> ORGANISM: Bordetella Pertussis

<400> SEQUENCE: 9

```
gtgcctcgtc ctacttcccg ccgtacgcgc cctgcgcgcc ggcaggcgca gcccgccttc     60

gtgcccgcgc tcttcatgct tgccctgggc gccgttgccg ccggcgcgcg cgcccagccc    120

gctgcggcgg gtgtcccgga tacgcaaggc gtggcgcaaa tgccggccgt cacggtcaac    180

gccgcgccgg tggacgacac gctggagcat ctggaggcgc cggtcgatac cggcgcgctg    240

ggacggcgca cccagctgga gacgcctttt tccaccacgg tggtgactgc ccgcgacatg    300

gaggagcgcc aggtcaacaa gctgggagac gtgttcgcgc tggatgcctc ggtgacggac    360

aacagcgcgt cctatggcgc gtgggccagc tacctgacgg tgcgcggcct gccgctggat    420

tggcagaatt cgtaccgcat cgatggccgg ccgttcctga gctacgtcac gacgctgccg    480

ttcgagcact tcgagcagat cgacctgctc aagggggcgt cgggcttcat gtacggtttc    540

ggctcgccgg gcggcctggt caactatgtc accaagaagc cgaccgacga agcggtgcgc    600

agcgtcgagc tgggctacgt gtccaagggg ttgctgcgcg agcacgtgga cctgggcggc    660

agggtgggcc agagcggcgc gtttggctat cggctgaatg ccacgcacga ggagggcaat    720
```

-continued

```
acctacaacg gtggatcgct gtaccgcgat tcggtgtcgc tggcgctgga tgcgcgcctg    780

agcgaccggt tgacctggga cttccaatcc atctaccagg accgcaaggc catcgggcag    840

gagcccacga tctatgcggg caccatggcc ggcagcgagt tgccatcgcc ggtgcgcaac    900

gacaatgaca ggctggtcgg gcagggaccg tatgcggaca atgcgttccg ctattactcg    960

accggcttga agtaccaatt ggcggacgaa tggacgctga gcaccaatta cagctacagc   1020

tccacgcgta cccgccgcaa cgagtcggtg ctgttcctgc gcgaccaggc gggcgactat   1080

gacgattacc gctcggacta tggcgaggcc tatggctaca accagtggca ggccatgctg   1140

gagggcaagt tcgctaccgg tcccttgaag caccacgtgg tggccggcgc gtcgtggcag   1200

aagcagaaga acgactacag cgccaacggg gtctatcaat tgcagggcac gggcaacctg   1260

cgcgcgcgca ataccaacac gtactacagc gaaggccagc tgcacctgta ccgcgcggcc   1320

gagatcacgc agaaggcgct gttcgccagc gacacggtcg acctgaccgg cggctggtcg   1380

gtgctgggcg ggctgcgcta tacgaattat gcgcagcaag gattcgatgc cacgggcgcg   1440

cgaacatcgc gctacgacaa gaacggcgtg ctgacgccga cctttgccct gatgtacaag   1500

ctgacgccgc gcaccatggc ctatgccagc tacatcgaat ccttggagcc gggctcgtcg   1560

gtgggcgccg cgtacgccaa cttcggcgca ttgctcgatc cgttgaagag caagcagtac   1620

gagctgggca tcaagaccga acaggacggc tgggccgcca cggcggcgct gtttcgcatc   1680

gagaagaagg cggaatacgc gaatgccgcc aacgagctgg tgcaggacgg caagacgctc   1740

tatcaggggt tggaactggg cgcctccacg cgtatcgccc gcgactggaa cgtgggaggc   1800

agcctgatgt tgctggattc ggaatacaag aaaggctcgg atttcaccgg caaccgcgtg   1860

gcgggagcgc cgaagttcgt ggcggccgcg caactggcgt actcggtgcc gcaggtgccg   1920

gggctgaagc tgcgcgccga tgtgaagtac accggcaaca cgatgctggg cgccagcaac   1980

cgggtgcagg tggacgacta cgccatcgtc aatatcggcg ccacctacga cacgcagatc   2040

cacggctacg aggcgacctt caccgccggc atcaacaacg tggccaacaa gcgctactgg   2100

ctgtaccagt cgtctgacta cgtgaaggcg ggcgacccgc ggacctatgg cctgacgtct   2160

atatccagat atccggatat ctggatataa                                    2190
```

<210> SEQ ID NO 10
<211> LENGTH: 729
<212> TYPE: PRT
<213> ORGANISM: Bordetella Pertussis

<400> SEQUENCE: 10

```
Val Pro Arg Pro Thr Ser Arg Arg Thr Arg Pro Ala Arg Arg Gln Ala
 1               5                  10                  15

Gln Pro Ala Phe Val Pro Ala Leu Phe Met Leu Ala Leu Gly Ala Val
            20                  25                  30

Ala Ala Gly Ala Arg Ala Gln Pro Ala Ala Ala Gly Val Pro Asp Thr
        35                  40                  45

Gln Gly Val Ala Gln Met Pro Ala Val Thr Val Asn Ala Ala Pro Val
    50                  55                  60

Asp Asp Thr Leu Glu His Leu Glu Ala Pro Val Asp Thr Gly Ala Leu
65                  70                  75                  80

Gly Arg Arg Thr Gln Leu Glu Thr Pro Phe Ser Thr Thr Val Val Thr
                85                  90                  95

Ala Arg Asp Met Glu Glu Arg Gln Val Asn Lys Leu Gly Asp Val Phe
            100                 105                 110

Ala Leu Asp Ala Ser Val Thr Asp Asn Ser Ala Ser Tyr Gly Ala Trp
```

```
        115                 120                 125

Ala Ser Tyr Leu Thr Val Arg Gly Leu Pro Leu Asp Trp Gln Asn Ser
    130                 135                 140

Tyr Arg Ile Asp Gly Arg Pro Phe Leu Ser Tyr Val Thr Thr Leu Pro
145                 150                 155                 160

Phe Glu His Phe Glu Gln Ile Asp Leu Leu Lys Gly Ala Ser Gly Phe
                165                 170                 175

Met Tyr Gly Phe Gly Ser Pro Gly Gly Leu Val Asn Tyr Val Thr Lys
            180                 185                 190

Lys Pro Thr Asp Glu Ala Val Arg Ser Val Glu Leu Gly Tyr Val Ser
        195                 200                 205

Lys Gly Leu Leu Arg Glu His Val Asp Leu Gly Gly Arg Val Gly Gln
    210                 215                 220

Ser Gly Ala Phe Gly Tyr Arg Leu Asn Ala Thr His Glu Glu Gly Asn
225                 230                 235                 240

Thr Tyr Asn Gly Gly Ser Leu Tyr Arg Asp Ser Val Ser Leu Ala Leu
                245                 250                 255

Asp Ala Arg Leu Ser Asp Arg Leu Thr Trp Asp Phe Gln Ser Ile Tyr
            260                 265                 270

Gln Asp Arg Lys Ala Ile Gly Gln Glu Pro Thr Ile Tyr Ala Gly Thr
        275                 280                 285

Met Ala Gly Ser Glu Leu Pro Ser Pro Val Arg Asn Asp Asn Asp Arg
    290                 295                 300

Leu Val Gly Gln Gly Pro Tyr Ala Asp Asn Ala Phe Arg Tyr Tyr Ser
305                 310                 315                 320

Thr Gly Leu Lys Tyr Gln Leu Ala Asp Glu Trp Thr Leu Ser Thr Asn
                325                 330                 335

Tyr Ser Tyr Ser Ser Thr Arg Thr Arg Arg Asn Glu Ser Val Leu Phe
            340                 345                 350

Leu Arg Asp Gln Ala Gly Asp Tyr Asp Asp Tyr Arg Ser Asp Tyr Gly
        355                 360                 365

Glu Ala Tyr Gly Tyr Asn Gln Trp Gln Ala Met Leu Glu Gly Lys Phe
    370                 375                 380

Ala Thr Gly Pro Leu Lys His His Val Val Ala Gly Ala Ser Trp Gln
385                 390                 395                 400

Lys Gln Lys Asn Asp Tyr Ser Ala Asn Gly Val Tyr Gln Leu Gln Gly
                405                 410                 415

Thr Gly Asn Leu Arg Ala Arg Asn Thr Asn Thr Tyr Tyr Ser Glu Gly
            420                 425                 430

Gln Leu His Leu Tyr Arg Ala Ala Glu Ile Thr Gln Lys Ala Leu Phe
        435                 440                 445

Ala Ser Asp Thr Val Asp Leu Thr Gly Gly Trp Ser Val Leu Gly Gly
    450                 455                 460

Leu Arg Tyr Thr Asn Tyr Ala Gln Gln Gly Phe Asp Ala Thr Gly Ala
465                 470                 475                 480

Arg Thr Ser Arg Tyr Asp Lys Asn Gly Val Leu Thr Pro Thr Phe Ala
                485                 490                 495

Leu Met Tyr Lys Leu Thr Pro Arg Thr Met Ala Tyr Ala Ser Tyr Ile
            500                 505                 510

Glu Ser Leu Glu Pro Gly Ser Ser Val Gly Ala Ala Tyr Ala Asn Phe
        515                 520                 525

Gly Ala Leu Leu Asp Pro Leu Lys Ser Lys Gln Tyr Glu Leu Gly Ile
    530                 535                 540
```

```
Lys Thr Glu Gln Asp Gly Trp Ala Ala Thr Ala Ala Leu Phe Arg Ile
545                 550                 555                 560

Glu Lys Lys Ala Glu Tyr Ala Asn Ala Ala Asn Glu Leu Val Gln Asp
                565                 570                 575

Gly Lys Thr Leu Tyr Gln Gly Leu Glu Leu Gly Ala Ser Thr Arg Ile
            580                 585                 590

Ala Arg Asp Trp Asn Val Gly Gly Ser Leu Met Leu Leu Asp Ser Glu
        595                 600                 605

Tyr Lys Lys Gly Ser Asp Phe Thr Gly Asn Arg Val Ala Gly Ala Pro
    610                 615                 620

Lys Phe Val Ala Ala Ala Gln Leu Ala Tyr Ser Val Pro Gln Val Pro
625                 630                 635                 640

Gly Leu Lys Leu Arg Ala Asp Val Lys Tyr Thr Gly Asn Thr Met Leu
                645                 650                 655

Gly Ala Ser Asn Arg Val Gln Val Asp Asp Tyr Ala Ile Val Asn Ile
            660                 665                 670

Gly Ala Thr Tyr Asp Thr Gln Ile His Gly Tyr Glu Ala Thr Phe Thr
        675                 680                 685

Ala Gly Ile Asn Asn Val Ala Asn Lys Arg Tyr Trp Leu Tyr Gln Ser
    690                 695                 700

Ser Asp Tyr Val Lys Ala Gly Asp Pro Arg Thr Tyr Gly Leu Thr Ser
705                 710                 715                 720

Ile Ser Arg Tyr Pro Asp Ile Trp Ile
                725
```

<210> SEQ ID NO 11
<211> LENGTH: 2067
<212> TYPE: DNA
<213> ORGANISM: Bordetella Pertussis

<400> SEQUENCE: 11

```
ttgcccgcca taagcgtcac gggtcgtgag atttccgacc tcaccgaggg tacaaacgcc      60

tacacaaccg aggccatgag cacggccacg ggcctgacac tctcgccacg cgaaacacca     120

caatccgtca gtgtggtcac ccgacagcag atcgaggatc agggcctcac cgacaccggc     180

gccatcctgg cgaccgcgcc agggatttcc gtcacgcgca gcgacagcaa ccgctattca     240

ttctcggccc gcggcttcac catcgacaac ttccagtttg acggcctggt atcgcccatc     300

ctgagccaat ggaactatgg ttcgaccgat atggacgccg ccatctacga tcacgtggaa     360

atcgtacgtg gcgccacagg cctgatgaca ggctcgggca atccttcagc cgccgtgaac     420

ttcgtgcgca agcgtccctt gcgtgagttc gcggctacgt tcaatgcgag tgtcggcagc     480

tgggactatg tgcgcggcga tgccgacatc tccgtgccca tcacggaaga cggcagaata     540

cggtcacgct tggtggccgc ctacagtcag ggcgacagct atgtgcactt tttagatacg     600

cgccggcgca cattctatgg cgtggtcagc gccgatctga cgccggatac ggtgctgacg     660

accagcgtgg agtaccagca caaccacagc aatgggtttg gcagcggctt tccgctgttc     720

tatagcgacg gttcgcgcac cgatttcaac cgctcggtgg ccaacaacgc tccctgggcc     780

cggcaggata ccgaagccac cacctatttc gtggacctca cgcaccgctt caccaatgac     840

tggaagctgc gcgcggccta tagccacact gatggccgct atctcatgaa acatgtgtac     900

cggggcggct accccgatcg ccatactggc atcatcgctg cccccccctgc attttccaac     960

tacgacggca acctcgatcg ggatgacatc catttttcct tgtccgctcc tttcgaggcc    1020

ttcggcctgc gccacgaagt tgccctgggc tggatgagca tcgacaacca tagcgacatc    1080
```

-continued

```
cagcgatacg caatggtcgg accggcccca gccatcggca gcttcttcga ctggcgccgc   1140

gcccacatcc aagagcccag ctgggccgac acgctgtcgc ccgccgacga cgtgcgcacc   1200

aagcagaccg gcgcctatct ggtcggccgg tttgcactag ccgaacccct gcacctcatc   1260

gtgggcgacc gttggagcga ctggaaaacc aaacagatgt attttggctc gcgccgcgaa   1320

tacaggatca agaatcagtt cacccoctat gccggtctga cctacgacat caacgacacc   1380

tacacggcgt acgccagcta tacggagatc ttccagccgc agaacgcgcg cgacaccagc   1440

ggcggcattc ttcctcccat caaaagcaag agctatgagc tgggtctgaa ggcagcctat   1500

ctggagggac ggctcaatac ctccgccgcg ctctttcaga cgcggcagga taacctggcc   1560

caggtcatcc cgggctcatc cattccgggc tttccgaaca tgcaggcctc acgtgccgcc   1620

tccggcgcca aggtcgaggg gatagacctg gaggccagcg gccagatcct gcccgactgg   1680

aacatcggcg ccagctatac acacttcacc accaaggacg ccagcggcaa ccccatcaac   1740

accaatcatc cgcgcagcct gttcaagctc tacaccacgt accgcctgcc gggcgccctg   1800

caccggctta ccgtgggcgg cggcgttgac tggcaaagtc gcatgtacca ggccgcagcc   1860

agtccgcgcg gcaatgtcga agtcgaacag gacagctacg cactcgtgag cctcatggcg   1920

cgcttcgact ttaacaaaaa actgtcggca acactgaacg tgaacaatct gttcgacaaa   1980

aagtactacg atcagatcgg cttctacagc cagggttggt ggggtgcgcc acgcaatgta   2040

atgctcaact tgcgggcgca gtattga                                       2067
```

<210> SEQ ID NO 12
<211> LENGTH: 688
<212> TYPE: PRT
<213> ORGANISM: Bordetella Pertussis

<400> SEQUENCE: 12

```
Leu Pro Ala Ile Ser Val Thr Gly Arg Glu Ile Ser Asp Leu Thr Glu
 1               5                  10                  15

Gly Thr Asn Ala Tyr Thr Thr Glu Ala Met Ser Thr Ala Thr Gly Leu
            20                  25                  30

Thr Leu Ser Pro Arg Glu Thr Pro Gln Ser Val Ser Val Val Thr Arg
        35                  40                  45

Gln Gln Ile Glu Asp Gln Gly Leu Thr Asp Thr Gly Ala Ile Leu Ala
    50                  55                  60

Thr Ala Pro Gly Ile Ser Val Thr Arg Ser Asp Ser Asn Arg Tyr Ser
65                  70                  75                  80

Phe Ser Ala Arg Gly Phe Thr Ile Asp Asn Phe Gln Phe Asp Gly Leu
                85                  90                  95

Val Ser Pro Ile Leu Ser Gln Trp Asn Tyr Gly Ser Thr Asp Met Asp
            100                 105                 110

Ala Ala Ile Tyr Asp His Val Glu Ile Val Arg Gly Ala Thr Gly Leu
        115                 120                 125

Met Thr Gly Ser Gly Asn Pro Ser Ala Ala Val Asn Phe Val Arg Lys
    130                 135                 140

Arg Pro Leu Arg Glu Phe Ala Ala Thr Phe Asn Ala Ser Val Gly Ser
145                 150                 155                 160

Trp Asp Tyr Val Arg Gly Asp Ala Asp Ile Ser Val Pro Ile Thr Glu
                165                 170                 175

Asp Gly Arg Ile Arg Ser Arg Leu Val Ala Ala Tyr Ser Gln Gly Asp
            180                 185                 190

Ser Tyr Val His Phe Leu Asp Thr Arg Arg Arg Thr Phe Tyr Gly Val
        195                 200                 205
```

```
Val Ser Ala Asp Leu Thr Pro Asp Thr Val Leu Thr Thr Ser Val Glu
    210                 215                 220

Tyr Gln His Asn His Ser Asn Gly Phe Gly Ser Gly Phe Pro Leu Phe
225                 230                 235                 240

Tyr Ser Asp Gly Ser Arg Thr Asp Phe Asn Arg Ser Val Ala Asn Asn
                245                 250                 255

Ala Pro Trp Ala Arg Gln Asp Thr Glu Ala Thr Thr Tyr Phe Val Asp
            260                 265                 270

Leu Thr His Arg Phe Thr Asn Asp Trp Lys Leu Arg Ala Ala Tyr Ser
        275                 280                 285

His Thr Asp Gly Arg Tyr Leu Met Lys His Val Tyr Arg Gly Gly Tyr
    290                 295                 300

Pro Asp Arg His Thr Gly Ile Ile Ala Ala Pro Pro Ala Phe Ser Asn
305                 310                 315                 320

Tyr Asp Gly Asn Leu Asp Arg Asp Asp Ile His Phe Ser Leu Ser Ala
                325                 330                 335

Pro Phe Glu Ala Phe Gly Leu Arg His Glu Val Ala Leu Gly Trp Met
            340                 345                 350

Ser Ile Asp Asn His Ser Asp Ile Gln Arg Tyr Ala Met Val Gly Pro
        355                 360                 365

Ala Pro Ala Ile Gly Ser Phe Phe Asp Trp Arg Arg Ala His Ile Gln
    370                 375                 380

Glu Pro Ser Trp Ala Asp Thr Leu Ser Pro Ala Asp Asp Val Arg Thr
385                 390                 395                 400

Lys Gln Thr Gly Ala Tyr Leu Val Gly Arg Phe Ala Leu Ala Glu Pro
                405                 410                 415

Leu His Leu Ile Val Gly Asp Arg Trp Ser Asp Trp Lys Thr Lys Gln
            420                 425                 430

Met Tyr Phe Gly Ser Arg Arg Glu Tyr Arg Ile Lys Asn Gln Phe Thr
        435                 440                 445

Pro Tyr Ala Gly Leu Thr Tyr Asp Ile Asn Asp Thr Tyr Thr Ala Tyr
    450                 455                 460

Ala Ser Tyr Thr Glu Ile Phe Gln Pro Gln Asn Ala Arg Asp Thr Ser
465                 470                 475                 480

Gly Gly Ile Leu Pro Pro Ile Lys Ser Lys Ser Tyr Glu Leu Gly Leu
                485                 490                 495

Lys Ala Ala Tyr Leu Glu Gly Arg Leu Asn Thr Ser Ala Ala Leu Phe
            500                 505                 510

Gln Thr Arg Gln Asp Asn Leu Ala Gln Val Ile Pro Gly Ser Ser Ile
        515                 520                 525

Pro Gly Phe Pro Asn Met Gln Ala Ser Arg Ala Ala Ser Gly Ala Lys
    530                 535                 540

Val Glu Gly Ile Asp Leu Glu Ala Ser Gly Gln Ile Leu Pro Asp Trp
545                 550                 555                 560

Asn Ile Gly Ala Ser Tyr Thr His Phe Thr Thr Lys Asp Ala Ser Gly
                565                 570                 575

Asn Pro Ile Asn Thr Asn His Pro Arg Ser Leu Phe Lys Leu Tyr Thr
            580                 585                 590

Thr Tyr Arg Leu Pro Gly Ala Leu His Arg Leu Thr Val Gly Gly Gly
        595                 600                 605

Val Asp Trp Gln Ser Arg Met Tyr Gln Ala Ala Ala Ser Pro Arg Gly
    610                 615                 620

Asn Val Glu Val Glu Gln Asp Ser Tyr Ala Leu Val Ser Leu Met Ala
```

-continued

```
625                 630                 635                 640

Arg Phe Asp Phe Asn Lys Lys Leu Ser Ala Thr Leu Asn Val Asn Asn
                645                 650                 655

Leu Phe Asp Lys Lys Tyr Tyr Asp Gln Ile Gly Phe Tyr Ser Gln Gly
            660                 665                 670

Trp Trp Gly Ala Pro Arg Asn Val Met Leu Asn Leu Arg Ala Gln Tyr
        675                 680                 685


<210> SEQ ID NO 13
<211> LENGTH: 2232
<212> TYPE: DNA
<213> ORGANISM: Bordetella Pertussis

<400> SEQUENCE: 13

atgaagttct actcttccca tccgatgccc gagtcgctcg cggctgcgat cgcagtgcct     60

ctgttgggcc tgctgccggc ggcgcaggcc gcgtccacgg cggtccagct gccatccgtc    120

acggtcgagg gcgagtactc gtcctatcaa ccggaaagcg cccagtcgcc caagttcacc    180

gcgcccctgg cggacacgcc gcgcacggtg caggtcatcc ctgagcggct catccaggac    240

caggggggcca gcgacctcga agcggtactg cgcaatgcgc cagggatatc gatgaccgcc    300

ggcgaaggcg gccgtccggc cagcgacctg ccgttcatcc gcggccagaa ttcggccagc    360

agcctttttg tcgacggcct gcgcgatccc agcacgcaat cgcgcgatac cttcaacctg    420

gaacaggtcg acgtcgtcaa ggggcccgat tcggtatttt ccgggcgcgg cggcgccggc    480

ggaagcatca acctcgtcac caagacgccc aggaaccagg atttcaccga agtccaggcc    540

ggcatcggga cggccgagac ctaccgaggc accatagacg gcaactgggt gctgggcgag    600

aacacggcgc tgcgcctcaa cctgctgggc accagggaca ccgtgccggg ccgcgacaag    660

gcggtcgagt tcagccgcgt gggtatcgcg ccatcgctgc gcctgggcct gagcggcccc    720

acccgcgtga cgctgggcct gtaccactat cgccaccggc gggttcccga ttattcgatt    780

ccgtacgatc cgcgcaccgg cacgccgatc accgagacca tcggcgtcag ccgccgcaac    840

ttctacggcc tggtgcggcg cgactccggc gataccgagg actacgccgc caccgtcaaa    900

tgggagcacg acctcgccaa tggcttcaag gtggagaacc tggcgcgcta ctcgcgtgcc    960

acggtggagc agatcaccac catgcccgaa ctgaaaaccg ccgatctggc caaggggctg   1020

gtgtaccgca atctgcgcgc cagctaccag gtcaacgaca gtttcgccaa ccgcaccgac   1080

ctgcgcggta cattcgacac ggggcagtgg cgccatacct tcgatctggg cggggagttc   1140

gccaccagcc ggcgcagtcg cgaccgctac aagcaagaaa tccccgacgc cgccagtcct   1200

tgctcgcccg tgacggacgg caacaatccc gccctgtgcg cctcgctccg ggatccggat   1260

ccgcacgtgg atttcccggg aacggtgcgg cgcaaccata acccggcccg ctaccacacc   1320

gacatcctgt ccctgtacgg tttcgacacc atcgccttcg acgagcagtg gcagctgaat   1380

ctcggcctgc gctgggacca ctacaagacc agcggacgca acctgccggt acgaggcgcc   1440

aagccgcccg tctacgagcg tgccgcgcgc accgacaacc tgttcaacta ccagctcggc   1500

ctggtctaca agcctcgtcc ggacggctcg gtgtatgcga gttacggcac ggcgtccacg   1560

ccgtcggccg tgtccgacta cgccccggcg gacagcatct ccggcacaag ccagcagctc   1620

aagccggagc gcagcgaggc gatcgagatc gggaccaagt ggcaggtgct ggaccggcgg   1680

ctgctggtga cgggcgccat gttccgcgag acgcgcaaga acaccagcat cgaagtcgcc   1740

gaaggcctgc gcgcaccagc cggcaagagc cgcgtcaccg gcatggagct gggcgtggcg   1800

ggcagcctga cgccgcgctg ggacgtctac ggcggctacg cgctgctcga cagcaagctg   1860
```

```
gtcagggcca gccataagag cggggcgcaa ggccagccgc tgcccagcgc gccccggcac   1920

gcattcagca tctggagcac ctacaagctg ctgccggaac tgaccgtggg ggccggcgcg   1980

ttctatcgca gcaaggtcta tggcaacgca gatgccggct acaacaagga cggcacgccc   2040

aaggcgcgct gggtgccggc gtactggcgc ttcgacgcca tggcggcgta ccagcttaac   2100

aagcacctta cggcccagtt gaacgtctac aacctgctcg acaagaccta ttacgccaag   2160

acctaccgca gccattacgc ggcgctgggc ccggggcggt ccgccatgct gacgttcaag   2220

ctgagctact ga                                                         2232


<210> SEQ ID NO 14
<211> LENGTH: 743
<212> TYPE: PRT
<213> ORGANISM: Bordetella Pertussis

<400> SEQUENCE: 14

Met Lys Phe Tyr Ser Ser His Pro Met Pro Glu Ser Leu Ala Ala Ala
 1               5                  10                  15

Ile Ala Val Pro Leu Leu Gly Leu Leu Pro Ala Ala Gln Ala Ala Ser
            20                  25                  30

Thr Ala Val Gln Leu Pro Ser Val Thr Val Glu Gly Glu Tyr Ser Ser
        35                  40                  45

Tyr Gln Pro Glu Ser Ala Gln Ser Pro Lys Phe Thr Ala Pro Leu Ala
    50                  55                  60

Asp Thr Pro Arg Thr Val Gln Val Ile Pro Glu Arg Leu Ile Gln Asp
65                  70                  75                  80

Gln Gly Ala Ser Asp Leu Glu Ala Val Leu Arg Asn Ala Pro Gly Ile
                85                  90                  95

Ser Met Thr Ala Gly Glu Gly Gly Arg Pro Ala Ser Asp Leu Pro Phe
            100                 105                 110

Ile Arg Gly Gln Asn Ser Ala Ser Ser Leu Phe Val Asp Gly Leu Arg
        115                 120                 125

Asp Pro Ser Thr Gln Ser Arg Asp Thr Phe Asn Leu Glu Gln Val Asp
    130                 135                 140

Val Val Lys Gly Pro Asp Ser Val Phe Ser Gly Arg Gly Gly Ala Gly
145                 150                 155                 160

Gly Ser Ile Asn Leu Val Thr Lys Thr Pro Arg Asn Gln Asp Phe Thr
                165                 170                 175

Glu Val Gln Ala Gly Ile Gly Thr Ala Glu Thr Tyr Arg Gly Thr Ile
            180                 185                 190

Asp Gly Asn Trp Val Leu Gly Glu Asn Thr Ala Leu Arg Leu Asn Leu
        195                 200                 205

Leu Gly Thr Arg Asp Thr Val Pro Gly Arg Asp Lys Ala Val Glu Phe
    210                 215                 220

Ser Arg Val Gly Ile Ala Pro Ser Leu Arg Leu Gly Leu Ser Gly Pro
225                 230                 235                 240

Thr Arg Val Thr Leu Gly Leu Tyr His Tyr Arg His Arg Arg Val Pro
                245                 250                 255

Asp Tyr Ser Ile Pro Tyr Asp Pro Arg Thr Gly Thr Pro Ile Thr Glu
            260                 265                 270

Thr Ile Gly Val Ser Arg Arg Asn Phe Tyr Gly Leu Val Arg Arg Asp
        275                 280                 285

Ser Gly Asp Thr Glu Asp Tyr Ala Ala Thr Val Lys Trp Glu His Asp
    290                 295                 300
```

-continued

```
Leu Ala Asn Gly Phe Lys Val Glu Asn Leu Ala Arg Tyr Ser Arg Ala
305                 310                 315                 320

Thr Val Glu Gln Ile Thr Thr Met Pro Glu Leu Lys Thr Ala Asp Leu
                325                 330                 335

Ala Lys Gly Leu Val Tyr Arg Asn Leu Arg Ala Ser Tyr Gln Val Asn
            340                 345                 350

Asp Ser Phe Ala Asn Arg Thr Asp Leu Arg Gly Thr Phe Asp Thr Gly
        355                 360                 365

Gln Trp Arg His Thr Phe Asp Leu Gly Gly Glu Phe Ala Thr Ser Arg
    370                 375                 380

Arg Ser Arg Asp Arg Tyr Lys Gln Glu Ile Pro Asp Ala Ala Ser Pro
385                 390                 395                 400

Cys Ser Pro Val Thr Asp Gly Asn Asn Pro Ala Leu Cys Ala Ser Leu
                405                 410                 415

Arg Asp Pro Asp Pro His Val Asp Phe Pro Gly Thr Val Arg Arg Asn
            420                 425                 430

His Asn Pro Ala Arg Tyr His Thr Asp Ile Leu Ser Leu Tyr Gly Phe
        435                 440                 445

Asp Thr Ile Ala Phe Asp Glu Gln Trp Gln Leu Asn Leu Gly Leu Arg
    450                 455                 460

Trp Asp His Tyr Lys Thr Ser Gly Arg Asn Leu Pro Val Arg Gly Ala
465                 470                 475                 480

Lys Pro Pro Val Tyr Glu Arg Ala Ala Arg Thr Asp Asn Leu Phe Asn
                485                 490                 495

Tyr Gln Leu Gly Leu Val Tyr Lys Pro Arg Pro Asp Gly Ser Val Tyr
            500                 505                 510

Ala Ser Tyr Gly Thr Ala Ser Thr Pro Ser Ala Val Ser Asp Tyr Ala
        515                 520                 525

Pro Ala Asp Ser Ile Ser Gly Thr Ser Gln Gln Leu Lys Pro Glu Arg
    530                 535                 540

Ser Glu Ala Ile Glu Ile Gly Thr Lys Trp Gln Val Leu Asp Arg Arg
545                 550                 555                 560

Leu Leu Val Thr Gly Ala Met Phe Arg Glu Thr Arg Lys Asn Thr Ser
                565                 570                 575

Ile Glu Val Ala Glu Gly Leu Arg Ala Pro Ala Gly Lys Ser Arg Val
            580                 585                 590

Thr Gly Met Glu Leu Gly Val Ala Gly Ser Leu Thr Pro Arg Trp Asp
        595                 600                 605

Val Tyr Gly Gly Tyr Ala Leu Leu Asp Ser Lys Leu Val Arg Ala Ser
    610                 615                 620

His Lys Ser Gly Ala Gln Gly Gln Pro Leu Pro Ser Ala Pro Arg His
625                 630                 635                 640

Ala Phe Ser Ile Trp Ser Thr Tyr Lys Leu Leu Pro Glu Leu Thr Val
                645                 650                 655

Gly Ala Gly Ala Phe Tyr Arg Ser Lys Val Tyr Gly Asn Ala Asp Ala
            660                 665                 670

Gly Tyr Asn Lys Asp Gly Thr Pro Lys Ala Arg Trp Val Pro Ala Tyr
        675                 680                 685

Trp Arg Phe Asp Ala Met Ala Ala Tyr Gln Leu Asn Lys His Leu Thr
    690                 695                 700

Ala Gln Leu Asn Val Tyr Asn Leu Leu Asp Lys Thr Tyr Tyr Ala Lys
705                 710                 715                 720

Thr Tyr Arg Ser His Tyr Ala Ala Leu Gly Pro Gly Arg Ser Ala Met
                725                 730                 735
```

Leu Thr Phe Lys Leu Ser Tyr
740

<210> SEQ ID NO 15
<211> LENGTH: 2271
<212> TYPE: DNA
<213> ORGANISM: Bordetella Pertussis

<400> SEQUENCE: 15
atggagaagc cgttgaaatc cctggactcg tattcagcga gcacgctcgc caactcgctg 60
gccgccgcca ttgcggtgcc ggccctgtgc ctgatgcccg gtgctcaggc acagaccagc 120
gcgggcgtta cccaattggc gccggtgcag gtagagggcg aagcgtcccc ctatcaggcc 180
accaccgtcc agtcgtccaa gatgacggcg cccttgctgg atacgcccag gaccgtgcag 240
gtcgtgccgc agcaggtcat ccaggaccag gccgccacca atctgcagga cgtgctgcgc 300
aactcgccgg gcatcaccat gggcgccggc gagggcgggc gcgccggcgg cgacctgccc 360
atcatccggg gccagaatgc ggcgggcagc atcttcgtcg acggcgtgcg cgaccccagc 420
acccagatac gcgatacgtt caacctggag caggtcgaga tcatcaaggg gcctgattcg 480
gtctactccg gccgcggcgg agccggcggc agcatcaacc tggtcagcaa gacgccgaag 540
gcgcgcgact tcgccgaggg ctcggtgcag atcggcaccg acagcaatta ccgcgccacc 600
gccgacggca actggctgct gggcgacaac gccgccttcc gcctgaacct gatgggcaac 660
aagggcgacg tgccgggccg cgaccatgcg gtcgatttca gccgctgggg cgtggcgccc 720
accctgcaac tgggcgtggg cacgcccacc cgcatcaccc tggggtacta ccactaccag 780
gatgacagca tgcccgatta cgcgatcccg tacgatccga agtcggggca gccggtcacc 840
gagacccagg gcgtcagccg caagaatttc tacgggctga ccggccgcga cttcatgaag 900
tcgcgcgacg acgtggccac gctggccatc gatcacgatt tcagcagcaa gctgcgcctg 960
cgcaacgtca cccgctacgg gcgctcggtg accgactacg ccgccaccaa tccggatgac 1020
agcaagggca acgtgcccaa cgggctggtg taccgggcgc tgaaggcggg ctactacacc 1080
aacaagacgt tcaccaacca gaccgacctg agcggcgaat tcgagacggg cagcctgcag 1140
cactcgttcg acgtgggctt cgagtacagc aacatcaagc aggacaagga ctcgtatacc 1200
cagactatcg ccaagggcgc gatgccttgc aaggtgggcg ccaacgatgc cagcaatccg 1260
gccttgtgca cctcgctgtg ggatccggat ccgcatgact attatcccgg ccacctgtcg 1320
cgcaacgaca acccggcccg ctattccacc gacacgatcg cgctctacgg cttcgacacg 1380
atcaagttca acgagcaatg gcaggccagc gtcggactgc gttgggacaa ttaccgcgta 1440
agcggcagca atatcgcccg cggccgcaac gatcccgcca gcacgccggc gttctacagc 1500
accagccgcg aagacaatct gttcaattac cagctgggcc tggcctacaa gccggtgccc 1560
aacggcacga tctacgcctc gtatggcacc tcgtcgacgc cgtcggccgt cgccggctcg 1620
aacgtgagcg acgccgtgac ggtgagcaac gagtcgctgg cgccggagaa aagccgcacc 1680
gtcgaggtcg gcaccaagtg gcaattgttc gacgaccgcc tgaccctgtc gggcgcgttg 1740
ttccaggaca tccgcaagaa caccagcgtg gccgtgtcgg cgaccgaaac ggagcagatc 1800
ggcaaggcca aggtgcgcgg catcgaactg ggcttctcgg gcagcatcac gcccaagtgg 1860
aacgtctacg gcggctatac cttcatggac agcgaactgg tcgagggcgc ctacaacagc 1920
ggcgcggtgg gccaggacct gcccaacacg ccgcgcaatg ccttcagcct gtggaccacc 1980
tacaagctgg tgcctcagct gaccgtgggc ggcggcgcct attacgtgga caaggtatat 2040

-continued ggcaacgcgg acaacggtcg caatgccgac ggcacgccga aggcgcgctg ggtaccgtcg 2100
tactggcgct tcgacgccat ggccgcgtac gagttcaacg accacctgac cgcgcagctc 2160
aacgtgatga acatcttcga caagacgtac tacaccaagg cctacgcggc gcactacgcg 2220
gcgctgggca cgggccgcgc cgcggtgctg tcgttcaata tcaagtattg a 2271

<210> SEQ ID NO 16
<211> LENGTH: 756
<212> TYPE: PRT
<213> ORGANISM: Bordetella Pertussis

<400> SEQUENCE: 16

Met Glu Lys Pro Leu Lys Ser Leu Asp Ser Tyr Ser Ala Ser Thr Leu
1 5 10 15

Ala Asn Ser Leu Ala Ala Ala Ile Ala Val Pro Ala Leu Cys Leu Met
20 25 30

Pro Gly Ala Gln Ala Gln Thr Ser Ala Gly Val Thr Gln Leu Ala Pro
35 40 45

Val Gln Val Glu Gly Glu Ala Ser Pro Tyr Gln Ala Thr Thr Val Gln
50 55 60

Ser Ser Lys Met Thr Ala Pro Leu Leu Asp Thr Pro Arg Thr Val Gln
65 70 75 80

Val Val Pro Gln Gln Val Ile Gln Asp Gln Ala Ala Thr Asn Leu Gln
85 90 95

Asp Val Leu Arg Asn Ser Pro Gly Ile Thr Met Gly Ala Gly Glu Gly
100 105 110

Gly Arg Ala Gly Gly Asp Leu Pro Ile Ile Arg Gly Gln Asn Ala Ala
115 120 125

Gly Ser Ile Phe Val Asp Gly Val Arg Asp Pro Ser Thr Gln Ile Arg
130 135 140

Asp Thr Phe Asn Leu Glu Gln Val Glu Ile Ile Lys Gly Pro Asp Ser
145 150 155 160

Val Tyr Ser Gly Arg Gly Gly Ala Gly Gly Ser Ile Asn Leu Val Ser
165 170 175

Lys Thr Pro Lys Ala Arg Asp Phe Ala Glu Gly Ser Val Gln Ile Gly
180 185 190

Thr Asp Ser Asn Tyr Arg Ala Thr Ala Asp Gly Asn Trp Leu Leu Gly
195 200 205

Asp Asn Ala Ala Phe Arg Leu Asn Leu Met Gly Asn Lys Gly Asp Val
210 215 220

Pro Gly Arg Asp His Ala Val Asp Phe Ser Arg Trp Gly Val Ala Pro
225 230 235 240

Thr Leu Gln Leu Gly Val Gly Thr Pro Thr Arg Ile Thr Leu Gly Tyr
245 250 255

Tyr His Tyr Gln Asp Asp Ser Met Pro Asp Tyr Ala Ile Pro Tyr Asp
260 265 270

Pro Lys Ser Gly Gln Pro Val Thr Glu Thr Gln Gly Val Ser Arg Lys
275 280 285

Asn Phe Tyr Gly Leu Thr Gly Arg Asp Phe Met Lys Ser Arg Asp Asp
290 295 300

Val Ala Thr Leu Ala Ile Asp His Asp Phe Ser Ser Lys Leu Arg Leu
305 310 315 320

Arg Asn Val Thr Arg Tyr Gly Arg Ser Val Thr Asp Tyr Ala Ala Thr
325 330 335

Asn Pro Asp Asp Ser Lys Gly Asn Val Pro Asn Gly Leu Val Tyr Arg

-continued

```
            340                 345                 350

Ala Leu Lys Ala Gly Tyr Tyr Thr Asn Lys Thr Phe Thr Asn Gln Thr
        355                 360                 365

Asp Leu Ser Gly Glu Phe Glu Thr Gly Ser Leu Gln His Ser Phe Asp
    370                 375                 380

Val Gly Phe Glu Tyr Ser Asn Ile Lys Gln Asp Lys Asp Ser Tyr Thr
385                 390                 395                 400

Gln Thr Ile Ala Lys Gly Ala Met Pro Cys Lys Val Gly Ala Asn Asp
                405                 410                 415

Ala Ser Asn Pro Ala Leu Cys Thr Ser Leu Trp Asp Pro Asp Pro His
            420                 425                 430

Asp Tyr Tyr Pro Gly His Leu Ser Arg Asn Asp Asn Pro Ala Arg Tyr
        435                 440                 445

Ser Thr Asp Thr Ile Ala Leu Tyr Gly Phe Asp Thr Ile Lys Phe Asn
    450                 455                 460

Glu Gln Trp Gln Ala Ser Val Gly Leu Arg Trp Asp Asn Tyr Arg Val
465                 470                 475                 480

Ser Gly Ser Asn Ile Ala Arg Gly Arg Asn Asp Pro Ala Ser Thr Pro
                485                 490                 495

Ala Phe Tyr Ser Thr Ser Arg Glu Asp Asn Leu Phe Asn Tyr Gln Leu
            500                 505                 510

Gly Leu Ala Tyr Lys Pro Val Pro Asn Gly Thr Ile Tyr Ala Ser Tyr
        515                 520                 525

Gly Thr Ser Ser Thr Pro Ser Ala Val Ala Gly Ser Asn Val Ser Asp
    530                 535                 540

Ala Val Thr Val Ser Asn Glu Ser Leu Ala Pro Glu Lys Ser Arg Thr
545                 550                 555                 560

Val Glu Val Gly Thr Lys Trp Gln Leu Phe Asp Asp Arg Leu Thr Leu
                565                 570                 575

Ser Gly Ala Leu Phe Gln Asp Ile Arg Lys Asn Thr Ser Val Ala Val
            580                 585                 590

Ser Ala Thr Glu Thr Glu Gln Ile Gly Lys Ala Lys Val Arg Gly Ile
        595                 600                 605

Glu Leu Gly Phe Ser Gly Ser Ile Thr Pro Lys Trp Asn Val Tyr Gly
    610                 615                 620

Gly Tyr Thr Phe Met Asp Ser Glu Leu Val Glu Gly Ala Tyr Asn Ser
625                 630                 635                 640

Gly Ala Val Gly Gln Asp Leu Pro Asn Thr Pro Arg Asn Ala Phe Ser
                645                 650                 655

Leu Trp Thr Thr Tyr Lys Leu Val Pro Gln Leu Thr Val Gly Gly Gly
            660                 665                 670

Ala Tyr Tyr Val Asp Lys Val Tyr Gly Asn Ala Asp Asn Gly Arg Asn
        675                 680                 685

Ala Asp Gly Thr Pro Lys Ala Arg Trp Val Pro Ser Tyr Trp Arg Phe
    690                 695                 700

Asp Ala Met Ala Ala Tyr Glu Phe Asn Asp His Leu Thr Ala Gln Leu
705                 710                 715                 720

Asn Val Met Asn Ile Phe Asp Lys Thr Tyr Tyr Thr Lys Ala Tyr Ala
                725                 730                 735

Ala His Tyr Ala Ala Leu Gly Thr Gly Arg Ala Ala Val Leu Ser Phe
            740                 745                 750

Asn Ile Lys Tyr
        755
```

<210> SEQ ID NO 17
<211> LENGTH: 2109
<212> TYPE: DNA
<213> ORGANISM: Bordetella Pertussis

<400> SEQUENCE: 17

```
ttgcatactc gcacgccaca gcggcagcgc ccggtcgcgc cgcgcctgct gcatctatcg     60
ctggccgcct cgctggcggc cggcgccgcc caggcgcaga ccgccaccga agccaccacc    120
ctgcccaccg tgcaggtcac cggcaggggc gagaccgcca ccggcccggt cgacggctat    180
gccgccacgc gcagcgccac cgccaccaag accgataccc cgctgtcgga aaccccgcag    240
gccgtcacgg tgatcccgcg cgagcagatc atcgaccagg gcgcgcagaa cgtgcaggac    300
accatgaact acgccgcggg ggtgcgcccc aacgcctatg gcgtggacaa ccgcggcgac    360
tacgtgcggg tgcgcggggt ggagccggtc cagtatctcg acggcctgaa gcagttcttc    420
aactacaaca atccgcgcac cgaggtctac gggctcgagc gcgtcgaagt cctgcgcggc    480
ccggcctcga tgctgtacgg ccagggcagc accggcggcg tggtcaacct cgtcagcaag    540
cggccgcagc ccgaggccat gcgcgagatc ggcgtgaccg tgggcaacca caaccgcaag    600
gagatccagg ccgatctcac cggcccgctg accgaggacg gcacctggct gtaccaggtg    660
gtggccctcg gacgcgacag cgacacgcag gtccagtaca ccaaggacga ccgcatgatg    720
ctcgcgccgt cgctgacctg gcagcccagc gccgccacct cgctgacgct gcaggcctac    780
tggcagaagg acaagtcggg cacgacccag gccttcctgc cctggagcgg cacggtcagc    840
ggcaacccca acggccgcat ccccacccgc cgcttcacca gcgaacccgg cttcgaccgc    900
tacgacaccg agcaattcag cgtgggctgg cagttcgagc acaagttcaa cgacaactgg    960
aaagtgcgcc agaacctgcg ccacacatcc agcaaggtcg actacagcac gctgtatccg   1020
gcggtctacg gcaaccccga caatcccttc atcgacgccg accagcgcgt ggtcaatcgc   1080
tacctgtaca tcaagaaccc gcgcatgcgt tccttgctgg ccgaccagaa cctcgaaggc   1140
aaggtgaact ggggccgcgc cgaacatacc ctgctgatgg gcgtggacta cagccgctat   1200
cgcgagaccg gcgagaccgg cagcgggttc ggcgcgccgc tggacctgta ccagccggtc   1260
tacggcaccc tgcccgacta tgccatgtcg gacgtgccca agaacaagca gcagcagatc   1320
ggcgtctacc tgcaggacca gatcaagttc gaccgcaact ggatcgtggt ggcgggcctg   1380
cgccacgacc gcgtcgccaa cagcgtcgag ggcgccgaca aggaaaccga caacgccacc   1440
accaagcggc tgggcctgat gtacgccgcc gacaacggct ggtcgcccta cctcagctac   1500
agcgagtcgt tcacccccat cgccggcacc gacaacagcg gcaaccgctg ggtgccgatg   1560
cgcggcaagc aatgggaagc aggcctgaag tacatgccgc aggacaccgg ctatgaggcc   1620
accctggcgg cctacgacct gcgcgagcgc aaccgccaga ccaacgaccc gtccgatccc   1680
accaaccagg tgcagaccgg caagaccaag acgcgcggca tcgaactgga attccgcggc   1740
cgcgtcacgc cgcagatgga tgtgatcgcc aactacaact acaccgacat cgacccgcag   1800
ctcgaaggcc tgcccaagca cacgttctcg ctgtggagca aataccggtt cagcgtgggc   1860
gatgtgcatg gctttgccgc cggcgccggc gtgcgctacc tgaacgcgtt tcgcgacggg   1920
tccgcgcccg agaccggctc ggtggccctg ttcgacgcca tgctcagcta cgacaccggt   1980
tcgtggcgct atgcgctgaa cgtcgccaac atcgccgaca agacctacga ggtggtgtgc   2040
ctgcggcgcg gcgattgctt ctacggccag cgccgcacgg tcaccctgag cgccatgtac   2100
cgcttctag                                                           2109
```

<210> SEQ ID NO 18
<211> LENGTH: 702
<212> TYPE: PRT
<213> ORGANISM: Bordetella Pertussis

<400> SEQUENCE: 18

Leu His Thr Arg Thr Pro Gln Arg Gln Arg Pro Val Ala Pro Arg Leu
1 5 10 15

Leu His Leu Ser Leu Ala Ala Ser Leu Ala Ala Gly Ala Ala Gln Ala
20 25 30

Gln Thr Ala Thr Glu Ala Thr Thr Leu Pro Thr Val Gln Val Thr Gly
35 40 45

Arg Gly Glu Thr Ala Thr Gly Pro Val Asp Gly Tyr Ala Ala Thr Arg
50 55 60

Ser Ala Thr Ala Thr Lys Thr Asp Thr Pro Leu Ser Glu Thr Pro Gln
65 70 75 80

Ala Val Thr Val Ile Pro Arg Glu Gln Ile Ile Asp Gln Gly Ala Gln
85 90 95

Asn Val Gln Asp Thr Met Asn Tyr Ala Ala Gly Val Arg Pro Asn Ala
100 105 110

Tyr Gly Val Asp Asn Arg Gly Asp Tyr Val Arg Val Arg Gly Val Glu
115 120 125

Pro Val Gln Tyr Leu Asp Gly Leu Lys Gln Phe Phe Asn Tyr Asn Asn
130 135 140

Pro Arg Thr Glu Val Tyr Gly Leu Glu Arg Val Glu Val Leu Arg Gly
145 150 155 160

Pro Ala Ser Met Leu Tyr Gly Gln Gly Ser Thr Gly Gly Val Val Asn
165 170 175

Leu Val Ser Lys Arg Pro Gln Pro Glu Ala Met Arg Glu Ile Gly Val
180 185 190

Thr Val Gly Asn His Asn Arg Lys Glu Ile Gln Ala Asp Leu Thr Gly
195 200 205

Pro Leu Thr Glu Asp Gly Thr Trp Leu Tyr Gln Val Val Ala Leu Gly
210 215 220

Arg Asp Ser Asp Thr Gln Val Gln Tyr Thr Lys Asp Asp Arg Met Met
225 230 235 240

Leu Ala Pro Ser Leu Thr Trp Gln Pro Ser Ala Ala Thr Ser Leu Thr
245 250 255

Leu Gln Ala Tyr Trp Gln Lys Asp Lys Ser Gly Thr Thr Gln Ala Phe
260 265 270

Leu Pro Trp Ser Gly Thr Val Ser Gly Asn Pro Asn Gly Arg Ile Pro
275 280 285

Thr Arg Arg Phe Thr Ser Glu Pro Gly Phe Asp Arg Tyr Asp Thr Glu
290 295 300

Gln Phe Ser Val Gly Trp Gln Phe Glu His Lys Phe Asn Asp Asn Trp
305 310 315 320

Lys Val Arg Gln Asn Leu Arg His Thr Ser Ser Lys Val Asp Tyr Ser
325 330 335

Thr Leu Tyr Pro Ala Val Tyr Gly Asn Pro Asp Asn Pro Phe Ile Asp
340 345 350

Ala Asp Gln Arg Val Val Asn Arg Tyr Leu Tyr Ile Lys Asn Pro Arg
355 360 365

Met Arg Ser Leu Leu Ala Asp Gln Asn Leu Glu Gly Lys Val Asn Trp
370 375 380

-continued

```
Gly Arg Ala Glu His Thr Leu Leu Met Gly Val Asp Tyr Ser Arg Tyr
385                 390                 395                 400

Arg Glu Thr Gly Glu Thr Gly Ser Gly Phe Gly Ala Pro Leu Asp Leu
                405                 410                 415

Tyr Gln Pro Val Tyr Gly Thr Leu Pro Asp Tyr Ala Met Ser Asp Val
            420                 425                 430

Pro Lys Asn Lys Gln Gln Gln Ile Gly Val Tyr Leu Gln Asp Gln Ile
        435                 440                 445

Lys Phe Asp Arg Asn Trp Ile Val Val Ala Gly Leu Arg His Asp Arg
    450                 455                 460

Val Ala Asn Ser Val Glu Gly Ala Asp Lys Glu Thr Asp Asn Ala Thr
465                 470                 475                 480

Thr Lys Arg Leu Gly Leu Met Tyr Ala Ala Asp Asn Gly Trp Ser Pro
                485                 490                 495

Tyr Leu Ser Tyr Ser Glu Ser Phe Thr Pro Ile Ala Gly Thr Asp Asn
            500                 505                 510

Ser Gly Asn Arg Trp Val Pro Met Arg Gly Lys Gln Trp Glu Ala Gly
        515                 520                 525

Leu Lys Tyr Met Pro Gln Asp Thr Gly Tyr Glu Ala Thr Leu Ala Ala
    530                 535                 540

Tyr Asp Leu Arg Glu Arg Asn Arg Gln Thr Asn Asp Pro Ser Asp Pro
545                 550                 555                 560

Thr Asn Gln Val Gln Thr Gly Lys Thr Lys Thr Arg Gly Ile Glu Leu
                565                 570                 575

Glu Phe Arg Gly Arg Val Thr Pro Gln Met Asp Val Ile Ala Asn Tyr
            580                 585                 590

Asn Tyr Thr Asp Ile Asp Pro Gln Leu Glu Gly Leu Pro Lys His Thr
        595                 600                 605

Phe Ser Leu Trp Ser Lys Tyr Arg Phe Ser Val Gly Asp Val His Gly
    610                 615                 620

Phe Ala Ala Gly Ala Gly Val Arg Tyr Leu Asn Ala Phe Arg Asp Gly
625                 630                 635                 640

Ser Ala Pro Glu Thr Gly Ser Val Ala Leu Phe Asp Ala Met Leu Ser
                645                 650                 655

Tyr Asp Thr Gly Ser Trp Arg Tyr Ala Leu Asn Val Ala Asn Ile Ala
            660                 665                 670

Asp Lys Thr Tyr Glu Val Val Cys Leu Arg Arg Gly Asp Cys Phe Tyr
        675                 680                 685

Gly Gln Arg Arg Thr Val Thr Leu Ser Ala Met Tyr Arg Phe
    690                 695                 700


<210> SEQ ID NO 19
<211> LENGTH: 2613
<212> TYPE: DNA
<213> ORGANISM: Bordetella pertussis

<400> SEQUENCE: 19

atggtttacg cttgcgatca gggcgcccgc cgcgcccgtc ccgcgccgcc aaggcgcccc      60

caaacggcac tggccatgcg cggcgcgctg gcggcatgcg cactggccgg tacgctggcg     120

gccgctcccg ccgccgcgca gccgacggcg gcgcccgcat cggcgggcgc gcgcgcctgg     180

cacatcgacg ccggcccccct gggcgaggcc ctggcgcgct ttgccgacca ggccggcatt     240

accctgctgt acgaccccgc cgcggtgcgc ggccgcgcca gcgccggcct gcaaggcgtg     300

tactcggtgc ccgacggcct ggcgcgcctg ctcgatggca gcggcctgga cgcgcgccag     360
```

```
cgcggcgccg gcacctacgt gctgcaggcg ctgcccgccg gcccggtcgc ccagctggcg    420

ccggtcacca tcgaggctga cggcgtgcgc gccgatcccg cctgggcccg caccgccacg    480

cgccgcgagc tcgacgcgcg ccaggtgctc gactggagcg atatcggcaa gcgcgtcgat    540

cccggcgtca actacaaccg ccgcaccaag agcatcaaca tccgcggcct ggacgaaaac    600

cgcgtggtca cgcgcatcga cggcatccgc ctgccctggc tcgacgacgg cgcgcgcggc    660

atccagggcg ggctgaacgc ggtggacttc aacaccctgt cgcgcctgga cgtcgtgcgc    720

ggcgccgact ccagcgcggc cggctccggc gcgctgggcg gcctggccga cctgcgcacg    780

ctcgaacccg ccgacctgct gcgcgacggg cgccgcttcg gcgcgctggc caagtccgac    840

tatgactcgg ccgacgccag ctggggcctg aacgcggccc tggccgggca ggtccacgac    900

gacaccagct ggctgttgca ggcgggcacc cgcaatgggc acgacctgga caaccgcgcc    960

gacacgggcg gctacggcag caagcgcagc cagcccagcc ccgaggacta cgcccagaac   1020

aacttcctgc tcaagctgca gcagcgcatc gacggcggcc atcgcctcgg cctgacgggc   1080

gaatacttca agcgccgcgc cgacctcgac cagatgtacc agcagggcgc cggcaccagc   1140

taccagtacg gcgccaaccg cacccacgag gaaaccacgc gcaagcgcgt ctcgctggac   1200

taccagtaca acgccccgca ggccggcgcc gcgatcgaca gcgcccgggc catggtgtat   1260

tggcagcggc tgcggctgga cagctcgcag gacgcccgcc gcacgcgcga cgggcgcgcc   1320

tacgcccgcc ccggcgaccc gtacttctac ggctacccca gcggccccta cgggcgcagc   1380

aactcgatcc aggaatcgat cctcggcgtc aacggcgagc tctccagccg cttcgaaggc   1440

atggtgtcgc agcgcgtgac gataggcggc gaatggtacg gcaaccgcac cgagcagtac   1500

tcggacggct acgacaactg ccccgccatc ccgcccggca cgcccgcgcc gatggggccg   1560

cgcctgtgcg acatgctgca taccaaccag gccgacatgc cccgggtcaa gggcagccag   1620

tgggccatct gggcgcagga cgaaatcgcc ttcgccgacg ggcgctacat cctgaccccg   1680

tcactgcgct acgaccatta cgagcagaag ccgcagcaag gcggcggcta ccagaacaac   1740

cccaacgccg gcgcgctgcc gccgtcgtcg tcggggggcc gcttctcgcc caagctgctg   1800

ggcacctgga aggcgcgcga ggcgctgacg ctgtatgcgc aatacggctt cggctaccgg   1860

gcgccgtcgg ccaccgagct gtacaccaac tacggcggcc cgggaaccta tctgcgcgtg   1920

ggcaatccct ccttgaagcc cgagaccagc aagggctggg aactgggcgc ccgcctgggc   1980

gacgaccagt tgggaggcgc cgtatcgctg ttcgacaacc gctaccagaa cttcatcgac   2040

aagaacgtgc cgctgggcaa gggttcgccg caatggcagc cggcctggga cggccagtac   2100

ccgctgggcg tcaccgggct ggccaaccgg gcgcgcgtgc gcatctatgg cgccgaagcc   2160

tcggcgcact ggcggttcgc gcccaactgg cgcacctggg gctcgctggc ctgggccgtg   2220

ggcaaggacg aaaacaccgg ccagcacctg aattcggtgc cgccgctcaa ggccatcctc   2280

ggcctgggct accagcgcga cgaatggggc atcgacgcca tgctgacggc cgccacgcgc   2340

cgcgacgacg tgcaataccc cgaggcctcc gccagcgcgc gctacgccga tttccaggcc   2400

ccgggctacg gcgtggtgga tctgtccgcc tactggcgcc cggccgccgt caagggcctg   2460

cagctgcagg cgggcgtgtt caacctgttc gacaagaaat actgggaagc catcaacgtg   2520

cccacggcgg gtgccattgc gattccgcga ccgttagact ggtacaacga gccaggccgc   2580

agcgtgcgcg tatcgttgac ctaccagtat tga                                2613
```

<210> SEQ ID NO 20
<211> LENGTH: 870
<212> TYPE: PRT

<213> ORGANISM: Bordetella pertussis

<400> SEQUENCE: 20

Met Val Tyr Ala Cys Asp Gln Gly Ala Arg Arg Ala Arg Pro Ala Pro
1 5 10 15

Pro Arg Arg Pro Gln Thr Ala Leu Ala Met Arg Gly Ala Leu Ala Ala
20 25 30

Cys Ala Leu Ala Gly Thr Leu Ala Ala Ala Pro Ala Ala Ala Gln Pro
35 40 45

Thr Ala Ala Pro Ala Ser Ala Gly Ala Arg Ala Trp His Ile Asp Ala
50 55 60

Gly Pro Leu Gly Glu Ala Leu Ala Arg Phe Ala Asp Gln Ala Gly Ile
65 70 75 80

Thr Leu Leu Tyr Asp Pro Ala Ala Val Arg Gly Arg Ala Ser Ala Gly
85 90 95

Leu Gln Gly Val Tyr Ser Val Pro Asp Gly Leu Ala Arg Leu Leu Asp
100 105 110

Gly Ser Gly Leu Asp Ala Arg Gln Arg Gly Ala Gly Thr Tyr Val Leu
115 120 125

Gln Ala Leu Pro Ala Gly Pro Val Ala Gln Leu Ala Pro Val Thr Ile
130 135 140

Glu Ala Asp Gly Val Arg Ala Asp Pro Ala Trp Ala Arg Thr Ala Thr
145 150 155 160

Arg Arg Glu Leu Asp Ala Arg Gln Val Leu Asp Trp Ser Asp Ile Gly
165 170 175

Lys Arg Val Asp Pro Gly Val Asn Tyr Asn Arg Arg Thr Lys Ser Ile
180 185 190

Asn Ile Arg Gly Leu Asp Glu Asn Arg Val Val Thr Arg Ile Asp Gly
195 200 205

Ile Arg Leu Pro Trp Leu Asp Asp Gly Ala Arg Gly Ile Gln Gly Gly
210 215 220

Leu Asn Ala Val Asp Phe Asn Thr Leu Ser Arg Leu Asp Val Val Arg
225 230 235 240

Gly Ala Asp Ser Ser Ala Ala Gly Ser Gly Ala Leu Gly Gly Leu Ala
245 250 255

Asp Leu Arg Thr Leu Glu Pro Ala Asp Leu Leu Arg Asp Gly Arg Arg
260 265 270

Phe Gly Ala Leu Ala Lys Ser Asp Tyr Asp Ser Ala Asp Ala Ser Trp
275 280 285

Gly Leu Asn Ala Ala Leu Ala Gly Gln Val His Asp Asp Thr Ser Trp
290 295 300

Leu Leu Gln Ala Gly Thr Arg Asn Gly His Asp Leu Asp Asn Arg Ala
305 310 315 320

Asp Thr Gly Gly Tyr Gly Ser Lys Arg Ser Gln Pro Ser Pro Glu Asp
325 330 335

Tyr Ala Gln Asn Asn Phe Leu Leu Lys Leu Gln Gln Arg Ile Asp Gly
340 345 350

Gly His Arg Leu Gly Leu Thr Gly Glu Tyr Phe Lys Arg Arg Ala Asp
355 360 365

Leu Asp Gln Met Tyr Gln Gln Gly Ala Gly Thr Ser Tyr Gln Tyr Gly
370 375 380

Ala Asn Arg Thr His Glu Glu Thr Thr Arg Lys Arg Val Ser Leu Asp
385 390 395 400

Tyr Gln Tyr Asn Ala Pro Gln Ala Gly Ala Ala Ile Asp Ser Ala Arg

-continued

```
                405                 410                 415

Ala Met Val Tyr Trp Gln Arg Leu Arg Leu Asp Ser Ser Gln Asp Ala
            420                 425                 430

Arg Arg Thr Arg Asp Gly Arg Ala Tyr Ala Arg Pro Gly Asp Pro Tyr
        435                 440                 445

Phe Tyr Gly Tyr Pro Ser Gly Pro Tyr Gly Arg Ser Asn Ser Ile Gln
    450                 455                 460

Glu Ser Ile Leu Gly Val Asn Gly Glu Leu Ser Ser Arg Phe Glu Gly
465                 470                 475                 480

Met Val Ser Gln Arg Val Thr Ile Gly Gly Glu Trp Tyr Gly Asn Arg
                485                 490                 495

Thr Glu Gln Tyr Ser Asp Gly Tyr Asp Asn Cys Pro Ala Ile Pro Pro
            500                 505                 510

Gly Thr Pro Ala Pro Met Gly Pro Arg Leu Cys Asp Met Leu His Thr
        515                 520                 525

Asn Gln Ala Asp Met Pro Arg Val Lys Gly Ser Gln Trp Ala Ile Trp
    530                 535                 540

Ala Gln Asp Glu Ile Ala Phe Ala Asp Gly Arg Tyr Ile Leu Thr Pro
545                 550                 555                 560

Ser Leu Arg Tyr Asp His Tyr Glu Gln Lys Pro Gln Gln Gly Gly Gly
                565                 570                 575

Tyr Gln Asn Asn Pro Asn Ala Gly Ala Leu Pro Pro Ser Ser Ser Gly
            580                 585                 590

Gly Arg Phe Ser Pro Lys Leu Leu Gly Thr Trp Lys Ala Arg Glu Ala
        595                 600                 605

Leu Thr Leu Tyr Ala Gln Tyr Gly Phe Gly Tyr Arg Ala Pro Ser Ala
    610                 615                 620

Thr Glu Leu Tyr Thr Asn Tyr Gly Gly Pro Gly Thr Tyr Leu Arg Val
625                 630                 635                 640

Gly Asn Pro Ser Leu Lys Pro Glu Thr Ser Lys Gly Trp Glu Leu Gly
                645                 650                 655

Ala Arg Leu Gly Asp Asp Gln Leu Gly Gly Ala Val Ser Leu Phe Asp
            660                 665                 670

Asn Arg Tyr Gln Asn Phe Ile Asp Lys Asn Val Pro Leu Gly Lys Gly
        675                 680                 685

Ser Pro Gln Trp Gln Pro Ala Trp Asp Gly Gln Tyr Pro Leu Gly Val
    690                 695                 700

Thr Gly Leu Ala Asn Arg Ala Arg Val Arg Ile Tyr Gly Ala Glu Ala
705                 710                 715                 720

Ser Ala His Trp Arg Phe Ala Pro Asn Trp Arg Thr Trp Gly Ser Leu
                725                 730                 735

Ala Trp Ala Val Gly Lys Asp Glu Asn Thr Gly Gln His Leu Asn Ser
            740                 745                 750

Val Pro Pro Leu Lys Ala Ile Leu Gly Leu Gly Tyr Gln Arg Asp Glu
        755                 760                 765

Trp Gly Ile Asp Ala Met Leu Thr Ala Ala Thr Arg Arg Asp Asp Val
    770                 775                 780

Gln Tyr Pro Glu Ala Ser Ala Ser Ala Arg Tyr Ala Asp Phe Gln Ala
785                 790                 795                 800

Pro Gly Tyr Gly Val Val Asp Leu Ser Ala Tyr Trp Arg Pro Ala Ala
                805                 810                 815

Val Lys Gly Leu Gln Leu Gln Ala Gly Val Phe Asn Leu Phe Asp Lys
            820                 825                 830
```

-continued

```
Lys Tyr Trp Glu Ala Ile Asn Val Pro Thr Ala Gly Ala Ile Ala Ile
        835                 840                 845

Pro Arg Pro Leu Asp Trp Tyr Asn Glu Pro Gly Arg Ser Val Arg Val
    850                 855                 860

Ser Leu Thr Tyr Gln Tyr
865                 870
```

<210> SEQ ID NO 21
<211> LENGTH: 2283
<212> TYPE: DNA
<213> ORGANISM: Bordetella pertussis

<400> SEQUENCE: 21

```
ttgcggccgg gccggcggcg cgccgcgcgc tgcccgtcat cgacatgccc gccggctgcc     60

ggcgcggcgc cacaacgtgt gatcatgaaa cagacttccc tttactacgc caccctgggc    120

ctggtcggac tggcgctggc cgcgcccgcg cgcgcgcagg agcaatcgct tcccgtccaa    180

ctcgcgccgg tggtcgtgca tggcgcgccc gaggccaacg gcccgctgaa tctcgacgcg    240

gtcgacagca ccggcagccg cctgggcctg accctgcgcg agacgcccgc ctcggtgacc    300

gtcatcaacc gcgagcagat cgaggcgcgc ggcgcgctcg acacgcagga aatcgcccgc    360

ggcatcgtcg gcgtggacaa tgcctcgccg cccggctcgg ccggctcggt gagctaccgc    420

ggtttctcgg gttcgcaggt cagccagttg ttcaacggca tttcggtgca gtacgacgtg    480

gtcgccgcgc gtccgatcga cagctggatc tacgaccgcg tcgaagccat cggcgggccg    540

tccagcttcc tgttcggcgc gggcgcggtg ggcggcgcca tcaactacgt gaccaaggtg    600

gcgcagcgcg atacgttcta cgacggccag ctgcgcctgg gttcgtacgg cgcgcgccag    660

gcatccgtgg gccttaaccg gcaattggcc ggcgagccgg gcgggcgcgg ccagtacctg    720

cgcatcgacg ccaacgccaa cgcgagcgac ggctgggtcg acggcaatcg ctcgcacgcc    780

gagcaggtgg cggcctcgct gctgtcggac ctgggcgaac gcgtgaccca tacgctggcg    840

ctggagtacc agcacgagat ggtgcaccgg ccttactggg gtacgccgct gaccaccgac    900

ggcgacggcg tggtgcgcgg cgaaggccac atccgcggcg ggacgcgctg gaagaactac    960

aacgtcgacg acggccggta cgagcaatcg gtgtggtggc tgcgttcgct gaccgaatgg   1020

caggccagcg accgcctgag tttccgcaat acgctgtact actatcgcgc cgatcgcgat   1080

ttccagaacc tcgagaccta ccgctacaac ccgggcaaca gccaggtgct gcgctccggc   1140

gcgctgctgc agcgccacga gcagcgcctg ctgggcaacc gcatcgaagg cctgtaccac   1200

ggcagcctgg gcggcctgcg cagcgactgg tcgttcggcg ccgactacag cgtcaaccgc   1260

cagacgcgct accccaccag cgtggccggg caagtcgata gcgtggaccc gtacgagttc   1320

gacccgggcg agttctacga cattccgggc atgcggcgcg gccacgtgcc cgaccgcgac   1380

aacaaggtgc gcacgctggc cttcatgctg gaaaaccgca ccgaagtggg cggcggggtc   1440

gcgctggtga cggctctgcg gcacgacatc atcgacctgg acctgaccaa ccggcgcgcg   1500

gccagcgcgg cttcgcccgg gcacgcctcg cgccgctaca acccgaccac ggggcgcgtc   1560

gccgtcaatt gggaggtcag tcccggcgcg accctgtacg cgcaatacgc caccgccgcc   1620

gacccgcctt ccggcgtact gtcgaccgcg accttcgccg atgtgctgaa caacgacaag   1680

ctgaccaccg gcacccaggt cgaggccggc ggcaagttcg cgttctggga cggccgcggc   1740

acggcgaccg tggcggtcta cgagatcaag cgcaagaacc tcgccacgcc cgatcccctc   1800

aaccccggca gcagcctgcc ggtgggcagc cagtctgccc gcgggctgga gctggccggc   1860

ggattgcagt tgacgcgcgc cttgtcgctg caggccaacc tggcgctggt cgacccccgc   1920
```

```
tatgacgatt tctcgcagaa cgtcggcggg gtggcggtct cgcgcaacgg caaggtgccg   1980

gtcaacacgc cgcgccggct ggccaacgtg tggctggact acgccttcgc gcccgactgg   2040

cgcgccagcc tggcggcgcg ccacgtgggc aagacctatg cggacgcggc caatacggtg   2100

tgggcgccgg cctataccgt gttcgacgcg gcgctgtcgc atcgcatcga ccgccatttc   2160

agcgtgacgg cgcgggtgcg caacctgacc gacaaggtct atgccgccag cgtgaccggc   2220

gcgcccatgt attacctggg cgcgccgcgc agcgtcgaac tcgcgctgca ggcgcgcttc   2280

tga                                                                 2283


<210> SEQ ID NO 22
<211> LENGTH: 760
<212> TYPE: PRT
<213> ORGANISM: Bordetella pertussis

<400> SEQUENCE: 22

Leu Arg Pro Gly Arg Arg Arg Ala Ala Arg Cys Pro Ser Ser Thr Cys
 1               5                  10                  15

Pro Pro Ala Ala Gly Ala Ala Pro Gln Arg Val Ile Met Lys Gln Thr
            20                  25                  30

Ser Leu Tyr Tyr Ala Thr Leu Gly Leu Val Gly Leu Ala Leu Ala Ala
        35                  40                  45

Pro Ala Arg Ala Gln Glu Gln Ser Leu Pro Val Gln Leu Ala Pro Val
    50                  55                  60

Val Val His Gly Ala Pro Glu Ala Asn Gly Pro Leu Asn Leu Asp Ala
65                  70                  75                  80

Val Asp Ser Thr Gly Ser Arg Leu Gly Leu Thr Leu Arg Glu Thr Pro
                85                  90                  95

Ala Ser Val Thr Val Ile Asn Arg Glu Gln Ile Glu Ala Arg Gly Ala
            100                 105                 110

Leu Asp Thr Gln Glu Ile Ala Arg Gly Ile Val Gly Val Asp Asn Ala
        115                 120                 125

Ser Pro Pro Gly Ser Ala Gly Ser Val Ser Tyr Arg Gly Phe Ser Gly
    130                 135                 140

Ser Gln Val Ser Gln Leu Phe Asn Gly Ile Ser Val Gln Tyr Asp Val
145                 150                 155                 160

Val Ala Ala Arg Pro Ile Asp Ser Trp Ile Tyr Asp Arg Val Glu Ala
                165                 170                 175

Ile Gly Gly Pro Ser Ser Phe Leu Phe Gly Ala Gly Ala Val Gly Gly
            180                 185                 190

Ala Ile Asn Tyr Val Thr Lys Val Ala Gln Arg Asp Thr Phe Tyr Asp
        195                 200                 205

Gly Gln Leu Arg Leu Gly Ser Tyr Gly Ala Arg Gln Ala Ser Val Gly
    210                 215                 220

Leu Asn Arg Gln Leu Ala Gly Glu Pro Gly Gly Arg Gly Gln Tyr Leu
225                 230                 235                 240

Arg Ile Asp Ala Asn Ala Asn Ala Ser Asp Gly Trp Val Asp Gly Asn
                245                 250                 255

Arg Ser His Ala Glu Gln Val Ala Ala Ser Leu Leu Ser Asp Leu Gly
            260                 265                 270

Glu Arg Val Thr His Thr Leu Ala Leu Glu Tyr Gln His Glu Met Val
        275                 280                 285

His Arg Pro Tyr Trp Gly Thr Pro Leu Thr Thr Asp Gly Asp Gly Val
    290                 295                 300
```

-continued

```
Val Arg Gly Glu Gly His Ile Arg Gly Gly Thr Arg Trp Lys Asn Tyr
305                 310                 315                 320

Asn Val Asp Asp Gly Arg Tyr Glu Gln Ser Val Trp Trp Leu Arg Ser
                325                 330                 335

Leu Thr Glu Trp Gln Ala Ser Asp Arg Leu Ser Phe Arg Asn Thr Leu
            340                 345                 350

Tyr Tyr Tyr Arg Ala Asp Arg Asp Phe Gln Asn Leu Glu Thr Tyr Arg
        355                 360                 365

Tyr Asn Pro Gly Asn Ser Gln Val Leu Arg Ser Gly Ala Leu Leu Gln
    370                 375                 380

Arg His Glu Gln Arg Leu Leu Gly Asn Arg Ile Glu Gly Leu Tyr His
385                 390                 395                 400

Gly Ser Leu Gly Gly Leu Arg Ser Asp Trp Ser Phe Gly Ala Asp Tyr
                405                 410                 415

Ser Val Asn Arg Gln Thr Arg Tyr Pro Thr Ser Val Ala Gly Gln Val
            420                 425                 430

Asp Ser Val Asp Pro Tyr Glu Phe Asp Pro Gly Glu Phe Tyr Asp Ile
        435                 440                 445

Pro Gly Met Arg Arg Gly His Val Pro Asp Arg Asp Asn Lys Val Arg
    450                 455                 460

Thr Leu Ala Phe Met Leu Glu Asn Arg Thr Glu Val Gly Gly Gly Val
465                 470                 475                 480

Ala Leu Val Thr Ala Leu Arg His Asp Ile Ile Asp Leu Asp Leu Thr
                485                 490                 495

Asn Arg Arg Ala Ala Ser Ala Ala Ser Pro Gly His Ala Ser Arg Arg
            500                 505                 510

Tyr Asn Pro Thr Thr Gly Arg Val Ala Val Asn Trp Glu Val Ser Pro
        515                 520                 525

Gly Ala Thr Leu Tyr Ala Gln Tyr Ala Thr Ala Ala Asp Pro Pro Ser
    530                 535                 540

Gly Val Leu Ser Thr Ala Thr Phe Ala Asp Val Leu Asn Asn Asp Lys
545                 550                 555                 560

Leu Thr Thr Gly Thr Gln Val Glu Ala Gly Gly Lys Phe Ala Phe Trp
                565                 570                 575

Asp Gly Arg Gly Thr Ala Thr Val Ala Val Tyr Glu Ile Lys Arg Lys
            580                 585                 590

Asn Leu Ala Thr Pro Asp Pro Leu Asn Pro Gly Ser Ser Leu Pro Val
        595                 600                 605

Gly Ser Gln Ser Ala Arg Gly Leu Glu Leu Ala Gly Gly Leu Gln Leu
    610                 615                 620

Thr Arg Ala Leu Ser Leu Gln Ala Asn Leu Ala Leu Val Asp Pro Arg
625                 630                 635                 640

Tyr Asp Asp Phe Ser Gln Asn Val Gly Gly Val Ala Val Ser Arg Asn
                645                 650                 655

Gly Lys Val Pro Val Asn Thr Pro Arg Arg Leu Ala Asn Val Trp Leu
            660                 665                 670

Asp Tyr Ala Phe Ala Pro Asp Trp Arg Ala Ser Leu Ala Ala Arg His
        675                 680                 685

Val Gly Lys Thr Tyr Ala Asp Ala Ala Asn Thr Val Trp Ala Pro Ala
    690                 695                 700

Tyr Thr Val Phe Asp Ala Ala Leu Ser His Arg Ile Asp Arg His Phe
705                 710                 715                 720

Ser Val Thr Ala Arg Val Arg Asn Leu Thr Asp Lys Val Tyr Ala Ala
                725                 730                 735
```

```
Ser Val Thr Gly Ala Pro Met Tyr Tyr Leu Gly Ala Pro Arg Ser Val
            740                 745                 750

Glu Leu Ala Leu Gln Ala Arg Phe
        755                 760


<210> SEQ ID NO 23
<211> LENGTH: 1890
<212> TYPE: DNA
<213> ORGANISM: Bordetella pertussis

<400> SEQUENCE: 23

atgaaatccc gctcactccg gcgctgcgcc ggtgtcctgg cctgtgtcgc tccgttggcc     60

ggccacgccc aggccggcgc cgccgccggc caacccatcc ccgaactcga tccggtcgtc    120

gtcaccgccg cgcgatcgcc ccagctgctc aagaatgtgc tggccgacgc cagcgtgatc    180

gagcgcgata cgctggcgcg cgccggccag tccagcctgg ccgaagtgct ggcgcagcag    240

cacggcatcg aattcgccga cagcggcggc ccgcaaagcg tcaccagcct gttcatgcgc    300

ggcgccaaca gcaaccagac cctggtcctg ctcaacggcc agcgcatcaa caacgccaac    360

ggcggcggca ttgcgctcaa cgcgctgccg ccggaagcca tcgaacgcat cgagatcatg    420

cgtggcgcgg ccagcagcct gtacggggcc gacgcgatcg gcggcgtgat caacatcatt    480

acccgcgagc cgggcgacaa ggcgctgtcg gcctatgcca acgccggtta cggcacctac    540

ggcaccagcc gctacgacgc cggcgtctcg ggcgcggccg acggcttcag ctacagcctg    600

tccaccggct atggccagag ccatggcttc aacgccacca accgccgctc gttctcgtac    660

aacccggaca aggacagcta ctaccagaac tacgccaccg gcacgctggg ctacgaatgg    720

cggcccgagc agaaagtggt ggcgcaggtc taccgcagcc gcatcaacgg cggctacgac    780

gcctcggcct cgtacgacta caacgaccgc tacatccagg acctgcaggc ctattcgctg    840

gccagcgaaa accgcctgac ccgctactgg aagagcacgc tgcgcgccgg ctatgtggaa    900

gacaagaacg attcgcgcgc cgaaggcatg ttcgaagaca acaacacgcg cttccggacc    960

cgccagatgc agtacctgtg gcagaacgac ttcaccctgg ccgccggcca gacgctgacg   1020

ctggcctacg agcacctgga ccagcgcgcc gacggccaga tgagcaccgc caccggcatc   1080

ggcaactaca ccgagacgcg ccgccacgtg aactcgtaca ccggcgtcta cctgggcgat   1140

ttcggccgcc accatgtgca ggccagcctg cgcaacgaca acaactcgca gttcggcagc   1200

cacaccaccg gcggcctggc ctacgggttc gacctgacgc ccaacctgcg cgccaccgtg   1260

gccgccaaca cgggctttcg ggcgccgtcg ttcaacgatc tgtacacgcc gaccagcgcg   1320

ttcggctatc gcggcaaccc cgacctcaag ccggaagagt cgcgcaacgc cgagatcggc   1380

ctgaaatacc aggacgagga cagcgaactg ggcgtggtgt attaccagac ccgcatcaag   1440

aacctgatcc aggtgaccga ggacttcagc acggtcgaga acgtcgggcg cgcccgcctg   1500

caaggcttca ccatcagcgg cgcgcaccgc ttcggcaaca cgcgcctgcg cgccagcctg   1560

gacctgagca acccgcgcaa cgaagacacc ggcaagcaat tgctgcgccg cgcccgcacg   1620

gtgctgcgcg ccggcatcga ccatcgcttc gaccgcctgc tggtgggcgc cgagtggtac   1680

gcctcggacg agcgctacga ctacggcttc cccgaggaaa agcgcctggg cggctacggc   1740

ctggtcaacc tgaccgcggc ctacgacctg agccgcaaca tgcaggtgca ggtgcgctgg   1800

aacaacgtgc tcggccagcg ctacaccttg gccgacggct acaacacggc cggctcgaac   1860

gccttcgtca acccgtcgtg gcgcatgtag                                    1890
```

-continued

<210> SEQ ID NO 24
<211> LENGTH: 629
<212> TYPE: PRT
<213> ORGANISM: Bordetella pertussis

<400> SEQUENCE: 24

```
Met Lys Ser Arg Ser Leu Arg Arg Cys Ala Gly Val Leu Ala Cys Val
 1               5                  10                  15

Ala Pro Leu Ala Gly His Ala Gln Ala Gly Ala Ala Ala Gly Gln Pro
            20                  25                  30

Ile Pro Glu Leu Asp Pro Val Val Val Thr Ala Ala Arg Ser Pro Gln
        35                  40                  45

Leu Leu Lys Asn Val Leu Ala Asp Ala Ser Val Ile Glu Arg Asp Thr
    50                  55                  60

Leu Ala Arg Ala Gly Gln Ser Ser Leu Ala Glu Val Leu Ala Gln Gln
65                  70                  75                  80

His Gly Ile Glu Phe Ala Asp Ser Gly Gly Pro Gln Ser Val Thr Ser
                85                  90                  95

Leu Phe Met Arg Gly Ala Asn Ser Asn Gln Thr Leu Val Leu Leu Asn
            100                 105                 110

Gly Gln Arg Ile Asn Asn Ala Asn Gly Gly Gly Ile Ala Leu Asn Ala
        115                 120                 125

Leu Pro Pro Glu Ala Ile Glu Arg Ile Glu Ile Met Arg Gly Ala Ala
    130                 135                 140

Ser Ser Leu Tyr Gly Ala Asp Ala Ile Gly Gly Val Ile Asn Ile Ile
145                 150                 155                 160

Thr Arg Glu Pro Gly Asp Lys Ala Leu Ser Ala Tyr Ala Asn Ala Gly
                165                 170                 175

Tyr Gly Thr Tyr Gly Thr Ser Arg Tyr Asp Ala Gly Val Ser Gly Ala
            180                 185                 190

Ala Asp Gly Phe Ser Tyr Ser Leu Ser Thr Gly Tyr Gly Gln Ser His
        195                 200                 205

Gly Phe Asn Ala Thr Asn Arg Arg Ser Phe Ser Tyr Asn Pro Asp Lys
    210                 215                 220

Asp Ser Tyr Tyr Gln Asn Tyr Ala Thr Gly Thr Leu Gly Tyr Glu Trp
225                 230                 235                 240

Arg Pro Glu Gln Lys Val Val Ala Gln Val Tyr Arg Ser Arg Ile Asn
                245                 250                 255

Gly Gly Tyr Asp Ala Ser Ala Ser Tyr Asp Tyr Asn Asp Arg Tyr Ile
            260                 265                 270

Gln Asp Leu Gln Ala Tyr Ser Leu Ala Ser Glu Asn Arg Leu Thr Arg
        275                 280                 285

Tyr Trp Lys Ser Thr Leu Arg Ala Gly Tyr Val Glu Asp Lys Asn Asp
    290                 295                 300

Ser Arg Ala Glu Gly Met Phe Glu Asp Asn Asn Thr Arg Phe Arg Thr
305                 310                 315                 320

Arg Gln Met Gln Tyr Leu Trp Gln Asn Asp Phe Thr Leu Ala Ala Gly
                325                 330                 335

Gln Thr Leu Thr Leu Ala Tyr Glu His Leu Asp Gln Arg Ala Asp Gly
            340                 345                 350

Gln Met Ser Thr Ala Thr Gly Ile Gly Asn Tyr Thr Glu Thr Arg Arg
        355                 360                 365

His Val Asn Ser Tyr Thr Gly Val Tyr Leu Gly Asp Phe Gly Arg His
    370                 375                 380

His Val Gln Ala Ser Leu Arg Asn Asp Asn Asn Ser Gln Phe Gly Ser
```

```
385                 390                 395                 400

His Thr Thr Gly Gly Leu Ala Tyr Gly Phe Asp Leu Thr Pro Asn Leu
                405                 410                 415

Arg Ala Thr Val Ala Ala Asn Thr Gly Phe Arg Ala Pro Ser Phe Asn
            420                 425                 430

Asp Leu Tyr Thr Pro Thr Ser Ala Phe Gly Tyr Arg Gly Asn Pro Asp
        435                 440                 445

Leu Lys Pro Glu Glu Ser Arg Asn Ala Glu Ile Gly Leu Lys Tyr Gln
    450                 455                 460

Asp Glu Asp Ser Glu Leu Gly Val Val Tyr Tyr Gln Thr Arg Ile Lys
465                 470                 475                 480

Asn Leu Ile Gln Val Thr Glu Asp Phe Ser Thr Val Glu Asn Val Gly
                485                 490                 495

Arg Ala Arg Leu Gln Gly Phe Thr Ile Ser Gly Ala His Arg Phe Gly
            500                 505                 510

Asn Thr Arg Leu Arg Ala Ser Leu Asp Leu Ser Asn Pro Arg Asn Glu
        515                 520                 525

Asp Thr Gly Lys Gln Leu Leu Arg Arg Ala Arg Thr Val Leu Arg Ala
    530                 535                 540

Gly Ile Asp His Arg Phe Asp Arg Leu Leu Val Gly Ala Glu Trp Tyr
545                 550                 555                 560

Ala Ser Asp Glu Arg Tyr Asp Tyr Gly Phe Pro Glu Glu Lys Arg Leu
                565                 570                 575

Gly Gly Tyr Gly Leu Val Asn Leu Thr Ala Ala Tyr Asp Leu Ser Arg
            580                 585                 590

Asn Met Gln Val Gln Val Arg Trp Asn Asn Val Leu Gly Gln Arg Tyr
        595                 600                 605

Thr Leu Ala Asp Gly Tyr Asn Thr Ala Gly Ser Asn Ala Phe Val Asn
    610                 615                 620

Pro Ser Trp Arg Met
625


<210> SEQ ID NO 25
<211> LENGTH: 1734
<212> TYPE: DNA
<213> ORGANISM: Bordetella pertussis

<400> SEQUENCE: 25

atgattccac cttgccgctt atccctgatc ccggcgctgg ccgccatggc gctggcaggc     60

gcctttcccg cgccgagcgg ggccgcgccg gctgaattgg cgcccatcgc ggtcatcggc    120

gacgatcccg acgatccgcg ggtattcgaa ggcagcaccg ccacccgtac cgccacaccg    180

ctgcgggagg tgccgcagac ggtcgacacc gtgaaggtgc cggacgccct gaactatggc    240

gcgcgcacgc tgggcgaggc gctggccggc gtgcccaatg tcaccgacgc cagcgatacc    300

cgcttcgacg gcttgcgcat acgcgggttc gacgccggca gcgacttcta cctggacggg    360

gtgcgcgatg acagccagta cgtgcgcgac ctgcacaaca tcgagcgcat cgaggtgctc    420

aaggggccgg ccggcgttct gtacggccgc ggcagccagg gcggcatcgt caatcgggtg    480

agcaaggcgc ccgggccggg ccgcgcttcc accctcgaag tccggctggg cggcgaggac    540

tttcgcagcc tgtacgccga cctgagcgcg gacccttccg acacggtcag cctgcgcctg    600

aacgtgggcg gcgagaatgc gggcagtttc aggcacgggg tcagctcgcg ccgccgcctg    660

gcgtcgcccg ccttggcgtg gcgcattacg ccacggctcg attggctggc gcagtacgaa    720

cacagccgct acgaccgcgt gcccgaccgc ggcattccct cggtggacgg ccggcccgcg    780
```

-continued

```
ccggtcgggc gctcgaccgt ctacggcgac cccgggcgcg acaatatcga cgatcgggtc     840

caggtgctgc gctcgcgcct gcgctaccgg gcggccaatg gatgggagct gcgccatacc     900

ctgtcgacgt tccggctgca tagcgatttc gacaacacct atctgtccgg ctggcgcgcc     960

gagaccgggc tggtgcaacg ccagcgctgg cagcagcacc tgcgcgcccg gcatctttac    1020

aacgtcttcg aggccgaggg cacgttcgcc accggctggc tcgaacaccg cttgctggcc    1080

ggcgtcgagc tgggcagcca gcatcgcgat ccgacgctgc accgcgcggc caccaaaggc    1140

cccggcgcgc agccggtgcc cgggctggcg ctgcaccacc ccgacttgag ccagcagcac    1200

cacggccgca tggagcgcgc cagcgatgcg cgtcaccgcg tgcgtacgca aggctactac    1260

ttgcaggatc aactgcgatt gagcgagtcc tggcaggtgg tggcgggcgc gcgcctggac    1320

cggttcgggg tgcgcacgcg caatcgcctg ctgggcctgg aaggcagccg tggcgaccgc    1380

agtgtgagtc cgcgcctggg agtggtctgg acgccctggc cggcgcacgc gttctacgcg    1440

tcgtacagca agactttctc gcccaccggc ggcggcacca taggcatcac gccggacgcg    1500

cggggcaacg ccaatgatct gccgcccgaa catacgcgcc agtacgaagc cggggtcaag    1560

agcgactggc tggacgggcg cctgagcacc atgctggccg tctaccagct cgaactctac    1620

aaccgccgca cgcgcgcgcc ccacgatccc acgcggatac tcctgacggg cctgcagcgc    1680

tcgcgcggcc tggaaatgag cggggcgggg cggctagctg tgaagattca atag          1734
```

<210> SEQ ID NO 26
<211> LENGTH: 577
<212> TYPE: PRT
<213> ORGANISM: Bordetella pertussis

<400> SEQUENCE: 26

```
Met Ile Pro Pro Cys Arg Leu Ser Leu Ile Pro Ala Leu Ala Ala Met
 1               5                  10                  15

Ala Leu Ala Gly Ala Phe Pro Ala Pro Ser Gly Ala Ala Pro Ala Glu
            20                  25                  30

Leu Ala Pro Ile Ala Val Ile Gly Asp Asp Pro Asp Asp Pro Arg Val
        35                  40                  45

Phe Glu Gly Ser Thr Ala Thr Arg Thr Ala Thr Pro Leu Arg Glu Val
    50                  55                  60

Pro Gln Thr Val Asp Thr Val Lys Val Pro Asp Ala Leu Asn Tyr Gly
65                  70                  75                  80

Ala Arg Thr Leu Gly Glu Ala Leu Ala Gly Val Pro Asn Val Thr Asp
                85                  90                  95

Ala Ser Asp Thr Arg Phe Asp Gly Leu Arg Ile Arg Gly Phe Asp Ala
            100                 105                 110

Gly Ser Asp Phe Tyr Leu Asp Gly Val Arg Asp Asp Ser Gln Tyr Val
        115                 120                 125

Arg Asp Leu His Asn Ile Glu Arg Ile Glu Val Leu Lys Gly Pro Ala
    130                 135                 140

Gly Val Leu Tyr Gly Arg Gly Ser Gln Gly Gly Ile Val Asn Arg Val
145                 150                 155                 160

Ser Lys Ala Pro Gly Pro Gly Arg Ala Ser Thr Leu Glu Val Arg Leu
                165                 170                 175

Gly Gly Glu Asp Phe Arg Ser Leu Tyr Ala Asp Leu Ser Ala Asp Pro
            180                 185                 190

Ser Asp Thr Val Ser Leu Arg Leu Asn Val Gly Gly Glu Asn Ala Gly
        195                 200                 205
```

-continued

Ser Phe Arg His Gly Val Ser Ser Arg Arg Arg Leu Ala Ser Pro Ala
    210                 215                 220

Leu Ala Trp Arg Ile Thr Pro Arg Leu Asp Trp Leu Ala Gln Tyr Glu
225                 230                 235                 240

His Ser Arg Tyr Asp Arg Val Pro Asp Arg Gly Ile Pro Ser Val Asp
                245                 250                 255

Gly Arg Pro Ala Pro Val Gly Arg Ser Thr Val Tyr Gly Asp Pro Gly
            260                 265                 270

Arg Asp Asn Ile Asp Asp Arg Val Gln Val Leu Arg Ser Arg Leu Arg
        275                 280                 285

Tyr Arg Ala Ala Asn Gly Trp Glu Leu Arg His Thr Leu Ser Thr Phe
    290                 295                 300

Arg Leu His Ser Asp Phe Asp Asn Thr Tyr Leu Ser Gly Trp Arg Ala
305                 310                 315                 320

Glu Thr Gly Leu Val Gln Arg Gln Arg Trp Gln Gln His Leu Arg Ala
                325                 330                 335

Arg His Leu Tyr Asn Val Phe Glu Ala Glu Gly Thr Phe Ala Thr Gly
            340                 345                 350

Trp Leu Glu His Arg Leu Leu Ala Gly Val Glu Leu Gly Ser Gln His
        355                 360                 365

Arg Asp Pro Thr Leu His Arg Ala Ala Thr Lys Gly Pro Gly Ala Gln
    370                 375                 380

Pro Val Pro Gly Leu Ala Leu His His Pro Asp Leu Ser Gln Gln His
385                 390                 395                 400

His Gly Arg Met Glu Arg Ala Ser Asp Ala Arg His Arg Val Arg Thr
                405                 410                 415

Gln Gly Tyr Tyr Leu Gln Asp Gln Leu Arg Leu Ser Glu Ser Trp Gln
            420                 425                 430

Val Val Ala Gly Ala Arg Leu Asp Arg Phe Gly Val Arg Thr Arg Asn
        435                 440                 445

Arg Leu Leu Gly Leu Glu Gly Ser Arg Gly Asp Arg Ser Val Ser Pro
    450                 455                 460

Arg Leu Gly Val Val Trp Thr Pro Trp Pro Ala His Ala Phe Tyr Ala
465                 470                 475                 480

Ser Tyr Ser Lys Thr Phe Ser Pro Thr Gly Gly Gly Thr Ile Gly Ile
                485                 490                 495

Thr Pro Asp Ala Arg Gly Asn Ala Asn Asp Leu Pro Pro Glu His Thr
            500                 505                 510

Arg Gln Tyr Glu Ala Gly Val Lys Ser Asp Trp Leu Asp Gly Arg Leu
        515                 520                 525

Ser Thr Met Leu Ala Val Tyr Gln Leu Glu Leu Tyr Asn Arg Arg Thr
    530                 535                 540

Arg Ala Pro His Asp Pro Thr Arg Ile Leu Leu Thr Gly Leu Gln Arg
545                 550                 555                 560

Ser Arg Gly Leu Glu Met Ser Gly Ala Gly Arg Leu Ala Val Lys Ile
                565                 570                 575

Gln

<210> SEQ ID NO 27
<211> LENGTH: 1437
<212> TYPE: DNA
<213> ORGANISM: Bordetella pertussis

<400> SEQUENCE: 27
atgaacacgc tgcgacgcct gcgcatcctg ggcgccgccg ccacgctggg cgggccggcc      60

```
gccgcgcagg aggcgcccgc catgctggag ccggtgcgca tcagcggcac gcgcaccggc    120

acctcggtgc tcgatacgcc cgcgtccgtg gacgtggtcg atggccacga gctgcgcgcg    180

cgcaacctgc aggtcaacct gtccgaaggc ttggccggcg tgcccggact gcagctgcag    240

aaccgccaga attacgcgca ggacctgcag ctgtcgatac gcggcttcgg cgcgcgctcg    300

accttcggcg tgcgcggcgt gcggctgtac gtggacggca tcccggccac catgcccgac    360

ggccagggcc agacctcgaa catcgacatc ggctcggccg gccgcgtgga agtgctgcgc    420

ggcccgttct cggccctgta cggcaattcg tcgggcggcg tggtgcaggt gttcaccgaa    480

cagggcagcg atccgcccga ggcgacgggc agcgcggcgg cgggcagctt cggcacctgg    540

cgctacggcg ccaagctgcg cggcgccagc gcggcagacg gcctggatta cgtgctggac    600

ttcaatcgct tcacgaccga gggctatcgc gaccacagcg ccgcgcgcaa gaacctgggc    660

aacgcgcggc tgggcctgcg catggacgac ggcagccgcc tgacgctgag cgccaaccac    720

gtggacctga ccgcgcagga tccgctgggc ctgacgcgcg agcaattcga ggacgacccg    780

cgcagcgcgc cggtggccga gcgcttcgat acgcgcaaga ccgtgcgcca gacccagggc    840

ggcctgctgt acgagcgcgc cttcgacacg cgcaacgacc tgcgcgtgat gctgtactac    900

ggacaacgcc gcaccacgca ataccaatcc atcccggtgg ccgtgcagca aagccccacg    960

caggccggcg gcgtgatcga cctgggccgc gactacggcg gcgccgacct acgctggacc   1020

tcgcgccagc aggtggccgg cctgccgctg accctgatcg gcggactggc ctatgacacc   1080

atgaaggagc agcgccgcgg ctacgacaac tacaccggcc cgcccgctgc gcccaccggc   1140

catgggcgtc aagggcgcgt tgcggcgcga cgagaccaac acggtctaca acctggaccc   1200

gtacctgcag gcctcgtggc agttcgccga gcgctggacg ctggacgcgg ggctgcgcta   1260

cagcacggtg cgcttcgact cggacgatca ttaccaggcg ccgggcaacg gcgacgacag   1320

cggacgcgcc acctatcgca aggccttgcc ggtggcggcg ctgcgctatg cggccaacga   1380

gaacctgagc ctgtacgcct cgtacggacg cggcttcgag acgcccacgc tcaatga      1437
```

<210> SEQ ID NO 28
<211> LENGTH: 478
<212> TYPE: PRT
<213> ORGANISM: Bordetella pertussis

<400> SEQUENCE: 28

```
Met Asn Thr Leu Arg Arg Leu Arg Ile Leu Gly Ala Ala Ala Thr Leu
1               5                   10                  15

Gly Gly Pro Ala Ala Ala Gln Glu Ala Pro Ala Met Leu Glu Pro Val
            20                  25                  30

Arg Ile Ser Gly Thr Arg Thr Gly Thr Ser Val Leu Asp Thr Pro Ala
        35                  40                  45

Ser Val Asp Val Val Asp Gly His Glu Leu Arg Ala Arg Asn Leu Gln
    50                  55                  60

Val Asn Leu Ser Glu Gly Leu Ala Gly Val Pro Gly Leu Gln Leu Gln
65                  70                  75                  80

Asn Arg Gln Asn Tyr Ala Gln Asp Leu Gln Leu Ser Ile Arg Gly Phe
                85                  90                  95

Gly Ala Arg Ser Thr Phe Gly Val Arg Gly Val Arg Leu Tyr Val Asp
            100                 105                 110

Gly Ile Pro Ala Thr Met Pro Asp Gly Gln Gly Gln Thr Ser Asn Ile
        115                 120                 125

Asp Ile Gly Ser Ala Gly Arg Val Glu Val Leu Arg Gly Pro Phe Ser
```

130 135 140

Ala Leu Tyr Gly Asn Ser Ser Gly Gly Val Val Gln Val Phe Thr Glu
145 150 155 160

Gln Gly Ser Asp Pro Pro Glu Ala Thr Gly Ser Ala Ala Ala Gly Ser
165 170 175

Phe Gly Thr Trp Arg Tyr Gly Ala Lys Leu Arg Gly Ala Ser Ala Ala
180 185 190

Asp Gly Leu Asp Tyr Val Leu Asp Phe Asn Arg Phe Thr Thr Glu Gly
195 200 205

Tyr Arg Asp His Ser Ala Ala Arg Lys Asn Leu Gly Asn Ala Arg Leu
210 215 220

Gly Leu Arg Met Asp Asp Gly Ser Arg Leu Thr Leu Ser Ala Asn His
225 230 235 240

Val Asp Leu Thr Ala Gln Asp Pro Leu Gly Leu Thr Arg Glu Gln Phe
245 250 255

Glu Asp Asp Pro Arg Ser Ala Pro Val Ala Glu Arg Phe Asp Thr Arg
260 265 270

Lys Thr Val Arg Gln Thr Gln Gly Gly Leu Leu Tyr Glu Arg Ala Phe
275 280 285

Asp Thr Arg Asn Asp Leu Arg Val Met Leu Tyr Tyr Gly Gln Arg Arg
290 295 300

Thr Thr Gln Tyr Gln Ser Ile Pro Val Ala Val Gln Gln Ser Pro Thr
305 310 315 320

Gln Ala Gly Gly Val Ile Asp Leu Gly Arg Asp Tyr Gly Gly Ala Asp
325 330 335

Leu Arg Trp Thr Ser Arg Gln Gln Val Ala Gly Leu Pro Leu Thr Leu
340 345 350

Ile Gly Gly Leu Ala Tyr Asp Thr Met Lys Glu Gln Arg Arg Gly Tyr
355 360 365

Asp Asn Tyr Thr Gly Pro Pro Ala Ala Pro Thr Gly His Gly Arg Gln
370 375 380

Gly Arg Val Ala Ala Arg Arg Asp Gln His Gly Leu Gln Pro Gly Pro
385 390 395 400

Val Pro Ala Gly Leu Val Ala Val Arg Arg Ala Leu Asp Ala Gly Arg
405 410 415

Gly Ala Ala Leu Gln His Gly Ala Leu Arg Leu Gly Arg Ser Leu Pro
420 425 430

Gly Ala Gly Gln Arg Arg Arg Gln Arg Thr Arg His Leu Ser Gln Gly
435 440 445

Leu Ala Gly Gly Gly Ala Ala Leu Cys Gly Gln Arg Glu Pro Glu Pro
450 455 460

Val Arg Leu Val Arg Thr Arg Leu Arg Asp Ala His Ala Gln
465 470 475

<210> SEQ ID NO 29
<211> LENGTH: 2733
<212> TYPE: DNA
<213> ORGANISM: Bordetella pertussis

<400> SEQUENCE: 29
atgaacatgt ctctgtcacg cattgtcaag gcggcgcccc tgcgccgcac cacgctggcc 60
atggcgctgg gcgcgctggg cgccgccccg gcggcgcatg ccgactggaa caaccagtcc 120
atcgtcaaga ccggtgagcg ccagcatggc atccatatcc agggctccga cccgggcggc 180
gtacggaccg ccagcggaac caccatcaag gtaagcggcc gtcaggccca gggcatcctg 240

-continued

```
ctagaaaatc ccgcggccga gctgcagttc cggaacggca gtgtcacgtc gtcgggacag    300
ttgtccgacg atggcatccg gcgctttctg ggcaccgtca ccgtcaaggc cggcaagctg    360
gtcgccgatc acgccacgct ggccaacgtt ggcgacacct gggacgacga cggcatcgcg    420
ctctatgtgg ccggcgaaca ggcccaggcc agcatcgccg acagcaccct gcagggcgct    480
ggcggcgtgc agatcgagcg cggcgccaat gtcacggtcc aacgcagcgc catcgtcgac    540
gggggcttgc atatcggcgc cctgcagtca ttgcagccgg aagaccttcc gcccagccgg    600
gtggtgctgc gcgacaccaa cgtgaccgcc gtgcccgcca gcggcgcgcc cgcggcggtg    660
tctgtgttgg gggccagtga gcttacgctc gacggcgggc acatcaccgg cgggcgggca    720
gcgggggtgg cggccatgca aggggcggtc gtgcatctgc agcgcgcgac gatacggcgc    780
ggggacgcgc ctgccggcgg tgcggttccc ggcggtgcgg ttcccggtgg tgcggttccc    840
ggcggcttcg gtcccggcgg cttcggtccc gtcctcgacg gctggtatgg cgtggacgta    900
tcgggctcca gcgtggagct cgcccagtcg atcgtcgagg cgccggagct gggcgccgca    960
atccgggtgg gccgcggcgc cagggtgacg gtgtcgggcg gcagcttgtc cgcaccgcac   1020
ggcaatgtca tcgagaccgg cggcgcgcgt cgctttgcgc ctcaagccgc gcccctgtcg   1080
atcaccttgc aggccggcgc gcatgcccag gggaaagcgc tgctgtaccg ggtcctgccg   1140
gagcccgtga agctgacgct gaccgggggc gccgatgcgc agggcgacat cgtcgcgacg   1200
gagctgccct ccattcccgg cacgtcgatc gggccgctcg acgtggcgct ggccagccag   1260
gcccgatgga cgggcgctac ccgcgcggtc gactcgctgt ccatcgacaa cgccacctgg   1320
gtcatgacgg acaactcgaa cgtcggtgcg ctacggctgg ccagcgacgg cagcgtcgat   1380
ttccagcagc cggccgaagc tgggcggttc aaggtcctga cggtcaatac gctggcgggt   1440
tcggggctgt tccgcatgaa tgtcttcgcg gacctggggc tgagcgacaa gctggtcgtc   1500
atgcaggacg ccagcggcca gcacaggctg tgggtccgca acagcggcag cgagccggcc   1560
agcgccaaca ccctgctgct ggtgcagacg ccactaggca gcgcggcgac ctttaccctt   1620
gccaacaagg acggcaaggt cgatatcggt acctatcgct atcgattggc cgccaacggc   1680
aatgggcagt ggagcctggt gggcgcgaag gcgccgccgg cgcccaagcc cgcgccgcag   1740
ccgggtcccc agccgccgca gccgccgcag ccgcagccgg aagcgccggc gccgcaaccg   1800
ccggcgggca gggagttgtc cgccgccgcc aacgcggcgg tcaacacggg tggggtgggc   1860
ctggccagca cgctctggta cgccgaaagc aatgcgttgt ccaagcgcct gggcgagttg   1920
cgcctgaatc cggacgccgg cggcgcctgg ggccgcggct tcgcgcaacg ccagcagctg   1980
gacaaccgcg ccgggcggcg cttcgaccag aaggtggccg gcttcgagct gggcgccgac   2040
cacgcggtgg cggtggccgg cggacgctgg cacctgggcg ggctggccgg ctatacgcgc   2100
ggcgaccgcg gcttcaccgg cgacggcggc ggccacaccg acagcgtgca tgtcgggggc   2160
tatgccacat atatcgccga cagcggtttc tacctggacg cgacgctgcg cgccagccgc   2220
ctggagaatg acttcaaggt ggcgggcagc gacgggtacg cggtcaaggg caagtaccgc   2280
acccatgggg tgggcgcctc gctcgaggcg ggccggcgct ttacccatgc cgacggctgg   2340
ttcctcgagc cgcaggccga gctggcggta ttccgggccg gcggcggtgc gtaccgcgcg   2400
gccaacggcc tgcgggtgcg cgacgaaggc ggcagctcgg tgctgggtcg cctgggcctg   2460
gaggtcggca agcgcatcga actggcaggc ggcaggcagg tgcagccata catcaaggcc   2520
agcgtgctgc aggagttcga cggcgcgggt acggtacaca ccaacggcat cgcgcaccgc   2580
accgaactgc gcggcacgcg cgccgaactg ggcctgggca tggccgccgc gctgggccgc   2640
```

ggccacagcc tgtatgcctc gtacgagtac tccaagggcc cgaagctggc catgccgtgg 2700
accttccacg cgggctaccg gtacagctgg taa 2733

<210> SEQ ID NO 30
<211> LENGTH: 910
<212> TYPE: PRT
<213> ORGANISM: Bordetella pertussis

<400> SEQUENCE: 30

Met Asn Met Ser Leu Ser Arg Ile Val Lys Ala Ala Pro Leu Arg Arg
1 5 10 15

Thr Thr Leu Ala Met Ala Leu Gly Ala Leu Gly Ala Ala Pro Ala Ala
20 25 30

His Ala Asp Trp Asn Asn Gln Ser Ile Val Lys Thr Gly Glu Arg Gln
35 40 45

His Gly Ile His Ile Gln Gly Ser Asp Pro Gly Gly Val Arg Thr Ala
50 55 60

Ser Gly Thr Thr Ile Lys Val Ser Gly Arg Gln Ala Gln Gly Ile Leu
65 70 75 80

Leu Glu Asn Pro Ala Ala Glu Leu Gln Phe Arg Asn Gly Ser Val Thr
85 90 95

Ser Ser Gly Gln Leu Ser Asp Asp Gly Ile Arg Arg Phe Leu Gly Thr
100 105 110

Val Thr Val Lys Ala Gly Lys Leu Val Ala Asp His Ala Thr Leu Ala
115 120 125

Asn Val Gly Asp Thr Trp Asp Asp Asp Gly Ile Ala Leu Tyr Val Ala
130 135 140

Gly Glu Gln Ala Gln Ala Ser Ile Ala Asp Ser Thr Leu Gln Gly Ala
145 150 155 160

Gly Gly Val Gln Ile Glu Arg Gly Ala Asn Val Thr Val Gln Arg Ser
165 170 175

Ala Ile Val Asp Gly Gly Leu His Ile Gly Ala Leu Gln Ser Leu Gln
180 185 190

Pro Glu Asp Leu Pro Pro Ser Arg Val Val Leu Arg Asp Thr Asn Val
195 200 205

Thr Ala Val Pro Ala Ser Gly Ala Pro Ala Ala Val Ser Val Leu Gly
210 215 220

Ala Ser Glu Leu Thr Leu Asp Gly Gly His Ile Thr Gly Gly Arg Ala
225 230 235 240

Ala Gly Val Ala Ala Met Gln Gly Ala Val Val His Leu Gln Arg Ala
245 250 255

Thr Ile Arg Arg Gly Asp Ala Pro Ala Gly Gly Ala Val Pro Gly Gly
260 265 270

Ala Val Pro Gly Gly Ala Val Pro Gly Gly Phe Gly Pro Gly Gly Phe
275 280 285

Gly Pro Val Leu Asp Gly Trp Tyr Gly Val Asp Val Ser Gly Ser Ser
290 295 300

Val Glu Leu Ala Gln Ser Ile Val Glu Ala Pro Glu Leu Gly Ala Ala
305 310 315 320

Ile Arg Val Gly Arg Gly Ala Arg Val Thr Val Ser Gly Gly Ser Leu
325 330 335

Ser Ala Pro His Gly Asn Val Ile Glu Thr Gly Gly Ala Arg Arg Phe
340 345 350

Ala Pro Gln Ala Ala Pro Leu Ser Ile Thr Leu Gln Ala Gly Ala His

-continued

```
        355                 360                 365

Ala Gln Gly Lys Ala Leu Leu Tyr Arg Val Leu Pro Glu Pro Val Lys
    370                 375                 380

Leu Thr Leu Thr Gly Gly Ala Asp Ala Gln Gly Asp Ile Val Ala Thr
385                 390                 395                 400

Glu Leu Pro Ser Ile Pro Gly Thr Ser Ile Gly Pro Leu Asp Val Ala
                405                 410                 415

Leu Ala Ser Gln Ala Arg Trp Thr Gly Ala Thr Arg Ala Val Asp Ser
            420                 425                 430

Leu Ser Ile Asp Asn Ala Thr Trp Val Met Thr Asp Asn Ser Asn Val
        435                 440                 445

Gly Ala Leu Arg Leu Ala Ser Asp Gly Ser Val Asp Phe Gln Gln Pro
    450                 455                 460

Ala Glu Ala Gly Arg Phe Lys Val Leu Thr Val Asn Thr Leu Ala Gly
465                 470                 475                 480

Ser Gly Leu Phe Arg Met Asn Val Phe Ala Asp Leu Gly Leu Ser Asp
                485                 490                 495

Lys Leu Val Val Met Gln Asp Ala Ser Gly Gln His Arg Leu Trp Val
            500                 505                 510

Arg Asn Ser Gly Ser Glu Pro Ala Ser Ala Asn Thr Leu Leu Leu Val
        515                 520                 525

Gln Thr Pro Leu Gly Ser Ala Ala Thr Phe Thr Leu Ala Asn Lys Asp
    530                 535                 540

Gly Lys Val Asp Ile Gly Thr Tyr Arg Tyr Arg Leu Ala Ala Asn Gly
545                 550                 555                 560

Asn Gly Gln Trp Ser Leu Val Gly Ala Lys Ala Pro Pro Ala Pro Lys
                565                 570                 575

Pro Ala Pro Gln Pro Gly Pro Gln Pro Pro Gln Pro Pro Gln Pro Gln
            580                 585                 590

Pro Glu Ala Pro Ala Pro Gln Pro Pro Ala Gly Arg Glu Leu Ser Ala
        595                 600                 605

Ala Ala Asn Ala Ala Val Asn Thr Gly Gly Val Gly Leu Ala Ser Thr
    610                 615                 620

Leu Trp Tyr Ala Glu Ser Asn Ala Leu Ser Lys Arg Leu Gly Glu Leu
625                 630                 635                 640

Arg Leu Asn Pro Asp Ala Gly Gly Ala Trp Gly Arg Gly Phe Ala Gln
                645                 650                 655

Arg Gln Gln Leu Asp Asn Arg Ala Gly Arg Arg Phe Asp Gln Lys Val
            660                 665                 670

Ala Gly Phe Glu Leu Gly Ala Asp His Ala Val Ala Val Ala Gly Gly
        675                 680                 685

Arg Trp His Leu Gly Gly Leu Ala Gly Tyr Thr Arg Gly Asp Arg Gly
    690                 695                 700

Phe Thr Gly Asp Gly Gly Gly His Thr Asp Ser Val His Val Gly Gly
705                 710                 715                 720

Tyr Ala Thr Tyr Ile Ala Asp Ser Gly Phe Tyr Leu Asp Ala Thr Leu
                725                 730                 735

Arg Ala Ser Arg Leu Glu Asn Asp Phe Lys Val Ala Gly Ser Asp Gly
            740                 745                 750

Tyr Ala Val Lys Gly Lys Tyr Arg Thr His Gly Val Gly Ala Ser Leu
        755                 760                 765

Glu Ala Gly Arg Arg Phe Thr His Ala Asp Gly Trp Phe Leu Glu Pro
    770                 775                 780
```

```
Gln Ala Glu Leu Ala Val Phe Arg Ala Gly Gly Gly Ala Tyr Arg Ala
785                 790                 795                 800

Ala Asn Gly Leu Arg Val Arg Asp Glu Gly Gly Ser Ser Val Leu Gly
                805                 810                 815

Arg Leu Gly Leu Glu Val Gly Lys Arg Ile Glu Leu Ala Gly Gly Arg
            820                 825                 830

Gln Val Gln Pro Tyr Ile Lys Ala Ser Val Leu Gln Glu Phe Asp Gly
        835                 840                 845

Ala Gly Thr Val His Thr Asn Gly Ile Ala His Arg Thr Glu Leu Arg
    850                 855                 860

Gly Thr Arg Ala Glu Leu Gly Leu Gly Met Ala Ala Ala Leu Gly Arg
865                 870                 875                 880

Gly His Ser Leu Tyr Ala Ser Tyr Glu Tyr Ser Lys Gly Pro Lys Leu
                885                 890                 895

Ala Met Pro Trp Thr Phe His Ala Gly Tyr Arg Tyr Ser Trp
            900                 905                 910
```

<210> SEQ ID NO 31
<211> LENGTH: 2748
<212> TYPE: DNA
<213> ORGANISM: Bordetella pertussis

<400> SEQUENCE: 31

```
atggcaggac aagcgagggg atggtacggc gcaggcggac gccacccaat acattttcaa     60

atttcggcgg gcgctgcgtt gatgctgggc ctgctggacg tcgccggcgc cgccgctgtc    120

acggcagcgc agcgaataga tggcggcgcg gcgtttctgg gcgatgtcgc catagcgacg    180

accaaggcgt ccgagcacgg tatcaacgtg actggccgca cggcagaggt tcgggtgacg    240

ggcggcacca tacggacgag cggcaaccag gcccagggct tgcgggtcgg cacggagaat    300

gcaccggaca acaccgcgct gggcgcgtcg gtctttttgc agaacctgat catcgagact    360

tccgggaccg gggcattggg cgtctctgtc cacgagccac agggaggagg aggcacgcgc    420

ttgtccatgt ccgggacgac ggtgcgcacg cgcggcgatg acagtttcgc cctgcagctt    480

tcagggcctg ccagcgccac cttgaatgac gtggcgctgg agacggccgg ccagcaggcg    540

cccgcggtgg tgctgtggca aggcgcacag ttgaacgcac aggggctggt ggttcaggtc    600

aacggggcag gcgtttccgc gatacatgcg caggatgccg gcagcttcac gttgtcgggc    660

tcggatatta ccgcccgggg cctggaagtc gccgggatct atgtgcagga aggcatgcag    720

gggacgttga cgggtacgcg ggtcacgacg cagggcgata ccgcgcccgc cttgcaggtg    780

gaggacgcgg gtacgcacgt cagcatgaac ggcggcgcgt tgtcgacctc cggcgcgaat    840

tcgcccgctg catggctgct ggctggcggt tccgcgcagt tccgcgatac ggtattgagg    900

accgtcggcg aggcctcgca tggcgtggac gtcgctgcgc acagcgaggt cgaactggcg    960

catgcgcagg tgcgggccga cggcaaggg gctcatggcc tggtggtgac gcgaagcagc   1020

gcgatggtgc gggcgggttc actggtagag agcaccggag acggcgccgc ggcgctgctg   1080

gaaagcgggc atcttacggt ggacggcagc gtggtccatg gccacggcgc ggccgggttg   1140

gaggtcgacg gcgagagtaa tgtgtccctg ctcaacggcg cacgcctgtc gtcggaccag   1200

ccgacggcga tcaggctgat cgaccctcgg tcggtcctga acctcgacat caaggaccgg   1260

gcgcagctat tgggcgacat tgcgccagag gcgcagcagc cggacggttc gcccgagcag   1320

gccagggttc gtgtggcgct cgccgacggg gggacgtggg cgggccgcac ggacggcgcg   1380

gtccatacgg tgcgattgct cgatcgtggc gtctggaccg tgacgggcga ttcccgggtg   1440
```

-continued

```
gccgaggtca agctggaggg cggcacgctg gcgtttgcgc cacctgcgca gcccaagggc   1500

gctttcaaga cactggtcgc gacgcagggc atttccggta cgggcacgat agtcatgaat   1560

gcacatttgc ccagcggcac ggccgatgtg ctggtggcgc cgcagggatt cggcgaccgg   1620

caggtgctgg tggtcaacaa cacggatgat ggcaccgaga gcggcgcgac caaggtgccg   1680

ctgatcgaag acgaacaagg ccatacggcg ttcacgctgg gcaacatggg gggacgggtg   1740

gacgcgggtg cgcgccagta cgaattgacc gcgagcgagg cgcaggccga caaggcccgc   1800

acctggcagc tgacgccgac caacgagttg tccaccacgg cgaccgccgc cgtgaatgcg   1860

atggcgatcg cggcgtcgca gcgcatctgg caggccgaaa tggacgtgtt gctgcgccat   1920

atgagcggcc tgcattcgat cgggtcgccg ggcggattct gggcgcgcgg cctgagccag   1980

cgccagaggc tcgataccgg ttacggaccc tggcagaagc agaccgtcag cggaatagag   2040

ctgggcctcg acaggcgggt ggccggcggc gcaacgacgg cgtggtccgt cggcatgctg   2100

gccggctaca gcgagacccg gcgcgatggc ggcgcatacc gcgccgggca tgtgcacagc   2160

gcgcacgtcg gcgcgtatgt ctcctacctg aatgattcgg gctcgtatgt ggatggcgtg   2220

gtcaagtaca accgctttcg gcatggtttc gacattcgca cgaccgacct gaagcgggtc   2280

gatgccaagc accgcagcca cggcctgggc gcgttgctgc gcggcgggcg ccgtatcgat   2340

atcgatggcg gctggtatgt cgagccgcag gcttcggtgg cgtggttcca cgccggcggg   2400

agccgctatg aggccagcaa tggcctgcgc gtgcgcgccg acggcgcgca ttcatgggtg   2460

ttgcgcgccg gggcggaggc gggccggcag atgaggttgg ccaatggcaa tatcgttgaa   2520

ccctatgcgc gcttgggctg ggcccaggag ctgggggccg ataacgcggt ctacaccaac   2580

ggcatcaggc atgtcacgcg ttcgcgtggc ggattcgccg aggcccgcgt gggggtgggc   2640

gccttgctgg gcaagcggca tgccttgtac gccgactacg agtatgccaa gggcgcgcgg   2700

ttcgaggcgc cctggacctt gcagctgggg tatcgctaca gctggtga                2748
```

<210> SEQ ID NO 32
<211> LENGTH: 915
<212> TYPE: PRT
<213> ORGANISM: Bordetella pertussis

<400> SEQUENCE: 32

```
Met Ala Gly Gln Ala Arg Gly Trp Tyr Gly Ala Gly Gly Arg His Pro
 1               5                  10                  15

Ile His Phe Gln Ile Ser Ala Gly Ala Ala Leu Met Leu Gly Leu Leu
            20                  25                  30

Asp Val Ala Gly Ala Ala Ala Val Thr Ala Ala Gln Arg Ile Asp Gly
        35                  40                  45

Gly Ala Ala Phe Leu Gly Asp Val Ala Ile Ala Thr Thr Lys Ala Ser
    50                  55                  60

Glu His Gly Ile Asn Val Thr Gly Arg Thr Ala Glu Val Arg Val Thr
65                  70                  75                  80

Gly Gly Thr Ile Arg Thr Ser Gly Asn Gln Ala Gln Gly Leu Arg Val
                85                  90                  95

Gly Thr Glu Asn Ala Pro Asp Asn Thr Ala Leu Gly Ala Ser Val Phe
            100                 105                 110

Leu Gln Asn Leu Ile Ile Glu Thr Ser Gly Thr Gly Ala Leu Gly Val
        115                 120                 125

Ser Val His Glu Pro Gln Gly Gly Gly Gly Thr Arg Leu Ser Met Ser
    130                 135                 140

Gly Thr Thr Val Arg Thr Arg Gly Asp Asp Ser Phe Ala Leu Gln Leu
```

```
145                 150                 155                 160

Ser Gly Pro Ala Ser Ala Thr Leu Asn Asp Val Ala Leu Glu Thr Ala
                165                 170                 175

Gly Gln Gln Ala Pro Ala Val Val Leu Trp Gln Gly Ala Gln Leu Asn
            180                 185                 190

Ala Gln Gly Leu Val Val Gln Val Asn Gly Ala Gly Val Ser Ala Ile
        195                 200                 205

His Ala Gln Asp Ala Gly Ser Phe Thr Leu Ser Gly Ser Asp Ile Thr
    210                 215                 220

Ala Arg Gly Leu Glu Val Ala Gly Ile Tyr Val Gln Glu Gly Met Gln
225                 230                 235                 240

Gly Thr Leu Thr Gly Thr Arg Val Thr Thr Gln Gly Asp Thr Ala Pro
                245                 250                 255

Ala Leu Gln Val Glu Asp Ala Gly Thr His Val Ser Met Asn Gly Gly
            260                 265                 270

Ala Leu Ser Thr Ser Gly Ala Asn Ser Pro Ala Ala Trp Leu Leu Ala
        275                 280                 285

Gly Gly Ser Ala Gln Phe Arg Asp Thr Val Leu Arg Thr Val Gly Glu
    290                 295                 300

Ala Ser His Gly Val Asp Val Ala Ala His Ser Glu Val Glu Leu Ala
305                 310                 315                 320

His Ala Gln Val Arg Ala Asp Gly Gln Gly Ala His Gly Leu Val Val
                325                 330                 335

Thr Arg Ser Ser Ala Met Val Arg Ala Gly Ser Leu Val Glu Ser Thr
            340                 345                 350

Gly Asp Gly Ala Ala Ala Leu Leu Glu Ser Gly His Leu Thr Val Asp
        355                 360                 365

Gly Ser Val Val His Gly His Gly Ala Ala Gly Leu Glu Val Asp Gly
    370                 375                 380

Glu Ser Asn Val Ser Leu Leu Asn Gly Ala Arg Leu Ser Ser Asp Gln
385                 390                 395                 400

Pro Thr Ala Ile Arg Leu Ile Asp Pro Arg Ser Val Leu Asn Leu Asp
                405                 410                 415

Ile Lys Asp Arg Ala Gln Leu Leu Gly Asp Ile Ala Pro Glu Ala Gln
            420                 425                 430

Gln Pro Asp Gly Ser Pro Glu Gln Ala Arg Val Arg Val Ala Leu Ala
        435                 440                 445

Asp Gly Gly Thr Trp Ala Gly Arg Thr Asp Gly Ala Val His Thr Val
    450                 455                 460

Arg Leu Leu Asp Arg Gly Val Trp Thr Val Thr Gly Asp Ser Arg Val
465                 470                 475                 480

Ala Glu Val Lys Leu Glu Gly Gly Thr Leu Ala Phe Ala Pro Pro Ala
                485                 490                 495

Gln Pro Lys Gly Ala Phe Lys Thr Leu Val Ala Thr Gln Gly Ile Ser
            500                 505                 510

Gly Thr Gly Thr Ile Val Met Asn Ala His Leu Pro Ser Gly Thr Ala
        515                 520                 525

Asp Val Leu Val Ala Pro Gln Gly Phe Gly Asp Arg Gln Val Leu Val
    530                 535                 540

Val Asn Asn Thr Asp Asp Gly Thr Glu Ser Gly Ala Thr Lys Val Pro
545                 550                 555                 560

Leu Ile Glu Asp Glu Gln Gly His Thr Ala Phe Thr Leu Gly Asn Met
                565                 570                 575
```

-continued

```
Gly Gly Arg Val Asp Ala Gly Ala Arg Gln Tyr Glu Leu Thr Ala Ser
            580                 585                 590

Glu Ala Gln Ala Asp Lys Ala Arg Thr Trp Gln Leu Thr Pro Thr Asn
        595                 600                 605

Glu Leu Ser Thr Thr Ala Thr Ala Ala Val Asn Ala Met Ala Ile Ala
    610                 615                 620

Ala Ser Gln Arg Ile Trp Gln Ala Glu Met Asp Val Leu Leu Arg His
625                 630                 635                 640

Met Ser Gly Leu His Ser Ile Gly Ser Pro Gly Gly Phe Trp Ala Arg
                645                 650                 655

Gly Leu Ser Gln Arg Gln Arg Leu Asp Thr Gly Tyr Gly Pro Trp Gln
            660                 665                 670

Lys Gln Thr Val Ser Gly Ile Glu Leu Gly Leu Asp Arg Arg Val Ala
        675                 680                 685

Gly Gly Ala Thr Thr Ala Trp Ser Val Gly Met Leu Ala Gly Tyr Ser
    690                 695                 700

Glu Thr Arg Arg Asp Gly Gly Ala Tyr Arg Ala Gly His Val His Ser
705                 710                 715                 720

Ala His Val Gly Ala Tyr Val Ser Tyr Leu Asn Asp Ser Gly Ser Tyr
                725                 730                 735

Val Asp Gly Val Val Lys Tyr Asn Arg Phe Arg His Gly Phe Asp Ile
            740                 745                 750

Arg Thr Thr Asp Leu Lys Arg Val Asp Ala Lys His Arg Ser His Gly
        755                 760                 765

Leu Gly Ala Leu Leu Arg Gly Gly Arg Arg Ile Asp Ile Asp Gly Gly
    770                 775                 780

Trp Tyr Val Glu Pro Gln Ala Ser Val Ala Trp Phe His Ala Gly Gly
785                 790                 795                 800

Ser Arg Tyr Glu Ala Ser Asn Gly Leu Arg Val Arg Ala Asp Gly Ala
                805                 810                 815

His Ser Trp Val Leu Arg Ala Gly Ala Glu Ala Gly Arg Gln Met Arg
            820                 825                 830

Leu Ala Asn Gly Asn Ile Val Glu Pro Tyr Ala Arg Leu Gly Trp Ala
        835                 840                 845

Gln Glu Leu Gly Ala Asp Asn Ala Val Tyr Thr Asn Gly Ile Arg His
    850                 855                 860

Val Thr Arg Ser Arg Gly Gly Phe Ala Glu Ala Arg Val Gly Val Gly
865                 870                 875                 880

Ala Leu Leu Gly Lys Arg His Ala Leu Tyr Ala Asp Tyr Glu Tyr Ala
                885                 890                 895

Lys Gly Ala Arg Phe Glu Ala Pro Trp Thr Leu Gln Leu Gly Tyr Arg
            900                 905                 910

Tyr Ser Trp
        915
```

<210> SEQ ID NO 33
<211> LENGTH: 3033
<212> TYPE: DNA
<213> ORGANISM: Bordetella pertussis

<400> SEQUENCE: 33

```
atgtatctcg atagattccg tcaatgtccg tcttccttgc agatcccgcg ttccgcgtgg      60

cgcctgcatg cgctggccgc agctctggcg ctggccggca tggcccggct ggcgcccgcg     120

gcggcgcagg cgccgcagcc gcccgtggcc ggcgcgccgc atgcgcagga cgccgggcag     180
```

-continued

```
gaaggagagt tcgaccaccg ggacaacacg ctcattgcag tctttgacga cggcgtcggc    240
atcaatctcg acgacgatcc cgacgagctc ggcgagacgg cgccccccac gctcaaggac    300
atccacatct cggtggagca caagaacccg atgagcaagc cggccatcgg ggtgcgtgtc    360
agcggcgccg gccgcgcgct gacgctggcc ggctcgacca tcgatgccac cgagggcggc    420
attcccgcag tggtacggcg cggcggcacg ctggagctgg atggcgtcac cgtggcgggc    480
ggggaaggga tggagccgat gacggtctct gacgccggca gccgcctgag cgtgcgcggc    540
ggcgtgctgg gcggcgaagc gccgggcgtc ggcctggtcc gggccgcgca aggcggccag    600
gcgagcatca tcgacgcgac gctgcagagc atcctcgggc ccgcgctcat tgccgacggc    660
ggctccattt ccgtcgccgg cggttcgatc gacatggaca tgggcccggg attcccgccg    720
ccgcctccac cgcttcccgg ggcgccgctg gccgcgcatc cgccgctcga tcgcgttgcc    780
gcggtgcacg ccggccagga cggcaaggtg acactgcggg aggtggcgct gcgggctcac    840
gggccgcagg cgacgggcgt ctatgcgtat atgcctggca gcgaaatcac cctgcaggga    900
ggcacagtca gcgtgcaggg cgatgacggg gccggcgtgg tcgccggcgc gggcctgctc    960
gacgccttgc cgcccggcgg cacggtgcgg ctggacggaa ccacggtgtc gaccgatggc   1020
gccaacaccg atgccgtgct ggttcgcggc gacgcggcgc gcgccgaggt cgtcaacacc   1080
gtgctgcgca ccgccaagag cctggccgcc ggcgtatcgg cccagcatgg aggccgcgtc   1140
acgctgcggc agacccgcat cgagaccgcg ggcgcggggg ccgagggcat ctccgtgctg   1200
ggcttcgagc cgcagtccgg ctccggcccg gccagcgtcg acatgcaggg cggcagcatc   1260
accacgaccg gcaaccgcgc cgccggcatc gcgctcaccc acggcagcgc ccgcctggaa   1320
ggcgtggcgg tgcgcgccga gggcagcggc tcgagcgccg cgcagctggc caacggcacg   1380
ctggtcgtca gcgcagggtc gctggcctcg gcccagtccg gcgcgatcag cgtgaccgac   1440
acgccgctga agctgatgcc gggcgccctg gccagcagca cggtctcggt ccggttgacc   1500
gacggcgcca cggcgcaagg cggcaatggc gtgttcctcc agcagcattc caccattccg   1560
gtggcggttg ccctcgagag cggcgccctg gctcgcggcg atatcgtcgc cgacggcaac   1620
aagcccctcg atgccgggat ctccctcagc gtggccagcg gcgccgcctg gcacggcgcc   1680
acccaggtgc tccagtcggc cacgctgggc aagggcggaa cctgggtcgt gaacgccgac   1740
tcccgggtgc aggacatgtc gatgcgcggc gggcgggtcg aattccaggc gcccgcgccc   1800
gaggcctctt acaagaccct gaccctgcaa accctggacg gcaacggcgt gttcgtgctg   1860
aacaccaacg tcgccgccgg gcagaacgac cagttgcggg tcaccggccg cgccgatggc   1920
cagcaccgcg tgctggtgcg caatgccgga ggcgaggccg acagccgggg cgcccgcctg   1980
ggcctggtgc atacccaggg gcagggcaac gccaccttcc ggctggccaa cgtcggcaag   2040
gcggttgacc tgggcacgtg gcgctacagc ctggcggagg atccgaagac gcatgtctgg   2100
agcttgcagc gcgcgggcca ggccctgtcg gggcggccca atgccgccgt gaacgcggcg   2160
gatctttcca gcatcgccct ggccgagtcc aacgcgctgg acaagcgcct gggcgagctg   2220
cgcctgcgcg ccgacgccgg cgggccatgg gcgcgtacgt tcagcgagcg ccagcagatc   2280
agcaaccgcc acgcccgcgc ctacgaccag acggtcagcg ggctggagat cggcctggac   2340
cgtggctgga gcgcgtcggg cgggcgctgg tacgccggcg gcctgctcgg ctacacctat   2400
gccgaccgca cctatcccgg cgacggtggc ggcaaggtca agggcctgca cgtcggcggc   2460
tacgccgcct atgtcggcga tggcggctac tatctcgaca ccgtgctgcg gctgggccgc   2520
tacgatcagc aatacaacat tgccggcacc gatggcggcc gcgtcaccgc cgactaccgc   2580
```

-continued

```
acaagcggcg ccgcatggtc gctcgaaggc gggcgccggt tcgagctgcc caacgactgg   2640

ttcgccgaac cgcaggccga ggtcatgctg tggcgcacgt caggcaagcg ctatcgcgcc   2700

agcaatggcc tgcgcgtcaa ggtggacgcc aacaccgcca cgctgggccg cctgggcttg   2760

cgcttcggcc gccgcatcgc cctggccggc ggcaacatcg tgcagcccta cgccaggctc   2820

ggctggacgc aggagttcaa aagcacgggc gatgtgcgca ccaatggcat tggccatgcc   2880

ggcgcaggcc gccacggccg cgtggaactg ggcgcgggcg tcgacgccgc gttgggcaag   2940

gggcacaacc tctatgcttc gtacgagtac gcggcgggcg accggatcaa cattccgtgg   3000

tcgttccacg ccggctaccg ctacagcttc tga                                3033
```

```
<210> SEQ ID NO 34
<211> LENGTH: 1010
<212> TYPE: PRT
<213> ORGANISM: Bordetella pertussis

<400> SEQUENCE: 34

Met Tyr Leu Asp Arg Phe Arg Gln Cys Pro Ser Ser Leu Gln Ile Pro
1               5                   10                  15

Arg Ser Ala Trp Arg Leu His Ala Leu Ala Ala Ala Leu Ala Leu Ala
            20                  25                  30

Gly Met Ala Arg Leu Ala Pro Ala Ala Ala Gln Ala Pro Gln Pro Pro
        35                  40                  45

Val Ala Gly Ala Pro His Ala Gln Asp Ala Gly Gln Glu Gly Glu Phe
    50                  55                  60

Asp His Arg Asp Asn Thr Leu Ile Ala Val Phe Asp Asp Gly Val Gly
65                  70                  75                  80

Ile Asn Leu Asp Asp Asp Pro Asp Glu Leu Gly Glu Thr Ala Pro Pro
                85                  90                  95

Thr Leu Lys Asp Ile His Ile Ser Val Glu His Lys Asn Pro Met Ser
            100                 105                 110

Lys Pro Ala Ile Gly Val Arg Val Ser Gly Ala Gly Arg Ala Leu Thr
        115                 120                 125

Leu Ala Gly Ser Thr Ile Asp Ala Thr Glu Gly Gly Ile Pro Ala Val
    130                 135                 140

Val Arg Arg Gly Gly Thr Leu Glu Leu Asp Gly Val Thr Val Ala Gly
145                 150                 155                 160

Gly Glu Gly Met Glu Pro Met Thr Val Ser Asp Ala Gly Ser Arg Leu
                165                 170                 175

Ser Val Arg Gly Gly Val Leu Gly Gly Glu Ala Pro Gly Val Gly Leu
            180                 185                 190

Val Arg Ala Ala Gln Gly Gly Gln Ala Ser Ile Ile Asp Ala Thr Leu
        195                 200                 205

Gln Ser Ile Leu Gly Pro Ala Leu Ile Ala Asp Gly Gly Ser Ile Ser
    210                 215                 220

Val Ala Gly Gly Ser Ile Asp Met Asp Met Gly Pro Gly Phe Pro Pro
225                 230                 235                 240

Pro Pro Pro Pro Leu Pro Gly Ala Pro Leu Ala Ala His Pro Pro Leu
                245                 250                 255

Asp Arg Val Ala Ala Val His Ala Gly Gln Asp Gly Lys Val Thr Leu
            260                 265                 270

Arg Glu Val Ala Leu Arg Ala His Gly Pro Gln Ala Thr Gly Val Tyr
        275                 280                 285

Ala Tyr Met Pro Gly Ser Glu Ile Thr Leu Gln Gly Gly Thr Val Ser
    290                 295                 300
```

```
Val Gln Gly Asp Asp Gly Ala Gly Val Val Ala Gly Ala Gly Leu Leu
305                 310                 315                 320

Asp Ala Leu Pro Pro Gly Gly Thr Val Arg Leu Asp Gly Thr Thr Val
                325                 330                 335

Ser Thr Asp Gly Ala Asn Thr Asp Ala Val Leu Val Arg Gly Asp Ala
            340                 345                 350

Ala Arg Ala Glu Val Val Asn Thr Val Leu Arg Thr Ala Lys Ser Leu
        355                 360                 365

Ala Ala Gly Val Ser Ala Gln His Gly Gly Arg Val Thr Leu Arg Gln
    370                 375                 380

Thr Arg Ile Glu Thr Ala Gly Ala Gly Ala Glu Gly Ile Ser Val Leu
385                 390                 395                 400

Gly Phe Glu Pro Gln Ser Gly Ser Gly Pro Ala Ser Val Asp Met Gln
                405                 410                 415

Gly Gly Ser Ile Thr Thr Thr Gly Asn Arg Ala Ala Gly Ile Ala Leu
            420                 425                 430

Thr His Gly Ser Ala Arg Leu Glu Gly Val Ala Val Arg Ala Glu Gly
        435                 440                 445

Ser Gly Ser Ser Ala Ala Gln Leu Ala Asn Gly Thr Leu Val Val Ser
    450                 455                 460

Ala Gly Ser Leu Ala Ser Ala Gln Ser Gly Ala Ile Ser Val Thr Asp
465                 470                 475                 480

Thr Pro Leu Lys Leu Met Pro Gly Ala Leu Ala Ser Ser Thr Val Ser
                485                 490                 495

Val Arg Leu Thr Asp Gly Ala Thr Ala Gln Gly Gly Asn Gly Val Phe
            500                 505                 510

Leu Gln Gln His Ser Thr Ile Pro Val Ala Val Ala Leu Glu Ser Gly
        515                 520                 525

Ala Leu Ala Arg Gly Asp Ile Val Ala Asp Gly Asn Lys Pro Leu Asp
    530                 535                 540

Ala Gly Ile Ser Leu Ser Val Ala Ser Gly Ala Ala Trp His Gly Ala
545                 550                 555                 560

Thr Gln Val Leu Gln Ser Ala Thr Leu Gly Lys Gly Gly Thr Trp Val
                565                 570                 575

Val Asn Ala Asp Ser Arg Val Gln Asp Met Ser Met Arg Gly Gly Arg
            580                 585                 590

Val Glu Phe Gln Ala Pro Ala Pro Glu Ala Ser Tyr Lys Thr Leu Thr
        595                 600                 605

Leu Gln Thr Leu Asp Gly Asn Gly Val Phe Val Leu Asn Thr Asn Val
    610                 615                 620

Ala Ala Gly Gln Asn Asp Gln Leu Arg Val Thr Gly Arg Ala Asp Gly
625                 630                 635                 640

Gln His Arg Val Leu Val Arg Asn Ala Gly Gly Glu Ala Asp Ser Arg
                645                 650                 655

Gly Ala Arg Leu Gly Leu Val His Thr Gln Gly Gln Gly Asn Ala Thr
            660                 665                 670

Phe Arg Leu Ala Asn Val Gly Lys Ala Val Asp Leu Gly Thr Trp Arg
        675                 680                 685

Tyr Ser Leu Ala Glu Asp Pro Lys Thr His Val Trp Ser Leu Gln Arg
    690                 695                 700

Ala Gly Gln Ala Leu Ser Gly Ala Ala Asn Ala Ala Val Asn Ala Ala
705                 710                 715                 720

Asp Leu Ser Ser Ile Ala Leu Ala Glu Ser Asn Ala Leu Asp Lys Arg
```

-continued

```
                725                 730                 735

Leu Gly Glu Leu Arg Leu Arg Ala Asp Ala Gly Gly Pro Trp Ala Arg
            740                 745                 750

Thr Phe Ser Glu Arg Gln Gln Ile Ser Asn Arg His Ala Arg Ala Tyr
        755                 760                 765

Asp Gln Thr Val Ser Gly Leu Glu Ile Gly Leu Asp Arg Gly Trp Ser
    770                 775                 780

Ala Ser Gly Gly Arg Trp Tyr Ala Gly Gly Leu Leu Gly Tyr Thr Tyr
785                 790                 795                 800

Ala Asp Arg Thr Tyr Pro Gly Asp Gly Gly Gly Lys Val Lys Gly Leu
                805                 810                 815

His Val Gly Gly Tyr Ala Ala Tyr Val Gly Asp Gly Gly Tyr Tyr Leu
            820                 825                 830

Asp Thr Val Leu Arg Leu Gly Arg Tyr Asp Gln Gln Tyr Asn Ile Ala
        835                 840                 845

Gly Thr Asp Gly Gly Arg Val Thr Ala Asp Tyr Arg Thr Ser Gly Ala
    850                 855                 860

Ala Trp Ser Leu Glu Gly Gly Arg Arg Phe Glu Leu Pro Asn Asp Trp
865                 870                 875                 880

Phe Ala Glu Pro Gln Ala Glu Val Met Leu Trp Arg Thr Ser Gly Lys
                885                 890                 895

Arg Tyr Arg Ala Ser Asn Gly Leu Arg Val Lys Val Asp Ala Asn Thr
            900                 905                 910

Ala Thr Leu Gly Arg Leu Gly Leu Arg Phe Gly Arg Arg Ile Ala Leu
        915                 920                 925

Ala Gly Gly Asn Ile Val Gln Pro Tyr Ala Arg Leu Gly Trp Thr Gln
    930                 935                 940

Glu Phe Lys Ser Thr Gly Asp Val Arg Thr Asn Gly Ile Gly His Ala
945                 950                 955                 960

Gly Ala Gly Arg His Gly Arg Val Glu Leu Gly Ala Gly Val Asp Ala
                965                 970                 975

Ala Leu Gly Lys Gly His Asn Leu Tyr Ala Ser Tyr Glu Tyr Ala Ala
            980                 985                 990

Gly Asp Arg Ile Asn Ile Pro Trp Ser Phe His Ala Gly Tyr Arg Tyr
        995                 1000                1005

Ser Phe
    1010
```

<210> SEQ ID NO 35
<211> LENGTH: 1944
<212> TYPE: DNA
<213> ORGANISM: Bordetella pertussis

<400> SEQUENCE: 35

```
atgcacattt acggaaatat gaatcgagca acaccttgcc gcggtgcggt gcgtgccctt      60

gcgcttgccc tgctgggagc gggtatgtgg acactttctc ctccctcggc atgggcgctt     120

aagctcccgt cgctgctgac ggacgacgag ctgaagctgg ttctgccgac tggcatgtct     180

ctggaggatt tcaagcgcag ccttcaggag tccgcgccga gcgcgctggc aacgccgccg     240

tcgtcttcgc ctccggttgc gaagccaggt ccgggctccg ttgccgaggc tccgtcgggg     300

tcgggccaca aggacaaccc atcccctccc gtcgtcggcg tcggtccagg tatggcggag     360

tcgtctggcg gacataaccc cggcgtgggg gggggcacgc atgaaaatgg gttgcccggt     420

ataggaaagg tcggcgggtc tgcgcccgga ccggatacca gtacgggctc gggtcccgac     480
```

-continued

```
gccggcatgg cgtccggagc gggttcgacg tcgcccggcg catcgggtgg ggcgggcaag    540

gatgcgatgc cgccctcgga aggcgagagg ccggactccg gtatgtccga ttcggggcgg    600

ggtggcgaat cgtcggctgg aggcttgaat ccggacggcg ctggcaagcc accgcgggag    660

gaaggcgagc cgggttccaa gtctcctgcg gacggtggcc aggacgggcc gccgccgccc    720

cgggacggcg gcgatgcgga tccgcaacct ccgcgggacg atggcaatgg ggaacagcag    780

ccgcccaagg gcggcgggga tgaggggcag cgcccgccgc ctgccgccgg aaacggtggc    840

aacggtggca acgggaacgc gcagcttccc gagcgcggcg acgacgcggg tccgaagcct    900

cccgagggag agggcggcga tgaaggtccg caaccgccgc agggcggcgg cgagcaggac    960

gcgccggagg ttcctcccgt cgcgccggcg ccgcccgcgg gcaacggtgt ctatgacccg   1020

ggcacgcata ccttgaccac gccggcctct gcggcggtga gcctggccag cagttcgcat   1080

ggcgtatggc aggccgagat gaacgcgttg agcaagcgca tgggcgagtt gcgcctgacg   1140

ccggttgcgg gcggcgtatg ggccgcgct tttggccggc gccaggacgt cgacaaccgc    1200

gtgtcgcgcg agttccgcca gaccatcagc ggtttcgaac tgggcgccga taccgccttg   1260

ccggtggccg acgggcgctg gcacgtgggc gcggtggctg gctacaccaa cggccgcatc   1320

aagttcgacc ggggcggcac gggcgatgac gacagcgtgc acgtgggcgc ttacgctacc   1380

tacatcgagg acggcggttt ctatatggat ggcatcgtgc gggtcagccg cattcgccac   1440

gcgttcaagg tggacgacgc caagggccgg cgcgtgcgcg gccagtaccg cggcaatggc   1500

gtgggcgcgt cgctggaact gggcaagcgc ttcacgtggc ccggcgcctg gtacgtggag   1560

ccgcagctgg aggtggccgc cttccatgcg caaggggccg actacaccgc cagcaacggc   1620

ctgcgcatca aggacgacgg cacgaactcc atgctgggcc gcctgggcct gcacgtgggg   1680

cggcagttcg acctgggcga tggccgcgtg gtgcagccct acatgaagct gagctgggtg   1740

caggagttcg acggcaaggg cacggtgcgc accaacgaca tccggcacaa ggtgcggctc   1800

gatggcggcc gcaccgaact ggccgtaggg gtggcttcgc aactgggcaa gcacggcagc   1860

ctgttcggct cgtacgagta cgccaagggc agccgccaga ccatgccgtg gaccttccac   1920

gtcggctatc gctacgcctg gtag                                          1944
```

<210> SEQ ID NO 36
<211> LENGTH: 647
<212> TYPE: PRT
<213> ORGANISM: Bordetella pertussis

<400> SEQUENCE: 36

```
Met His Ile Tyr Gly Asn Met Asn Arg Ala Thr Pro Cys Arg Gly Ala
 1               5                  10                  15

Val Arg Ala Leu Ala Leu Ala Leu Leu Gly Ala Gly Met Trp Thr Leu
            20                  25                  30

Ser Pro Pro Ser Ala Trp Ala Leu Lys Leu Pro Ser Leu Leu Thr Asp
        35                  40                  45

Asp Glu Leu Lys Leu Val Leu Pro Thr Gly Met Ser Leu Glu Asp Phe
    50                  55                  60

Lys Arg Ser Leu Gln Glu Ser Ala Pro Ser Ala Leu Ala Thr Pro Pro
65                  70                  75                  80

Ser Ser Ser Pro Pro Val Ala Lys Pro Gly Pro Gly Ser Val Ala Glu
                85                  90                  95

Ala Pro Ser Gly Ser Gly His Lys Asp Asn Pro Ser Pro Pro Val Val
            100                 105                 110

Gly Val Gly Pro Gly Met Ala Glu Ser Ser Gly Gly His Asn Pro Gly
```

```
        115                 120                 125

Val Gly Gly Gly Thr His Glu Asn Gly Leu Pro Gly Ile Gly Lys Val
    130                 135                 140

Gly Gly Ser Ala Pro Gly Pro Asp Thr Ser Thr Gly Ser Gly Pro Asp
145                 150                 155                 160

Ala Gly Met Ala Ser Gly Ala Gly Ser Thr Ser Pro Gly Ala Ser Gly
                165                 170                 175

Gly Ala Gly Lys Asp Ala Met Pro Pro Ser Glu Gly Glu Arg Pro Asp
            180                 185                 190

Ser Gly Met Ser Asp Ser Gly Arg Gly Gly Glu Ser Ser Ala Gly Gly
        195                 200                 205

Leu Asn Pro Asp Gly Ala Gly Lys Pro Pro Arg Glu Glu Gly Glu Pro
    210                 215                 220

Gly Ser Lys Ser Pro Ala Asp Gly Gly Gln Asp Gly Pro Pro Pro Pro
225                 230                 235                 240

Arg Asp Gly Gly Asp Ala Asp Pro Gln Pro Pro Arg Asp Asp Gly Asn
                245                 250                 255

Gly Glu Gln Gln Pro Pro Lys Gly Gly Gly Asp Glu Gly Gln Arg Pro
            260                 265                 270

Pro Pro Ala Ala Gly Asn Gly Gly Asn Gly Gly Asn Gly Asn Ala Gln
        275                 280                 285

Leu Pro Glu Arg Gly Asp Asp Ala Gly Pro Lys Pro Pro Glu Gly Glu
    290                 295                 300

Gly Gly Asp Glu Gly Pro Gln Pro Pro Gln Gly Gly Gly Glu Gln Asp
305                 310                 315                 320

Ala Pro Glu Val Pro Pro Val Ala Pro Ala Pro Pro Ala Gly Asn Gly
                325                 330                 335

Val Tyr Asp Pro Gly Thr His Thr Leu Thr Thr Pro Ala Ser Ala Ala
            340                 345                 350

Val Ser Leu Ala Ser Ser Ser His Gly Val Trp Gln Ala Glu Met Asn
        355                 360                 365

Ala Leu Ser Lys Arg Met Gly Glu Leu Arg Leu Thr Pro Val Ala Gly
    370                 375                 380

Gly Val Trp Gly Arg Ala Phe Gly Arg Arg Gln Asp Val Asp Asn Arg
385                 390                 395                 400

Val Ser Arg Glu Phe Arg Gln Thr Ile Ser Gly Phe Glu Leu Gly Ala
                405                 410                 415

Asp Thr Ala Leu Pro Val Ala Asp Gly Arg Trp His Val Gly Ala Val
            420                 425                 430

Ala Gly Tyr Thr Asn Gly Arg Ile Lys Phe Asp Arg Gly Gly Thr Gly
        435                 440                 445

Asp Asp Asp Ser Val His Val Gly Ala Tyr Ala Thr Tyr Ile Glu Asp
    450                 455                 460

Gly Gly Phe Tyr Met Asp Gly Ile Val Arg Val Ser Arg Ile Arg His
465                 470                 475                 480

Ala Phe Lys Val Asp Asp Ala Lys Gly Arg Arg Val Arg Gly Gln Tyr
                485                 490                 495

Arg Gly Asn Gly Val Gly Ala Ser Leu Glu Leu Gly Lys Arg Phe Thr
            500                 505                 510

Trp Pro Gly Ala Trp Tyr Val Glu Pro Gln Leu Glu Val Ala Ala Phe
        515                 520                 525

His Ala Gln Gly Ala Asp Tyr Thr Ala Ser Asn Gly Leu Arg Ile Lys
    530                 535                 540
```

```
Asp Asp Gly Thr Asn Ser Met Leu Gly Arg Leu Gly Leu His Val Gly
545                 550                 555                 560

Arg Gln Phe Asp Leu Gly Asp Gly Arg Val Val Gln Pro Tyr Met Lys
                565                 570                 575

Leu Ser Trp Val Gln Glu Phe Asp Gly Lys Gly Thr Val Arg Thr Asn
            580                 585                 590

Asp Ile Arg His Lys Val Arg Leu Asp Gly Gly Arg Thr Glu Leu Ala
        595                 600                 605

Val Gly Val Ala Ser Gln Leu Gly Lys His Gly Ser Leu Phe Gly Ser
    610                 615                 620

Tyr Glu Tyr Ala Lys Gly Ser Arg Gln Thr Met Pro Trp Thr Phe His
625                 630                 635                 640

Val Gly Tyr Arg Tyr Ala Trp
                645


<210> SEQ ID NO 37
<211> LENGTH: 1257
<212> TYPE: DNA
<213> ORGANISM: Bordetella pertussis

<400> SEQUENCE: 37

atgaaaccga cttccatcct ggcacgtttg ccccgctatc tcggcgcctg cgcgctggcc     60

gcgctggccg cgctggctgt cgcgccgctc gcgccggcgc aggcacagac tccgctgccc    120

gcgggactcg gcgccgccga ggtgcggcag tatttgtccg gcctgccgtc cgatgccctg    180

cgccagcagg cgtcgtggct ggcgccggcg ctgttgcgcc cctatctgtc aggcctgacg    240

gatgcgcaat tgcggcaata tgtgcaggcg ctgacacccg ggcagatcac gcaggggctg    300

gcggcgttga cgcctgcgca gcgtgcgcgg ctgcagcgcg aattcgaacg gcaggcgcgc    360

cggcaggtgc agcaggcggt acgggccgag gtcgccgcgc gcagcgcgcg ggcggtggcg    420

atggggcaga gcgcatcgat gctgctgctc gacgccgaga tgggaaccct ggcgcaacgc    480

cagggcgatc tgcgccgcgg ccacgacgag ggcgccttct gggcgcgcgg cagcgcgaac    540

cgcttcaagg tcgatacgcc ggacacaccg gcgttcgacc tgcgcgtgga gtacctgacg    600

ctgggcgccg accatggctg gcgcctggac acggggcggc tctatctggg cgcctacgcc    660

ggcgtctcgc gcgcccgcat ggatgacaac gacatcatgc acggccggat cgaaagccgg    720

ttcctgggca cgtacctgac ttatgtggac aacggcgggt tctacgtcga tgcggtcagc    780

aagctggggc gtatcgacga gtccgtgtcg ttcgacctgc cgctggggct gggcgactac    840

gacgacgata tatcgcatac aacgtatacg ggcagtgccg aggccggcta tcacttcaag    900

ttgccgcaac gctggttcgt cgagccgcag gcgcaggtga tctactcgcg cagcagccag    960

acgtcggtgc aggggcgggc cggcgtgcgc gccggccggg atttcaccct ggccggcggc   1020

gcgaccttgc gtccttatgt cagcgcctcg tacctgcacg agttctcgca cgacgactcg   1080

gtcgatttcg gcggcaagtc gtacgatgcc gaactgcccg gcagccgctg gcagctgggt   1140

gccggcgcgg cgctggacgt gggggcgcat cgcgcctacg cggatctgcg ctatgggcac   1200

ggcgccaaca tcagccagga cctgtcgctg aacatcggct acgcgtaccg cttctag      1257


<210> SEQ ID NO 38
<211> LENGTH: 418
<212> TYPE: PRT
<213> ORGANISM: Bordetella pertussis

<400> SEQUENCE: 38

Met Lys Pro Thr Ser Ile Leu Ala Arg Leu Pro Arg Tyr Leu Gly Ala
```

-continued

```
1               5                   10                  15

Cys Ala Leu Ala Ala Leu Ala Ala Leu Ala Val Ala Pro Leu Ala Pro
            20                  25                  30

Ala Gln Ala Gln Thr Pro Leu Pro Ala Gly Leu Gly Ala Ala Glu Val
        35                  40                  45

Arg Gln Tyr Leu Ser Gly Leu Pro Ser Asp Ala Leu Arg Gln Gln Ala
    50                  55                  60

Ser Trp Leu Ala Pro Ala Leu Leu Arg Pro Tyr Leu Ser Gly Leu Thr
65                  70                  75                  80

Asp Ala Gln Leu Arg Gln Tyr Val Gln Ala Leu Thr Pro Gly Gln Ile
                85                  90                  95

Thr Gln Gly Leu Ala Ala Leu Thr Pro Ala Gln Arg Ala Arg Leu Gln
            100                 105                 110

Arg Glu Phe Glu Arg Gln Ala Arg Arg Gln Val Gln Gln Ala Val Arg
        115                 120                 125

Ala Glu Val Ala Ala Arg Ser Ala Arg Ala Val Ala Met Gly Gln Ser
    130                 135                 140

Ala Ser Met Leu Leu Leu Asp Ala Glu Met Gly Thr Leu Ala Gln Arg
145                 150                 155                 160

Gln Gly Asp Leu Arg Arg Gly His Asp Glu Gly Ala Phe Trp Ala Arg
                165                 170                 175

Gly Ser Ala Asn Arg Phe Lys Val Asp Thr Pro Asp Thr Pro Ala Phe
            180                 185                 190

Asp Leu Arg Val Glu Tyr Leu Thr Leu Gly Ala Asp His Gly Trp Arg
        195                 200                 205

Leu Asp Thr Gly Arg Leu Tyr Leu Gly Ala Tyr Ala Gly Val Ser Arg
    210                 215                 220

Ala Arg Met Asp Asp Asn Asp Ile Met His Gly Arg Ile Glu Ser Arg
225                 230                 235                 240

Phe Leu Gly Thr Tyr Leu Thr Tyr Val Asp Asn Gly Gly Phe Tyr Val
                245                 250                 255

Asp Ala Val Ser Lys Leu Gly Arg Ile Asp Glu Ser Val Ser Phe Asp
            260                 265                 270

Leu Pro Leu Gly Leu Gly Asp Tyr Asp Asp Asp Ile Ser His Thr Thr
        275                 280                 285

Tyr Thr Gly Ser Ala Glu Ala Gly Tyr His Phe Lys Leu Pro Gln Arg
    290                 295                 300

Trp Phe Val Glu Pro Gln Ala Gln Val Ile Tyr Ser Arg Ser Ser Gln
305                 310                 315                 320

Thr Ser Val Gln Gly Arg Ala Gly Val Arg Ala Gly Arg Asp Phe Thr
                325                 330                 335

Leu Ala Gly Gly Ala Thr Leu Arg Pro Tyr Val Ser Ala Ser Tyr Leu
            340                 345                 350

His Glu Phe Ser His Asp Asp Ser Val Asp Phe Gly Gly Lys Ser Tyr
        355                 360                 365

Asp Ala Glu Leu Pro Gly Ser Arg Trp Gln Leu Gly Ala Gly Ala Ala
    370                 375                 380

Leu Asp Val Gly Ala His Arg Ala Tyr Ala Asp Leu Arg Tyr Gly His
385                 390                 395                 400

Gly Ala Asn Ile Ser Gln Asp Leu Ser Leu Asn Ile Gly Tyr Ala Tyr
                405                 410                 415

Arg Phe
```

<210> SEQ ID NO 39
<211> LENGTH: 2712
<212> TYPE: DNA
<213> ORGANISM: Bordetella pertussis

<400> SEQUENCE: 39

```
atggtcggca ggagttgtca tcgtgcaggg tggttatacc gggcgacctt cctcttatac     60
gccgcaaact gtgcttatcc cgcgaacgcc caatcggttt ctggttccgg tcaggtgtcg    120
aacgggccga tcacgtcacc gcactgggtg gtgggcgggg aactgatcgt cggggatacg    180
ggcgccggga ccttgctcat cgaggccggc ggtaccgtgc tcaacgactg ggcctatatc    240
ggcagtgaca atggcgctgt gggcaccctg acggtgtcgg gccgcgacgg cgccggggcc    300
gcgtcgacct ggacgactgt cgacgatgtg tcgatcggcg ttgcggcggg cagcaggggc    360
acgctcgagg tgctcggcgg ggccagggcg caaagcggat ggggcaccat cggcgtcgct    420
gcaggcagcg tcggaagcgt gaccgtgtcc gggcccgggt cggtgtggaa tatcgccacg    480
gtcaattcgt tccagatcgg ctcgggcggc agcgggacgc tgtggatcga ccagggcggc    540
gcagtgtata gcgggcaggg cgtcatcggt tggaaccccg gcagcgacgg gcacgtcacg    600
gtattgggtc cggcaacggt atggaacccg ctgaacaata tctatgtcgg tctcggcggg    660
actggtgaac tggatatccg ggacggcgcg gccgttgcga ctgcagggtc gagcccgccg    720
ggcgccgcgg catcgatcta catcgggacg agcgcaggga gcgccggcac ggtaacggtg    780
tcgagcgcga cggccgtcac ctcgacgctc acgtcgaccg accgtatcga aatcggctcg    840
gccggcgccg gggtgctgac tgtcgccaaa ggcgggatgg tgggcgtcgc cagcgacgcc    900
tggatagcca tcaccggcac gtcctccgga acgctgaacc tgaccggcga tgccagcggc    960
cgaggcgtgc tggaaacggg ctcggtcatc aagggcgccg gcaacgcgac cttcaacctg   1020
gatggcgggg tcctgcgcgc caatcgtgac gaggccaatt tcctcaatgg tttctccacg   1080
caggcggtgg gaagcggcgg cgcctggttc gatacgaatg cccatgacgt gggcgttgtc   1140
accgccttct cgggtacgtc cagcttcaac aagctgggag ccggcacgct gacgctgtca   1200
ggcaacagcg ccgcgttcac ggggaacacc gatatccagg ccggaacgct gcaggtggac   1260
ggcgttcttg gcgggccggt ggatgtgctg gcgggggcgc ggttgaccgg taccgggcgc   1320
gtcggtgcga cggccaacaa gggcaccatt gcgccgggcc cgcgcagcgg ctttggcacc   1380
ctgacgatcg ccggggatta cgcggcccag ggcggcaacc tggaaatccg tacgcagctt   1440
ggcgccgacg actcgccgac cgacaggctg gtgatcacgg gcgccagcgc tggcgtgaca   1500
ccggtcacgg tcgagaatat cggcggcacg ggcgcctcga cccagcgggg catacaggtc   1560
gtgcaggtca atggcgcttc ggcaggccgg ttcaacctcg ccaacggcga ttacgtcatc   1620
gaggggcgtc cggcgctggt ggccggcgcc tatggctatg tgctgcagca ggacgccgcc   1680
gacggcgatt ggtatctgaa atcgtcgctg cccgaccctg gggctcccca aggcgggggc   1740
ggtctgccgg gcgccgggga gcccgtgctt tatcagcccg gcgtgccggt ctatgaagcc   1800
tatgccaaca cgctgctgca tctgagccgg ctttccacct tgcgccaacg ggtcggcaat   1860
cgcctttatg atccggcaga tgtcggccgc aacggcgtat ggagccgcgt cgagggctcc   1920
gcgagccagc tcgatccttc cgcgtccacg actggcgaac gccaggacgt cgatagctgg   1980
aaagtgcagt tcggtgtcga ccgtatcctg gccggcgggc aagagggctc ccgcctggtg   2040
ggcggattgg cgctgcagta cggcaaggcc gacacgcgcg tgtcgtcgat atacggcaat   2100
ggcactgtcg acgccacggc ctatggcctg accccgacgc tgacctggta cggcagggac   2160
ggcgcctatg tcgatgccca ggcccaggcg atctggttcg acagcgacct gagttcacgg   2220
```

ctggccggca agctcaagga tggccggaaa gcgcatggct atgggctggg tatcgaagcg 2280
ggcaaggcct tcggattgcg ggaggggctg gccctgatcc cgcaggcgca attgtcgtac 2340
gcatcgaccc gcttcgacag cttcgacgac agattcggcg cccgcgtcga agacgataag 2400
ggcgacagcc tgcagggccg tctcggcatc gcgctggact acaagagcag ctggcaagcg 2460
ggcggcgcga accgggagtc gagtgtcttc ggcatcgtca atgtgaagca tgagttcctg 2520
gatggcacgc gcgtgcgcgt tgccggcgtg ccggtaagca gccgcatggc gcgcacctgg 2580
ggcagcgtgg gagtgggggc cgattacggt tggggagaac gctacgccat ttacggccag 2640
gtggacgccg atgcagattt cgccggcagc tacatcgtca ccgcgaccgc ggggttcagg 2700
atgatgttct ag 2712

<210> SEQ ID NO 40
<211> LENGTH: 903
<212> TYPE: PRT
<213> ORGANISM: Bordetella pertussis

<400> SEQUENCE: 40

Met Val Gly Arg Ser Cys His Arg Ala Gly Trp Leu Tyr Arg Ala Thr
1 5 10 15

Phe Leu Leu Tyr Ala Ala Asn Cys Ala Tyr Pro Ala Asn Ala Gln Ser
20 25 30

Val Ser Gly Ser Gly Gln Val Ser Asn Gly Pro Ile Thr Ser Pro His
35 40 45

Trp Val Val Gly Gly Glu Leu Ile Val Gly Asp Thr Gly Ala Gly Thr
50 55 60

Leu Leu Ile Glu Ala Gly Gly Thr Val Leu Asn Asp Trp Ala Tyr Ile
65 70 75 80

Gly Ser Asp Asn Gly Ala Val Gly Thr Leu Thr Val Ser Gly Arg Asp
85 90 95

Gly Ala Gly Ala Ala Ser Thr Trp Thr Thr Val Asp Asp Val Ser Ile
100 105 110

Gly Val Ala Ala Gly Ser Arg Gly Thr Leu Glu Val Leu Gly Gly Ala
115 120 125

Arg Ala Gln Ser Gly Trp Gly Thr Ile Gly Val Ala Ala Gly Ser Val
130 135 140

Gly Ser Val Thr Val Ser Gly Pro Gly Ser Val Trp Asn Ile Ala Thr
145 150 155 160

Val Asn Ser Phe Gln Ile Gly Ser Gly Gly Ser Gly Thr Leu Trp Ile
165 170 175

Asp Gln Gly Gly Ala Val Tyr Ser Gly Gln Gly Val Ile Gly Trp Asn
180 185 190

Pro Gly Ser Asp Gly His Val Thr Val Leu Gly Pro Ala Thr Val Trp
195 200 205

Asn Pro Leu Asn Asn Ile Tyr Val Gly Leu Gly Gly Thr Gly Glu Leu
210 215 220

Asp Ile Arg Asp Gly Ala Ala Val Ala Thr Ala Gly Ser Ser Pro Pro
225 230 235 240

Gly Ala Ala Ala Ser Ile Tyr Ile Gly Thr Ser Ala Gly Ser Ala Gly
245 250 255

Thr Val Thr Val Ser Ser Ala Thr Ala Val Thr Ser Thr Leu Thr Ser
260 265 270

Thr Asp Arg Ile Glu Ile Gly Ser Ala Gly Ala Gly Val Leu Thr Val
275 280 285

```
Ala Lys Gly Gly Met Val Gly Val Ala Ser Asp Ala Trp Ile Ala Ile
    290                 295                 300

Thr Gly Thr Ser Ser Gly Thr Leu Asn Leu Thr Gly Asp Ala Ser Gly
305                 310                 315                 320

Arg Gly Val Leu Glu Thr Gly Ser Val Ile Lys Gly Ala Gly Asn Ala
                325                 330                 335

Thr Phe Asn Leu Asp Gly Gly Val Leu Arg Ala Asn Arg Asp Glu Ala
            340                 345                 350

Asn Phe Leu Asn Gly Phe Ser Thr Gln Ala Val Gly Ser Gly Gly Ala
        355                 360                 365

Trp Phe Asp Thr Asn Ala His Asp Val Gly Val Val Thr Ala Phe Ser
    370                 375                 380

Gly Thr Ser Ser Phe Asn Lys Leu Gly Ala Gly Thr Leu Thr Leu Ser
385                 390                 395                 400

Gly Asn Ser Ala Ala Phe Thr Gly Asn Thr Asp Ile Gln Ala Gly Thr
                405                 410                 415

Leu Gln Val Asp Gly Val Leu Gly Gly Pro Val Asp Val Leu Ala Gly
            420                 425                 430

Ala Arg Leu Thr Gly Thr Gly Arg Val Gly Ala Thr Ala Asn Lys Gly
        435                 440                 445

Thr Ile Ala Pro Gly Pro Arg Ser Gly Phe Gly Thr Leu Thr Ile Ala
    450                 455                 460

Gly Asp Tyr Ala Ala Gln Gly Gly Asn Leu Glu Ile Arg Thr Gln Leu
465                 470                 475                 480

Gly Ala Asp Asp Ser Pro Thr Asp Arg Leu Val Ile Thr Gly Ala Ser
                485                 490                 495

Ala Gly Val Thr Pro Val Thr Val Glu Asn Ile Gly Gly Thr Gly Ala
            500                 505                 510

Ser Thr Gln Arg Gly Ile Gln Val Val Gln Val Asn Gly Ala Ser Ala
        515                 520                 525

Gly Arg Phe Asn Leu Ala Asn Gly Asp Tyr Val Ile Glu Gly Arg Pro
    530                 535                 540

Ala Leu Val Ala Gly Ala Tyr Gly Tyr Val Leu Gln Gln Asp Ala Ala
545                 550                 555                 560

Asp Gly Asp Trp Tyr Leu Lys Ser Ser Leu Pro Asp Pro Gly Ala Pro
                565                 570                 575

Gln Gly Gly Gly Gly Leu Pro Gly Ala Gly Glu Pro Val Leu Tyr Gln
            580                 585                 590

Pro Gly Val Pro Val Tyr Glu Ala Tyr Ala Asn Thr Leu Leu His Leu
        595                 600                 605

Ser Arg Leu Ser Thr Leu Arg Gln Arg Val Gly Asn Arg Leu Tyr Asp
    610                 615                 620

Pro Ala Asp Val Gly Arg Asn Gly Val Trp Ser Arg Val Glu Gly Ser
625                 630                 635                 640

Ala Ser Gln Leu Asp Pro Ser Ala Ser Thr Thr Gly Glu Arg Gln Asp
                645                 650                 655

Val Asp Ser Trp Lys Val Gln Phe Gly Val Asp Arg Ile Leu Ala Gly
            660                 665                 670

Gly Gln Glu Gly Ser Arg Leu Val Gly Gly Leu Ala Leu Gln Tyr Gly
        675                 680                 685

Lys Ala Asp Thr Arg Val Ser Ser Ile Tyr Gly Asn Gly Thr Val Asp
    690                 695                 700

Ala Thr Ala Tyr Gly Leu Thr Pro Thr Leu Thr Trp Tyr Gly Arg Asp
```

-continued

```
705                 710                 715                 720

Gly Ala Tyr Val Asp Ala Gln Ala Gln Ala Ile Trp Phe Asp Ser Asp
                725                 730                 735

Leu Ser Ser Arg Leu Ala Gly Lys Leu Lys Asp Gly Arg Lys Ala His
            740                 745                 750

Gly Tyr Gly Leu Gly Ile Glu Ala Gly Lys Ala Phe Gly Leu Arg Glu
        755                 760                 765

Gly Leu Ala Leu Ile Pro Gln Ala Gln Leu Ser Tyr Ala Ser Thr Arg
    770                 775                 780

Phe Asp Ser Phe Asp Asp Arg Phe Gly Ala Arg Val Glu Asp Asp Lys
785                 790                 795                 800

Gly Asp Ser Leu Gln Gly Arg Leu Gly Ile Ala Leu Asp Tyr Lys Ser
                805                 810                 815

Ser Trp Gln Ala Gly Gly Ala Asn Arg Glu Ser Ser Val Phe Gly Ile
            820                 825                 830

Val Asn Val Lys His Glu Phe Leu Asp Gly Thr Arg Val Arg Val Ala
        835                 840                 845

Gly Val Pro Val Ser Ser Arg Met Ala Arg Thr Trp Gly Ser Val Gly
    850                 855                 860

Val Gly Ala Asp Tyr Gly Trp Gly Glu Arg Tyr Ala Ile Tyr Gly Gln
865                 870                 875                 880

Val Asp Ala Asp Ala Asp Phe Ala Gly Ser Tyr Ile Val Thr Ala Thr
                885                 890                 895

Ala Gly Phe Arg Met Met Phe
            900
```

<210> SEQ ID NO 41
<211> LENGTH: 1449
<212> TYPE: DNA
<213> ORGANISM: Bordetella pertussis

<400> SEQUENCE: 41

```
atgccgtcac ccgatgcctt gccgcacacg ccgcctgctt caggcggcga tcgcgtgatc     60

agcgggatcc tgcagcagga cctcggcagt tggctggcgc cggatgccgc aaagcgcagc    120

ccctccgagc ctggcaaggc ggccgaaaaa atcggggtaa tgccgaacga ggacctcggc    180

aagtggctgg ttccgggggc gcaaaagaac aatccgcccg agcctggcaa gacgctggac    240

gaaatccgtg cgggtctcga aaaatgggtg gcgcccgggt ccaagccgcc cgtcgaaccg    300

gatccggaca aggcgacgca ggcgtatcgc aaagacctcg ataaatggct ggcgcctccg    360

gccaagtccg gcccgcccga agcgccaccc gtcgtccaac ccgaagcgcc gccgcaagcg    420

caacctgagg cgccgcctgt cgtgccgccg ccggccgagc cgccagcagc tcgaccgccg    480

gccgttccgc ccgcgcggcc ggccggcgac gcggtgtacg tgccgggcac gcgcacgctg    540

acgccgacgg ccaacgcggc ggtgggcacg gccagcgccg cgcaaggtct gtggcaggcc    600

gagatgaacg cgttgagcaa gcgcatgggc gagttgcgcc tgacgccggt tgcgggcggc    660

gtatggggcc gcgcttttgg ccggcgccag gacgtcgaca accgcgtgtc gcgcgagttc    720

cgccagacca tcagcggttt cgaactgggc gccgataccg ccttgccggt ggccgacggg    780

cgctggcacg tgggcgcggt ggctggctac accaacggcc gcatcaagtt cgaccggggc    840

ggcacgggcg atgacgacag cgtgcacgtg ggcgcttacg ctacctacat cgaggacggc    900

ggtttctata tggatggcat cgtgcgggtc agccgcattc gccacgcgtt caaggtggac    960

gacgccaagg gccggcgcgt gcgcggccag taccgcggca atggcgtggg cgcgtcgctg   1020
```

-continued gaactgggca agcgcttcac gtggcccggc gcctggtacg tggagccgca gctggaggtg 1080
gccgccttcc atgcgcaagg ggccgactac accgccagca acggcctgcg catcaaggac 1140
gacggcacga actccatgct gggccgcctg ggcctgcacg tggggcggca gttcgacctg 1200
ggcgatggcc gcgtggtgca gccctacatg aagctgagct gggtgcagga gttcgacggc 1260
aagggcacgg tgcgcaccaa cgacatccgg cacaaggtgc ggctcgatgg cggccgcacc 1320
gaactggccg taggggtggc ttcgcaactg ggcaagcacg gcagcctgtt cggctcgtac 1380
gagtacgcca agggcagccg ccagaccatg ccgtggacct tccacgtcgg ctatcgctac 1440
gcctggtag 1449

<210> SEQ ID NO 42
<211> LENGTH: 482
<212> TYPE: PRT
<213> ORGANISM: Bordetella pertussis

<400> SEQUENCE: 42

Met Pro Ser Pro Asp Ala Leu Pro His Thr Pro Pro Ala Ser Gly Gly
1 5 10 15

Asp Arg Val Ile Ser Gly Ile Leu Gln Gln Asp Leu Gly Ser Trp Leu
20 25 30

Ala Pro Asp Ala Ala Lys Arg Ser Pro Ser Glu Pro Gly Lys Ala Ala
35 40 45

Glu Lys Ile Gly Val Met Pro Asn Glu Asp Leu Gly Lys Trp Leu Val
50 55 60

Pro Gly Ala Gln Lys Asn Asn Pro Pro Glu Pro Gly Lys Thr Leu Asp
65 70 75 80

Glu Ile Arg Ala Gly Leu Glu Lys Trp Val Ala Pro Gly Ser Lys Pro
85 90 95

Pro Val Glu Pro Asp Pro Asp Lys Ala Thr Gln Ala Tyr Arg Lys Asp
100 105 110

Leu Asp Lys Trp Leu Ala Pro Pro Ala Lys Ser Gly Pro Pro Glu Ala
115 120 125

Pro Pro Val Val Gln Pro Glu Ala Pro Pro Gln Ala Gln Pro Glu Ala
130 135 140

Pro Pro Val Val Pro Pro Pro Ala Glu Pro Pro Ala Ala Arg Pro Pro
145 150 155 160

Ala Val Pro Pro Ala Arg Pro Ala Gly Asp Ala Val Tyr Val Pro Gly
165 170 175

Thr Arg Thr Leu Thr Pro Thr Ala Asn Ala Ala Val Gly Thr Ala Ser
180 185 190

Ala Ala Gln Gly Leu Trp Gln Ala Glu Met Asn Ala Leu Ser Lys Arg
195 200 205

Met Gly Glu Leu Arg Leu Thr Pro Val Ala Gly Gly Val Trp Gly Arg
210 215 220

Ala Phe Gly Arg Arg Gln Asp Val Asp Asn Arg Val Ser Arg Glu Phe
225 230 235 240

Arg Gln Thr Ile Ser Gly Phe Glu Leu Gly Ala Asp Thr Ala Leu Pro
245 250 255

Val Ala Asp Gly Arg Trp His Val Gly Ala Val Ala Gly Tyr Thr Asn
260 265 270

Gly Arg Ile Lys Phe Asp Arg Gly Gly Thr Gly Asp Asp Asp Ser Val
275 280 285

His Val Gly Ala Tyr Ala Thr Tyr Ile Glu Asp Gly Gly Phe Tyr Met
290 295 300

Asp Gly Ile Val Arg Val Ser Arg Ile Arg His Ala Phe Lys Val Asp
305 310 315 320

Asp Ala Lys Gly Arg Arg Val Arg Gly Gln Tyr Arg Gly Asn Gly Val
325 330 335

Gly Ala Ser Leu Glu Leu Gly Lys Arg Phe Thr Trp Pro Gly Ala Trp
340 345 350

Tyr Val Glu Pro Gln Leu Glu Val Ala Ala Phe His Ala Gln Gly Ala
355 360 365

Asp Tyr Thr Ala Ser Asn Gly Leu Arg Ile Lys Asp Asp Gly Thr Asn
370 375 380

Ser Met Leu Gly Arg Leu Gly Leu His Val Gly Arg Gln Phe Asp Leu
385 390 395 400

Gly Asp Gly Arg Val Val Gln Pro Tyr Met Lys Leu Ser Trp Val Gln
405 410 415

Glu Phe Asp Gly Lys Gly Thr Val Arg Thr Asn Asp Ile Arg His Lys
420 425 430

Val Arg Leu Asp Gly Gly Arg Thr Glu Leu Ala Val Gly Val Ala Ser
435 440 445

Gln Leu Gly Lys His Gly Ser Leu Phe Gly Ser Tyr Glu Tyr Ala Lys
450 455 460

Gly Ser Arg Gln Thr Met Pro Trp Thr Phe His Val Gly Tyr Arg Tyr
465 470 475 480

Ala Trp

<210> SEQ ID NO 43
<211> LENGTH: 2280
<212> TYPE: DNA
<213> ORGANISM: Bordetella pertussis

<400> SEQUENCE: 43
atgtgcgaca cctgcagaga tgatgatggc acctcgcctt cgattcgcgt ccaaggcggg 60
gttgttcagg gcggcatggg tgcaaataac gtcgctgtgg tggcaacagg gtctggaaag 120
gtcgcgatcg agaatgcgga actgctcgga gccagcggca tgtacgccac gttcggcgcg 180
caggtcgata tgaaaggcgg gcgcattctg gcgcacaaca ccaatatcct gggaagccag 240
ggttacgccg atggtcccta tggcggcgtg gtcgtgacag aggacggtca agtcaacctg 300
gagggcgcca aggtcagtgc aactggcctg ggggccgccg gcttgtggtt gctgggcgac 360
aaggacacca gcccgcgagc cagcctgcgc aacaccgacg tccacggaga ggtcgccgcc 420
attgcgctgg ggttcaatgg cgaggcgaac atctcgggcg gcagcttgag cgtagaggat 480
ggggccgtgc tcaccaccct gacgcccgat gcagtcgagt attactacga ctacgccttg 540
tccatggagc atctgccagc tgatgcgccg ttgacgccgg tccgcgtcac gctgtccgat 600
ggcgcgcgcg ccagcggaga aacgttgatc gcgcatggcg ggttgttgcc catgacgctg 660
cgcttgagca gcggggtcga cgcccgcggc gacatcgtca cgctgccgcc ttccgcgccg 720
cccgattccg cggagcaacc ggatgccgag ccggaaccgg atgccgagct ggaaccggac 780
gccgcggcgc agtcggacgc caaggcgaat gcgcgggtca tggcgcaggt agatggcggg 840
gaacctgttg ccgtgccgat cccggcccct tcgcatcccg atgccccgat cgacgtgttc 900
atcgacagcg gtgcccaatg gcggggcatg accaagaccg tcaatgcgtt gcgcatcgag 960
gacggcacct ggaccgtcac cgggtcgtcc acggtgaaca gcctgcacct gcaggcaggc 1020
aaggtggcgt acgcaacgcc tgccgaaagc gacggagaat tcaaacacct gcgggtcaag 1080

```
accctctcgg gaagcggcct gttcgagatg aacgccagcg ccgacctgag cgatggcgac   1140

ctgctggtcg tgtccgacga ggccagcggg cagcacaagg tgctggtgcg aggagccggc   1200

acggaaccca ccggtgtgga aagcctgacg ctggtcgagc tgcccgaggg cagccagacg   1260

aagttcacgc ttgccaaccg gggcggggtg gtcgacgccg gcgcgttccg ctatcgcctg   1320

acgccggaca acggtgtctg gggcctggaa cggaccagcc agctttcggc cgtcgccaac   1380

gcggccttga ataccggggg cgtgggcgcg gccagcagca tctggtatgc ggaaggcaat   1440

gcgctctcca agcgcctggg cgagttgcgg ctcgatcccg gcgcgggcgg cttctggggg   1500

cgcacgttcg cccagaagca gcagctcgac aacaaggctg gccgacgctt cgaccagaag   1560

gtgtacggtt tcgagctggg ggccgaccat gccatcgcag gacagcaagg gcgctggcac   1620

gtgggcggcc tgctgggcta tacccgcgca aggcgcagct tcatcgatga cggcgccggg   1680

cataccgaca gcgcgcatat cggggcctac gcggcgtacg tggcggacaa cggcttctat   1740

ttcgattcga ccctgcgcgc cagccgcttc gagaacgact tcacggtaac ggccaccgac   1800

gccgtttccg tacggggcaa gtaccgggcc aatggggtag gcgccacctt ggaggccggc   1860

aaacgtttca cgttgcacga cggctggttc gtcgaacctc agtccgaggt gtcgctgttc   1920

catgccagcg gcggaaccta ccgtgccgcg aacaacctgt cggtcaagga cgaaggcggc   1980

acctccgccg tgctgcgcct gggcttggcg gccgggcgac gcatcgacct gggcaaggac   2040

cgcgtgatcc agccctatgc caccctgagc tggctgcagg aattcaaagg cgtcacgacc   2100

gttcgcacca acgggtacgg gctgcgcacc gacctgagcg gtggccgggc tgaattggcg   2160

ctgggcctgg ccgccgcgtt ggggcgcggc caccagctct acacttcgta cgagtacgcc   2220

aagggcaaca agctgacctt gccttggacg ttccacctgg gctatcgcta cacctggtag   2280
```

<210> SEQ ID NO 44
<211> LENGTH: 759
<212> TYPE: PRT
<213> ORGANISM: Bordetella pertussis

<400> SEQUENCE: 44

```
Met Cys Asp Thr Cys Arg Asp Asp Asp Gly Thr Ser Pro Ser Ile Arg
 1               5                  10                  15

Val Gln Gly Gly Val Val Gln Gly Gly Met Gly Ala Asn Asn Val Ala
            20                  25                  30

Val Val Ala Thr Gly Ser Gly Lys Val Ala Ile Glu Asn Ala Glu Leu
        35                  40                  45

Leu Gly Ala Ser Gly Met Tyr Ala Thr Phe Gly Ala Gln Val Asp Met
    50                  55                  60

Lys Gly Gly Arg Ile Leu Ala His Asn Thr Asn Ile Leu Gly Ser Gln
65                  70                  75                  80

Gly Tyr Ala Asp Gly Pro Tyr Gly Gly Val Val Val Thr Glu Asp Gly
                85                  90                  95

Gln Val Asn Leu Glu Gly Ala Lys Val Ser Ala Thr Gly Leu Gly Ala
            100                 105                 110

Ala Gly Leu Trp Leu Leu Gly Asp Lys Asp Thr Ser Pro Arg Ala Ser
        115                 120                 125

Leu Arg Asn Thr Asp Val His Gly Glu Val Ala Ala Ile Ala Leu Gly
    130                 135                 140

Phe Asn Gly Glu Ala Asn Ile Ser Gly Gly Ser Leu Ser Val Glu Asp
145                 150                 155                 160

Gly Ala Val Leu Thr Thr Leu Thr Pro Asp Ala Val Glu Tyr Tyr Tyr
                165                 170                 175
```

-continued

```
Asp Tyr Ala Leu Ser Met Glu His Leu Pro Ala Asp Ala Pro Leu Thr
            180                 185                 190

Pro Val Arg Val Thr Leu Ser Asp Gly Ala Arg Ala Ser Gly Glu Thr
        195                 200                 205

Leu Ile Ala His Gly Gly Leu Leu Pro Met Thr Leu Arg Leu Ser Ser
    210                 215                 220

Gly Val Asp Ala Arg Gly Asp Ile Val Thr Leu Pro Pro Ser Ala Pro
225                 230                 235                 240

Pro Asp Ser Ala Glu Gln Pro Asp Ala Glu Pro Glu Pro Asp Ala Glu
                245                 250                 255

Leu Glu Pro Asp Ala Ala Ala Gln Ser Asp Ala Lys Ala Asn Ala Arg
            260                 265                 270

Val Met Ala Gln Val Asp Gly Gly Glu Pro Val Ala Val Pro Ile Pro
        275                 280                 285

Ala Pro Ser His Pro Asp Ala Pro Ile Asp Val Phe Ile Asp Ser Gly
    290                 295                 300

Ala Gln Trp Arg Gly Met Thr Lys Thr Val Asn Ala Leu Arg Ile Glu
305                 310                 315                 320

Asp Gly Thr Trp Thr Val Thr Gly Ser Ser Thr Val Asn Ser Leu His
                325                 330                 335

Leu Gln Ala Gly Lys Val Ala Tyr Ala Thr Pro Ala Glu Ser Asp Gly
            340                 345                 350

Glu Phe Lys His Leu Arg Val Lys Thr Leu Ser Gly Ser Gly Leu Phe
        355                 360                 365

Glu Met Asn Ala Ser Ala Asp Leu Ser Asp Gly Asp Leu Leu Val Val
    370                 375                 380

Ser Asp Glu Ala Ser Gly Gln His Lys Val Leu Val Arg Gly Ala Gly
385                 390                 395                 400

Thr Glu Pro Thr Gly Val Glu Ser Leu Thr Leu Val Glu Leu Pro Glu
                405                 410                 415

Gly Ser Gln Thr Lys Phe Thr Leu Ala Asn Arg Gly Gly Val Val Asp
            420                 425                 430

Ala Gly Ala Phe Arg Tyr Arg Leu Thr Pro Asp Asn Gly Val Trp Gly
        435                 440                 445

Leu Glu Arg Thr Ser Gln Leu Ser Ala Val Ala Asn Ala Ala Leu Asn
    450                 455                 460

Thr Gly Gly Val Gly Ala Ala Ser Ser Ile Trp Tyr Ala Glu Gly Asn
465                 470                 475                 480

Ala Leu Ser Lys Arg Leu Gly Glu Leu Arg Leu Asp Pro Gly Ala Gly
                485                 490                 495

Gly Phe Trp Gly Arg Thr Phe Ala Gln Lys Gln Gln Leu Asp Asn Lys
            500                 505                 510

Ala Gly Arg Arg Phe Asp Gln Lys Val Tyr Gly Phe Glu Leu Gly Ala
        515                 520                 525

Asp His Ala Ile Ala Gly Gln Gln Gly Arg Trp His Val Gly Gly Leu
    530                 535                 540

Leu Gly Tyr Thr Arg Ala Arg Arg Ser Phe Ile Asp Asp Gly Ala Gly
545                 550                 555                 560

His Thr Asp Ser Ala His Ile Gly Ala Tyr Ala Ala Tyr Val Ala Asp
                565                 570                 575

Asn Gly Phe Tyr Phe Asp Ser Thr Leu Arg Ala Ser Arg Phe Glu Asn
            580                 585                 590

Asp Phe Thr Val Thr Ala Thr Asp Ala Val Ser Val Arg Gly Lys Tyr
```

```
        595                 600                 605

Arg Ala Asn Gly Val Gly Ala Thr Leu Glu Ala Gly Lys Arg Phe Thr
    610                 615                 620

Leu His Asp Gly Trp Phe Val Glu Pro Gln Ser Glu Val Ser Leu Phe
625                 630                 635                 640

His Ala Ser Gly Gly Thr Tyr Arg Ala Ala Asn Asn Leu Ser Val Lys
                645                 650                 655

Asp Glu Gly Gly Thr Ser Ala Val Leu Arg Leu Gly Leu Ala Ala Gly
            660                 665                 670

Arg Arg Ile Asp Leu Gly Lys Asp Arg Val Ile Gln Pro Tyr Ala Thr
        675                 680                 685

Leu Ser Trp Leu Gln Glu Phe Lys Gly Val Thr Thr Val Arg Thr Asn
    690                 695                 700

Gly Tyr Gly Leu Arg Thr Asp Leu Ser Gly Gly Arg Ala Glu Leu Ala
705                 710                 715                 720

Leu Gly Leu Ala Ala Ala Leu Gly Arg Gly His Gln Leu Tyr Thr Ser
                725                 730                 735

Tyr Glu Tyr Ala Lys Gly Asn Lys Leu Thr Leu Pro Trp Thr Phe His
            740                 745                 750

Leu Gly Tyr Arg Tyr Thr Trp
        755
```

<210> SEQ ID NO 45
<211> LENGTH: 1548
<212> TYPE: DNA
<213> ORGANISM: Bordetella pertussis

<400> SEQUENCE: 45

```
ttgcgccaga ccacgccggt gccggtgcgg ctcgtcctgc gcggcgcggc ggtcgcgcag     60

ggcgatgtcg tgcgcgcgcc cgagacggcg ccggagaagg atgggttcgg cacgcccgtg    120

cggccgggct tgcgcgtcgg gctggaccag gcgccgctcg agctcgatgt ggccgacggc    180

gcgcagtggc atggcgcgac tcagtcgctt gacaggctgg ccctgggcgc gggcggccaa    240

tggcgcatga gcgcggcatc cagcgtgggc gaactgagca tggagcctgg cgcggccgtc    300

gtgttcggcg atgcggccgg accgggtttt caaacgctga cggtgcgcac cctggcgggc    360

gccggttcgt tcgagatgcg tgcggacgcc gcgctggagc atgccgatca actggtggtg    420

accgaccagg ccgaagggcg gcatcgcgtg tggttgcgcg cgccggccgg cgccgagccg    480

tcgaaggcac aggccgtgct ggtgcgcgcg cccgcagacg gcaaggccag tttcgaactc    540

gacggcagcg acggcagggc cgacttcggc acctatcgct acgggctggc gcagcagccg    600

ggcggcgcct ggggcctagt caggacgggg tattcgtcca ccgccgccgc ggcgctggat    660

accggcggac tgggcgcggt gcaggggttg tggtatgccg aatccaacgc gttgggcaag    720

cgcatgggcg aattgcgcct gaacccggac gccggcggcg cctggggccg ggcgttcagc    780

cagcgccagc gcatcagtcc gcgcgcgggc cggcatttcc agcaaggcgt cagcggcatc    840

gagctgggcg ccgaccgggc ctggcccgtg gccggcggcc gttggcatgc gggctggttg    900

ctgggctaca cgcgcgcgtc acgcgggttt tccggccagg gaaaggggca caccgacagc    960

gtgcacgtgg gcggctatgc cacctatatc ggcgccaatg gcgtgtacgc cgatgccacg   1020

ctgcgcgcca gccgcttcga gaattcgttc gacgcacctg gctgggcggg gcgcaccgtg   1080

tccggcagct accgcgccaa tggcgtgggc gtgacgctgg aggccggccg gcgtctggcg   1140

ctggaccggc actggttcgt cgagccgcag gccgaactgg cgtggtttcg tgccggcggc   1200
```

ggtacgtaca cggccagcaa tggcctgcgt atcgaggatg acggcggcac gtcgctgcag 1260
gcgcgggtag gcgcgcaagc cggccgccgc ttcgacttgc gcggcggcgc ggtggtgcag 1320
ccctacgcgc agctgagttg ggtgcaggaa ctcaagggcg tgagcacggt gcgcaccaac 1380
ggcatcgcgc accgtaccga cctgggcgcg ggccgcgtcg aactgggact gggcgtggcg 1440
gccgcgctgg gcaagggcca caatctgtac gcgtcgtacg agtacgcgca cgggcccagg 1500
ctcagcctgc cgtggaccgt gcagctgggt taccgctacg cttggtaa 1548

<210> SEQ ID NO 46
<211> LENGTH: 515
<212> TYPE: PRT
<213> ORGANISM: Bordetella pertussis

<400> SEQUENCE: 46

Leu Arg Gln Thr Thr Pro Val Pro Val Arg Leu Val Leu Arg Gly Ala
1 5 10 15

Ala Val Ala Gln Gly Asp Val Val Arg Ala Pro Glu Thr Ala Pro Glu
20 25 30

Lys Asp Gly Phe Gly Thr Pro Val Arg Pro Gly Leu Arg Val Gly Leu
35 40 45

Asp Gln Ala Pro Leu Glu Leu Asp Val Ala Asp Gly Ala Gln Trp His
50 55 60

Gly Ala Thr Gln Ser Leu Asp Arg Leu Ala Leu Gly Ala Gly Gly Gln
65 70 75 80

Trp Arg Met Ser Ala Ala Ser Ser Val Gly Glu Leu Ser Met Glu Pro
85 90 95

Gly Ala Ala Val Val Phe Gly Asp Ala Ala Gly Pro Gly Phe Gln Thr
100 105 110

Leu Thr Val Arg Thr Leu Ala Gly Ala Gly Ser Phe Glu Met Arg Ala
115 120 125

Asp Ala Ala Leu Glu His Ala Asp Gln Leu Val Val Thr Asp Gln Ala
130 135 140

Glu Gly Arg His Arg Val Trp Leu Arg Ala Pro Ala Gly Ala Glu Pro
145 150 155 160

Ser Lys Ala Gln Ala Val Leu Val Arg Ala Pro Ala Asp Gly Lys Ala
165 170 175

Ser Phe Glu Leu Asp Gly Ser Asp Gly Arg Ala Asp Phe Gly Thr Tyr
180 185 190

Arg Tyr Gly Leu Ala Gln Gln Pro Gly Gly Ala Trp Gly Leu Val Arg
195 200 205

Thr Gly Tyr Ser Ser Thr Ala Ala Ala Ala Leu Asp Thr Gly Gly Leu
210 215 220

Gly Ala Val Gln Gly Leu Trp Tyr Ala Glu Ser Asn Ala Leu Gly Lys
225 230 235 240

Arg Met Gly Glu Leu Arg Leu Asn Pro Asp Ala Gly Gly Ala Trp Gly
245 250 255

Arg Ala Phe Ser Gln Arg Gln Arg Ile Ser Pro Arg Ala Gly Arg His
260 265 270

Phe Gln Gln Gly Val Ser Gly Ile Glu Leu Gly Ala Asp Arg Ala Trp
275 280 285

Pro Val Ala Gly Gly Arg Trp His Ala Gly Trp Leu Leu Gly Tyr Thr
290 295 300

Arg Ala Ser Arg Gly Phe Ser Gly Gln Gly Lys Gly His Thr Asp Ser
305 310 315 320

```
Val His Val Gly Gly Tyr Ala Thr Tyr Ile Gly Ala Asn Gly Val Tyr
                325                 330                 335

Ala Asp Ala Thr Leu Arg Ala Ser Arg Phe Glu Asn Ser Phe Asp Ala
            340                 345                 350

Pro Gly Trp Ala Gly Arg Thr Val Ser Gly Ser Tyr Arg Ala Asn Gly
        355                 360                 365

Val Gly Val Thr Leu Glu Ala Gly Arg Arg Leu Ala Leu Asp Arg His
    370                 375                 380

Trp Phe Val Glu Pro Gln Ala Glu Leu Ala Trp Phe Arg Ala Gly Gly
385                 390                 395                 400

Gly Thr Tyr Thr Ala Ser Asn Gly Leu Arg Ile Glu Asp Asp Gly Gly
                405                 410                 415

Thr Ser Leu Gln Ala Arg Val Gly Ala Gln Ala Gly Arg Arg Phe Asp
            420                 425                 430

Leu Arg Gly Gly Ala Val Val Gln Pro Tyr Ala Gln Leu Ser Trp Val
        435                 440                 445

Gln Glu Leu Lys Gly Val Ser Thr Val Arg Thr Asn Gly Ile Ala His
    450                 455                 460

Arg Thr Asp Leu Gly Ala Gly Arg Val Glu Leu Gly Leu Gly Val Ala
465                 470                 475                 480

Ala Ala Leu Gly Lys Gly His Asn Leu Tyr Ala Ser Tyr Glu Tyr Ala
                485                 490                 495

His Gly Pro Arg Leu Ser Leu Pro Trp Thr Val Gln Leu Gly Tyr Arg
            500                 505                 510

Tyr Ala Trp
        515
```

<210> SEQ ID NO 47
<211> LENGTH: 1194
<212> TYPE: DNA
<213> ORGANISM: Bordetella pertussis

<400> SEQUENCE: 47

```
ttgccttcgc cgcccgaaga ggcgcctcag gcggggcccg acgcgtccaa gcagcggccg     60

gagggcctgc ccgcgcccga tgccaatccc caacccgatg caaagcccgg agctgagatg    120

aaaccccggc ctggggtgga acccggacct gaggcggaac ctggtccgca ggggcagcct    180

ggcccccagc ctggagcccg gccgcaggac gagccgcacg cgcagccgct gccgcccgcc    240

ggcaaccccg gcgctgggat ttacatgccc cgcagcggca tcttgaccgc accggttctg    300

gccgtgctgg gcacggccag tgcgccgcaa ggtatctggc aggcagagat gaacgccctg    360

agcaagcgca tgggtgaatt gcggcttacg ccggcagccg gcggcgtgtg ggcacgctcg    420

ttcgcgcaac gccaacgcct ggacaatcag gtggtggaca ggttcaccca gaccgtgggc    480

gggatcgaga ttggcgccga cacggccttg ccggcggccg aggggcgctg gcatgtaggc    540

gcggtggccg gctacagccg tgcgcgccgc aagctggcgc acagcgcccg tggcaacagc    600

gacagcctgc atgtgggcgc ctatgcgacg tatatcggcg acggcggctt ctacctcgac    660

gggattgtgc gggtgaaccg ctacgagcac gatttcaggg ctgacggcca gcgcggcgcg    720

cgcgtgacgg gcaagtatcg cgccaatggc atcgggctgt cgctggagac cggcaggcgt    780

ttcacatggg ccggcgactg gttcgtggaa ccgcaggtcg aagtggcgtt gttccgttcg    840

ggcggggcag actacacggc cagcaatggc gtgcgcgtcg acgtggcaag caccaagtcg    900

ttgctgggcc gggcaggcct gcaggtggga cgcaagctgg atctgggcaa cggcaaactg    960

gtgcagccgt acgccaagct gagctggttg caggagttcg atggcgtggg caaggtgcgc   1020
```

```
accaacgata tcggccatga cgtcaaactg cggggcgggc gcgccgaact cgacttgggc   1080

gtggccgcgg cgcttggcag gcacagcagc ctgtttgctt cgtacgagta cagcaagggc   1140

agccgcttga ccattccgtg gagctttcac gtcggctatc gatacgcctg gtaa         1194


<210> SEQ ID NO 48
<211> LENGTH: 397
<212> TYPE: PRT
<213> ORGANISM: Bordetella pertussis

<400> SEQUENCE: 48

Leu Pro Ser Pro Pro Glu Glu Ala Pro Gln Ala Gly Pro Asp Ala Ser
1               5                   10                  15

Lys Gln Arg Pro Glu Gly Leu Pro Ala Pro Asp Ala Asn Pro Gln Pro
            20                  25                  30

Asp Ala Lys Pro Gly Ala Glu Met Lys Pro Arg Pro Gly Val Glu Pro
        35                  40                  45

Gly Pro Glu Ala Glu Pro Gly Pro Gln Gly Gln Pro Gly Pro Gln Pro
    50                  55                  60

Gly Ala Arg Pro Gln Asp Glu Pro His Ala Gln Pro Leu Pro Pro Ala
65                  70                  75                  80

Gly Asn Pro Gly Ala Gly Ile Tyr Met Pro Arg Ser Gly Ile Leu Thr
                85                  90                  95

Ala Pro Val Leu Ala Val Leu Gly Thr Ala Ser Ala Pro Gln Gly Ile
            100                 105                 110

Trp Gln Ala Glu Met Asn Ala Leu Ser Lys Arg Met Gly Glu Leu Arg
        115                 120                 125

Leu Thr Pro Ala Ala Gly Gly Val Trp Ala Arg Ser Phe Ala Gln Arg
    130                 135                 140

Gln Arg Leu Asp Asn Gln Val Val Asp Arg Phe Thr Gln Thr Val Gly
145                 150                 155                 160

Gly Ile Glu Ile Gly Ala Asp Thr Ala Leu Pro Ala Ala Glu Gly Arg
                165                 170                 175

Trp His Val Gly Ala Val Ala Gly Tyr Ser Arg Ala Arg Arg Lys Leu
            180                 185                 190

Ala His Ser Ala Arg Gly Asn Ser Asp Ser Leu His Val Gly Ala Tyr
        195                 200                 205

Ala Thr Tyr Ile Gly Asp Gly Gly Phe Tyr Leu Asp Gly Ile Val Arg
    210                 215                 220

Val Asn Arg Tyr Glu His Asp Phe Arg Ala Asp Gly Gln Arg Gly Ala
225                 230                 235                 240

Arg Val Thr Gly Lys Tyr Arg Ala Asn Gly Ile Gly Leu Ser Leu Glu
                245                 250                 255

Thr Gly Arg Arg Phe Thr Trp Ala Gly Asp Trp Phe Val Glu Pro Gln
            260                 265                 270

Val Glu Val Ala Leu Phe Arg Ser Gly Gly Ala Asp Tyr Thr Ala Ser
        275                 280                 285

Asn Gly Val Arg Val Asp Val Ala Ser Thr Lys Ser Leu Leu Gly Arg
    290                 295                 300

Ala Gly Leu Gln Val Gly Arg Lys Leu Asp Leu Gly Asn Gly Lys Leu
305                 310                 315                 320

Val Gln Pro Tyr Ala Lys Leu Ser Trp Leu Gln Glu Phe Asp Gly Val
                325                 330                 335

Gly Lys Val Arg Thr Asn Asp Ile Gly His Asp Val Lys Leu Arg Gly
            340                 345                 350
```

```
Gly Arg Ala Glu Leu Asp Leu Gly Val Ala Ala Ala Leu Gly Arg His
        355                 360                 365

Ser Ser Leu Phe Ala Ser Tyr Glu Tyr Ser Lys Gly Ser Arg Leu Thr
    370                 375                 380

Ile Pro Trp Ser Phe His Val Gly Tyr Arg Tyr Ala Trp
385                 390                 395


<210> SEQ ID NO 49
<211> LENGTH: 6903
<212> TYPE: DNA
<213> ORGANISM: Bordetella pertussis

<400> SEQUENCE: 49

atgagacggt taaaggccca ggctttcgag ggcagccgca gcaggccggc aggacatggg     60

gtggcgccta ccttgctggc gctggccctg ggttccagg gggcggcggc gtgggccaat    120

tgcacgacgt caaacggtgc taccacttgc accaacgcca acggctctca taccaacaag    180

gtgggcagtg gaccgagcgg gatgaacgaa cgcgtcaccg tgaatcaggg ggcgcgcatc    240

gagacaaacg ccagcgcggc gatcagtgtg ggaacgagcg ggcaggtacg aatcgagggc    300

ggtgcagtag tgcaaagcac ggtcaatact gctgcgtccg gccagtacgc caaaacgctg    360

gaagcagcaa gcaataacaa tatttccatc caagtaaacg cgcagctcct ggccaagggc    420

agcgcttcgc agtccagcgc gttgggattg tcaggcgccg gcaataccgt caccaaccat    480

ggcacgatcc gggccgataa tgccgcggca atctgggtca ctgccaatac cgccaatgcg    540

gccaatacca tcgataacta cgggactatc gaaacagtgc tcaatggcgg ctacgccaac    600

gccatcggca gcacgcggaa caacagtgcc acgggcgctg gcgtgacggt acgcaatcat    660

gccaacggac gcatcgtcgg caacgtgaag ttcgaggctg gcgacgacag cgtcatactc    720

gacggcggct ctaccatcac cggatccttg aacggtggca gcggcaacaa cagcctgacg    780

ctgaaagccg gcgacggcac gctgggccgc gcaatccgca acttcggcac gatcaccaag    840

caggaggctg gaacctggac cctgaatggc caggtcggcc gcaacgacaa caacctcaag    900

tccacggtca aggtggaggg cggcacgctg gtcttgcgcg gcgataacag cggcgccacc    960

cagggcggcg tgttgcaggt gtccgccggc gctacggcgg acgtaactgc cgccagcgcc   1020

atgcagtcca tcagcaacgc cggcacggtt cagttcacgc aggacagcaa tgccgcctac   1080

gccggcgtgc tgagcgggac cgggagcatc gtcaagcgcg gcggcggcga cctgacgttg   1140

acgggcaaca acacccatac cggcaaggtg gtggtggagg cgggcagcct cagcgtatcg   1200

gcggccaaca acctgggtgg cgcaggtagt tcggtacagc tcaagggcgg cgccctcgcc   1260

ctcaagaaaa ccatcgtcgt caatcgcggc ctgacgctcg attccggggc gcagacgttg   1320

atcatcgagc cgggaacaac cacgacctgg caaggccagg ttagcggcgc cggcaaactg   1380

gtgacccagg gcggcacgct ggtgctggag cacgcgtcca atacgtatag cggcggtacg   1440

gagatcaaca acggaacgct gcgggcggcg catgatgcca gcctgggttc cggcacgttg   1500

gcgctcaaga acagccagct ggccgccacg gacagcttca cggccacgcg tgcattgacg   1560

ctcgctggaa acgaaagcat agacgtcgca gccaccaaga tactcagttg gaacggcgaa   1620

atcagcggcg ccggcaccct ggtgaaggaa ggccagggga ccttgctgct gcgcggaacc   1680

aatcagcaaa atggcggcac gaccgtcaat gccggtacgc tgcagatatc ccgcgacgcc   1740

aatcttggcc gaggggcgct ggcgctgaac gacggcacgc tgcagagcac cggcagcttc   1800

gcgacctcgc gcgcggccac cttgcgcggc caggccacca tggaggtcga cgcttcgcat   1860
```

-continued

```
accgtgacct ggaatggcga gctgagcggc ggcggcatgt tgcgcaagtc aggccagggc   1920
acgctggtcc tggccggcgc caacacgtac tcgggtggca cggtggtcga ggccggcgcg   1980
cttcgggcag gacacgaaga caacctggga cggggcgcaa taaccctgca gggcggagat   2040
ctgcttgccg gcggcagttt ttcgagcaac cgcgatctca cgcttgtccg cggttccttg   2100
gacgtggctc gcgacgctac cctgacctgg agcggcgcga tatcgggcgc cggcgatctg   2160
gtcaagaaag gggacgggcg cctgacactc acgggcgtca acgagtacgc cggccagacc   2220
gtgctccggg gcggcaagct gcgtgtggcc agggacgaaa acctgggccg cggagcactg   2280
gtgctggaag acaataccgt gttcgagagc atgggctcgc atgccgccac gcggcaggtc   2340
acgctcaagg gcgcgcccaa ggtagagacg cttgacggca ctacgctcga atggcgcggc   2400
acggtcgacg gcgacggcaa gctgtacaag caaggcggcg gcacgctcgt gctgagcggc   2460
aacaatacct acgccaaggg cgtcgaggtc tggggcgggg tcgtgcaagt ctctcgcgac   2520
cagaacctgg gcgcggccaa tggcgcggtc acgctcaacg gcggcgggtt ggcggccaac   2580
ggggatttca ccagcaatcg ccagctggag ctgaccgccg gggccaaggc catcgacgtc   2640
gcggccggca aggacgtgac gtggcgcggt gtcgtcaacg gcgccggcgc gctgaccaag   2700
gccggcgacg gtacgctggc gctggccggc gccaacacct acaccggcgg cacgcgcttg   2760
cagggcggca ccgtgcaggt atcgcgcgac aacaacctcg gccaggccgc cggcgcggtc   2820
acgttcgacg gcgggcggct ggccaacacg ggcagctttg cgaccgcgcg cacggccacg   2880
ctcaacaagg ctggccagat cgataccgac cggggcacca cgctgacatg gaacggcgcc   2940
atcggcggca agggcgagct gcgcaagcaa ggggcgggca ccctggtgct gggcggagcc   3000
aacacttacc agggcgacac ccgcgtcgag gccggcacgc tgcaagtgtc ggccgacgcc   3060
aatctgggcc agggcgccgt gcatctgcac gacagccggc tggcgacgac cggtacgttc   3120
gcgacctcgc gccgtctgga gttgaccgga cgtggcgcgg tgcaagcggc tgccgccgcc   3180
acgctggatt ggcgcgggac ggtcgctggc gccggcacgc tggtcaagga gggcgcaggc   3240
acgctggtgc tggccggtga caaccagcat gccggcggca ccgaggtcag ggccggcacg   3300
ctgcaggtat cgcgcgccac caacctgggg cccggcgcgc tggcgctgga gaacgcggcg   3360
ctggccacga ccgccagctt cacggccacg caggcagcca ccctgactgg caacgccgcc   3420
atcgacacgg ccgccggcac cacgctggga tgggaggggg ccatcggcgg aaccggcagc   3480
ctgcacaaaa agggcgaggg caagctggtg ctggtcaagg acaaccacca tgacggcggc   3540
accacgatcc acgccggtac cctgcaggtg tcgcgcgacg ccaacctggg ctcgggacag   3600
agcgcggtga cgctggatgg cggcgccctg gcggtttctg ccgggttctc cagcgggcgc   3660
gagatcgtcg tgggcgccgg gcacggcgcg ctttcggtga cgggcggcca caccctgcaa   3720
tggcagggcc aggtcggcgg ggcgggggcg ttgaccaaga cgggcgacgg cacgctcgtg   3780
ctggagcacg acaataccca cgccggcggt acccggatta ccggcggggt gctgcgcgtc   3840
tcgcgcgatg agaacctggg cgaggcgcat ggcatgctga cgctcgacgg cggcacgctg   3900
tcgaccaccg ccgggttcgc gagccggcgc aacgccaccg tgggcaacgg cggcggccgg   3960
atcgtcgtcg ccgacgccgc cacgctggat ttgcagggcg acgttgccgg cgcgggccgg   4020
ctggtcaaag agggcgcggg cacgctggcc ttgggcggca cgaacaccta tgccggcggc   4080
accgtggtcg aggccggcac gctgcgggtc gcgcgcgacg ccaacctggg cggcggcgcg   4140
ctgaccctga acaacagccg cctgcatgcg accgccggct ttgccaccgg ccgcgatgcg   4200
accctctccg ggcgcgcctc gatcgacacc gacgaccggg cgacgctgca atggcgcggc   4260
```

-continued

```
acggtcaatg gcgccggcag gctggtcaag cagggcctgg gcaccctggt actggacggc   4320
gacaaccggt acgcgggagg caccgaggtc aatgccggca cgctgcaggt cgcgcgcgac   4380
gccaacctgg gcgcgggcga cgtggcgctc aatggcagca gcctggccgc gaccgccagc   4440
ttcgccaccg cgcgcacggc cacgctgagc ggcgcggccg ccatcgacac ggccgacggc   4500
gccaccttgg actggaatgg cctgctcgac ggtgacggcg ccctggtcaa gcagggcaac   4560
ggcaccctgg cgctggccgc ggccaaccgc tatggcggcg gcaccatcgt caaggcgggc   4620
gccgtgcgga tcgcccgcga cgccaacctg gggcgggccg gcaccggcgt aacgctggac   4680
ggcggcgcgc tggccaccac ggcggatctc gcgaccggcc gcgcggcgac cctgggcgcg   4740
gccaacggca cgctggacgt ggccgccggc acccgcctgg actggaacgg ggcgatcggc   4800
ggcgccggcg cgctgaccaa gaccggcgcc ggcaccctgg cgctcaacca cgacaaccag   4860
catgccggcg gcaccctggt ccatggcggc acgctgcgga tcgcccgcga cgccaacctg   4920
ggcgcggcgg gcacggcggt gacgctggac ggcggcacgc tggccaccac ggcgtcgttg   4980
gcgcccgagc gcgcgctgcg cgtcggggcg cgcaacggcg tattgctgcc ggacgcgggc   5040
acgaccctgg attggcgggg cgtggtcgcc ggcgcgggca agctgaccaa ggccggtccg   5100
ggcacgctgg tgctcagcgc cgataaccgc catggcggcg gcacggcagt caccggcggt   5160
acgctgcaag tttcgcgcga cgccaacctg ggcgcggcgg ccggcgccct gacgctggac   5220
ggcggcacct tgctgagcac cgccagcttt gcctcggcgc gtgtcgccac cctcgatgcc   5280
gcgggcggca ccttcgtcac ccgcgacggc acccggctgg attgggacgg cgcgataggc   5340
ggggcgggtg gcctggtcaa ggaaggcgcc ggcgagctgc ggcttggcaa tgccaatacc   5400
taccaggggc cgacccgcat cgccgccggc cgcctggccg tcaacggcag catcgccagc   5460
ccggtcacgg tcgagcaggc cggcgtgctg ggcggcacgg gccgcatcgt cggggatgtg   5520
gccaaccgcg gcgtggtcgc gccgggcaac tcgatcggcg cgttgacggt ggccggcaat   5580
tacgctggta cgggcggcag cctggaagtg gaggcggtgc ttggcggcga cgccgcgccg   5640
gccgatcggc tggtgctcga cggcggcgcg gccagcggcg tcacgccggt cgtagtcaag   5700
ccgcagggcg gggtgggcgg cctgaccctg cgcggcattc cggtggtcgt ggcccagggt   5760
ggcgccacga ccgcgcccgg ggccttccgc ctggcgcagc cgctggtcgc gggcgcctac   5820
gagtaccagt tgctgcgcgg cgcgggcgac ggcgccgcgg cgcaggcgca agactggtac   5880
ctgcgtacct cccgcgtcga gcgcgacaag gcgggcagga tcgtcaaggt cgtgcccttc   5940
taccggcccg aggtggcgct gtatgccggc acgcccatgc tgatgcgcat ggtcggcacg   6000
gaagcgctgg gcagctaccg cgaacgcgcg ggccagcccg gcgcggccgc gcccgaggca   6060
ggcgccgcag cccggcgtgg cgtgtgggca cgtaccttcg ggcgtcgttt cgagcgctcc   6120
gcgggcagcg aagcggcgcc gtccttcaac ggcagcctgg ccggcatgca gctgggcgcg   6180
gacctctaca cgcgtcgctc ggccacccgg catgccgacg ccttcggcgt gttcggcgga   6240
tacgccacgg cccgcggcga tgtgcggggc ctggcgcgcg gcgagatcca ggcggtgggc   6300
acgtccacgc tgcgggccgc ccagctgggc gcctactgga cgcacactgg tccgagcggc   6360
tggtacgtcg acacggtgct ggcgggcacg cgctacaagc agcagaccag ctcgtcggcc   6420
catgtcggcg cgaccagccg cggctggggc atgatggcct cggtggaggc cggctacccg   6480
tggcagctca atccgcgctg gcaaatcgag ccgcaggccc agttggtgta tcagcagctt   6540
ggcatcgcca atggcgccga ccgcgtgtct tcggtgtcgt acaagacgcc cgatgcgctg   6600
acggggcggc tgggcacgcg cctggcgggc cagtacgcat acgggaaggc gcagttgcgg   6660
```

```
ccgttcatgg gcgtatcgct gctgcacgat ttcaccggcg ccgacaccgt cacgttcgcg   6720

ggcgtgcaca gcgtacgcgc cagccgccag aacacggccg tggatctgaa ggcgggcgtg   6780

gacacgcagc tgggcaagag cgtaggcctg tgggggcagg tcggctacgg caagtcggtc   6840

ggcagcggcg acggcagcga ccgtggctgg agcgccaacc tggggctgcg cgtggcgtat   6900

tga                                                               6903


<210> SEQ ID NO 50
<211> LENGTH: 2300
<212> TYPE: PRT
<213> ORGANISM: Bordetella pertussis

<400> SEQUENCE: 50

Met Arg Arg Leu Lys Ala Gln Ala Phe Glu Gly Ser Arg Ser Arg Pro
1               5                   10                  15

Ala Gly His Gly Val Ala Pro Thr Leu Leu Ala Leu Ala Leu Gly Phe
            20                  25                  30

Gln Gly Ala Ala Ala Trp Ala Asn Cys Thr Thr Ser Asn Gly Ala Thr
        35                  40                  45

Thr Cys Thr Asn Ala Asn Gly Ser His Thr Asn Lys Val Gly Ser Gly
    50                  55                  60

Pro Ser Gly Met Asn Glu Arg Val Thr Val Asn Gln Gly Ala Arg Ile
65                  70                  75                  80

Glu Thr Asn Ala Ser Ala Ala Ile Ser Val Gly Thr Ser Gly Gln Val
                85                  90                  95

Arg Ile Glu Gly Gly Ala Val Val Gln Ser Thr Val Asn Thr Ala Ala
            100                 105                 110

Ser Gly Gln Tyr Ala Lys Thr Leu Glu Ala Ala Ser Asn Asn Asn Ile
        115                 120                 125

Ser Ile Gln Val Asn Ala Gln Leu Leu Ala Lys Gly Ser Ala Ser Gln
    130                 135                 140

Ser Ser Ala Leu Gly Leu Ser Gly Ala Gly Asn Thr Val Thr Asn His
145                 150                 155                 160

Gly Thr Ile Arg Ala Asp Asn Ala Ala Ala Ile Trp Val Thr Ala Asn
                165                 170                 175

Thr Ala Asn Ala Ala Asn Thr Ile Asp Asn Tyr Gly Thr Ile Glu Thr
            180                 185                 190

Val Leu Asn Gly Gly Tyr Ala Asn Ala Ile Gly Ser Thr Arg Asn Asn
        195                 200                 205

Ser Ala Thr Gly Ala Gly Val Thr Val Arg Asn His Ala Asn Gly Arg
    210                 215                 220

Ile Val Gly Asn Val Lys Phe Glu Ala Gly Asp Asp Ser Val Ile Leu
225                 230                 235                 240

Asp Gly Gly Ser Thr Ile Thr Gly Ser Leu Asn Gly Gly Ser Gly Asn
                245                 250                 255

Asn Ser Leu Thr Leu Lys Ala Gly Asp Gly Thr Leu Gly Arg Ala Ile
            260                 265                 270

Arg Asn Phe Gly Thr Ile Thr Lys Gln Glu Ala Gly Thr Trp Thr Leu
        275                 280                 285

Asn Gly Gln Val Gly Arg Asn Asp Asn Asn Leu Lys Ser Thr Val Lys
    290                 295                 300

Val Glu Gly Gly Thr Leu Val Leu Arg Gly Asp Asn Ser Gly Ala Thr
305                 310                 315                 320

Gln Gly Gly Val Leu Gln Val Ser Ala Gly Ala Thr Ala Asp Val Thr
                325                 330                 335
```

```
Ala Ala Ser Ala Met Gln Ser Ile Ser Asn Ala Gly Thr Val Gln Phe
            340                 345                 350

Thr Gln Asp Ser Asn Ala Ala Tyr Ala Gly Val Leu Ser Gly Thr Gly
        355                 360                 365

Ser Ile Val Lys Arg Gly Gly Gly Asp Leu Thr Leu Thr Gly Asn Asn
    370                 375                 380

Thr His Thr Gly Lys Val Val Val Glu Ala Gly Ser Leu Ser Val Ser
385                 390                 395                 400

Ala Ala Asn Asn Leu Gly Gly Ala Gly Ser Ser Val Gln Leu Lys Gly
                405                 410                 415

Gly Ala Leu Ala Leu Lys Lys Thr Ile Val Val Asn Arg Gly Leu Thr
            420                 425                 430

Leu Asp Ser Gly Ala Gln Thr Leu Ile Ile Glu Pro Gly Thr Thr Thr
        435                 440                 445

Thr Trp Gln Gly Gln Val Ser Gly Ala Gly Lys Leu Val Thr Gln Gly
    450                 455                 460

Gly Thr Leu Val Leu Glu His Ala Ser Asn Thr Tyr Ser Gly Gly Thr
465                 470                 475                 480

Glu Ile Asn Asn Gly Thr Leu Arg Ala Ala His Asp Ala Ser Leu Gly
                485                 490                 495

Ser Gly Thr Leu Ala Leu Lys Asn Ser Gln Leu Ala Ala Thr Asp Ser
            500                 505                 510

Phe Thr Ala Thr Arg Ala Leu Thr Leu Ala Gly Asn Glu Ser Ile Asp
        515                 520                 525

Val Ala Ala Thr Lys Ile Leu Ser Trp Asn Gly Glu Ile Ser Gly Ala
    530                 535                 540

Gly Thr Leu Val Lys Glu Gly Gln Gly Thr Leu Leu Leu Arg Gly Thr
545                 550                 555                 560

Asn Gln Gln Asn Gly Gly Thr Thr Val Asn Ala Gly Thr Leu Gln Ile
                565                 570                 575

Ser Arg Asp Ala Asn Leu Gly Arg Gly Ala Leu Ala Leu Asn Asp Gly
            580                 585                 590

Thr Leu Gln Ser Thr Gly Ser Phe Ala Thr Ser Arg Ala Ala Thr Leu
        595                 600                 605

Arg Gly Gln Ala Thr Met Glu Val Asp Ala Ser His Thr Val Thr Trp
    610                 615                 620

Asn Gly Glu Leu Ser Gly Gly Gly Met Leu Arg Lys Ser Gly Gln Gly
625                 630                 635                 640

Thr Leu Val Leu Ala Gly Ala Asn Thr Tyr Ser Gly Gly Thr Val Val
                645                 650                 655

Glu Ala Gly Ala Leu Arg Ala Gly His Glu Asp Asn Leu Gly Arg Gly
            660                 665                 670

Ala Ile Thr Leu Gln Gly Gly Asp Leu Leu Ala Gly Gly Ser Phe Ser
        675                 680                 685

Ser Asn Arg Asp Leu Thr Leu Val Arg Gly Ser Leu Asp Val Ala Arg
    690                 695                 700

Asp Ala Thr Leu Thr Trp Ser Gly Ala Ile Ser Gly Ala Gly Asp Leu
705                 710                 715                 720

Val Lys Lys Gly Asp Gly Arg Leu Thr Leu Thr Gly Val Asn Glu Tyr
                725                 730                 735

Ala Gly Gln Thr Val Leu Arg Gly Gly Lys Leu Arg Val Ala Arg Asp
            740                 745                 750

Glu Asn Leu Gly Arg Gly Ala Leu Val Leu Glu Asp Asn Thr Val Phe
```

```
        755                 760                 765

Glu Ser Met Gly Ser His Ala Ala Thr Arg Gln Val Thr Leu Lys Gly
    770                 775                 780

Ala Pro Lys Val Glu Thr Leu Asp Gly Thr Thr Leu Glu Trp Arg Gly
785                 790                 795                 800

Thr Val Asp Gly Asp Gly Lys Leu Tyr Lys Gln Gly Gly Gly Thr Leu
                805                 810                 815

Val Leu Ser Gly Asn Asn Thr Tyr Ala Lys Gly Val Glu Val Trp Gly
            820                 825                 830

Gly Val Val Gln Val Ser Arg Asp Gln Asn Leu Gly Ala Ala Asn Gly
        835                 840                 845

Ala Val Thr Leu Asn Gly Gly Gly Leu Ala Ala Asn Gly Asp Phe Thr
    850                 855                 860

Ser Asn Arg Gln Leu Glu Leu Thr Ala Gly Ala Lys Ala Ile Asp Val
865                 870                 875                 880

Ala Ala Gly Lys Asp Val Thr Trp Arg Gly Val Val Asn Gly Ala Gly
                885                 890                 895

Ala Leu Thr Lys Ala Gly Asp Gly Thr Leu Ala Leu Ala Gly Ala Asn
            900                 905                 910

Thr Tyr Thr Gly Gly Thr Arg Leu Gln Gly Gly Thr Val Gln Val Ser
        915                 920                 925

Arg Asp Asn Asn Leu Gly Gln Ala Ala Gly Ala Val Thr Phe Asp Gly
    930                 935                 940

Gly Arg Leu Ala Asn Thr Gly Ser Phe Ala Thr Ala Arg Thr Ala Thr
945                 950                 955                 960

Leu Asn Lys Ala Gly Gln Ile Asp Thr Asp Arg Gly Thr Thr Leu Thr
                965                 970                 975

Trp Asn Gly Ala Ile Gly Gly Lys Gly Glu Leu Arg Lys Gln Gly Ala
            980                 985                 990

Gly Thr Leu Val Leu Gly Gly Ala Asn Thr Tyr Gln Gly Asp Thr Arg
        995                 1000                1005

Val Glu Ala Gly Thr Leu Gln Val Ser Ala Asp Ala Asn Leu Gly Gln
    1010                1015                1020

Gly Ala Val His Leu His Asp Ser Arg Leu Ala Thr Thr Gly Thr Phe
1025                1030                1035                1040

Ala Thr Ser Arg Arg Leu Glu Leu Thr Gly Arg Gly Ala Val Gln Ala
                1045                1050                1055

Ala Ala Ala Ala Thr Leu Asp Trp Arg Gly Thr Val Ala Gly Ala Gly
            1060                1065                1070

Thr Leu Val Lys Glu Gly Ala Gly Thr Leu Val Leu Ala Gly Asp Asn
        1075                1080                1085

Gln His Ala Gly Gly Thr Glu Val Arg Ala Gly Thr Leu Gln Val Ser
    1090                1095                1100

Arg Ala Thr Asn Leu Gly Pro Gly Ala Leu Ala Leu Glu Asn Ala Ala
1105                1110                1115                1120

Leu Ala Thr Thr Ala Ser Phe Thr Ala Thr Gln Ala Ala Thr Leu Thr
                1125                1130                1135

Gly Asn Ala Ala Ile Asp Thr Ala Ala Gly Thr Thr Leu Gly Trp Glu
            1140                1145                1150

Gly Ala Ile Gly Gly Thr Gly Ser Leu His Lys Lys Gly Glu Gly Lys
        1155                1160                1165

Leu Val Leu Val Lys Asp Asn His His Asp Gly Gly Thr Thr Ile His
    1170                1175                1180
```

```
Ala Gly Thr Leu Gln Val Ser Arg Asp Ala Asn Leu Gly Ser Gly Gln
1185                1190                1195                1200

Ser Ala Val Thr Leu Asp Gly Gly Ala Leu Ala Val Ser Ala Gly Phe
                1205                1210                1215

Ser Ser Gly Arg Glu Ile Val Val Gly Ala Gly His Gly Ala Leu Ser
            1220                1225                1230

Val Thr Gly Gly His Thr Leu Gln Trp Gln Gly Gln Val Gly Gly Ala
        1235                1240                1245

Gly Ala Leu Thr Lys Thr Gly Asp Gly Thr Leu Val Leu Glu His Asp
    1250                1255                1260

Asn Thr His Ala Gly Gly Thr Arg Ile Thr Gly Gly Val Leu Arg Val
1265                1270                1275                1280

Ser Arg Asp Glu Asn Leu Gly Glu Ala His Gly Met Leu Thr Leu Asp
                1285                1290                1295

Gly Gly Thr Leu Ser Thr Thr Ala Gly Phe Ala Ser Arg Arg Asn Ala
            1300                1305                1310

Thr Val Gly Asn Gly Gly Gly Arg Ile Val Val Ala Asp Ala Ala Thr
        1315                1320                1325

Leu Asp Leu Gln Gly Asp Val Ala Gly Ala Gly Arg Leu Val Lys Glu
    1330                1335                1340

Gly Ala Gly Thr Leu Ala Leu Gly Gly Thr Asn Thr Tyr Ala Gly Gly
1345                1350                1355                1360

Thr Val Val Glu Ala Gly Thr Leu Arg Val Ala Arg Asp Ala Asn Leu
                1365                1370                1375

Gly Gly Gly Ala Leu Thr Leu Asn Asn Ser Arg Leu His Ala Thr Ala
            1380                1385                1390

Gly Phe Ala Thr Gly Arg Asp Ala Thr Leu Ser Gly Arg Ala Ser Ile
        1395                1400                1405

Asp Thr Asp Asp Arg Ala Thr Leu Gln Trp Arg Gly Thr Val Asn Gly
    1410                1415                1420

Ala Gly Arg Leu Val Lys Gln Gly Leu Gly Thr Leu Val Leu Asp Gly
1425                1430                1435                1440

Asp Asn Arg Tyr Ala Gly Gly Thr Glu Val Asn Ala Gly Thr Leu Gln
                1445                1450                1455

Val Ala Arg Asp Ala Asn Leu Gly Ala Gly Asp Val Ala Leu Asn Gly
            1460                1465                1470

Ser Ser Leu Ala Ala Thr Ala Ser Phe Ala Thr Ala Arg Thr Ala Thr
        1475                1480                1485

Leu Ser Gly Ala Ala Ala Ile Asp Thr Ala Asp Gly Ala Thr Leu Asp
    1490                1495                1500

Trp Asn Gly Leu Leu Asp Gly Asp Gly Ala Leu Val Lys Gln Gly Asn
1505                1510                1515                1520

Gly Thr Leu Ala Leu Ala Ala Ala Asn Arg Tyr Gly Gly Gly Thr Ile
                1525                1530                1535

Val Lys Ala Gly Ala Val Arg Ile Ala Arg Asp Ala Asn Leu Gly Arg
            1540                1545                1550

Ala Gly Thr Gly Val Thr Leu Asp Gly Gly Ala Leu Ala Thr Thr Ala
        1555                1560                1565

Asp Leu Ala Thr Gly Arg Ala Ala Thr Leu Gly Ala Ala Asn Gly Thr
    1570                1575                1580

Leu Asp Val Ala Ala Gly Thr Arg Leu Asp Trp Asn Gly Ala Ile Gly
1585                1590                1595                1600

Gly Ala Gly Ala Leu Thr Lys Thr Gly Ala Gly Thr Leu Ala Leu Asn
                1605                1610                1615
```

```
His Asp Asn Gln His Ala Gly Gly Thr Leu Val His Gly Gly Thr Leu
            1620                1625                1630

Arg Ile Ala Arg Asp Ala Asn Leu Gly Ala Ala Gly Thr Ala Val Thr
        1635                1640                1645

Leu Asp Gly Gly Thr Leu Ala Thr Thr Ala Ser Leu Ala Pro Glu Arg
    1650                1655                1660

Ala Leu Arg Val Gly Ala Arg Asn Gly Val Leu Leu Pro Asp Ala Gly
1665                1670                1675                1680

Thr Thr Leu Asp Trp Arg Gly Val Val Ala Gly Ala Gly Lys Leu Thr
                1685                1690                1695

Lys Ala Gly Pro Gly Thr Leu Val Leu Ser Ala Asp Asn Arg His Gly
            1700                1705                1710

Gly Gly Thr Ala Val Thr Gly Gly Thr Leu Gln Val Ser Arg Asp Ala
        1715                1720                1725

Asn Leu Gly Ala Ala Ala Gly Ala Leu Thr Leu Asp Gly Gly Thr Leu
    1730                1735                1740

Leu Ser Thr Ala Ser Phe Ala Ser Ala Arg Val Ala Thr Leu Asp Ala
1745                1750                1755                1760

Ala Gly Gly Thr Phe Val Thr Arg Asp Gly Thr Arg Leu Asp Trp Asp
                1765                1770                1775

Gly Ala Ile Gly Gly Ala Gly Gly Leu Val Lys Glu Gly Ala Gly Glu
            1780                1785                1790

Leu Arg Leu Gly Asn Ala Asn Thr Tyr Gln Gly Pro Thr Arg Ile Ala
        1795                1800                1805

Ala Gly Arg Leu Ala Val Asn Gly Ser Ile Ala Ser Pro Val Thr Val
    1810                1815                1820

Glu Gln Ala Gly Val Leu Gly Gly Thr Gly Arg Ile Val Gly Asp Val
1825                1830                1835                1840

Ala Asn Arg Gly Val Val Ala Pro Gly Asn Ser Ile Gly Ala Leu Thr
                1845                1850                1855

Val Ala Gly Asn Tyr Ala Gly Thr Gly Gly Ser Leu Glu Val Glu Ala
            1860                1865                1870

Val Leu Gly Gly Asp Ala Ala Pro Ala Asp Arg Leu Val Leu Asp Gly
        1875                1880                1885

Gly Ala Ala Ser Gly Val Thr Pro Val Val Val Lys Pro Gln Gly Gly
    1890                1895                1900

Val Gly Gly Leu Thr Leu Arg Gly Ile Pro Val Val Val Ala Gln Gly
1905                1910                1915                1920

Gly Ala Thr Thr Ala Pro Gly Ala Phe Arg Leu Ala Gln Pro Leu Val
                1925                1930                1935

Ala Gly Ala Tyr Glu Tyr Gln Leu Leu Arg Gly Ala Gly Asp Gly Ala
            1940                1945                1950

Ala Ala Gln Ala Gln Asp Trp Tyr Leu Arg Thr Ser Arg Val Glu Arg
        1955                1960                1965

Asp Lys Ala Gly Arg Ile Val Lys Val Val Pro Phe Tyr Arg Pro Glu
    1970                1975                1980

Val Ala Leu Tyr Ala Gly Thr Pro Met Leu Met Arg Met Val Gly Thr
1985                1990                1995                2000

Glu Ala Leu Gly Ser Tyr Arg Glu Arg Ala Gly Gln Pro Gly Ala Ala
                2005                2010                2015

Ala Pro Glu Ala Gly Ala Ala Ala Arg Arg Gly Val Trp Ala Arg Thr
            2020                2025                2030

Phe Gly Arg Arg Phe Glu Arg Ser Ala Gly Ser Glu Ala Ala Pro Ser
```

-continued 2035 2040 2045

Phe Asn Gly Ser Leu Ala Gly Met Gln Leu Gly Ala Asp Leu Tyr Thr
2050 2055 2060

Arg Arg Ser Ala Thr Arg His Ala Asp Ala Phe Gly Val Phe Gly Gly
2065 2070 2075 2080

Tyr Ala Thr Ala Arg Gly Asp Val Arg Gly Leu Ala Arg Gly Glu Ile
2085 2090 2095

Gln Ala Val Gly Thr Ser Thr Leu Arg Ala Ala Gln Leu Gly Ala Tyr
2100 2105 2110

Trp Thr His Thr Gly Pro Ser Gly Trp Tyr Val Asp Thr Val Leu Ala
2115 2120 2125

Gly Thr Arg Tyr Lys Gln Gln Thr Ser Ser Ser Ala His Val Gly Ala
2130 2135 2140

Thr Ser Arg Gly Trp Gly Met Met Ala Ser Val Glu Ala Gly Tyr Pro
2145 2150 2155 2160

Trp Gln Leu Asn Pro Arg Trp Gln Ile Glu Pro Gln Ala Gln Leu Val
2165 2170 2175

Tyr Gln Gln Leu Gly Ile Ala Asn Gly Ala Asp Arg Val Ser Ser Val
2180 2185 2190

Ser Tyr Lys Thr Pro Asp Ala Leu Thr Gly Arg Leu Gly Thr Arg Leu
2195 2200 2205

Ala Gly Gln Tyr Ala Tyr Gly Lys Ala Gln Leu Arg Pro Phe Met Gly
2210 2215 2220

Val Ser Leu Leu His Asp Phe Thr Gly Ala Asp Thr Val Thr Phe Ala
2225 2230 2235 2240

Gly Val His Ser Val Arg Ala Ser Arg Gln Asn Thr Ala Val Asp Leu
2245 2250 2255

Lys Ala Gly Val Asp Thr Gln Leu Gly Lys Ser Val Gly Leu Trp Gly
2260 2265 2270

Gln Val Gly Tyr Gly Lys Ser Val Gly Ser Gly Asp Gly Ser Asp Arg
2275 2280 2285

Gly Trp Ser Ala Asn Leu Gly Leu Arg Val Ala Tyr
2290 2295 2300

<210> SEQ ID NO 51
<211> LENGTH: 2622
<212> TYPE: DNA
<213> ORGANISM: Bordetella pertussis

<400> SEQUENCE: 51
atgttgcgaa ctggagcccc gatgcgtagc gcccgccgcc gtaccccagc acgacttgcc 60
ccgttgccgg ccatgctggc cgccgccggc ctgctgcaat ccttgggcgc gacgcccgcg 120
gccgcggcct gtgcgcccac gctggcgcca gccagcgggc agagcgtgca atgcgacggc 180
gccgtggtca accagtcggt cgaggcggcg gccggcagcc agaacgtaac catcacggtg 240
gcgcccggcg cgctgttctc gaccaacgcg acgcgggcgc tgtcggtcga tgaccgcagc 300
cgtatcgtca acgagggcac gatccagatg gccggcggcg ccggcgcctc gcgcggcgcc 360
atggtgggtt tcggcgacaa caaccagttg atcaaccgcg gatcgatcac gacatcgggc 420
agcggcgtgc gcggcatctc ggtgcccaac gtcggcagta ccgggacgct ggtcgacaac 480
agcggcagca tccgcaccca gggcgccagc gcgcacggca tcgccatcaa cggcccgggc 540
aaccgcgtcc agaacagcgg cgccatcacc gtcaacggca ccgacgccaa gggcgtgtat 600
ctgcaaggcg gcagccccgc ggccaacgta ctggtcaacg gcggcaccat ccatgcgcgc 660

-continued

```
ggcgccagca gcaacggcat attcggcccc gacggcgtgc atgtgaacac caccaacgcc    720

aacggctttc atgcccgcgt cgagaacctg cccggcgggc gcatcctcag cgatcactcg    780

tatgcgctgc gcgggcagaa cggcaacgat accttcatca acgccggcta cctgcaaggg    840

cacggcgggg ccggccgcga cacggccgtc tacatgggcc cccagggcac gggcacgctg    900

atcctgcgca ccggctcggc catcgccggc ctggccgacg gcggcggggc ggccagccat    960

gcgtatctgg agggcagcgg cacggtggac aaccggttcg ccaacttccg caccctgacc   1020

atgcgcggcg ccgactggcg ctggacctcg gacgccgcgt tcaccgaaag cgtggacctg   1080

cgcaccggca cattctttct tgccggcacg ctcgccagcc cggccaaccg cctggccgcc   1140

ggcgcggtgc tggccggcac cggcacgctg gccggcgcat tgcgcaacgc cggcgaaatc   1200

cggcccggcc cgaacgacgg cagcggctac ggcgcgctga cggtgcgcgg cgattacacc   1260

ggcgcgggcg gcgcgctgcg cgtcaacacg gtgctggccg gcgacggggc cgcctcggac   1320

aggctggtca tcgatggcgg gcacgccggc ggcagcaccc cggtcacggt ggtcaaccgg   1380

ggcgggcagg gcgcgctgac cgcggccgac ggcatcctgg tggtccaggc catcaatggc   1440

gcaagctcgg acgccggcgc cttctcgctg gccgcccccc tcaacgccgg cgcatacgag   1500

tacaggctgt accgcggcgg cgccacgggc gccgcgccgg acagctggta cctgcgctcg   1560

cgggcctatc tggtcgagga ccaactggcc ggcagccttg ccgaagccga ggcgatcgcc   1620

gacgacatcg gccggcgcac cggcgagcgg ccgagcatcg aggacacgcc gctgtaccgg   1680

cccgaggtgg cgctgtacag cagcattccc atgctggcgc ggcgcatggg cctggcccag   1740

ctgggcacct tccacgaacg gcagggcaac caggcgctgc tggcgcgcga cggcgaacgc   1800

gtcgcggcct gggcgcgcgc ctatggcggc aacagcaagc aggcgctcga cggcgatgcg   1860

caacccggca tcgacgcccg cctggccggc gtgcaactgg ggcaggacct ctacagcagc   1920

gtgcgcccgg acggcggaca gcaccgcttc gggctgttcg gcggctatgg ccaggcgcgc   1980

ggcgacaccc acggctcggc cggcggcgag cgcgacgccg ctaccggccg gctgaccatc   2040

gacggctaca gcgtcggcgg ctactggacc tatgtcggcc cgcgcgggtg gtacgtggat   2100

gccgtgctgg ccaacacctg gatggacatc gacaccgact ccaaggccgg gcgcgacgcc   2160

gatacgcgcg gccaggcgtt cacggcttcg ctggaaagtg gctacccgct ggcgctgtcc   2220

gagcgctgga cgctggagcc gcaggcgcag ctcatctacc agcacacgcg cgtcgacggt   2280

ttctcggacg ccgtgtccga ggtgcgcatc cgcgacgaca acgcgctgac cgcccgcctg   2340

ggcgcccggc tgcagggcga gtacgcggcc gccgcgcagg tgtggcgccc ctacgcggcg   2400

ctgaatttct ggcgcacctt cagcggcgag aacaccgtcg tgctgggcga agacagcatc   2460

gatacccggc gcggcgcgac ctcgctcgaa ctggcggccg gcgccagcgt gacgctggcc   2520

cgcagcctgg ccctctacgg caggctggcc tatgccacca gcatcgacag ccagtatctg   2580

cgcggcgctt cggcgcagct ggggatgcgc tacacctggt aa                       2622


<210> SEQ ID NO 52
<211> LENGTH: 873
<212> TYPE: PRT
<213> ORGANISM: Bordetella pertussis

<400> SEQUENCE: 52

Met Leu Arg Thr Gly Ala Pro Met Arg Ser Ala Arg Arg Arg Thr Pro
 1               5                   10                  15

Ala Arg Leu Ala Pro Leu Pro Ala Met Leu Ala Ala Ala Gly Leu Leu
            20                  25                  30
```

```
Gln Ser Leu Gly Ala Thr Pro Ala Ala Ala Ala Cys Ala Pro Thr Leu
        35                  40                  45

Ala Pro Ala Ser Gly Gln Ser Val Gln Cys Asp Gly Ala Val Val Asn
    50                  55                  60

Gln Ser Val Glu Ala Ala Ala Gly Ser Gln Asn Val Thr Ile Thr Val
65                  70                  75                  80

Ala Pro Gly Ala Leu Phe Ser Thr Asn Ala Thr Arg Ala Leu Ser Val
                85                  90                  95

Asp Asp Arg Ser Arg Ile Val Asn Glu Gly Thr Ile Gln Met Ala Gly
            100                 105                 110

Gly Ala Gly Ala Ser Arg Gly Ala Met Val Gly Phe Gly Asp Asn Asn
        115                 120                 125

Gln Leu Ile Asn Arg Gly Ser Ile Thr Thr Ser Gly Ser Gly Val Arg
    130                 135                 140

Gly Ile Ser Val Pro Asn Val Gly Ser Thr Gly Thr Leu Val Asp Asn
145                 150                 155                 160

Ser Gly Ser Ile Arg Thr Gln Gly Ala Ser Ala His Gly Ile Ala Ile
                165                 170                 175

Asn Gly Pro Gly Asn Arg Val Gln Asn Ser Gly Ala Ile Thr Val Asn
            180                 185                 190

Gly Thr Asp Ala Lys Gly Val Tyr Leu Gln Gly Gly Ser Pro Ala Ala
        195                 200                 205

Asn Val Leu Val Asn Gly Gly Thr Ile His Ala Arg Gly Ala Ser Ser
    210                 215                 220

Asn Gly Ile Phe Gly Pro Asp Gly Val His Val Asn Thr Thr Asn Ala
225                 230                 235                 240

Asn Gly Phe His Ala Arg Val Glu Asn Leu Pro Gly Gly Arg Ile Leu
                245                 250                 255

Ser Asp His Ser Tyr Ala Leu Arg Gly Gln Asn Gly Asn Asp Thr Phe
            260                 265                 270

Ile Asn Ala Gly Tyr Leu Gln Gly His Gly Gly Ala Gly Arg Asp Thr
        275                 280                 285

Ala Val Tyr Met Gly Pro Gln Gly Thr Gly Thr Leu Ile Leu Arg Thr
    290                 295                 300

Gly Ser Ala Ile Ala Gly Leu Ala Asp Gly Gly Gly Ala Ala Ser His
305                 310                 315                 320

Ala Tyr Leu Glu Gly Ser Gly Thr Val Asp Asn Arg Phe Ala Asn Phe
                325                 330                 335

Arg Thr Leu Thr Met Arg Gly Ala Asp Trp Arg Trp Thr Ser Asp Ala
            340                 345                 350

Ala Phe Thr Glu Ser Val Asp Leu Arg Thr Gly Thr Phe Phe Leu Ala
        355                 360                 365

Gly Thr Leu Ala Ser Pro Ala Asn Arg Leu Ala Ala Gly Ala Val Leu
    370                 375                 380

Ala Gly Thr Gly Thr Leu Ala Gly Ala Leu Arg Asn Ala Gly Glu Ile
385                 390                 395                 400

Arg Pro Gly Pro Asn Asp Gly Ser Gly Tyr Gly Ala Leu Thr Val Arg
                405                 410                 415

Gly Asp Tyr Thr Gly Ala Gly Gly Ala Leu Arg Val Asn Thr Val Leu
            420                 425                 430

Ala Gly Asp Gly Ala Ala Ser Asp Arg Leu Val Ile Asp Gly Gly His
        435                 440                 445

Ala Gly Gly Ser Thr Pro Val Thr Val Val Asn Arg Gly Gly Gln Gly
    450                 455                 460
```

```
Ala Leu Thr Ala Ala Asp Gly Ile Leu Val Val Gln Ala Ile Asn Gly
465                 470                 475                 480

Ala Ser Ser Asp Ala Gly Ala Phe Ser Leu Ala Ala Pro Leu Asn Ala
                485                 490                 495

Gly Ala Tyr Glu Tyr Arg Leu Tyr Arg Gly Gly Ala Thr Gly Ala Ala
            500                 505                 510

Pro Asp Ser Trp Tyr Leu Arg Ser Arg Ala Tyr Leu Val Glu Asp Gln
        515                 520                 525

Leu Ala Gly Ser Leu Ala Glu Ala Glu Ala Ile Ala Asp Asp Ile Gly
    530                 535                 540

Arg Arg Thr Gly Glu Arg Pro Ser Ile Glu Asp Thr Pro Leu Tyr Arg
545                 550                 555                 560

Pro Glu Val Ala Leu Tyr Ser Ser Ile Pro Met Leu Ala Arg Arg Met
                565                 570                 575

Gly Leu Ala Gln Leu Gly Thr Phe His Glu Arg Gln Gly Asn Gln Ala
            580                 585                 590

Leu Leu Ala Arg Asp Gly Glu Arg Val Ala Ala Trp Ala Arg Ala Tyr
        595                 600                 605

Gly Gly Asn Ser Lys Gln Ala Leu Asp Gly Asp Ala Gln Pro Gly Ile
    610                 615                 620

Asp Ala Arg Leu Ala Gly Val Gln Leu Gly Gln Asp Leu Tyr Ser Ser
625                 630                 635                 640

Val Arg Pro Asp Gly Gly Gln His Arg Phe Gly Leu Phe Gly Gly Tyr
                645                 650                 655

Gly Gln Ala Arg Gly Asp Thr His Gly Ser Ala Gly Gly Glu Arg Asp
            660                 665                 670

Ala Ala Thr Gly Arg Leu Thr Ile Asp Gly Tyr Ser Val Gly Gly Tyr
        675                 680                 685

Trp Thr Tyr Val Gly Pro Arg Gly Trp Tyr Val Asp Ala Val Leu Ala
    690                 695                 700

Asn Thr Trp Met Asp Ile Asp Thr Asp Ser Lys Ala Gly Arg Asp Ala
705                 710                 715                 720

Asp Thr Arg Gly Gln Ala Phe Thr Ala Ser Leu Glu Ser Gly Tyr Pro
                725                 730                 735

Leu Ala Leu Ser Glu Arg Trp Thr Leu Glu Pro Gln Ala Gln Leu Ile
            740                 745                 750

Tyr Gln His Thr Arg Val Asp Gly Phe Ser Asp Ala Val Ser Glu Val
        755                 760                 765

Arg Ile Arg Asp Asp Asn Ala Leu Thr Ala Arg Leu Gly Ala Arg Leu
    770                 775                 780

Gln Gly Glu Tyr Ala Ala Ala Ala Gln Val Trp Arg Pro Tyr Ala Ala
785                 790                 795                 800

Leu Asn Phe Trp Arg Thr Phe Ser Gly Glu Asn Thr Val Val Leu Gly
                805                 810                 815

Glu Asp Ser Ile Asp Thr Arg Arg Gly Ala Thr Ser Leu Glu Leu Ala
            820                 825                 830

Ala Gly Ala Ser Val Thr Leu Ala Arg Ser Leu Ala Leu Tyr Gly Arg
        835                 840                 845

Leu Ala Tyr Ala Thr Ser Ile Asp Ser Gln Tyr Leu Arg Gly Ala Ser
    850                 855                 860

Ala Gln Leu Gly Met Arg Tyr Thr Trp
865                 870
```

<210> SEQ ID NO 53
<211> LENGTH: 3120
<212> TYPE: DNA
<213> ORGANISM: Bordetella pertussis

<400> SEQUENCE: 53
atgcctgctc aacgcactcc tcgcaccgcg gtttgtgagg ccaccgtccg ttcatcgcca 60
cgttggatcc attgcaccgg attcgtgctg tgcgcgctgc tggcggcatg cggaggcggt 120
ggcggcggag gtggcggcgg aggcggtggc ggcagcccgg gcggccgtgc gccatcggcg 180
ccgcaacccg ccccttcgcc acgccccgaa cctgcacccg agccggcacc caatcctgcg 240
cccaggcctg ctccgcaacc gccggcgccc gcgcctggag cgccccgtcc tcccgcgccg 300
ccaccggagg ctcccccgcc cgtgatgccg ccgccggccg tgccgcctca gctgcccgaa 360
gtgccggccg cagacctgcc ccgcgtgcgc gcgccgctgt cgacataccg gcggccgcaa 420
cgcaccgact tcgtcacgcc caccggcggg ccgttcttcg ccaagcagga caaagccctc 480
aacaccatcg acctgaagat ggcgcacgac ctgaagctgc ggggctaccg cgtcaaagtc 540
gcggtcgtcg acgaaggcgt gcgcagcgac catccgctcc tgaacgtcga gaagaaatac 600
ggtggcgatt acatggccga cggcacccgc acctaccccg accccaagcg ccagggcagg 660
cacggaacct cggtcgccct ggtactggcc ggacaggaca ccgacacgta tcgcggcggc 720
gttgcgccca atgccgacct ctattcggcc aacatcggca cgcgggccgg ccacgtctcc 780
gacgaagccg cattccacgc ctggaacgac ctgctcgggc acggcatcaa gatcttcaac 840
aacagtttcg ccaccgaagg tccggaaggc gagcagcgcg tcaaggagga ccgcaacgaa 900
taccatagcg ccgccaacaa gcagaacacc tacatcggac ggctcgatcg cctggtgcgc 960
gacggcgcgc tcctcatttt cgccgccggc aacggcaggc catcgggtcg cgcctacagt 1020
gaggtcggct cggtcggacg cacccctcgc gtcgagccgc acctgcaacg cggcctgatc 1080
gtggtcaccg cggtggacga aaacggcagg ctcgaaacat gggccaaccg ctgcgggcaa 1140
gcgcagcaat ggtgcctggc cgcgcccagc accgcctacc tgcccggcct cgacaaggac 1200
aaccccgaca gcatccacgt cgaacagggc acgtcgctat ccgcgccgct ggtcaccggc 1260
gccgccgtac tggtgcagga tcgctttcgc tggatggaca acgacaacct gcgcaccacc 1320
ttgctgacca cggcgcagga caagggcccg tacggcgtcg acccgcagta cggctggggc 1380
gtgctcgacg tgggccgcgc cgtgcagggc ccggcgcagt tcgccttcgg cgacttcgtc 1440
gcccgggtta cggatacctc cacgttcggc aacgacatct ccggcgccgg cgggctggtc 1500
gtcgacggcc ccggcgcgct ggtcctggcc ggctccaata cctatgccgg ccgcaccacc 1560
atcaagcgcg gcaccctcga cgtctttggc agcgtcacgt ccgccgtcac cgtcgagcct 1620
ggcggcacgc tgaccggcat cggcaccgtc ggcacggtga ccaaccaggg cacggtggtc 1680
aacaaggagg ccggcctgca cgtcaaggga gattactcac agaccgcgca gggcctgctg 1740
gtcaccgaca tcggctcgct gctcgacgta tccggcaggg ccagcctggc cggccggctg 1800
catgtggacg acatccgccc cggctacgtc ggcggcgacg ggaaaagcgt cccggtcatc 1860
aaggccggcg cggtgtccgg cgtcttcgcc acgctgacgc gcagtccggg cctgctgctc 1920
aacgcccggc tggactaccg gccccaggcc gtctacctga ccatgcggcg cgccgagcgc 1980
gtccatgccg cggcgcagcg gggcgcggac gacgggcgtc gcgcgtcggt gctggccgtg 2040
gccgagcggc tcgacgccgc gatgcgcgaa ctcgatgccc tgcccgagtc gcagcgcgac 2100
gccgcggcgc cggcggccgc catcggacgc atccagcgcg tgcaaagccg caaggtgctg 2160
caggacaacc tgtattcgct ggccggcgcc acctacgcca acgccgccgc ggtcaacacg 2220

```
ctggagcaga accgctggat ggaccgcctc gagaaccacc tggcccaggc cggcggcgag   2280

cgcgtggcgg ccatcgccga gtatcgccac ggccagttgc gctggcgccc cgatggcctg   2340

caaggccgcc agcgcggcaa cggcatcatg ctgggcctgg cgcgcgaagt ctcggccggc   2400

ctgagcctgg ccgcggcgct gacccacagc cgcacgcact gggacgagtc gtccggcgcg   2460

ccggcccgcg acaacgccgc catgaccacg ccgggcgtac tgctgggcgc gcgccgcgcc   2520

tgggaggacg gctggttcgt gcagggcgca ctgggctata gccgctaccg caaccaggcc   2580

acgcgccaca tctcgctcgg cgatgccggc cacaccgtcg gcgccaccgc ccggggccac   2640

gtctggcagg ccgacgccgg cctgggacgc cagtggacgc tcgcccccgg acacacgctg   2700

gcgcctcggg cgggcctgca actcacgcat ctgcgccagc aaggtttcag cgagagcggc   2760

gcgcaaggac tggggctgcg cgcccacgcc ttgacgcgca ccgtgcccac gctgtgggcg   2820

caactgcaaa gccgccatgc cttcatgctg ggagccacgc ccatgacggc gcagctgcaa   2880

ctgggcgtct ggcatgacct gcgcgcgcgg cgctacgccg cctccggcgg tttcgccggc   2940

ctggcgcagg accagggcgc cagcggctac tggcccgtgc cgcgcacacg cgtacagggc   3000

gcgctcggcc tgcgcgccga gttcgcgcca ggcctcgtgc tggggctggg ctacacgggc   3060

cagcttgcca cgcactgggt cgatcaccag ctcagcgcca gcctcactta ccgctactga   3120
```

<210> SEQ ID NO 54
<211> LENGTH: 1039
<212> TYPE: PRT
<213> ORGANISM: Bordetella pertussis

<400> SEQUENCE: 54

```
Met Pro Ala Gln Arg Thr Pro Arg Thr Ala Val Cys Glu Ala Thr Val
 1               5                  10                  15

Arg Ser Ser Pro Arg Trp Ile His Cys Thr Gly Phe Val Leu Cys Ala
            20                  25                  30

Leu Leu Ala Ala Cys Gly Gly Gly Gly Gly Gly Gly Gly Gly Gly Gly
        35                  40                  45

Gly Gly Gly Ser Pro Gly Gly Arg Ala Pro Ser Ala Pro Gln Pro Ala
    50                  55                  60

Pro Ser Pro Arg Pro Glu Pro Ala Pro Glu Pro Ala Pro Asn Pro Ala
65                  70                  75                  80

Pro Arg Pro Ala Pro Gln Pro Pro Ala Pro Ala Pro Gly Ala Pro Arg
                85                  90                  95

Pro Pro Ala Pro Pro Pro Glu Ala Pro Pro Pro Val Met Pro Pro Pro
            100                 105                 110

Ala Val Pro Pro Gln Leu Pro Glu Val Pro Ala Ala Asp Leu Pro Arg
        115                 120                 125

Val Arg Ala Pro Leu Ser Thr Tyr Arg Arg Pro Gln Arg Thr Asp Phe
    130                 135                 140

Val Thr Pro Thr Gly Gly Pro Phe Phe Ala Lys Gln Asp Lys Ala Leu
145                 150                 155                 160

Asn Thr Ile Asp Leu Lys Met Ala His Asp Leu Lys Leu Arg Gly Tyr
                165                 170                 175

Arg Val Lys Val Ala Val Val Asp Glu Gly Val Arg Ser Asp His Pro
            180                 185                 190

Leu Leu Asn Val Glu Lys Lys Tyr Gly Gly Asp Tyr Met Ala Asp Gly
        195                 200                 205

Thr Arg Thr Tyr Pro Asp Pro Lys Arg Gln Gly Arg His Gly Thr Ser
    210                 215                 220
```

```
Val Ala Leu Val Leu Ala Gly Gln Asp Thr Asp Thr Tyr Arg Gly Gly
225                 230                 235                 240

Val Ala Pro Asn Ala Asp Leu Tyr Ser Ala Asn Ile Gly Thr Arg Ala
                245                 250                 255

Gly His Val Ser Asp Glu Ala Ala Phe His Ala Trp Asn Asp Leu Leu
            260                 265                 270

Gly His Gly Ile Lys Ile Phe Asn Asn Ser Phe Ala Thr Glu Gly Pro
        275                 280                 285

Glu Gly Glu Gln Arg Val Lys Glu Asp Arg Asn Glu Tyr His Ser Ala
    290                 295                 300

Ala Asn Lys Gln Asn Thr Tyr Ile Gly Arg Leu Asp Arg Leu Val Arg
305                 310                 315                 320

Asp Gly Ala Leu Leu Ile Phe Ala Ala Gly Asn Gly Arg Pro Ser Gly
                325                 330                 335

Arg Ala Tyr Ser Glu Val Gly Ser Val Gly Arg Thr Pro Arg Val Glu
            340                 345                 350

Pro His Leu Gln Arg Gly Leu Ile Val Val Thr Ala Val Asp Glu Asn
        355                 360                 365

Gly Arg Leu Glu Thr Trp Ala Asn Arg Cys Gly Gln Ala Gln Gln Trp
    370                 375                 380

Cys Leu Ala Ala Pro Ser Thr Ala Tyr Leu Pro Gly Leu Asp Lys Asp
385                 390                 395                 400

Asn Pro Asp Ser Ile His Val Glu Gln Gly Thr Ser Leu Ser Ala Pro
                405                 410                 415

Leu Val Thr Gly Ala Ala Val Leu Val Gln Asp Arg Phe Arg Trp Met
            420                 425                 430

Asp Asn Asp Asn Leu Arg Thr Thr Leu Leu Thr Thr Ala Gln Asp Lys
        435                 440                 445

Gly Pro Tyr Gly Val Asp Pro Gln Tyr Gly Trp Gly Val Leu Asp Val
    450                 455                 460

Gly Arg Ala Val Gln Gly Pro Ala Gln Phe Ala Phe Gly Asp Phe Val
465                 470                 475                 480

Ala Arg Val Thr Asp Thr Ser Thr Phe Gly Asn Asp Ile Ser Gly Ala
                485                 490                 495

Gly Gly Leu Val Val Asp Gly Pro Gly Ala Leu Val Leu Ala Gly Ser
            500                 505                 510

Asn Thr Tyr Ala Gly Arg Thr Thr Ile Lys Arg Gly Thr Leu Asp Val
        515                 520                 525

Phe Gly Ser Val Thr Ser Ala Val Thr Val Glu Pro Gly Gly Thr Leu
    530                 535                 540

Thr Gly Ile Gly Thr Val Gly Thr Val Thr Asn Gln Gly Thr Val Val
545                 550                 555                 560

Asn Lys Glu Ala Gly Leu His Val Lys Gly Asp Tyr Ser Gln Thr Ala
                565                 570                 575

Gln Gly Leu Leu Val Thr Asp Ile Gly Ser Leu Leu Asp Val Ser Gly
            580                 585                 590

Arg Ala Ser Leu Ala Gly Arg Leu His Val Asp Asp Ile Arg Pro Gly
        595                 600                 605

Tyr Val Gly Gly Asp Gly Lys Ser Val Pro Val Ile Lys Ala Gly Ala
    610                 615                 620

Val Ser Gly Val Phe Ala Thr Leu Thr Arg Ser Pro Gly Leu Leu Leu
625                 630                 635                 640

Asn Ala Arg Leu Asp Tyr Arg Pro Gln Ala Val Tyr Leu Thr Met Arg
```

```
                645                 650                 655

Arg Ala Glu Arg Val His Ala Ala Ala Gln Arg Gly Ala Asp Asp Gly
            660                 665                 670

Arg Arg Ala Ser Val Leu Ala Val Ala Glu Arg Leu Asp Ala Ala Met
        675                 680                 685

Arg Glu Leu Asp Ala Leu Pro Glu Ser Gln Arg Asp Ala Ala Ala Pro
    690                 695                 700

Ala Ala Ala Ile Gly Arg Ile Gln Arg Val Gln Ser Arg Lys Val Leu
705                 710                 715                 720

Gln Asp Asn Leu Tyr Ser Leu Ala Gly Ala Thr Tyr Ala Asn Ala Ala
                725                 730                 735

Ala Val Asn Thr Leu Glu Gln Asn Arg Trp Met Asp Arg Leu Glu Asn
            740                 745                 750

His Leu Ala Gln Ala Gly Gly Glu Arg Val Ala Ala Ile Ala Glu Tyr
        755                 760                 765

Arg His Gly Gln Leu Arg Trp Arg Pro Asp Gly Leu Gln Gly Arg Gln
    770                 775                 780

Arg Gly Asn Gly Ile Met Leu Gly Leu Ala Arg Glu Val Ser Ala Gly
785                 790                 795                 800

Leu Ser Leu Ala Ala Ala Leu Thr His Ser Arg Thr His Trp Asp Glu
                805                 810                 815

Ser Ser Gly Ala Pro Ala Arg Asp Asn Ala Ala Met Thr Thr Pro Gly
            820                 825                 830

Val Leu Leu Gly Ala Arg Arg Ala Trp Glu Asp Gly Trp Phe Val Gln
        835                 840                 845

Gly Ala Leu Gly Tyr Ser Arg Tyr Arg Asn Gln Ala Thr Arg His Ile
    850                 855                 860

Ser Leu Gly Asp Ala Gly His Thr Val Gly Ala Thr Ala Arg Gly His
865                 870                 875                 880

Val Trp Gln Ala Asp Ala Gly Leu Gly Arg Gln Trp Thr Leu Ala Pro
                885                 890                 895

Gly His Thr Leu Ala Pro Arg Ala Gly Leu Gln Leu Thr His Leu Arg
            900                 905                 910

Gln Gln Gly Phe Ser Glu Ser Gly Ala Gln Gly Leu Gly Leu Arg Ala
        915                 920                 925

His Ala Leu Thr Arg Thr Val Pro Thr Leu Trp Ala Gln Leu Gln Ser
    930                 935                 940

Arg His Ala Phe Met Leu Gly Ala Thr Pro Met Thr Ala Gln Leu Gln
945                 950                 955                 960

Leu Gly Val Trp His Asp Leu Arg Ala Arg Arg Tyr Ala Ala Ser Gly
                965                 970                 975

Gly Phe Ala Gly Leu Ala Gln Asp Gln Gly Ala Ser Gly Tyr Trp Pro
            980                 985                 990

Val Pro Arg Thr Arg Val Gln Gly Ala Leu Gly Leu Arg Ala Glu Phe
        995                 1000                1005

Ala Pro Gly Leu Val Leu Gly Leu Gly Tyr Thr Gly Gln Leu Ala Thr
    1010                1015                1020

His Trp Val Asp His Gln Leu Ser Ala Ser Leu Thr Tyr Arg Tyr
1025                1030                1035
```

<210> SEQ ID NO 55
<211> LENGTH: 2244
<212> TYPE: DNA
<213> ORGANISM: Bordetella pertussis -continued

<400> SEQUENCE: 55

```
atgtcgtccc cgcgtccccc cgcaccttgg cgcgcaccgc tcgcgcttgc cggcctgtcg      60
cttggttgcg ctgccggcgc atacggcgcg cccgcgccgg cacaaaccgt cgtcaccctg     120
cccgcgcaag aggtcatcgg cgacagcgtc gcggcggccc ggtccgtgct gcgcctgccg     180
gagatcgagc gcgcgcaggc cgacaacttc gcctccctgg tcgatcagct gccgggcatc     240
tcgatggccg gctctccgcg ccccggcggg caaagcctga acatctgggg catgggcgat     300
accgaggacg tgaaaatcgt cctcgatggc gcgcccaagg gtttcgagaa gtaccgccag     360
ggctcggtct tcatcgaacc cgaactgatc cggcgcatcg aggtcgacaa ggggccgcac     420
aacctggtcg acggcaatgg cgggttcggc ggcaccgtca agatcgatac caaggatgcg     480
gccgacctgt tgccgccggg cgcgcgcttc ggcgcgctgg ccaagtacgg ccgccattcg     540
aacgacggcc aggacatcta cagcgtggcg ctgtacggcc gcacccgcgc cgacggggcc     600
gacggcctgc tgtatgccaa ccgccgcgac ggcggcgatc tgcgccgccc cgacggcacc     660
cgcttcgcat actcgcgcaa caaccagcgc tcgctgctcg ccaaggtcaa cctctatccg     720
gacgacgccc agaccatcac cctgtcggcc atgcgttcga atgcggcggg ttggcaaccc     780
ttcgcggcca agcgcgacga tcttcccgcg ccttcgcagg ccgatatcga ccgctacggc     840
ctgaccgaag catggcggcg caagctggtc catcgcgacc agctcgacca gaactacagc     900
gcgaaatgga acatcgcccc atccgcccat ccctgggtga acctcacgct ggcctatgcc     960
cgctcggaca cccggcagcg cgaccggcgc tcgtcccggg cgtcgcagtc ggcctttctc    1020
ggcacgctgg gcaacaagag ttgggtcgac taccgcgacg accggttcga cctcagcaac    1080
gaaagccacg tggccctggg cacggccgag catgtcctgc tggcgggcct gcgctggcac    1140
cggcatcgcc gcgacacgct catgtactac ccgcccggcc gcggcgagcc cgattacaac    1200
cacgggtact tccagccgca ctacatgcct tcgggcacgc agaccgtgcg cagcctgtac    1260
ctgcaggacg ccgtcaccgt cggcggcctt accgtcacgc ccggcgtgcg gtacgaccat    1320
gtcgccaata ccggcaggcc aaacgacgcg ccccgctaca acaaccccgc ccccgtggcc    1380
gggcatgact accgccgcgt ctcgtacgcg ggctggaccc cgcacctggg cgtggtctgg    1440
aaggcggcgc gaggcgtggc gctgttcgcc gacgccggcc gcacctggcg cgcacccgtc    1500
atcgacgaac agtacgaagt gcaatatgcg aagtccaatg tgtcgggcag cagccgggcg    1560
ctgcggcccg agcgcatcgt gggcctgcgc gccggcgccg tactggatta caacgatatc    1620
gcgacgcgcg gcgacagcgt gcagatacgg accacgctgt ttcgcaatcg cggcaagcac    1680
gagatcttcc agcgccgtgg cgtggcatgc cgcgggcagg ccgagggcgg cgccgcctcg    1740
gactgcccca agcccttgtc caactaccgc aacctgcccg gctacaccat cgaagggctg    1800
gaactggaga cctactacga cagcccggcg atgttcgcca gcctgtcgct ttcggccatg    1860
cgcgggcacc gcgacgcctc gccgcgcgat ccatgggggc cgcgcacctg gatcgccgag    1920
atcccgccgg tctcggcgcg cgcgatgctg ggcgtgaaac tgccgcgcct ggacatggtc    1980
ctgggatggc gcggcgaatt cgtgcgccgc caggaccgct cgccgaccga cggcgacccg    2040
ctggccggct actgggcctt gcccaagacc gccggctacg cgctgcacgg cctgttcgca    2100
agctggcaac cccggcatgt caaaggcctg gacgtgcgcc tggccgccga caacctcttc    2160
aaccggccct atcatcccta cctgggcgaa gcggtatcgg gcacgggccg caacatcaag    2220
ctgagcatcg cccagcgctt ctag                                           2244
```

<210> SEQ ID NO 56

<211> LENGTH: 747
<212> TYPE: PRT
<213> ORGANISM: Bordetella pertussis

<400> SEQUENCE: 56

```
Met Ser Ser Pro Arg Pro Pro Ala Pro Trp Arg Ala Pro Leu Ala Leu
 1               5                  10                  15

Ala Gly Leu Ser Leu Gly Cys Ala Ala Gly Ala Tyr Gly Ala Pro Ala
            20                  25                  30

Pro Ala Gln Thr Val Val Thr Leu Pro Ala Gln Glu Val Ile Gly Asp
        35                  40                  45

Ser Val Ala Ala Ala Arg Ser Val Leu Arg Leu Pro Glu Ile Glu Arg
    50                  55                  60

Ala Gln Ala Asp Asn Phe Ala Ser Leu Val Asp Gln Leu Pro Gly Ile
65                  70                  75                  80

Ser Met Ala Gly Ser Pro Arg Pro Gly Gly Gln Ser Leu Asn Ile Trp
                85                  90                  95

Gly Met Gly Asp Thr Glu Asp Val Lys Ile Val Leu Asp Gly Ala Pro
            100                 105                 110

Lys Gly Phe Glu Lys Tyr Arg Gln Gly Ser Val Phe Ile Glu Pro Glu
        115                 120                 125

Leu Ile Arg Arg Ile Glu Val Asp Lys Gly Pro His Asn Leu Val Asp
    130                 135                 140

Gly Asn Gly Gly Phe Gly Gly Thr Val Lys Ile Asp Thr Lys Asp Ala
145                 150                 155                 160

Ala Asp Leu Leu Pro Pro Gly Ala Arg Phe Gly Ala Leu Ala Lys Tyr
                165                 170                 175

Gly Arg His Ser Asn Asp Gly Gln Asp Ile Tyr Ser Val Ala Leu Tyr
            180                 185                 190

Gly Arg Thr Arg Ala Asp Gly Ala Asp Gly Leu Leu Tyr Ala Asn Arg
        195                 200                 205

Arg Asp Gly Gly Asp Leu Arg Arg Pro Asp Gly Thr Arg Phe Ala Tyr
    210                 215                 220

Ser Arg Asn Asn Gln Arg Ser Leu Leu Ala Lys Val Asn Leu Tyr Pro
225                 230                 235                 240

Asp Asp Ala Gln Thr Ile Thr Leu Ser Ala Met Arg Ser Asn Ala Ala
                245                 250                 255

Gly Trp Gln Pro Phe Ala Ala Lys Arg Asp Asp Leu Pro Ala Pro Ser
            260                 265                 270

Gln Ala Asp Ile Asp Arg Tyr Gly Leu Thr Glu Ala Trp Arg Arg Lys
        275                 280                 285

Leu Val His Arg Asp Gln Leu Asp Gln Asn Tyr Ser Ala Lys Trp Asn
    290                 295                 300

Ile Ala Pro Ser Ala His Pro Trp Val Asn Leu Thr Leu Ala Tyr Ala
305                 310                 315                 320

Arg Ser Asp Thr Arg Gln Arg Asp Arg Arg Ser Ser Arg Ala Ser Gln
                325                 330                 335

Ser Ala Phe Leu Gly Thr Leu Gly Asn Lys Ser Trp Val Asp Tyr Arg
            340                 345                 350

Asp Asp Arg Phe Asp Leu Ser Asn Glu Ser His Val Ala Leu Gly Thr
        355                 360                 365

Ala Glu His Val Leu Leu Ala Gly Leu Arg Trp His Arg His Arg Arg
    370                 375                 380

Asp Thr Leu Met Tyr Tyr Pro Pro Gly Arg Gly Glu Pro Asp Tyr Asn
385                 390                 395                 400
```

```
His Gly Tyr Phe Gln Pro His Tyr Met Pro Ser Gly Thr Gln Thr Val
                405                 410                 415

Arg Ser Leu Tyr Leu Gln Asp Ala Val Thr Val Gly Gly Leu Thr Val
            420                 425                 430

Thr Pro Gly Val Arg Tyr Asp His Val Ala Asn Thr Gly Arg Pro Asn
        435                 440                 445

Asp Ala Pro Arg Tyr Asn Asn Pro Ala Pro Val Ala Gly His Asp Tyr
    450                 455                 460

Arg Arg Val Ser Tyr Ala Gly Trp Thr Pro His Leu Gly Val Val Trp
465                 470                 475                 480

Lys Ala Ala Arg Gly Val Ala Leu Phe Ala Asp Ala Gly Arg Thr Trp
                485                 490                 495

Arg Ala Pro Val Ile Asp Glu Gln Tyr Glu Val Gln Tyr Ala Lys Ser
            500                 505                 510

Asn Val Ser Gly Ser Ser Arg Ala Leu Arg Pro Glu Arg Ile Val Gly
        515                 520                 525

Leu Arg Ala Gly Ala Val Leu Asp Tyr Asn Asp Ile Ala Thr Arg Gly
    530                 535                 540

Asp Ser Val Gln Ile Arg Thr Thr Leu Phe Arg Asn Arg Gly Lys His
545                 550                 555                 560

Glu Ile Phe Gln Arg Arg Gly Val Ala Cys Arg Gly Gln Ala Glu Gly
                565                 570                 575

Gly Ala Ala Ser Asp Cys Pro Lys Pro Leu Ser Asn Tyr Arg Asn Leu
            580                 585                 590

Pro Gly Tyr Thr Ile Glu Gly Leu Glu Leu Glu Thr Tyr Tyr Asp Ser
        595                 600                 605

Pro Ala Met Phe Ala Ser Leu Ser Leu Ser Ala Met Arg Gly His Arg
    610                 615                 620

Asp Ala Ser Pro Arg Asp Pro Trp Gly Pro Arg Thr Trp Ile Ala Glu
625                 630                 635                 640

Ile Pro Pro Val Ser Ala Arg Ala Met Leu Gly Val Lys Leu Pro Arg
                645                 650                 655

Leu Asp Met Val Leu Gly Trp Arg Gly Glu Phe Val Arg Arg Gln Asp
            660                 665                 670

Arg Ser Pro Thr Asp Gly Asp Pro Leu Ala Gly Tyr Trp Ala Leu Pro
        675                 680                 685

Lys Thr Ala Gly Tyr Ala Leu His Gly Leu Phe Ala Ser Trp Gln Pro
    690                 695                 700

Arg His Val Lys Gly Leu Asp Val Arg Leu Ala Ala Asp Asn Leu Phe
705                 710                 715                 720

Asn Arg Pro Tyr His Pro Tyr Leu Gly Glu Ala Val Ser Gly Thr Gly
                725                 730                 735

Arg Asn Ile Lys Leu Ser Ile Ala Gln Arg Phe
            740                 745
```

<210> SEQ ID NO 57
<211> LENGTH: 1578
<212> TYPE: DNA
<213> ORGANISM: Bordetella pertussis

<400> SEQUENCE: 57

```
atgaaggcgc ggcgcctggc catggcgggt ctgtcgctgg cgctcggcgg ctgctcgctg      60

tcgcagcaga tgcaggccat gcgcgacgcc gcgacgtccc tgcgcgcacg cctgctcgaa     120

gggcagcagg ccgtgggccg ggccggcgag cggccggcgc gcgaagccgc ccaggacgtc     180
```

gcgcggccct ggctggccgg gcgcgcccag ccgctggcac gcgaggtgct gctgccgccg 240
gcgctgcgcg ccgatgtcga tacgaccctg ctgttcgcgg gcaaggccac gctgcccgtg 300
ctggccgagc gcctgcatcg cgccaccggc atcgccgtgc gcgtgcatcc cgacgcgctg 360
ctgccgcgcg ccgccttcct gccgcgcctg gcggggcagg ccgagctggc ggccgagcct 420
cccgcccagg ccgaactgcg ggccgggccg cgtccgctgg ccgacacgct cgacgcgctg 480
gccgcgcagc tgtacgtgca ctggcgctac catcgcggcg ccatcgagtt ctaccgcacc 540
gaaacgcggg tcttcgatgt gcgcacgctg gcgctggccg ccagcgcgca ggctcggctg 600
ggccgcgccg gcagcggcga gacgggcagt ttcgaccatg cctcgagcac ggtgctcagc 660
gccgacgccg gcaaggcgct gcaggccgtg cgggaccgcg tcgccgcttt cctgacgcgc 720
gccggcgtca tcgccgagat cgaggcgggc ggaagcacgc tcgcggtcac ggatacgccg 780
gaggcgctcg cgcgcatcga aaaatacctg caaggcgaga accgcgccct gacgcgccgg 840
gtacgcctgg tgttcgaaga gctcacggtg cgcaccacgg ccgccgccga aggcggcatc 900
gattggcagg cggtctacgc cagcgcgcgc gccgcggcgt cgtacgccat gcccggcggg 960
gccggcgcgg caggcgcgct cggggcccgc gtgctggccg ggccctggcg cgacgcgcgc 1020
gccctgatcg ccgcgctgag caccatggga gcggtactgc gccatcgcag catacccatg 1080
ctgacgctga accggcgcgc cgtcacccac gccgtgcgca ccacgttttc ctacgtggac 1140
caggtgcagc gcctgagccc gaccgcggcg gcgcccggtg ggcgcgatgc cgtgcccggg 1200
ctggcggtgc agcagaagcg cgagacggtg ggcacgttcc tcacgctgtt gcccgaggcg 1260
cgcgatgacg gccgcatcct gctctccatt tcctatgaca acaccattgc ccagccgctg 1320
cgcaccctga ccttcggcga gggcggccag caagtgtcgc tgcagcagat cgccatcgac 1380
ggcagcggca tcgtgcagca ggtcgagctg ctgcccggcc agcccgtcat cctgtcgggc 1440
ttcgaccaca gcgaagacca atacgaacgc caccgcctgt ttcccgatgc gccgctcgcg 1500
gccggcgggc acgaccgcac ggcgcgcgag cgggtcacga ccgtggtcat ggtcaccgcg 1560
cagatcgacg agggttga 1578

<210> SEQ ID NO 58
<211> LENGTH: 525
<212> TYPE: PRT
<213> ORGANISM: Bordetella pertussis

<400> SEQUENCE: 58

Met Lys Ala Arg Arg Leu Ala Met Ala Gly Leu Ser Leu Ala Leu Gly
1 5 10 15

Gly Cys Ser Leu Ser Gln Gln Met Gln Ala Met Arg Asp Ala Ala Thr
20 25 30

Ser Leu Arg Ala Arg Leu Leu Glu Gly Gln Gln Ala Val Gly Arg Ala
35 40 45

Gly Glu Arg Pro Ala Arg Glu Ala Ala Gln Asp Val Ala Arg Pro Trp
50 55 60

Leu Ala Gly Arg Ala Gln Pro Leu Ala Arg Glu Val Leu Leu Pro Pro
65 70 75 80

Ala Leu Arg Ala Asp Val Asp Thr Thr Leu Leu Phe Ala Gly Lys Ala
85 90 95

Thr Leu Pro Val Leu Ala Glu Arg Leu His Arg Ala Thr Gly Ile Ala
100 105 110

Val Arg Val His Pro Asp Ala Leu Leu Pro Arg Ala Ala Phe Leu Pro
115 120 125

```
Arg Leu Ala Gly Gln Ala Glu Leu Ala Ala Glu Pro Pro Ala Gln Ala
    130                 135                 140

Glu Leu Arg Ala Gly Pro Arg Pro Leu Ala Asp Thr Leu Asp Ala Leu
145                 150                 155                 160

Ala Ala Gln Leu Tyr Val His Trp Arg Tyr His Arg Gly Ala Ile Glu
                165                 170                 175

Phe Tyr Arg Thr Glu Thr Arg Val Phe Asp Val Arg Thr Leu Ala Leu
            180                 185                 190

Ala Ala Ser Ala Gln Ala Arg Leu Gly Arg Ala Gly Ser Gly Glu Thr
        195                 200                 205

Gly Ser Phe Asp His Ala Ser Ser Thr Val Leu Ser Ala Asp Ala Gly
    210                 215                 220

Lys Ala Leu Gln Ala Val Arg Asp Arg Val Ala Ala Phe Leu Thr Arg
225                 230                 235                 240

Ala Gly Val Ile Ala Glu Ile Glu Ala Gly Gly Ser Thr Leu Ala Val
                245                 250                 255

Thr Asp Thr Pro Glu Ala Leu Ala Arg Ile Glu Lys Tyr Leu Gln Gly
            260                 265                 270

Glu Asn Arg Ala Leu Thr Arg Arg Val Arg Leu Val Phe Glu Glu Leu
        275                 280                 285

Thr Val Arg Thr Thr Ala Ala Ala Glu Gly Gly Ile Asp Trp Gln Ala
    290                 295                 300

Val Tyr Ala Ser Ala Arg Ala Ala Ala Ser Tyr Ala Met Pro Gly Gly
305                 310                 315                 320

Ala Gly Ala Ala Gly Ala Leu Gly Ala Arg Val Leu Ala Gly Pro Trp
                325                 330                 335

Arg Asp Ala Arg Ala Leu Ile Ala Ala Leu Ser Thr Met Gly Ala Val
            340                 345                 350

Leu Arg His Arg Ser Ile Pro Met Leu Thr Leu Asn Arg Arg Ala Val
        355                 360                 365

Thr His Ala Val Arg Thr Thr Phe Ser Tyr Val Asp Gln Val Gln Arg
    370                 375                 380

Leu Ser Pro Thr Ala Ala Ala Pro Gly Gly Arg Asp Ala Val Pro Gly
385                 390                 395                 400

Leu Ala Val Gln Gln Lys Arg Glu Thr Val Gly Thr Phe Leu Thr Leu
                405                 410                 415

Leu Pro Glu Ala Arg Asp Asp Gly Arg Ile Leu Leu Ser Ile Ser Tyr
            420                 425                 430

Asp Asn Thr Ile Ala Gln Pro Leu Arg Thr Leu Thr Phe Gly Glu Gly
        435                 440                 445

Gly Gln Gln Val Ser Leu Gln Gln Ile Ala Ile Asp Gly Ser Gly Ile
    450                 455                 460

Val Gln Gln Val Glu Leu Leu Pro Gly Gln Pro Val Ile Leu Ser Gly
465                 470                 475                 480

Phe Asp His Ser Glu Asp Gln Tyr Glu Arg His Arg Leu Phe Pro Asp
                485                 490                 495

Ala Pro Leu Ala Ala Gly Gly His Asp Arg Thr Ala Arg Glu Arg Val
            500                 505                 510

Thr Thr Val Val Met Val Thr Ala Gln Ile Asp Glu Gly
        515                 520                 525
```

<210> SEQ ID NO 59
<211> LENGTH: 1512
<212> TYPE: DNA

<213> ORGANISM: Bordetella pertussis

<400> SEQUENCE: 59

```
gtgaccatgt tcatccgctg gctcattctc tccgcctgcc tgctgctggc cgcctgcagc      60
cgcgctcccg ataccgagat cctgcagcgc gatgtcggcc agaccctggc cgccacgtac     120
ggcccggacc tgttcgacat cgtcgcgctg cgccgcatgg gctcggccac cgacagcacg     180
gccccgccgg gccagacgcg ccgggtggtc tattacgatg tggtgctggg cctgaagaag     240
gacctcaccc tgggcgcctg ggaccagccc ggcgccgccg cgctggtcag cctgctgggc     300
gccgggccgc gcagcatctc gggggtgaaa tccagcggca atgccgccgg cgaccagatc     360
gtcgcccacg ccagcgccat ctaccagcgc gacgcagagc aatgggtgca cgtcgccccg     420
gccagcttca cggccaccga agcgccctcg ctggacaccg gcgcgccgcc gccggtgacg     480
cgccagctgc tccagacgct ggagcagatc acgcgttccg tgccctacag cgcctccagc     540
accgcccagc acgtggtgca acaggagctg gagcgctcgg tggcgcgcat caatggccgg     600
cttgcccgcc tgcaaaaggg ctacccgctg gcgaccggcc ccgacaaggg cgagtacctg     660
gcgttcggcc aggcgctggc cgcgatcggg cgcaacgagc aggtgcgcgt cattcccctc     720
attaccggcg gcagcgcgga caacatggcc atgctgcgca gcggcgcggc ggtggccgcc     780
ctgtcgcagg ccgacatcgc gcaactggcc tacgagggca aggggccgtt cgaaagccag     840
ggaccgttct ccgggttgcg cgcgctgggc agcctgtatc cggagctggt gcacatcgtg     900
gtgcgccagg gcgatggcat cgccacggtg ggcgcgctgc gcggcaagaa gattgccctg     960
ggcccgtcgg gctcggcggt acgcaccacg ctggagaccg tgctggcagc ccatgggctg    1020
cagccggggc gcgactatgc agtcatcgac acgccggccg ccgcggccct gccgcagctg    1080
agcgaaggac gggtcgacgc ggtggcgcag gtcatcggta cgccggccgc gcccttgcgc    1140
gcggcgctga cccaggcgcg cctggcgctg ctgccgctgg accgggctgc gatcgacaag    1200
ctggtgcagg ccgatccgac cctgatggcg ctggacatcc cggccaacac ctaccccagc    1260
caggccgcgg ccatccccac ggtgggcatg gcggcgctgc tggtcaccac ggccgatctg    1320
acgcgcgacg aggccgcgca tatggtggac gtggtatacc gggccgggca ggacctgctg    1380
gccgccgggt ccgcgcaggg cgcgcaggta tccgcggcca acgccgggcg cggattgagc    1440
attcccctgc acgacggcgc cgtggaagcc ttcgagaaac tgggcgcgcc gcccctgccc    1500
gagggcaggt ag                                                        1512
```

<210> SEQ ID NO 60
<211> LENGTH: 503
<212> TYPE: PRT
<213> ORGANISM: Bordetella pertussis

<400> SEQUENCE: 60

```
Val Thr Met Phe Ile Arg Trp Leu Ile Leu Ser Ala Cys Leu Leu Leu
 1               5                  10                  15

Ala Ala Cys Ser Arg Ala Pro Asp Thr Glu Ile Leu Gln Arg Asp Val
            20                  25                  30

Gly Gln Thr Leu Ala Ala Thr Tyr Gly Pro Asp Leu Phe Asp Ile Val
        35                  40                  45

Ala Leu Arg Arg Met Gly Ser Ala Thr Asp Ser Thr Ala Pro Pro Gly
    50                  55                  60

Gln Thr Arg Arg Val Val Tyr Tyr Asp Val Val Leu Gly Leu Lys Lys
65                  70                  75                  80

Asp Leu Thr Leu Gly Ala Trp Asp Gln Pro Gly Ala Ala Ala Leu Val
```

```
                85                  90                  95

Ser Leu Leu Gly Ala Gly Pro Arg Ser Ile Ser Gly Val Lys Ser Ser
            100                 105                 110

Gly Asn Ala Ala Gly Asp Gln Ile Val Ala His Ala Ser Ala Ile Tyr
        115                 120                 125

Gln Arg Asp Ala Glu Gln Trp Val His Val Ala Pro Ala Ser Phe Thr
    130                 135                 140

Ala Thr Glu Ala Pro Ser Leu Asp Thr Gly Ala Pro Pro Pro Val Thr
145                 150                 155                 160

Arg Gln Leu Leu Gln Thr Leu Glu Gln Ile Thr Arg Ser Val Pro Tyr
                165                 170                 175

Ser Ala Ser Ser Thr Ala Gln His Val Val Gln Gln Glu Leu Glu Arg
            180                 185                 190

Ser Val Ala Arg Ile Asn Gly Arg Leu Ala Arg Leu Gln Lys Gly Tyr
        195                 200                 205

Pro Leu Ala Thr Gly Pro Asp Lys Gly Glu Tyr Leu Ala Phe Gly Gln
    210                 215                 220

Ala Leu Ala Ala Ile Gly Arg Asn Glu Gln Val Arg Val Ile Pro Leu
225                 230                 235                 240

Ile Thr Gly Gly Ser Ala Asp Asn Met Ala Met Leu Arg Ser Gly Ala
                245                 250                 255

Ala Val Ala Ala Leu Ser Gln Ala Asp Ile Ala Gln Leu Ala Tyr Glu
            260                 265                 270

Gly Lys Gly Pro Phe Glu Ser Gln Gly Pro Phe Ser Gly Leu Arg Ala
        275                 280                 285

Leu Gly Ser Leu Tyr Pro Glu Leu Val His Ile Val Val Arg Gln Gly
    290                 295                 300

Asp Gly Ile Ala Thr Val Gly Ala Leu Arg Gly Lys Lys Ile Ala Leu
305                 310                 315                 320

Gly Pro Ser Gly Ser Ala Val Arg Thr Thr Leu Glu Thr Val Leu Ala
                325                 330                 335

Ala His Gly Leu Gln Pro Gly Arg Asp Tyr Ala Val Ile Asp Thr Pro
            340                 345                 350

Ala Ala Ala Ala Leu Pro Gln Leu Ser Glu Gly Arg Val Asp Ala Val
        355                 360                 365

Ala Gln Val Ile Gly Thr Pro Ala Ala Pro Leu Arg Ala Ala Leu Thr
    370                 375                 380

Gln Ala Arg Leu Ala Leu Leu Pro Leu Asp Arg Ala Ala Ile Asp Lys
385                 390                 395                 400

Leu Val Gln Ala Asp Pro Thr Leu Met Ala Leu Asp Ile Pro Ala Asn
                405                 410                 415

Thr Tyr Pro Ser Gln Ala Ala Ala Ile Pro Thr Val Gly Met Ala Ala
            420                 425                 430

Leu Leu Val Thr Thr Ala Asp Leu Thr Arg Asp Glu Ala Ala His Met
        435                 440                 445

Val Asp Val Val Tyr Arg Ala Gly Gln Asp Leu Leu Ala Ala Gly Ser
    450                 455                 460

Ala Gln Gly Ala Gln Val Ser Ala Ala Asn Ala Gly Arg Gly Leu Ser
465                 470                 475                 480

Ile Pro Leu His Asp Gly Ala Val Glu Ala Phe Glu Lys Leu Gly Ala
                485                 490                 495

Pro Pro Leu Pro Glu Gly Arg
            500
```

<210> SEQ ID NO 61
<211> LENGTH: 1494
<212> TYPE: DNA
<213> ORGANISM: Bordetella pertussis

<400> SEQUENCE: 61

```
atgatccgta tgcctggttt ccgattctcc gttccgccgc gccgccggct ggccgtcgcg      60
gcgctgtgcg cggcgctggg cggctgtgcg gtcgggcccg actaccagcg acccgccatc     120
gacgtggggg ccgcctacaa ggaggccgcc gcgccgcagc ccggctggac gcccgcgcag     180
cccagcgacg agagcgcgcg cgggcaatgg tggcaggtgt atggcgaccc ggtgctcgac     240
ggcctggtgc agcaattgaa ccagggcaac tactccgtgg cgcaggccga ggccaattat     300
cgccaggccc aggcgctggt gcgcaatgcg cgcgccggct tcttccccac cataggcgcg     360
ggcgccgacg tgacgcggtc cggctcgggc ggcggcagcg gcgccggctc gaacggcagc     420
tcggtcggca accagtactc gctcagtggg tcggtcagct gggaagtcga tgtgtggggc     480
cgggtgcgcc gcgaagtcga gtccagccgc gccgaggcgc aggccagcgc ggcggacctg     540
gccgtcaccc gcctgagcgc gcaggccgcc ctggtgcaga actacctgca attgcgcgtg     600
ctcgacgagc agaaacgcct gctcgacgcc acggtgctgg cctacgagcg ctcgctgcgc     660
ctgacgcaga accgctacga agccggcgtg gtgggcaagt ccgacgtggc ggtggcgcgc     720
acccagctgg agaacacgcg ggcccagtcc atcgacctgg actggcagcg cggccagttc     780
gagcacgcca tcgcggtgct gatggggcag gcgccttcgc gcttcgccct gccggcgcag     840
ccgttcgcgc agcaactgcc ggacatcccg gcgggcctgc cctcgcaact gctggagcgc     900
cggcccgacg tggcggccgc cgagcggcgc gcggccgccg ccaatgcgca gatcggcgtg     960
gcgcaggcgg cctggttccc ggacctgacc ttgtcggcca gcggcggttt tcgcagcggc    1020
cagttcgccg agtggctgac cgcgccggcg cgcttctgga ccctcggccc ggcgctggcc    1080
atgacgctgt tcgacggcgg cgcgcgttcg gcgcgcgtcg agcaggcccg cgccgcctat    1140
gacgcgcagg cggccgccta ccgccagagc gtgctgacgg cgctgcgcga ggtggaggat    1200
tacctggtgc agctgcgcgt gatggagcac gagcagcagg tgcagcgcaa tgcgctcgag    1260
tccgcgcgcg aatcgctgcg cctggcgcgc aaccagtacg agcaggggct gatcgactac    1320
ctgagcgtgg cggtgctgga aaccaccgcg ctgaacaccg agcgcaacgc catcagcctg    1380
ctgggcagcc ggctcaacgc cagcgtgcag ctgatcgcgg cgctgggcgg cgggtggcag    1440
ggcttgccgg ccgaggcggc ggccagcgcg gcggccgagc cgtccgcgcc ctag          1494
```

<210> SEQ ID NO 62
<211> LENGTH: 497
<212> TYPE: PRT
<213> ORGANISM: Bordetella pertussis

<400> SEQUENCE: 62

```
Met Ile Arg Met Pro Gly Phe Arg Phe Ser Val Pro Pro Arg Arg Arg
 1               5                  10                  15

Leu Ala Val Ala Ala Leu Cys Ala Ala Leu Gly Gly Cys Ala Val Gly
            20                  25                  30

Pro Asp Tyr Gln Arg Pro Ala Ile Asp Val Gly Ala Ala Tyr Lys Glu
        35                  40                  45

Ala Ala Ala Pro Gln Pro Gly Trp Thr Pro Ala Gln Pro Ser Asp Glu
    50                  55                  60

Ser Ala Arg Gly Gln Trp Trp Gln Val Tyr Gly Asp Pro Val Leu Asp
65                  70                  75                  80
```

```
Gly Leu Val Gln Gln Leu Asn Gln Gly Asn Tyr Ser Val Ala Gln Ala
                85                  90                  95

Glu Ala Asn Tyr Arg Gln Ala Gln Ala Leu Val Arg Asn Ala Arg Ala
            100                 105                 110

Gly Phe Phe Pro Thr Ile Gly Ala Gly Ala Asp Val Thr Arg Ser Gly
        115                 120                 125

Ser Gly Gly Gly Ser Gly Ala Gly Ser Asn Gly Ser Ser Val Gly Asn
    130                 135                 140

Gln Tyr Ser Leu Ser Gly Ser Val Ser Trp Glu Val Asp Val Trp Gly
145                 150                 155                 160

Arg Val Arg Arg Glu Val Glu Ser Ser Arg Ala Glu Ala Gln Ala Ser
                165                 170                 175

Ala Ala Asp Leu Ala Val Thr Arg Leu Ser Ala Gln Ala Ala Leu Val
            180                 185                 190

Gln Asn Tyr Leu Gln Leu Arg Val Leu Asp Glu Gln Lys Arg Leu Leu
        195                 200                 205

Asp Ala Thr Val Leu Ala Tyr Glu Arg Ser Leu Arg Leu Thr Gln Asn
    210                 215                 220

Arg Tyr Glu Ala Gly Val Val Gly Lys Ser Asp Val Ala Val Ala Arg
225                 230                 235                 240

Thr Gln Leu Glu Asn Thr Arg Ala Gln Ser Ile Asp Leu Asp Trp Gln
                245                 250                 255

Arg Gly Gln Phe Glu His Ala Ile Ala Val Leu Met Gly Gln Ala Pro
            260                 265                 270

Ser Arg Phe Ala Leu Pro Ala Gln Pro Phe Ala Gln Gln Leu Pro Asp
        275                 280                 285

Ile Pro Ala Gly Leu Pro Ser Gln Leu Leu Glu Arg Arg Pro Asp Val
    290                 295                 300

Ala Ala Ala Glu Arg Arg Ala Ala Ala Ala Asn Ala Gln Ile Gly Val
305                 310                 315                 320

Ala Gln Ala Ala Trp Phe Pro Asp Leu Thr Leu Ser Ala Ser Gly Gly
                325                 330                 335

Phe Arg Ser Gly Gln Phe Ala Glu Trp Leu Thr Ala Pro Ala Arg Phe
            340                 345                 350

Trp Thr Leu Gly Pro Ala Leu Ala Met Thr Leu Phe Asp Gly Gly Ala
        355                 360                 365

Arg Ser Ala Arg Val Glu Gln Ala Arg Ala Ala Tyr Asp Ala Gln Ala
    370                 375                 380

Ala Ala Tyr Arg Gln Ser Val Leu Thr Ala Leu Arg Glu Val Glu Asp
385                 390                 395                 400

Tyr Leu Val Gln Leu Arg Val Met Glu His Glu Gln Gln Val Gln Arg
                405                 410                 415

Asn Ala Leu Glu Ser Ala Arg Glu Ser Leu Arg Leu Ala Arg Asn Gln
            420                 425                 430

Tyr Glu Gln Gly Leu Ile Asp Tyr Leu Ser Val Ala Val Leu Glu Thr
        435                 440                 445

Thr Ala Leu Asn Thr Glu Arg Asn Ala Ile Ser Leu Leu Gly Ser Arg
    450                 455                 460

Leu Asn Ala Ser Val Gln Leu Ile Ala Ala Leu Gly Gly Gly Trp Gln
465                 470                 475                 480

Gly Leu Pro Ala Glu Ala Ala Ala Ser Ala Ala Ala Glu Pro Ser Ala
                485                 490                 495

Pro
```

<210> SEQ ID NO 63
<211> LENGTH: 1494
<212> TYPE: DNA
<213> ORGANISM: Bordetella pertussis

<400> SEQUENCE: 63

```
atgacgcatc ccgtcccgac gacctttgca cgtaccgccg gcgcgctgct tgccgcgctg      60

gcgctggccg gctgcgccgt ggggccgcag taccaggcgc ccacgcccgc gccggtgaag     120

ctggccagcc ccgaacaggc gctgttctcg gccgaccggt tgcaacgcga atggtggcgc     180

cagttgcagg atgcccggct ggacgcgttg atcggcctgg cgctggcgcg caacctcgat     240

atcggcctgg cgctggcgcg caacctcgat atccgccagg cgcaggcgcg cctgcgcgaa     300

gcgcgcgccg cgctcgacga aaaggaactg gaccgctggc cgaccgtgac cgcggccggc     360

ggctacacgc gcagcctgtc gcagatcaac cccggccccg accagcgcaa cctcgcgcaa     420

agctaccgcg cgggcttcga cgcgacctgg gaaatcgatt tgttcggccg cctgcagcga     480

cgggccgagg ccgcggccgc gcgcgaccag gccgccgccg ccgacctggc ccagacgcgc     540

ctggtggtgg tggccgagct ggcacgcaac tatttcgaga tgcgcggcgc cgagcaacgg     600

ctggccgtgg cgcgcgccaa cctcgccacc cagcaggaga cgctgcgcgt caccgcggcg     660

ctggtggaaa ccggccgcgg ctatgccggc gacctggcca gcgcacgggc cgagctggcc     720

ggcacgcggg cgctgctcgc gccgctggag acgcaacggc gcctggccca gtaccacatc     780

gccgtcctgg cggccatgcg gccggccgag ctgggcgagc tgcggcagga gcagccgctg     840

gcgccgctgg ccgcgcaatt gcccatcggc gacgtggcca tgctgctgca acgccgcccc     900

gacgtgcgcg ccgccgagcg cctgctggcc gccaccaacg ccgacgtcgg cgccatcacc     960

gccgaactgt atccgcgcat cgacctgggc gggttcctcg gtttcattgc cttgcgcggc    1020

ggcgacctgg gccaggccag cagcaaggcc ttcgcgctgg cgccgacgat cagctggccg    1080

gcgttgcacc tgggcagcgt ccaggcgcag ctgcgcgcgg gccaggcccg gcacgacgcg    1140

gcgcgggcgc gctacgaaca ggtggcgctg caggccatcg aggaagtgga aggcgcgttg    1200

acgcgctatg gacagaacca gcagcggctg cgcgacctgc ttgacagcgc cacgcagagc    1260

cagcgcgccg ccgacctggc gcaaacgcgc tatcgtgaag ggccgcgcgc gtatttgacg    1320

gtgctggacg cgcagcgtac tcttttgcgc gcacaggatg ccgtggcgca atccgagtcg    1380

gagtcctata ccagcctggt cgcgctctac aaggccctgg gcggaggctg gaataccgac    1440

gccgccgcgc ccgcccgttc cgcccgcacc gccgccctgc cggccagccc ctga          1494
```

<210> SEQ ID NO 64
<211> LENGTH: 497
<212> TYPE: PRT
<213> ORGANISM: Bordetella pertussis

<400> SEQUENCE: 64

```
Met Thr His Pro Val Pro Thr Thr Phe Ala Arg Thr Ala Gly Ala Leu
1               5                   10                  15

Leu Ala Ala Leu Ala Leu Ala Gly Cys Ala Val Gly Pro Gln Tyr Gln
            20                  25                  30

Ala Pro Thr Pro Ala Pro Val Lys Leu Ala Ser Pro Glu Gln Ala Leu
        35                  40                  45

Phe Ser Ala Asp Arg Leu Gln Arg Glu Trp Trp Arg Gln Leu Gln Asp
    50                  55                  60

Ala Arg Leu Asp Ala Leu Ile Gly Leu Ala Leu Ala Arg Asn Leu Asp
```

-continued

```
65                  70                  75                  80

Ile Gly Leu Ala Leu Ala Arg Asn Leu Asp Ile Arg Gln Ala Gln Ala
                85                  90                  95

Arg Leu Arg Glu Ala Arg Ala Ala Leu Asp Glu Lys Glu Leu Asp Arg
            100                 105                 110

Trp Pro Thr Val Thr Ala Ala Gly Gly Tyr Thr Arg Ser Leu Ser Gln
        115                 120                 125

Ile Asn Pro Gly Pro Asp Gln Arg Asn Leu Ala Gln Ser Tyr Arg Ala
    130                 135                 140

Gly Phe Asp Ala Thr Trp Glu Ile Asp Leu Phe Gly Arg Leu Gln Arg
145                 150                 155                 160

Arg Ala Glu Ala Ala Ala Ala Arg Asp Gln Ala Ala Ala Ala Asp Leu
                165                 170                 175

Ala Gln Thr Arg Leu Val Val Val Ala Glu Leu Ala Arg Asn Tyr Phe
            180                 185                 190

Glu Met Arg Gly Ala Glu Gln Arg Leu Ala Val Ala Arg Ala Asn Leu
        195                 200                 205

Ala Thr Gln Gln Glu Thr Leu Arg Val Thr Ala Ala Leu Val Glu Thr
    210                 215                 220

Gly Arg Gly Tyr Ala Gly Asp Leu Ala Ser Ala Arg Ala Glu Leu Ala
225                 230                 235                 240

Gly Thr Arg Ala Leu Leu Ala Pro Leu Glu Thr Gln Arg Arg Leu Ala
                245                 250                 255

Gln Tyr His Ile Ala Val Leu Ala Ala Met Arg Pro Ala Glu Leu Gly
            260                 265                 270

Glu Leu Arg Gln Glu Gln Pro Leu Ala Pro Leu Ala Ala Gln Leu Pro
        275                 280                 285

Ile Gly Asp Val Ala Met Leu Leu Gln Arg Arg Pro Asp Val Arg Ala
    290                 295                 300

Ala Glu Arg Leu Leu Ala Ala Thr Asn Ala Asp Val Gly Ala Ile Thr
305                 310                 315                 320

Ala Glu Leu Tyr Pro Arg Ile Asp Leu Gly Gly Phe Leu Gly Phe Ile
                325                 330                 335

Ala Leu Arg Gly Gly Asp Leu Gly Gln Ala Ser Ser Lys Ala Phe Ala
            340                 345                 350

Leu Ala Pro Thr Ile Ser Trp Pro Ala Leu His Leu Gly Ser Val Gln
        355                 360                 365

Ala Gln Leu Arg Ala Gly Gln Ala Arg His Asp Ala Ala Arg Ala Arg
    370                 375                 380

Tyr Glu Gln Val Ala Leu Gln Ala Ile Glu Glu Val Glu Gly Ala Leu
385                 390                 395                 400

Thr Arg Tyr Gly Gln Asn Gln Gln Arg Leu Arg Asp Leu Leu Asp Ser
                405                 410                 415

Ala Thr Gln Ser Gln Arg Ala Ala Asp Leu Ala Gln Thr Arg Tyr Arg
            420                 425                 430

Glu Gly Ala Ala Pro Tyr Leu Thr Val Leu Asp Ala Gln Arg Thr Leu
        435                 440                 445

Leu Arg Ala Gln Asp Ala Val Ala Gln Ser Glu Ser Glu Ser Tyr Thr
    450                 455                 460

Ser Leu Val Ala Leu Tyr Lys Ala Leu Gly Gly Gly Trp Asn Thr Asp
465                 470                 475                 480

Ala Ala Ala Pro Ala Arg Ser Ala Arg Thr Ala Ala Leu Pro Ala Ser
                485                 490                 495
```

Pro

<210> SEQ ID NO 65
<211> LENGTH: 1383
<212> TYPE: DNA
<213> ORGANISM: Bordetella pertussis

<400> SEQUENCE: 65

```
atgaaacctg tcgtcatgag aaccttgttg tcccttgccg tggccacggc cctggccggc     60

tgctcgctgg cgcccaccta cgagcgcccg caggcgccgg tcgacgcggc ctatccgtcc    120

ggcccggcct acggcgcgcc gggccaggcc gccgcgggcg cgccggccgc cgccgacgtg    180

ggctggcgcg acttcttcgg cgacccgctg ctgcaggagc tgctggcgct gtcgctggcc    240

aacaaccgcg acctgcgggt cgccgcgctc aacgtggagg cggcgcgcct caacccgagc    300

ggacaggccg gcatcagccg cagctaccag gtcggtgcca gcctgtcgac ctgggagctg    360

gacctgttcg ggcgcatccg cagcctcagc gaacaggcgc tgcagctcta tctggcccag    420

gacgaaacgc gcctggccac ccagctgacg ctggtggccg agaccgccaa cgcctacccg    480

accctgcgcg ccgaccagga actgctggcg ctgacgcgcc agacgctggc ggcccagcag    540

gagtcgtaca agctgacccg ccagagctac gacctgggcg tggcgaccga gctggacctg    600

agccaggccg agatttcgct gcgcaccgcc gagcgcaatc tgtcgcagta cacgcgcatg    660

gcggcgcagg accgcaacgc gctggtgctg ctggtgggcc agccgctgcc ggccggcatc    720

ggcgcgcagc tggaccaggc cgtggcgctg cccgacggcg tggtcctggc cgacctgccg    780

gcgggcctgc cgtcggatct gctcgcgcgc cggccggata tccgcgcggc ggagcaccag    840

ctgcaagccg ccaacgccag catcggcgcg gcgcgcgcgg cgttcttccc gcgcatcagc    900

ctgaccggct cggccggcac ggccagcgcc agcctgggcg gcctgttcga tgccgggtcg    960

ggggcctgga gtttcgcgcc gcagatcagc gtgccgatct tcgcgggcgg ggcgctgcgc   1020

gccagcctgg acctggccaa gatccagaag gacatcggca tcgcgcgcta cgagcaggcc   1080

atccagagcg ggttccgcga ggtctccgac gcgctggccg gccgcggcac attgcaggag   1140

cagatccggt cgcaggaact gctggtgcag gccaaccagc gcgcctacga cctgtcgcag   1200

cagcgttacc agcagggcat cgacaactat ctcagcgtgc tggattcgca gcgttcgctg   1260

tatacggcgc agcagacgct ggtcgagacg cggctggcgc gcctgtccaa cctgatccag   1320

ctctacaagg cgctgggcgg cggctggtcc gagcgcacgg tggcggcggc gcaggccggc   1380

tga                                                                 1383
```

<210> SEQ ID NO 66
<211> LENGTH: 460
<212> TYPE: PRT
<213> ORGANISM: Bordetella pertussis

<400> SEQUENCE: 66

```
Met Lys Pro Val Val Met Arg Thr Leu Leu Ser Leu Ala Val Ala Thr
 1               5                  10                  15

Ala Leu Ala Gly Cys Ser Leu Ala Pro Thr Tyr Glu Arg Pro Gln Ala
            20                  25                  30

Pro Val Asp Ala Ala Tyr Pro Ser Gly Pro Ala Tyr Gly Ala Pro Gly
        35                  40                  45

Gln Ala Ala Ala Gly Ala Pro Ala Ala Ala Asp Val Gly Trp Arg Asp
    50                  55                  60

Phe Phe Gly Asp Pro Leu Leu Gln Glu Leu Leu Ala Leu Ser Leu Ala
65                  70                  75                  80
```

```
Asn Asn Arg Asp Leu Arg Val Ala Ala Leu Asn Val Glu Ala Ala Arg
                85                  90                  95

Leu Asn Pro Ser Gly Gln Ala Gly Ile Ser Arg Ser Tyr Gln Val Gly
            100                 105                 110

Ala Ser Leu Ser Thr Trp Glu Leu Asp Leu Phe Gly Arg Ile Arg Ser
        115                 120                 125

Leu Ser Glu Gln Ala Leu Gln Leu Tyr Leu Ala Gln Asp Glu Thr Arg
    130                 135                 140

Leu Ala Thr Gln Leu Thr Leu Val Ala Glu Thr Ala Asn Ala Tyr Pro
145                 150                 155                 160

Thr Leu Arg Ala Asp Gln Glu Leu Leu Ala Leu Thr Arg Gln Thr Leu
                165                 170                 175

Ala Ala Gln Gln Glu Ser Tyr Lys Leu Thr Arg Gln Ser Tyr Asp Leu
            180                 185                 190

Gly Val Ala Thr Glu Leu Asp Leu Ser Gln Ala Glu Ile Ser Leu Arg
        195                 200                 205

Thr Ala Glu Arg Asn Leu Ser Gln Tyr Thr Arg Met Ala Ala Gln Asp
    210                 215                 220

Arg Asn Ala Leu Val Leu Leu Val Gly Gln Pro Leu Pro Ala Gly Ile
225                 230                 235                 240

Gly Ala Gln Leu Asp Gln Ala Val Ala Leu Pro Asp Gly Val Val Leu
                245                 250                 255

Ala Asp Leu Pro Ala Gly Leu Pro Ser Asp Leu Leu Ala Arg Arg Pro
            260                 265                 270

Asp Ile Arg Ala Ala Glu His Gln Leu Gln Ala Ala Asn Ala Ser Ile
        275                 280                 285

Gly Ala Ala Arg Ala Ala Phe Phe Pro Arg Ile Ser Leu Thr Gly Ser
    290                 295                 300

Ala Gly Thr Ala Ser Ala Ser Leu Gly Gly Leu Phe Asp Ala Gly Ser
305                 310                 315                 320

Gly Ala Trp Ser Phe Ala Pro Gln Ile Ser Val Pro Ile Phe Ala Gly
                325                 330                 335

Gly Ala Leu Arg Ala Ser Leu Asp Leu Ala Lys Ile Gln Lys Asp Ile
            340                 345                 350

Gly Ile Ala Arg Tyr Glu Gln Ala Ile Gln Ser Gly Phe Arg Glu Val
        355                 360                 365

Ser Asp Ala Leu Ala Gly Arg Gly Thr Leu Gln Glu Gln Ile Arg Ser
    370                 375                 380

Gln Glu Leu Leu Val Gln Ala Asn Gln Arg Ala Tyr Asp Leu Ser Gln
385                 390                 395                 400

Gln Arg Tyr Gln Gln Gly Ile Asp Asn Tyr Leu Ser Val Leu Asp Ser
                405                 410                 415

Gln Arg Ser Leu Tyr Thr Ala Gln Gln Thr Leu Val Glu Thr Arg Leu
            420                 425                 430

Ala Arg Leu Ser Asn Leu Ile Gln Leu Tyr Lys Ala Leu Gly Gly Gly
        435                 440                 445

Trp Ser Glu Arg Thr Val Ala Ala Ala Gln Ala Gly
    450                 455                 460
```

<210> SEQ ID NO 67
<211> LENGTH: 1350
<212> TYPE: DNA
<213> ORGANISM: Bordetella pertussis

<400> SEQUENCE: 67

```
atgaaacagc ataaggtcgg caggcactgg gcaggatggg cgatggcgct ggcgtgcctg      60

ggcgcggccg cgccgctggc ggcgcagccg gcggcaccag ctggggccgc gcaggcgcgc     120

gaactgctgc tggaggtcaa gggccagcag ccgttgcgcc tggacgccgc gccatcgcgc     180

gtggcgatcg ccgatccgca ggtcgccgac gtcaaggtgc tggcgcccgg cgtgggccgc     240

ccgggcgagg tgctgctgat cggccggcag gccggcacca ccgagctgcg ggtctggagc     300

cgcggctcgc gcgacccgca ggtctggacc gtgcgcgtgc tgccgcaagt gcaggccgcg     360

ctggcgcggc gcggcgtcgg cggcggcgcg caggtcgaca tggctggcga cagcggcgtg     420

gtcaccggca tggcgccctc ggccgaggcg catcgcggcg cggccgaggc tgccgcggcc     480

gccgcgggcg gcaacgacaa ggtggtcgac atgtcgcaga tcaacaccag cggcgtggtg     540

caggtggaag tgaaagtggt cgagctggcg cgctcggtca tgaaggatgt cgggatcaat     600

ttcagggccg acagcggccc gtggtcgggc ggcgtgtcgc tgctgccgga cctggccagc     660

ggcggcatgt tcggcatgct gtcctatacc agccgcgatt tcagcgcgtc gctggcgctg     720

ctgcaaaaca acggcatggc gcgcgtcctg gccgagccga cgctgctggc catgtcgggc     780

cagagcgcca gcttcctggc cggcggcgag attccgattc cggtatcggc cggcctgggt     840

acgacctcgg tgcagttcaa gcccttcggc atcggcctga cggtcacgcc cacggtcatc     900

tcgcgcgagc gcatcgcgct gaaggtggcg cccgaagcca gcgagctgga ctacgccaac     960

ggcatttcca gcatcgacag caacaatcgc atcacggtga tcccggcgtt gcgaacccgc    1020

aaggccgaca ccatggtgga gctgggcgat ggcgagacat tcgtcatcag cggcctggtt    1080

tcgcgccaga ccaaggccag cgtcaacaag gtgccgctgt tgggcgacct gcccatcatc    1140

ggggcgttct tccgcaacgt gcagtattcc caggaggatc gcgaattggt gatcgtggtc    1200

acgccgcgcc tggttcgccc catcgcgcgc ggtgtcacgc tgcccttgcc gggcgcgcgc    1260

caggaggtca gcgacgctgg cttcaacgcc tggggctatt acctgctggg tccgatgagc    1320

ggccagcaga tgccgggctt ttcacagtga                                      1350
```

<210> SEQ ID NO 68
<211> LENGTH: 449
<212> TYPE: PRT
<213> ORGANISM: Bordetella pertussis

<400> SEQUENCE: 68

```
Met Lys Gln His Lys Val Gly Arg His Trp Ala Gly Trp Ala Met Ala
1               5                   10                  15

Leu Ala Cys Leu Gly Ala Ala Ala Pro Leu Ala Ala Gln Pro Ala Ala
            20                  25                  30

Pro Ala Gly Ala Ala Gln Ala Arg Glu Leu Leu Leu Glu Val Lys Gly
        35                  40                  45

Gln Gln Pro Leu Arg Leu Asp Ala Ala Pro Ser Arg Val Ala Ile Ala
    50                  55                  60

Asp Pro Gln Val Ala Asp Val Lys Val Leu Ala Pro Gly Val Gly Arg
65                  70                  75                  80

Pro Gly Glu Val Leu Leu Ile Gly Arg Gln Ala Gly Thr Thr Glu Leu
                85                  90                  95

Arg Val Trp Ser Arg Gly Ser Arg Asp Pro Gln Val Trp Thr Val Arg
            100                 105                 110

Val Leu Pro Gln Val Gln Ala Ala Leu Ala Arg Arg Gly Val Gly Gly
        115                 120                 125

Gly Ala Gln Val Asp Met Ala Gly Asp Ser Gly Val Val Thr Gly Met
```

```
    130                 135                 140

Ala Pro Ser Ala Glu Ala His Arg Gly Ala Ala Glu Ala Ala Ala Ala
145                 150                 155                 160

Ala Ala Gly Gly Asn Asp Lys Val Val Asp Met Ser Gln Ile Asn Thr
                165                 170                 175

Ser Gly Val Val Gln Val Glu Val Lys Val Val Glu Leu Ala Arg Ser
            180                 185                 190

Val Met Lys Asp Val Gly Ile Asn Phe Arg Ala Asp Ser Gly Pro Trp
        195                 200                 205

Ser Gly Gly Val Ser Leu Leu Pro Asp Leu Ala Ser Gly Gly Met Phe
    210                 215                 220

Gly Met Leu Ser Tyr Thr Ser Arg Asp Phe Ser Ala Ser Leu Ala Leu
225                 230                 235                 240

Leu Gln Asn Asn Gly Met Ala Arg Val Leu Ala Glu Pro Thr Leu Leu
                245                 250                 255

Ala Met Ser Gly Gln Ser Ala Ser Phe Leu Ala Gly Gly Glu Ile Pro
            260                 265                 270

Ile Pro Val Ser Ala Gly Leu Gly Thr Thr Ser Val Gln Phe Lys Pro
        275                 280                 285

Phe Gly Ile Gly Leu Thr Val Thr Pro Thr Val Ile Ser Arg Glu Arg
    290                 295                 300

Ile Ala Leu Lys Val Ala Pro Glu Ala Ser Glu Leu Asp Tyr Ala Asn
305                 310                 315                 320

Gly Ile Ser Ser Ile Asp Ser Asn Asn Arg Ile Thr Val Ile Pro Ala
                325                 330                 335

Leu Arg Thr Arg Lys Ala Asp Thr Met Val Glu Leu Gly Asp Gly Glu
            340                 345                 350

Thr Phe Val Ile Ser Gly Leu Val Ser Arg Gln Thr Lys Ala Ser Val
        355                 360                 365

Asn Lys Val Pro Leu Leu Gly Asp Leu Pro Ile Ile Gly Ala Phe Phe
    370                 375                 380

Arg Asn Val Gln Tyr Ser Gln Glu Asp Arg Glu Leu Val Ile Val Val
385                 390                 395                 400

Thr Pro Arg Leu Val Arg Pro Ile Ala Arg Gly Val Thr Leu Pro Leu
                405                 410                 415

Pro Gly Ala Arg Gln Glu Val Ser Asp Ala Gly Phe Asn Ala Trp Gly
            420                 425                 430

Tyr Tyr Leu Leu Gly Pro Met Ser Gly Gln Gln Met Pro Gly Phe Ser
        435                 440                 445

Gln
```

<210> SEQ ID NO 69
<211> LENGTH: 1290
<212> TYPE: DNA
<213> ORGANISM: Bordetella pertussis

<400> SEQUENCE: 69

```
atgaagcgac ttctctgtct gtccctgctg tccgtattgc tggcggcgtg cacgacccca      60

tcgcagattc cgcccgagac ggcgcccggc ggcgtgccgc cggcggccga aggtccgctg     120

gtcgtgccgc cgctgtcggc gctgtccgac accccgccgc gcgcgctggc cgggcgctac     180

cagcgcgttg cctggaccga gctgcccaac tgggagagcg acgacctgtc gcgctggtgg     240

ccgctgttcc tgcgcaattg caaaggcctg atgcggccga ccagcggtaa cctggcggcg     300

ccggcacgcg ccacgccgcg cgcctggcag cccgtgtgcg cggcggcggt cgacccgtcc     360
```

```
aaggcgccgg ccgccggcga cagcgcggcg gtgcggcgct tcctgcagac ctggctgcag    420

ccctggcgca tcgccggcgc cgacggccgt cccgccacca ataccgtcac cggctactac    480

gagccgctgg tgcgcggctc gcgccgccag ggcggccgct accagtggcc gctgtatgcc    540

gtgccggccg acctgctcgt cgtcgacctg ggctcggtct atcccgacct gaccggcaag    600

cgcgtgcgcg gccggctcga cggccgccgg gtcgtgccct acgacacgcg cgccgcgatc    660

gaggcgggcg accgcaagcc gccggccatc gtctgggtgg acgatccggt cgacaatttc    720

ttcctgcagg tccaggggtc gggccgggtg cagctgaccg atggccccga ccgcggcacc    780

acgatccgcg tcgcgtacgc cgaccataac ggccagccct atgcctccat cggccgctgg    840

ctcatcgaca agggcgagct gcgcgccgac caggcatcga tgcagaacat ccgtgcctgg    900

gcccaacgca atccctcgcg cgtgcaggaa atgctcaacg ccaacccggc ggtggtcttc    960

ttccgcgaag aggcggtggt cgatccggag caagggccca agggggccta tggcatcccg   1020

ttggcgccgc agcgctcgat cgcggtcgac gccggtttcg tgccgctggg cacgccggtc   1080

tacctgtcga ccacgctgcc ggcctccgac cggcccctgc agcgcaccgt gttcgcgcag   1140

gacaccggca cggccattcg cggcgcggcg cgcgccgact tctattgggg ctacggcgag   1200

gaagccggcc agcaggccgg gcgcatgaag cagcgcggcc agatgtggct gctgtggccc   1260

aagcaggccg gggagccgtc ggcgcgatga                                    1290
```

```
<210> SEQ ID NO 70
<211> LENGTH: 429
<212> TYPE: PRT
<213> ORGANISM: Bordetella pertussis

<400> SEQUENCE: 70

Met Lys Arg Leu Leu Cys Leu Ser Leu Leu Ser Val Leu Leu Ala Ala
 1               5                  10                  15

Cys Thr Thr Pro Ser Gln Ile Pro Pro Glu Thr Ala Pro Gly Gly Val
            20                  25                  30

Pro Pro Ala Ala Glu Gly Pro Leu Val Val Pro Pro Leu Ser Ala Leu
        35                  40                  45

Ser Asp Thr Pro Pro Arg Ala Leu Ala Gly Arg Tyr Gln Arg Val Ala
    50                  55                  60

Trp Thr Glu Leu Pro Asn Trp Glu Ser Asp Asp Leu Ser Arg Trp Trp
65                  70                  75                  80

Pro Leu Phe Leu Arg Asn Cys Lys Gly Leu Met Arg Pro Thr Ser Gly
                85                  90                  95

Asn Leu Ala Ala Pro Ala Arg Ala Thr Pro Arg Ala Trp Gln Pro Val
            100                 105                 110

Cys Ala Ala Ala Val Asp Pro Ser Lys Ala Pro Ala Ala Gly Asp Ser
        115                 120                 125

Ala Ala Val Arg Arg Phe Leu Gln Thr Trp Leu Gln Pro Trp Arg Ile
    130                 135                 140

Ala Gly Ala Asp Gly Arg Pro Ala Thr Asn Thr Val Thr Gly Tyr Tyr
145                 150                 155                 160

Glu Pro Leu Val Arg Gly Ser Arg Arg Gln Gly Gly Arg Tyr Gln Trp
                165                 170                 175

Pro Leu Tyr Ala Val Pro Ala Asp Leu Leu Val Val Asp Leu Gly Ser
            180                 185                 190

Val Tyr Pro Asp Leu Thr Gly Lys Arg Val Arg Gly Arg Leu Asp Gly
        195                 200                 205
```

```
Arg Arg Val Val Pro Tyr Asp Thr Arg Ala Ala Ile Glu Ala Gly Asp
    210                 215                 220

Arg Lys Pro Pro Ala Ile Val Trp Val Asp Asp Pro Val Asp Asn Phe
225                 230                 235                 240

Phe Leu Gln Val Gln Gly Ser Gly Arg Val Gln Leu Thr Asp Gly Pro
                245                 250                 255

Asp Arg Gly Thr Thr Ile Arg Val Ala Tyr Ala Asp His Asn Gly Gln
            260                 265                 270

Pro Tyr Ala Ser Ile Gly Arg Trp Leu Ile Asp Lys Gly Glu Leu Arg
        275                 280                 285

Ala Asp Gln Ala Ser Met Gln Asn Ile Arg Ala Trp Ala Gln Arg Asn
    290                 295                 300

Pro Ser Arg Val Gln Glu Met Leu Asn Ala Asn Pro Ala Val Val Phe
305                 310                 315                 320

Phe Arg Glu Glu Ala Val Val Asp Pro Glu Gln Gly Pro Lys Gly Ala
                325                 330                 335

Tyr Gly Ile Pro Leu Ala Pro Gln Arg Ser Ile Ala Val Asp Ala Gly
            340                 345                 350

Phe Val Pro Leu Gly Thr Pro Val Tyr Leu Ser Thr Thr Leu Pro Ala
        355                 360                 365

Ser Asp Arg Pro Leu Gln Arg Thr Val Phe Ala Gln Asp Thr Gly Thr
    370                 375                 380

Ala Ile Arg Gly Ala Ala Arg Ala Asp Phe Tyr Trp Gly Tyr Gly Glu
385                 390                 395                 400

Glu Ala Gly Gln Gln Ala Gly Arg Met Lys Gln Arg Gly Gln Met Trp
                405                 410                 415

Leu Leu Trp Pro Lys Gln Ala Gly Glu Pro Ser Ala Arg
            420                 425
```

<210> SEQ ID NO 71
<211> LENGTH: 1146
<212> TYPE: DNA
<213> ORGANISM: Bordetella pertussis

<400> SEQUENCE: 71

```
atgttcaact gtcggcgatt cctgcaaatc ggcacgctgt cggccctgct ggccggctgt      60

gccacctcca gccaaacacc ccaagcccag catcttcccg cgcaggccgc cacaggccag     120

gccgaccgcg tccgcatcgg cccggacaaa cccgtatcga gcgacgaagg ccccgccacg     180

ctgacgccga ccggcgaact gcggcccgac gtccgcgcct tcgccgaaca gctggcggcg     240

cagcgcgagc tgcccctgcc gcaagtgctg gccagcctgg aaagcacgcg ctacaacgcg     300

accgtcgccc gcctcatcgc cccgtccggc gcgtcgggca agaaaatctg gcgcagctgg     360

ctgacctatc gcgggcgttt cgtcgaaccc aagcgcatcg cctggggcgt ggaattctgg     420

aacgccaacc aggacctgct caaccgcgcc gcccagcgct acggcgtgcc ggcctcgatc     480

atcgcctcca tcatcggcgt ggaaaccctg tatggccgca acgtgggcaa cttccgcgtg     540

gtcgacgccc tggcgacgct ggcattcgac tacctcgatc ccgccaagcc cgagcgcgcc     600

gacatgttcc gcggccagct cggcgacttc atcaccctgg cgctgcagga caagctggac     660

cccgagacgc gcggctcgta cgccggcgcc atcggcatgc cgcaattcat gcccggcagc     720

atcatgcgct atgcggtcga tggcgatgac gacggccaca tcgacctgac caacagcgtc     780

gcggacgcgg tcatgtcggt gggcaacttc ctggtcgaac atggctggca gcgcggcctg     840

ccggtgttcg cgccggtcgc gctgccggcc gatccggcgc cgctggtggc cggcggcctt     900
```

-continued

```
acgccgacgc tggactggaa cggcctgcag gccgccggcg cgcgcccggc ggcgggcgcc    960

ggacgcggcg cctggcagga gcaccccatg ggcatcgtgg acctggtcga ggaagcgcgc   1020

ggcaccgtgc aataccgtac cgccacgccc aatttctttg ccctgacgca atacaaccgc   1080

agctacttct atgccacggc ggtggccgac ctggcggccg aactgcaggc ccgcacgggc   1140

tattga                                                              1146
```

<210> SEQ ID NO 72
<211> LENGTH: 381
<212> TYPE: PRT
<213> ORGANISM: Bordetella pertussis

<400> SEQUENCE: 72

```
Met Phe Asn Cys Arg Arg Phe Leu Gln Ile Gly Thr Leu Ser Ala Leu
 1               5                  10                  15

Leu Ala Gly Cys Ala Thr Ser Ser Gln Thr Pro Gln Ala Gln His Leu
            20                  25                  30

Pro Ala Gln Ala Ala Thr Gly Gln Ala Asp Arg Val Arg Ile Gly Pro
        35                  40                  45

Asp Lys Pro Val Ser Ser Asp Glu Gly Pro Ala Thr Leu Thr Pro Thr
    50                  55                  60

Gly Glu Leu Arg Pro Asp Val Arg Ala Phe Ala Glu Gln Leu Ala Ala
65                  70                  75                  80

Gln Arg Glu Leu Pro Leu Pro Gln Val Leu Ala Ser Leu Glu Ser Thr
                85                  90                  95

Arg Tyr Asn Ala Thr Val Ala Arg Leu Ile Ala Pro Ser Gly Ala Ser
            100                 105                 110

Gly Lys Lys Ile Trp Arg Ser Trp Leu Thr Tyr Arg Gly Arg Phe Val
        115                 120                 125

Glu Pro Lys Arg Ile Ala Trp Gly Val Glu Phe Trp Asn Ala Asn Gln
    130                 135                 140

Asp Leu Leu Asn Arg Ala Ala Gln Arg Tyr Gly Val Pro Ala Ser Ile
145                 150                 155                 160

Ile Ala Ser Ile Ile Gly Val Glu Thr Leu Tyr Gly Arg Asn Val Gly
                165                 170                 175

Asn Phe Arg Val Val Asp Ala Leu Ala Thr Leu Ala Phe Asp Tyr Leu
            180                 185                 190

Asp Pro Ala Lys Pro Glu Arg Ala Asp Met Phe Arg Gly Gln Leu Gly
        195                 200                 205

Asp Phe Ile Thr Leu Ala Leu Gln Asp Lys Leu Asp Pro Glu Thr Arg
    210                 215                 220

Gly Ser Tyr Ala Gly Ala Ile Gly Met Pro Gln Phe Met Pro Gly Ser
225                 230                 235                 240

Ile Met Arg Tyr Ala Val Asp Gly Asp Asp Asp Gly His Ile Asp Leu
                245                 250                 255

Thr Asn Ser Val Ala Asp Ala Val Met Ser Val Gly Asn Phe Leu Val
            260                 265                 270

Glu His Gly Trp Gln Arg Gly Leu Pro Val Phe Ala Pro Val Ala Leu
        275                 280                 285

Pro Ala Asp Pro Ala Pro Leu Val Ala Gly Gly Leu Thr Pro Thr Leu
    290                 295                 300

Asp Trp Asn Gly Leu Gln Ala Ala Gly Ala Arg Pro Ala Ala Gly Ala
305                 310                 315                 320

Gly Arg Gly Ala Trp Gln Glu His Pro Met Gly Ile Val Asp Leu Val
                325                 330                 335
```

```
Glu Glu Ala Arg Gly Thr Val Gln Tyr Arg Thr Ala Thr Pro Asn Phe
            340                 345                 350

Phe Ala Leu Thr Gln Tyr Asn Arg Ser Tyr Phe Tyr Ala Thr Ala Val
        355                 360                 365

Ala Asp Leu Ala Ala Glu Leu Gln Ala Arg Thr Gly Tyr
    370                 375                 380


<210> SEQ ID NO 73
<211> LENGTH: 1098
<212> TYPE: DNA
<213> ORGANISM: Bordetella pertussis

<400> SEQUENCE: 73

atgaaccata gactcatacg ttgcctgagc atcgcgctgc tggccctgct gtcgggctgc      60

agcattctct ccgggtcggg cccgacgcga tcggccatca tggacggcgg gtcgaccgac     120

gcgaccggcg ccaagctcgg ctcctacgac ctggtggacc tgcgcgccga caccattgcg     180

ccctatgtgc tggtcaaggc ggtgtccaag gatggcgcca cctcggacgg ctacgtgggc     240

aatatgcgcg tgatgccggg cgatgtgctg cgcatcctgg tagccgacag catggagacc     300

ggactgttcg cgccgctggc cgccggcggc acggtgttcg aagccgtgcg ggtcgcggcc     360

gacggcagca tctcgctgcc ctatgcgggc cgcctgaaag tgcagggcaa gtcgctggcg     420

cagatcgagc agctcgtcaa gggcagcctg cgcaataccg cggcggtgca gccgcaggcc     480

atggtggatc tggccgacga ccgctccaat tcggtgctgg tggccggggc ggtgccgcgc     540

ccgggacgct tcggcggcaa caagggcccg ctgacggcgc tggatgcgat cacgcaggcg     600

ggcggctcga ccctgccggc ttaccaggcc gacgtagtga tccggactgg cagcaaggtg     660

cagcgcattc cttaccagca attgctcaac ggccgcaacg tggcggtgga gccgcgctcc     720

gaactggtgg tcgaaccgaa cctgaagcgt ttcgtggcga tgggggccct taccaagccg     780

ggcctgcacg aactgccgtc gaaccagacc aatctgctcg acgccctggg cgtggccgga     840

ggcctgaacg accgcgcggc cgacgccacc ggggtattcg tttttcgcct ggacggccgc     900

aacgccgatg gccgcccgcg gcccacggtg ttcaggctga atatgcgcaa tccggagtcc     960

atgttcctgg ccaagcaatt cgagctgctg ccggaggacg tggtgtatgt cagtaatgcg    1020

cccatgtacg aatgggaaaa gatcattacg cctatcgtgc aggtcctgat cgtgggccaa    1080

cgcgtgggta cttactaa                                                  1098


<210> SEQ ID NO 74
<211> LENGTH: 365
<212> TYPE: PRT
<213> ORGANISM: Bordetella pertussis

<400> SEQUENCE: 74

Met Asn His Arg Leu Ile Arg Cys Leu Ser Ile Ala Leu Leu Ala Leu
 1               5                  10                  15

Leu Ser Gly Cys Ser Ile Leu Ser Gly Ser Gly Pro Thr Arg Ser Ala
            20                  25                  30

Ile Met Asp Gly Gly Ser Thr Asp Ala Thr Gly Ala Lys Leu Gly Ser
        35                  40                  45

Tyr Asp Leu Val Asp Leu Arg Ala Asp Thr Ile Ala Pro Tyr Val Leu
    50                  55                  60

Val Lys Ala Val Ser Lys Asp Gly Ala Thr Ser Asp Gly Tyr Val Gly
65                  70                  75                  80

Asn Met Arg Val Met Pro Gly Asp Val Leu Arg Ile Leu Val Ala Asp
```

```
                85                  90                  95

Ser Met Glu Thr Gly Leu Phe Ala Pro Leu Ala Ala Gly Gly Thr Val
            100                 105                 110

Phe Glu Ala Val Arg Val Ala Ala Asp Gly Ser Ile Ser Leu Pro Tyr
        115                 120                 125

Ala Gly Arg Leu Lys Val Gln Gly Lys Ser Leu Ala Gln Ile Glu Gln
    130                 135                 140

Leu Val Lys Gly Ser Leu Arg Asn Thr Ala Ala Val Gln Pro Gln Ala
145                 150                 155                 160

Met Val Asp Leu Ala Asp Asp Arg Ser Asn Ser Val Leu Val Ala Gly
                165                 170                 175

Ala Val Pro Arg Pro Gly Arg Phe Gly Gly Asn Lys Gly Pro Leu Thr
            180                 185                 190

Ala Leu Asp Ala Ile Thr Gln Ala Gly Gly Ser Thr Leu Pro Ala Tyr
        195                 200                 205

Gln Ala Asp Val Val Ile Arg Thr Gly Ser Lys Val Gln Arg Ile Pro
    210                 215                 220

Tyr Gln Gln Leu Leu Asn Gly Arg Asn Val Ala Val Glu Pro Arg Ser
225                 230                 235                 240

Glu Leu Val Val Glu Pro Asn Leu Lys Arg Phe Val Ala Met Gly Ala
                245                 250                 255

Leu Thr Lys Pro Gly Leu His Glu Leu Pro Ser Asn Gln Thr Asn Leu
            260                 265                 270

Leu Asp Ala Leu Gly Val Ala Gly Gly Leu Asn Asp Arg Ala Ala Asp
        275                 280                 285

Ala Thr Gly Val Phe Val Phe Arg Leu Asp Gly Arg Asn Ala Asp Gly
    290                 295                 300

Arg Pro Arg Pro Thr Val Phe Arg Leu Asn Met Arg Asn Pro Glu Ser
305                 310                 315                 320

Met Phe Leu Ala Lys Gln Phe Glu Leu Leu Pro Glu Asp Val Val Tyr
                325                 330                 335

Val Ser Asn Ala Pro Met Tyr Glu Trp Glu Lys Ile Ile Thr Pro Ile
            340                 345                 350

Val Gln Val Leu Ile Val Gly Gln Arg Val Gly Thr Tyr
        355                 360                 365
```

<210> SEQ ID NO 75
<211> LENGTH: 900
<212> TYPE: DNA
<213> ORGANISM: Bordetella pertussis

<400> SEQUENCE: 75

```
atgcaacgtc tcatgcccat cctggtcgga ctgctcgtcg tcctggccgt cctgtcttca     60

tgcgtcttcg tggtccgcga gcgcgactac gccctggtgt tctcgctggg cgaggtgcgc    120

caggtcatca gcgagcctgg cctgtatttc aaggcgccgc cgccgttcca gaacgtcgtc    180

acgctggaca agcgcatcct caccatcgag tccagcgatg ccgagcgcat ccagacctcc    240

gagaagaaga acctgctgat cgactcgtac gtcaagtggc gcatcgccga tccgcgcctg    300

tactacgtga ccttcggcgg caacgagcgc gccgcccagg agcgtctgca ggcgcagatc    360

cgcgacgcgc tgaacgcggc ggtcaacgtg cgcacggtca aggacgtggt ctcggccgag    420

cgtgacaagg tcatggccga aatcctcacc aacgtcgtca agcgcgccga gccgctgggc    480

gtgcaggtgg tcgacgtgcg cctgcgccgc atcgagttcg cgcccgagat ttccgagtcg    540

gtctatcgcc gcatggaagc cgagcgcacc cgcgtggcca acgagctgcg ttcgatcggc    600
```

gcggccgaaa gcgagaagat ccgcgccgag gccgaccgcc agcgcgaggt catcgtggcc 660
caggcctatg cgcgcgccca gggcatcatg ggcgagggcg acgcccaggc cggcagcatc 720
tacgcccagg ccttcggccg caataccgag ttctacacct attacaagag cctggaagcc 780
tatcgcgccg cgttcggcaa aaccggtgac gtattggtgg tcgatccgac gtcggagttc 840
ttccagttct tcaagaaccc cggcaagggc gcggcgggcg ccccggcacc ggcgaattga 900

<210> SEQ ID NO 76
<211> LENGTH: 299
<212> TYPE: PRT
<213> ORGANISM: Bordetella pertussis

<400> SEQUENCE: 76

Met Gln Arg Leu Met Pro Ile Leu Val Gly Leu Leu Val Val Leu Ala
1 5 10 15

Val Leu Ser Ser Cys Val Phe Val Val Arg Glu Arg Asp Tyr Ala Leu
20 25 30

Val Phe Ser Leu Gly Glu Val Arg Gln Val Ile Ser Glu Pro Gly Leu
35 40 45

Tyr Phe Lys Ala Pro Pro Pro Phe Gln Asn Val Val Thr Leu Asp Lys
50 55 60

Arg Ile Leu Thr Ile Glu Ser Ser Asp Ala Glu Arg Ile Gln Thr Ser
65 70 75 80

Glu Lys Lys Asn Leu Leu Ile Asp Ser Tyr Val Lys Trp Arg Ile Ala
85 90 95

Asp Pro Arg Leu Tyr Tyr Val Thr Phe Gly Gly Asn Glu Arg Ala Ala
100 105 110

Gln Glu Arg Leu Gln Ala Gln Ile Arg Asp Ala Leu Asn Ala Ala Val
115 120 125

Asn Val Arg Thr Val Lys Asp Val Val Ser Ala Glu Arg Asp Lys Val
130 135 140

Met Ala Glu Ile Leu Thr Asn Val Val Lys Arg Ala Glu Pro Leu Gly
145 150 155 160

Val Gln Val Val Asp Val Arg Leu Arg Arg Ile Glu Phe Ala Pro Glu
165 170 175

Ile Ser Glu Ser Val Tyr Arg Arg Met Glu Ala Glu Arg Thr Arg Val
180 185 190

Ala Asn Glu Leu Arg Ser Ile Gly Ala Ala Glu Ser Glu Lys Ile Arg
195 200 205

Ala Glu Ala Asp Arg Gln Arg Glu Val Ile Val Ala Gln Ala Tyr Ala
210 215 220

Arg Ala Gln Gly Ile Met Gly Glu Gly Asp Ala Gln Ala Gly Ser Ile
225 230 235 240

Tyr Ala Gln Ala Phe Gly Arg Asn Thr Glu Phe Tyr Thr Tyr Tyr Lys
245 250 255

Ser Leu Glu Ala Tyr Arg Ala Ala Phe Gly Lys Thr Gly Asp Val Leu
260 265 270

Val Val Asp Pro Thr Ser Glu Phe Phe Gln Phe Phe Lys Asn Pro Gly
275 280 285

Lys Gly Ala Ala Gly Ala Pro Ala Pro Ala Asn
290 295

<210> SEQ ID NO 77
<211> LENGTH: 855
<212> TYPE: DNA

<213> ORGANISM: Bordetella pertussis

<400> SEQUENCE: 77

```
ttgcccaggg aggcaaccat gaaacccgtc atccagactt tcctgcgcgc cgccgccgtg     60

gccggcctgg cgctgctggc cggctgcgcc ggcgtcagca cgacgcagtc cggcgcgatc    120

ggcgtggacc gcacccaata catgtcgagc ctggtgcccg agcaggcgct ggtgcaggag    180

gccgggcagc agtatgccga gatcgtccag gaggcccgcg ccaaggggct gcttgaccgc    240

gacccggcgc aattgtcgcg cgtgcgcgcc atttcccagc gcctgatcgc gcagaccggg    300

gtgtttcgcg ccgacgcggc caactggcca tgggaagtgc atgtgctgtc ggtcgacgag    360

gtcaacgcct ggtgcatgcc cggcggcaag attgccgtct acacgggcct gctcgcccat    420

atcaagccga ccgacgacga actggcggcg gtgctgggcc acgagatcgc gcatgcgttg    480

cgcgagcacg cgcgcgagcg cgtctcgcag cagatggcga ccagcatcgg cctgtcggtg    540

ctgtccatgg ccaccggttc gcccggcgcg tccgacctgg gcggcaagct gaccgaagtc    600

atgttcacct tgcccaacag ccgcacgcac gagaccgagg ccgatcgcat gggcgtcgaa    660

ctggccgcgc gcgccggttt cgatccgcgc gccgccgtca cgctgtggca gaaaatgggc    720

gcggccgacg gcaatgcgcc gccggagttc ctgtccaccc acccgtcggc cagtacccgc    780

atcggcgaat tgcagcaggc cttgcagaag gtattgccgc tgtacgagca ggcgcgcggc    840

caggccgcca aatag                                                     855
```

<210> SEQ ID NO 78
<211> LENGTH: 284
<212> TYPE: PRT
<213> ORGANISM: Bordetella pertussis

<400> SEQUENCE: 78

```
Leu Pro Arg Glu Ala Thr Met Lys Pro Val Ile Gln Thr Phe Leu Arg
 1               5                  10                  15

Ala Ala Ala Val Ala Gly Leu Ala Leu Leu Ala Gly Cys Ala Gly Val
            20                  25                  30

Ser Thr Thr Gln Ser Gly Ala Ile Gly Val Asp Arg Thr Gln Tyr Met
        35                  40                  45

Ser Ser Leu Val Pro Glu Gln Ala Leu Val Gln Glu Ala Gly Gln Gln
    50                  55                  60

Tyr Ala Glu Ile Val Gln Glu Ala Arg Ala Lys Gly Leu Leu Asp Arg
65                  70                  75                  80

Asp Pro Ala Gln Leu Ser Arg Val Arg Ala Ile Ser Gln Arg Leu Ile
                85                  90                  95

Ala Gln Thr Gly Val Phe Arg Ala Asp Ala Ala Asn Trp Pro Trp Glu
            100                 105                 110

Val His Val Leu Ser Val Asp Glu Val Asn Ala Trp Cys Met Pro Gly
        115                 120                 125

Gly Lys Ile Ala Val Tyr Thr Gly Leu Leu Ala His Ile Lys Pro Thr
    130                 135                 140

Asp Asp Glu Leu Ala Ala Val Leu Gly His Glu Ile Ala His Ala Leu
145                 150                 155                 160

Arg Glu His Ala Arg Glu Arg Val Ser Gln Gln Met Ala Thr Ser Ile
                165                 170                 175

Gly Leu Ser Val Leu Ser Met Ala Thr Gly Ser Pro Gly Ala Ser Asp
            180                 185                 190

Leu Gly Gly Lys Leu Thr Glu Val Met Phe Thr Leu Pro Asn Ser Arg
        195                 200                 205
```

```
Thr His Glu Thr Glu Ala Asp Arg Met Gly Val Glu Leu Ala Ala Arg
    210                 215                 220

Ala Gly Phe Asp Pro Arg Ala Ala Val Thr Leu Trp Gln Lys Met Gly
225                 230                 235                 240

Ala Ala Asp Gly Asn Ala Pro Pro Glu Phe Leu Ser Thr His Pro Ser
                245                 250                 255

Ala Ser Thr Arg Ile Gly Glu Leu Gln Gln Ala Leu Gln Lys Val Leu
            260                 265                 270

Pro Leu Tyr Glu Gln Ala Arg Gly Gln Ala Ala Lys
        275                 280


<210> SEQ ID NO 79
<211> LENGTH: 849
<212> TYPE: DNA
<213> ORGANISM: Bordetella pertussis

<400> SEQUENCE: 79

gtgactcacc gtcccgctgc actctcgaag cccgcctccc gccgcggggt ggccctgcgc      60

gcggcgatcg cgctgtcaac cattctgatc gtggccggct gcggctcgtc aagcaccaaa     120

tacgacaaga ccgcgggctg gagcgccgaa cagttgtacg ccgacgccaa gcaggaagtc     180

gcggcgggca actggaccga tgcccgggag cgcctgaccg ccatcgaaag ccgctacccg     240

ttcggcacgt acgcccagca ggccctgatc gaactggctt acgtcaactg gaaagacggc     300

gagaacgaac aggcgctggc cgccatcgac cgcttccagc agctctatcc caaccacccg     360

ggcacggact acgtgctgta cctgaagggg ctggtcaact tcacgccggc cagcgccttc     420

atgagcaacc tgaccggcca ggaccccgcc gagcgcgatc ccaagggcct gcgcgcgtcc     480

tacgatgcgt tcaacgaact ggtccagcgc ttccccaaca gcaagtacac gcccgatgcg     540

cagaagcgca tgacctggct ggtcaacgcc atcgccatga acgaagtcca cgtggcgcgc     600

tactactacg agcggggcgc ctacgtggcg gccgccaacc gggcgcagac cgtgatcacc     660

gatttcgagg gggcccccgc ctcggaagaa gcgctctata tcatggtcga gtcgtatgac     720

aagctgggaa tgaccgaact gaagggcgac gccgaacgcg tgctcgacca gaactatccc     780

aacagcaaat tcaagacgca aggcctgtcg gccgacaaga gctggtggaa cccgttctcg     840

tggcgctga                                                              849


<210> SEQ ID NO 80
<211> LENGTH: 282
<212> TYPE: PRT
<213> ORGANISM: Bordetella pertussis

<400> SEQUENCE: 80

Val Thr His Arg Pro Ala Ala Leu Ser Lys Pro Ala Ser Arg Arg Gly
 1               5                  10                  15

Val Ala Leu Arg Ala Ala Ile Ala Leu Ser Thr Ile Leu Ile Val Ala
            20                  25                  30

Gly Cys Gly Ser Ser Ser Thr Lys Tyr Asp Lys Thr Ala Gly Trp Ser
        35                  40                  45

Ala Glu Gln Leu Tyr Ala Asp Ala Lys Gln Glu Val Ala Ala Gly Asn
    50                  55                  60

Trp Thr Asp Ala Arg Glu Arg Leu Thr Ala Ile Glu Ser Arg Tyr Pro
65                  70                  75                  80

Phe Gly Thr Tyr Ala Gln Gln Ala Leu Ile Glu Leu Ala Tyr Val Asn
                85                  90                  95
```

-continued

```
Trp Lys Asp Gly Glu Asn Glu Gln Ala Leu Ala Ala Ile Asp Arg Phe
            100                 105                 110

Gln Gln Leu Tyr Pro Asn His Pro Gly Thr Asp Tyr Val Leu Tyr Leu
        115                 120                 125

Lys Gly Leu Val Asn Phe Thr Pro Ala Ser Ala Phe Met Ser Asn Leu
    130                 135                 140

Thr Gly Gln Asp Pro Ala Glu Arg Asp Pro Lys Gly Leu Arg Ala Ser
145                 150                 155                 160

Tyr Asp Ala Phe Asn Glu Leu Val Gln Arg Phe Pro Asn Ser Lys Tyr
                165                 170                 175

Thr Pro Asp Ala Gln Lys Arg Met Thr Trp Leu Val Asn Ala Ile Ala
            180                 185                 190

Met Asn Glu Val His Val Ala Arg Tyr Tyr Tyr Glu Arg Gly Ala Tyr
        195                 200                 205

Val Ala Ala Ala Asn Arg Ala Gln Thr Val Ile Thr Asp Phe Glu Gly
    210                 215                 220

Ala Pro Ala Ser Glu Glu Ala Leu Tyr Ile Met Val Glu Ser Tyr Asp
225                 230                 235                 240

Lys Leu Gly Met Thr Glu Leu Lys Gly Asp Ala Glu Arg Val Leu Asp
                245                 250                 255

Gln Asn Tyr Pro Asn Ser Lys Phe Lys Thr Gln Gly Leu Ser Ala Asp
            260                 265                 270

Lys Ser Trp Trp Asn Pro Phe Ser Trp Arg
        275                 280
```

<210> SEQ ID NO 81
<211> LENGTH: 816
<212> TYPE: DNA
<213> ORGANISM: Bordetella pertussis

<400> SEQUENCE: 81

```
ttgcccccac aggttgacct tgccatgacg aagcactctg ccgctcgaat cgccaccatc      60

gccgccgcag gcgtcctgct ggccggctgc gcagcgccca agaaccccga tccgcgcgat     120

ccctgggaag gcttcaaccg gggcgtctac aagttcaacg acacggtcga ccgcgcgctg     180

ttcaagccgg tggcccaggc ctataccttc gtcaccccgc agccggtgcg cagctgcgtg     240

cacaatatgt tcagcaacgt gggcgacctg tggtcggcca ccaacagctt cctgcaaggc     300

cgcgggcacg atttcgtcaa cacgatcggc cgcttcctgt tcaataccac catggggatc     360

ggcggctgct tcgacgtcgc gtcgaccacc ggggcgcgca agatccccaa cgacttcggc     420

gtgacgctgg gcgtctgggg cttcggccag ggaccgtacc tggtgctgcc gatctggggc     480

gccagcagcc tgcgcgacgg cgtcggcctg atcggcgact ggaccggcaa ccagggcgcg     540

accatcggcg cgatcgacaa cgtgccgctg cgcaactcgc tgtggggcct ggaggccgtc     600

gacctgcgcg ccagcctgct cgataccacc gacaccgtgg accgcgtggc gctggatccc     660

tacagcttcg tgcgcgacgc ctacctgcag cgccgcgccg ccatggtgcg cggcaccaag     720

acgggcgacg acacgctgcc cacctatgaa gacgagggcg atgacgacgc ggcccccgcc     780

gcgccggccg cccagccggc cgcccagccg cagtaa                               816
```

<210> SEQ ID NO 82
<211> LENGTH: 271
<212> TYPE: PRT
<213> ORGANISM: Bordetella pertussis

<400> SEQUENCE: 82

-continued

```
Leu Pro Pro Gln Val Asp Leu Ala Met Thr Lys His Ser Ala Ala Arg
 1               5                  10                  15

Ile Ala Thr Ile Ala Ala Ala Gly Val Leu Leu Ala Gly Cys Ala Ala
            20                  25                  30

Pro Lys Asn Pro Asp Pro Arg Asp Pro Trp Glu Gly Phe Asn Arg Gly
        35                  40                  45

Val Tyr Lys Phe Asn Asp Thr Val Asp Arg Ala Leu Phe Lys Pro Val
    50                  55                  60

Ala Gln Ala Tyr Thr Phe Val Thr Pro Gln Pro Val Arg Ser Cys Val
65                  70                  75                  80

His Asn Met Phe Ser Asn Val Gly Asp Leu Trp Ser Ala Thr Asn Ser
                85                  90                  95

Phe Leu Gln Gly Arg Gly His Asp Phe Val Asn Thr Ile Gly Arg Phe
            100                 105                 110

Leu Phe Asn Thr Thr Met Gly Ile Gly Gly Cys Phe Asp Val Ala Ser
        115                 120                 125

Thr Thr Gly Ala Arg Lys Ile Pro Asn Asp Phe Gly Val Thr Leu Gly
    130                 135                 140

Val Trp Gly Phe Gly Gln Gly Pro Tyr Leu Val Leu Pro Ile Trp Gly
145                 150                 155                 160

Ala Ser Ser Leu Arg Asp Gly Val Gly Leu Ile Gly Asp Trp Thr Gly
                165                 170                 175

Asn Gln Gly Ala Thr Ile Gly Ala Ile Asp Asn Val Pro Leu Arg Asn
            180                 185                 190

Ser Leu Trp Gly Leu Glu Ala Val Asp Leu Arg Ala Ser Leu Leu Asp
        195                 200                 205

Thr Thr Asp Thr Val Asp Arg Val Ala Leu Asp Pro Tyr Ser Phe Val
    210                 215                 220

Arg Asp Ala Tyr Leu Gln Arg Arg Ala Ala Met Val Arg Gly Thr Lys
225                 230                 235                 240

Thr Gly Asp Asp Thr Leu Pro Thr Tyr Glu Asp Glu Gly Asp Asp Asp
                245                 250                 255

Ala Ala Pro Ala Ala Pro Ala Ala Gln Pro Ala Ala Gln Pro Gln
            260                 265                 270
```

<210> SEQ ID NO 83
<211> LENGTH: 804
<212> TYPE: DNA
<213> ORGANISM: Bordetella pertussis

<400> SEQUENCE: 83

```
atggcaacaa agtgcctgct ccaggggagt tttccggatg ccagcccgat aatgccggca      60

atgcgtagtg gcgccgcatg ggtgctggaa gggaggttta tgcggtttgg atggggattg     120

ccggcgctgg ccgtcgtgct tgcgctggcc ggatgcgtga atcgcgagcc agaggagcgc     180

gcggccttca tcgcgtatct ggaacaagtg gccgcgccgc aggcgggcgt cgtggccgcg     240

ccgcccgacc cgcccacgcg caaggccctg ggcgactacg aggcgcagta cgagccgatg     300

gaagcggcgc acgccgccgt gcgcgaagcg ttggcggcgc agcaggcggc gctgcaggcg     360

ctgcggctgc attcggtcga cgagatcgtc gcacgccagg acggctggga caggctggcc     420

gagcgcctgg cggccgcgcg caccgggctc gaacaggcgc gcgccgccgc cgacgccgcg     480

cgcgccggga tggagcagcc tcccgacctg cgcaacgcct acgcgcgcgc ctatgaacac     540

agcgtcacgg cgccggcaca ggccttggcg cggatatccg gcctgctcga acccgccgtg     600

gaggatgcgc ggcgcgtggc cgggttcgtt gcgcgccatc gcgatcaggt cgataccgat     660
```

ggtccgctga cccaggtgcg cgatccctcg gtgcgcagcg agctcaatgt actgctgcag 720
gcgctcaatg gccgctccga ccaggtttcg caggcgcagg ccttgctcaa tggcctggcg 780
ggaccggctc gccaggcgcc ctga 804

<210> SEQ ID NO 84
<211> LENGTH: 267
<212> TYPE: PRT
<213> ORGANISM: Bordetella pertussis

<400> SEQUENCE: 84

Met Ala Thr Lys Cys Leu Leu Gln Gly Ser Phe Pro Asp Ala Ser Pro
1 5 10 15

Ile Met Pro Ala Met Arg Ser Gly Ala Ala Trp Val Leu Glu Gly Arg
20 25 30

Phe Met Arg Phe Gly Trp Gly Leu Pro Ala Leu Ala Val Val Leu Ala
35 40 45

Leu Ala Gly Cys Val Asn Arg Glu Pro Glu Glu Arg Ala Ala Phe Ile
50 55 60

Ala Tyr Leu Glu Gln Val Ala Ala Pro Gln Ala Gly Val Val Ala Ala
65 70 75 80

Pro Pro Asp Pro Pro Thr Arg Lys Ala Leu Gly Asp Tyr Glu Ala Gln
85 90 95

Tyr Glu Pro Met Glu Ala Ala His Ala Ala Val Arg Glu Ala Leu Ala
100 105 110

Ala Gln Gln Ala Ala Leu Gln Ala Leu Arg Leu His Ser Val Asp Glu
115 120 125

Ile Val Ala Arg Gln Asp Gly Trp Asp Arg Leu Ala Glu Arg Leu Ala
130 135 140

Ala Ala Arg Thr Gly Leu Glu Gln Ala Arg Ala Ala Ala Asp Ala Ala
145 150 155 160

Arg Ala Gly Met Glu Gln Pro Pro Asp Leu Arg Asn Ala Tyr Ala Arg
165 170 175

Ala Tyr Glu His Ser Val Thr Ala Pro Ala Gln Ala Leu Ala Arg Ile
180 185 190

Ser Gly Leu Leu Glu Pro Ala Val Glu Asp Ala Arg Arg Val Ala Gly
195 200 205

Phe Val Ala Arg His Arg Asp Gln Val Asp Thr Asp Gly Pro Leu Thr
210 215 220

Gln Val Arg Asp Pro Ser Val Arg Ser Glu Leu Asn Val Leu Leu Gln
225 230 235 240

Ala Leu Asn Gly Arg Ser Asp Gln Val Ser Gln Ala Gln Ala Leu Leu
245 250 255

Asn Gly Leu Ala Gly Pro Ala Arg Gln Ala Pro
260 265

<210> SEQ ID NO 85
<211> LENGTH: 693
<212> TYPE: DNA
<213> ORGANISM: Bordetella pertussis

<400> SEQUENCE: 85
gtgatgctga agaccgtatt gcgcctgccg gtctgcgccg cgctgctggc gctggccgcg 60
ggctgcgcga tgattccgcc cgaaccggtg gtgatctgtc cgctgaccgc gccgcctccg 120
tcgccgccgc aaccctcggc gcggcccaac ggctcgatct accagccttc ggcctacggc 180

-continued

```
aactatccgc tgttcgagga ccgccggccg cgcaacgtgg gcgacatcgt caccatcgtg    240

ctggaggaaa agaccaacgc cgccaagggc gtggccacca ataccagccg cgacggctcg    300

gccacgctgg gcgtggcggc cgcgccgcgc ttcatggacg gcatcatcaa cgacaagctg    360

gataccgata tctcgggcgg caataccgcc aacggcaccg gcaagagcag cgccaacaac    420

accttcaccg gcaccatcac gaccaccgtg atcggggtgc tgcccaacgg caatctgcag    480

atcgccggcg agaagcagat cgccatcaac cgcggcagcg agtacgtgcg cttctcgggc    540

gtggtcgacc cgcgatcgat caccggcagc aatacggtgt cgtcgacccg ggtggccgac    600

gcgcgcatcg aataccgcag caagggcgtc atggacgaag tccagaccat gggctggctg    660

caacgctttt tcctgatcgc ttcgccgttc tga                                 693
```

<210> SEQ ID NO 86
<211> LENGTH: 230
<212> TYPE: PRT
<213> ORGANISM: Bordetella pertussis

<400> SEQUENCE: 86

```
Val Met Leu Lys Thr Val Leu Arg Leu Pro Val Cys Ala Ala Leu Leu
 1               5                  10                  15

Ala Leu Ala Ala Gly Cys Ala Met Ile Pro Pro Glu Pro Val Val Ile
            20                  25                  30

Cys Pro Leu Thr Ala Pro Pro Pro Ser Pro Pro Gln Pro Ser Ala Arg
        35                  40                  45

Pro Asn Gly Ser Ile Tyr Gln Pro Ser Ala Tyr Gly Asn Tyr Pro Leu
    50                  55                  60

Phe Glu Asp Arg Arg Pro Arg Asn Val Gly Asp Ile Val Thr Ile Val
65                  70                  75                  80

Leu Glu Glu Lys Thr Asn Ala Ala Lys Gly Val Ala Thr Asn Thr Ser
                85                  90                  95

Arg Asp Gly Ser Ala Thr Leu Gly Val Ala Ala Ala Pro Arg Phe Met
            100                 105                 110

Asp Gly Ile Ile Asn Asp Lys Leu Asp Thr Asp Ile Ser Gly Gly Asn
        115                 120                 125

Thr Ala Asn Gly Thr Gly Lys Ser Ser Ala Asn Asn Thr Phe Thr Gly
    130                 135                 140

Thr Ile Thr Thr Thr Val Ile Gly Val Leu Pro Asn Gly Asn Leu Gln
145                 150                 155                 160

Ile Ala Gly Glu Lys Gln Ile Ala Ile Asn Arg Gly Ser Glu Tyr Val
                165                 170                 175

Arg Phe Ser Gly Val Val Asp Pro Arg Ser Ile Thr Gly Ser Asn Thr
            180                 185                 190

Val Ser Ser Thr Arg Val Ala Asp Ala Arg Ile Glu Tyr Arg Ser Lys
        195                 200                 205

Gly Val Met Asp Glu Val Gln Thr Met Gly Trp Leu Gln Arg Phe Phe
    210                 215                 220

Leu Ile Ala Ser Pro Phe
225                 230
```

<210> SEQ ID NO 87
<211> LENGTH: 681
<212> TYPE: DNA
<213> ORGANISM: Bordetella pertussis

<400> SEQUENCE: 87

```
atgaagtcgt ccctgtatcg aatcgcagcg ctcagcgccg ctgccctgtt gctggccggc     60
```

-continued

```
tgcgccaacc agcgcgctcc gaaggagtcg ggcttcctcg gcgattactc gcagttgcgc    120

gaggagcagg tgcccggcgg cgcgcggctg atctaccgcg acgccgcgct caagccgcgc    180

cagtacaccg ccatgtggct gtcgccggtc gagtactacc ccagcccgca accgtcggcg    240

caggtgtcga tggaaacgct gaccgaactg cagaactacc tggaccagtc gctgcgccgc    300

aagatcggcc gcgagatccg cctggtcaac ggcccggcc cgggcgtggc caaggcgcgc     360

atcgcgatca cagcggtcgg cagcgaaagc gaggcgctgg cggcctacca gtacatcccc    420

gtggcgctgg ccgtcaccgg cgccagggcc gtgctggaag gcggccggcc gcagcaggcc    480

accatcgcga tcgaaagcaa ggtcaccgac agccagacgg gccagctgct gtgggcgtcg    540

gtgcgcgggg gcaccggcga gcgcgtacgc gccatcgccc agggccaggc ctcggtgccg    600

gcctcggcgc tcaagccgct gatcgacgaa tggaccgata acgtcgcacg tgaaatacgc    660

aactacgtgc gcagcaaata a                                               681
```

<210> SEQ ID NO 88
<211> LENGTH: 226
<212> TYPE: PRT
<213> ORGANISM: Bordetella pertussis

<400> SEQUENCE: 88

```
Met Lys Ser Ser Leu Tyr Arg Ile Ala Ala Leu Ser Ala Ala Ala Leu
 1               5                  10                  15

Leu Leu Ala Gly Cys Ala Asn Gln Arg Ala Pro Lys Glu Ser Gly Phe
            20                  25                  30

Leu Gly Asp Tyr Ser Gln Leu Arg Glu Glu Gln Val Pro Gly Gly Ala
        35                  40                  45

Arg Leu Ile Tyr Arg Asp Ala Ala Leu Lys Pro Arg Gln Tyr Thr Ala
    50                  55                  60

Met Trp Leu Ser Pro Val Glu Tyr Tyr Pro Ser Pro Gln Pro Ser Ala
65                  70                  75                  80

Gln Val Ser Met Glu Thr Leu Thr Glu Leu Gln Asn Tyr Leu Asp Gln
                85                  90                  95

Ser Leu Arg Arg Lys Ile Gly Arg Glu Ile Arg Leu Val Asn Gly Pro
            100                 105                 110

Gly Pro Gly Val Ala Lys Ala Arg Ile Ala Ile Thr Ala Val Gly Ser
        115                 120                 125

Glu Ser Glu Ala Leu Ala Ala Tyr Gln Tyr Ile Pro Val Ala Leu Ala
    130                 135                 140

Val Thr Gly Ala Arg Ala Val Leu Glu Gly Gly Arg Pro Gln Gln Ala
145                 150                 155                 160

Thr Ile Ala Ile Glu Ser Lys Val Thr Asp Ser Gln Thr Gly Gln Leu
                165                 170                 175

Leu Trp Ala Ser Val Arg Gly Gly Thr Gly Glu Arg Val Arg Ala Ile
            180                 185                 190

Ala Gln Gly Gln Ala Ser Val Pro Ala Ser Ala Leu Lys Pro Leu Ile
        195                 200                 205

Asp Glu Trp Thr Asp Asn Val Ala Arg Glu Ile Arg Asn Tyr Val Arg
    210                 215                 220

Ser Lys
225
```

<210> SEQ ID NO 89
<211> LENGTH: 561
<212> TYPE: DNA

<213> ORGANISM: Bordetella pertussis

<400> SEQUENCE: 89
gtgaaccaac gtggggccct tttacccgtt aacacgtgtg actctctttg caaaggaact 60
atcatgaagt cgcgcattgc caaaagccta accatagctg cgctggccgc cacgctggca 120
gcctgcagtt ccgtccctct cgacgacaag gcaggtcaag ctggaggctc cggccagggt 180
tcggcctccg gccagatcct ggatcccttc aacccgcaaa gcattctggc gcaacagcgc 240
tcggtgtact ttgacttcga cagctatacg gtgtcggaac agtatcgcgg cctggtcgaa 300
acccacgccc gctacctggc ttcgaacaac cagcagcgca tcaagatcga aggcaatacc 360
gacgaacgcg gcggcgccga gtacaacctc gcactgggcc aacgccgtgc cgacgctgtc 420
cgtcgcatga tgaccctgct gggtgtgtcg gacaaccaga tcgaaaccat tagtttcggc 480
aaggaaaagc cgaaggcgac gggttcgagc gaggctgatt tcgccgagaa ccgccgcgcc 540
gatatcgttt atcagcgcta a 561

<210> SEQ ID NO 90
<211> LENGTH: 186
<212> TYPE: PRT
<213> ORGANISM: Bordetella pertussis

<400> SEQUENCE: 90

Val Asn Gln Arg Gly Ala Leu Leu Pro Val Asn Thr Cys Asp Ser Leu
1               5                   10                  15

Cys Lys Gly Thr Ile Met Lys Ser Arg Ile Ala Lys Ser Leu Thr Ile
            20                  25                  30

Ala Ala Leu Ala Ala Thr Leu Ala Ala Cys Ser Ser Val Pro Leu Asp
        35                  40                  45

Asp Lys Ala Gly Gln Ala Gly Gly Ser Gly Gln Gly Ser Ala Ser Gly
    50                  55                  60

Gln Ile Leu Asp Pro Phe Asn Pro Gln Ser Ile Leu Ala Gln Gln Arg
65                  70                  75                  80

Ser Val Tyr Phe Asp Phe Asp Ser Tyr Thr Val Ser Glu Gln Tyr Arg
                85                  90                  95

Gly Leu Val Glu Thr His Ala Arg Tyr Leu Ala Ser Asn Asn Gln Gln
            100                 105                 110

Arg Ile Lys Ile Glu Gly Asn Thr Asp Glu Arg Gly Gly Ala Glu Tyr
        115                 120                 125

Asn Leu Ala Leu Gly Gln Arg Arg Ala Asp Ala Val Arg Arg Met Met
    130                 135                 140

Thr Leu Leu Gly Val Ser Asp Asn Gln Ile Glu Thr Ile Ser Phe Gly
145                 150                 155                 160

Lys Glu Lys Pro Lys Ala Thr Gly Ser Ser Glu Ala Asp Phe Ala Glu
                165                 170                 175

Asn Arg Arg Ala Asp Ile Val Tyr Gln Arg
            180                 185

<210> SEQ ID NO 91
<211> LENGTH: 555
<212> TYPE: DNA
<213> ORGANISM: Bordetella pertussis

<400> SEQUENCE: 91
gtgtccatga tcgcacgtat ttccctgcgg cctctgaagg ggctcgcggt ggctgtcctg 60
gcagcctccg ccctgaccgc ctgctcgtcc ggcaaatggg gattccccta caaggccggc 120
gtccagcaag gcaactggat caccaaagag caggtcgccc tgctgcagca aggcatgtcg 180
cgcgaacagg tgcgcttcgc cctgggcagc cccacgctga ccagcgtgct gcacgccgat 240
cgctgggatt acccctacta cttcaagccc ggctacggca aggcgcagga acgccagttc 300
accgtgtggt tcgagaacga ccacctggta cgctggagcg gggatgaaca gcccgacctc 360
cagccgttcc agatcgagaa agtgaacgcc aaacaggaag aaaaagccga cgcccaggtg 420
gatacggccg agaagcgcca ggaaggcatc gacaaggctg aaaaagtccg gccccatgtc 480
gatgtcacga cgccggacaa ccccaccctc gactacccgg gcgagccggg ccaaaccttc 540
gaaccgctca agtaa 555

<210> SEQ ID NO 92
<211> LENGTH: 184
<212> TYPE: PRT
<213> ORGANISM: Bordetella pertussis

<400> SEQUENCE: 92

Val Ser Met Ile Ala Arg Ile Ser Leu Arg Pro Leu Lys Gly Leu Ala
1               5                   10                  15

Val Ala Val Leu Ala Ala Ser Ala Leu Thr Ala Cys Ser Ser Gly Lys
            20                  25                  30

Trp Gly Phe Pro Tyr Lys Ala Gly Val Gln Gln Gly Asn Trp Ile Thr
        35                  40                  45

Lys Glu Gln Val Ala Leu Leu Gln Gln Gly Met Ser Arg Glu Gln Val
    50                  55                  60

Arg Phe Ala Leu Gly Ser Pro Thr Leu Thr Ser Val Leu His Ala Asp
65                  70                  75                  80

Arg Trp Asp Tyr Pro Tyr Tyr Phe Lys Pro Gly Tyr Gly Lys Ala Gln
                85                  90                  95

Glu Arg Gln Phe Thr Val Trp Phe Glu Asn Asp His Leu Val Arg Trp
            100                 105                 110

Ser Gly Asp Glu Gln Pro Asp Leu Gln Pro Phe Gln Ile Glu Lys Val
        115                 120                 125

Asn Ala Lys Gln Glu Glu Lys Ala Asp Ala Gln Val Asp Thr Ala Glu
    130                 135                 140

Lys Arg Gln Glu Gly Ile Asp Lys Ala Glu Lys Val Arg Pro His Val
145                 150                 155                 160

Asp Val Thr Thr Pro Asp Asn Pro Thr Leu Asp Tyr Pro Gly Glu Pro
                165                 170                 175

Gly Gln Thr Phe Glu Pro Leu Lys
            180

<210> SEQ ID NO 93
<211> LENGTH: 549
<212> TYPE: DNA
<213> ORGANISM: Bordetella pertussis

<400> SEQUENCE: 93
atggcgaccc atcctgtcgg gccaacgttg ctggcggcgc tgacgctgct tgccgcctgc 60
agcggttcca tggcgcaaga gccgccctac aagagcacga tactgggctt gcaggcgacc 120
atcctggacc tgaagggctt gccgtccgac accgacggcg gcatatcgga cctgagcgcc 180
caagtgggtg cgctggccgc gcgccatgaa ggcgtgtcgg tacggcaggg caaggatgcc 240
gtcaccatcg ccatgatggg cgacgtactc ttcgatttcg acaaggccga catactcgcc 300
gcggccgaac ccactctgcg ggacatcgcg gagctgatca aatcccccgc caccggcatc 360

```
gtcgccattg aaggtcacac ggactccaag ggctcggatt cctataacaa gggcctgtca    420

ttgcgacggg cccaggccgt tgcgcagtgg ctgggcgctc acggggtgga tgcagcgaaa    480

ctgtcggtca ggggcctggg ggctgccagg cccgtacagc ccaaccagct agctgtgaag    540

attcaatag                                                            549
```

<210> SEQ ID NO 94
<211> LENGTH: 182
<212> TYPE: PRT
<213> ORGANISM: Bordetella pertussis

<400> SEQUENCE: 94

```
Met Ala Thr His Pro Val Gly Pro Thr Leu Leu Ala Ala Leu Thr Leu
 1               5                  10                  15

Leu Ala Ala Cys Ser Gly Ser Met Ala Gln Glu Pro Pro Tyr Lys Ser
            20                  25                  30

Thr Ile Leu Gly Leu Gln Ala Thr Ile Leu Asp Leu Lys Gly Leu Pro
        35                  40                  45

Ser Asp Thr Asp Gly Gly Ile Ser Asp Leu Ser Ala Gln Val Gly Ala
    50                  55                  60

Leu Ala Ala Arg His Glu Gly Val Ser Val Arg Gln Gly Lys Asp Ala
65                  70                  75                  80

Val Thr Ile Ala Met Met Gly Asp Val Leu Phe Asp Phe Asp Lys Ala
                85                  90                  95

Asp Ile Leu Ala Ala Ala Glu Pro Thr Leu Arg Asp Ile Ala Glu Leu
            100                 105                 110

Ile Lys Ser Pro Ala Thr Gly Ile Val Ala Ile Glu Gly His Thr Asp
        115                 120                 125

Ser Lys Gly Ser Asp Ser Tyr Asn Lys Gly Leu Ser Leu Arg Arg Ala
    130                 135                 140

Gln Ala Val Ala Gln Trp Leu Gly Ala His Gly Val Asp Ala Ala Lys
145                 150                 155                 160

Leu Ser Val Arg Gly Leu Gly Ala Ala Arg Pro Val Gln Pro Asn Gln
                165                 170                 175

Leu Ala Val Lys Ile Gln
            180
```

<210> SEQ ID NO 95
<211> LENGTH: 504
<212> TYPE: DNA
<213> ORGANISM: Bordetella pertussis

<400> SEQUENCE: 95

```
atgaactata tgcattcccc ctctgtagtt gccgggcgcg cccgccgcct gctggcggta     60

gcggcggttg ccggctcggt ggccgttctg gccggctgcg ccaatcccag cgcatcgagt    120

ggggtgtaca cgtacggcca ggcgcagcgc gagcagatcg tgcgcaccgg cacggtcacc    180

ggcgtgcgtc cgattaccat ccagaacgac aagtccagcg gcgtcggctt ggtggccggt    240

ggcgcgctgg gcggggtagc gggcaatgcc gtcggcggcg gcaccggccg caccatcgcc    300

acggtgggcg gcgtcatcct cggcgcgctg gcgggcaacg ccatcgagaa ccgcgcgggc    360

aagtcctccg gctacgaaat cacggtgcgc ctggacaacg gcgaaacccg ggtcgtggcg    420

caggaagccg acgtgcccat cagcgtgggc cagcgcgtgc aggtcatcag cggcgcgggc    480

ccgacccgcg tgacaccgta ttga                                           504
```

<210> SEQ ID NO 96

<211> LENGTH: 167
<212> TYPE: PRT
<213> ORGANISM: Bordetella pertussis

<400> SEQUENCE: 96

```
Met Asn Tyr Met His Ser Pro Ser Val Val Ala Gly Arg Ala Arg Arg
 1               5                  10                  15

Leu Leu Ala Val Ala Ala Val Ala Gly Ser Val Ala Val Leu Ala Gly
            20                  25                  30

Cys Ala Asn Pro Ser Ala Ser Ser Gly Val Tyr Thr Tyr Gly Gln Ala
        35                  40                  45

Gln Arg Glu Gln Ile Val Arg Thr Gly Thr Val Thr Gly Val Arg Pro
    50                  55                  60

Ile Thr Ile Gln Asn Asp Lys Ser Ser Gly Val Gly Leu Val Ala Gly
65                  70                  75                  80

Gly Ala Leu Gly Gly Val Ala Gly Asn Ala Val Gly Gly Gly Thr Gly
                85                  90                  95

Arg Thr Ile Ala Thr Val Gly Gly Val Ile Leu Gly Ala Leu Ala Gly
            100                 105                 110

Asn Ala Ile Glu Asn Arg Ala Gly Lys Ser Ser Gly Tyr Glu Ile Thr
        115                 120                 125

Val Arg Leu Asp Asn Gly Glu Thr Arg Val Val Ala Gln Glu Ala Asp
    130                 135                 140

Val Pro Ile Ser Val Gly Gln Arg Val Gln Val Ile Ser Gly Ala Gly
145                 150                 155                 160

Pro Thr Arg Val Thr Pro Tyr
                165
```

<210> SEQ ID NO 97
<211> LENGTH: 459
<212> TYPE: DNA
<213> ORGANISM: Bordetella pertussis

<400> SEQUENCE: 97

```
ttggcgttga tcagcaaaaa ggagcgcatc ttgaaaaccc tgctacccgt attggcgctt      60

gccgccctgc tgtcggcctg caacgcgaac gccccctcgg atacgcccga gggcgcgccg     120

ccgcccgata cgcatacctc gcgcaattcg ctggactggc aaggcacgta ccagggcgtg     180

ctgccgtgcg ccgactgccc cggcatccgc acggtgctga ccctgcgcgc cgacaacacc     240

taccagttgc agacccagta cctggagcgc cagccccgcc cggacacggt gcaaggcaga     300

ttcggctggc tgacgggcga caacgccatc gagctcgaca gcgccggcga tcactaccgt     360

taccaggtcg gcgaaaaccg gctgaccatg atgtcgcaag acggcaccct gcccagcggc     420

ccgttggccg agcactacgt gctcaagcgc agccagtga                            459
```

<210> SEQ ID NO 98
<211> LENGTH: 152
<212> TYPE: PRT
<213> ORGANISM: Bordetella pertussis

<400> SEQUENCE: 98

```
Leu Ala Leu Ile Ser Lys Lys Glu Arg Ile Leu Lys Thr Leu Leu Pro
 1               5                  10                  15

Val Leu Ala Leu Ala Ala Leu Leu Ser Ala Cys Asn Ala Asn Ala Pro
            20                  25                  30

Ser Asp Thr Pro Glu Gly Ala Pro Pro Pro Asp Thr His Thr Ser Arg
        35                  40                  45
```

-continued

```
Asn Ser Leu Asp Trp Gln Gly Thr Tyr Gln Gly Val Leu Pro Cys Ala
    50                  55                  60

Asp Cys Pro Gly Ile Arg Thr Val Leu Thr Leu Arg Ala Asp Asn Thr
65                  70                  75                  80

Tyr Gln Leu Gln Thr Gln Tyr Leu Glu Arg Gln Pro Arg Pro Asp Thr
                85                  90                  95

Val Gln Gly Arg Phe Gly Trp Leu Thr Gly Asp Asn Ala Ile Glu Leu
            100                 105                 110

Asp Ser Ala Gly Asp His Tyr Arg Tyr Gln Val Gly Glu Asn Arg Leu
        115                 120                 125

Thr Met Met Ser Gln Asp Gly Thr Leu Pro Ser Gly Pro Leu Ala Glu
    130                 135                 140

His Tyr Val Leu Lys Arg Ser Gln
145                 150
```

<210> SEQ ID NO 99
<211> LENGTH: 5310
<212> TYPE: DNA
<213> ORGANISM: Bordetella pertussis

<400> SEQUENCE: 99

```
atgagacggt taaaggccca ggctttcgaa ggcagccgca gcaggccggc aggacatggg     60

gtggcgccta ccttgctggc gctggccctg gggttccagg gggcggcggc gtgggccaat    120

tgcaccacct cggggtccaa caccacttgc accgcagccg gcggagcgca tcgcgccaag    180

gtagggggcg gctctaccgg gaacaaccaa cacgtcacgg tgcaggccgg tgcgcggatc    240

gaggccggcg acagcggggc catcagcgtg ggcaataaca gccgagtcca gatccaggac    300

ggcgccgtcg tgcaaagcac ggtcaatact gctgcgtccg gccagtacgc caaaacgctg    360

gaagcagcaa gcaataacaa tatttccatc caagtaggcg cgcagctcct ggccaagggc    420

agcgcttcgc agtccagcgc gttgggattg tcaggcgccg gcaataccgt caccaaccat    480

ggcacgatcc gggccgataa tgccgcggca atctggatca ctgccaatac cgccaatgcg    540

gccaatacca tcgataacta cgggactatc gaaacagtgc tcaatggcgg ctacgccaac    600

gccatcggca gcacgcggaa caacagcgcc acgggcgctg gcgtgacggt acgcaatcat    660

gccaacgggc gcatcgtcgg caacgtgaag ttcgaggctg gcgacgacag cgtcatactc    720

gacggcggct ctaccatcac cggatccttg aacggtggca gcggcaacaa cagcctgacg    780

ctgaaagccg gcgacggcac gctgggccgc gcaatccgca acttcggcac gatcaccaag    840

caggaggctg gaacctggac cctgaatggc caggtcggcc gcaacgacaa caacttcaag    900

tccacggtca aggtggaggg cggcacgctg gtcttgcgcg gcgataacag cggcgccacc    960

cagggcggcg tgttgcaggt gtccgccggc gctacggcgg acgtaactgc cgccagcgcc   1020

atgcagtcca tcagcaacgc cggcacggtt cagttcacgc aggacagcaa tgccgcctac   1080

gccggcgtgc tgagcgggac cgggagcatc gtcaagcgcg gcggcggcga cctgacgttg   1140

acgggcaaca acacccatac cggcaaggtg gtggtggagg cgggcagcct cagcgtatcg   1200

gcggccaaca acctgggtgg cgcaggtagt tcggtacagc tcaagggcgg cgccctcgcc   1260

ctcaagaaaa ccatcgccgt caatcgcggc ctgacgctcg attccggggc gcagacgttg   1320

atcatcgagc cgggaacaac cacgacctgg caaggccagg tcagtggcgc cggcaaactg   1380

gtgacccagg gcggcacgct ggtgctggag cacgcgtcca atacgtatag cggcggtacg   1440

gagatcaaca acggaacgct gcgggcggcg catgacgcca gcctgggttc cggcacgttg   1500

gcgctcaaga acagccagct ggccgccacg gacagcttca cggccacgcg tgcattgacg   1560
```

-continued ctcgctggaa acgaaagcat agacgtcgca gccaccaaga tactcagttg gaacggagaa 1620
atcagcggcg ccggcaccct ggtgaaggaa ggccagggga ccttgctgct gcgcggaacc 1680
aatcagcaaa atggcggcac gaccgtcaat gccggtacgc tgcagatatc ccgcgacgcc 1740
aatcttggcc gaggggcgct ggcgctgaac gacggcacgc tgcagagcac cggcagcttc 1800
gcgacctcgc gcgcggccac cttgcgcggc caggccacca tggaggtcga cgcttcgcat 1860
accgtgacct ggaatggcga gctgagcggc ggcggcatgt tgcgcaagtc aggccagggc 1920
acgctggccc tggccggcgc caacacgtac tcgggtggca cggtggtcga ggccggcgcg 1980
cttcgggcag gacacgaaga caacctggga cggggcgcaa taaccctgca gggcggagat 2040
ctgcttgccg gcggcagttt ttcgagcaac cgcgatctca cgcttgtccg cggttccttg 2100
gacgtggctc gcgacgctac cctgacctgg aacggtgcga tatcgggcgc cggcgatctg 2160
gtcaaaacgg gggacgggac cctggcgctc actggcgtca acgagtacgc cggccagacc 2220
gtgctcaggc aaggcaagct gcgcgtggcc agggaagaaa gcctgggcgg cgctgcgctg 2280
gtgctggaaa acaatacggt gttcgagagt gcgggctcgt atgccatcgg gcggcgagtc 2340
acgctcaagg gcgcgcccaa ggtggcaacg cccgcgggcg acacgctcga atggcgcggc 2400
acggtcgacg gcgacggcaa gctgtacaag caaggcggcg gcacgctcgt gctgagcggc 2460
aacaatacct acgccaaggg cgtcgaggtc tggggcgggg tcgtgcaagt ctctcgcgac 2520
cagaacctgg gcgcggccaa tggcgcggtc acgctcaacg gcggcgggtt ggcggccaac 2580
ggggatttca ccagcaatcg ccagctggag ctgaccgccg gggccaaggc catcgacgtc 2640
gcggccggca aggacgtgac gtggcgcggt gtcgtcaacg gcgccggcgc gctgaccaag 2700
gccggcgacg gcaccttgag gttggagagc gtcaacacct acaccggtgg cacgcgcttg 2760
cagggcggca ccgtgcaggt atcgcgcgac aacaacctag gccaggccgc cggcgcggtc 2820
acgttcgacg gcgggcggct ggccagcacc ggcagctttg cgaccgcacg cgcggccacg 2880
ctcaacaacg ccggccagat cgataccgcc cagggcacca cgctgacgtg gaacggcgcc 2940
attggcggca agggcgagct gcgcaagcaa ggggcgggca ccctggtgct gggcggcgcc 3000
aacacttacc agggcgacac ccgcgtcgag gctggcacgc tgcaggtgtc ggccgacgcc 3060
aatctgggcc agggcgccgt gcatctgcac gacagccggc tggcgacgac cggtaccttc 3120
gcgacctcgc gccgtctgga gttgaccgga cgtggcacgg tgcaagcggc tgccgccgcc 3180
acgctggatt ggcgcgggac ggtggctggc gccggcacgc tggtcaagga aggcgcaggc 3240
acgctggtgc tggccggcga caaccagcat gccggcggca ccctggtcca cggcggcacg 3300
ctgcgcatcg cccgcgacgc caacctgggc gcggcgggca cggcggtgac gctggacggc 3360
ggcacgctgg ccaccacggc atcgttggcg ctggatcgcg cgctgcgcgt cggggcgcgc 3420
aatggcgtat tgctgccgga cgcgggcacg accctggatt ggcggggcgt ggtcgccggc 3480
gcgggcaagc tgaccaaggc cggtccgggc atgctggtgc tcagcgccga caaccgccat 3540
ggcggcggca cggcagtcac cggcggtacg ctgcaagtct cgcgcgacgc caacctgggc 3600
gcggcggccg gcgccctgac gctggacggc ggcactttgc tgagcaccgc cagctttgcc 3660
tcggcgcgtg ccgccaccct cgatgccgcg ggcggcacct tcgtcacccg cgacggcacc 3720
cggctggatt gggacggcgc gataggcggg gcgggtggcc tggtcaagga gggcgccggc 3780
gagctgcggc ttggcaatgc caatacctac caggggccga cccgcatcgc cgccggccgc 3840
ctggccgtca acggcagcat cgccagcccg gtcacggtcg agcaggctgg cgtgctgggc 3900
ggcacgggcc gcatcgtcgg ggatgtggcc aaccgcggcg tggtcgcgcc gggcaactcg 3960
atcggcgcgt tgacggtagc cggcaattac gctggtaccg gcggcagcct ggaagtggag 4020
gcggtgcttg gcggcgacgc cgcgccggcc gatcggctgg tgcttgacgg cggcgcggcc 4080
agcggtgtca cgccggtcgt ggtcaagccg cagggcgggg tgggcggcct gaccctgcgc 4140
ggcattccgg tggtcgtggc ccagggtggc gccacgaccg cgcccggggc cttccgcctg 4200
gcgcagccgc tggtcgcggg cgcctacgag taccagttgc tgcgcggcgc gggcgacggc 4260
gccgcggcgc aggcgcagga ctggtacctg cgtacgtccc gcgtcgagcg cgacaaggcg 4320
ggcaggatcg tcaaggtcgt gcccttctac cggcccgagg tggcgctgta tgccggcacg 4380
ccgatgctga tgcgcatgac aggcacggaa atgctgggca gctatcgcga gcgggcgggc 4440
cagactggtg cggtgtcgcc cgaagcgggc gccacggccg cgcgcggtgg atgggcgcgc 4500
accttcggcc gccgtttcga gcgttccgcc ggcggcgagg ccgcgccgtc cttcgacggc 4560
catttggccg gcgcgcaact gggcgcggac ctctacgcgc gcagctcggg cacgcggcat 4620
accgacgcct tcggggtgtt cggcggatat gccacggtgc gcggcgacgt gcatggcctg 4680
gcgcgtggcg aaatccaggc cgtggggacg tccacgctgc gggccaccca attgggcgcc 4740
tattggaccc acactggtcc gggcggctgg tacatcgaca cggtgctggc cggcacgcgc 4800
tacaggcagc agacgaagtc gtccgctcag gtcggcgctg tcagccgcgg ctgggggatg 4860
acggcttcgg tggaggcggg ctatccgtgg cagctcaacc cgcgctggcg catcgaaccg 4920
caggcccagg tggtgtatca gcaactgggc attgccaatg gcgccgaccg cgtgtccacg 4980
gtgtcgtaca agacgcccga tgcgctgacg gctcggttag gtacgcgcct gtcgggccag 5040
tacgcatacg ggaaggcgca gttgcggccg ttcatgggcg tatcgctgct gcacgatttc 5100
accggcgcgg acaccgtcac gttcgcgggc gcgcatggcg tacgcgccag ccgccagaac 5160
acggccgtgg atctgaaggc gggcgtggac acgcagctgg gcaagagcgt aggcctgtgg 5220
gggcaggtag gctacggcaa gtcggtcggc agcggcgacg gcagcgaccg tggctggagc 5280
gccaacctgg ggctgcgcgt ggcgtattga 5310

<210> SEQ ID NO 100
<211> LENGTH: 1769
<212> TYPE: PRT
<213> ORGANISM: Bordetella pertussis

<400> SEQUENCE: 100

Met Arg Arg Leu Lys Ala Gln Ala Phe Glu Gly Ser Arg Ser Arg Pro
1 5 10 15

Ala Gly His Gly Val Ala Pro Thr Leu Leu Ala Leu Ala Leu Gly Phe
20 25 30

Gln Gly Ala Ala Ala Trp Ala Asn Cys Thr Thr Ser Gly Ser Asn Thr
35 40 45

Thr Cys Thr Ala Ala Gly Gly Ala His Arg Ala Lys Val Gly Gly Gly
50 55 60

Ser Thr Gly Asn Asn Gln His Val Thr Val Gln Ala Gly Ala Arg Ile
65 70 75 80

Glu Ala Gly Asp Ser Gly Ala Ile Ser Val Gly Asn Asn Ser Arg Val
85 90 95

Gln Ile Gln Asp Gly Ala Val Val Gln Ser Thr Val Asn Thr Ala Ala
100 105 110

Ser Gly Gln Tyr Ala Lys Thr Leu Glu Ala Ala Ser Asn Asn Asn Ile
115 120 125

Ser Ile Gln Val Gly Ala Gln Leu Leu Ala Lys Gly Ser Ala Ser Gln

-continued

```
    130                 135                 140

Ser Ser Ala Leu Gly Leu Ser Gly Ala Gly Asn Thr Val Thr Asn His
145                 150                 155                 160

Gly Thr Ile Arg Ala Asp Asn Ala Ala Ala Ile Trp Ile Thr Ala Asn
                165                 170                 175

Thr Ala Asn Ala Ala Asn Thr Ile Asp Asn Tyr Gly Thr Ile Glu Thr
            180                 185                 190

Val Leu Asn Gly Gly Tyr Ala Asn Ala Ile Gly Ser Thr Arg Asn Asn
        195                 200                 205

Ser Ala Thr Gly Ala Gly Val Thr Val Arg Asn His Ala Asn Gly Arg
    210                 215                 220

Ile Val Gly Asn Val Lys Phe Glu Ala Gly Asp Asp Ser Val Ile Leu
225                 230                 235                 240

Asp Gly Gly Ser Thr Ile Thr Gly Ser Leu Asn Gly Gly Ser Gly Asn
                245                 250                 255

Asn Ser Leu Thr Leu Lys Ala Gly Asp Gly Thr Leu Gly Arg Ala Ile
            260                 265                 270

Arg Asn Phe Gly Thr Ile Thr Lys Gln Glu Ala Gly Thr Trp Thr Leu
        275                 280                 285

Asn Gly Gln Val Gly Arg Asn Asp Asn Asn Phe Lys Ser Thr Val Lys
    290                 295                 300

Val Glu Gly Gly Thr Leu Val Leu Arg Gly Asp Asn Ser Gly Ala Thr
305                 310                 315                 320

Gln Gly Gly Val Leu Gln Val Ser Ala Gly Ala Thr Ala Asp Val Thr
                325                 330                 335

Ala Ala Ser Ala Met Gln Ser Ile Ser Asn Ala Gly Thr Val Gln Phe
            340                 345                 350

Thr Gln Asp Ser Asn Ala Ala Tyr Ala Gly Val Leu Ser Gly Thr Gly
        355                 360                 365

Ser Ile Val Lys Arg Gly Gly Gly Asp Leu Thr Leu Thr Gly Asn Asn
    370                 375                 380

Thr His Thr Gly Lys Val Val Val Glu Ala Gly Ser Leu Ser Val Ser
385                 390                 395                 400

Ala Ala Asn Asn Leu Gly Gly Ala Gly Ser Ser Val Gln Leu Lys Gly
                405                 410                 415

Gly Ala Leu Ala Leu Lys Lys Thr Ile Ala Val Asn Arg Gly Leu Thr
            420                 425                 430

Leu Asp Ser Gly Ala Gln Thr Leu Ile Ile Glu Pro Gly Thr Thr Thr
        435                 440                 445

Thr Trp Gln Gly Gln Val Ser Gly Ala Gly Lys Leu Val Thr Gln Gly
    450                 455                 460

Gly Thr Leu Val Leu Glu His Ala Ser Asn Thr Tyr Ser Gly Gly Thr
465                 470                 475                 480

Glu Ile Asn Asn Gly Thr Leu Arg Ala Ala His Asp Ala Ser Leu Gly
                485                 490                 495

Ser Gly Thr Leu Ala Leu Lys Asn Ser Gln Leu Ala Ala Thr Asp Ser
            500                 505                 510

Phe Thr Ala Thr Arg Ala Leu Thr Leu Ala Gly Asn Glu Ser Ile Asp
        515                 520                 525

Val Ala Ala Thr Lys Ile Leu Ser Trp Asn Gly Glu Ile Ser Gly Ala
    530                 535                 540

Gly Thr Leu Val Lys Glu Gly Gln Gly Thr Leu Leu Leu Arg Gly Thr
545                 550                 555                 560
```

-continued

```
Asn Gln Gln Asn Gly Gly Thr Thr Val Asn Ala Gly Thr Leu Gln Ile
                565                 570                 575

Ser Arg Asp Ala Asn Leu Gly Arg Gly Ala Leu Ala Leu Asn Asp Gly
            580                 585                 590

Thr Leu Gln Ser Thr Gly Ser Phe Ala Thr Ser Arg Ala Ala Thr Leu
        595                 600                 605

Arg Gly Gln Ala Thr Met Glu Val Asp Ala Ser His Thr Val Thr Trp
    610                 615                 620

Asn Gly Glu Leu Ser Gly Gly Gly Met Leu Arg Lys Ser Gly Gln Gly
625                 630                 635                 640

Thr Leu Ala Leu Ala Gly Ala Asn Thr Tyr Ser Gly Gly Thr Val Val
                645                 650                 655

Glu Ala Gly Ala Leu Arg Ala Gly His Glu Asp Asn Leu Gly Arg Gly
            660                 665                 670

Ala Ile Thr Leu Gln Gly Gly Asp Leu Leu Ala Gly Gly Ser Phe Ser
        675                 680                 685

Ser Asn Arg Asp Leu Thr Leu Val Arg Gly Ser Leu Asp Val Ala Arg
    690                 695                 700

Asp Ala Thr Leu Thr Trp Asn Gly Ala Ile Ser Gly Ala Gly Asp Leu
705                 710                 715                 720

Val Lys Thr Gly Asp Gly Thr Leu Ala Leu Thr Gly Val Asn Glu Tyr
                725                 730                 735

Ala Gly Gln Thr Val Leu Arg Gln Gly Lys Leu Arg Val Ala Arg Glu
            740                 745                 750

Glu Ser Leu Gly Gly Ala Ala Leu Val Leu Glu Asn Asn Thr Val Phe
        755                 760                 765

Glu Ser Ala Gly Ser Tyr Ala Ile Gly Arg Arg Val Thr Leu Lys Gly
    770                 775                 780

Ala Pro Lys Val Ala Thr Pro Ala Gly Asp Thr Leu Glu Trp Arg Gly
785                 790                 795                 800

Thr Val Asp Gly Asp Gly Lys Leu Tyr Lys Gln Gly Gly Gly Thr Leu
                805                 810                 815

Val Leu Ser Gly Asn Asn Thr Tyr Ala Lys Gly Val Glu Val Trp Gly
            820                 825                 830

Gly Val Val Gln Val Ser Arg Asp Gln Asn Leu Gly Ala Ala Asn Gly
        835                 840                 845

Ala Val Thr Leu Asn Gly Gly Gly Leu Ala Ala Asn Gly Asp Phe Thr
    850                 855                 860

Ser Asn Arg Gln Leu Glu Leu Thr Ala Gly Ala Lys Ala Ile Asp Val
865                 870                 875                 880

Ala Ala Gly Lys Asp Val Thr Trp Arg Gly Val Val Asn Gly Ala Gly
                885                 890                 895

Ala Leu Thr Lys Ala Gly Asp Gly Thr Leu Arg Leu Glu Ser Val Asn
            900                 905                 910

Thr Tyr Thr Gly Gly Thr Arg Leu Gln Gly Gly Thr Val Gln Val Ser
        915                 920                 925

Arg Asp Asn Asn Leu Gly Gln Ala Ala Gly Ala Val Thr Phe Asp Gly
    930                 935                 940

Gly Arg Leu Ala Ser Thr Gly Ser Phe Ala Thr Ala Arg Ala Ala Thr
945                 950                 955                 960

Leu Asn Asn Ala Gly Gln Ile Asp Thr Ala Gln Gly Thr Thr Leu Thr
                965                 970                 975

Trp Asn Gly Ala Ile Gly Gly Lys Gly Glu Leu Arg Lys Gln Gly Ala
            980                 985                 990
```

```
Gly Thr Leu Val Leu Gly Gly Ala Asn Thr Tyr Gln Gly Asp Thr Arg
        995                 1000                1005

Val Glu Ala Gly Thr Leu Gln Val Ser Ala Asp Ala Asn Leu Gly Gln
    1010                1015                1020

Gly Ala Val His Leu His Asp Ser Arg Leu Ala Thr Thr Gly Thr Phe
1025                1030                1035                1040

Ala Thr Ser Arg Arg Leu Glu Leu Thr Gly Arg Gly Thr Val Gln Ala
                1045                1050                1055

Ala Ala Ala Ala Thr Leu Asp Trp Arg Gly Thr Val Ala Gly Ala Gly
            1060                1065                1070

Thr Leu Val Lys Glu Gly Ala Gly Thr Leu Val Leu Ala Gly Asp Asn
        1075                1080                1085

Gln His Ala Gly Gly Thr Leu Val His Gly Gly Thr Leu Arg Ile Ala
    1090                1095                1100

Arg Asp Ala Asn Leu Gly Ala Ala Gly Thr Ala Val Thr Leu Asp Gly
1105                1110                1115                1120

Gly Thr Leu Ala Thr Thr Ala Ser Leu Ala Leu Asp Arg Ala Leu Arg
                1125                1130                1135

Val Gly Ala Arg Asn Gly Val Leu Leu Pro Asp Ala Gly Thr Thr Leu
            1140                1145                1150

Asp Trp Arg Gly Val Val Ala Gly Ala Gly Lys Leu Thr Lys Ala Gly
        1155                1160                1165

Pro Gly Met Leu Val Leu Ser Ala Asp Asn Arg His Gly Gly Gly Thr
    1170                1175                1180

Ala Val Thr Gly Gly Thr Leu Gln Val Ser Arg Asp Ala Asn Leu Gly
1185                1190                1195                1200

Ala Ala Ala Gly Ala Leu Thr Leu Asp Gly Gly Thr Leu Leu Ser Thr
                1205                1210                1215

Ala Ser Phe Ala Ser Ala Arg Ala Ala Thr Leu Asp Ala Ala Gly Gly
            1220                1225                1230

Thr Phe Val Thr Arg Asp Gly Thr Arg Leu Asp Trp Asp Gly Ala Ile
        1235                1240                1245

Gly Gly Ala Gly Gly Leu Val Lys Glu Gly Ala Gly Glu Leu Arg Leu
    1250                1255                1260

Gly Asn Ala Asn Thr Tyr Gln Gly Pro Thr Arg Ile Ala Ala Gly Arg
1265                1270                1275                1280

Leu Ala Val Asn Gly Ser Ile Ala Ser Pro Val Thr Val Glu Gln Ala
                1285                1290                1295

Gly Val Leu Gly Gly Thr Gly Arg Ile Val Gly Asp Val Ala Asn Arg
            1300                1305                1310

Gly Val Val Ala Pro Gly Asn Ser Ile Gly Ala Leu Thr Val Ala Gly
        1315                1320                1325

Asn Tyr Ala Gly Thr Gly Gly Ser Leu Glu Val Glu Ala Val Leu Gly
    1330                1335                1340

Gly Asp Ala Ala Pro Ala Asp Arg Leu Val Leu Asp Gly Gly Ala Ala
1345                1350                1355                1360

Ser Gly Val Thr Pro Val Val Val Lys Pro Gln Gly Gly Val Gly Gly
                1365                1370                1375

Leu Thr Leu Arg Gly Ile Pro Val Val Val Ala Gln Gly Gly Ala Thr
            1380                1385                1390

Thr Ala Pro Gly Ala Phe Arg Leu Ala Gln Pro Leu Val Ala Gly Ala
        1395                1400                1405

Tyr Glu Tyr Gln Leu Leu Arg Gly Ala Gly Asp Gly Ala Ala Ala Gln
```

-continued

```
    1410                1415                1420

Ala Gln Asp Trp Tyr Leu Arg Thr Ser Arg Val Glu Arg Asp Lys Ala
1425                1430                1435                1440

Gly Arg Ile Val Lys Val Val Pro Phe Tyr Arg Pro Glu Val Ala Leu
                1445                1450                1455

Tyr Ala Gly Thr Pro Met Leu Met Arg Met Thr Gly Thr Glu Met Leu
            1460                1465                1470

Gly Ser Tyr Arg Glu Arg Ala Gly Gln Thr Gly Ala Val Ser Pro Glu
        1475                1480                1485

Ala Gly Ala Thr Ala Ala Arg Gly Gly Trp Ala Arg Thr Phe Gly Arg
    1490                1495                1500

Arg Phe Glu Arg Ser Ala Gly Gly Glu Ala Ala Pro Ser Phe Asp Gly
1505                1510                1515                1520

His Leu Ala Gly Ala Gln Leu Gly Ala Asp Leu Tyr Ala Arg Ser Ser
                1525                1530                1535

Gly Thr Arg His Thr Asp Ala Phe Gly Val Phe Gly Gly Tyr Ala Thr
            1540                1545                1550

Val Arg Gly Asp Val His Gly Leu Ala Arg Gly Glu Ile Gln Ala Val
        1555                1560                1565

Gly Thr Ser Thr Leu Arg Ala Thr Gln Leu Gly Ala Tyr Trp Thr His
    1570                1575                1580

Thr Gly Pro Gly Gly Trp Tyr Ile Asp Thr Val Leu Ala Gly Thr Arg
1585                1590                1595                1600

Tyr Arg Gln Gln Thr Lys Ser Ser Ala Gln Val Gly Ala Val Ser Arg
                1605                1610                1615

Gly Trp Gly Met Thr Ala Ser Val Glu Ala Gly Tyr Pro Trp Gln Leu
            1620                1625                1630

Asn Pro Arg Trp Arg Ile Glu Pro Gln Ala Gln Val Val Tyr Gln Gln
        1635                1640                1645

Leu Gly Ile Ala Asn Gly Ala Asp Arg Val Ser Thr Val Ser Tyr Lys
    1650                1655                1660

Thr Pro Asp Ala Leu Thr Ala Arg Leu Gly Thr Arg Leu Ser Gly Gln
1665                1670                1675                1680

Tyr Ala Tyr Gly Lys Ala Gln Leu Arg Pro Phe Met Gly Val Ser Leu
                1685                1690                1695

Leu His Asp Phe Thr Gly Ala Asp Thr Val Thr Phe Ala Gly Ala His
            1700                1705                1710

Gly Val Arg Ala Ser Arg Gln Asn Thr Ala Val Asp Leu Lys Ala Gly
        1715                1720                1725

Val Asp Thr Gln Leu Gly Lys Ser Val Gly Leu Trp Gly Gln Val Gly
    1730                1735                1740

Tyr Gly Lys Ser Val Gly Ser Gly Asp Gly Ser Asp Arg Gly Trp Ser
1745                1750                1755                1760

Ala Asn Leu Gly Leu Arg Val Ala Tyr
                1765
```

<210> SEQ ID NO 101
<211> LENGTH: 582
<212> TYPE: DNA
<213> ORGANISM: Bordetella pertussis

<400> SEQUENCE: 101

```
atgaacaaac cctccaaatt cgctctggcg ctcgccttcg ccgctgttac ggcctctggt      60

gcagcttccg cgcaaaccgt ggacaactgg cgcaatccgt ttggcgacgt ttggaagaac     120
```

```
ggcaccaatg aactgtgctg gcgcgatgcg ttctggaccc cggctaccgg catccccggt    180

tgcgacggcg ttccggtcgc tcagaaggaa aagtccgctc ccatggccgc caaggtcgtg    240

ttcaatgctg acaccttctt cgacttcgac aagtcgacgc tgaagccgga aggccgccag    300

ctgctggatc aagtcgccca gcaagccggc acgatcgatc tggaaacgat catcgccgtt    360

ggccacacgg actcgatcgg caccgaagcc tacaaccaga agctgtccga gcgccgtgcc    420

gctgcggtca agacctacct ggtcagcaag ggtatcgacc ccaaccgtat ctacacggaa    480

ggcaagggcg aactgcaacc gatcgcttcg aacaagacgc gtgaaggccg tgcccagaac    540

cgtcgcgtgg aaatcgaaat cgtcggtagc cgcaagaact aa                       582
```

<210> SEQ ID NO 102
<211> LENGTH: 193
<212> TYPE: PRT
<213> ORGANISM: Bordetella pertussis

<400> SEQUENCE: 102

```
Met Asn Lys Pro Ser Lys Phe Ala Leu Ala Leu Ala Phe Ala Ala Val
 1               5                  10                  15

Thr Ala Ser Gly Ala Ala Ser Ala Gln Thr Val Asp Asn Trp Arg Asn
            20                  25                  30

Pro Phe Gly Asp Val Trp Lys Asn Gly Thr Asn Glu Leu Cys Trp Arg
        35                  40                  45

Asp Ala Phe Trp Thr Pro Ala Thr Gly Ile Pro Gly Cys Asp Gly Val
    50                  55                  60

Pro Val Ala Gln Lys Glu Lys Ser Ala Pro Met Ala Ala Lys Val Val
65                  70                  75                  80

Phe Asn Ala Asp Thr Phe Phe Asp Phe Asp Lys Ser Thr Leu Lys Pro
                85                  90                  95

Glu Gly Arg Gln Leu Leu Asp Gln Val Ala Gln Gln Ala Gly Thr Ile
            100                 105                 110

Asp Leu Glu Thr Ile Ile Ala Val Gly His Thr Asp Ser Ile Gly Thr
        115                 120                 125

Glu Ala Tyr Asn Gln Lys Leu Ser Glu Arg Arg Ala Ala Ala Val Lys
    130                 135                 140

Thr Tyr Leu Val Ser Lys Gly Ile Asp Pro Asn Arg Ile Tyr Thr Glu
145                 150                 155                 160

Gly Lys Gly Glu Leu Gln Pro Ile Ala Ser Asn Lys Thr Arg Glu Gly
                165                 170                 175

Arg Ala Gln Asn Arg Arg Val Glu Ile Glu Ile Val Gly Ser Arg Lys
            180                 185                 190

Asn
```

<210> SEQ ID NO 103
<211> LENGTH: 582
<212> TYPE: DNA
<213> ORGANISM: Bordetella pertussis

<400> SEQUENCE: 103

```
atgaacaaac cctccaaatt cgctctggcg ctcgccttcg ccgctgttac ggcctctggt     60

gcagcttccg cgcaaaccgt ggacaactgg cgcaatccgt ttggcgacgt ttggaagaac    120

ggcaccaatg aactgtgctg gcgcgatgcg ttctggaccc cggctaccgg catccccggt    180

tgcgacggcg ttccggtcgc tcagaaggaa aagcccgctc ccatggccgc caaggtcgtg    240

ttcaatgctg acaccttctt cgacttcgac aagtcgacgc tgaagccgga aggccgccag    300
```

ctgctggatc aagtcgccca gcaagccggc acgatcgatc tggaaacgat catcgccgtt 360
ggccacacgg actcgatcgg caccgaagcc tacaaccaga agctgtccga gcgccgtgcc 420
gctgcggtca agacctacct ggtcagcaag ggtatcgacc ccaaccgtat ctacacggaa 480
ggcaagggcg aactgcaacc gatcgcttcg aacaagacgc gtgaaggccg tgcccagaac 540
cgtcgcgtgg aaatcgagat cgtcggtagc cgcaagaact aa 582

<210> SEQ ID NO 104
<211> LENGTH: 193
<212> TYPE: PRT
<213> ORGANISM: Bordetella pertussis

<400> SEQUENCE: 104

```
Met Asn Lys Pro Ser Lys Phe Ala Leu Ala Leu Ala Phe Ala Ala Val
 1               5                  10                  15

Thr Ala Ser Gly Ala Ala Ser Ala Gln Thr Val Asp Asn Trp Arg Asn
            20                  25                  30

Pro Phe Gly Asp Val Trp Lys Asn Gly Thr Asn Glu Leu Cys Trp Arg
        35                  40                  45

Asp Ala Phe Trp Thr Pro Ala Thr Gly Ile Pro Gly Cys Asp Gly Val
    50                  55                  60

Pro Val Ala Gln Lys Glu Lys Pro Ala Pro Met Ala Ala Lys Val Val
65                  70                  75                  80

Phe Asn Ala Asp Thr Phe Phe Asp Phe Asp Lys Ser Thr Leu Lys Pro
                85                  90                  95

Glu Gly Arg Gln Leu Leu Asp Gln Val Ala Gln Gln Ala Gly Thr Ile
            100                 105                 110

Asp Leu Glu Thr Ile Ile Ala Val Gly His Thr Asp Ser Ile Gly Thr
        115                 120                 125

Glu Ala Tyr Asn Gln Lys Leu Ser Glu Arg Arg Ala Ala Ala Val Lys
    130                 135                 140

Thr Tyr Leu Val Ser Lys Gly Ile Asp Pro Asn Arg Ile Tyr Thr Glu
145                 150                 155                 160

Gly Lys Gly Glu Leu Gln Pro Ile Ala Ser Asn Lys Thr Arg Glu Gly
                165                 170                 175

Arg Ala Gln Asn Arg Arg Val Glu Ile Glu Ile Val Gly Ser Arg Lys
            180                 185                 190

Asn
```

<210> SEQ ID NO 105
<211> LENGTH: 2232
<212> TYPE: DNA
<213> ORGANISM: Bordetella pertussis

<400> SEQUENCE: 105
atgaagttct acccttccca tccgatgccc gagtcgctcg cggctgcgat cgcagtgcct 60
ctgttgggcc tgctgccggc ggcgcaggcc gcgtccacgg cggtccagct gccatccgtc 120
acggtcgagg gcgagtactc gtcctatcaa ccggaaagcg cccagtcgcc caagttcacc 180
gcgcccctgg cggacacgcc gcgcacggtg caggtcatcc ctgagcggct catccaggac 240
cagggggcca gcgacctcga agcggtactg cgcaatgcgc cagggatatc gatgaccgcc 300
ggcgaaggcg gccgtccggc cagcgacctg ccgttcatcc gcggccagaa ttcggccagc 360
agcctgtttg tcgacggcct gcgcgatccc agcacgcaat cgcgcgatac cttcaacctg 420
gaacaggtcg acgtcgtcaa ggggcccgat tcggtatttt ccgggcgcgg cggcgccggc 480

```
ggaagcatca acctcgtcac caagacgccc aggaaccagg atttcaccga agtccaggcc    540

ggcatcggga cggccgagac ctaccgaggc accatagacg gcaactgggt gctgggcgag    600

aacacggcgc tgcgcctcaa cctgctgggc accaggggca ccgtgccggg ccgcgacaag    660

gcggtcgagt tcagccgcgt gggtatcgcg ccatcgctgc gcctgggcct gagcggcccc    720

acccgcgtga cgctgggcct gtacctctat cgccaccggc gggttcccga ttattcgatt    780

ccgtacgatc cgcgcaccgg cacgccgatc accgagacca tcggggtcag ccgccgcaac    840

ttctacggcc tggtgcagcg cgactccggc gataccgagg actacgccgc caccgtcaaa    900

tgggagcacg acctcgccaa tggcttcaag gtggagaacc tggcgcgcta ctcgcgcgcc    960

acggtggagc agatcaccac catccccgaa ctgaaaaccg ccgatctggc caaagggctg   1020

gtgtaccgca atctgcgcgc cagctaccag gtcaacgaca gtttcgccaa ccgcaccgac   1080

ctgcgcggca cattcgacac ggggcagtgg cgccatacct tcgatctggg cggggagttc   1140

gccaccagcc ggcgcagtcg cgaccgctac aagcaggaaa tccccgacgc cgccagtcct   1200

tgctcgcccg tgacgggcgg caacaatccc gccctgtgcg cctcgctccg ggatccggat   1260

ccgcacgtgg atttcccggg aacggtgcgg cgcaaccata acccggcccg ctaccacacc   1320

gacatcctgt ccctgtacgg tttcgacacc atcgccttcg acgagcagtg gcagctgaat   1380

ctcggcctgc gctgggacca ctacaagacc agcggacgca acctgccggt acgaggcgcc   1440

aagccgcccg tctacgagag cgccgcgcgt accgacaacc tgttcaacta ccagctcggc   1500

ctggtctaca agcctcgtcc ggacggctcg gtgtatgcga gctacggcac ggcgtccacg   1560

ccgtcggccg tgtccgacta cgcccccggcg gacaacatct ccggcacaag ccagcagttc   1620

aagccggagc gcagcgaggt gatcgaggtc gggaccaagt ggcaggtgct ggaccggcgg   1680

ctgctggtga cgggcgccat gttccgcgaa acgcgcaaga acaccagcat cgaagtcgcc   1740

gaaggcctgc gcgcaccggc cggcaagagc cgcgtcaccg gcatggagct gggcgtggcg   1800

ggcagcctga cgccgcgctg ggacgtctac ggcggctacg cgctgctcga cagcaagctg   1860

gtcagggcca gccataacag cggggcgcaa ggccagccgc tgcccagcgc gccccggcac   1920

gcattcagca tctggagcac ctacaagctg ctgccggagc tgaccgtggg ggccggcgcg   1980

ttctatcgca gcaaggtcta tggcaacgca gatgccggcc acaacaagga cggcacgccc   2040

aaggcgcgct gggtgccggc gtactggcgc ttcgacgcca tggcggcgta ccagctcaac   2100

aagcacctta cggcccagtt gaacgtctac aacctgctcg acaagaccta ttacgccaag   2160

acctaccgca gccattacgc ggcgctgggt ccggggcggt ccgccatgct gacgttcaag   2220

ctgagctact ga                                                        2232
```

<210> SEQ ID NO 106
<211> LENGTH: 743
<212> TYPE: PRT
<213> ORGANISM: Bordetella pertussis

<400> SEQUENCE: 106

```
Met Lys Phe Tyr Pro Ser His Pro Met Pro Glu Ser Leu Ala Ala Ala
 1               5                  10                  15

Ile Ala Val Pro Leu Leu Gly Leu Leu Pro Ala Ala Gln Ala Ala Ser
            20                  25                  30

Thr Ala Val Gln Leu Pro Ser Val Thr Val Glu Gly Glu Tyr Ser Ser
        35                  40                  45

Tyr Gln Pro Glu Ser Ala Gln Ser Pro Lys Phe Thr Ala Pro Leu Ala
    50                  55                  60
```

-continued

```
Asp Thr Pro Arg Thr Val Gln Val Ile Pro Glu Arg Leu Ile Gln Asp
65                  70                  75                  80

Gln Gly Ala Ser Asp Leu Glu Ala Val Leu Arg Asn Ala Pro Gly Ile
                85                  90                  95

Ser Met Thr Ala Gly Glu Gly Gly Arg Pro Ala Ser Asp Leu Pro Phe
            100                 105                 110

Ile Arg Gly Gln Asn Ser Ala Ser Ser Leu Phe Val Asp Gly Leu Arg
        115                 120                 125

Asp Pro Ser Thr Gln Ser Arg Asp Thr Phe Asn Leu Glu Gln Val Asp
    130                 135                 140

Val Val Lys Gly Pro Asp Ser Val Phe Ser Gly Arg Gly Gly Ala Gly
145                 150                 155                 160

Gly Ser Ile Asn Leu Val Thr Lys Thr Pro Arg Asn Gln Asp Phe Thr
                165                 170                 175

Glu Val Gln Ala Gly Ile Gly Thr Ala Glu Thr Tyr Arg Gly Thr Ile
            180                 185                 190

Asp Gly Asn Trp Val Leu Gly Glu Asn Thr Ala Leu Arg Leu Asn Leu
        195                 200                 205

Leu Gly Thr Arg Gly Thr Val Pro Gly Arg Asp Lys Ala Val Glu Phe
    210                 215                 220

Ser Arg Val Gly Ile Ala Pro Ser Leu Arg Leu Gly Leu Ser Gly Pro
225                 230                 235                 240

Thr Arg Val Thr Leu Gly Leu Tyr Leu Tyr Arg His Arg Arg Val Pro
                245                 250                 255

Asp Tyr Ser Ile Pro Tyr Asp Pro Arg Thr Gly Thr Pro Ile Thr Glu
            260                 265                 270

Thr Ile Gly Val Ser Arg Arg Asn Phe Tyr Gly Leu Val Gln Arg Asp
        275                 280                 285

Ser Gly Asp Thr Glu Asp Tyr Ala Ala Thr Val Lys Trp Glu His Asp
    290                 295                 300

Leu Ala Asn Gly Phe Lys Val Glu Asn Leu Ala Arg Tyr Ser Arg Ala
305                 310                 315                 320

Thr Val Glu Gln Ile Thr Thr Ile Pro Glu Leu Lys Thr Ala Asp Leu
                325                 330                 335

Ala Lys Gly Leu Val Tyr Arg Asn Leu Arg Ala Ser Tyr Gln Val Asn
            340                 345                 350

Asp Ser Phe Ala Asn Arg Thr Asp Leu Arg Gly Thr Phe Asp Thr Gly
        355                 360                 365

Gln Trp Arg His Thr Phe Asp Leu Gly Gly Glu Phe Ala Thr Ser Arg
    370                 375                 380

Arg Ser Arg Asp Arg Tyr Lys Gln Glu Ile Pro Asp Ala Ala Ser Pro
385                 390                 395                 400

Cys Ser Pro Val Thr Gly Gly Asn Asn Pro Ala Leu Cys Ala Ser Leu
                405                 410                 415

Arg Asp Pro Asp Pro His Val Asp Phe Pro Gly Thr Val Arg Arg Asn
            420                 425                 430

His Asn Pro Ala Arg Tyr His Thr Asp Ile Leu Ser Leu Tyr Gly Phe
        435                 440                 445

Asp Thr Ile Ala Phe Asp Glu Gln Trp Gln Leu Asn Leu Gly Leu Arg
    450                 455                 460

Trp Asp His Tyr Lys Thr Ser Gly Arg Asn Leu Pro Val Arg Gly Ala
465                 470                 475                 480

Lys Pro Pro Val Tyr Glu Ser Ala Ala Arg Thr Asp Asn Leu Phe Asn
                485                 490                 495
```

```
Tyr Gln Leu Gly Leu Val Tyr Lys Pro Arg Pro Asp Gly Ser Val Tyr
            500                 505                 510

Ala Ser Tyr Gly Thr Ala Ser Thr Pro Ser Ala Val Ser Asp Tyr Ala
        515                 520                 525

Pro Ala Asp Asn Ile Ser Gly Thr Ser Gln Gln Phe Lys Pro Glu Arg
    530                 535                 540

Ser Glu Val Ile Glu Val Gly Thr Lys Trp Gln Val Leu Asp Arg Arg
545                 550                 555                 560

Leu Leu Val Thr Gly Ala Met Phe Arg Glu Thr Arg Lys Asn Thr Ser
                565                 570                 575

Ile Glu Val Ala Glu Gly Leu Arg Ala Pro Ala Gly Lys Ser Arg Val
            580                 585                 590

Thr Gly Met Glu Leu Gly Val Ala Gly Ser Leu Thr Pro Arg Trp Asp
        595                 600                 605

Val Tyr Gly Gly Tyr Ala Leu Leu Asp Ser Lys Leu Val Arg Ala Ser
    610                 615                 620

His Asn Ser Gly Ala Gln Gly Gln Pro Leu Pro Ser Ala Pro Arg His
625                 630                 635                 640

Ala Phe Ser Ile Trp Ser Thr Tyr Lys Leu Leu Pro Glu Leu Thr Val
                645                 650                 655

Gly Ala Gly Ala Phe Tyr Arg Ser Lys Val Tyr Gly Asn Ala Asp Ala
            660                 665                 670

Gly His Asn Lys Asp Gly Thr Pro Lys Ala Arg Trp Val Pro Ala Tyr
        675                 680                 685

Trp Arg Phe Asp Ala Met Ala Ala Tyr Gln Leu Asn Lys His Leu Thr
    690                 695                 700

Ala Gln Leu Asn Val Tyr Asn Leu Leu Asp Lys Thr Tyr Tyr Ala Lys
705                 710                 715                 720

Thr Tyr Arg Ser His Tyr Ala Ala Leu Gly Pro Gly Arg Ser Ala Met
                725                 730                 735

Leu Thr Phe Lys Leu Ser Tyr
            740


<210> SEQ ID NO 107
<211> LENGTH: 1158
<212> TYPE: DNA
<213> ORGANISM: Bordetella pertussis

<400> SEQUENCE: 107

atgaaaaaga ctctgctcgc tgccgccctg ctcgccggtt tcgccggtgc cgctcaggca     60

gaaacgtcgg tcaccctgta cggtatcatc gacacgggta tcggctacaa cgatgtcgat    120

ttcaaggtga aaggcgctaa cgccgacgac agcgacttca agtacaacca cagccgcttc    180

ggcatgatca acggcgtgca gaacggttcg cgctggggtc tgcgtggtac ggaagatctg    240

ggtgacggcc tgcaagctgt gttccaactg gaatcgggct tcaactcggg caacggtaac    300

tcggcccaag acggccgcct gttcggtcgc caagccacca tcggtctgca aagcgaaagc    360

tggggccgtc tggacttcgg tcgccaaacc aacatcgcct cgaagtactt cggctcgatc    420

gatccgttcg gcgctggctt cggtcaagcc aacatcggca tgggcatgag cgcgatgaac    480

accgttcgct acgacaacat ggtcatgtac cagaccccgt cgtacagcgg cttccagttc    540

ggtatcggct actcgttcag cgcgaacgac aaggatgctg acgccgtcaa ccgcgttggc    600

ttcgccaccg ccgacaacgt tcgtgccatc acgaccggtc tgcgctacgt gaacggcccg    660

ctgaacgtcg ctctgtcgta cgaccagctg aacgcctcga acaaccaagc ccaaggcgaa    720
```

-continued

```
gttgacgcga ccccgcgcag ctacggcctc ggcggttcgt atgacttcga agtcgtgaag    780

ctggctctgg cctacgctcg cacgaccgac ggctggttcg gtggccaagg ctacccggtc    840

gccgtcacgc tgccctcggg cgacaagttc ggcggcttcg gcgtgaacac cttcgctgac    900

ggcttcaagg ccaactcgta catggtcggc ctgtcggccc ccatcggcgg cgccagcaac    960

gtgttcggtt cgtggcagat ggttgacccc aagctgaccg gcggcgacga gaagatgaac   1020

gtcttctcgc tgggctacac ctacgacctg tccaagcgca ccaacctgta cgcctacggt   1080

tcgtacgcca agaacttcgc gttcctggaa gatgccaagt cgaccgctgt cggcgtcggt   1140

atccgtcacc gcttctaa                                                 1158
```

<210> SEQ ID NO 108
<211> LENGTH: 385
<212> TYPE: PRT
<213> ORGANISM: Bordetella pertussis

<400> SEQUENCE: 108

```
Met Lys Lys Thr Leu Leu Ala Ala Ala Leu Leu Ala Gly Phe Ala Gly
 1               5                  10                  15

Ala Ala Gln Ala Glu Thr Ser Val Thr Leu Tyr Gly Ile Ile Asp Thr
            20                  25                  30

Gly Ile Gly Tyr Asn Asp Val Asp Phe Lys Val Lys Gly Ala Asn Ala
        35                  40                  45

Asp Asp Ser Asp Phe Lys Tyr Asn His Ser Arg Phe Gly Met Ile Asn
    50                  55                  60

Gly Val Gln Asn Gly Ser Arg Trp Gly Leu Arg Gly Thr Glu Asp Leu
65                  70                  75                  80

Gly Asp Gly Leu Gln Ala Val Phe Gln Leu Glu Ser Gly Phe Asn Ser
                85                  90                  95

Gly Asn Gly Asn Ser Ala Gln Asp Gly Arg Leu Phe Gly Arg Gln Ala
            100                 105                 110

Thr Ile Gly Leu Gln Ser Glu Ser Trp Gly Arg Leu Asp Phe Gly Arg
        115                 120                 125

Gln Thr Asn Ile Ala Ser Lys Tyr Phe Gly Ser Ile Asp Pro Phe Gly
    130                 135                 140

Ala Gly Phe Gly Gln Ala Asn Ile Gly Met Gly Met Ser Ala Met Asn
145                 150                 155                 160

Thr Val Arg Tyr Asp Asn Met Val Met Tyr Gln Thr Pro Ser Tyr Ser
                165                 170                 175

Gly Phe Gln Phe Gly Ile Gly Tyr Ser Phe Ser Ala Asn Asp Lys Asp
            180                 185                 190

Ala Asp Ala Val Asn Arg Val Gly Phe Ala Thr Ala Asp Asn Val Arg
        195                 200                 205

Ala Ile Thr Thr Gly Leu Arg Tyr Val Asn Gly Pro Leu Asn Val Ala
    210                 215                 220

Leu Ser Tyr Asp Gln Leu Asn Ala Ser Asn Asn Gln Ala Gln Gly Glu
225                 230                 235                 240

Val Asp Ala Thr Pro Arg Ser Tyr Gly Leu Gly Gly Ser Tyr Asp Phe
                245                 250                 255

Glu Val Val Lys Leu Ala Leu Ala Tyr Ala Arg Thr Thr Asp Gly Trp
            260                 265                 270

Phe Gly Gly Gln Gly Tyr Pro Val Ala Val Thr Leu Pro Ser Gly Asp
        275                 280                 285

Lys Phe Gly Gly Phe Gly Val Asn Thr Phe Ala Asp Gly Phe Lys Ala
```

```
    290                 295                 300

Asn Ser Tyr Met Val Gly Leu Ser Ala Pro Ile Gly Gly Ala Ser Asn
305                 310                 315                 320

Val Phe Gly Ser Trp Gln Met Val Asp Pro Lys Leu Thr Gly Gly Asp
                325                 330                 335

Glu Lys Met Asn Val Phe Ser Leu Gly Tyr Thr Tyr Asp Leu Ser Lys
            340                 345                 350

Arg Thr Asn Leu Tyr Ala Tyr Gly Ser Tyr Ala Lys Asn Phe Ala Phe
        355                 360                 365

Leu Glu Asp Ala Lys Ser Thr Ala Val Gly Val Gly Ile Arg His Arg
    370                 375                 380

Phe
385
```

<210> SEQ ID NO 109
<211> LENGTH: 1167
<212> TYPE: DNA
<213> ORGANISM: Bordetella pertussis

<400> SEQUENCE: 109

```
atgaaaaaga ctctgctcgc tgccgccctg ctcgccggtt tcgccggtgc cgctcaggca      60

gaaacgtcgg tcaccctgta cggtatcatc gacacgggta tcggctacaa cgatgtcgat     120

ttcaaggtga aaggcgctaa cgccgacggc agcgacttca agtacaacca cagccgcttc     180

ggcatgatca acggcgtgca gaacggttcg cgctggggtc tgcgtggtac ggaagatctg     240

ggtgacggcc tgcaagctgt gttccaactg gaatcgggct tcagctcggc caacggtaac     300

tcggcccaag acggtcgcct gttcggtcgt caagccacca tcggtctgca aagcgaaagc     360

tggggccgtc tggacttcgg tcgccaaacc aacatcgcct cgaagtactt cggctcgatc     420

gatccgttcg gcgctggctt cggtcaagcc aacatcggca tgggcatgag cgcgatgaac     480

accgttcgct acgacaacat ggtcatgtac cagaccccgt cgtacagcgg cttccagttc     540

ggtatcggct actcgttcag cgcgaacgac aaggacgctg acgccgtcaa ccgcgttggc     600

ttcgccaccg ccgacaacgt tcgtgccatc acgaccggtc tgcgctacgt gaacggcccg     660

ctgaacgtcg ctctgtcgta cgaccagctg aacgcctcga acaaccaagc ccaagacgaa     720

gttgacgcca ccccgcgcag ctacggcatc ggcggttcgt atgacttcga agtcgtgaag     780

ctggctctgg cctacgctcg cacgaccgac ggctggttcg gtggccaagg ctacccggtc     840

gctgtcacgc tgccctcggg cgacaagttc ggcggcttcg gcgtgaacac cttcgctgac     900

ggcttcaagg ccaactccta cctgttgggc ctgtcggctc cgatcggcgg cgccagcaac     960

gtgttcggtt cgtggcagat ggttgacccc agcaacgaca agctgaccgg cggcgacgag    1020

aagatgaacg tcttctcgct gggctacacc tacgacctgt ccaagcgcac caacctgtac    1080

gcctacggtt cgtacgccaa gaacttcgcg ttcctggaag atgccaagtc gaccgctgtc    1140

ggcgtcggta tccgtcaccg cttctaa                                        1167
```

<210> SEQ ID NO 110
<211> LENGTH: 388
<212> TYPE: PRT
<213> ORGANISM: Bordetella pertussis

<400> SEQUENCE: 110

```
Met Lys Lys Thr Leu Leu Ala Ala Ala Leu Leu Ala Gly Phe Ala Gly
 1               5                  10                  15

Ala Ala Gln Ala Glu Thr Ser Val Thr Leu Tyr Gly Ile Ile Asp Thr
```

-continued

```
            20                  25                  30

Gly Ile Gly Tyr Asn Asp Val Asp Phe Lys Val Lys Gly Ala Asn Ala
        35                  40                  45

Asp Gly Ser Asp Phe Lys Tyr Asn His Ser Arg Phe Gly Met Ile Asn
    50                  55                  60

Gly Val Gln Asn Gly Ser Arg Trp Gly Leu Arg Gly Thr Glu Asp Leu
65                  70                  75                  80

Gly Asp Gly Leu Gln Ala Val Phe Gln Leu Glu Ser Gly Phe Ser Ser
                85                  90                  95

Ala Asn Gly Asn Ser Ala Gln Asp Gly Arg Leu Phe Gly Arg Gln Ala
            100                 105                 110

Thr Ile Gly Leu Gln Ser Glu Ser Trp Gly Arg Leu Asp Phe Gly Arg
        115                 120                 125

Gln Thr Asn Ile Ala Ser Lys Tyr Phe Gly Ser Ile Asp Pro Phe Gly
    130                 135                 140

Ala Gly Phe Gly Gln Ala Asn Ile Gly Met Gly Met Ser Ala Met Asn
145                 150                 155                 160

Thr Val Arg Tyr Asp Asn Met Val Met Tyr Gln Thr Pro Ser Tyr Ser
                165                 170                 175

Gly Phe Gln Phe Gly Ile Gly Tyr Ser Phe Ser Ala Asn Asp Lys Asp
            180                 185                 190

Ala Asp Ala Val Asn Arg Val Gly Phe Ala Thr Ala Asp Asn Val Arg
        195                 200                 205

Ala Ile Thr Thr Gly Leu Arg Tyr Val Asn Gly Pro Leu Asn Val Ala
    210                 215                 220

Leu Ser Tyr Asp Gln Leu Asn Ala Ser Asn Asn Gln Ala Gln Asp Glu
225                 230                 235                 240

Val Asp Ala Thr Pro Arg Ser Tyr Gly Ile Gly Gly Ser Tyr Asp Phe
                245                 250                 255

Glu Val Val Lys Leu Ala Leu Ala Tyr Ala Arg Thr Thr Asp Gly Trp
            260                 265                 270

Phe Gly Gly Gln Gly Tyr Pro Val Ala Val Thr Leu Pro Ser Gly Asp
        275                 280                 285

Lys Phe Gly Gly Phe Gly Val Asn Thr Phe Ala Asp Gly Phe Lys Ala
    290                 295                 300

Asn Ser Tyr Leu Leu Gly Leu Ser Ala Pro Ile Gly Gly Ala Ser Asn
305                 310                 315                 320

Val Phe Gly Ser Trp Gln Met Val Asp Pro Ser Asn Asp Lys Leu Thr
                325                 330                 335

Gly Gly Asp Glu Lys Met Asn Val Phe Ser Leu Gly Tyr Thr Tyr Asp
            340                 345                 350

Leu Ser Lys Arg Thr Asn Leu Tyr Ala Tyr Gly Ser Tyr Ala Lys Asn
        355                 360                 365

Phe Ala Phe Leu Glu Asp Ala Lys Ser Thr Ala Val Gly Val Gly Ile
    370                 375                 380

Arg His Arg Phe
385
```